US010954304B2

(12) United States Patent
Nishimura et al.

(10) Patent No.: US 10,954,304 B2
(45) Date of Patent: Mar. 23, 2021

(54) NEUTRALIZING ANTIBODIES TO THE αVβ8 INTEGRIN COMPLEX FOR IMMUNOTHERAPY

(71) Applicant: The Regents of the University of California, Oakland, CA (US)

(72) Inventors: Stephen L. Nishimura, San Francisco, CA (US); Jianlong Lou, San Francisco, CA (US); James D. Marks, San Francisco, CA (US); Jody L. Baron, San Francisco, CA (US); Yifan Cheng, San Francisco, CA (US); Shenping Wu, San Francisco, CA (US); Anthony Cormier, San Francisco, CA (US); Naoki Takasaka, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/331,902

(22) PCT Filed: Sep. 29, 2017

(86) PCT No.: PCT/US2017/054306
§ 371 (c)(1),
(2) Date: Mar. 8, 2019

(87) PCT Pub. No.: WO2018/064478
PCT Pub. Date: Apr. 5, 2018

(65) Prior Publication Data
US 2019/0218298 A1    Jul. 18, 2019

Related U.S. Application Data

(60) Provisional application No. 62/401,570, filed on Sep. 29, 2016, provisional application No. 62/529,381, filed on Jul. 6, 2017.

(51) Int. Cl.
*C07K 16/00* (2006.01)
*C07K 16/46* (2006.01)
*C07K 16/28* (2006.01)
*A61P 31/20* (2006.01)
*A61P 35/04* (2006.01)
*A61P 37/04* (2006.01)
*A61P 1/04* (2006.01)
*C07K 14/705* (2006.01)
*C07K 16/22* (2006.01)
*G01N 33/563* (2006.01)
*A61K 39/00* (2006.01)

(52) U.S. Cl.
CPC ............ *C07K 16/2839* (2013.01); *A61P 1/04* (2018.01); *A61P 31/20* (2018.01); *A61P 35/04* (2018.01); *A61P 37/04* (2018.01); *C07K 14/705* (2013.01); *C07K 16/22* (2013.01); *G01N 33/563* (2013.01); *A61K 2039/505* (2013.01); *C07K 2317/24* (2013.01); *C07K 2317/34* (2013.01); *C07K 2317/56* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 2012/0251523 A1 | 10/2012 | Unutmaz et al. |
| 2013/0064837 A1 | 3/2013 | Nishimura et al. |
| 2014/0271478 A1 | 9/2014 | Nishimura et al. |
| 2016/0040839 A1 | 2/2016 | Driscoll |

FOREIGN PATENT DOCUMENTS

| EP | 1957522 A2 | 8/2008 | |
| WO | 2011103490 A2 | 8/2011 | |
| WO | 2014165524 A2 | 10/2014 | |
| WO | WO-2014165524 A2 * | 10/2014 | ......... C07K 16/2839 |

OTHER PUBLICATIONS

Takasaka et al. Integrin αvβ8-expressing tumor cells evade host immunity by regulating TGF-β activation in immune cells. JCI Insight. 2018;3(20):e122591. (Year: 2018).*
International Search Report and Written Opinion dated Mar. 8, 2018 for PCT/US2017/054306.
Stockis, et al., "Blocking Immunosuppression by Human Tregs In Vivo With Antibodies Targeting Integrin αVβ8," Proceedings of the National Academy of Sciences, Nov. 21, 2017 (Nov. 21, 2017), vol. 114, No. 47, 1-161-10168. Entire document.
Worthington, et al., "Integrin αVβ8-Mediated TGF-62 Activation by Effector Regulatory T Cells is Essential for Suppression of T-Cell-Mediated Inflammation," Immunity, May 19, 2015 (May 19, 2015), vol. 42, pp. 1-13. Entire document.
Wu, "Fab assisted CryoEM of asymmetrical membrane proteins," UCSF, presentation at Yale University on Jan. 2017, pp. 1-48.

(Continued)

Primary Examiner — Maher M Haddad
(74) Attorney, Agent, or Firm — Kilpatrick Townsend & Stockton LLP

(57) ABSTRACT

Provided is an antibody that specifically binds human αvββ and blocks binding of TGFp peptide to αvβ8, wherein the antibody binds to the specificity determining loop (SDL) of human β8. In some embodiments, the antibody further binds to one, two, or all three of the human av-head domain, the al helix of human β8, or the al helix of human β8. In some embodiments, the antibody is humanized or chimeric. In some embodiments, the antibody is linked to a detectable label. Also provided is a method of enhancing an immune response in a human individual, comprising administering a sufficient amount of the antibody to the individual, thereby enhancing an immune response. Also provided are pharmaceutical compositions comprising the anti-αvββ antibodies or antigen-binding molecules thereof.

15 Claims, 68 Drawing Sheets
Specification includes a Sequence Listing.

(56) References Cited

OTHER PUBLICATIONS

Shunsuke, Minagawa, et al., "Selective Targeting of TGF-beta Activation to Treat Fibroinflammatory Airway Disease," Science Translation Medicine, American Association for the Advancement of Science, Jun. 18, 2014, vol. 6, No. 241, 14 pages.

Eberlein, C., et al., "A human monoclonal antibody 264RAD targeting [alpha]v&bgr;6 integrin reduces tumour growth and metastasis, and modulates key biomarkers in vivo," Oncogene, Sep. 12, 2013, vol. 32, No. 37, pp. 4406-4416.

Koopman Van Aarsen, Louise A., et al., "Antibody-mediated blockade of integrin alpha(v)beta(6) inhibits tumor progression in vivo by a transforming growth factor-beta-regulated mechanism," Cancer Research, American Association for Cancer Research, Jan. 15, 2008, vol. 68, No. 2, pp. 561-570.

Supplementary European Search Report dated Apr. 21, 2020 in European Patent Application EP17857499, 12 pages.

\* cited by examiner

| VH | Framework 1 | CDR1 | Framework 2 | CDR2 | Framework 3 | CDR3 | Framework 4 |
|---|---|---|---|---|---|---|---|
| (Mouse Hybridoma Name) | | | | | | | |
| B13C4 15-8 | EVQLQQSGPELKKPGETVKISCKASGY | TFTDYSMH | WVKQAPGKGLKWMG | WIKTETGEPTYADDFKG | REAFSLETSATTAYLQINNLKNEDTAKYFCAI | YYYGRDS | WGQGTTLTVSS |
| B13C4 15-10 | QIQLLQSGPELKKPGETVKISCKASGY | TFTDYSMH | WVKQAPGKGLKWMG | WIKTETGEPTYADDFKG | REAFSLETSATTAYLQINNLKNEDTAKYFCAI | YYYGRDS | WGQGTTLTVSS |
| B13H3.2 | QIQLLQSGPELKKPGETVKISCKASGY | TFTDYSMH | WVKQAPGKGLKWMG | WIKTETGEPTYADDFKG | REAFSLETSASTANLQINNLKNEDTATYFCAI | YYYGRDS | WGQGTTLTVSS |
| B13C1231015 | QIQLLQSGPELKKPGETVKISCKASGY | TFTDYSIH | WVKQAPGKGLKWMG | WIKTETDEPTYADDFKE | REAFSLETSASTAYLQIINLKNEDTATYFCAI | YYYGRDS | WGQGTTLTVSS |
| B15B11Vh | QIQLLQSGPELKKPGETVKISCKASGY | TFTDYSMH | WVKQAPGKGLKWVA | WIKTETGEPTYADDNG | REAFSLETSASTAYLQINNLKNEDTATYFCAI | YYYGRDS | WGQGTTLTVSS |
| B2B2 15-9 | QIQLLQSGPELKKPGETVKISCLASGY | TFTDYSMH | WVKQAPGKGLKWVA | RINTETGEPTFADDFRG | REAVSLETSASTAYLQINNLKNEDTATYFCAI | YYYGRDS | WGQGTTLTVSS |
| R1D12715.3 | EVQLVESGGGLVQPGGSLKLSCAASGF | TFSSFGMS | WVRQTPDKRLELVA | TINSNGGSTYYPDNMKG | RFTISRDNAKNTILQMSSLKSEDTAMYYCAS | ACYRYGAFFDY | WGQGTTLTVSS |
| (Produced Rabbit IgG clone name) | | | | | | | |
| RSDlVH-1 | EVQLLESGPELKKPGETVKISCKASGY | TFTDYSIH | WVKQAPGKGLKWMG | WIKTETGEPTYADDFKG | REAFSLETSASTAYLQINNLKNEDTATYFCAI | YYYGRDS | WGQGTTLTVSS |
| RSDlVH-3 | QVQIMQSGPELKKPGETVKISCKASGY | TFTDYSIH | WVKQAPGKGLKWMG | WIKTETGEPTYADDPNG | REAFSLETSASTAYLQINNLKNEDTATYFCAI | YYYGRDS | WGQGTTLTVSS |
| RSDlVH-16 | QIQLQQSGPELKKPGETVKISCKASGY | TFTDYSMH | WVKQAPGKGLKWVA | RINTETGEPTFADDFRG | REAFSLETSASTAYLQINNLKNEDTATYFCAI | YYYGRDS | WGQGTTLTVSS |
| (scFv clone from Yeast Display library) | | | | | | | |
| 29 | QIQLLQSGPELKKPGETVKISCKASGY | TFTDYSMH | WVKQAPGKGLKWVA | RINTETGEPTFADDFRG | REAVSLETSASTAYLQINNLKNEDTATYFCAI | YYYGRDS | WGQGTTLTVSS |
| 44 | QIQLLQSGPELKKPGETVKISCKASGY | TFTDYSMH | WVKQAPGKGLKWVA | RINTETGEPTFADDFRG | REAVSLETSATTAYLQINNLKNEDTAKYFCAI | YYYGRDS | WGQGTTLTVSS |
| A1=B4=F9 | QIQLLQSGPELKKPGETVKISCKASGY | TFTDYSMH | WVKQAPGKGLKWVA | RINTETGEPTFADDFRG | REAVSLETSASTAYLQINNLKNEDTATYFCAI | YYYGRDS | WGQGTTLTVSS |
| A5=C6 | QIQLLQSGPELKKPGETVKISCKASGY | TFTDYSMH | WVKQAPGKGLKWVA | RINTETGEPTFADDFRG | REAVSLETSASTAYLQINNLKNEDTATYFCAI | YYYGRDT | WGQGTALTVSS |
| D4=E6 | QIQLLQSGPELKKPGETVKISCKASGY | TFTDYSMH | WVKQAPGKGLKWVA | RINTETGEPTFADDFRG | REAVSLETSASTAYLQINNLKNEDTATYFCAI | FYYGRDS | WGQGTTLTVSS |
| Final clone for in vivo/in vitro Functional test in IgG format | | | | | | | |
| C6D4 | QIQLLQSGPELKKPGETVKISCKASGY | TFTDYSMH | WVKQAPGKGLKWVA | RINTETGEPTFADDFRG | REAVSLETSASTAYLQINNLKNEDTATYFCAI | FYYGRDS | WGQGTTLTVSS |

FIG. 1

| VH | Framework 1 | CDR1 | Framework 2 | CDR2 | Framework 3 | CDR3 | Framework 4 |
|---|---|---|---|---|---|---|---|
| (Mouse Hybridoma Name) | | | | | | | |
| B2B2 35-20 | DIVMSQSPSSMYASLGERVTITC | KASQDINSYLS | WFQQKPGKSPKTLIY | RANRLVD | GVPSRFSGSSSGQDYSLTISSLEYEDMGIYYC | LQYDEFPPLT | FGAGTKLELKA |
| B2B2 35-26 | QIVLTQSPSSMYASLGERVTITC | KASQDINSYLS | WFQQKGASPKTLIY | RANRLVD | GVPSRFSGSGSGGQDYSLTISSLEYEDMGIYYC | LQYDEFPPLT | FGAGTKLELKR |
| B15B1vk34-26 | QIVLTQSPAIMSASPGEKVTMTC | SASSSVSYMH | WYQQKPGTSPKLWIY | DTSNLAS | GVPARFSGSGSGTSYSLTISMEAEDAATYYC | QQWSSNPLT | FGAGTKLELKA |
| B15B1vk33-24 | EIVLTQSPAIMSASPGEKVTMTC | SASSSVSYMH | WYQQKPGSSPKLWIY | DTSNLAS | GVPARFSGSGSGTSYSLTISSMEAEDAATYYC | QQWSSNPHT | FGSGTKLELKA |
| B15B1vk35-26 | QIVLTQSPAIMSASPGEKVTMTC | SASSSVSYMH | WYQQKSGTSPKLWIY | DTSNLAS | GVPARFSGSGSGTSYSLTISSMEAEDAATYYC | QQWSSNPPT | FGDGTRLELKA |
| B13C12134-25 | DIKMTQSPAIMSASPGEKVTMTC | SASSSVSYMH | WYQQKSGTSPKRWIY | DTSKLAS | GVPARFSGSGSGTSYSLTISSMEAEDAATYYC | QQWSSNPFT | FGSGTKLELKA |
| B13C12133-26 | QMVLTHSPAIMSASPGEKVTMTC | SASSSVSYMH | WYQQKPGSSPKPWIY | GTSNLAS | GVPARFSGSGSGTSYSLTISSMEAEDAATYYC | QQWSSNPPT | FGDGTRLELKA |
| B13C4 35-20 | DIVMSQSPSSLAVSAGEKVTMSC | KSSQSLLNSRTRKNYLA | WYQQKPGQSPRLLIY | WASTRES | GVPDRFTGSSGTDFTLTISSVQAEDLAVYYC | KQSYNLLT | FGAGTKLELKA |
| B15B1vk35-20 | DIVMSQSPSSLAVSAGENVTVSC | KSSQSLLNSRTRKNYLA | WYQQKPGQSPRLLIY | WASTRES | GVPDRFTGSSGTDFTLTISSVQAEDLAVYFC | KQSYNLLT | FGAGTKLELKR |
| B13C12335-25 | DIKMTQSPSSLAVSPGEKVTMSC | KSSQSLHSRTRKNYLA | WYQQKPGQSPKLLIY | WASTRES | GVPDRFTGSSGTDFTLTISSVQAEDLAVYFC | KQSYNLLT | FGAGTKLELKR |
| B13C1233520 | DIVMSQSPSSLAVSPGEKVTMSC | KSSQSLHSRTRKNYLA | WYQQKPGQSPKLLIY | WASTRES | GVPDRFTGSSGTDFTLTISSVQAEDLAVYYC | KQSYNLLT | FGAGTKLELKA |
| (Produced Rabbit IgG clone name) | | | | | | | |
| RSDLVK-1 | DIVMTQSPSSLAVSAGEKVTMSC | KSSQSLLNSRTRKNYLA | WYQQKPGQSPRLLIY | WASTRES | GVPDRFTGSSGTDFTLTISSVQAEDLAVYYC | KQSYNLLT | FGAGTKLELKR |
| RSDLVK-6 | DIVMTQSPSSLAVSAGENVTVSC | KSSQSLLNSRTRKNYLA | WYQQKPGQSPRLLIY | WASTRES | GVPDRFTGSSGTDFTLTISSVQAEDLAVYYC | KQSYNLLT | FGAGTRLELKR |
| RSDLVK-10 | DIVMTQSPSSLAVSAGENVTVSC | KSSQSLLNSRTRKNYLA | WYQQKPGQSPKLLIY | WASTRES | GVPDRFTGSSGTGFTLTISSVQAEDLAVYFC | KQSYNLLT | FGAGTKLELKR |
| RSDLVK-13 | DIVMSQSPSSLAVSPGEKVTMSC | KSSQSLHSRTRKNYLA | WYQQKPGQSPKLLIY | WASTRES | GVPDRFTGSSGTDFTLTISSVQAEDLAVYFC | KQSYNLLT | FGAGTKLELKR |
| (scFv clone from Yeast Display library) | | | | | | | |
| 29 | DIVMSQSPSSLAVSAGEKVTMSC | KSSQSLLNSRTRKNYLA | WYQQKPGQSPRLLIY | WASTRES | GVPDRFTGSSGTDFTLTISSVQAEDLAVYYC | KQSYNLLT | FGAGTKLELKA |
| 44 | DIVMSQSPSSLAVSAGEKVTMSC | KSSQSLLNSRTRKNYLA | WYQQKPGQSPRLLIY | WASTRES | GVPDRFTGSSGTDFTLTISSVQAEDLAVYYC | KQSYNLLT | FGAGTKLELKA |
| A1=B4=F9 | DIVMSQSPSSLAVSAGEKVTMSC | KSSQSLLNSRTRKNYLA | WYQQKPGQSPRLLIY | WASTRES | GVPDRFTGSSGTDFTLTISSVQDEDLAVYYC | KQSYNLLT | FGAGTKLELKA |
| A5=C6 | DIVMSQSPSSLAVSAGEKVTMSC | KSSQSLLNSRTRKNYLA | WYQQKPGQSPRLLIY | WASTRES | GVPDRFTGSSGTDFTLTISSVQAEDLAVYYC | KQSYNLLT | FGAGTKLELKA |
| D4=E6 | DIVMSQSPSSLAVSAGEKVTMSC | KSSQSLLNSRTRKNYLA | WYQQKPGQXPRLLIY | WASTRES | GVPDRFTGSSGTDFTLTISSVQDEDLAVYYC | KQSYNLLS | FGAGTKLELKA |
| Final clone for in vivo/in vitro Functional test in IgG format | | | | | | | |
| C6D4 | DIVMTQSPSSLAVSAGEKVTMSC | KSSQSLLNSRTRKNYLA | WYQQKPGQSPRLLIY | WASTRES | GVPDRFTGSSGTDFTLTISSVQAEDLAVYYC | KQSYNLLS | FGAGTKLELKR |

FIG. 2

```
Human     αv         FLQDGTKTVEYAPCRSQDI DADG QGFCQGGFSIDFTKADRVLLGGPGSF YWQGQ
Chimp     αv         FLQDGTKTVEYAPCRSQDI DADG QGFCQGGFSIDFTKADRVLLGGPGSF YWQGQ
Rhesus    αv         FLQDGTKTVEYAPCRSQDI DADG QGFCQGGFSIDFTKADRVLLGGPGSF YWQGQ
Cyno      αv         FLQDGTKTVEYAPCRSQDI DADG QGFCQGGFSIDFTKADRVLLGGPGSF YWQGQ
Cow       αv         FLQDGTKTVEYAPCRSKNI DADG QGFCQGGFSIDFTKADRVLLGGPGSF YWQGQ
Pig       αv         FLQDGTKTVEYAPCRSKNI DADG QGFCQGGFSIDFTKADRVLLGGPGSF YWQGQ
Horse     αv         FLQDGAKTVEYAPCRSKNI DADG QGFCQGGFSIDFTKADRVLLGGPGSF YWQGQ
Mouse     αv         FLQDGTKTVEYAPCRSKNI DADG QGFCQGGFSIDFTKADRVLLGGPGSF YWQGQ
Rat       αv         FLQDGTKTVEYAPCRSKNI DADG QGFCQGGFSIDFTKADRVLLGGPGSF YWQGQ
Armadillo αv         FLQDGTKTVEYAPCRSRSI DADG QGFCQGGFSIDFTKADRVLLGGPGSF YWQGQ
Platypus  αv         FLQDGTKTVEYAPCRSRSI DADG QGFCQGGFSIDFTKADRVLLGGPGSF YWQGQ
```

Integrin αv: Epitope for C6D4 in Bold Underlined Italics

```
Human     β8         SASMHNNIEKLNSVGNDLSRKMAFFSRDFRLGFGSYVDKTVSPYISIHPERIHNQC SDYNLD CMPPHGYIHVLSLTENITEFEKAV HRQ KIS
Chimp     β8         SASMHNNIEKLNSVGNDLSRKMAFFSRDFRLGFGSYVDKTVSPYISIHPERIHNQC SDYNLD CMPPHGYIHVLSLTENITEFEKAV HRQ KIS
Rhesus    β8         SASMHNNIEKLNSVGNDLSRKMAFFSRDFRLGFGSYVDKTVSPYISIHPERIHNQC SDYNLD CMPPHGYIHVLSLTENITEFEKAV HRQ KIS
Cyno      β8         SASMHNNIEKLNSVGNDLSRKMAFFSRDFRLGFGSYVDKTVSPYISIHPERIHNQC SDYNLD CMPPHGYIHVLSLTENITEFEKAV HRQ KIS
Cow       β8         SASMHNNIEKLNSVGNDLSRKMAFFSRDFRLGFGSYVDKTVSPYISIHPERIHNQC SDYNLD CMPPHGYIHVLSLTENITEFEKAV HRQ KIS
Pig       β8         SASMHNIEKLNTVGNDLSRKMAFFSRDFRLGFGSYVDKTVSPYISIHPERIHNQC SDYNLD CMPPHGYIHVLSLTENITEFEKAV HRQ KIS
Horse     β8         SASMHNNIEKLNSVGNDLSRKMAFFSRDFRLGFGSYVDKTVSPYISIHPERIHNQC SDYNLD CMPPHGYIHVLSLTENITEFERAV HRQ KIS
Mouse     β8         SASMHNNIEKLNSVGNDLSKKMALYSRDFRLGFGSYVDKTVSPYISIHPERIHNQC SDYNLD CMPPHGYIHVLSLTENITEFEKAV HRQ KIS
Rat       β8         SASMHNNIEKLNSVGNDLSKKMALFSHDFRLGFGSYVDKTVSPYISIHPERIHNQC SDYNLD CMPPHGYIHVLSLTENITEFEKAV HRQ KIS
Armadillo β8         SASMHNNIEKLNSVGNDLSRKMAFFSLDFRLGFGSYVDKTVSPYISIHPERIHNQC SDYNLD CMPPHGYIHVLSLTENITEFAKAV HRQ KIS
Platypus  β8         SASMHNNIEKLNSVGNDLSQKMADFTRDFRLGFGSYVDKTVSPYISIHPGRIRNQC SQYDLD CMPPHGYIHVLPLTENVTEFEKAV NKQ KIS
```

FIG. 4

```
  1  FNLDVDSPAEYSGPEGSYFGFAVDFFVPSASSRMFLLVGAPKANTTQPGI    50
 51  VEGGQVLKCDWSSTRRCQPIEFDATGNRDYAKDDPLEFKSHQWFGASVRS   100
101  KQDKILACAPLYHWRTEMKQEREPVGTCFLQDGTKTVEYAPCRSQDI*DAD*  150
151  *G*QGFCQGGFSIDFTKADRVLLGGPGSF*Y*WQGQLISDQVAEIVSKYDPNVY  200
201  SIKYNNQLATRTAQAIFDDSYLGYSVAVGDFNGDGIDDFVSGVPRAARTL   250
251  GMVYIYDGKNMSSLYNFTGEQMAAYFGFSVAATDINGDDYADVFIGAPLF   300
301  MDRGSDGKLQEVGQVSVSLQRASGDFQTTKLNGFEVFARFGSAIAPLGDL   350
351  DQDGFNDIAIAAPYGGEDKKGIVYIFNGRSTGLNAVPSQILEGQWAARSM   400
401  PPSFGYSMKGATDIDKNGYPDLIVGAFGVDRAILYRARPVITVNAGLEVY   450
451  PSILNQDNKTCSLPGTALKVSCFNVRFCLKADGKGVLPRKLNFQVELLLD   500
501  KLKQKGAIRRALFLYSRSPSHSKNMTISRGGLMQCEELIAYLRDESEFRD   550
551  KLTPITIFMEYRLDYRTAADTTGLQPILNQFTPANISRQAHILLDCGEDN   600
601  VCKPKLEVSVDSDQKKIYIGDDNPLTLIVKAQNQGEGAYEAELIVSIPLQ   650
651  ADFIGVVRNNEALARLSCAFKTENQTRQVVCDLGNPMKAGTQLLAGLRFS   700
701  VHQQSEMDTSVKFDLQIQSSNLFDKVSPVVSHKVDLAVLAAVEIRGVSSP   750
751  DHVFLPIPNWEHKENPETEEDVGPVVQHIYELRNNGPSSFSKAMLHLQWP   800
801  YKYNNNTLLYILHYDIDGPMNCTSDMEINPLRIKISSLQTTEKNDTVAGQ   850
851  GERDHLITKRDLALSEGDIHTLGCGVAQCLKIVCQVGRLDRGKSAILYVK   900
901  SLLWTETFMNKENQNHSYSLKSSASFNVIEFPYKNLPIEDITNSTLVTTN   950
951  VTWGIQPAPMPVPVWVIILAVLAGLLLLAVLVFVMYRMGFFKRVRPPQEE  1000
1001 QEREQLQPHENGEGNSET                                  1018
```

Integrin AlphaV (Human, No Signal Peptide) –
Epitope for C6D4 in _Bold Underlined Italics_

```
  1  EDNRCASSNAASCARCLALGPECGWCVQEDFISGGSRSERCDIVSNLISK    50
 51  GCSVDSIEYPSVHVIIPTENEINTQVTPGEVSIQLRPGAEANFMLKVHPL   100
101  KKYPVDLYYLVDVSASM*H*NNIEKLNSVGNDLSRKMAFFSRDFRLGFGSYV  150
151  DKTVSPYISIHPERIHNQC***SDYNLD***CMPPHGYIHVLSLTENITEFEKAVH*  200
201  *R*QKISGNIDTPEGGFDAMLQAAVCESHIGWRKEAKRLLLVMTDQTSHLAL  250
251  DSKLAGIVVPNDGNCHLKNNVYVKSTTMEHPSLGQLSEKLIDNNINVIFA   300
301  VQGKQFHWYKDLLPLLPGTIAGEIESKAANLNNLVVEAYQKLISEVKVQV   350
351  ENQVQGIYFNITAICPDGSRKPGMEGCRNVTSNDEVLFNVTVTMKKCDVT   400
401  GGKNYAIIKPIGFNETAKIHIHRNCSQCEDNRGPKGKCVDETFLDSKCF    450
451  QCDENKCHFDEDQFSSESCKSHKDQPVCSGRGVCVCGKCSCHKIKLGKVY   500
501  GKYCEKDDFSCPYHHGNLCAGHGECEAGRCQCFSGWEGDRCQCPSAAAQH   550
551  CVNSKGQVCSGRGTCVCGRCECTDPRSIGRFCEHCPTCYTACKENWNCMQ   600
601  CLHPHNLSQAILDQCKTSCALMEQQHYVDQTSECFSSPSYLRIFFIIFIV   650
651  TFLIGLLKVLIIRQVILQWNSNKIKSSSDYRVSASKKDKLILQSVCTRAV   700
701  TYRREKPEEIKMDISKLNAHETFRCNF                         727
```

Integrin Beta8 (Human, No Signal Peptide) –
Epitope for C6D4 in _Bold Underlined Italics_

FIG. 5

| PBS | ALT Day 0 | HBSag ELISA | ALT Day 7 | HBSag ELISA | ALT Day 14 | HBSag ELISA |
|---|---|---|---|---|---|---|
| 1 | 71 | POS | 33 | POS | 68 | POS |
| 2 | 77 | POS | 10 | POS | 27 | POS |
| 3 | 20 | POS | 16 | POS | 38 | POS |
| 4 | 33 | POS | 17 | POS | 51 | POS |
| 5 | 28 | POS | 14 | POS | 31 | POS |
| C6D4 | | | | | | |
| 1 | 38 | POS | 23 | NEG | 26 | NEG |
| 2 | 31 | POS | 24 | NEG | 20 | NEG |
| 3 | 24 | POS | 59 | NEG | 31 | NEG |
| 4 | 28 | POS | 24 | POS | 20 | POS |

FIG. 10

| VH | Framework 1 | CDR1 | Framework 2 | CDR2 | Framework 3 | CDR3 | Framework 4 |
|---|---|---|---|---|---|---|---|
| (Mouse Hybridoma clone Name) | | | | | | | |
| 4F1 | QVQLQQSGAELVRPGTSVKVSCKASGY | AFTDYLIE | WVKQRPGQGLEWIG | VINPGTGGTNYNKKFKV | KATLTADKSSSTAVMQLGGLTFDDSAVYFCAR | EGNARTYYYAMDY | WGQGTSVTVSS |
| 6B9 | QVQLQQSGAELVRPGTSVKVSCKASGY | AFTDYLIE | WVKQRPGQGLEWIG | VINPETGGTNYNAKFRG | KATLTADKSSSTAVMQLSSLTSGDSAVYFCAR | EAGNYIYAMDY | WGQGTSVTVSS |
| (scFv clone Name from yeast display library) | | | | | | | |
| 6B9.1 | QVQLQQSGAELVRPGTSVKVSCKASGY | AFTDYLIE | WVKQRPGQGLEWIG | VINPETGGTNYNAKFRG | KATLTADKSSSSAVMQLSSLTSGDSAVYFCAR | EAGNYIYAMDY | WGQGTSVTVSS |
| A1 | QVQLQQSGAELVRPGASVKVSCKASGY | AFTDYLIE | WVRQRPGQGLEWIG | VINPETGGTNYNAKFRG | KATLTADKSSSSVAVMQLSSLTSGDSAVYFCAR | EAGNYIYAMDY | WGQGTSVTVSS |
| A2 | QVQLQQSGAELVRPGTSVKVSCKASGY | AFTDYLIE | WVRQRPGQGLEWIG | VINPETGGTNYNAKFRG | KATLTADKSSSSTAVMQLSSLTSGDSAVYFCAR | EAGNYIYAMDY | WGQGTSVTVSS |
| A8 | QVQLQQSGAELVRPGTSVKVSCKASGY | AFTDYLIE | WVRQRPGQGLEWIG | VINPETGGTNYNAKFRG | KATLTADKSSSSAVMQLSGLTSGDSAVYFCAR | EAGNYIYAMDY | WGQGTSVTVSS |
| A11 | QVQLQQSGAELVRPGTSVKVSCKASGY | AFTDNLIE | WVRQRPGQGLEWIG | VINPETGGTNYNAKFRG | KATLTADKSSSSAVMQLSSLTSGDSAVYFCAR | EAGNYIYAMDY | WGQGTSVTVSS |
| B1 | QVQLQQSGAELVRPGTSVKVSCKASGY | AFTDYLIE | WVKQRPGQGLEWIG | VINPETGGTNYNAKFRG | KATLTADKSSSSAVMQLSSLTSGDSAVYFCAR | EAGNYIYAMDY | WGQGTSVTVSS |
| B3 | QVQLQQSGAELVRPGTSVKVSCKASGY | AFTDYLIE | WVRQRPGQGLEWIG | VINPETGGTNYNAKFRG | KATLTADKSSSSAVMQLSGLTSGDSAVYFCAR | EAGNYIYAMDY | WGQGTSVTVSS |
| C4=F10 | QVQLQQSGAELVRPGTSVKVSCKASGY | AFTDYLIE | WVRQRPGQGLEWIG | VINPETGGTNYNAKFRG | RATLTADKSSSSAVMQLSSLTSGDSAVYFCAR | EAGNYIYAMDY | WGQGTSVTVSS |
| C7=D1 | QVQLQQSGAELVRPGTSVKVSCKASGY | AFTDYLIE | WVRQRPGQGLEWIG | VINPETGGTNYNAKFRG | KATLTADKSSSSAVMQLSSLTSGDSAVYFCAR | EAGNYIYAMDY | WGQGTSVTVSS |
| D3=F1 | QVQLQQSGAELVRPGTSVKVSCKASGY | AFTDYLIE | WVRQRPGQGLEWIG | VINPETGGTNYNAKFRG | KATLTADKSSSSAVMQLSSLTSDDSAVYFCAR | EAGNYIYAMDY | WGQGTSVTVSS |
| D10=E5 | QVQLQQSGAELVRPGTSVKVSCKASGY | AFTDYLIE | WVRQRPGQGLEWIG | VINPETGGTNYNAKFRG | KVTLTADKSSSSAVMQLSSLTSGDSAVYFCAR | EAGNYIYAMDY | WGQGTSVTVSS |
| G4 | QVQLQQSGAELVRPGTSVKVSCKASGY | AFTDYLIE | WVRQRPGQGLEWIG | VINPETGGTNYNAKFRG | KVTLTADKSSSSAVMQLNSLTSGDSAVYFCAR | EAGNYIYAMDY | WGQGTSVTVSS |
| (Produced Rabbit IgG clone name) | | | | | | | |
| C4 | QVQLQQSGAELVRPGTSVKVSCKASGY | AFTDYLIE | WVRQRPGQGLEWIG | VINPETGGTNYNAKFRG | RATLTADKSSSSAVMQLSSLTSGDSAVYFCAR | EAGNYIYAMDY | WGQGTSVTVSS |
| D10 | QVQLQQSGAELVRPGTSVKVSCKASGY | AFTDYLIE | WVRQRPGQGLEWIG | VINPETGGTNYNAKFRG | KVTLTADKTSSSAVMQLSSLTSGDSAVYFCAR | EAGNYIYAMDY | WGQGTSVTVSS |
| (scFv clone from Phage Display library) | | | | | | | |
| 4F1A11 | QVQLQQSGAELVRPGTSVKVSCKASGY | AFTDYLIE | WVKQRPGQGLEWIG | VINPETGGTNYNAKFRG | RATLTADKSSSSAVMQLSSLTSGDSAVYFCAR | EAGNYIYAMDY | WGQGTSVTVSS |
| 4F1E1 | QVQLQQSGAELVRPGTSVKVSCKASGY | AFTDYLIQ | WVKQRPGQGLEWIG | VINPETGGTNYNAKFRG | KATLTADKSSSSAVMQLSSLTSGDSAVYFCAR | EAGNYIYAMDY | WGQGTSVTVSS |
| 4F1G3 | QVQLQQSGAELVRPGTSVKVRCKASGY | AFTDYLIQ | WVKQRPGQGLEWIG | VINPETGGTNYNAKFRG | KATLTADKTSSSAVMQLSSLTSGDSAVYFCAR | EAGNYIYAMDY | WGQGTSVTVSS |
| 4F1G10 | QVQLQQSGAELVRPGTSVKVSCKASGY | AFTDYLIQ | WVKQRPGQGLEWIG | VINPETGGTNYNAKFRG | KATLTANKSSSSAVMQLSSLTSGDSAVYFCAR | EAGNYIYAMDY | WGQGTSVTVSS |
| 4F1E10 | QVQLQQSGAELVRPGTSVKVPCKASGY | AFTDYLIQ | WVKQRPGQGLEWIG | VINPETGGTNYNAKFRG | KATLTADKSSSSAVMQLSSLTSGDSAVYFCAR | EAGNYIYAMDY | WGQGTSVTVSS |
| 4F1E9 | QVQLQQSGAELVRPGTSVKVSCKASGY | AFTDYLIE | WVKQRPGQGLEWIG | VINPETGGTNYNAKFRG | KATLTADKSSSSAVMQLSSLTSGDSAVYFCAR | EAGNYIYAMDY | WGQGTSVTVSS |
| 4F1H12 | QVQLQQSGAELVRPGTSVKVSCKASGY | AFTDYLIQ | WVKQRPGQGLEWIG | VINPETGGTNYNAKFRG | KATLTADKSSSATLQSSLTSGDSAVYFCAR | EAGNYIYAMDY | WGQGTSVTVSS |
| Final clone for in vitro Functional test in IgG format | | | | | | | |
| F9 | QVQLQQSGAELVRPGTSVKVSCKASGY | AFTDYLIQ | WVKQRPGQGLEWIG | VINPETGGTNYNAKFRG | KATLTADKSSSAVMQLSSLTSGDSAVYFCAR | EAGNYIYAMDY | WGQGTSVTVSS |

FIG. 11A

| VL | Framework 1 | CDR1 | Framework2 | CDR2 | Framework3 | CDR3 | Framework 4 |
|---|---|---|---|---|---|---|---|
| (Mouse Hybridoma clone Name) | | | | | | | |
| 4F1 | DIQMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKA |
| 689 | DIEMTQTPASLSASVGETVTITC | RASENIYSYLV | WYQQKQGKSPQVLVY | NAKTLAE | GVPSRFSGSGSGTQFSLKINSLQPEDFGSYYC | QHHNGTPYT | FGGGTKLEIKA |
| (scFv clone Name from yeast display library) | | | | | | | |
| 6B9.1 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKA |
| A1 = A2 = C4 = C7 = D1 = D10 = E5 = F1 = F10 = G4 : | | | | | | | |
| A8 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKA |
| A11 | HIVMTQSPASLSASVGETVTITC | RASVNIYSYLV | WYQQKQGKSPQLLVH | NAKTLAE | GVPSRFSGSGSGTQFSLKINSVQPEDFGSYYC | QHHHGTPYT | FGGGTKLEIKA |
| B1 | DIVMTQSPASLSASVGETVTITC | RASVNIYSYLV | WYQQKQGKSPQLLVH | NAKTLAE | GVPSRFSGSGSGTQFSLKINSLQPEDFGSYCY | QHHHGTPYT | FGGGTKLEIKA |
| B3 | DIVMTQSPASLSASVGETVTITC | RASVNIYSYLV | WYQQKQGKSPQLLVH | NAKTLAA | GVPSRFSGSGSGTQFSLKINSLQPEDVGSYYC | QHHHGTPYT | FGGGTKLEIKA |
| D10=E5 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKA |
| (Produced Rabbit IgG clone name) | | | | | | | |
| C4 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| D10 | DIEMTQTPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| (scFv clone from Phage Display library) | | | | | | | |
| 4F1E1 = 4F1G3 = 4F1B5 = 4F1G11 = 4F1A9 = 4F1A9 = 4F1H9 = 4F1D10 = 4F1E9 = 4F1F10 = 4F1H11 = 4F1H12 : | | | | | | | |
| | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKA |
| 4FA11 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKA |
| Final clone for in vitro Functional test in IgG format | | | | | | | |
| F9 | DIVMTQSPAHLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |

FIG. 11B

C6D4 binds integrin αVβ8 at the head domain

Zoom-in onto the integrin αVβ8 head domains and bound Fab C6D4

C6D4, Vk, CDR1: KSSQSLLNSRTRKNYLA
αV, β-propeller domain, blade W3: ...DIDADGQG...SFYWQ...

Interacting residues are in bold

C6D4, Vh, CDR1: DYSMH    CDR3: FYYGRDS
β8, SDL: 153 TVSPYISIHPERIHNQCSDYNLDCMPPH 180
C6D4, Vk, CDR1: KSSQSLLNSRTRKNYLA    CDR2: WASTRES    CDR3: KQSYNLLS

Interacting residues are in bold

This residue is technically outside of the CDR
C6D4, Vk, CDR2: YWASTRES
β8, α1 helix: 114 SASMHNNIEKLNSVGNDLSRKMAFFS 139
Interacting residues are in bold C6D4, Vh, CDR1: YTFTDYSMH
β8, α2 helix: 191 NITEFEKAVHR 201

This residue is technically outside of the CDR

Interacting residues are in bold

β8 integrin subunit is increased in expression in the crypt epithelial cells of patients infected with H. Pylori H. Pylori Normal Lung Adenocarcinoma: β8 expression inversely correlates with PD-PL1 expression
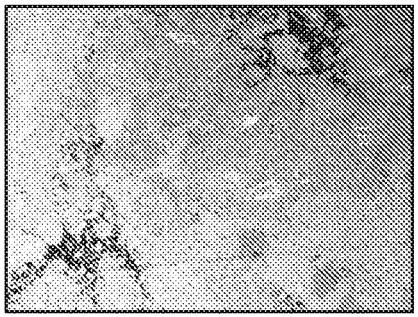
FIG. 32A
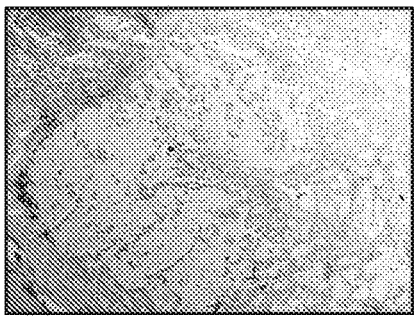
FIG. 32B
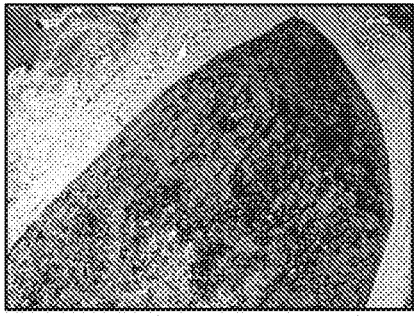
FIG. 32C
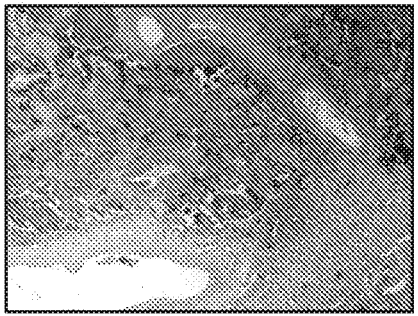
FIG. 32D
anti-PD-L1 (E1L3N)
FIG. 32E
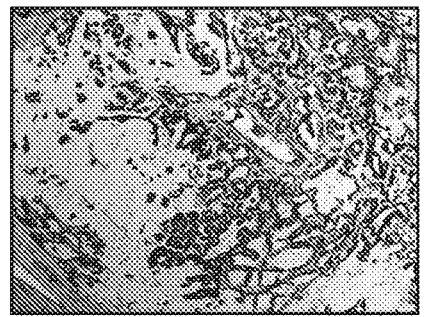
FIG. 32F
FIG. 32G
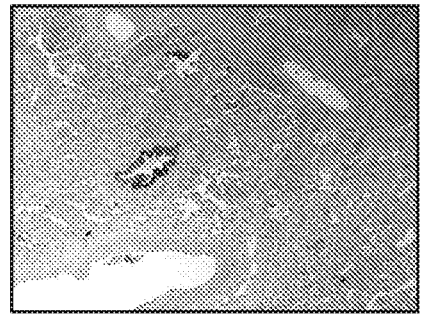
FIG. 32H
anti-β8 (F9)

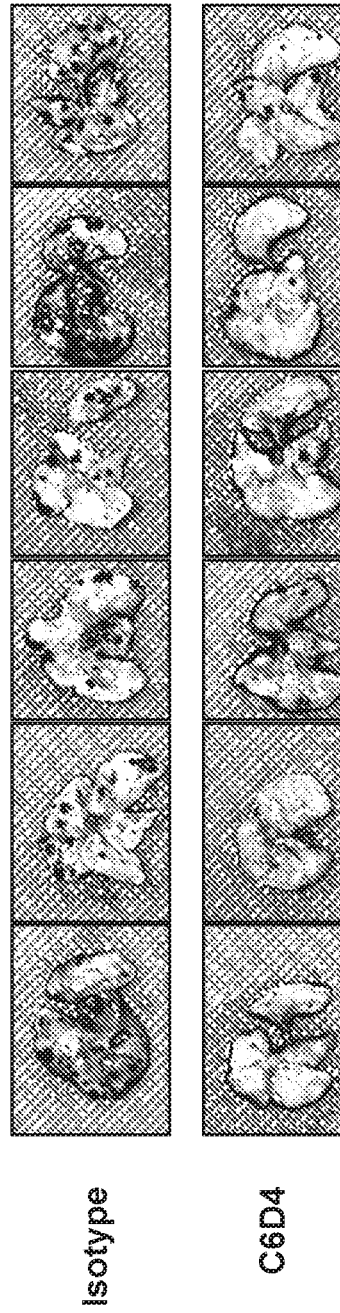
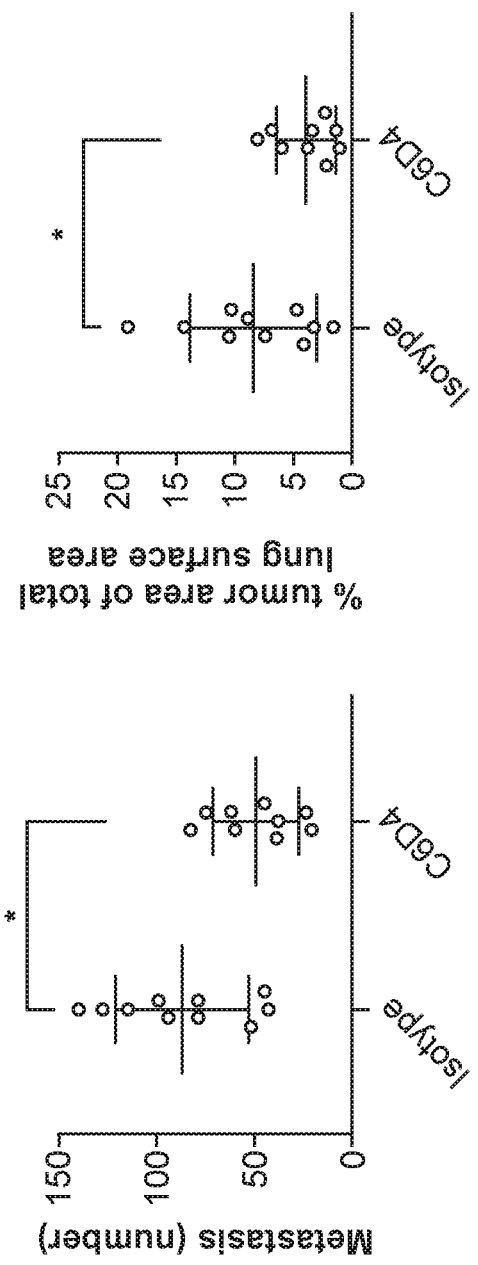
FIG. 34A
FIG. 34B
FIG. 34C

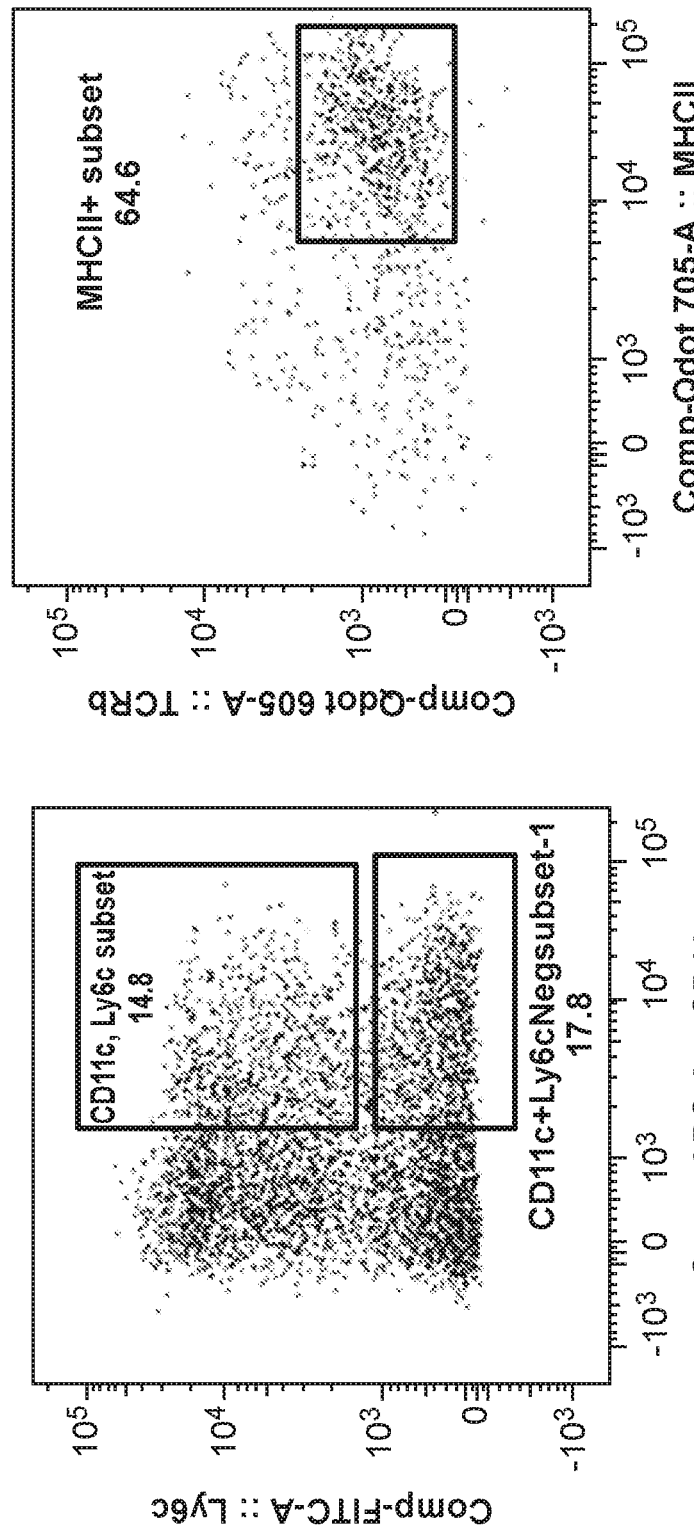

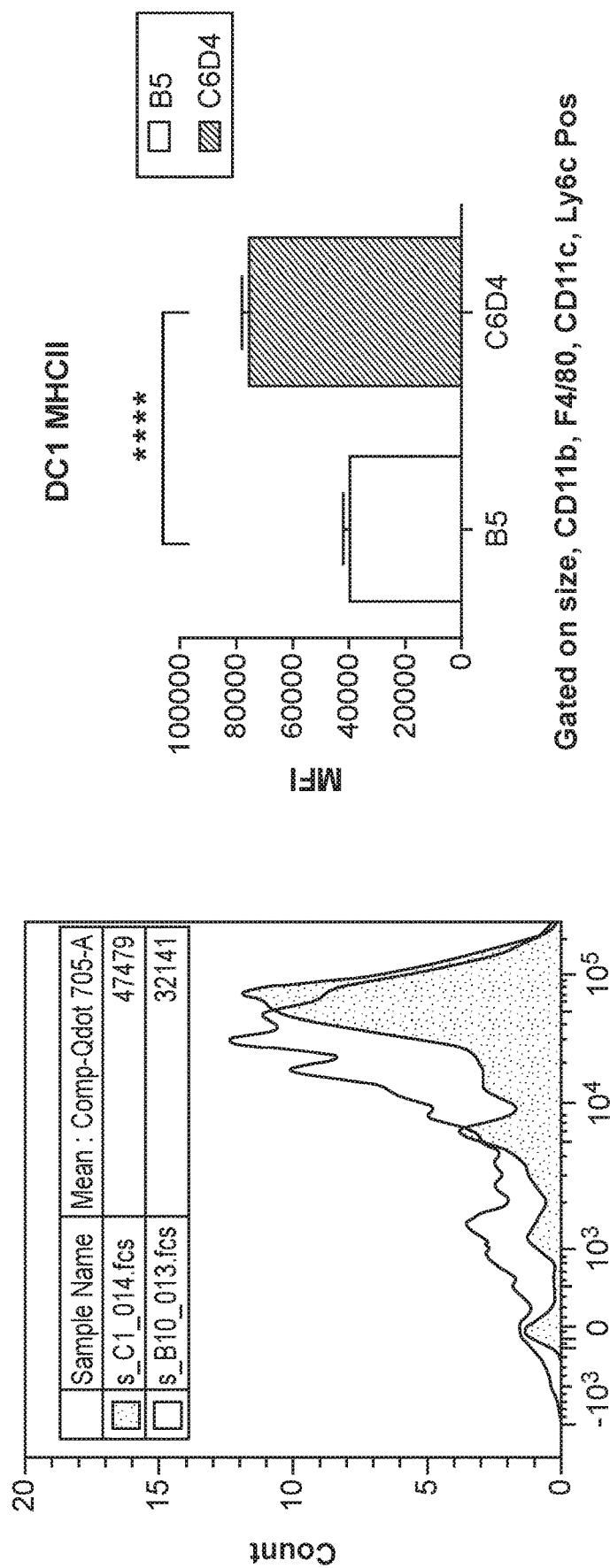

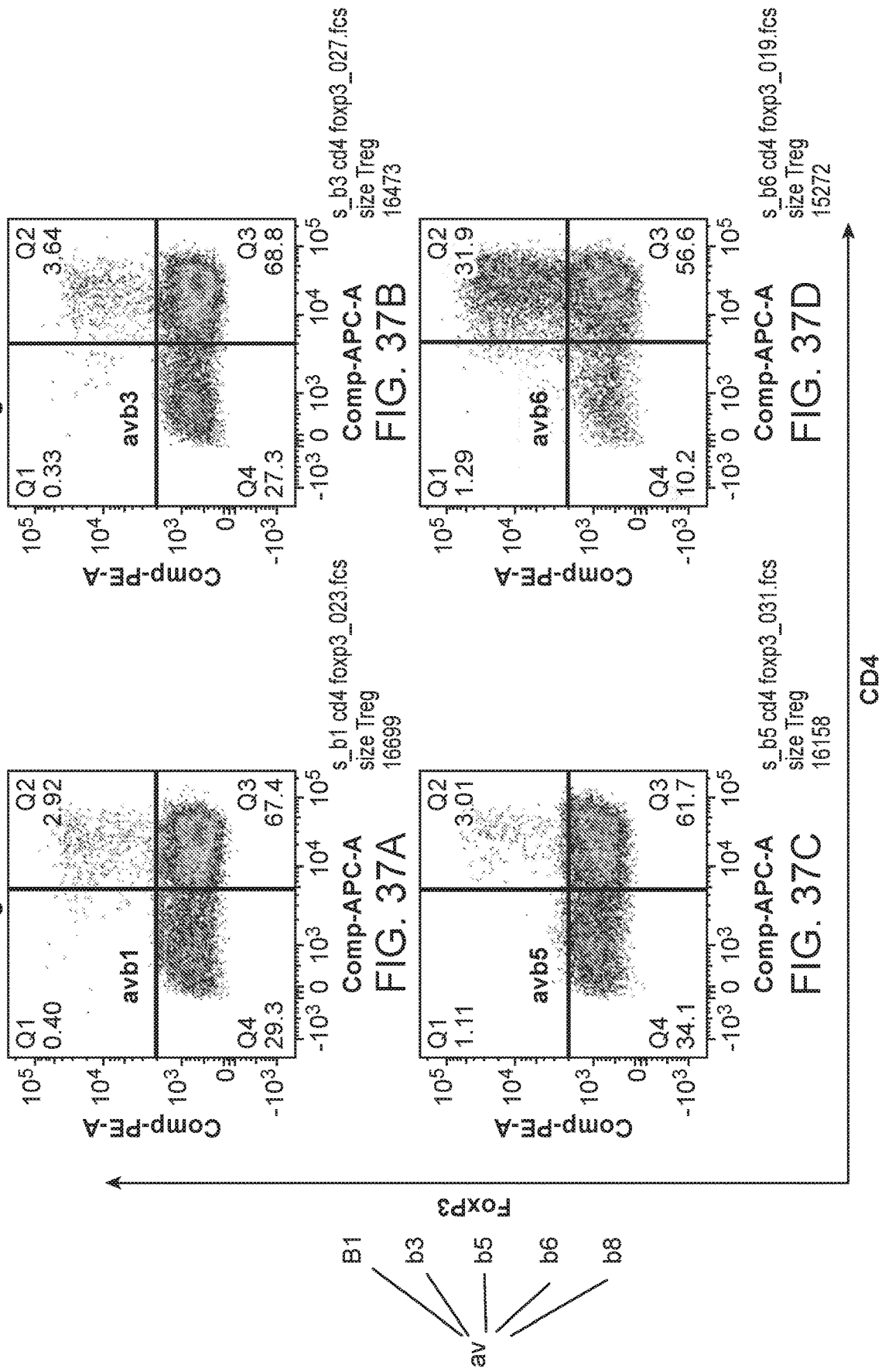

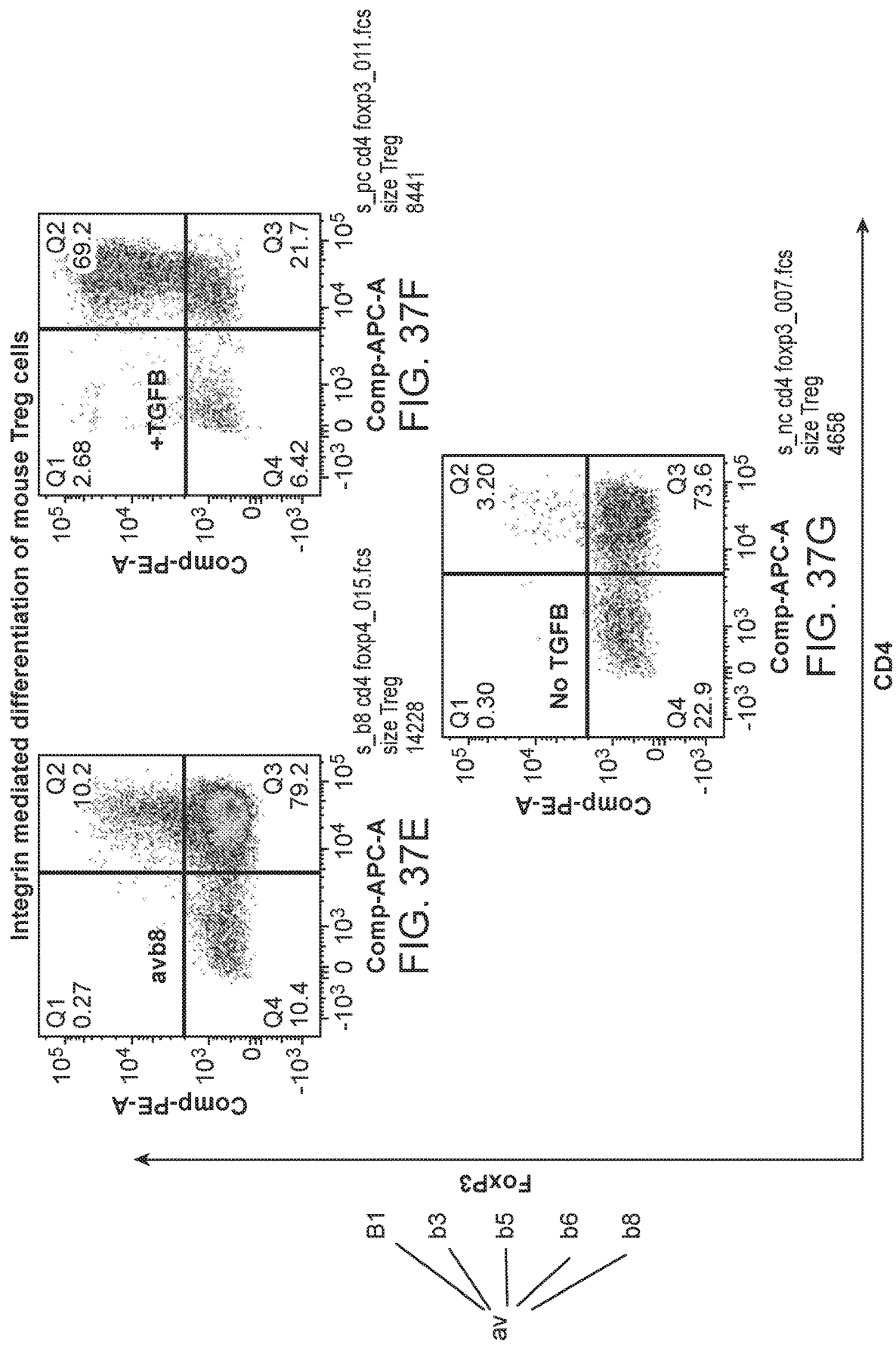

Structure based development of a C6D4 derivative (C6D4-RGD3)
that is cross-reactive to both avb6 and avb8

αVβ6: GRGDLGRLKK
αIIbβ3: GRGDSP
αIIbβ3: AKQRGDV

Structure based development of a C6D4 derivative (C6D4-RGD3) that is cross-reactive to both avb6 and avb8

C6D4_vk
DIVMTQSPSSLAVSAGEKVTMSCKSSQSLLNSRTRKNYLAWYQQKPGQSPRLLIYWASTRESGVPDRFTGSGSGTDFTLTISSVQAEDLAVYYCKQSYNLLSFGAGTKLE
LKAADAAPTVSIFPPSSEQLTSGASVVCFLNNFYPKDINVKWKIDGSERQNGVLNSWTDQDSKDSTYSMSSTLTLTKDEYERHNSYTCEATHKTSTSPIVKSENRNEC

C6D4-RGD1  KSSQSLLGRGDLIGNALA   (17aa)
C6D4-RGD2  KSSQSLLNSGRGDLIGNALA  (19aa)
C6D4-RGD3  KSSQSLLGRG

FIG. 39

Vk CDR1/RGD mutant binding to avb8 expressing cells compared to WT C6D4 n=4

C6D4 binding to αvβ8 is not enhanced by cations C6D4-RGD3 binding to αvβ8 is enhanced by cations and cation-dependent to αvβ6

| Mab (5 ug/ml) | Receptor | Binding in EDTA buffer (% compared with binding to anti-av clone 11D12V2) | Binding in Mg buffer relative to clone 68 (% compared with binding to anti-av clone 11D12V2 |
|---|---|---|---|
| C6D4 | avb8 | 105% | 103% |
| C6D4 | avb6 | 0% | 0% |
| RGD3 | avb8 | 11% | 98% |
| RGD3 | avb6 | 0% | 120% |

FIG. 42

3G9 and RGD3 similarly inhibit avb6 function
RGD3 and C6D4 similarly inhibit avb8 function TGFb activation of LTGFcells to avb8

| | RGD3 | C6D4 |
|---|---|---|
| EC50 | 0.8538 | 1.044 |

FIG. 44C

TGFb activation of LTGFcells to avb6

| | 3G9 | RGD3 |
|---|---|---|
| EC50 | 0.9221 | 0.4124 |

FIG. 44D

Humanization of C6D4

C6D4 Humanization design and FACS Screened based on risk factor and germline (VH1/VK3) picking results with yeast scFv KD data

| VH (Mouse IgG2a) | Framework 1 | CDR1 | Framework 2 | CDR2 | Framework 3 | CDR3 | Framework 4 | scFv KD (nM) |
|---|---|---|---|---|---|---|---|---|
| C6D4 | QIQLVQSGPELKKPGETVKISCKASGYTFT | DYSMH | WVKQAPGKGLKWVA | RINTETGEPTFADDFRG | REAVSLETSASTAYLQINNLKNEDTATYFCAI | FYYGRDS | WGQGTTLTVSS | 7.2507 |
| HuC6D4 V1 | QIQLVQSGAEVKKPGASVKISCKASGYTFT | DYSMH | WVRQAPGQGLEWVA | RINTETGEPTFADDFRG | RFTVTLDTSTAVLEIRSLRSDTAVYFCAI | FYYGRDS | WGQGTTLTVSS | 15.571 |
| Mutclone A3 | QIQLVQSGAEVKKPGASVKISCKASGYTFT | DYSMH | WVRQAPGQGLEWVA | RINTETGEPTFADDFRG | RFSVTLDTSTAVLEIRSLRSDTAVYFCAI | FYYGRDS | WGQGTTLTVSS | 7.4638 |
| Mutclone B7 | QIQLVQSGAEVKKPGASVKISCKASGYTFT | DYSMH | WVRQAPGQGLEWVA | RINTETGEPTFADDFRG | RFSVTLDTSTAVLEITSLRSDTAVYFCAI | FYYGRDT | WGQGTALTVSS | 6.9373 |
| Mutclone E5 | QIQLVQSGAEVKKPGASVKISCKASGYTFT | DYSMH | WVRQAPGQGLEWVA | RINTETGEPTFADDFRG | RFTVTLDTSTAVLEIRSLRSDTAVYFCAI | FYYGRDT | WGQGTTLTVSS | 6.5826 |

| VK (Mouse IgG2a) | Framework 1 | CDR1 | Framework 2 | CDR2 | Framework 3 | CDR3 | Framework 4 | scFv KD (nM) |
|---|---|---|---|---|---|---|---|---|
| C6D4 | DIVMTQSPSSLAVSAGEKVTMSC | KSSQSLLNSRTRKNYLA | WYQQKPGQSPRLLIY | WASTRES | GVPDRFTGSGSGTDFTLTISSVQAEDLAVYYC | KQSYNLLS | FGAGTKLELKR | 7.2507 |
| HuC6D4 V1 | EIVMTQSPATLSVSPGERVTMSC | KSSQSLLNSRTRKNYLA | WYQQKPGQAPRLLIY | WASTRES | GVPARFSGSGSGTEFTLTISSVQSEDFAVYYC | KQSYNLLS | FGQGTVLEIKR | 15.571 |
| Mutclone A3 | EIVMTQSPATLSVSPGEIVMSC | KSSQSLLNSRSRKNYLA | WYQQKPGQAPRLLIY | WASTRES | GVPARFSGSGSGTEFTLTISSVQSEDFAVYYC | KQSYNLLS | FGQGTVLEIKR | 7.4638 |
| Mutclone B7 | EIVMTQSPATLSVSPEGERVTMSC | KSSQSLLNSRTRKNYLA | WYQQKPGQAPRLLIY | WASTRES | GVPARFSGSGSGTEFTLTISSVQSEDFAVYYC | KQSSNLLS | FGQGTVLEIKR | 6.9373 |
| Mutclone E5 | EIVMTQTPVTLSVSPGERVTMSC | KSSQSLLNSRSRKNYLA | WYQQKPGQAPRLLIY | WASTRES | DVPARFSGSGSGTEFTLTISSVQSEDFAVYYC | KQSYNLLS | FGQGTVLEIKR | 6.5826 |

FIG. 46

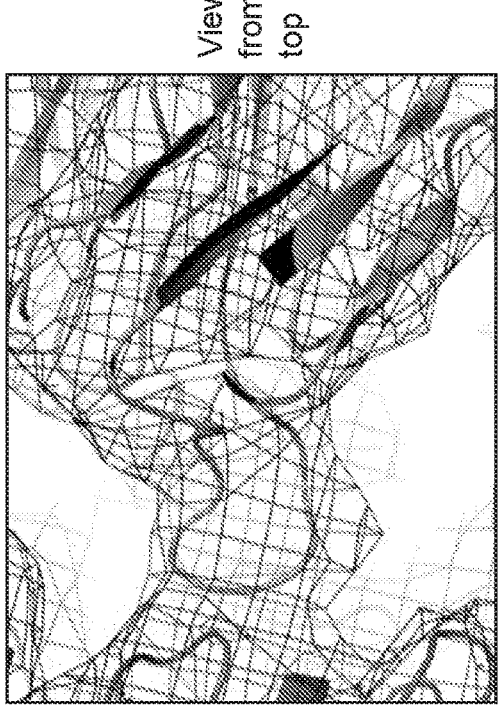
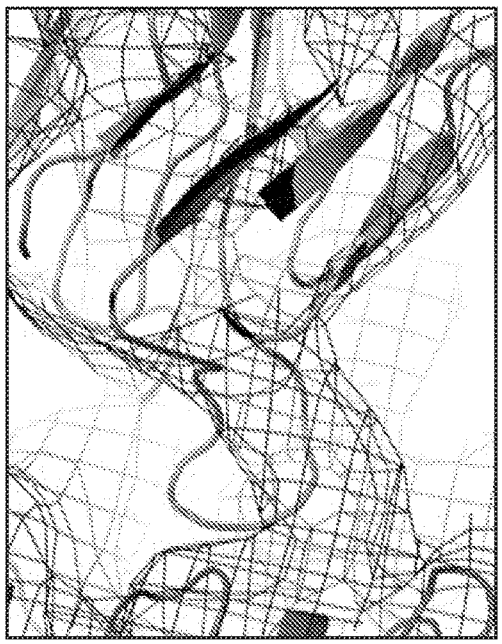
FIG. 48A
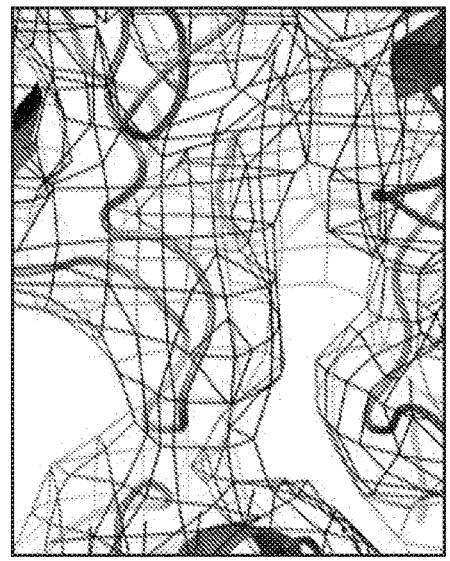
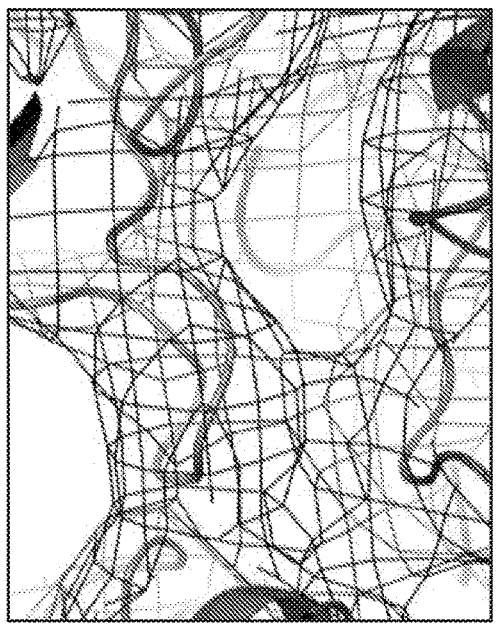
FIG. 48C
FIG. 48B
FIG. 48D

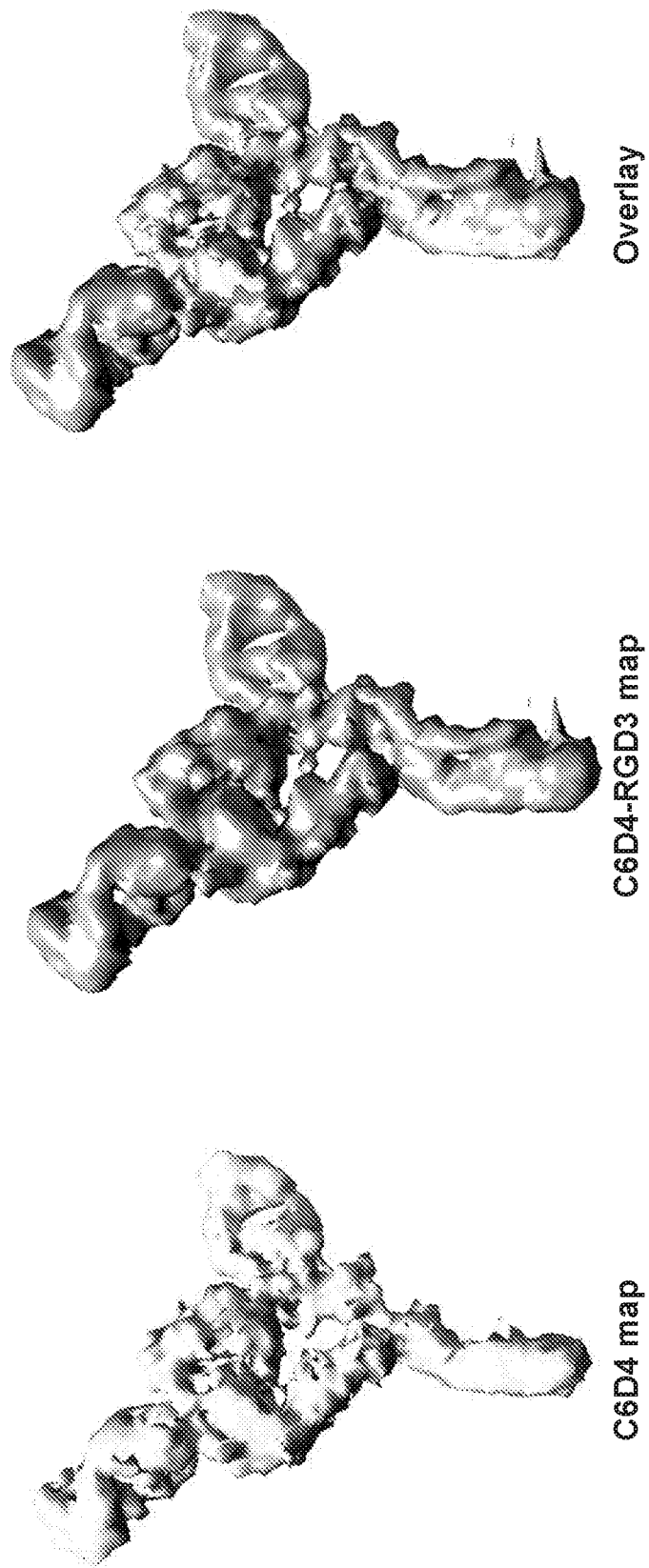

| VH (Mouse Hybridoma Name) | Framework 1 | CDR1 | Framework 2 | CDR2 | Framework 3 | CDR3 | Framework 4 |
|---|---|---|---|---|---|---|---|
| HuC6D4V1 | QIQLVQSGAEVKKPGASVKISCKASGYTFT | DYSMH | WVRQAPGQGLEWVA | RINTETGEPTFADDFRG | RFTVTLDTSTSTAYLEIRSLRSDDTAVYFCAI | FYYGRDS | WGQGTTLTVSS |
| HuC6D4A3 | QIQLVQSGAEVKKPGASVKISCKASGYTFT | DYSMH | WVRQAPGQGLEWVA | RINTETGEPTFADDFRG | RFTVTLDTSTAYLEIRSLRSDDTAVYFCAI | FYYGRDS | WGQGTTLTVSS |
| HuC6D4B7 | QIQLVQSGAKVKKPGASVKISCKASGYTFT | DYSMH | WVRQAPGQGLEWVA | RINTETGEPTFADDFRG | RFSVTLDTSTAYLEITSLRSDDTAVYFCAI | FYYGRDT | WGQGTALTVSS |
| HuC6D4E5 | QIQLVQSGAEVKKPGASVKISCKASGYTFT | DYSMH | WVRQAPGQGLEWVA | RINTETGEPTFADDFRG | RFTVTLDTSTSTAYLRSLRSDDTAVYFCAI | FYYGRDT | WGQGTTLTVSS |

Final clone for in vivo/in vitro Functional test in IgG format

| VH (Mouse Hybridoma Name) | Framework 1 | CDR1 | Framework 2 | CDR2 | Framework 3 | CDR3 | Framework 4 |
|---|---|---|---|---|---|---|---|
| C6D4 | QIQLLQSGPELKKPGETVKISCKASGYTFT | DYSMH | WVRQAPGKGLKWVA | RINTETGEPTFADDFRG | RFAVSLETSASTAYLQINLKNEDTATYFCAI | FYYGRDS | WGQGTTLTVSS |
| HuC6D4 | QIQLVQSGAEVKKPGASVKISCKASGYTFT | DYSMH | WVRQAPGQGLEWVA | RINTETGEPTFADDFRG | RFTVTLDTSTAYLEIRSLRSDDTAVYFCAI | FYYGRDT | WGQGTTLTVSS |
| C6D4-RGD3 | QIQLLQSGPELKKPGETVKISCKASGYTFT | DYSMH | WVRQAPGKGLKWVA | RINTETGEPTFADDFRG | RFAVSLETSASTAYLQINNLKNEDTATYFCAI | FYYGRDS | WGQGTTLTVSS |
| HuC6D4-RGD3 | QIQLVQSGAEVKKPGASVKISCKASGYTFT | DYSMH | WVRQAPGQGLEWVA | RINTETGEPTFADDFRG | RFTVTLDTSTSTAYLEIRSLRSDDTAVYFCAI | FYYGRDT | WGQGTTLTVSS |

Consensus sequence of HuC6D4 related clones:

Consensus VH: QIQLx1QSGx2x3x34KKPGx4x5VKISCKASGYTFT DYSMH WVx6QAPGx7GxL8Wx9x10 x11x12TETx13EPTx14ADDFx15x16 RFx17x18x19Lx20TSx21x22TAx23Lx24Ix25x26Lx27x28x29DTAx30YFCAI x31YYGRDx32 WGQGTx33LVTVSS where x1 = V or L, x2 = A or P, x3 = E or K, x4 = A or E, x5 = S or T, x6 = R or K, x7 = Q or K, x8 = E or K, x9 = V or M, x10 = A or G x11 = R or W,
x12 = N or K, x13 = G or D, x14 = F or Y, x15 = R, N, K or G, x16 = G or E, x17 = T, A, or S, x18 = V or F, x19 = T or S, x20 = D or E, x21 = T or A,
x22 = S or T, x23 = Y or N, x24 = E or Q, x25 = R, N, I or T, x26 = S or N, x27 = R or K, x28 = S or N, x29 = D or E, x30 = V, T, or K, x31 = F or Y,
x32 = T or S, x33 = T or A, x34 = V or L.

FIG. 50

| VL (Mouse Hybridoma Name) | Framework 1 | CDR1 | Framework 2 | CDR2 | Framework 3 | CDR3 | Framework 4 |
|---|---|---|---|---|---|---|---|
| HuC6D4V1 | EIVMTQSPATLSVSPGERVTMSC | KSSQSLLNSRTRKNYLA | WYQQKPGQAPRLLIY | WASTRES | GVPARFSGSGSGTEFTLTISSVQSEDFAVYYC | KQSYNLLS | FGQGTVLEIKR |
| HuC6D4A3 | EIVMTQSPATLSVSPGEIVTMSC | KSSQSLLNSRSRKNYLA | WYQQKPGQAPRLLIY | WASTRES | GVPARFSGSGSGTEFTLTISSVQSEDFAVYYC | KQSYNLIS | FGQGTVLEIKR |
| HuC6D4B7 | EIVMTQSPATQPVTLSVSPGERVTMSC | KSSQSLLNSRTRKNYLA | WYQQKPGQAPRLLIY | WASTRES | GVPARFSGSGSGTEFTLTISSVQSEDFAVYYC | KQSSNLIS | FGQGTVLEIKR |
| HuC6D4E5 | EIVMTQSPATLSVSPGERVTMSC | KSSQSLLNSRSRKNYLA | WYQQKPGQAPRLLIY | WASTRES | DVPARFSGSGSGTEFTLTISSVQSEDFAVYYC | KQSYNLLS | FGQGTVLEIKR |

Final clone for in vivo/in vitro Functional test in IgG format:

| VL (Mouse Hybridoma Name) | Framework 1 | CDR1 | Framework 2 | CDR2 | Framework 3 | CDR3 | Framework 4 |
|---|---|---|---|---|---|---|---|
| C6D4 | DIVMTQSPSSLAVSAGEKVTMSC | KSSQSLLNSRTRKNYLA | WYQQKPGQSPRLLIY | WASTRES | GVPDRFTGSGSGTDFTLTISSVQAEDLAVYYC | KQSYNLLS | FGAGTKLELKR |
| HuC6D4 | EIVMTQSPATLSVSPGERVTMSC | KSSQSLLNSRSRKNYLA | WYQQKPGQAPRLLIY | WASTRES | GVPARFSGSGSGTEFTLTISSVQSEDFAVYYC | KQSYNLLS | FGQGTVLEIKR |
| C6D4-RGD3 | DIVMTQSPSSLAVSAGEKVTMSC | KSSQLLGRGDLGRLKKNALA | WYQQKPGQSPRLLIY | WASTRES | GVPDRFTGSGSGTDFTLTISSVQAEDLAVYYC | KQSYNLLS | FGAGTKLELKR |
| HuC6D4-RGD3 | EIVMTQSPATLSVSPGERVTMSC | KSSQLLGRGDLGRLKKNALA | WYQQKPGQAPRLLIY | WASTRES | GVPARFSGSGSGTEFTLTISSVQSEDFAVYYC | KQSYNLLS | FGQGTVLEIKR |

Consensus sequence of HuC6D4 related clones:

Consensus VL: x40IVMx41Qx42Px43x44Lx45VSx46GEx47VTMSC KSSQSLLNSRx48RKNYLA WYQQKPGQx49PRLLIY WASTRES x50VPx51RFx52GSGSGTx53FLTISSVQx54EDx55AVYYC KQSYNLLS FGx56GTx57LEx58KR where x40 = E or D, x41 = T or S, x42 = S or V, x43 = A, S or T, x44 = T, S, x45 = S or A, x46 = P or A, x47 = R, K or L, x48 = S or T, x49 = A or S, x50 = G or D, x51 = A or D, x52 = S or T, x53 = E or D, x54 = S, D or A, x55 = F or L, x56 = Q or A, x57 = V or K, x58 = I or L.

RGD3 loop: GRGDLGRLK inside VL CDR1

FIG. 51

F9 Variants and parents Confirmed sequence

| VH | Framework 1 | CDR1 | Framework 2 | CDR2 | Framework 3 | CDR3 | Framework 4 |
|---|---|---|---|---|---|---|---|
| (Mouse Hybridoma clone Name) | | | | | | | |
| 4F1 | QVQLQQSGAELVRPGTSVKVSCKASGY | AFTNYLIE | WVKQRPGQGLEWIG | VINPGTGTNYNKKFKV | KATLTADKSSSTAYMQLGLITFDDSAVYFCAR | EGNARTYYAMDY | WGQGTSVTVSS |
| 6B9 | QVQLQQSGAELVRPGASVKVSCKASGY | AFTDYLIE | WVKQRPGQGLEWIG | VINPETGTNYNAKFRG | KATLTADKSSSTAYMQLSSLTSGDSAVYFCAR | EAGNYIYAMDY | WGQGTSVTVSS |
| (scFv clone Name from yeast display library) | | | | | | | |
| 6B9.1 | QVQLQQSGAELVRPGTSVKVSCKASGY | AFTDYLIE | WVKQRPGQGLEWIG | VINPETGTNYNAKFRG | KATLTADKSSSSAYMQLSSLTSGDSAVYFCAR | EAGNYIYAMDY | WGQGTSVTVSS |
| A1 | QVQLQQSGAELVRPGASVKVSCKASGY | AFTDYLIE | WVKQRPGQGLEWIG | VINPETGGTNYNAKFRG | KATLTADKSSSSVYMQLSSLTSGDSAVYFCAR | EAGNYIYAMDY | WGQGTSVTVSS |
| A2 | QVQLQQSGAELVRPGTSVKVSCKASGY | AFTDYLIE | WVRQRPGQGLEWIG | VINPETGGTNYNAKFRG | KATLTADKSSSTAYMQLSSLTSGDSAVYFCAR | EAGNYIYAMDY | WGQGTSVTVSS |
| A8 | QVQLQQSGAELVRPGTSVKVSCKASGY | AFTDYLIE | WVRQRPGQGLEWIG | VINPETGGTNYNAKFRG | KATLTADKSSSSAYMQLSSLTSGDSAVYFCAR | EAGNYIYAMDY | WGQGTSVTVSS |
| A11 | QVQLQQSGAELVRPGTSVKVSCKASGY | AFTDNLIE | WVRQRPGQGLEWIG | VINPETGGTNYNAKFRG | KATLTADKSSSSAYMQLSSLTSGDSAVYFCAR | EAGNYIYAMDY | WGQGTSVTVSS |
| B1 | QVQLQQSGAELVRPGTSVKVSCKASGY | AFTDYLIE | WVKQRPGQGLEWIG | VINPETGGTNYNAKFRG | KATLTADKSSSSAYMQLSLSGDSAVYFCAR | EAGNYIYAMDY | WGQGTSVTVSS |
| B3 | QVQLQQSGAELVRPGTSVKVSCKASGY | AFTDYLIE | WVRQRPGQGLEWIG | VINPETGGTNYNAKFRG | KATLTADKSSSSAYMQLSSLTSGDSAVYFCAR | EAGNYIYAMDY | WGQGTSVTVSS |
| C4=F10 | QVQLQQSGAELVRPGTSVKVSCKASGY | AFTDYLIE | WVRQRPGQGLEWIG | VINPETGGTNYNAKFRG | RATLTADKSSSSAYMQLSSLTSGDSAVYFCAR | EAGNYIYAMDY | WGQGTSVTVSS |
| C7=D1 | QVQLQQSGAELVRPGTSVKVSCKASGY | AFTDYLIE | WVRQRPGQGLEWIG | VINPETGGTNYNAKFRG | KATLTADKSSSSAYMQLSSLTSGDSAVYFCAR | EAGNYIYAMDY | WGQGTSVTVSS |
| D3=F1 | QVQLQQSGAELVRPGTSVKVSCKASGY | AFTDYLIE | WVRQRPGQGLEWIG | VINPETGGTNYNAKFRG | KATLTADKSSSSAYMQLSSLTDDSAVYFCAR | EAGNYIYAMDY | WGQGTSVTVSS |
| D10=E5 | QVQLQQSGAELVRPGTSVKVSCKASGY | AFTDYLIE | WVKQRPGQGLEWIG | VINPETGGTNYNAKFRG | KVTLTADKTSSSAYMQLSSLTSGDSAVYFCAR | EAGNYIYAMDY | WGQGTSVTVSS |
| E8 | QVQLQQSGAELVRPGTSVKVSCKASGY | AFTDYLIE | WVRQRPGQGLEWIG | VINPETGGTNYNAKFRG | KATLTADKSSSSAYMQLSSLTSGDSAVYFCAR | EAGNYIYAMDY | WGQGTSVTVSS |
| F2 | QVQLQQSGAELVRPGTSVKVSCKASGY | AFTDYLIE | WVKQRPGQGLEWIG | VINPETGGTNYNAKFRG | KATLTADKSSSSAYMQLSSLTSGDSAVYFCAR | EAGNYIYAMDY | WGQGTSVTVSS |
| G4 | QVQLQQSGAELVRPGTSVKVSCKASGY | AFTDYLIE | WVRQRPGQGLEWIG | VINPETGGTNYNAKFRG | KVTLTADKSSSSAYMQLNSLTSGDSAVYFCAR | EAGNYIYAMDY | WGQGTSVTVSS |

FIG. 52

| (Produced Rabbit IgG clone name) | | | | | | |
|---|---|---|---|---|---|---|
| C4 | QVQLQQSGAELVRPGTSVKVSCKASGY | AFTDYLIE | WVRQRPGQGLEWIG | VINPETGTNYNAKFRG | RATLTADKSSSSAYMQLSSLTSGDSAVYFCAR | EAGNYIYAMDY | WGQGTSVTVSS |
| D10 | QVQLQQSGAELVRPGTSVKVSCKASGY | AFTDYLIE | WVRQRPGQGLEWIG | VINPETGGTNYNAKFRG | KVTLTADKTSSSAYMQLSSLTSGDSAVYFCAR | EAGNYIYAMDY | WGQGTSVTVSS |
| (scFv clone from Phage Display library) | | | | | | | |
| 4F1E1 | QVQLQQSGAELVRPGTSVKVSCKASGY | AFTDYLI* | WVKQRPGQGLEWIG | VINPETGGTNYNAKFRG | KATLTADKSSSSAYMQLSSLTSGDSAVYFCAR | EAGNYIYAMDY | WGQGTSVTVSS |
| 4F1G3 | QVQLQQSGAELVRPGTSVKVSCKASGY | AFTDYLI* | WVKQRPGQGLEWIG | VINPETGGTNYNAKFRG | KATLTPANKSSSSAYMQLSLTSGDSAVYFCAR | EAGNYIYAMDY | WGQGTSVTVSS |
| 4F1B5 | QVQLQQSGAELVRPGTSVKVSCKASGY | AFTDYLI* | WVKQRPGQGLEWIG | VINPETGGTNYNAKFRG | KATLTADKSSSSAYMQLSLTSGDSAVYFCAR | EAGNYIYAMDY | WGQGTSVTVSS |
| 4F1G11 | QVQLQQSGAELVRPGTSVKVSCKASGY | AFTDYLI* | WVKQRPGQGLEWIG | VINPETGGTNYNAKFRG | KATLTADKSSSSAYMQLSSLTSGDSAVYFCAR | EAGNYIYAMDY | WGQGTSVTVSS |
| 4F1A9 | QVQLQQSGAELVRPGTSVKVSCKASGY | AFTDYLI* | WVKQRPGQGLEWIG | VINPETGGTNYNAKFRG | KATLTADKSSSSAYMQLSSLTSGDSAVYFCAR | EAGNYIYAMDY | WGQGTSVTVSS |
| 4F1B9 | QVQLQQSGAELVRPGTSVKVSCKASGY | AFTDYLI* | WVKQRPGQGLEWIG | VINPETGGTNYNAKFRG | KATLTADKSSSSAYMQLSSLTSGDSAVYFCAR | EAGNYIYAMDY | WGQGTSVTVSS |
| 4F1F9 | QVQLQQSGAELVRPGTSVKVSCKASGY | AFTDYLI* | WVKQRPGQGLEWIG | VINPETGGTNYNAKFRG | KATLTADKSSSSAYMQLSSLTSGDSAVYFCAR | EAGNYIYAMDY | WGQGTSVTVSS |
| 4F1H9 | QVQLQQSGAELVRPGTSVKVSCKASGY | AFTDYLI* | WVKQRPGQGLEWIG | VINPETGGTNYNAKFRG | KATLTADKSSSSAYMQLSSLTSGDSAVYFCAR | EAGNYIYAMDY | WGQGTSVTVSS |
| 4F1D10 | QVQLQQSGAELVRPGTSVKVSCKASGY | AFTDYLI* | WVKQRPGQGLEWIG | VINPETGGTNYNAKFRG | KATLTADKSSSSAYMQLSSLTSGDSAVYFCAR | EAGNYIYAMDY | WGQGTSVTVSS |
| 4F1E10 | QVQLQQSGAELVRPGTSVKVSCKASGY | AFTDYLI* | WVKQRPGQGLEWIG | VINPETGGTNYNAKFRG | KATLTADKSSSSAYMQLSSLTSGDSAVYFCAR | EAGNYIYAMDY | WGQGTSVTVSS |
| 4F1F10 | QVQLQQSGAELVRPGTSVKVSCKASPY | AFTDYLI* | WVKQRPGQGLEWIG | VINPETGGTNYNAKFRG | KATLTADKSSSSAYMQLSSLTSGDSAVYFCAR | EAGNYIYAMDY | WGQGTSVTVSS |
| 4F1H12 | QVQLQQSGAELVRPGTSVKVSCKASGY | AFTDYLI* | WVKQRPGQGLEWIG | VINPETGGTNYNAKFRG | KATLTADKSSSSAYLQLSSLTSGDSAVYFCAR | EAGNYIYAMDY | WGQGTSVTVSS |
| 4F1E9 | QVQLQQSGAELVRPGTSVKVSCKASGY | AFTDYLI* | WVKQRPGQGLEWIG | VINPETGGTNYNAKFRG | KATLTADKSSSSAYMQLSSLTSGDSAVYFCAR | EAGNYIYAMDY | WGQGTSVTVSS |
| 4FA11 | QVQL*QSGAELVRPGTSVKVSCKASGY | AFTDYLIE | WVKQRPGQGLEWIG | VINPETGGTNYNAKFRG | RATLTADKSSSSAYMQLSSLTSGDSAVYFCAR | EAGNYIYAMDY | WGQGTSVTVSS |
| 4FH11 | QVQLQQSGAELVRPGTSVKVSCKASGY | AFTDYLIE | WVKQRPGQGLEWIG | VINPETGGTNYNAKFRG | KATLTADKSSSSAYMQLSSLTSGDSAVYFCAR | EAGNYIYAMDY | WGQGTSVTVSS |
| Final clone for in vitro Functional test in IgG format | | | | | | | |
| F9 | QVQLQQSGAELVRPGTSVKVSCKASGY | AFTDYLIQ | WVKQRPGQGLEWIG | VINPETGGTNYNAKFRG | KATLTADKSSSSAYMQLSSLTSGDSAVYFCAR | EAGNYIYAMDY | WGQGTSVTVSS |

FIG. 52 (Cont.)

F9 Variants and parents Confirmed sequence

| VH (Mouse Hybridoma clone Name) | Framework 1 | CDR1 | Framework 2 | CDR2 | Framework 3 | CDR3 | Framework 4 |
|---|---|---|---|---|---|---|---|
| 4F1 | DIQMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKA |
| 6B9 | DIEMTQTPASLSASVGETVTITC | RASENIYSYLV | WYQQKQGKSPQVLVY | NAKTLAE | GVPSRFSGSGSGTQFSLKINSLQPEDFGSYYC | QHHNGTPYT | FGGGTKLEIKA |

(scFv clone Name from yeast display library)

| | Framework 1 | CDR1 | Framework 2 | CDR2 | Framework 3 | CDR3 | Framework 4 |
|---|---|---|---|---|---|---|---|
| 6B9.1 | DIVMTQSPASLSASVGETVTITC | RASVNIYSYLV | WYQQKQGKSPQLLVH | NAKTLAE | GVPSRFSGSGSGTQFSLKINSVQPEDFGSYYC | QHHHGTPYT | FGGGTKLEIKR |
| A1 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| A2 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| A8 | DIVMTQSPASLSASVGETVTITC | RASVNIYSYLV | WYQQKQGKSPQLLVH | NAKTLAE | GVPSRFSGSGSGTQFSLKINSVQPEDFGSYYC | QHHHGTPYT | FGGGTKLEIKR |
| A11 | HIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| B1 | DIVMTQSPASLSASVGETVTITC | RASVNIYSYLV | WYQQKQGKSPQLLVH | NAKTLAE | GVPSRFSGSGSGTQFSLKINSLQPEDVGSYYC | QHHHGTPYT | FGGGTKLEIKR |
| B3 | DIVMTQSPASLSASVGETVTITC | RASVNIYSYLV | WYQQKQGKSPQLLVH | NAKTLAA | GVPSRFSGSGSGTQFSLKINSLQPEDFGSYYC | QHHHGTPYT | FGGGTKLEIKR |
| C4=F10 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| C7=D1 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| D3=F1 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| D10=E5 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| E8 | DIVMTQSPASLSASVGETVTITC | RASVNIYSYLV | WYQQKQGKSPQLLVH | NAKTLAE | GVPSRFSGSGSGTRFSLKINSLQPEDFGSYYC | QHHHGTPYT | FGGGTKLEIKR |
| F2 | DIVMTQSPASLSASVGETVTITC | RASVNIYSYLV | WYQQKQGKSPQLLVH | NAKTLAE | GVPSRFSGSGSGTQFSLKISSLQPEDFGSYYC | QHHHGTPYT | FGGGTKLEIKR |
| G4 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |

FIG. 53

| | | | | | | |
|---|---|---|---|---|---|---|
| (Produced Rabbit IgG clone name) | | | | | | |
| C4 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIKR |
| D10 | DIEMTQTPASLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIK |
| (scFv clone from Phage Display library) | | | | | | |
| 4F1E1 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIK |
| 4F1G3 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIK |
| 4F1B5 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIK |
| 4F1G11 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIK |
| 4F1A9 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIK |
| 4F1B9 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIK |
| 4F1F9 | DIVMTQSPAFLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIK |
| 4F1H9 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIK |
| 4F1D10 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIK |
| 4F1E10 | DIVMTQSPASLSASVGETVTITC | RASVNIYSYLV | WYQQKQGKSPQLLVH | NAKTLAE | GVPSRFSGSGSGTXFSLKINSLQPEDFGSYYC | QHHHGTPYT FGGGTKLEIK |
| 4F1F10 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIK |
| 4F1H12 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIK |
| 4F1E9 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIK |
| 4FA11 | DIVVTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIK |
| 4FH11 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIK |
| Final clone for in vitro Functional test in IgG format | | | | | | |
| F9 | DIVMTQSPAFLSASVGETVTITC | RASVNIYSYLV | WYQQKQGKSPQLLVH | NAKTLAE | GVPSRFSGSGSGTQFSLKINSLQPEDFGSYYC | QHHHGTPYT FGGGTKLEIKR |

FIG. 53 (Cont.)

NEUTRALIZING ANTIBODIES TO THE αVβ8 INTEGRIN COMPLEX FOR IMMUNOTHERAPY

CROSS-REFERENCE TO RELATED PATENT APPLICATIONS

This application is a US National Stage entry of International Application No. PCT/US2017/054306, filed Sep. 29, 2017, which claims benefit of priority to U.S. Provisional Patent Application No. 62/401,570, filed Sep. 29, 2016 and U.S. Provisional Patent Application No. 62/529,381, filed Jul. 6, 2017, both of which are incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under grant no. U54 HL119893, awarded by the National Institutes of Health. The government has certain rights in the invention.

REFERENCE TO A "SEQUENCE LISTING" SUBMITTED AS ASCII TEXT FILES VIA EFS-WEB

The Sequence Listing written in file 081906-1062335 (224020PC)_SequenceListing.txt created on Sep. 29, 2017, 396,159 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

Transforming growth factor β (TGFβ) was originally characterized as an oncogene capable of inducing a transformed phenotype in non-neoplastic cells. A number of TGFβ family members have since been characterized, based on the presence of similar amino acid domains.

Some TGF-β isoforms are expressed ubiquitously in mammals (TGF-β 1-3), but are maintained in an inactive form by non-covalent interaction with a propeptide, the latency associated domain of TGF-β (LAP). For TGFβ to signal, it must be released from its inactive complex by a process called TGFβ activation. The latent TGF complex includes 3 components: the active (mature) TGFβ dimmer, LAP (latency associated peptide) and LTBP (latent TGFβ binding protein). LAP is a dimer, linked by a disulfide bond, that represents the N-terminal end of the TGFβ precursor protein. The mature TGFβ protein represents the C terminal end (about 25 kD) of the precursor. The bond between the TGFβs and LAP is proteolytically cleaved within the Golgi, but the TGF-β propeptide remains bound to TGFβ by non-covalent interactions. The complex of TGFβ and LAP is called the small latent complex (SLC). It is the association of LAP and TGFβ that confers latency. LAP-TGF binding is reversible and the isolated purified components can recombine to form an inactive SLC. Both the SLC and the larger complex are referred to herein as latent TGFβ, as both are inactive.

In general, integrins are adhesion molecules and mediate the attachment of cells to extracellular matrix proteins. Integrin αvβ8 binds to the LAP of TGF-β and mediates the activation of TGF-β1 and 3 (Mu et al. (2002) *J. Cell Biol.* 159:493). Integrin αvβ8-mediated activation of TGF-β is required for in vivo activation of TGF-β (i.e., release of the mature TGF-β polypeptide), thus αvβ8 is a gatekeeper of TGF-β function. Integrin αvβ8 is expressed in normal epithelia (e.g., airway epithelia), mesenchymal cells, and neuronal tissues.

The integrin β8 (Itgb8) has been associated with forkhead box P3 (Foxp3)-positive T cells and T-regulatory-specific epigenetic remodeling. See, e.g., Vandenbon, et al., *Proc. Natl. Acad. Sci. USA* vol. 113 no. 17 pp. E2393-E2402 (2016). FoxP3 is a transcription factor involved in the development of T-regulatory (Treg) cells. Human and mouse effector Treg cells express functional TGF-β-activating integrin αvβ8. See, Worthington, *Immunity* Volume 42, Issue 5, pp. 903-915 (May 2015). Treg cell integrin αvβ8-mediated TGF-0 activation is not needed for T cell homeostasis and integrin αvβ8 expression by Treg cells suppresses active inflammation.

Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

The terms "anti-αvβ8 antibody," "αvβ8 specific antibody," "αvβ8 antibody," and "anti-αvβ8" are used synonymously herein to refer to an antibody that specifically binds to αvβ8. Similarly, an anti-β8 antibody (and like terms) refer to an antibody that specifically binds to β8. The anti-αvβ8 antibodies and anti-β8 antibodies described herein bind to the protein expressed on αvβ8 expressing cells.

An αvβ8-associated disorder is a condition characterized by the presence of αvβ8-expressing cells, either cells expressing an increased level of αvβ8, or increased number of αvβ8-expressing cells relative to a normal, non-diseased control. TGFβ-associated disorders (disorders characterized by higher than normal TGFβ activity) include αvβ8-associated disorders, as αvβ8 is involved in activating TGFβ in certain circumstances, as described herein.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The words "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following amino acids are typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The terms "identical" or "percent identity," in the context of two or more nucleic acids, or two or more polypeptides, refer to two or more sequences or subsequences that are the same or have a specified percentage of nucleotides, or amino acids, that are the same (i.e., about 60% identity, preferably 65%, 70%, 75%, 80%, 85%, 90%, 91%, 92%, 93%, 94%, 95%, 96%, 97%, 98%, 99/o, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical." This definition also refers to, or may be applied to, the compliment of a nucleotide test sequence. The definition also includes sequences that have deletions and/or additions, as well as those that have substitutions. As described below, the algorithms can account for gaps and the like. Typically, identity exists over a region comprising an antibody epitope, or a sequence that is at least about 25 amino acids or nucleotides in length, or over a region that is 50-100 amino acids or nucleotides in length, or over the entire length of the reference sequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "isolated," when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "antibody" refers to a polypeptide comprising a framework region encoded by an immunoglobulin gene, or fragments thereof, that specifically bind and recognize an antigen, e.g., human αvβ8, a particular cell surface marker, or any desired target. Typically, the "variable region" contains the antigen-binding region of the antibody (or its functional equivalent) and is most critical in specificity and affinity of binding. See Paul, *Fundamental Immunology* (2003).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

An "isotype" is a class of antibodies defined by the heavy chain constant region. Antibodies described herein can be of any isotype of isotype class. Immunoglobulin genes include the kappa, lambda, alpha, gamma, delta, epsilon, and mu constant region genes. Light chains are classified as either kappa or lambda. Heavy chains are classified as gamma, mu, alpha, delta, or epsilon, which in turn define the isotype classes, IgG, IgM, IgA, IgD and IgE, respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4:72 (1983); Cole et al., Monoclonal Antibodies and Cancer Therapy, pp. 77-96. Alan R. Liss, Inc. 1985). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., supra; Marks et al., *Biotechnology*, 10:779-783, (1992)).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some complementary determining region ("CDR") residues and possibly some framework ("FR") residues are substituted by residues from analogous sites in rodent antibodies.

Antibodies or antigen-binding molecules of the invention further includes one or more immunoglobulin chains that are chemically conjugated to, or expressed as, fusion proteins with other proteins. It also includes bispecific antibody. A bispecific or bifunctional antibody is an artificial hybrid antibody having two different heavy/light chain pairs and two different binding sites. Other antigen-binding fragments or antibody portions of the invention include bivalent scFv (diabody), bispecific scFv antibodies where the antibody molecule recognizes two different epitopes, single binding domains (dAbs), and minibodies.

The various antibodies or antigen-binding fragments described herein can be produced by enzymatic or chemical modification of the intact antibodies, or synthesized de novo using recombinant DNA methodologies (e.g., single chain Fv), or identified using phage display libraries (see, e.g., McCafferty et al., Nature 348:552-554, 1990). For example, minibodies can be generated using methods described in the art, e.g., Vaughan and Sollazzo, Comb Chem High Throughput Screen. 4:417-30 2001. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). Single chain antibodies can be identified using phage display libraries or ribosome display libraries, gene shuffled libraries. Such libraries can be constructed from synthetic, semi-synthetic or native and immunocompetent sources.

A "monoclonal antibody" refers to a clonal preparation of antibodies with a single binding specificity and affinity for a given epitope on an antigen. A "polyclonal antibody" refers to a preparation of antibodies that are raised against a single antigen, but with different binding specificities and affinities.

As used herein, "V-region" refers to an antibody variable region domain comprising the segments of Framework 1, CDR1, Framework 2, CDR2, Framework 3, CDR3, and Framework 4. These segments are included in the V-segment as a consequence of rearrangement of the heavy chain and light chain V-region genes during B-cell differentiation.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson and Wu, *Nucleic Acids Res.* 2000 Jan. 1; 28(1): 214-218 and Johnson et al., Nucleic Acids Res., 29:205-206 (2001); Chothia & Lesk, (1987) *J. Mol. Biol.* 196, 901-917; Chothia et al. (1989) Nature 342, 877-883; Chothia et al. (1992) J. Mol. Biol. 227, 799-817; Al-Lazikani et al., *J. Mol. Biol* 1997, 273(4)). Unless otherwise indicated, CDRs are determined according to Kabat. Definitions of antigen combining sites are also described in the following: Ruiz et al. *Nucleic Acids Res.*, 28, 219-221 (2000); and Lefranc *Nucleic Acids Res. Jan.* 1; 29(1):207-9 (2001); MacCallum et al., *J. Mol. Biol.,* 262: 732-745 (1996); and Martin et al, *Proc. Natl Acad. Sci. USA,* 86, 9268-9272 (1989); Martin, et al, *Methods Enzymol.,* 203: 121-153, (1991); Pedersen et al, *Immunomethods,* 1, 126, (1992); and Rees et al, In Sternberg M. J. E. (ed.), Protein Structure Prediction. Oxford University Press, Oxford, 141-172 1996).

A "chimeric antibody" is an antibody molecule in which (a) the constant region, or a portion thereof, is altered, replaced or exchanged so that the antigen binding site (variable region, CDR, or portion thereof) is linked to a constant region of a different or altered class, effector function and/or species, or an entirely different molecule which confers new properties to the chimeric antibody (e.g., an enzyme, toxin, hormone, growth factor, drug, etc.); or (b) the variable region, or a portion thereof, is altered, replaced or exchanged with a variable region having a different or altered antigen specificity (e.g., CDR and framework regions from different species).

A "humanized" antibody is an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., *Proc. Natl. Acad. Sci. USA,* 81:6851-6855 (1984); Morrison and Oi, *Adv. Immunol.,* 44:65-92 (1988); Verhoeyen et al., *Science,* 239:1534-1536 (1988); Padlan, *Molec. Immun.,* 28:489-498 (1991); Padlan, *Molec. Immun.,* 31(3):169-217 (1994).

The antibody binds to an "epitope" on the antigen. The epitope is the specific antibody binding interaction site on the antigen, and can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures.

The term "specifically bind" refers to a molecule (e.g., antibody or antibody fragment) that binds to a target with at least 2-fold greater affinity than non-target compounds, e.g., at least 4-fold, 5-fold, 6-fold, 7-fold, 8-fold, 9-fold, 10-fold, 20-fold, 25-fold, 50-fold, or 100-fold greater affinity. For example, an antibody that specifically binds β8 will typically bind to β8 with at least a 2-fold greater affinity than a non-β8 target (e.g., a different integrin subunit, e.g., β6).

The term "binds" with respect to a cell type (e.g., an antibody that binds fibrotic cells, hepatocytes, chondrocytes, etc.), typically indicates that an agent binds a majority of the cells in a pure population of those cells. For example, an antibody that binds a given cell type typically binds to at least ⅔ of the cells in a population of the indicated cells (e.g., 75, 80, 85, 90, 91, 92, 93, 94, 95, 96, 97, 98, 99, or 100%). One of skill will recognize that some variability will arise depending on the method and/or threshold of determining binding.

As used herein, a first antibody, or an antigen-binding portion thereof, "competes" for binding to a target with a second antibody, or an antigen-binding portion thereof, when binding of the second antibody with the target is detectably decreased in the presence of the first antibody compared to the binding of the second antibody in the absence of the first antibody. The alternative, where the binding of the first antibody to the target is also detectably decreased in the presence of the second antibody, can, but need not be the case. That is, a second antibody can inhibit the binding of a first antibody to the target without that first antibody inhibiting the binding of the second antibody to the target. However, where each antibody detectably inhibits the binding of the other antibody to its cognate epitope or ligand, whether to the same, greater, or lesser extent, the antibodies are said to "cross-compete" with each other for binding of their respective epitope(s). Both competing and cross-competing antibodies are encompassed by the present invention. The term "competitor" antibody can be applied to the first or second antibody as can be determined by one of skill in the art. In some cases, the presence of the competitor antibody (e.g., the first antibody) reduces binding of the second antibody to the target by at least 10%, e.g., 20%, 30%, 40%, 50%, 60%, 70%, 80%, or more, e.g., so that binding of the second antibody to target is undetectable in the presence of the first (competitor) antibody.

The term "differentially expressed" or "differentially regulated" refers generally to a protein or nucleic acid biomarker that is overexpressed (upregulated) or underexpressed (downregulated) in one sample compared to at least one other sample. In the context of the present invention, the term generally refers to overexpression of a biomarker (e.g., αvβ8) on a diseased cell compared to a normal cell.

For example, the terms "overexpressed" or "upregulated" interchangeably refer to a protein or nucleic acid, generally a biomarker, that is transcribed or translated at a detectably greater than control level. The term includes overexpression due to transcription, post transcriptional processing, translation, post-translational processing, cellular localization (e.g., organelle, cytoplasm, nucleus, cell surface), and RNA and protein stability. Overexpression can be detected using conventional techniques for detecting biomarkers, whether mRNA (i.e., RT-PCR, hybridization) or protein (i.e., flow cytometry, imaging, ELISA, immunohistochemical techniques). Overexpression can be 100/%, 20%, 30%, 40%, 50%, 60%, 70%, 800/0, 90% or more in comparison to a normal cell.

The terms "agonist," "activator," "inducer" and like terms refer to molecules that increase activity or expression as compared to a control. Agonists are agents that, e.g., bind to, stimulate, increase, activate, enhance activation, sensitize or upregulate the activity of the target. The expression or activity can be increased 10%, 20%, 30%, 40%, 50%, 60%, 70%, 80%, 90% 100% or more than that in a control. In certain instances, the activation is 1.5-fold, 2-fold, 3-fold, 4-fold, 5-fold, 10-fold, or more in comparison to a control.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, *Bioconjugate Techniques* 1996, Academic Press, Inc., San Diego.

A "labeled" molecule (e.g., nucleic acid, protein, or antibody) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

The term "diagnosis" refers to a relative probability that a disorder such as cancer or an inflammatory condition is present in the subject. Similarly, the term "prognosis" refers to a relative probability that a certain future outcome may occur in the subject. For example, prognosis can refer to the likelihood that an individual will develop a TGFβ or αvβ8 associated disorder, have recurrence, or the likely severity of the disease (e.g., severity of symptoms, rate of functional decline, survival, etc.). The terms are not intended to be absolute, as will be appreciated by any one of skill in the field of medical diagnostics.

"Biopsy" or "biological sample from a patient" as used herein refers to a sample obtained from a patient having, or suspected of having, a TGFβ or αvβ8 associated disorder. In some embodiments, the sample may be a tissue biopsy, such as needle biopsy, fine needle biopsy, surgical biopsy, etc. The sample can also be a blood sample or blood fraction, e.g., white blood cell fraction, serum, or plasma. The sample can comprise a tissue sample harboring a lesion or suspected lesion, although the biological sample may be also be derived from another site, e.g., a site of suspected metastasis, a lymph node, or from the blood. In some cases, the biological sample may also be from a region adjacent to the lesion or suspected lesion.

A "biological sample" can be obtained from a patient, e.g., a biopsy, from an animal, such as an animal model, or from cultured cells, e.g., a cell line or cells removed from a patient and grown in culture for observation. Biological samples include tissues and bodily fluids, e.g., blood, blood fractions, lymph, saliva, urine, feces, etc.

The terms "therapy," "treatment," and "amelioration" refer to any reduction in the severity of symptoms. In the case of treating an inflammatory condition, the treatment can refer to reducing, e.g., blood levels of inflammatory cytokines, blood levels of active mature TGFβ, pain, swelling, recruitment of immune cells, etc. In the case of treating cancer, treatment can refer to reducing, e.g., tumor size, number of cancer cells, growth rate, metastatic activity, cell death of non-cancer cells, etc. As used herein, the terms "treat" and "prevent" are not intended to be absolute terms. Treatment and prevention can refer to any delay in onset, amelioration of symptoms, improvement in patient survival, increase in survival time or rate, etc. Treatment and prevention can be complete (no detectable symptoms remaining) or partial, such that symptoms are less frequent of severe than in a patient without the treatment described herein. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The terms "effective amount," "effective dose," "therapeutically effective amount," etc. refer to that amount of the therapeutic agent sufficient to ameliorate a disorder, as described above. For example, for the given parameter, a therapeutically effective amount will show an increase or decrease of therapeutic effect at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

As used herein, the term "pharmaceutically acceptable" is used synonymously with physiologically acceptable and pharmacologically acceptable. A pharmaceutical composition will generally comprise agents for buffering and preservation in storage, and can include buffers and carriers for appropriate delivery, depending on the route of administration.

The terms "dose" and "dosage" are used interchangeably herein. A dose refers to the amount of active ingredient given to an individual at each administration. For the present invention, the dose can refer to the concentration of the antibody or associated components, e.g., the amount of therapeutic agent or dosage of radiolabel. The dose will vary depending on a number of factors, including frequency of administration; size and tolerance of the individual; severity of the condition; risk of side effects; the route of administration; and the imaging modality of the detectable moiety (if present). One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

"Subject," "patient," "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically refers to an individual under medical supervision. A patient can be an individual that is seeking treatment, monitoring, adjustment or modification of an existing therapeutic regimen, etc.

An "inflammatory condition" refers to any inflammation in an individual, and can be transient (e.g., in response to exposure to a pathogen or allergen) or chronic. Inflammation is characterized by inflammatory cytokines such as IFN-gamma, IL-6, and TNF-alpha that recruit and activate macrophages and other leukocytes. In some cases, inflammation can develop into a chronic, harmful condition or autoimmune condition (e.g., MS, lupus, rheumatoid arthritis, Crohn's disease). Inflammation can be evident locally (e.g., at a localized site of infection or exposure) or systemically (e.g., atherosclerosis, high blood pressure). In some embodiments, the antibody compositions and methods described herein can be used to treat inflammatory conditions.

"Cancer", "tumor," "transformed" and like terms include precancerous, neoplastic, transformed, and cancerous cells, and can refer to a solid tumor, or a non-solid cancer (see, e.g., Edge et al. *AJCC Cancer Staging Manual* ($7^{th}$ ed. 2009); Cibas and Ducatman *Cytology: Diagnostic principles and clinical correlates* ($3^{rd}$ ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, *Culture of Animal Cells a Manual of Basic Technique* ($3^{rd}$ ed. 1994)). Although transformation can arise from infection with a transforming virus and incorporation of new genomic DNA, or uptake of exogenous DNA, it can also arise spontaneously or following exposure to a carcinogen.

The term "cancer" can refer to carcinomas, sarcomas, adenocarcinomas, lymphomas, leukemias, solid and lymphoid cancers, etc. Examples of different types of cancer include, but are not limited to, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma; head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia (AML), chronic myeloid leukemia (CML), and multiple myeloma. In some embodiments, the antibody compositions and methods described herein can be used for treating cancer.

The term "co-administer" refers to the simultaneous presence of two active agents in the blood of an individual. Active agents that are co-administered can be concurrently or sequentially delivered.

BRIEF SUMMARY OF THE INVENTION

In some aspects, an antibody is provided that specifically binds human αvβ8 and blocks binding of TGFβ peptide to αvβ8, wherein the antibody binds to an epitope on human αvβ8 comprising amino acids D148, A149, D150, G151, and Y178 of human αv as occurs in SEQ ID NO:393 and amino acids H118, S170, D171, Y172, N173 L174, D175, H200, and R201 of human β8 as occurs in SEQ ID NO:394.

In some embodiments, an antibody (optionally a chimeric or humanized antibody) is provided that comprises heavy chain CDRs SEQ ID NO:562, SEQ ID NO: 563, and SEQ ID NO; 564 and light chain CDRs SEQ ID NO:569, SEQ ID NO: 570, and SEQ ID NO: 571.

In some embodiments, an antibody (optionally a chimeric or humanized antibody) is provided that comprises:
heavy chain CDRs SEQ ID NO:313, SEQ ID NO:314, and SEQ ID NO:315; and light chain CDRs SEQ ID NO:334, SEQ ID NO:335, and SEQ ID NO:336; or
heavy chain CDRs SEQ ID NO:319, SEQ ID NO:320, and SEQ ID NO:321; and light chain CDRs SEQ ID NO:340, SEQ ID NO:341, and SEQ ID NO:342; or
heavy chain CDRs SEQ ID NO:316, SEQ ID NO:317, and SEQ ID NO:318; and light chain CDRs SEQ ID NO:337, SEQ ID NO:338, and SEQ ID NO:339; or
heavy chain CDRs SEQ ID NO:322, SEQ ID NO:323, and SEQ ID NO:324; and light chain CDRs SEQ ID NO:343, SEQ ID NO:344, and SEQ ID NO:345; or
heavy chain CDRs SEQ ID NO:322, SEQ ID NO:323, and SEQ ID NO:324; and light chain CDRs SEQ ID NO:346, SEQ ID NO:347, and SEQ ID NO:348; or
heavy chain CDRs SEQ ID NO:322, SEQ ID NO:323, and SEQ ID NO:324; and light chain CDRs SEQ ID NO:349, SEQ ID NO:350, and SEQ ID NO:351; or
heavy chain CDRs SEQ ID NO:325, SEQ ID NO:326, and SEQ ID NO:327; and light chain CDRs SEQ ID NO:352, SEQ ID NO:353, and SEQ ID NO:354; or
heavy chain CDRs SEQ ID NO:325, SEQ ID NO:326, and SEQ ID NO:327; and light chain CDRs SEQ ID NO:355, SEQ ID NO:356, and SEQ ID NO:357; or
heavy chain CDRs SEQ ID NO:325, SEQ ID NO:326, and SEQ ID NO:327; and light chain CDRs SEQ ID NO:358, SEQ ID NO:359, and SEQ ID NO:360; or
heavy chain CDRs SEQ ID NO:367, SEQ ID NO:368, and SEQ ID NO:369; and light chain CDRs SEQ ID NO:373, SEQ ID NO:374, and SEQ ID NO:375; or
heavy chain CDRs SEQ ID NO:364, SEQ ID NO:365, and SEQ ID NO:366; and light chain CDRs SEQ ID NO:373, SEQ ID NO:374, and SEQ ID NO:375; or
heavy chain CDRs SEQ ID NO:367, SEQ ID NO:368, and SEQ ID NO:369; and light chain CDRs SEQ ID NO:376, SEQ ID NO:377, and SEQ ID NO:378; or heavy chain CDRs SEQ ID NO:370, SEQ ID NO:371, and SEQ ID NO:372; and light chain CDRs SEQ ID NO:373, SEQ ID NO:374, and SEQ ID NO:375; or
heavy chain CDRs SEQ ID NO:331, SEQ ID NO:332, and SEQ ID NO:333; and light chain CDRs SEQ ID NO:382, SEQ ID NO:383, and SEQ ID NO:384; or
heavy chain CDRs SEQ ID NO:379, SEQ ID NO:380, and SEQ ID NO:381; and light chain CDRs SEQ ID NO:361, SEQ ID NO:362, and SEQ ID NO:363; or
heavy chain CDRs SEQ ID NO:331, SEQ ID NO:332, and SEQ ID NO:333; and light chain CDRs SEQ ID NO:361, SEQ ID NO:362, and SEQ ID NO:363; or
heavy chain CDRs SEQ ID NO:508, SEQ ID NO:509, and SEQ ID NO:510; and light chain CDRs SEQ ID NO:529, SEQ ID NO:530, and SEQ ID NO:531; or
heavy chain CDRs SEQ ID NO:511, SEQ ID NO:512, and SEQ ID NO:513; and light chain CDRs SEQ ID NO:532, SEQ ID NO:533, and SEQ ID NO:534; or
heavy chain CDRs SEQ ID NO:514, SEQ ID NO:515, and SEQ ID NO:516; and light chain CDRs SEQ ID NO:535, SEQ ID NO:536, and SEQ ID NO:537; or
heavy chain CDRs SEQ ID NO:517, SEQ ID NO:518, and SEQ ID NO:519; and light chain CDRs SEQ ID NO:538, SEQ ID NO:539, and SEQ ID NO:540; or
heavy chain CDRs SEQ ID NO: 520, SEQ ID NO:521, and SEQ ID NO:522; and light chain CDRs SEQ ID NO:541, SEQ ID NO:542, and SEQ ID NO:543; or
heavy chain CDRs SEQ ID NO: 523, SEQ ID NO:524, and SEQ ID NO:525; and light chain CDRs SEQ ID NO:544, SEQ ID NO:545, and SEQ ID NO:546; or
heavy chain CDRs SEQ ID NO: 526, SEQ ID NO:527, and SEQ ID NO:528; and light chain CDRs SEQ ID NO:547, SEQ ID NO:548, and SEQ ID NO:549; or
other antibodies described herein.

In some embodiments, the antibody is linked to a detectable label.

In some embodiments, the antibody further comprises heavy chain framework sequences FR1, FR2, FR3, and FR4 as SEQ ID NO: 558, SEQ ID NO: 559, SEQ ID NO: 560, and SEQ ID NO: 561, respectively, and light chain framework sequences FR1, FR2, FR3, and FR4 as SEQ ID NO: 565, SEQ ID NO: 566, SEQ ID NO: 567, and SEQ ID NO: 568, respectively.

In some embodiments, the antibody further comprises heavy chain framework sequences FR1, FR2, FR3, and FR4 as SEQ ID NO: 550, SEQ ID NO: 551, SEQ ID NO: 552, and SEQ ID NO: 553, respectively, and light chain framework sequences FR1, FR2, FR3, and FR4 as SEQ ID NO: 554, SEQ ID NO: 555, SEQ ID NO: 556, and SEQ ID NO: 557, respectively.

In some embodiments, the antibody is humanized. In some embodiments, the humanized antibody comprises SEQ ID NO:395, SEQ ID NO:403, SEQ ID NO:411; SEQ ID NO:419, SEQ ID NO:427, SEQ ID NO:443, SEQ ID NO:451, SEQ ID NO:459, SEQ ID NO:467; SEQ ID NO:475, SEQ ID NO:484, or SEQ ID NO:500.

Also provided is an antibody that binds to αvβ8 and αvβ6 and comprising a light chain CDR1 comprising the sequence RGDL. In some embodiments, the antibody comprises variable regions comprising heavy chain CDRs SEQ ID NO:523, SEQ ID NO:524, and SEQ ID NO:525; and light chain CDRs SEQ ID NO:544, SEQ ID NO:545, and SEQ ID NO:546; or heavy chain CDRs SEQ ID NO:526, SEQ ID NO:527, and SEQ ID NO:528; and light chain CDRs SEQ ID NO:547, SEQ ID NO:548, and SEQ ID NO:549.

In some embodiments, the antibody further comprises heavy chain framework sequences FR1, FR2, FR3, and FR4 as SEQ ID NO: 558, SEQ ID NO: 559, SEQ ID NO: 560, and SEQ ID NO: 561, respectively, and light chain framework sequences FR1, FR2, FR3, and FR4 as SEQ ID NO: 565, SEQ ID NO: 566, SEQ ID NO: 567, and SEQ ID NO: 568, respectively.

In some embodiments, the antibody further comprises heavy chain framework sequences FR1, FR2, FR3, and FR4 as SEQ ID NO: 550, SEQ ID NO: 551, SEQ ID NO: 552, and SEQ ID NO: 553, respectively, and light chain framework sequences FR1, FR2, FR3, and FR4 as SEQ ID NO: 554, SEQ ID NO: 555, SEQ ID NO: 556, and SEQ ID NO: 557, respectively.

In some embodiments, the antibody is humanized.

In some embodiments, the antibody is linked to a detectable label.

Also provided is an antibody that specifically binds human αvβ8 and blocks binding of TGFβ peptide to αvβ8, wherein the antibody binds to the specificity determining loop (SDL) of human β8. In some embodiments, the antibody further binds to one, two, or all three of the human αv-head domain, the α1 helix of human β8, or the α2 helix of human β8. In some embodiments, the antibody is humanized or chimeric. In some embodiments, the antibody is linked to a detectable label.

Also provided is a pharmaceutical composition comprising an antibody as described above or elsewhere herein in a pharmaceutically acceptable excipient.

Also provided is a method of enhancing an immune response to a viral infection in a human individual. In some embodiments, the method comprises administering a sufficient amount of an antibody as described above or elsewhere herein to the individual, thereby enhancing an immune response to the viral infection.

In some embodiments, the viral infection is a hepatitis infection. In some embodiments, the viral infection is a hepatitis B infection.

Also provided is a method of enhancing an immune response to a viral infection in a human individual, the method comprising administering a sufficient amount of the antibody to the individual, wherein the antibody specifically binds to human αvβ8 and blocks binding of TGFβ peptide to αvβ8 or blocks activation of αvβ8 by binding of TGFβ human αvβ8, thereby enhancing an immune response to the viral infection.

Also provided is a method of enhancing an immune response to cancer in a human individual, the method comprising administering a sufficient amount of an antibody as described above or elsewhere herein to the individual, thereby enhancing an immune response to the cancer.

In some embodiments, the cancer is lung cancer. In some embodiments, the cancer is a metastatic cancer. In some embodiments, the cancer is a primary cancer.

Also provided is a method of enhancing an immune response to *H. pyroli* in a human individual, the method comprising administering a sufficient amount of an antibody as described above or elsewhere herein to the individual, thereby enhancing an immune response to *H. pyroli*.

In some embodiments, the human individual has a peptide ulcer, gastric carcinoma or MALT lymphoma.

Also provided is an antibody that specifically binds to human αvβ8 and that comprises human heavy chain CDRs SEQ ID NO:299, SEQ ID NO:301, and SEQ ID NO:303; and light chain CDRs SEQ ID NO:307, SEQ ID NO:309, and SEQ ID NO:311. Alternatively, any antibodies having heavy chain CDRs or a heavy chain variable region as set forth in FIG. 53 and light chain CDRs or a light chain variable region from a corresponding sequence as set forth in FIG. 54 can be used In some embodiments, the antibody is linked to a detectable label.

Also provided is a method of detecting the presence, absence, or quantity of human in a sample, the method comprising, contacting to the sample an antibody that specifically binds to human αvβ8 and that comprises human heavy chain CDRs SEQ ID NO:299, SEQ ID NO:301, and SEQ ID NO:303; and light chain CDRs SEQ ID NO:307, SEQ ID NO:309, and SEQ ID NO:311, and detecting or quantifying binding of the antibody to the sample.

In some embodiments, the sample is a formalin-fixed sample.

BRIEF DESCRIPTION OF THE DRAWINGS

FIG. 1 illustrates heavy chain amino acid sequences for clones used in the construction of the composite antibody C6D4. B13C4 15-8: all sequences (SEQ ID NO: 1), Framework 1 (SEQ ID NO:2), CDR1 (SEQ ID NO:3), Framework 2 (SEQ ID NO:4), CDR2 (SEQ ID NO:5), Framework 3 (SEQ ID NO:6), CRD3 (SEQ ID NO:7), and Framework 4 (SEQ ID NO:8); B13C4 15-10: all sequences (SEQ ID NO:9), Framework 1 (SEQ ID NO:10), CDR1 (SEQ ID NO:11), Framework 2 (SEQ ID NO:12), CDR2 (SEQ ID NO:13), Framework 3 (SEQ ID NO:14), CRD3 (SEQ ID NO:15), and Framework 4 (SEQ ID NO:16); B13H3.2: all sequences (SEQ ID NO:17), Framework 1 (SEQ ID NO:18), CDR1 (SEQ ID NO:19), Framework 2 (SEQ ID NO:20), CDR2 (SEQ ID NO:21), Framework 3 (SEQ ID NO:22), CRD3 (SEQ ID NO:23), and Framework 4 (SEQ ID NO:24); B13C1231015: all sequences (SEQ ID NO:25), Framework 1 (SEQ ID NO:26), CDR1 (SEQ ID NO:27), Framework 2 (SEQ ID NO:28), CDR2 (SEQ ID NO:29), Framework 3 (SEQ ID NO:30), CRD3 (SEQ ID NO:31), and Framework 4 (SEQ ID NO:32); B15B11Vh: all sequences (SEQ ID NO:33), Framework 1 (SEQ ID NO:34), CDR1 (SEQ ID NO:35), Framework 2 (SEQ ID NO:36), CDR2 (SEQ ID NO:37), Framework 3 (SEQ ID NO:38), CRD3 (SEQ ID NO:39), and Framework 4 (SEQ ID NO:40); B2B2 15-9: all sequences (SEQ ID NO:41), Framework 1 (SEQ ID NO:42), CDR1 (SEQ ID NO:43), Framework 2 (SEQ ID NO:44), CDR2 (SEQ ID NO:45), Framework 3 (SEQ ID NO:46), CRD3 (SEQ ID NO:47), and Framework 4 (SEQ ID NO:48); R11D12715.3: all sequences (SEQ ID NO:49), Framework 1 (SEQ ID NO:50), CDR1 (SEQ ID NO:51), Framework 2 (SEQ ID NO:52), CDR2 (SEQ ID NO:53), Framework 3 (SEQ ID NO:54), CRD3 (SEQ ID NO:55), and Framework 4 (SEQ ID NO:56); RSDLVH-1: all sequences (SEQ ID NO:57 and SEQ ID NO:65), Framework 1 (SEQ ID NO:58 and SEQ ID NO:66), CDR1 (SEQ ID NO:59 and SEQ ID NO:67), Framework 2 (SEQ ID NO:60 and SEQ ID NO:68), CDR2 (SEQ ID NO:61 and SEQ ID NO:69), Framework 3 (SEQ ID NO:62 and SEQ ID NO:70), CRD3 (SEQ ID NO:63 and SEQ ID NO:71), and Framework 4 (SEQ ID NO:64 and SEQ ID NO:72); RSDLVH-3: all sequences (SEQ ID NO:73), Framework 1 (SEQ ID NO:74), CDR1 (SEQ ID NO:75), Framework 2 (SEQ ID NO:76), CDR2 (SEQ ID NO:77), Framework 3 (SEQ ID NO:78), CRD3 (SEQ ID NO:79), and Framework 4 (SEQ ID NO:80); RSDLVH-16: all sequences (SEQ ID NO:81), Framework 1 (SEQ ID NO:82), CDR1 (SEQ ID NO:83), Framework 2 (SEQ ID NO:84), CDR2 (SEQ ID NO:85), Framework 3 (SEQ ID NO:86), CRD3 (SEQ ID NO:87), and Framework 4 (SEQ ID NO:88); both 29 and 44: all sequences (SEQ ID NO:89), Framework 1 (SEQ ID NO:90), CDR1 (SEQ ID NO:91), Framework 2 (SEQ ID NO:92), CDR2 (SEQ ID NO:93), Framework 3 (SEQ ID NO:94), CRD3 (SEQ ID NO:95), and Framework 4 (SEQ ID NO:96); A1=B4=F9: all sequences (SEQ ID NO:97), Framework 1 (SEQ ID NO:98), CDR1 (SEQ ID NO:99), Framework 2 (SEQ ID NO:100), CDR2 (SEQ ID NO:101), Framework 3 (SEQ ID NO:102), CRD3 (SEQ ID NO:103), and Framework 4 (SEQ ID NO:104); A5=C6: all sequences (SEQ ID NO:105), Framework 1 (SEQ ID NO:106), CDR1 (SEQ ID NO:107), Framework 2 (SEQ ID NO: 108), CDR2 (SEQ ID NO: 109), Framework 3 (SEQ ID NO:110), CRD3 (SEQ ID NO: 111), and Framework 4 (SEQ ID NO: 112); D4=E6: all sequences (SEQ ID NO:113), Framework 1 (SEQ ID NO:114), CDR1 (SEQ ID NO:115), Framework 2 (SEQ ID NO: 116), CDR2 (SEQ ID NO: 117), Framework 3 (SEQ ID NO: 118), CRD3 (SEQ ID NO: 119), and Framework 4 (SEQ ID NO: 120); and C6D4: all sequences (SEQ ID NO: 121), Framework 1 (SEQ ID NO:122), CDR1 (SEQ ID NO:123), Framework 2 (SEQ ID NO: 124), CDR2 (SEQ ID NO:125), Framework 3 (SEQ ID NO: 126), CRD3 (SEQ ID NO:127), and Framework 4 (SEQ ID NO: 128).

FIG. 2 illustrates light chain amino acid sequences for clones used in the construction of the composite antibody C6D4. B2B2 35-20: all sequences (SEQ ID NO: 129), Framework 1 (SEQ ID NO:130), CDR1 (SEQ ID NO:131), Framework 2 (SEQ ID NO: 132), CDR2 (SEQ ID NO:133), Framework 3 (SEQ ID NO: 134), CRD3 (SEQ ID NO:135), and Framework 4 (SEQ ID NO: 136); B2B2 35-26: all sequences (SEQ ID NO: 137), Framework 1 (SEQ ID NO: 138), CDR1 (SEQ ID NO:139), Framework 2 (SEQ ID NO:140), CDR2 (SEQ ID NO:141), Framework 3 (SEQ ID NO: 142), CRD3 (SEQ ID NO:143), and Framework 4 (SEQ ID NO:144); B15B11vk34-26: all sequences (SEQ ID NO: 145), Framework 1 (SEQ ID NO:146), CDR1 (SEQ ID NO: 147), Framework 2 (SEQ ID NO: 148), CDR2 (SEQ ID NO: 149), Framework 3 (SEQ ID NO:150), CRD3 (SEQ ID NO: 151), and Framework 4 (SEQ ID NO: 152); B15B11vk33-24: all sequences (SEQ ID NO: 153), Framework 1 (SEQ ID NO: 154), CDR1 (SEQ ID NO:155), Framework 2 (SEQ ID NO: 156), CDR2 (SEQ ID NO: 157), Framework 3 (SEQ ID NO:158), CRD3 (SEQ ID NO:159), and Framework 4 (SEQ ID NO:160); B15B11vk35-26: all sequences (SEQ ID NO:161), Framework 1 (SEQ ID NO: 162), CDR1 (SEQ ID NO:163), Framework 2 (SEQ ID NO:164), CDR2 (SEQ ID NO:165), Framework 3 (SEQ ID NO:166), CRD3 (SEQ ID NO:167), and Framework 4 (SEQ ID NO:168); B13C12134-25: all sequences (SEQ ID NO:169), Framework 1 (SEQ ID NO:170), CDR1 (SEQ ID NO:171), Framework 2 (SEQ ID NO:172), CDR2 (SEQ ID NO:173), Framework 3 (SEQ ID NO:174), CRD3 (SEQ ID NO: 175), and Framework 4 (SEQ ID NO: 176); B13C12133-26: all sequences (SEQ ID NO: 177), Framework 1 (SEQ ID NO: 178), CDR1 (SEQ ID NO: 179), Framework 2 (SEQ ID NO:180), CDR2 (SEQ ID NO:181), Framework 3 (SEQ ID NO:182), CRD3 (SEQ ID NO:183), and Framework 4 (SEQ ID NO:184); B13C4 35-20: all sequences (SEQ ID NO:185), Framework 1 (SEQ ID NO: 186), CDR1 (SEQ ID NO: 187), Framework 2 (SEQ ID NO: 188), CDR2 (SEQ ID NO:189), Framework 3 (SEQ ID NO:190), CRD3 (SEQ ID NO:191), and Framework 4 (SEQ ID NO: 192); B15B11vk35-20: all sequences (SEQ ID NO: 193), Framework 1 (SEQ ID NO: 194), CDR1 (SEQ ID NO: 195), Framework 2 (SEQ ID NO: 196), CDR2 (SEQ ID NO: 197), Framework 3 (SEQ ID NO: 198), CRD3 (SEQ ID NO:199), and Framework 4 (SEQ ID NO:200);

B13C12335-25: all sequences (SEQ ID NO:201), Framework 1 (SEQ ID NO:202), CDR1 (SEQ ID NO:203), Framework 2 (SEQ ID NO:204), CDR2 (SEQ ID NO:205), Framework 3 (SEQ ID NO:206), CRD3 (SEQ ID NO:207), and Framework 4 (SEQ ID NO:208); B13C1233520: all sequences (SEQ ID NO:209), Framework 1 (SEQ ID NO:210), CDR1 (SEQ ID NO:211), Framework 2 (SEQ ID NO:212), CDR2 (SEQ ID NO:213), Framework 3 (SEQ ID NO:214), CRD3 (SEQ ID NO:215), and Framework 4 (SEQ ID NO:216); RSDLVK-1: all sequences (SEQ ID NO:217), Framework 1 (SEQ ID NO:218), CDR1 (SEQ ID NO:219), Framework 2 (SEQ ID NO:220), CDR2 (SEQ ID NO:221), Framework 3 (SEQ ID NO:222), CRD3 (SEQ ID NO:223), and Framework 4 (SEQ ID NO:224); RSDLVK-6: all sequences (SEQ ID NO:225), Framework 1 (SEQ ID NO:226), CDR1 (SEQ ID NO:227), Framework 2 (SEQ ID NO:228), CDR2 (SEQ ID NO:229), Framework 3 (SEQ ID NO:230), CRD3 (SEQ ID NO:231), and Framework 4 (SEQ ID NO:232); RSDLVK-10: all sequences (SEQ ID NO:233), Framework 1 (SEQ ID NO:234), CDR1 (SEQ ID NO:235), Framework 2 (SEQ ID NO:236), CDR2 (SEQ ID NO:237), Framework 3 (SEQ ID NO:238), CRD3 (SEQ ID NO:239), and Framework 4 (SEQ ID NO:240); RSDLVK-13: all sequences (SEQ ID NO:241), Framework 1 (SEQ ID NO:242), CDR1 (SEQ ID NO:243), Framework 2 (SEQ ID NO:244), CDR2 (SEQ ID NO:245), Framework 3 (SEQ ID NO:246), CRD3 (SEQ ID NO:247), and Framework 4 (SEQ ID NO:248); 29: all sequences (SEQ ID NO:249), Framework 1 (SEQ ID NO:250), CDR1 (SEQ ID NO:251), Framework 2 (SEQ ID NO:252), CDR2 (SEQ ID NO:253), Framework 3 (SEQ ID NO:254), CRD3 (SEQ ID NO:255), and Framework 4 (SEQ ID NO:256); 44: all sequences (SEQ ID NO:257), Framework 1 (SEQ ID NO:258), CDR1 (SEQ ID NO:259), Framework 2 (SEQ ID NO:260), CDR2 (SEQ ID NO:261), Framework 3 (SEQ ID NO:262), CRD3 (SEQ ID NO:263), and Framework 4 (SEQ ID NO:264); A1=B4=F9: all sequences (SEQ ID NO:265), Framework 1 (SEQ ID NO:266), CDR1 (SEQ ID NO:267), Framework 2 (SEQ ID NO:268), CDR2 (SEQ ID NO:269), Framework 3 (SEQ ID NO:270), CRD3 (SEQ ID NO:271), and Framework 4 (SEQ ID NO:272); A5=C6: all sequences (SEQ ID NO:273), Framework 1 (SEQ ID NO:274), CDR1 (SEQ ID NO:275), Framework 2 (SEQ ID NO:276), CDR2 (SEQ ID NO:277), Framework 3 (SEQ ID NO:278), CRD3 (SEQ ID NO:279), and Framework 4 (SEQ ID NO:280); D4=E6: all sequences (SEQ ID NO:281), Framework 1 (SEQ ID NO:282), CDR1 (SEQ ID NO:283), Framework 2 (SEQ ID NO:284), CDR2 (SEQ ID NO:285), Framework 3 (SEQ ID NO:286), CRD3 (SEQ ID NO:287), and Framework 4 (SEQ ID NO:288); and C6D4: all sequences (SEQ ID NO:289), Framework 1 (SEQ ID NO:290), CDR1 (SEQ ID NO:291), Framework 2 (SEQ ID NO:292), CDR2 (SEQ ID NO:293), Framework 3 (SEQ ID NO:294), CRD3 (SEQ ID NO:295), and Framework 4 (SEQ ID NO:296).

Figure 3:
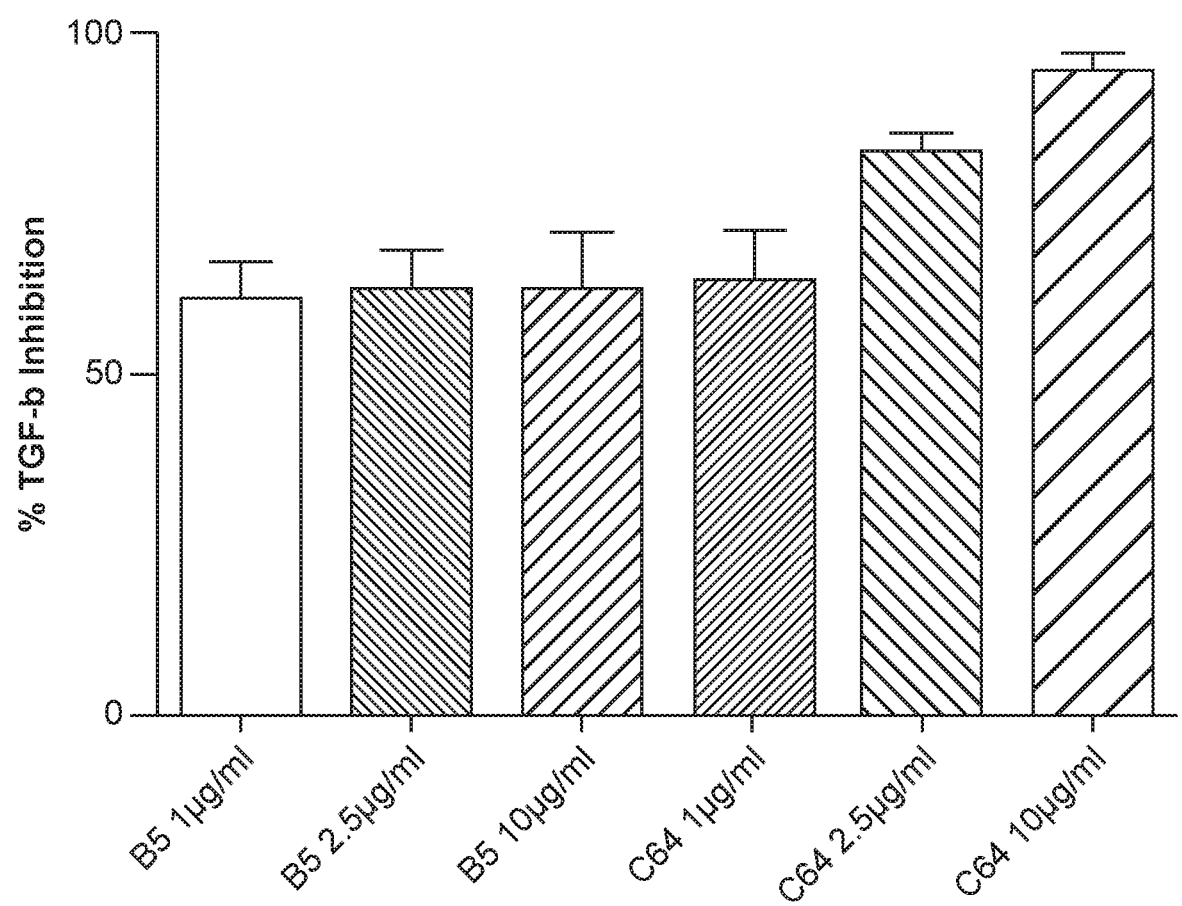

FIG. 3 is a plot of transforming growth factor-beta (TGF-β) binding inhibition percentages for different concentrations of the allosteric inhibitor B5 and the composite antibody C6D4.

FIG. 4 illustrates conservation of epitope among mammals, indicating the antibodies can be useful in multiple preclinical animal models and have broad utility, including in veterinary applications. Human αv (SEQ ID NO:591); Chimp αv (SEQ ID NO:592); Rhesus av (SEQ ID NO:593); Cyno αv (SEQ ID NO:594); Cow αv (SEQ ID NO:595); Pig αv (SEQ ID NO:596); Horse αv (SEQ ID NO:597); Mouse αv (SEQ ID NO:598); Rat αv (SEQ ID NO:599); Armadillo αv (SEQ ID NO:600); Platypus αv (SEQ ID NO:601); Human β8 (SEQ ID NO:602); Chimp β8 (SEQ ID NO:603); Rhesus β8 (SEQ ID NO:604); Cyno β8 (SEQ ID NO:605); Cow β8 (SEQ ID NO:606); Pig β8 (SEQ ID NO:607); Horse β8 (SEQ ID NO:608); Mouse β8 (SEQ ID NO:609); Rat β8 (SEQ ID NO:610); Armadillo β8 (SEQ ID NO:611); and Platypus β8 (SEQ ID NO:612).

FIG. 5 illustrates integrin alphaV (SEQ ID NO:394) and beta8 (SEQ ID NO:395) sequences. The epitope for C6D4 is in bold underlined italics.

Figure 6:
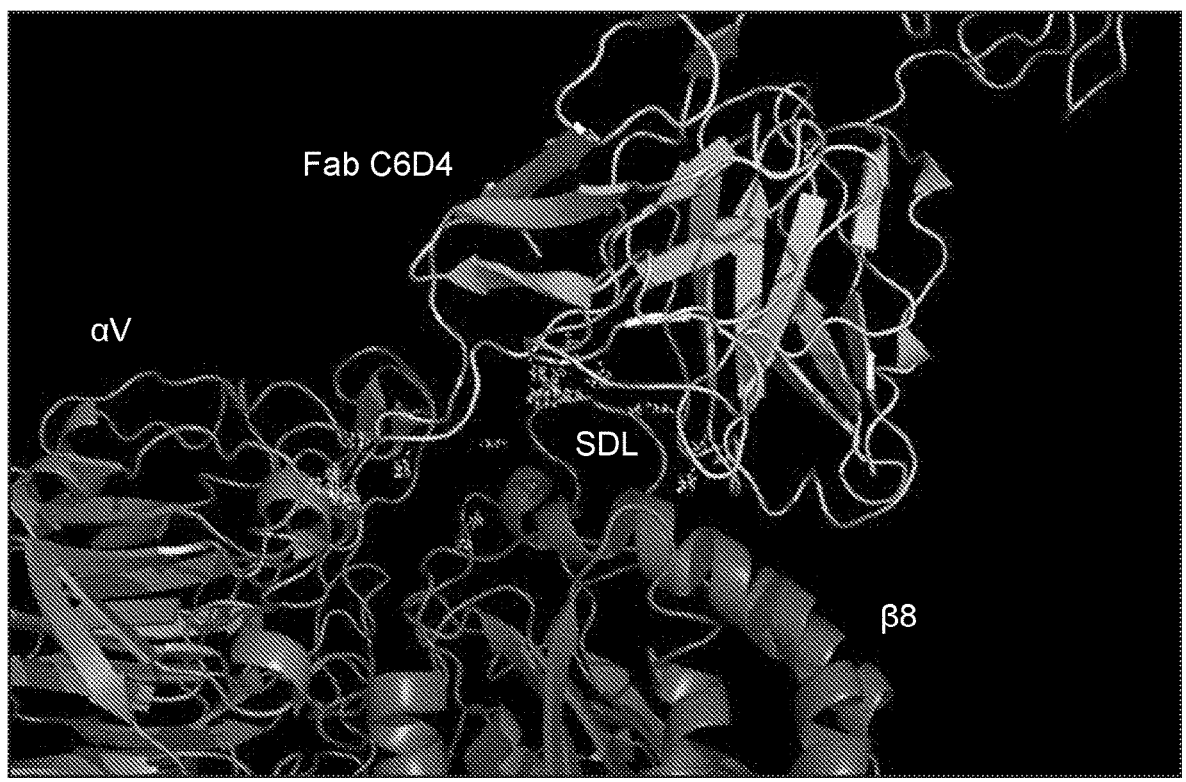

FIG. 6 illustrates cryoEM results, highlighting the interactions between C6D4 and the (SDL) loop of β8, the α1 and α2 helices of β8, and the head of αv.

Figure 7:
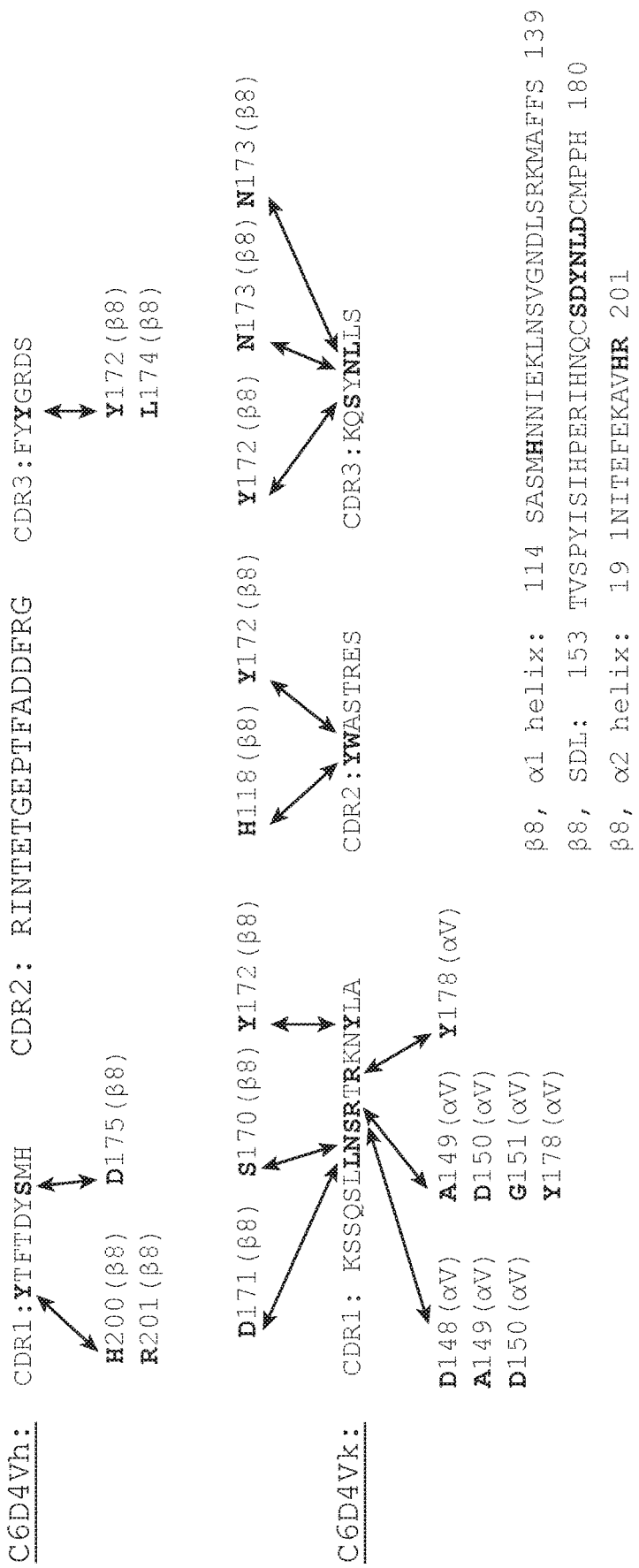

FIG. 7 illustrates the residues of the SDL and β8α1 and α2 helices and αv head of integrin αvβ8 that directly interact with C6D4 upon binding. The head sequence of integrin αv is FNLDVDSPAEYSGPEGSYFGFAVDFFVP-SASSRMFLLVGAPKANTTQPGIVEGGQVLKC DWSSTRRCQPIEFDATGNRDYAKDDPLEFKSHQWF-GASVRSKQDKILACAPLYHWRTE MKQEREPVGTCFLQDGTKTVEYAPCRSQDI-DADGQGFCQGGFSIDFTKADRVLLGGPGS FYWQGQLISDQVAEIVSKYDPNVYSIKYNNQLATR-TAQAIFDDSYLGYSVAVGDFNGD GIDDFVSGVPRAARTLGMVYIYDGKNMSSLYNFT-GEQMAAYFGFSVAATDINGDDYAD VFI-GAPLFMDRGSDGKLQEVGQVSVSLQRASGDFQTT-KLNGFEVFARFGSAIAPLGDLD QDGFNDIAIAAPY-GGEDKKGIVYIFNGRSTGLNAVPSQI-LEGQWAARSMPPSFGYSMKG ATDIDKNGYPDLIVGAFGVDRAILYRARP (SEQ ID NO:623). Sequences C6D4 Vh CDR1 (SEQ ID NO:613); C6D4 Vh CDR2 (SEQ ID NO:614); C6D4 Vh CDR3 (SEQ ID NO:615); C6D4 Vk CDR1 (SEQ ID NO:616); C6D4 Vk CDR2 (SEQ ID NO:617); C6D4 Vk CDR3 (SEQ ID NO:618); β8, α1 helix (SEQ ID NO:619); 08, SDL (SEQ ID NO:620); β8, α2 helix (SEQ ID NO:621); and αV, β-propeller domain blade W3 (SEQ ID NO:622).

Figure 8:
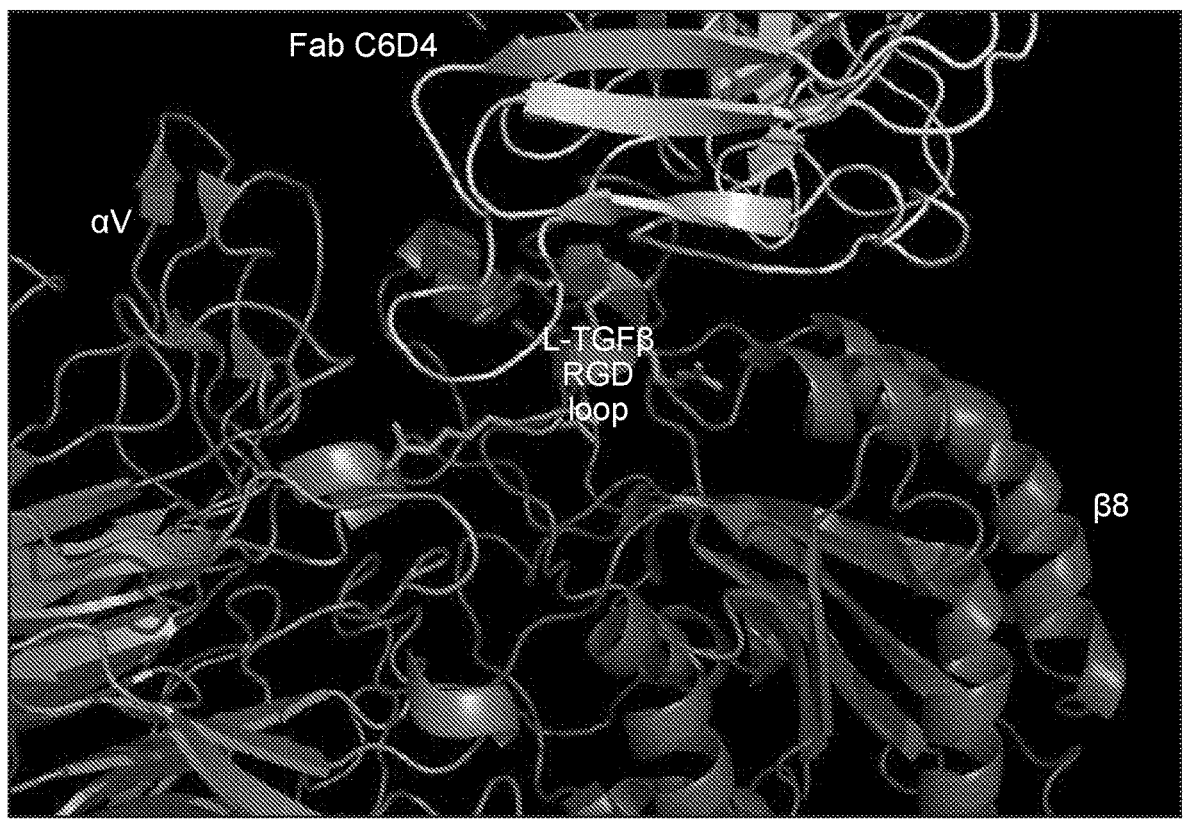

FIG. 8 illustrates the overlapping of the C6D4 epitope with the ligand binding pocket of integrin αvβ8, in relation to the association of the integrin with latent TGF-β.

Figure 9:
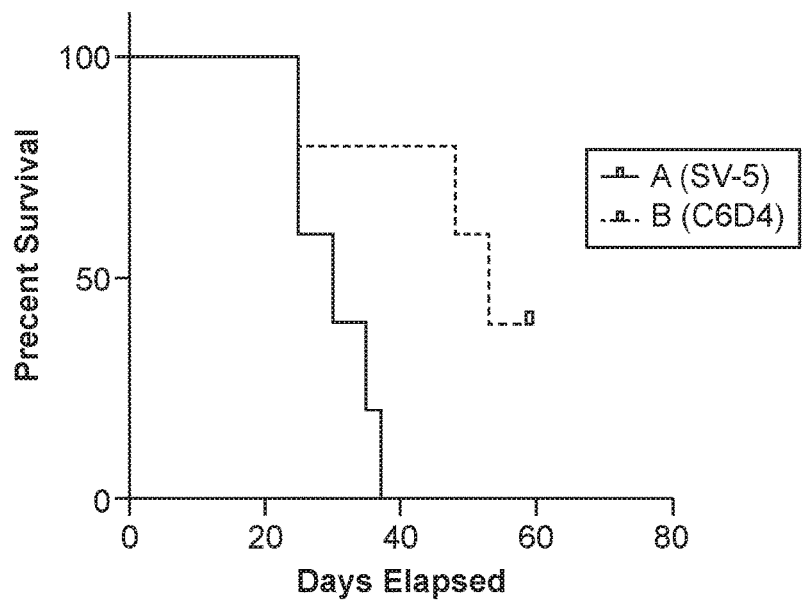

FIG. 9 is a plot of percent survival of mice injected with Lewis lung carcinoma (LLC) cells. The primary tumors were removed and the animals treated with C6D4 murine IgG2a or SV5 isotype control at a dosage of 7 mg/kg once per week. In this model, mice are euthanized after losing 20% body weight due to recurrence of the primary tumor or due to metastasis.

FIG. 10 is a table of HepB surface antigen (HBSag) clearance from a chronic infection mouse model as a result of treatment with C6D4.

FIG. 11A-B illustrate amino acid sequences for clones used in the construction of the engineered antibody 4F1F9, an antibody used for detection of αvβ8 in human tissues. FIG. 11A Sequences—4F1: all sequences (SEQ ID NO:624), Framework 1 (SEQ ID NO:625), CDR1 (SEQ ID NO:628), Framework 2 (SEQ ID NO:632), CDR2 (SEQ ID NO:634), Framework 3 (SEQ ID NO:637), CDR3 (SEQ ID NO:651), Framework 4 (SEQ ID NO:655), 6B9: all sequences (SEQ ID NO:656), Framework 1 (SEQ ID NO:625), CDR1 (SEQ ID NO:629), Framework 2 (SEQ ID NO:632), CDR2 (SEQ ID NO:635), Framework 3 (SEQ ID NO:638), CDR3 (SEQ ID NO:652), Framework 4 (SEQ ID NO:655), 6B9.1: all sequences (SEQ ID NO:657), Framework 1 (SEQ ID NO:625), CDR1 (SEQ ID NO:629), Framework 2 (SEQ ID NO:632), CDR2 (SEQ ID NO:636), Framework 3 (SEQ ID NO:638), CDR3 (SEQ ID NO:653), Framework 4 (SEQ ID NO:655), A1: all sequences (SEQ ID NO:658), Framework 1 (SEQ ID NO:626), CDR1 (SEQ ID NO:629), Framework 2 (SEQ ID NO:633), CDR2 (SEQ ID NO:636), Framework 3 (SEQ ID NO:639), CDR3 (SEQ ID NO:654), Framework 4 (SEQ ID NO:655), A2: all sequences (SEQ ID NO:659), Framework 1 (SEQ ID NO:625), CDR1 (SEQ ID NO:629), Framework 2 (SEQ ID NO:633), CDR2 (SEQ ID NO:636), Framework 3 (SEQ ID NO:640), CDR3 (SEQ ID NO:654), Framework 4 (SEQ ID NO:655), A8: all sequences (SEQ ID NO:660), Framework 1 (SEQ ID NO:625), CDR1 (SEQ ID NO:629), Framework 2 (SEQ ID NO:633), CDR2 (SEQ ID NO:636), Framework 3 (SEQ ID NO:641), CDR3 (SEQ ID NO:654), Framework 4 (SEQ ID NO:655), A11: all sequences (SEQ ID NO:661), Framework 1 (SEQ ID NO:625), CDR1 (SEQ ID NO:630), Framework 2 (SEQ ID NO:633), CDR2 (SEQ ID NO:636), Framework 3 (SEQ ID NO:638), CDR3 (SEQ ID NO:654), Framework 4 (SEQ ID NO:655), B1: all sequences (SEQ ID NO:662), Framework 1 (SEQ ID NO:625), CDR1 (SEQ ID NO:629), Framework 2 (SEQ ID NO:632), CDR2 (SEQ ID NO:636), Framework 3 (SEQ ID NO:642), CDR3 (SEQ ID NO:654), Framework 4 (SEQ ID NO:655), B3: all sequences (SEQ ID NO:663), Framework 1 (SEQ ID NO:625), CDR1 (SEQ ID NO:629), Framework 2 (SEQ ID NO:633), CDR2 (SEQ ID NO:636), Framework 3 (SEQ ID NO:643), CDR3 (SEQ ID NO:654), Framework 4 (SEQ ID NO:655), C4=F10: all sequences (SEQ ID NO:664), Framework 1 (SEQ ID NO:625), CDR1 (SEQ ID NO:629), Framework 2 (SEQ ID NO:633), CDR2 (SEQ ID NO:636), Framework 3 (SEQ ID NO:644), CDR3 (SEQ ID NO:654), Framework 4 (SEQ ID NO:655), C7=D1: all sequences (SEQ ID NO:665), Framework 1 (SEQ ID NO:625), CDR1 (SEQ ID NO:629), Framework 2 (SEQ ID NO:633), CDR2 (SEQ ID NO:636), Framework 3 (SEQ ID NO:644), CDR3 (SEQ ID NO:654), Framework 4 (SEQ ID NO:655), D3=F1: all sequences (SEQ ID NO:666), Framework 1 (SEQ ID NO:625), CDR1 (SEQ ID NO:629), Framework 2 (SEQ ID NO:633), CDR2 (SEQ ID NO:636), Framework 3 (SEQ ID NO:645), CDR3 (SEQ ID NO:654), Framework 4 (SEQ ID NO:655), D10=E5: all sequences (SEQ ID NO:667), Framework 1 (SEQ ID NO:625), CDR1 (SEQ ID NO:629), Framework 2 (SEQ ID NO:633), CDR2 (SEQ ID NO:636), Framework 3 (SEQ ID NO:646), CDR3 (SEQ ID NO:654), Framework 4 (SEQ ID NO:655), G4: all sequences (SEQ ID NO:668), Framework 1 (SEQ ID NO:625), CDR1 (SEQ ID NO:629), Framework 2 (SEQ ID NO:633), CDR2 (SEQ ID NO:636), Framework 3 (SEQ ID NO:647), CDR3 (SEQ ID NO:654), Framework 4 (SEQ ID NO:655), C4: all sequences (SEQ ID NO:669), Framework 1 (SEQ ID NO:625), CDR1 (SEQ ID NO:629), Framework 2 (SEQ ID NO:633), CDR2 (SEQ ID NO:636), Framework 3 (SEQ ID NO:650), CDR3 (SEQ ID NO:654), Framework 4 (SEQ ID NO:655), D10: all sequences (SEQ ID NO:670), Framework 1 (SEQ ID NO:625), CDR1 (SEQ ID NO:629), Framework 2 (SEQ ID NO:633), CDR2 (SEQ ID NO:636), Framework 3 (SEQ ID NO:646), CDR3 (SEQ ID NO:654), Framework 4 (SEQ ID NO:655), 4F1A11: all sequences (SEQ ID NO:671), Framework 1 (SEQ ID NO:625), CDR1 (SEQ ID NO:629), Framework 2 (SEQ ID NO:632), CDR2 (SEQ ID NO:636), Framework 3 (SEQ ID NO:650), CDR3 (SEQ ID NO:654), Framework 4 (SEQ ID NO:655), 4F1E1: all sequences (SEQ ID NO:672), Framework 1 (SEQ ID NO:625), CDR1 (SEQ ID NO:631), Framework 2 (SEQ ID NO:632), CDR2 (SEQ ID NO:636), Framework 3 (SEQ ID NO:638), CDR3 (SEQ ID NO:654), Framework 4 (SEQ ID NO:655), 4F1G3: all sequences (SEQ ID NO:673), Framework 1 (SEQ ID NO:625), CDR1 (SEQ ID NO:631), Framework 2 (SEQ ID NO:632), CDR2 (SEQ ID NO:636), Framework 3 (SEQ ID NO:648), CDR3 (SEQ ID NO:654), Framework 4 (SEQ ID NO:655), 4F1E10: all sequences (SEQ ID NO:674), Framework 1 (SEQ ID NO:627), CDR1 (SEQ ID NO:631), Framework 2 (SEQ ID NO:632), CDR2 (SEQ ID NO:636), Framework 3 (SEQ ID NO:638), CDR3 (SEQ ID NO:654), Framework 4 (SEQ ID NO:655), 4F1E9: all sequences (SEQ ID NO:675), Framework 1 (SEQ ID NO:625), CDR1 (SEQ ID NO:629), Framework 2 (SEQ ID NO:632), CDR2 (SEQ ID NO:636), Framework 3 (SEQ ID NO:638), CDR3 (SEQ ID NO:654), Framework 4 (SEQ ID NO:655), 4F1H12: all sequences (SEQ ID NO:676), Framework 1 (SEQ ID NO:625), CDR1 (SEQ ID NO:631), Framework 2 (SEQ ID NO:632), CDR2 (SEQ ID NO:636), Framework 3 (SEQ ID NO:649), CDR3 (SEQ ID NO:654), Framework 4 (SEQ ID NO:655), F9: all sequences (SEQ ID NO:677), Framework 1 (SEQ ID NO:625), CDR1 (SEQ ID NO:631), Framework 2 (SEQ ID NO:632), CDR2 (SEQ ID NO:636), Framework 3 (SEQ ID NO:638), CDR3 (SEQ ID NO:654), and Framework 4 (SEQ ID NO:655). FIG. 11B Sequences—4F1: all sequences (SEQ ID NO:678), Framework 1 (SEQ ID NO:692), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), 6B9: all sequences (SEQ ID NO:679), Framework 1 (SEQ ID NO:699), CDR1 (SEQ ID NO:700), Framework 2 (SEQ ID NO:701), CDR2 (SEQ ID NO:695), Framework 3 (SEQ ID NO:696), CDR3 (SEQ ID NO:702), Framework 4 (SEQ ID NO:698), 6B9.1: all sequences (SEQ ID NO:680), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), A1=A2=C4=C7=D1=D10=E5=F1=F10=G4: all sequences (SEQ ID NO:681), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), A8: all sequences (SEQ ID NO:682), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), A11: all sequences (SEQ ID NO:683), Framework 1 (SEQ ID NO:704), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), B1: all sequences (SEQ ID NO:684), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), B3: all sequences (SEQ ID NO:685), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), D10=E5: all sequences (SEQ ID NO:686), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), C4: all sequences (SEQ ID NO:687), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:706), D10: all sequences (SEQ ID NO:688), Framework 1 (SEQ ID NO:699), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:706), 4F1E1=1F1G3=4F1B5=4F1G11=4F1A9=4F1B9= 4F1H9=4F1D10=4F1E9=4F1F10=4FH11=4F1H12: all sequences (SEQ ID NO:689), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), 4FA11: all sequences (SEQ ID NO:690), Framework 1 (SEQ ID NO:705), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), F9: all sequences (SEQ ID NO:691), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), and Framework 4 (SEQ ID NO:706).

Figure 12:
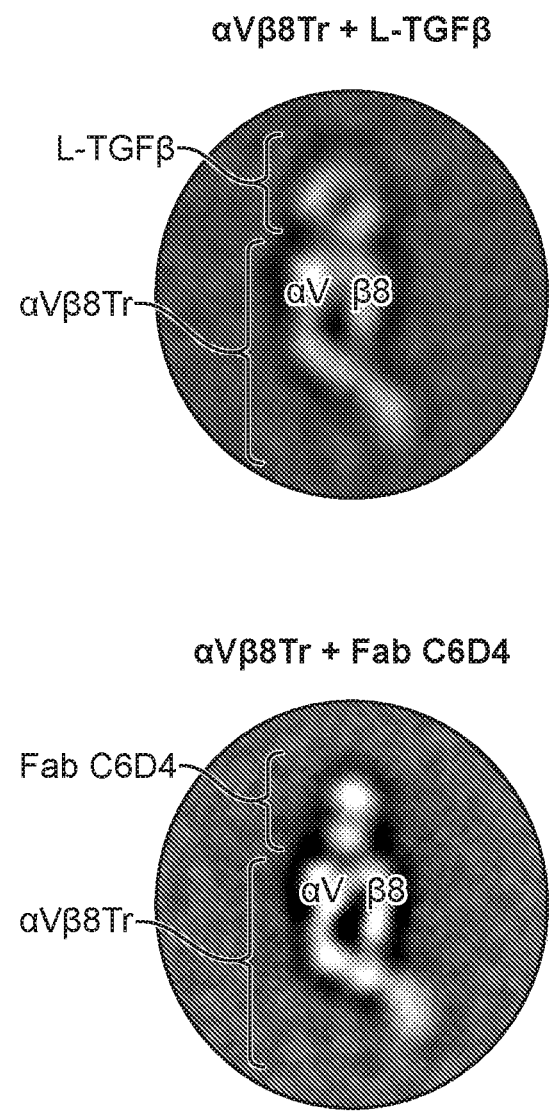

FIG. 12 demonstrates how the C6D4 epitope overlaps directly with the ligand binding pocket of integrin αVβ8, preventing association of integrin αVβ8 with L-TGFβ and thus activation of L-TGFβ. Representative class averages of integrin complexes observed by negative staining electron microscopy.

FIG. 13 illustrates a model of how the complex is generated from the crystal structure of αVβ3 (PDB ID: 3IJE), with the 08 model based on 03 using CHIMERA and MODELLER (Yang et al., *J Struct Biol.* 2012 Sep.; 179(3): 269-78). Refinement of the model to the cryo-electron microscopy map is done in rigid body in COOT (Emsley P, et al., *Acta Crystallographica Section D—Biological Crystallography.* 2010, 66:486-501), followed by complete refinement in PHENIX (Adams et al., *Acta Cryst.* 2010; D66:213-221).

Figure 14:
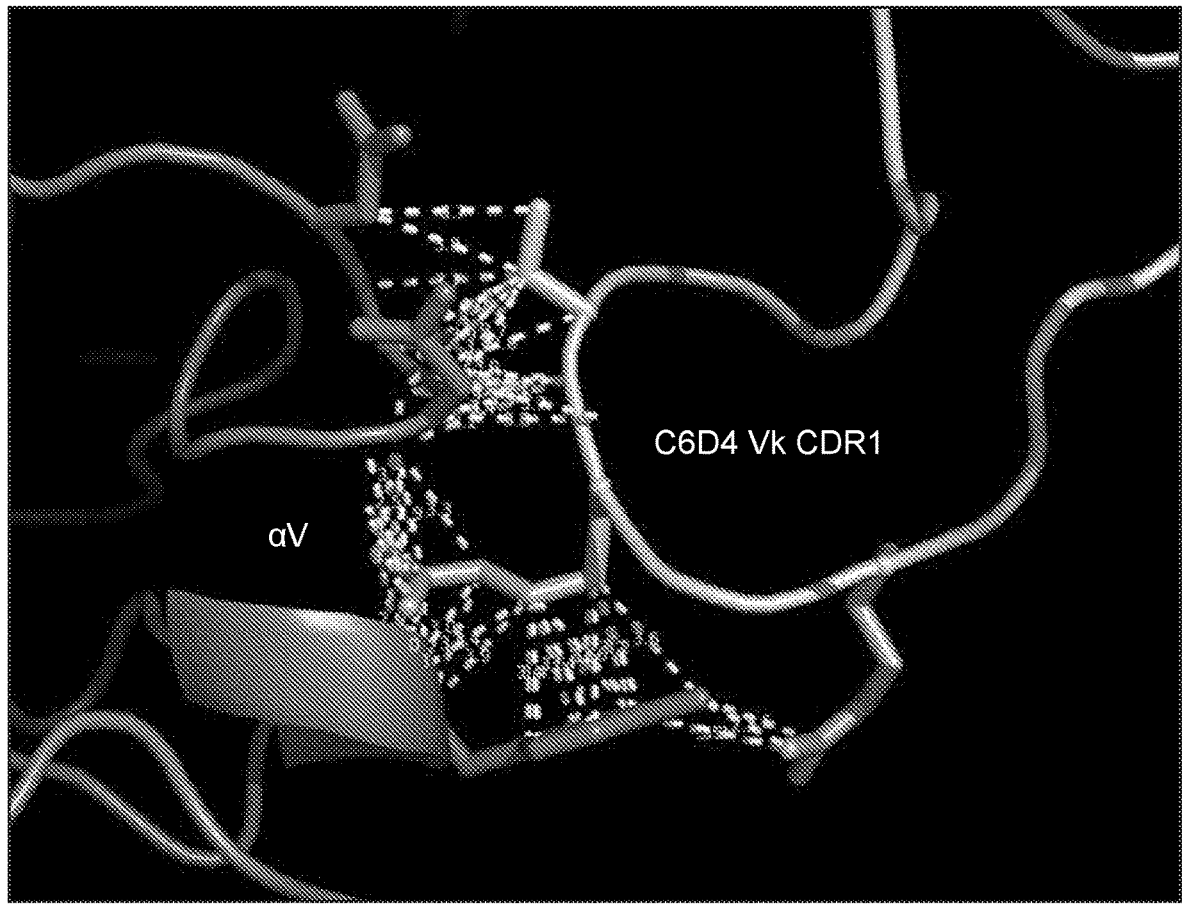

FIG. 14 illustrates interaction of C6D4 Vk CDR1 (SEQ ID NO:616) with integrin αV (SEQ ID NO:622, positions 46-52 and 75-79): Model of the αVβ8/C6D4 Fab complex. Interacting residues are represented as sticks. The dashed lines represent inter-atom distances comprised between 2.5 and 4.0 Å indicating potential interactions.

Figure 15:
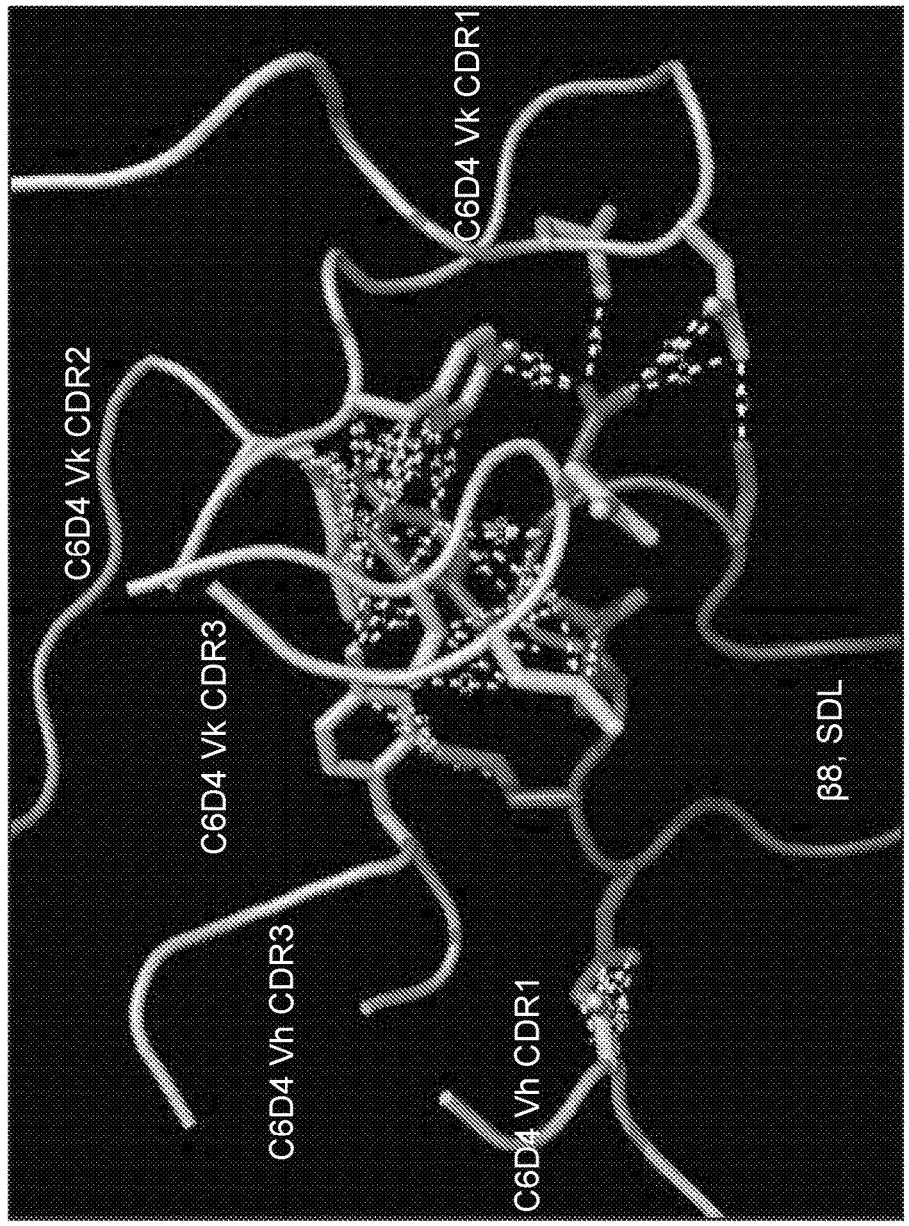

FIG. 15 illustrates interaction of C6D4 with the SDL region of integrin β8: Model of the αVβ8/C6D4 Fab complex. Interacting residues are represented as sticks. The dashed lines represent inter-atom distances comprised between 2.5 and 4.0 Å indicating potential interactions. C6D4 Vh CDR1 (SEQ ID NO:707), C6D4 Vh CDR3 (SEQ ID NO:615), β8, SDL (SEQ ID NO:620), C6D4 Vk CDR1 (SEQ ID NO:616), C6D4 Vk CDR2 (SEQ ID NO:708), and C6D4 Vk CDR3 (SEQ ID NO:618).

Figure 16:
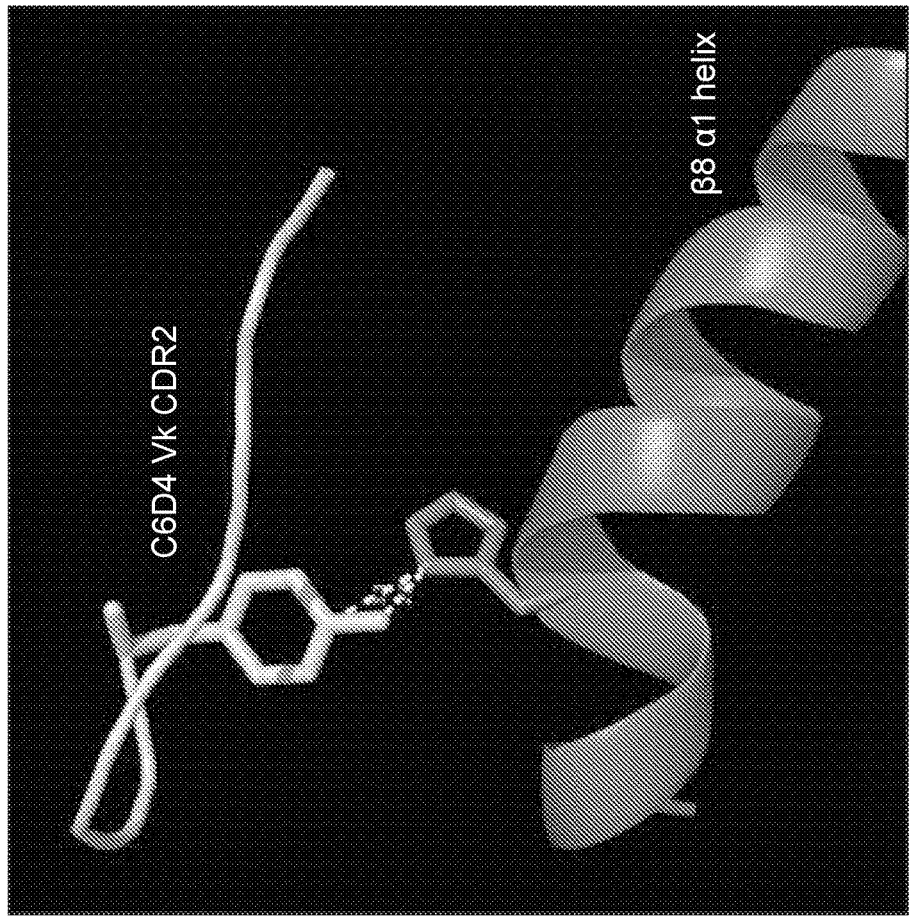

FIG. 16 illustrates interaction of C6D4 Vk CDR2 (SEQ ID NO:617) with the α1 helix of integrin β8 (SEQ ID NO:619): Model of the αVβ8/C6D4 Fab complex. Interacting residues are represented as sticks. The dashed lines represent inter-atom distances comprised between 2.5 and 4.0 Å indicating potential interactions.

Figure 17:
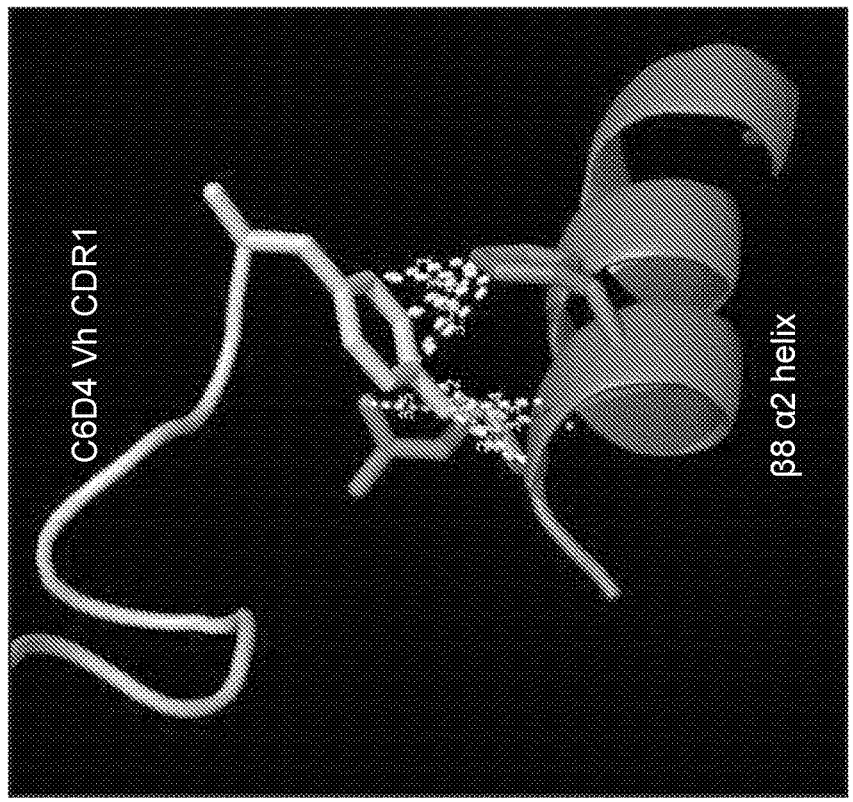

FIG. 17 illustrates interaction of C6D4 Vk CDR1 (SEQ ID NO:613) with the α2 helix of integrin β8 (SEQ ID NO:621): Model of the αVβ8/C6D4 Fab complex. Interacting residues are represented as sticks. The dashed lines represent inter-atom distances comprised between 2.5 and 4.0 Å indicating potential interactions.

Figure 18:
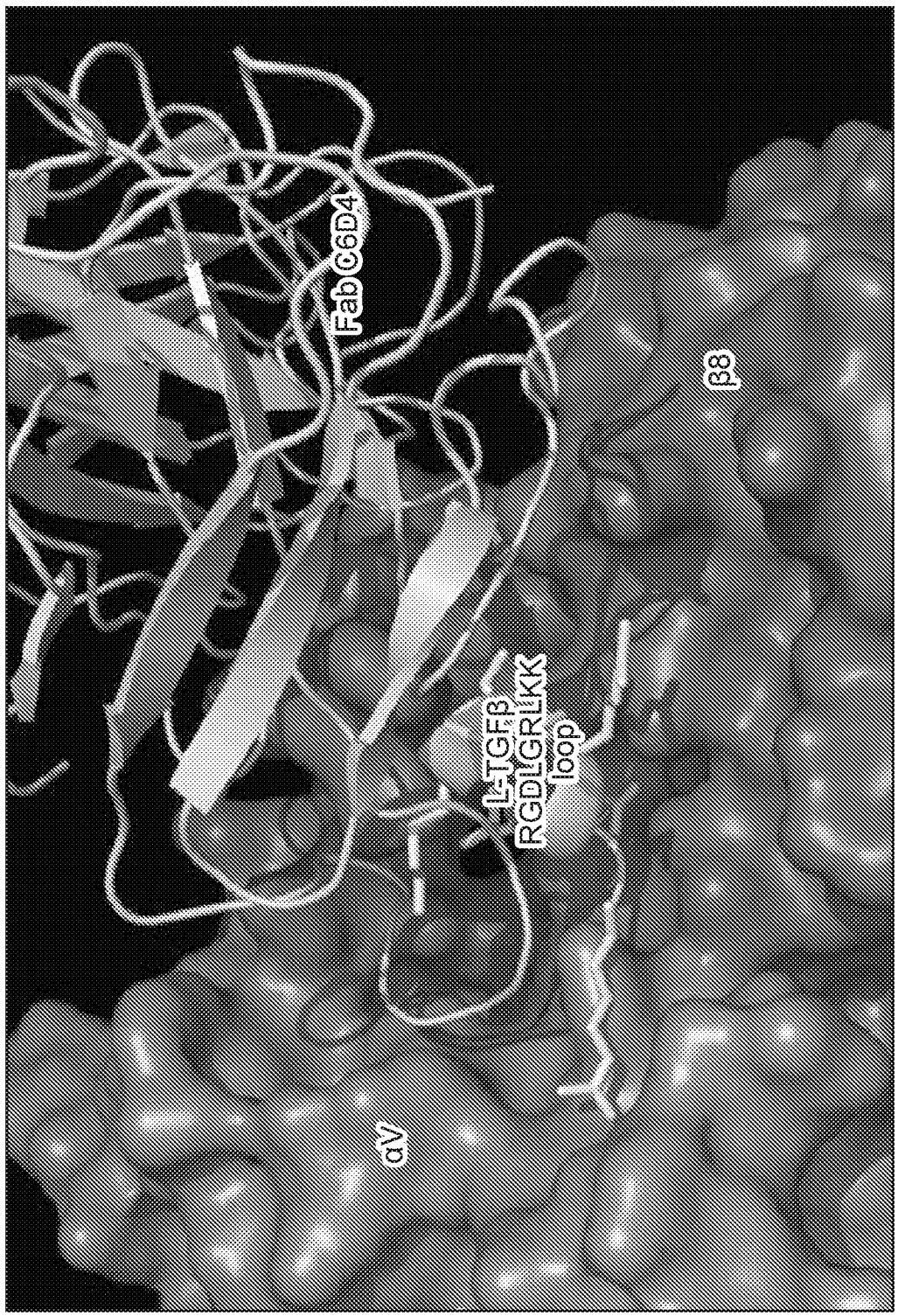

FIG. 18 illustrates that C6D4 blocks the access of L-TGFβ to the ligand binding pocket of integrin β8 and C6D4 bound to integrin αVβ8 directly clashes with the position of the RGDLGRLKK loop of L-TGFβ (SEQ ID NO:712). The surface of the αVβ8/C6D4 Fab complex is shown. The surface is αVβ8, while the cartoon is C6D4. In sticks are superimposed the residues RGDLGRLKK (SEQ ID NO:712) from the integrin binding loop of L-TGFβ as found when bound to integrin αVβ6 (PDB 4UM9) ((4) Structural determinants of integrin 1-subunit specificity for latent TGF-β. Dong X, et al. *Nat. Struct. Mol. Biol.* 2014 Dec.; 21(12):1091-6).

Figure 19:
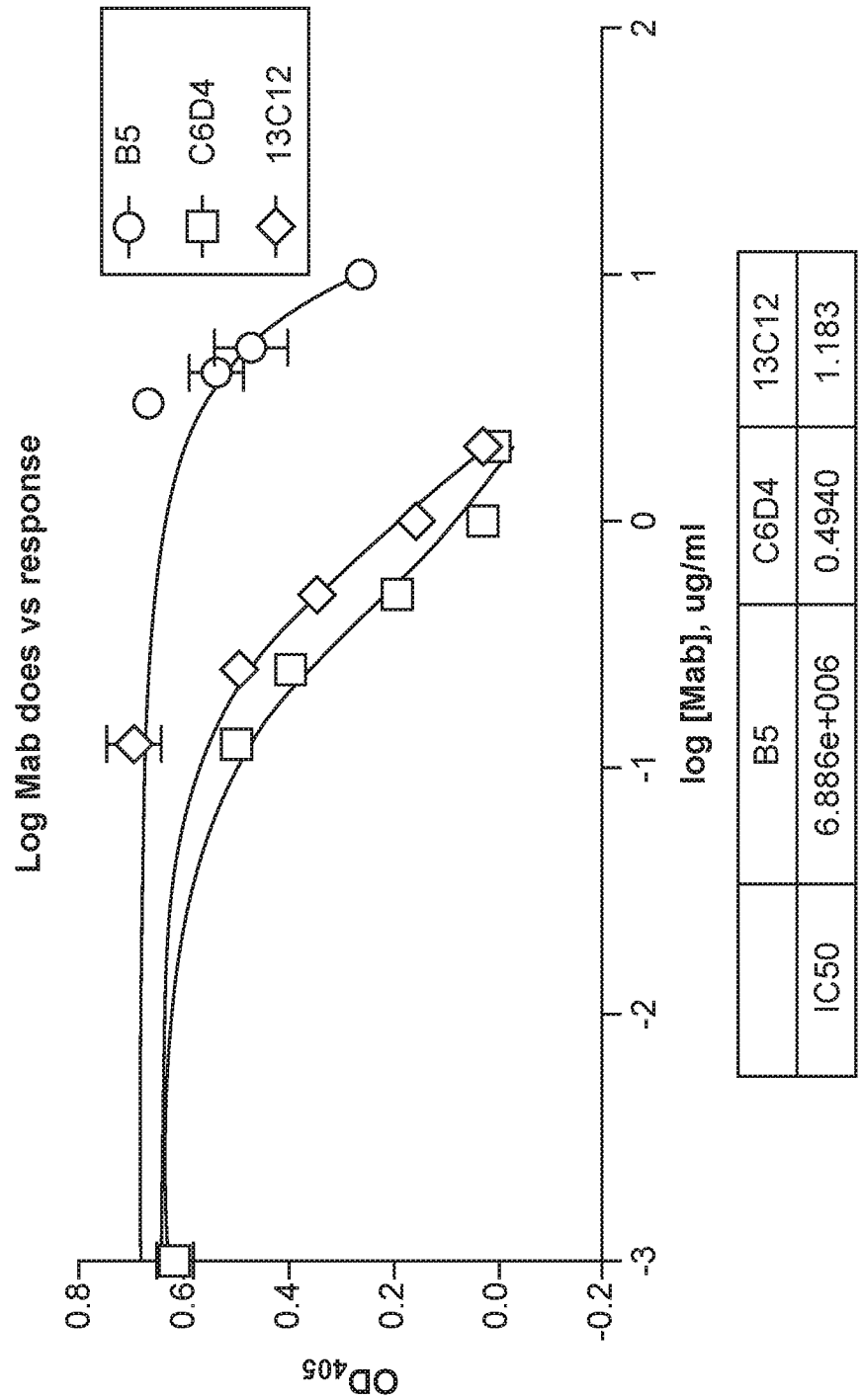

FIG. 19 shows that C6D4 is a potent inhibitor of binding of secreted αVβ8 to L-TGF-b3 peptide.

Figure 20:
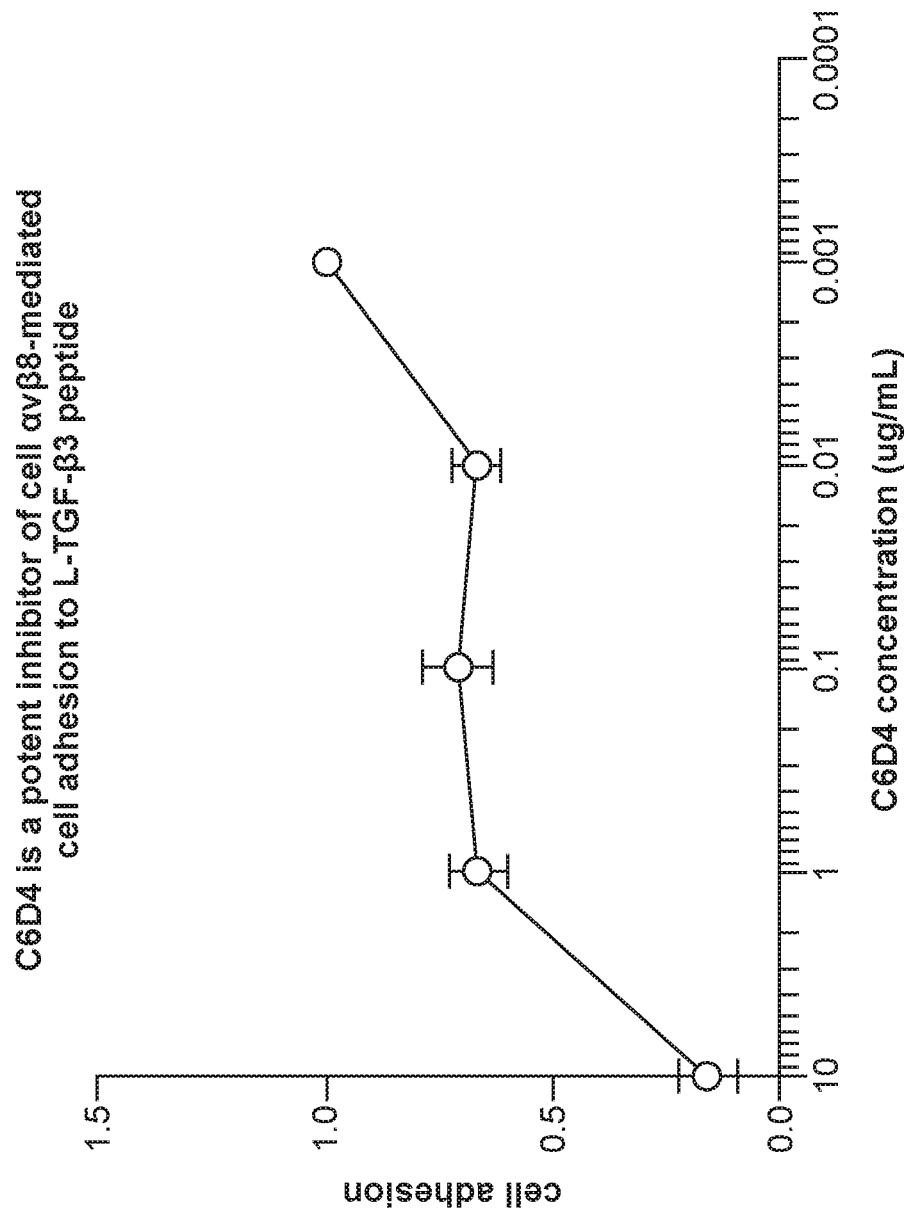
Figure 21A:
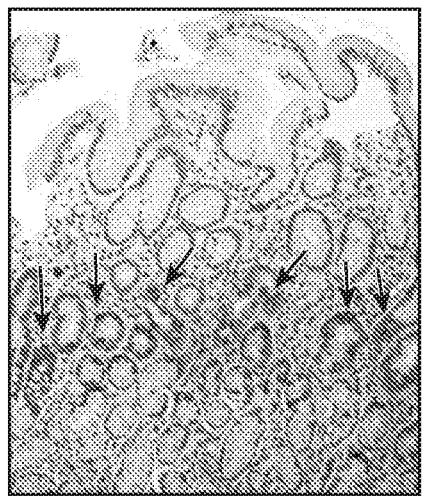
Figure 21B:
Figure 21C:
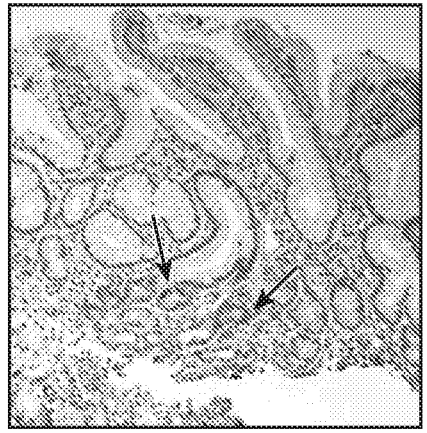
Figure 21D:
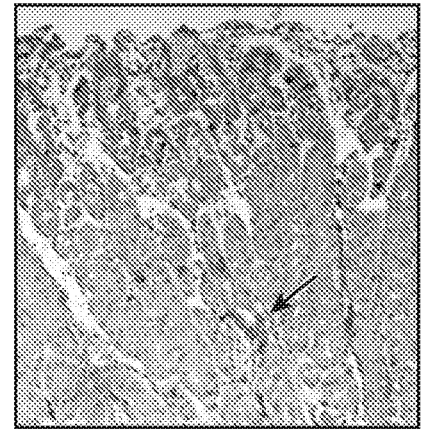

FIG. 20 shows that C6D4 is a potent inhibitor of cell αVβ8-mediated cell adhesion to L-TGF-b3 peptide.

FIG. 21 shows immunodetection of the integrin b8 subunit in formalin fixed paraffin embedded sections from patient infected with *H. Pylori* (A,B) or showing normal histology (C,D). The sections were stained with clone F9 in rabbit IgG format and detected using TSA signal amplification (Perkin Elmer). The brown precipitate indicates positive staining and the nuclei are counterstained with hematoxylin. The arrows indicate examples of positive crypts with stained crypt epithelial cells. The results show that the b8 integrin subunit is increased in expression in the stomachs of patients with *H. Pylori*.

Figure 22:
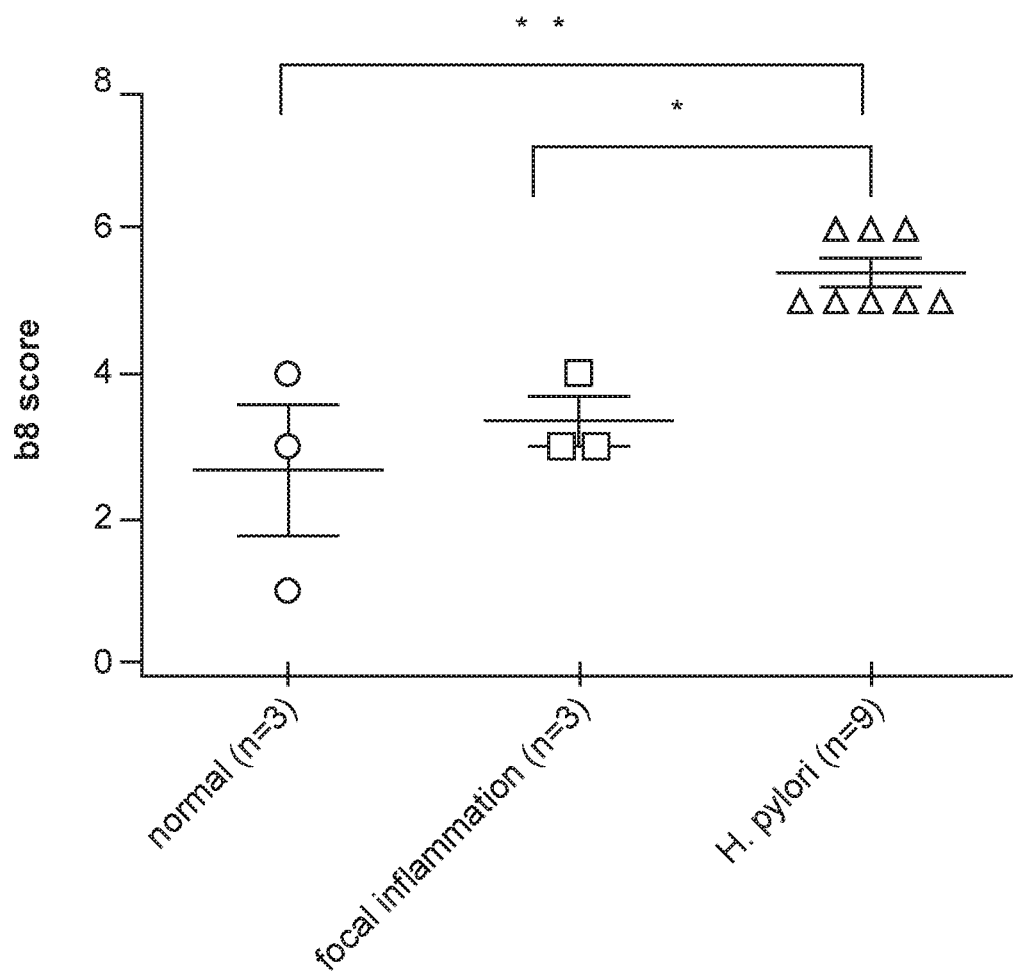
Figure 23:
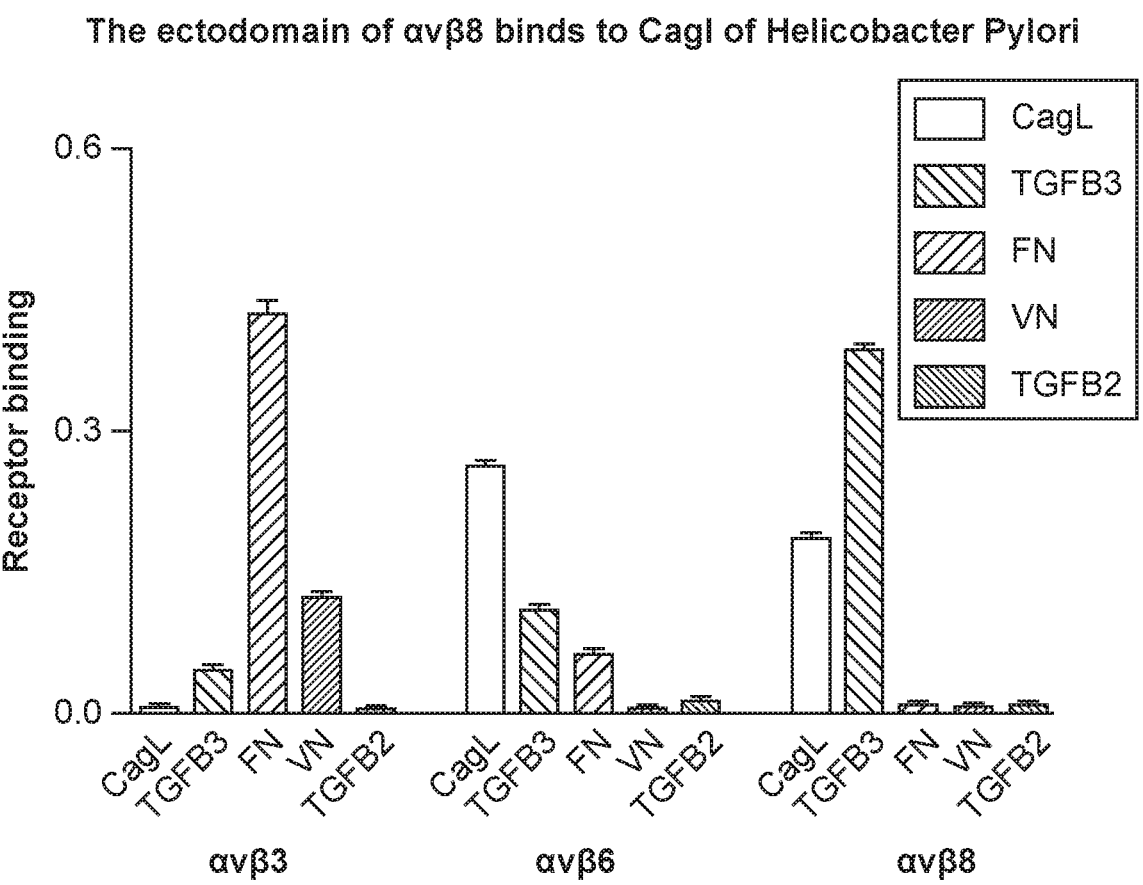

FIG. 22 shows quantification of Immunodetection of the integrin b8 subunit in formalin fixed paraffin embedded sections from patient infected with *H. Pylori*, showing normal histology or mild chronic inflammation. The sections were stained with clone F9 in rabbit IgG format and detected using TSA signal amplification (Perkin Elmer). The following scoring system was devised to capture the crypto-epithelial staining, 0=no stain, 1=just contrast+, 2=scattered, 3=diffuse and stromal staining, 0=no stain, 1=just contrast+, 2=scattered, 3=diffuse. Shown is a combined score and the n is shown. ANOVA with Sidak's multiple comparisons test. $**p<0.01$, $*p<0.05$ FIG. 23 shows binding assay of alkaline phosphatase (AP) αvβ3, αvβ6 and αvβ8 fusion proteins to CagL, the MAP RGD peptide derived from the TGFB3 sequence DDHGRGDLGRLK (SEQ ID NO:713), Fibronectin, Vitronectin or a MAP peptide derived from the TGFB2 sequence that corresponds to the RGD containing sequence of TGFB1 and TGFB3. All proteins are coated on ELISA plates at 5 ug/ml and input of AP receptors are normalized to AP activity. Results shown represent signal above BSA coated wells. The results show that αvβ8 (and αvβ6) binds to CagL as well as to TGFb3 peptide, whereas αvβ3 binds to FN and VN, poorly to TGFB3 and not at all to CagL. αvβ3 and αvβ8 show no binding and αvβ6 shows very weak binding to the control TGFb2 peptide. Shown are S.E.M.

Figure 24:
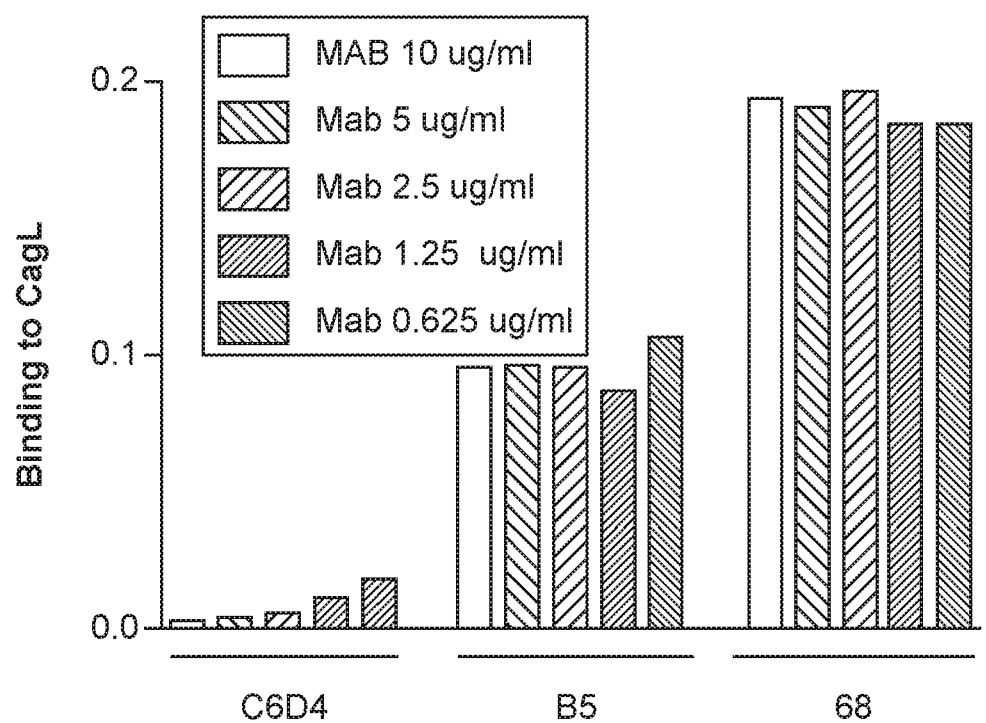

FIG. 24 shows binding assay of alkaline phosphatase (AP) αvβ8 fusion protein to CagL in the presence of C6D4, an allosteric inhibitor, B5, or a non-blocking antibody to the same epitope as B5, clone 68 which serves as a negative control. CagL is coated on ELISA plates at 5 ug/ml. Results shown represent signal above BSA coated wells. The results show that αvβ8 binding to CagL is completely inhibited by C6D4 and are partially inhibited by B5.

Figure 25:
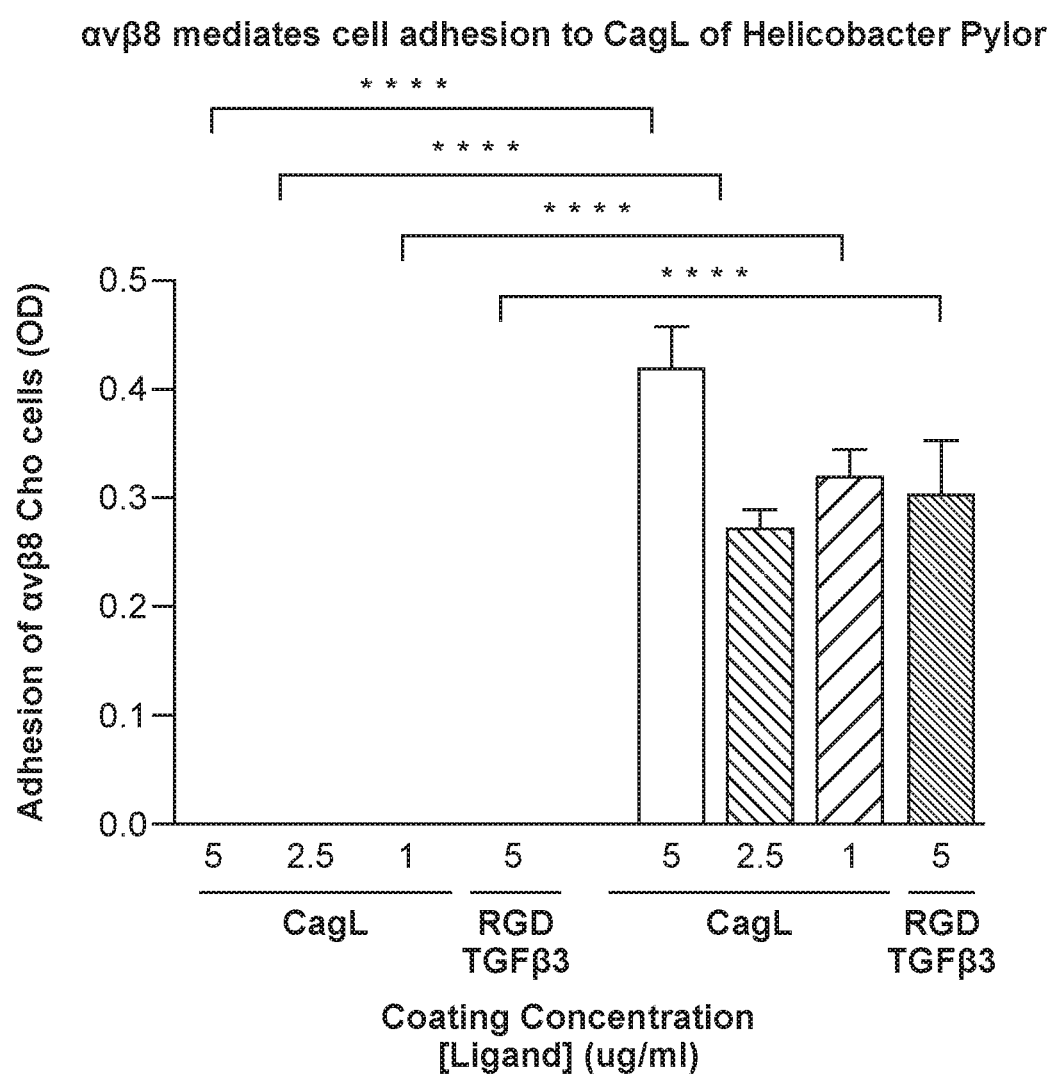
Figure 26:
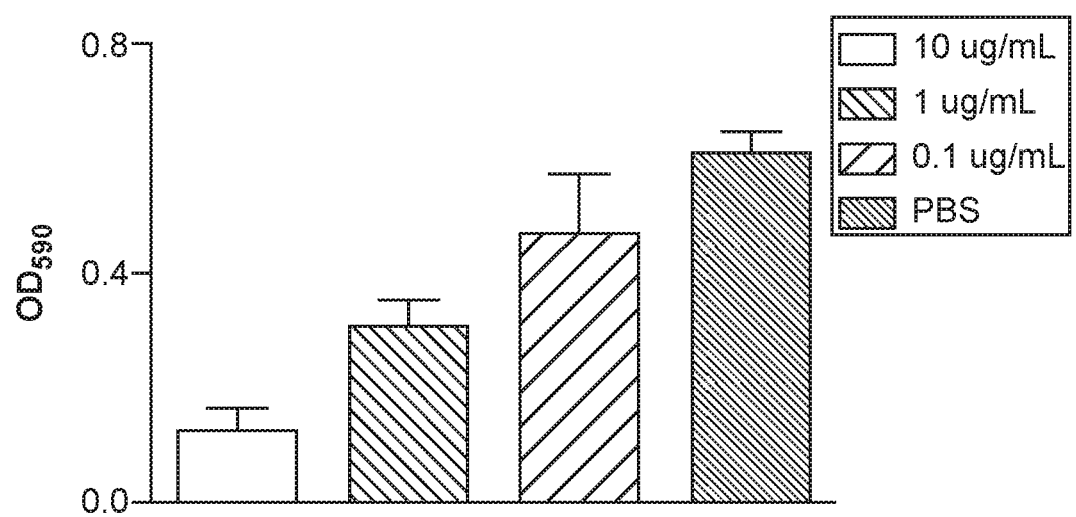

FIG. 25 shows adhesion assay of Cho Lec cells stably expressing human ITGAV and ITGB8 to recombinant CagL protein at the indicated concentrations (gift of Eric. Sundberg, University of Maryland, Md.). Binding is compared to wells coated with a multiple antigen presenting peptide containing the RGD peptide derived from the TGFB3 sequence DDHGRGDLGRLK (SEQ ID NO:713), which corresponds to as 257-268 of human TGF-b3 (NP_003230). $50 \times 10^3$ cells were allowed to attach to the wells for 30 min at RT. Unbound cells were washed off with PBS. Results were presented as stained cells detected after staining with crystal violet (OD590). Results shown represent signal above the nominal binding of mock transfected Cho Lec cells to CagL or TGFB3 peptide coated wells (5 ug·ml). The results show that αvβ8 mediates cell adhesion to CagL as well as to TGFb3 peptide. Shown are S.E.M. Significance was determined by ANOVA and Sidak's multiple comparison test. $****=p<0.00001$ FIG. 26 shows adhesion assay of Cho Lec cells stably expressing human ITGAV and ITGB8 to the TGF-b3 RGD MAP peptide (DDHGRGDLGRLK (SEQ ID NO:713)) (coating concentration 5 ug/ml). 50×10^3 cells were preincubated with cagL at the indicated concentrations of CagL vs PBS control for 15 min at RT and then the cells allowed to attach to the wells for 30 min at RT. Unbound cells were washed off with PBS. Results were presented as stained cells detected after staining with crystal violet (OD590). Results shown represent signal above the nominal binding of mock transfected Cho Lec cells to TGFB3 peptide coated wells (5 ug/ml). The results show that αvβ8 mediates cell adhesion to CagL is RGD dependent. Shown are S.E.M. N=3

Figure 27:
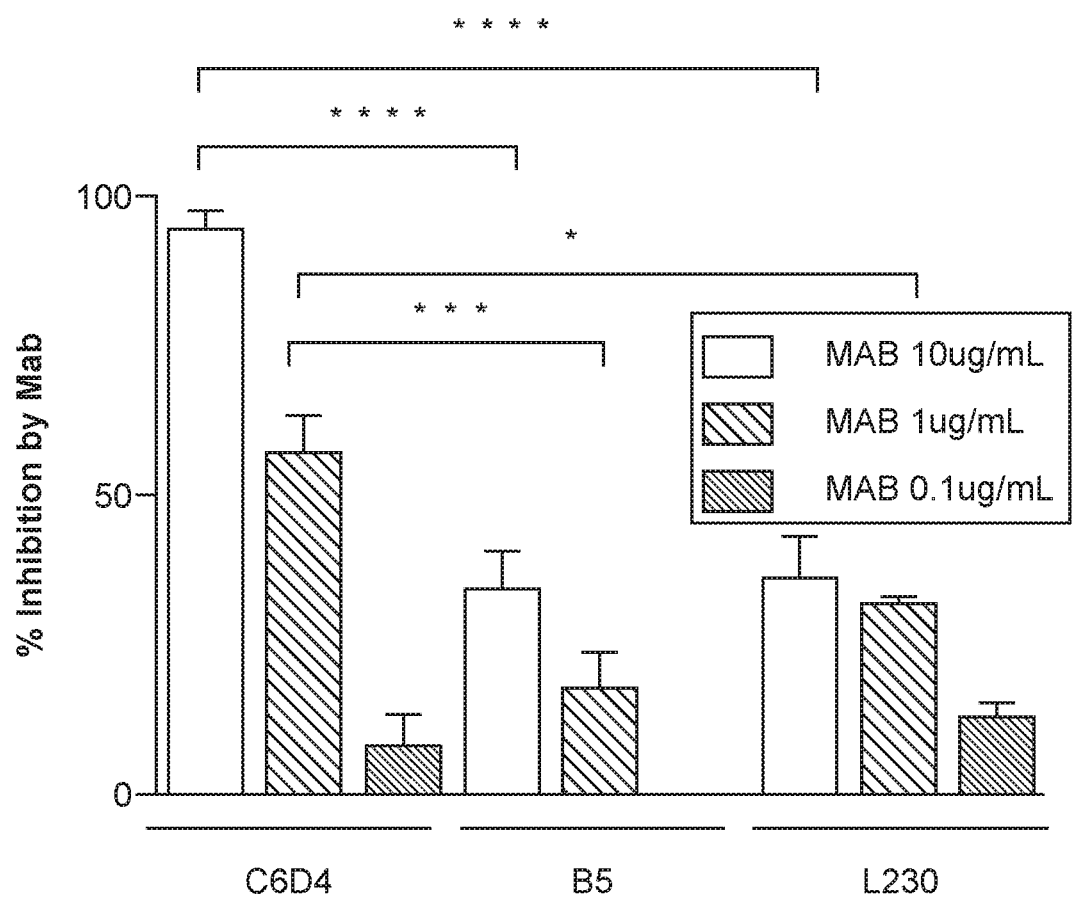

FIG. 27 shows adhesion assay of modified Chinese Hamster Ovary Cells (Cho Lec) cells stably expressing human ITGAV and ITGB8 to recombinant CagL protein at 5 ug/ml coating concentration, 50×10^3 cells were mixed with the Mabs at the indicated concentrations and allowed to attach to the wells for 30 min at RT. B5 is a previously described allosteric inhibitor of αvβ8-binding to TGF-B and L230 is a previously described anti-av blocking antibody. Unbound cells were washed off with PBS. Results are presented as stained cells detected after staining with crystal violet (OD590). Results shown represent % inhibition relative to the control binding defined by binding in presence of an isotype control antibody (anti-SV5) at the same concentration. Shown are S.E.M. Significance was determined by ANOVA and Sidak's multiple comparison test. **=p<0.00001, *p<0.001, *<0.05. The results show that C6D4 more efficiently blocks αvβ8 mediates cell adhesion to CagL than B5 or L230.

Figure 28:
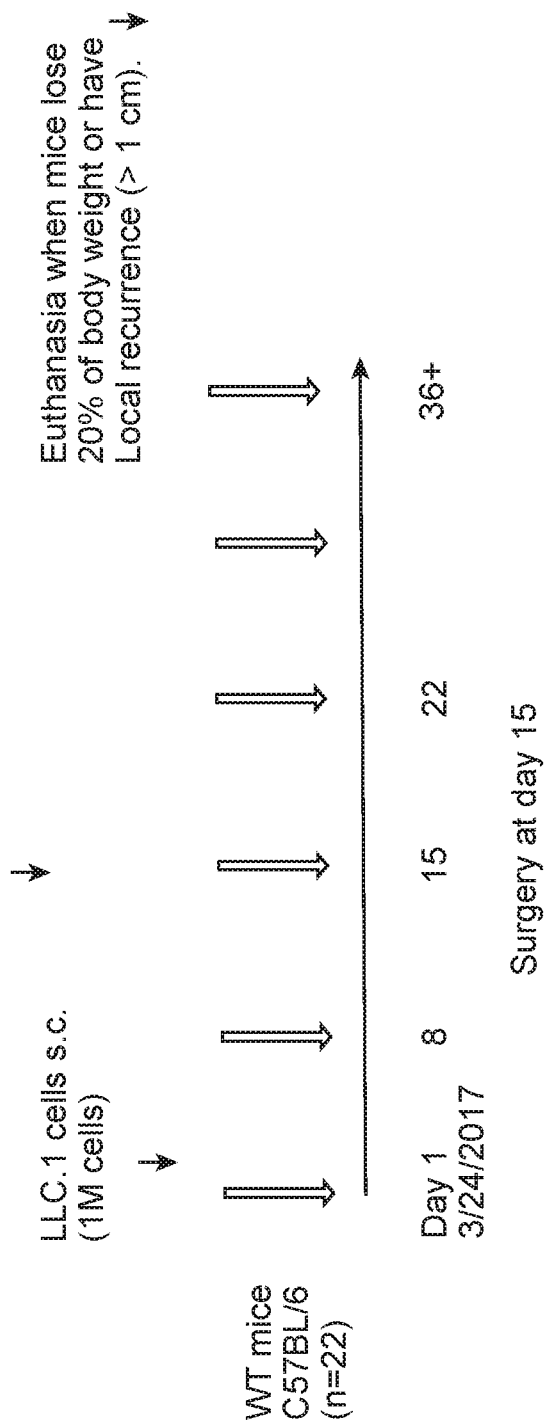

FIG. 28 shows a mouse model for evaluating lung metastasis using the LLC tumor cell line which does not express integrins αvβ6 or αvβ8. The LLC tumor cell line is syngenic to the host C57B/6 strain. The LLC. 1 cell line has been passed though mice one time and regrown from lung metastasis. After two weeks, subcutaneously injected tumor (1×10^6) LLC.1 cells form large tumor nodules (~1 cm). The tumors are removed surgically and when animals lose 20% body weight they are euthanized.

Figure 29A:
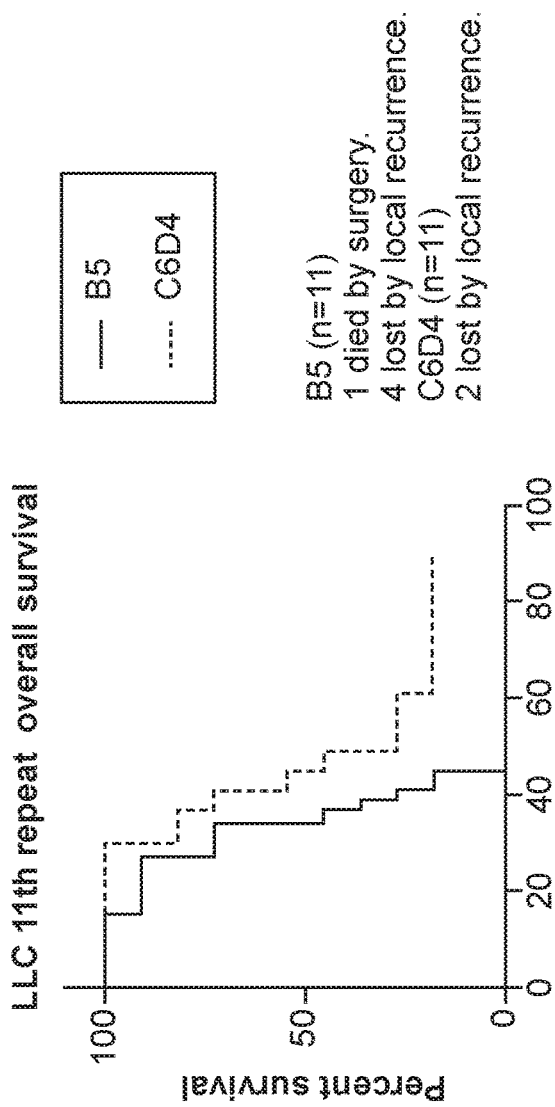
Figure 29B:
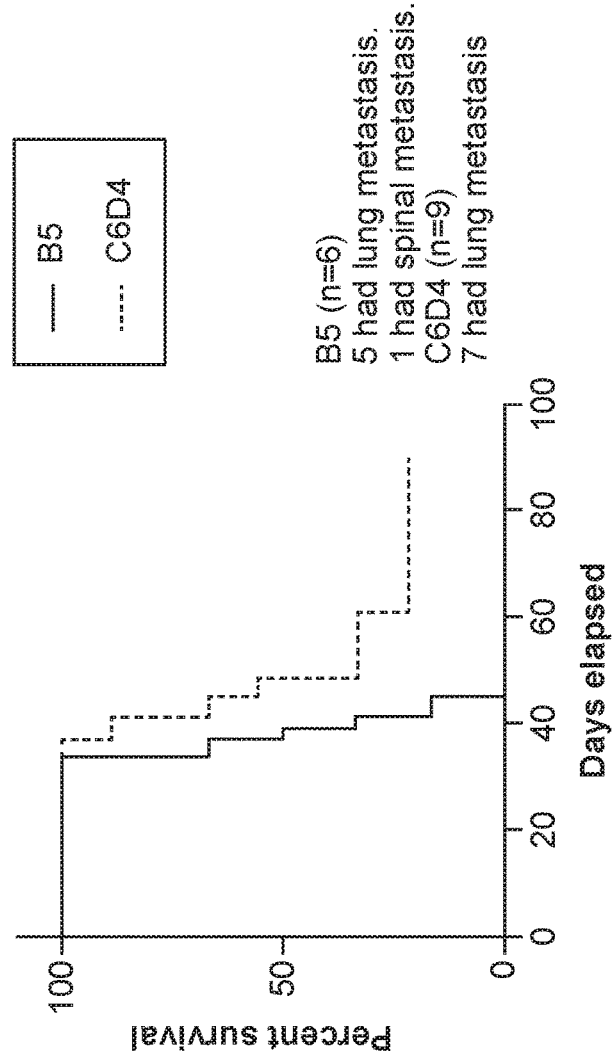
Figure 30A:
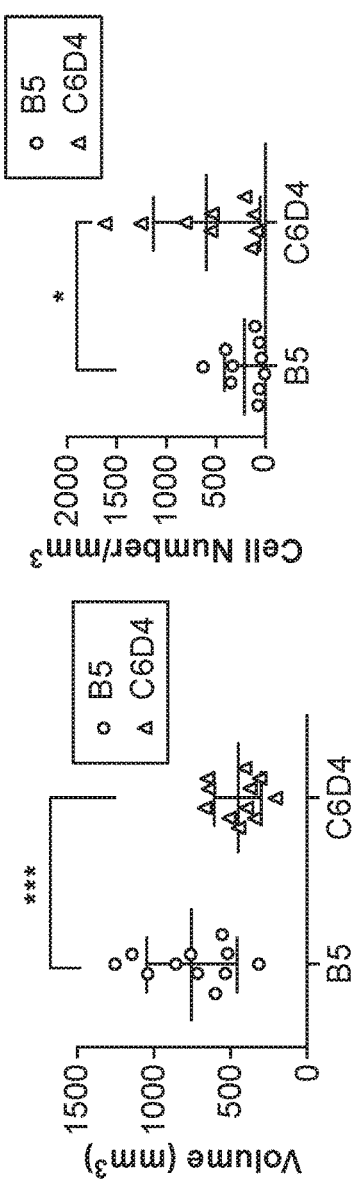
Figure 30B:
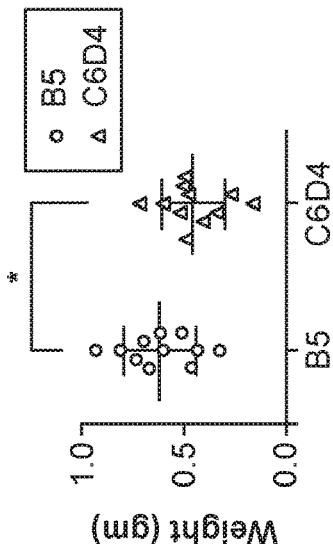
Figure 30C:
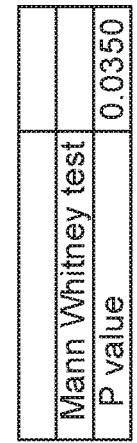
Figures 30D, 30E, 30F:
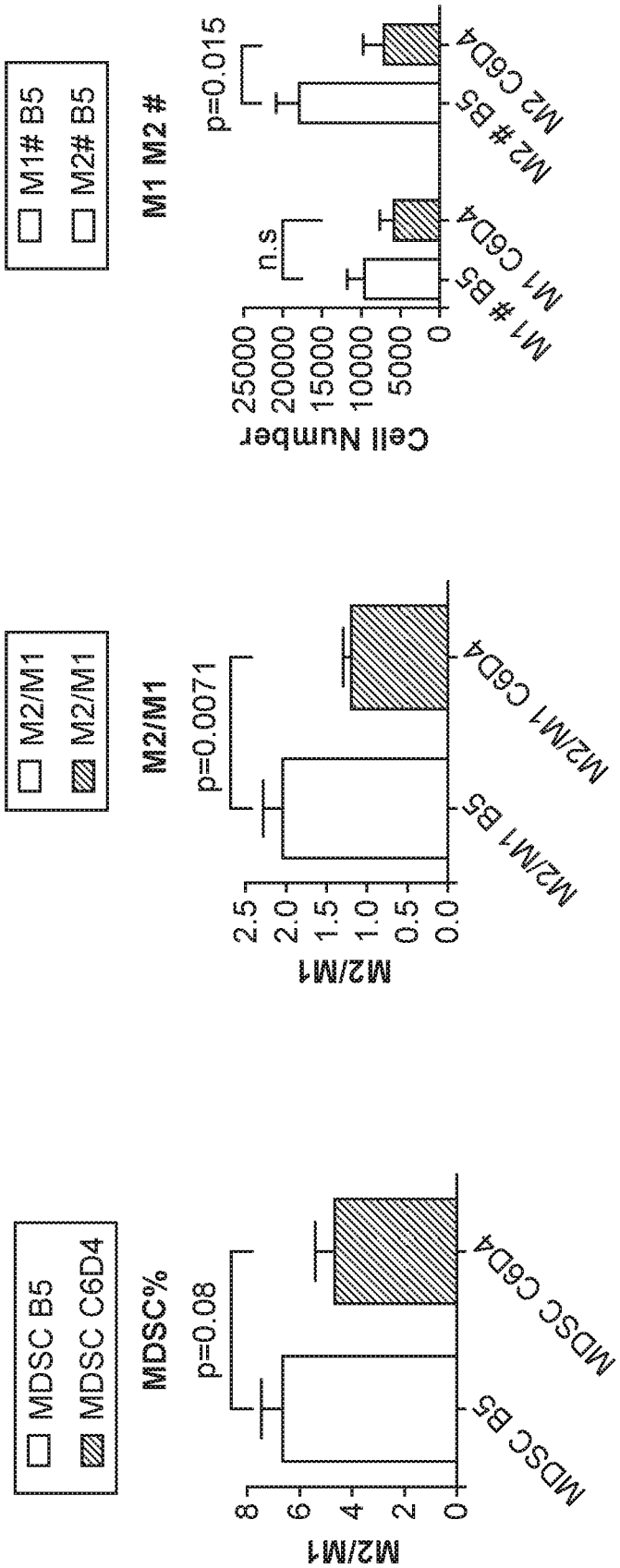

FIGS. 29A and 29B show the effect of C6D4 on mouse survival using the LLC tumor cell line model set forth in FIG. 28. Survival curves (FIG. 29A) represent mice euthanized for reasons of local recurrence or weight loss. FIG. 29B shows the survival curve when animals removed for local recurrence are excluded. At autopsy, the animals with 20% weight loss all have metastatic implants in their lungs. Here, C6D4 antibodies have been injected for up to 90 days in surviving animals. This experiment was performed eleven times, each time providing similar results (data not shown). Additionally, post-mortem examination did not reveal any abnormal inflammatory response in the tissues examined.

FIGS. 30A-F show the effect of CD64 on tumor growth and tumor immune response using the LLC tumor cell line model set forth in FIG. 28. Here, resected LLC. 1 primary tumors in mice that received two injections of isotype control (B5, which only reacts with human and not mouse b8) or C6D4 (which cross reacts with mouse and human), the primary tumor weights are recorded, dimensions are measured, and tumors are enzymatically disaggregated and immune cells isolated and counted. Flow cytometry was performed on the tumor infiltrating immune cells, and the tumor infiltrating immune cells are separated from tumor cells using Percoll gradient centrifugation. Shown here is one of three experiments each providing similar results. In each group n is equal to or greater than 10.

Figure 31:
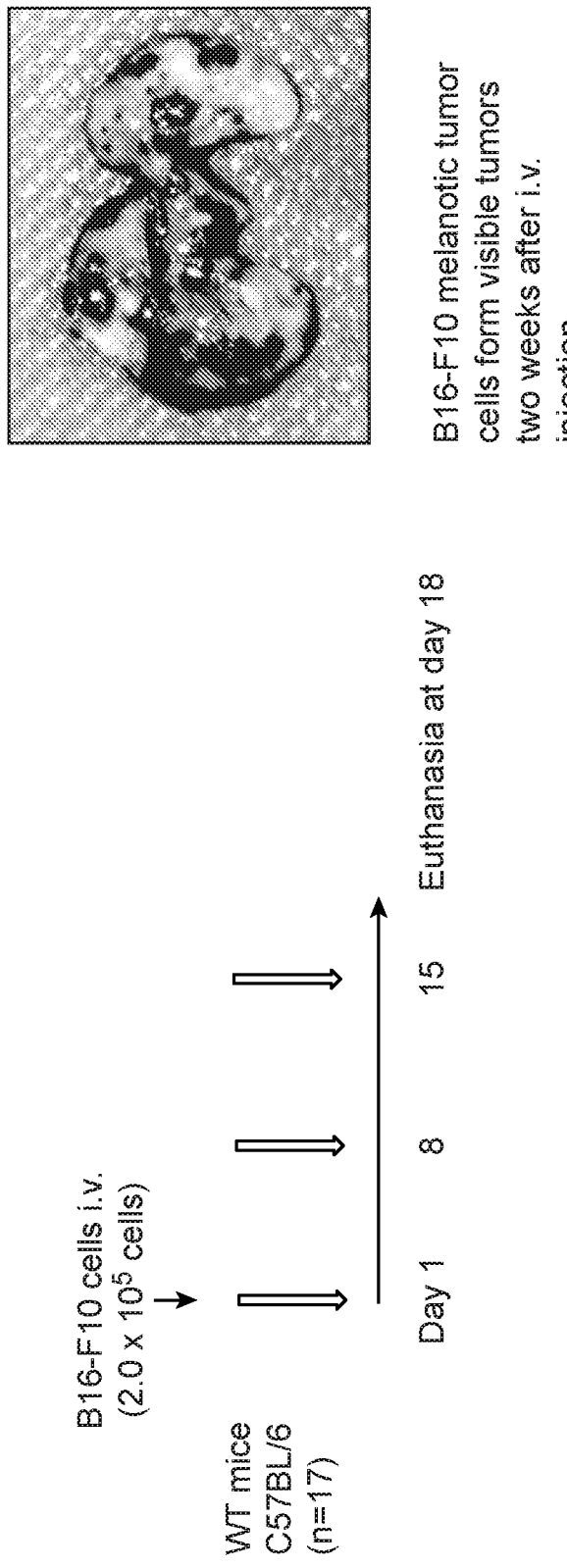

FIG. 31 shows a mouse model for evaluating metastatic disease using B16-F10 tumor cells. The B16-F10 highly metastatic tumor cell line is syngenic to the host C57B/6 strain. This line does not express integrins αvβ6 or αvβ8. The B16-F0 was transfected with murine itgb8 and after selection and sorting expresses surface αvβ8 at high levels. When injected intravenously via the tail vein, visible lung metastases appear by 14 days.

FIGS. 32A-H are lung adenocarcinoma samples stained with anti-b8 (FIGS. 32E-H) or anti-PD-L1 (E1L3N, Cell signaling) FIG. 32A-D. Here, it was observed that beta 8 expression inversely correlated with PD-L1 expression.

Figures 33A, 33B:
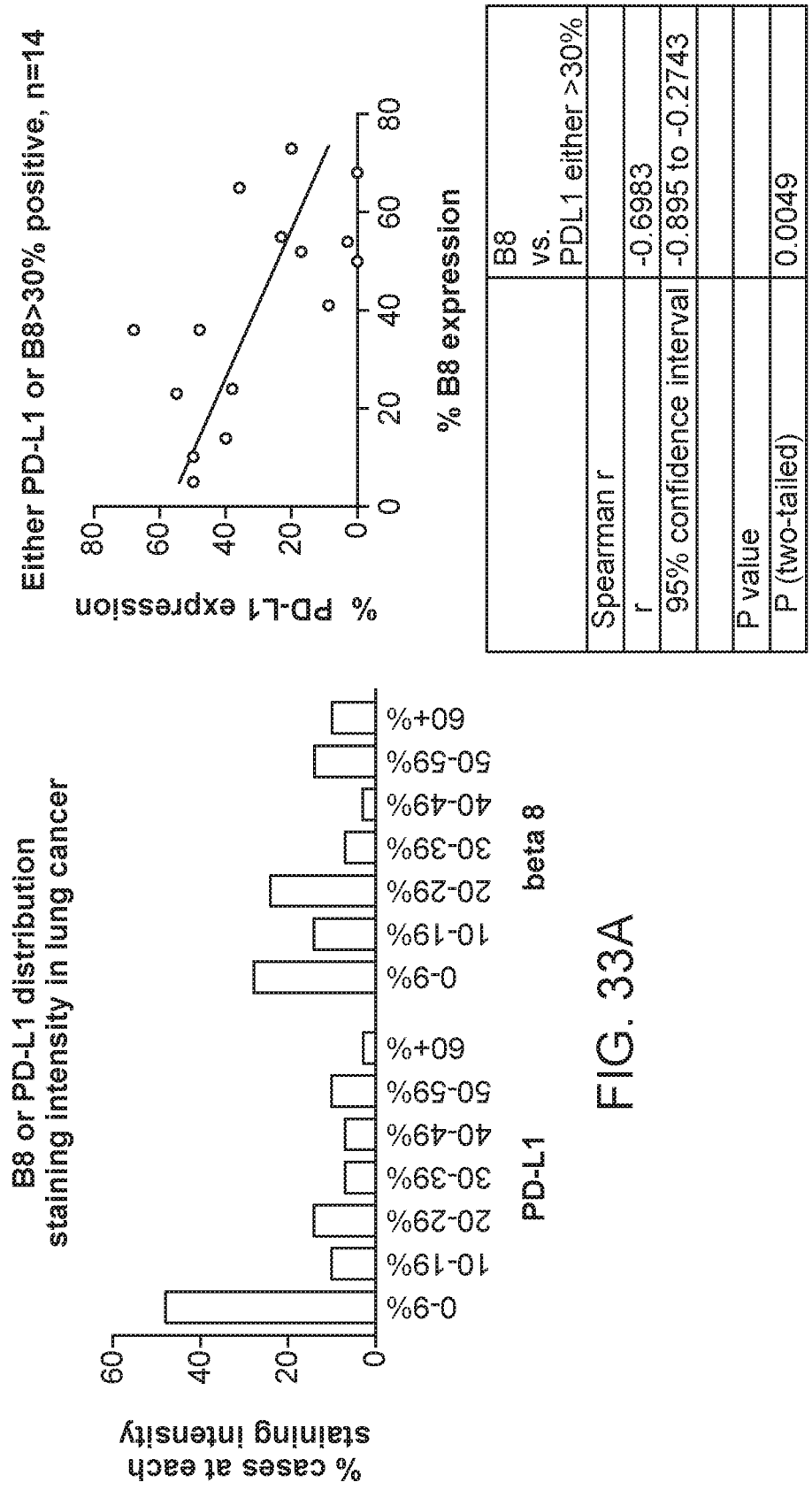
Figures 35A, 35B:
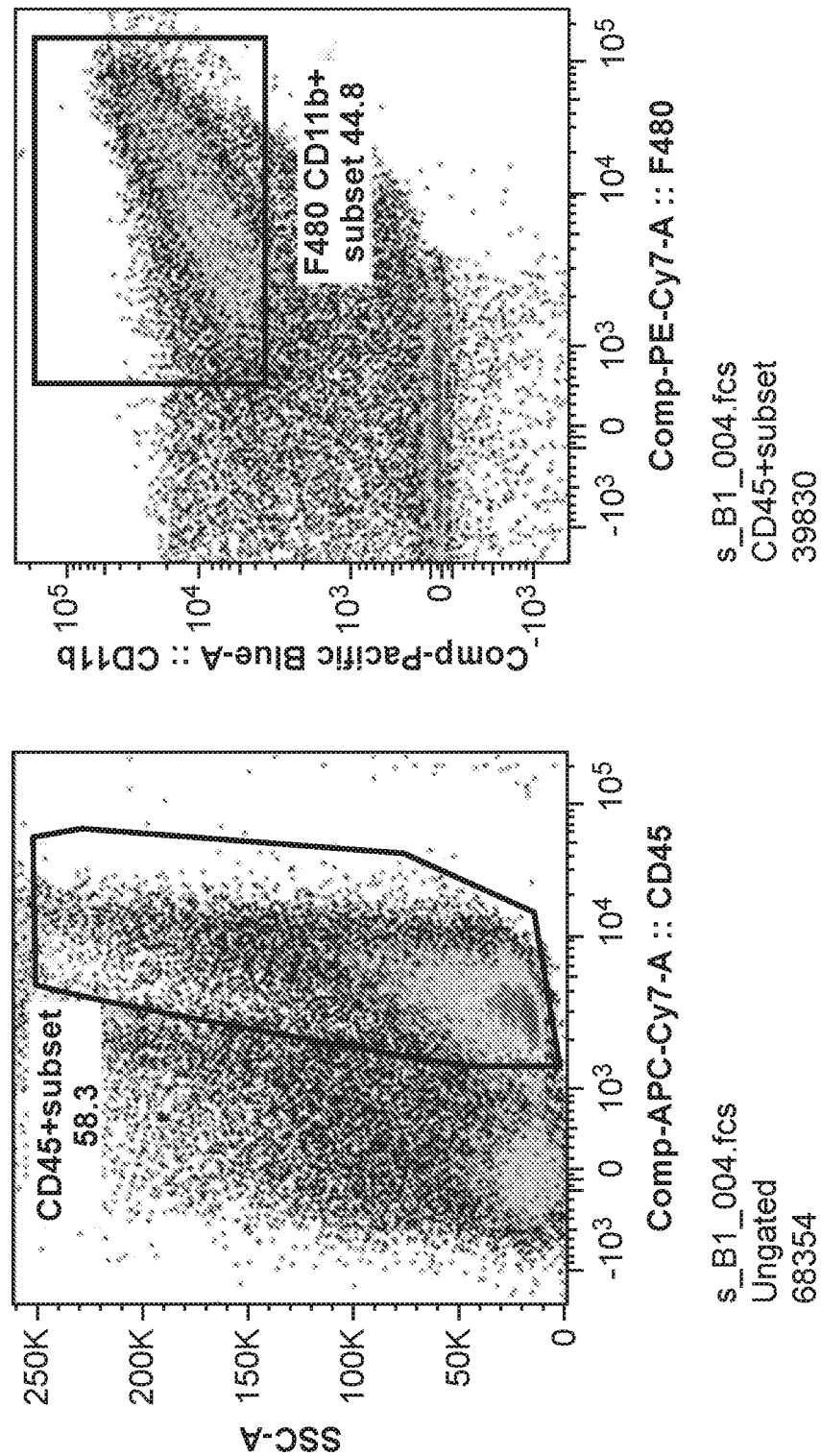
Figure 35C:
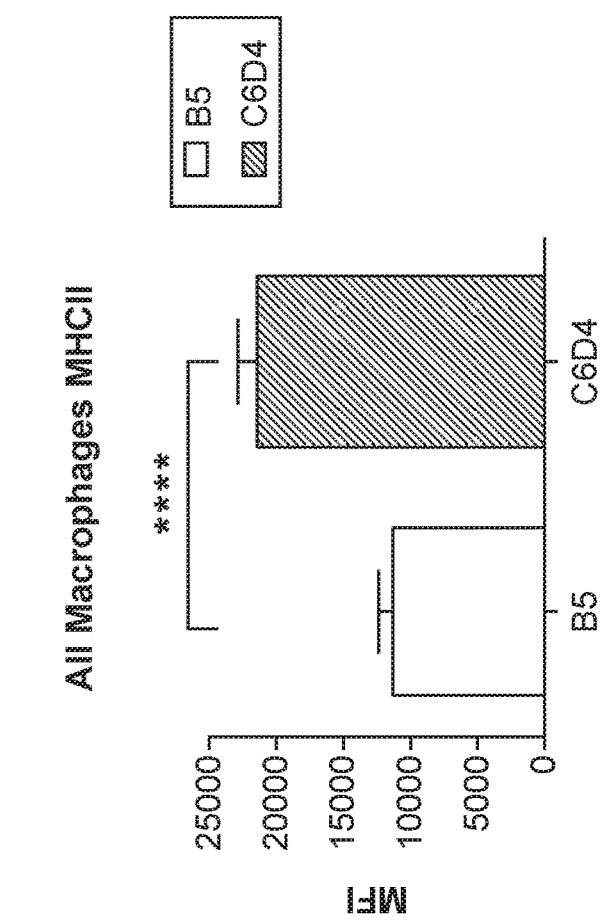
Figure 35D:
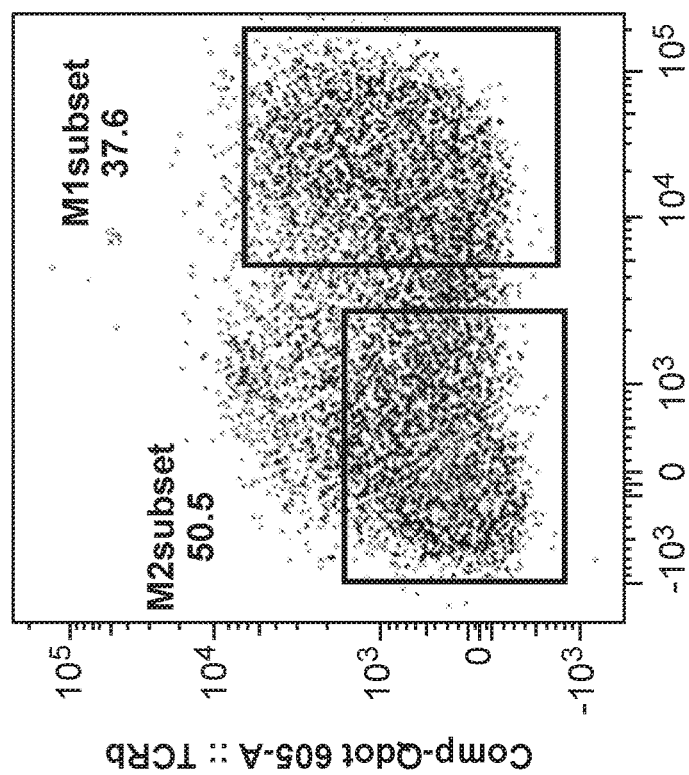
Figures 35E, 35F:
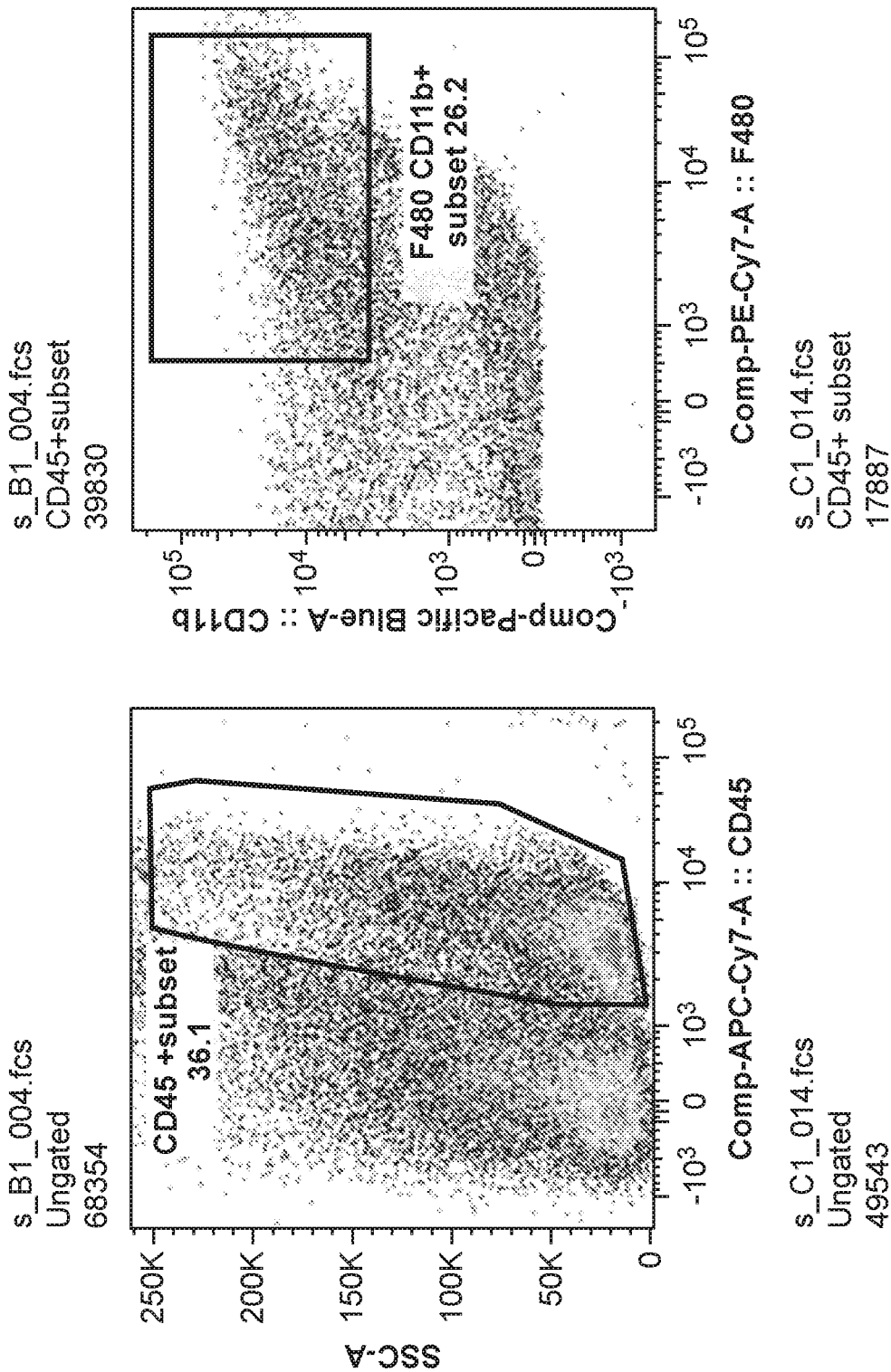
Figure 35H:
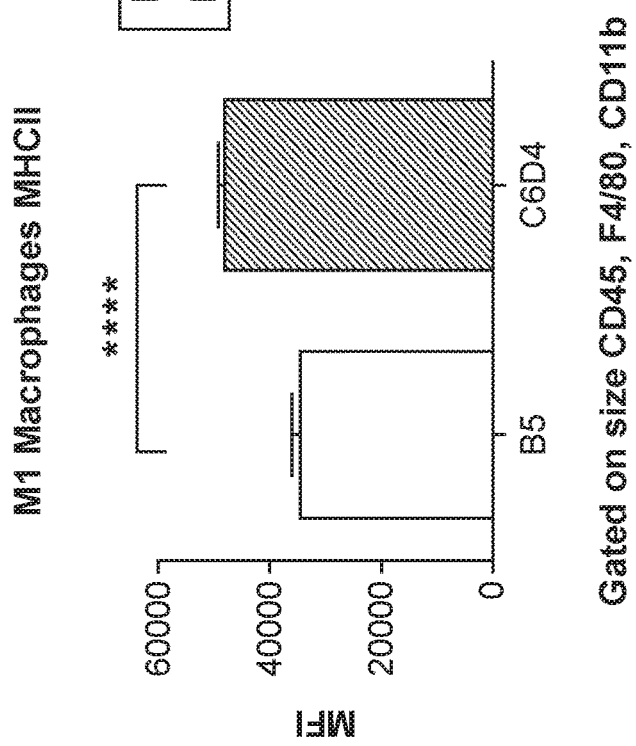
Figure 35G:
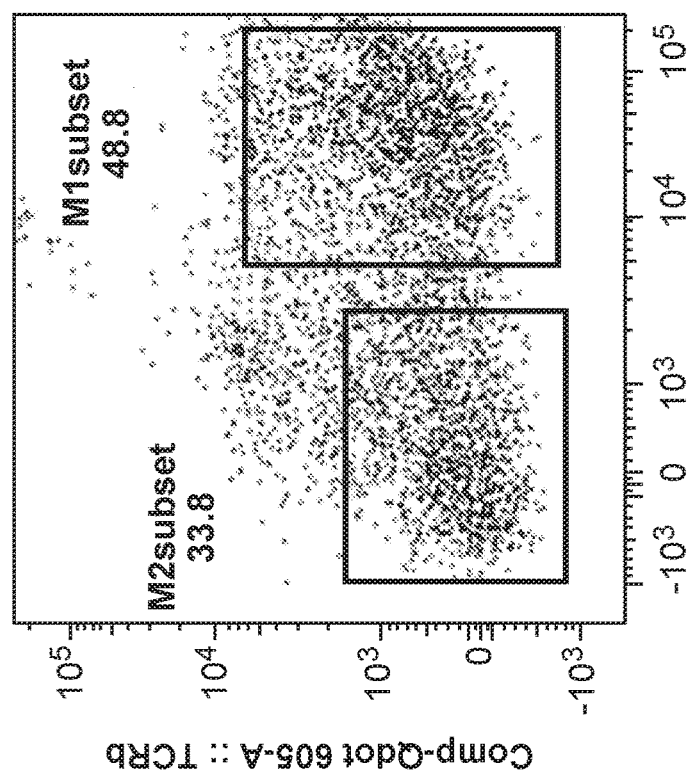
Figures 36A, 36B:
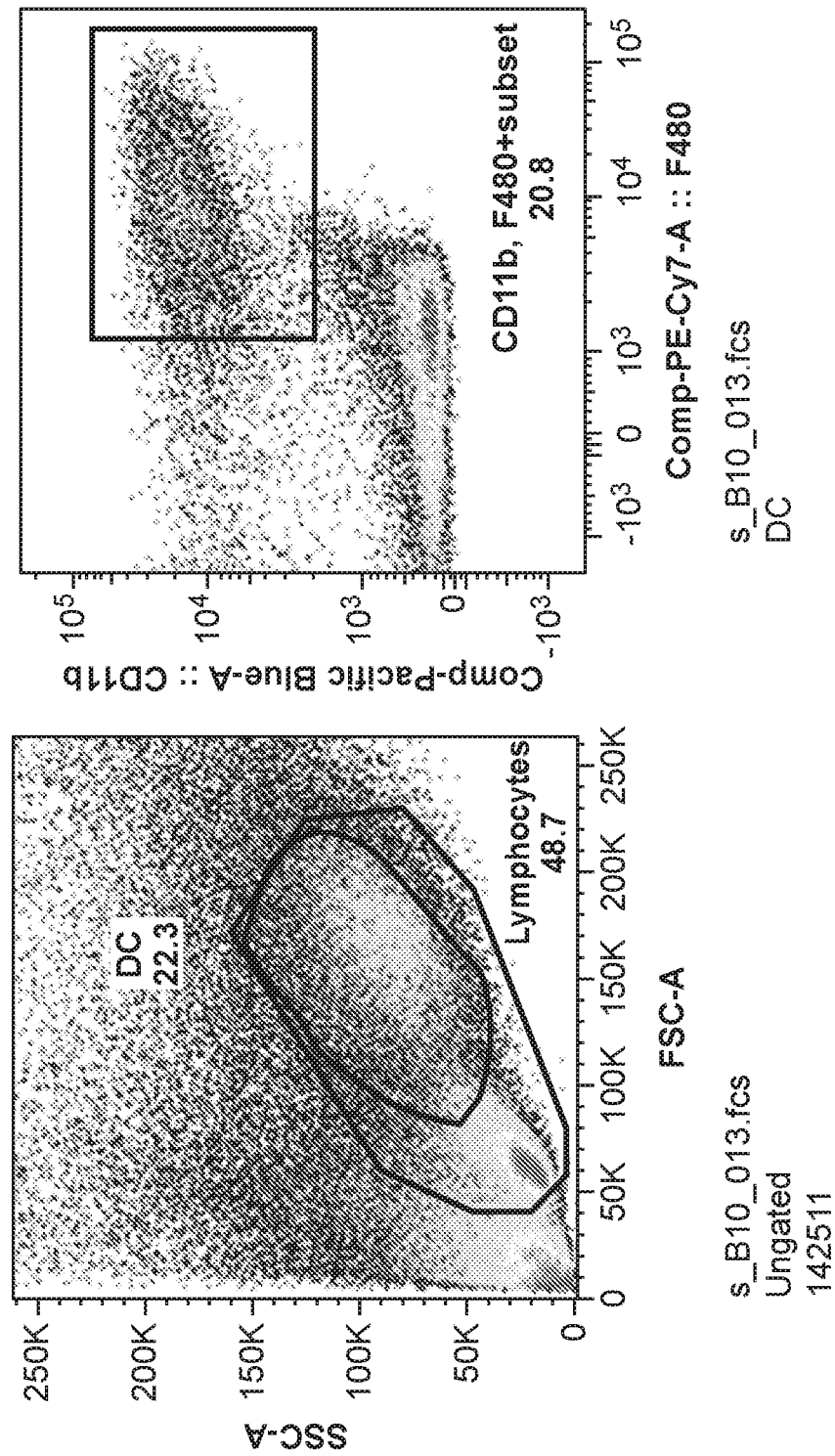

FIG. 33A shows distribution of lung adenocarcinoma samples of FIG. 32 (n=29) with staining for either PD-L1 or beta 8. FIG. 33B shows in all cases that stained at least 300% for beta 8 or PD-L were grouped together and the staining proportions were correlated.

FIGS. 34A-C shows the inhibition of B16 lung metastases as compared to an isotype sample. FIG. 34A are photographs of representative lungs in anterior and posterior views and visible lung metastases were counted and the total lung surface area involved with metastases was assessed. FIG. 34B shows the effect of C6D4 on total number of lung metastases. The B16-F10 highly metastatic tumor cell line is syngenic to the host C57B/6 strain and does not express integrins αvβ6 or αvβ8. The B16-F10 tumor cells were transfected with murine itgb8. After selection in G418 and two rounds of sorting a pool of high expressing αvβ8 cells was injected intravenously via the tail vein. After three injections (i.p.) of isotype control (SV5) or C6D4, both at 7 mg/kg at days 0, 7 and 14, the mice were euthanized at day 18. FIG. 34C shows the effect of C6D4 as measured by percentage of total lung surface area involved by metastatic melanoma.

FIGS. 35A-H show that C6D4 effects macrophage polarization to a proinflammatory phenotype. Increases in MHCII expression by tumor associated macrophages and dendritic cells is important in host immune responses to tumor antigens.

FIGS. 36A-F shows that C6D4 increases MHCII expression by tumor associated dendritic cells. Increases in MHCII by antigen presenting cells will increase antigen presentation.

FIGS. 37A-G are scatterplots showing integrin mediated differentiation of mouse Treg cells. Tumor associated CD4+ T regulatory cells play an important role in suppressing the host immune response and help tumors escape immune surveillance. The differentiation of Treg requires TGF-beta. It is thought that TGF-beta provided by mechanisms such as integrin αvβ8 mediated activation are important for Treg differentiation and function. Here, we immobilized the ectodomains of various integrins (2 mg/ml) on ELISA plates (co-coated with anti-CD3) and plate naïve murine splenic CD4+ cells with hIL-2 and retinoic acid. After 5 days the cells were fixed, permeabilized and stained with anti-CD4 and FoxP3. As a positive and negative control, cells were plated on wells with only anti-CD3 (no integrin) in the presence (+) or absence (−) of rTGF-b. The percentage of FoxP3 expressing cells are shown in each of the scatterplots (Q2).

Figure 38B:
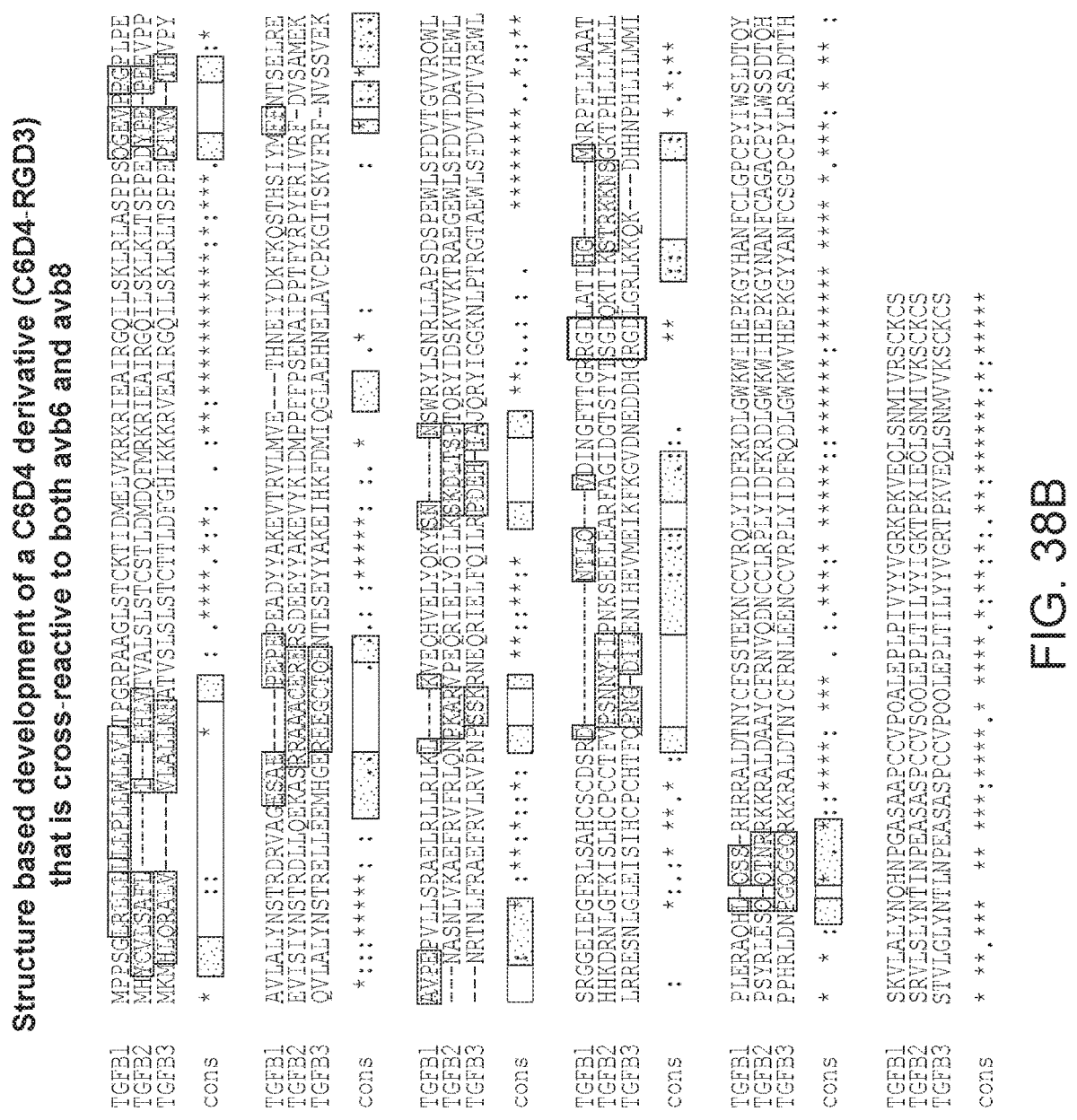

FIGS. 38A-D shows structural representations of a C6D4 derivative (termed "RGD3" or "CD64-RGD3") that is cross-reactive to αvβ6 and αvβ8 but not αvβ1, αvβ3, or αvβ5. FIG. 38A shows a close-up view of C6D4-RGD3 (gold) in complex with αvβ8 derived from cryoEM maps. Green is the αv subunit and blue is the β8 subunit. Shown in red is the LTGF-B1 peptide derived from structures of Latent- TGFB1 in complex with the integrin αvβ6. (αvβ6 (SEQ ID NO:709), αIIbβ3 (SEQ ID NO:710 (GRGDSP) and SEQ ID NO:711 (AKQRGDV). FIG. 38B shows sequence alignments of hTGFβ1-3 and the position of the RGD domains in TGFβ1 (SEQ ID NO:714) and TGFβ3 (SEQ ID NO:715). TGFβ2 (SEQ ID NO:716) does not have an RGD sequence. FIG. 38C shows the sequence of three mutant D4 Vk CDR1 loops containing portions of the hTGFB3 RGD sequence (in red) developed herein (C6D4 vk (SEQ ID NO:717); C6D4-RDG1 (SEQ ID NO:718); C6D4-RDG2 (SEQ ID NO:719); and C6D4-RDG3 (SEQ ID NO:720). FIG. 38D shows a zoomed image of the D4 loop (shown in gold) and the clash with the position of the bound RGD sequence of TGFβ1 in complex with integrin αvβ6.

FIG. 39 shows cell surface staining experiments of C6Vh expressed with either RGD1, RGD2 or RGD3 mutants (as set forth in FIG. 38) as rabbit IgG. Binding to human Cho cells expressing αvβ8 was expressed as a percentage of binding of C6D4.

FIG. 40 shows cell surface staining experiments of C6Vh expressed with either D4 Vk or RGD1, RGD2 or RGD3 mutants as rabbit IgG. Binding to Cho cells expressing human αvβ8 or SW480 cells expressing αvβ6 are shown. Relative binding is defined as staining compared to staining of non-transfected Cho or SW480 cells.

FIG. 41 shows binding experiments of C6Vh expressed with either D4 Vk or RGD1, RGD2 or RGD3 mutants as rabbit IgG, to various αv-integrins. All integrins were coated on ELISA plates at 2 mg/ml, blocked with BSA, and antibodies were allowed to bind. Binding of C6D4 and C6D4-RGD3 were detected with anti-rabbit HRP. The results are shown relative to control wells coated with anti-αv (clone 8B8) where αv-integrins were detected with another αv-antibody recognizing an non-overlapping epitope (L230-biotin), followed by SA-HRP.

FIG. 42 shows the effect of cations on the binding of C6D4 and C6D4-RGD3 to various receptors. Binding in EDTA containing buffer defines cation-dependence because EDTA binds to $Ca^{++}$ and $Mg^{++}$. Magnesium cation buffers contains 1 mM $Ca^{++}$ and 1 mM $Mg^{++}$. Here, the results are relative to anti-av, clone 11D12V2. All antibodies were coated on ELISA plates at 5 μg/ml. The αvβ8 or αvβ6 receptors (0.5 μg/ml) were bound for 1 hour and were then detected with biotinylated anti-av clone 8B8. The small amount of αvβ8 binding to C6D4-RGD3 in EDTA buffer (compared with no αvβ6 binding to C6D4-RGD3 in EDTA buffer) suggests that the binding to αvβ6 is more dependent on the RGD binding loop of Vk CDR1 than the binding to αvβ8.

FIGS. 43A and 43B show inhibition of αvβ8 adhesion and TGF-beta activation. Cho 3.2.8.1 cells transfected with b8 were used in adhesion assays to wells coated with branched GRGDLGRLK peptide (SEQ ID NO:721) (10 ug/ml). Cho-b8 cells were allowed to bind in adhesion assays (FIG. 43A) in the presence of C6D4, RGD3 or control Mab at various concentrations. Cho-b8 cells were allowed to attach to wells with TMLC TGF-β reporter cells in the presence of C6D4, RGD3 or control Mab at various concentrations (FIG. 43B). The values are shown as a proportion of control Mab (SV5) control. The results indicate that C6D4-RGD3 and C6D4 block αvβ8 function similarly.

FIGS. 44A-B show adhesion assays and FIGS. 44C-D show TGF-beta activation. Here, Cho3.2.8.1 cells were transfected with GARP and LTGFB1. GARP (LRRC32) is a cell surface scaffolding molecule present on the surface of Treg cells and binds LTGF-b to the cell surface. Upper panels (FIGS. 44A and 44B) show adhesion assays of Cho cells expressing GARP/LTGFB adhering to immobilized αvβ8 (FIG. 44A) or αvβ6 (FIG. 44B) performed in the presence of anti-β8 (C6D4), 3G9 (anti-β6) or the bispecific antibody RGD3 (anti-β6 and anti-β8). In the lower panels (FIGS. 44C and 44D), the TGF-beta reporters cells TMLC, were added to each well to determine the amount of TGF-β activation in response to αvβ8 (FIG. 44C) or αvβ6 (FIG. 44D) performed in the presence of anti-β8 (C6D4), 3G9 (anti-β6) or the bispecific antibody RGD3 (anti-β6 and anti-β8). The results are reported as relative luciferase activity to wells treated with isotype control antibody (SV5). Below each graph is the EC50 of each inhibitory antibody.

FIG. 45 shows binding assay of αvβ6 to TGFβ3 peptide. Mab 3G9 is a potent inhibitor of αvβ6-mediated TGF-b activation. C6D4-RGD3 shows cross-competition with 3G9 binding suggesting that they have overlapping binding footprints or allosterically influence each other's binding. However, these antibodies have different modes of action as 3G9 binding to αvβ6 is not cation-dependent while C6D4-RGD3 binding is cation dependent.

FIG. 46 illustrates heavy and light chain amino acid sequences for clones used in the construction of the composite humanized antibody C6D4. VH sequences—C6D4: all sequences (SEQ ID NO:722), Framework 1 (SEQ ID NO:732), CDR1 (SEQ ID NO:733), Framework 2 (SEQ ID NO:734), CDR2 (SEQ ID NO:735), Framework 3 (SEQ ID NO:736), CDR3 (SEQ ID NO:737), Framework 4 (SEQ ID NO:738); HuC6D4 V1: all sequences (SEQ ID NO:723), Framework 1 (SEQ ID NO:739), CDR1 (SEQ ID NO:733), Framework 2 (SEQ ID NO:740), CDR2 (SEQ ID NO:735), Framework 3 (SEQ ID NO:741), CDR3 (SEQ ID NO:737), Framework 4 (SEQ ID NO:738); Mutclone A3: all sequences (SEQ ID NO:724), Framework 1 (SEQ ID NO:739), CDR1 (SEQ ID NO:733), Framework 2 (SEQ ID NO:740), CDR2 (SEQ ID NO:735), Framework 3 (SEQ ID NO:741), CDR3 (SEQ ID NO:737), Framework 4 (SEQ ID NO:738); Mutclone B7: all sequences (SEQ ID NO:725), Framework 1 (SEQ ID NO:742), CDR1 (SEQ ID NO:733), Framework 2 (SEQ ID NO:740), CDR2 (SEQ ID NO:735), Framework 3 (SEQ ID NO:743), CDR3 (SEQ ID NO:744), Framework 4 (SEQ ID NO:738); Mutclone E5: all sequences (SEQ ID NO:726), Framework 1 (SEQ ID NO:739), CDR1 (SEQ ID NO:733), Framework 2 (SEQ ID NO:740), CDR2 (SEQ ID NO:735), Framework 3 (SEQ ID NO:741), CDR3 (SEQ ID NO:744), and Framework 4 (SEQ ID NO:738). VK sequences—C6D4: all sequences (SEQ ID NO:727), Framework 1 (SEQ ID NO:745), CDR1 (SEQ ID NO:746), Framework 2 (SEQ ID NO:747), CDR2 (SEQ ID NO:748), Framework 3 (SEQ ID NO:749), CDR3 (SEQ ID NO:750), Framework 4 (SEQ ID NO:751); HuC6D4 V1: all sequences (SEQ ID NO:728), Framework 1 (SEQ ID NO:752), CDR1 (SEQ ID NO:746), Framework 2 (SEQ ID NO:747), CDR2 (SEQ ID NO:748), Framework 3 (SEQ ID NO:753), CDR3 (SEQ ID NO:750), Framework 4 (SEQ ID NO:754); Mutclone A3: all sequences (SEQ ID NO:729), Framework 1 (SEQ ID NO:755), CDR1 (SEQ ID NO:756), Framework 2 (SEQ ID NO:747), CDR2 (SEQ ID NO:748), Framework 3 (SEQ ID NO:753), CDR3 (SEQ ID NO:750), Framework 4 (SEQ ID NO:754); Mutclone B7: all sequences (SEQ ID NO:730), Framework 1 (SEQ ID NO:757), CDR1 (SEQ 1D NO:746), Framework 2 (SEQ ID NO:747), CDR2 (SEQ ID NO:748), Framework 3 (SEQ ID NO:758), CDR3 (SEQ ID NO:750), Framework 4 (SEQ ID NO:754); Mutclone E5: all sequences (SEQ ID NO:731), Framework 1 (SEQ ID NO:752), CDR1 (SEQ ID NO:756), Framework 2 (SEQ ID NO:747), CDR2 (SEQ ID NO:748), Framework 3 (SEQ ID NO:753), CDR3 (SEQ ID NO:750), and Framework 4 (SEQ ID NO:754).

Figure 47:
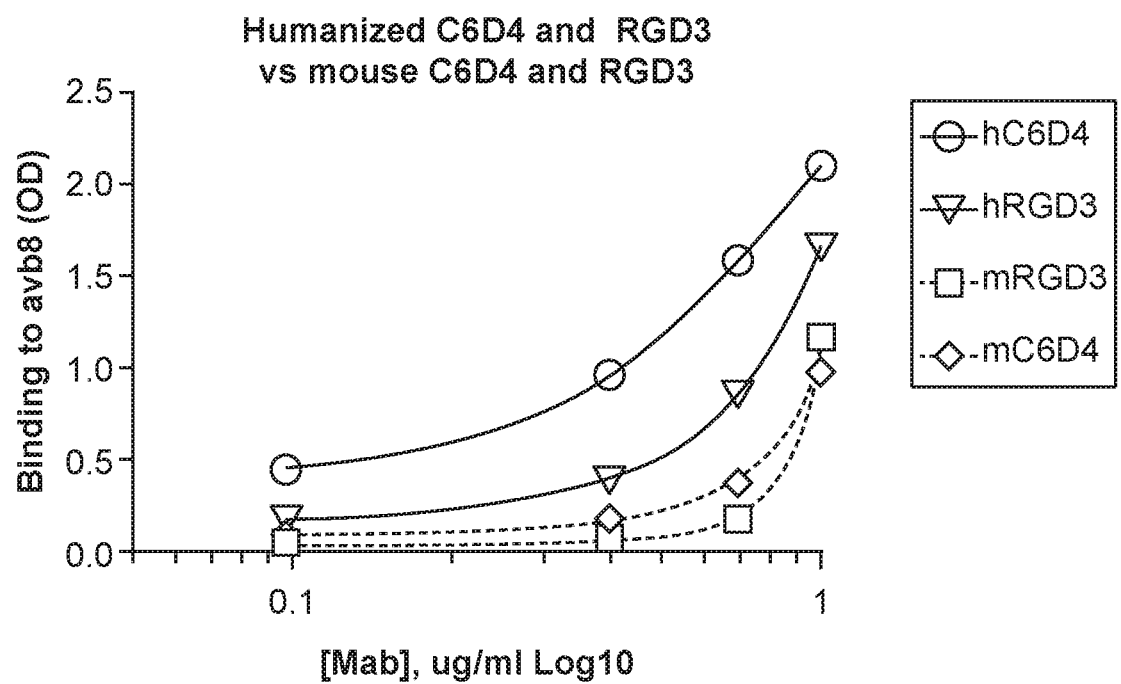
Figure 54A:
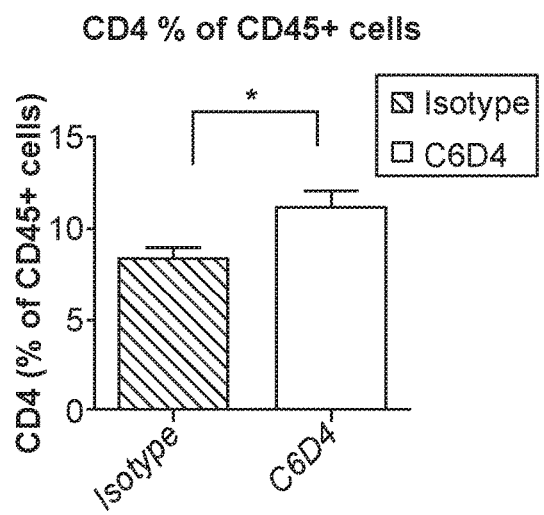
Figure 54B:
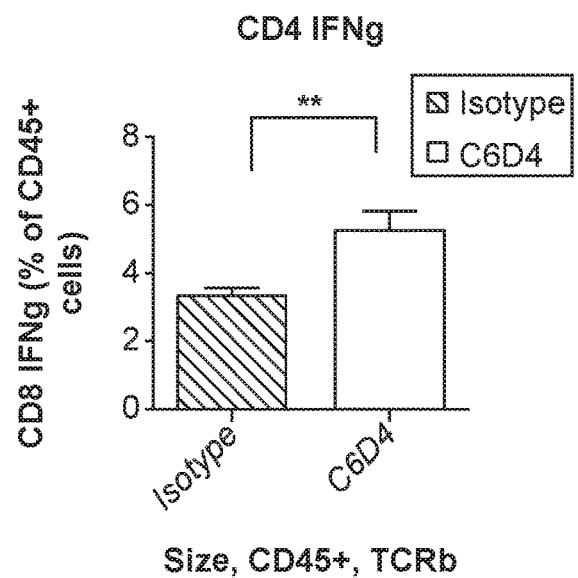
Figure 54C:
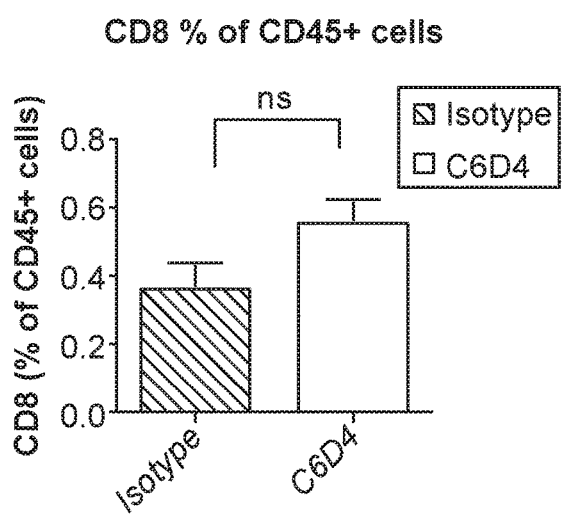
Figure 54D:
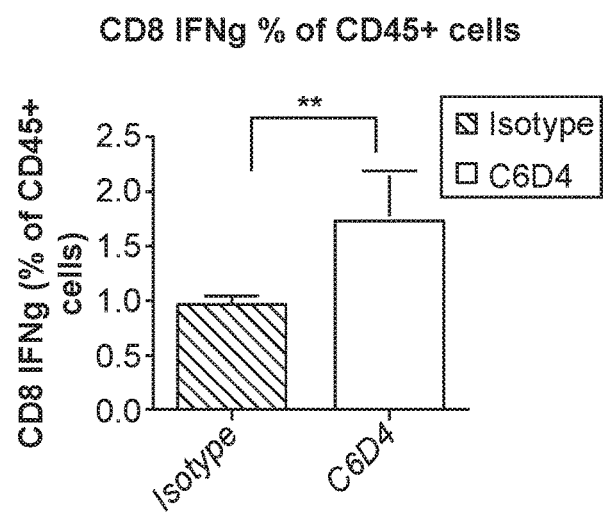

FIG. 47 shows binding assay of humanized C6D4 or RDG3 to recombinant αvβ8. Humanized C6D4 or RGD3 (Frameworks and CH1 are human; hinge and CH2-3 are mouse) were immobilized on ELISA plates at the indicated concentrations. As a negative control, some wells were coated with anti-SV5 at the same concentrations. Nonspecific binding sites were blocked with BSA. Recombinant αvβ8 ectodomain (0.5 ug/ml) was added to each well and after binding and washing in binding buffer (1 mM Ca and Mg), the bound αvβ8 was detected with biotinylated anti-αv (8b8) and detected with SA-HRP. Results are shown as specific binding (minus SV5 control).

FIG. 48 shows superposition of C6D4/αvβ8 cartoon model with wire map of C6D4/αvβ8 (FIGS. 48A and 48C) compared to a superposition of the same C6D4/αvβ8 cartoon model with wire map of C6D4-RGD3/αvβ8 (FIGS. 48B and D). The comparison of the two maps shows a different orientation of the CDR1 Vk loop of C6D4-RGD3 towards the beta8 subunit ligand binding site.

FIGS. 49A-C shows CryoEM maps of C6D4 and C6D4-RGD αvβ8 complexes having similar positioning. Here, C6D4 Fab-αvβ8 (FIG. 49A) is compared with RGD3-αvβ8 map (FIG. 49B), or in overlay (FIG. 49C), based on cryoEM derived density maps. The anti-av 11D12V2 Fab was used to increase molecular mass of the complex and to assist in particle orientation.

FIG. 50 illustrates heavy chain amino acid sequences for clones used in the construction of the composite humanized antibodies C6D4 and C6D4-RGD3. Consensus sequences for the humanized version of C6D4 and C6D4-RGD3 are provided. VH sequences—HuC6D4V1: all (SEQ ID NO:395), Framework 1 (SEQ ID NO:396), CDR1 (SEQ ID NO:397), Framework 2 (SEQ ID NO:398), CDR2 (SEQ ID NO:399), Framework 3 (SEQ ID NO:400), CDR3 (SEQ ID NO:401), and Framework 4 (SEQ ID NO:402); HuC6D4A3: all (SEQ ID NO:403), Framework 1 (SEQ ID NO:404), CDR1 (SEQ ID NO:405), Framework 2 (SEQ ID NO:406), CDR2 (SEQ ID NO:407), Framework 3 (SEQ ID NO:408), CDR3 (SEQ ID NO:409), and Framework 4 (SEQ ID NO:410); HuC6D4B7: all (SEQ ID NO:411), Framework 1 (SEQ ID NO:412), CDR1 (SEQ ID NO:413), Framework 2 (SEQ ID NO:414), CDR2 (SEQ ID NO:415), Framework 3 (SEQ ID NO:416), CDR3 (SEQ ID NO:417), and Framework 4 (SEQ ID NO:418); HuC6D4E5: all (SEQ ID NO:419), Framework 1 (SEQ ID NO:420), CDR1 (SEQ ID NO:421), Framework 2 (SEQ ID NO:422), CDR2 (SEQ ID NO:423), Framework 3 (SEQ ID NO:424), CDR3 (SEQ ID NO:425), and Framework 4 (SEQ ID NO:426); C6D4: all sequences (SEQ ID NO:722), Framework 1 (SEQ ID NO:732), CDR1 (SEQ ID NO:733), Framework 2 (SEQ ID NO:734), CDR2 (SEQ ID NO:735), Framework 3 (SEQ ID NO:736), CDR3 (SEQ ID NO: 737), and Framework 4 (SEQ ID NO:738); HuC6D4: all (SEQ ID NO:427), Framework 1 (SEQ ID NO:428), CDR1 (SEQ ID NO:429), Framework 2 (SEQ ID NO:430), CDR2 (SEQ ID NO:431), Framework 3 (SEQ ID NO:432), CDR3 (SEQ ID NO:433), and Framework 4 (SEQ ID NO:434); C6D4-RGD3: all (SEQ ID NO:435), Framework 1 (SEQ ID NO:436), CDR1 (SEQ ID NO:437), Framework 2 (SEQ ID NO:438), CDR2 (SEQ ID NO:439), Framework 3 (SEQ ID NO:440), CDR3 (SEQ ID NO:441), and Framework 4 (SEQ ID NO:442); HuC6D4-RGD3: all (SEQ ID NO:443), Framework 1 (SEQ ID NO:444), CDR1 (SEQ ID NO:445), Framework 2 (SEQ ID NO:446), CDR2 (SEQ ID NO:447), Framework 3 (SEQ ID NO:448), CDR3 (SEQ ID NO:449), and Framework 4 (SEQ ID NO:450); and Consensus VH: Framework 1 (SEQ ID NO:558), CDR1 (SEQ ID NO:563), Framework 2 (SEQ ID NO:559), CDR2 (SEQ ID NO:563), Framework 3 (SEQ ID NO:560), CDR3 (SEQ ID NO:564), and Framework 4 (SEQ ID NO:561).

FIG. 51 illustrates light chain amino acid sequences for clones used in the construction of the composite humanized antibodies C6D4 and C6D4-RGD3. Consensus sequences for the humanized version of C6D4 and C6D4-RGD3 are provided. VL sequences—HuC6D4V1: all (SEQ ID NO:451), Framework 1 (SEQ ID NO:452), CDR1 (SEQ ID NO:453), Framework 2 (SEQ ID NO:454), CDR2 (SEQ ID NO:455), Framework 3 (SEQ ID NO:456), CDR3 (SEQ ID NO:457), and Framework 4 (SEQ ID NO:458); HuC6D4A3: all (SEQ ID NO:459), Framework 1 (SEQ ID NO:460), CDR1 (SEQ ID NO:461), Framework 2 (SEQ ID NO:462), CDR2 (SEQ ID NO:463), Framework 3 (SEQ ID NO:464), CDR3 (SEQ ID NO:465), and Framework 4 (SEQ ID NO:466); HuC6D4B7: all (SEQ ID NO:467), Framework 1 (SEQ ID NO:468), CDR1 (SEQ ID NO:469), Framework 2 (SEQ ID NO:470), CDR2 (SEQ ID NO:471), Framework 3 (SEQ ID NO:472), CDR3 (SEQ ID NO:473), and Framework 4 (SEQ ID NO:474); HuC6D4E5: all (SEQ ID NO:475), Framework 1 (SEQ ID NO:476), CDR1 (SEQ ID NO:478), Framework 2 (SEQ ID NO:479), CDR2 (SEQ ID NO:480), Framework 3 (SEQ ID NO:481), CDR3 (SEQ ID NO:482), and Framework 4 (SEQ ID NO:483); C6D4: all sequences (SEQ ID NO:727), Framework 1 (SEQ ID NO:745), CDR1 (SEQ ID NO:746), Framework 2 (SEQ ID NO:747), CDR2 (SEQ ID NO:748), Framework 3 (SEQ ID NO:749), CDR3 (SEQ ID NO:750), and Framework 4 (SEQ ID NO:751); HuC6D4: all sequences (SEQ ID NO:484), Framework 1 (SEQ ID NO:485), CDR1 (SEQ ID NO:486), Framework 2 (SEQ ID NO:487), CDR2 (SEQ ID NO:488), Framework 3 (SEQ ID NO:489), CDR3 (SEQ ID NO:490), and Framework 4 (SEQ ID NO:491); C6D4-RGD3: all (SEQ ID NO:492), Framework 1 (SEQ ID NO:493), CDR1 (SEQ ID NO:494), Framework 2 (SEQ ID NO:495), CDR2 (SEQ ID NO:496), Framework 3 (SEQ ID NO:497), CDR3 (SEQ ID NO:498), and Framework 4 (SEQ ID NO:499); HuC6D4-RGD3: all (SEQ ID NO:500), Framework 1 (SEQ ID NO:501), CDR1 (SEQ ID NO:502), Framework 2 (SEQ ID NO:503), CDR2 (SEQ ID NO:504), Framework 3 (SEQ ID NO:505), CDR3 (SEQ ID NO: 506), and Framework 4 (SEQ ID NO:507); and Consensus VL: Framework 1 (SEQ ID NO:565), CDR1 (SEQ ID NO:569), Framework 2 (SEQ ID NO:566), CDR2 (SEQ ID NO:570), Framework 3 (SEQ ID NO:567), CDR3 (SEQ ID NO:571), and Framework 4 (SEQ ID NO:568). RDG3 loop (SEQ ID NO:721).

FIG. 52 illustrates heavy chain amino acid sequences for clones used in the construction of the composite antibody F9. Sequences—4F1: all sequences (SEQ ID NO:624), Framework 1 (ID NO:625), CDR1 (SEQ ID NO:628), Framework 2 (SEQ ID NO:632), CDR2 (SEQ ID NO:634), Framework 3 (SEQ ID NO:637), CDR3 (SEQ ID NO:651), Framework 4 (SEQ ID NO:655), 6B9: all sequences (SEQ ID NO:656, Framework 1 (SEQ ID NO:625), CDR1 (SEQ ID NO:629), Framework 2 (SEQ ID NO:632), CDR2 (SEQ ID NO:635), Framework 3 (SEQ ID NO:638), CDR3 (SEQ ID NO:652), Framework 4 (SEQ ID NO:655), 6B9.1: all sequences (SEQ ID NO:657), Framework 1 (SEQ ID NO:625), CDR1 (SEQ ID NO:629), Framework 2 (SEQ ID NO:632), CDR2 (SEQ ID NO:636), Framework 3 (SEQ ID NO:638), CDR3 (SEQ ID NO:653), Framework 4 (SEQ ID NO:655), A1: all sequences (SEQ ID NO:658), Framework 1 (SEQ ID NO:626), CDR1 (SEQ ID NO:629), Framework 2 (SEQ ID NO:633), CDR2 (SEQ ID NO:636), Framework 3 (SEQ ID NO:639), CDR3 (SEQ ID NO:654), Framework 4 (SEQ ID NO:655), A2: all sequences (SEQ ID NO:659), Framework 1 (SEQ ID NO:625), CDR1 (SEQ ID NO:629), Framework 2 (SEQ ID NO:633), CDR2 (SEQ ID NO:636), Framework 3 (SEQ ID NO:640), CDR3 (SEQ ID NO:654), Framework 4 (SEQ ID NO:655), A8: all sequences (SEQ ID NO:660), Framework 1 (SEQ ID NO:625), CDR1 (SEQ ID NO:629), Framework 2 (SEQ ID NO:633), CDR2 (SEQ ID NO:636), Framework 3 (SEQ ID NO:641), CDR3 (SEQ ID NO:654), Framework 4 (SEQ ID NO:655), A11: all sequences (SEQ ID NO:661), Framework 1 (SEQ ID NO:625), CDR1 (SEQ ID NO:630), Framework 2 (SEQ ID NO:633), CDR2 (SEQ ID NO:636), Framework 3 (SEQ ID NO:638), CDR3 (SEQ ID NO:654), Framework 4 (SEQ ID NO:655), B1: all sequences (SEQ ID NO:662), Framework 1 (SEQ ID NO:625), CDR1 (SEQ ID NO:629), Framework 2 (SEQ ID NO:632), CDR2 (SEQ ID NO:636), Framework 3 (SEQ ID NO:642), CDR3 (SEQ ID NO:654), Framework 4 (SEQ ID NO:655), B3: all sequences (SEQ ID NO:663), Framework 1 (SEQ ID NO:625), CDR1 (SEQ ID NO:629), Framework 2 (SEQ ID NO:633), CDR2 (SEQ ID NO:636), Framework 3 (SEQ ID NO:643), CDR3 (SEQ ID NO:654), Framework 4 (SEQ ID NO:655), C4=F10: all sequences (SEQ ID NO:664), Framework 1 (SEQ ID NO:625), CDR1 (SEQ ID NO:629), Framework 2 (SEQ ID NO:633), CDR2 (SEQ ID NO:636), Framework 3 (SEQ ID NO:644), CDR3 (SEQ ID NO:654), Framework 4 (SEQ ID NO:655), C7=D1: all sequences (SEQ ID NO:665), Framework 1 (SEQ ID NO:625), CDR1 (SEQ ID NO:629), Framework 2 (SEQ ID NO:633), CDR2 (SEQ ID NO:636), Framework 3 (SEQ ID NO:644), CDR3 (SEQ ID NO:654), Framework 4 (SEQ ID NO:655), D3=F1: all sequences (SEQ ID NO:666), Framework 1 (SEQ ID NO:625), CDR1 (SEQ ID NO:629), Framework 2 (SEQ ID NO:633), CDR2 (SEQ ID NO:636), Framework 3 (SEQ ID NO:645), CDR3 (SEQ ID NO:654), Framework 4 (SEQ ID NO:655), D10=E5: all sequences (SEQ ID NO:667), Framework 1 (SEQ ID NO:625), CDR1 (SEQ ID NO:629), Framework 2 (SEQ ID NO:633), CDR2 (SEQ ID NO:636), Framework 3 (SEQ ID NO:646), CDR3 (SEQ ID NO:654), Framework 4 (SEQ ID NO:655), E8: all sequences (SEQ ID NO:667), Framework 1 (SEQ ID NO:625), CDR1 (SEQ ID NO:629), Framework 2 (SEQ ID NO:633), CDR2 (SEQ ID NO:636), Framework 3 (SEQ ID NO:646), CDR3 (SEQ ID NO:654), Framework 4 (SEQ ID NO:655), F2: all sequences (SEQ ID NO:667), Framework 1 (SEQ ID NO:625), CDR1 (SEQ ID NO:629), Framework 2 (SEQ ID NO:633), CDR2 (SEQ ID NO:636), Framework 3 (SEQ ID NO:646), CDR3 (SEQ ID NO:654), Framework 4 (SEQ ID NO:655), G4: all sequences (SEQ ID NO:668), Framework 1 (SEQ ID NO:625), CDR1 (SEQ ID NO:629), Framework 2 (SEQ ID NO:633), CDR2 (SEQ ID NO:636), Framework 3 (SEQ ID NO:647), CDR3 (SEQ ID NO:654), Framework 4 (SEQ ID NO:655), C4: all sequences (SEQ ID NO:669), Framework 1 (SEQ ID NO:625), CDR1 (SEQ ID NO:629), Framework 2 (SEQ ID NO:633), CDR2 (SEQ ID NO:636), Framework 3 (SEQ ID NO:650), CDR3 (SEQ ID NO:654), Framework 4 (SEQ ID NO:655), D10: all sequences (SEQ ID NO:670), Framework 1 (SEQ ID NO:625), CDR1 (SEQ ID NO:629), Framework 2 (SEQ ID NO:633), CDR2 (SEQ ID NO:636), Framework 3 (SEQ ID NO:646), CDR3 (SEQ ID NO:654), Framework 4 (SEQ ID NO:655), 4F1A11: all sequences (SEQ ID NO:671), Framework 1 (SEQ ID NO:625), CDR1 (SEQ ID NO:629), Framework 2 (SEQ ID NO:632), CDR2 (SEQ ID NO:636), Framework 3 (SEQ ID NO:650), CDR3 (SEQ ID NO:654), Framework 4 (SEQ ID NO:655), 4F1E1: all sequences (SEQ ID NO:672), Framework 1 (SEQ ID NO:625), CDR1 (SEQ ID NO:631), Framework 2 (SEQ ID NO:632), CDR2 (SEQ ID NO:636), Framework 3 (SEQ ID NO:638), CDR3 (SEQ ID NO:654), Framework 4 (SEQ ID NO:655), 4F1G3: all sequences (SEQ ID NO:673), Framework 1 (SEQ ID NO:625), CDR1 (SEQ ID NO:631), Framework 2 (SEQ ID NO:632), CDR2 (SEQ ID NO:636), Framework 3 (SEQ ID NO:648), CDR3 (SEQ ID NO:654), Framework 4 (SEQ ID NO:655), 4F1E10: all sequences (SEQ ID NO:674), Framework 1 (SEQ ID NO:627), CDR1 (SEQ ID NO:631), Framework 2 (SEQ ID NO:632), CDR2 (SEQ ID NO:636), Framework 3 (SEQ ID NO:638), CDR3 (SEQ ID NO:654), Framework 4 (SEQ ID NO:655), 4F1E9: all sequences (SEQ ID NO:675), Framework 1 (SEQ ID NO:625), CDR1 (SEQ ID NO:629), Framework 2 (SEQ ID NO:632), CDR2 (SEQ ID NO:636), Framework 3 (SEQ ID NO:638), CDR3 (SEQ ID NO:654), Framework 4 (SEQ ID NO:655), 4F1H12: all sequences (SEQ ID NO:676), Framework 1 (SEQ ID NO:625), CDR1 (SEQ ID NO:631), Framework 2 (SEQ ID NO:632), CDR2 (SEQ ID NO:636), Framework 3 (SEQ ID NO:649), CDR3 (SEQ ID NO:654), Framework 4 (SEQ ID NO:655), F9: all sequences (SEQ ID NO:677), Framework 1 (SEQ ID NO:625), CDR1 (SEQ ID NO:631), Framework 2 (SEQ ID NO:632), CDR2 (SEQ ID NO:636), Framework 3 (SEQ ID NO:638), CDR3 (SEQ ID NO:654), and Framework 4 (SEQ ID NO:655).

FIG. 53 illustrates light chain amino acid sequences for clones used in the construction of the composite antibody F9. VL Sequences—4F1: all sequences (SEQ ID NO:678), Framework 1 (SEQ ID NO:692), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), 6B9: all sequences (SEQ ID NO:679), Framework 1 (SEQ ID NO:699), CDR1 (SEQ ID NO:700), Framework 2 (SEQ ID NO:701), CDR2 (SEQ ID NO:695), Framework 3 (SEQ ID NO:696), CDR3 (SEQ ID NO:702), Framework 4 (SEQ ID NO:698), 6B9.1: all sequences (SEQ ID NO:680), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), A1: all sequences (SEQ ID NO:681), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), A2: all sequences (SEQ ID NO:681), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), A8: all sequences (SEQ ID NO:682), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), A11: all sequences (SEQ ID NO:683), Framework 1 (SEQ ID NO:704), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), B1: all sequences (SEQ ID NO:684), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), B3: all sequences (SEQ ID NO:685), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), C4=F10: all sequences (SEQ ID NO:681), Framework 1 (SEQ ID NO:703), CDR1

(SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), C7=D1: all sequences (SEQ ID NO:681), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), D3=F1: all sequences (SEQ ID NO:681), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), D10=E5: all sequences (SEQ ID NO:686), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), E8: all sequences (SEQ ID NO:686), Framework 1 (SEQ ID NO:703), CDR1 (SEQ ID NO:693), Framework 2 (SEQ ID NO:694), CDR2 (SEQ ID NO:695), Framework 3 (SEQ ID NO:755), CDR3 (SEQ ID NO:697), Framework 4 (SEQ ID NO:698), F2: all sequences (SEQ ID NO:681), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), G4: all sequences (SEQ ID NO:681), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), C4: all sequences (SEQ ID NO:687), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:706), D10: all sequences (SEQ ID NO:688), Framework 1 (SEQ ID NO:699), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:706), 4F1E1=1F1G3=4F1B5=4F1G11=4F1A9=4F1B9=4F1H9=4F1D10=4F1E9=4F1F0=4F1H11=4F1H12: all sequences (SEQ ID NO:689), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), 4FA1: all sequences (SEQ ID NO:690), Framework 1 (SEQ ID NO:705), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), F9: all sequences (SEQ ID NO:691), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), and Framework 4 (SEQ ID NO:706).

FIG. 54A-54D are graphs showing percentage of cells staining positive for various cell surface markers. Mice were injected with Lewis lung carcinoma (LLC) cells and SV5 (isotype control) or C6D4 at a dosage of 7 mg/kg once per week.

DETAILED DESCRIPTION OF THE INVENTION

I. Introduction

The inventors have discovered certain antibodies that bind to human integrin αvβ8 and cause at least partial reduction in ligand binding function. Based on that discovery, they have developed detailed structural models to aid in the discovery of antibodies that bind to integrin αvβ8 at particular epitopes that optimally block the ligand binding site of integrin αvβ8. Some of the antibodies identified bind to both the αv-integrin subunit head domain and the β8-integrin subunit head domain to effectively cover the ligand binding site of the integrin αvβ8 without engaging to the ligand binding site itself (i.e. acting as a ligand-mimetic).

Further, the inventors have discovered that blocking ligand binding to integrin αvβ8 is effective in inhibiting cancer (including but not limited to metastatic cancer) and also is effective in treating viral infections. Without intending to limit the scope of the described invention, it is believed that integrin αvβ8 plays a role in blocking regulatory T cells (Tregs) function and/or development and thus that the antibodies described herein stimulate immunity to tumor cells and viruses. Accordingly, antibodies and methods of their use, among other aspects, are provided herein.

The inventors have also identified introduced an "RGDL" sequence (SEQ ID NO:756) into a CDR of the anti-αvβ8 antibody and have shown that such an introduction renders the antibody able to bind αvβ6 while maintaining substantially the same binding activity for αvβ8.

II. Antibodies

Provided herein are antibodies that bind human (and in some embodiments other mammalian, e.g., such as mouse, guinea pig, pig, and rabbit) integrin αvβ8. In some embodiments, the antibodies are isolated, are chimeric (comprising at least some heterologous amino acid sequence), are labeled or covalently linked to another molecule such a cytotoxic agent or a combination thereof. In some embodiments, the antibodies specifically bind human integrin αvβ8 and block binding of a ligand to human integrin αvβ8. Exemplary ligands can include, for example, TGFβ and LAP. In some embodiments, the antibodies bind in a cation-dependent manner or have enhanced binding in the presence of cations.

In some embodiments the epitope bound by the antibodies described herein on human integrin αvβ8 comprise amino acids in (1) the specificity determining loop (SDL) of the integrin β8 protein (e.g., TVSPYISIHPERIHNQCSDYNLDCMPPH (SEQ ID NO:620)), (2) in the cal (e.g., SASMHNNIEKLNSVGNDLSRKMAFFS (SEQ ID NO:619)) or α2 (e.g., NITEFEKAVHR (SEQ ID NO:621)) helices of the β8 integrin protein, (3) the head of the αv protein (e.g., DADGQ (SEQ ID NO:757); SFYWQ (SEQ ID NO:758); FDDSY (SEQ ID NO:759)) or other portions of KQDKILACAPLYHWR-TEMKQEREPVGTCFLQDGTKTVEYAPCRSQDI-DADGQGFCQGG FSIDFTKADRVLLGGPGSFYWQGQLISDQVAEIVSKY-DPNVYSIKYNNQLATRTAQAIFD (SEQ ID NO:760) or (4) a combination thereof (e.g., 1 and 2, 2 and 3, 1 and 3, or 1, 2, and 3) as they occur in the native human integrin αvβ8 protein, including for example to all of the listed portions of human integrin αvβ8. In some embodiments, the antibody binds to one or more or all amino acid in the SDL selected from: D175 (e.g., in NLDCM (SEQ ID NO:761)), L174 (e.g., in YNLDC (SEQ ID NO:762)), or S170, D171, or Y172 (e.g., in QCSDYNL (SEQ ID NO:763)), or combinations thereof, wherein the numbering is based on the human integrin β8 protein (SEQ ID NO:394). See, e.g., FIG. 7. In some embodiments, the antibody binds to the amino acid H118 (e.g., in SMHNN) (SEQ ID NO:764) in the α1 helix of the β8 integrin protein), wherein the numbering is based on the human integrin β8 protein (SEQ ID NO:394). In some embodiments, the antibody binds to the amino acid H200 or R201 (e.g., in AVHRJQ) in the α2 helix of the β8 integrin protein, or combinations thereof, wherein the numbering is based on the human integrin β8 protein (SEQ ID NO:394).

In some embodiments, the antibody binds to one or more or all amino acid (underlined) in the head of the αv protein selected from: D148, A149, D150, G151, or Y178 (e.g., in SFYWQ (SEQ ID NO:758)) or combinations thereof, wherein the numbering is based on the human integrin aov protein (SEQ ID NO:393). In some embodiments, the antibody binds to each of the above indicated (underlined) amino acids described in this paragraph. As can be seen from FIGS. 12-18, interaction with the above-described domains of integrin αvβ8 is beneficial.

As noted above, in some embodiments, the antibodies specifically bind human integrin αvβ8 and block binding of a ligand to human integrin αvβ8. The ability of an antibody to block αvβ8 integrin binding of a ligand can be determined by inhibition of binding of a soluble form of αvβ8 or a full-length form of αvβ8 expressed on the surface of cells to immobilized latent-TGF-beta or a portion thereof containing the sequence RGDL See, e.g., Ozawa, A, et al. *J Biol Chem.* 291(22):11551-65 (2016).

In some embodiments, the antibodies comprise one or more CDR (or all of the heavy chain CDRs of a clone, or all of the light chain CDRs of a clone) as follows:

| Heavy Chains | Clone name | CDR1 Vh (SEQ ID:) | CDR2 Vh (SEQ ID:) | CDR3 Vh (SEQ ID:) |
|---|---|---|---|---|
| Heavy | B2B2 | TFTDYSMH (313) | RINTETGEPTFADDFGG (314) | YYYGRDS (315) |
| Heavy | B13C4 | TFTDYSMH (316) | WIKTETGEPTYADDFKG (317) | YYYGRDS (318) |
| Heavy | B13H3 | TFTDYSMH (319) | WIKTETDEPTYADDFKE (320) | YYYGRDS (321) |
| Heavy | B15B11 | TFTDYSMH (322) | RINTETGEPTFADDFRG (323) | YYYGRDS (324) |
| Heavy | B13C12 | TFTDYSIH (325) | WIKTETGEPTYADDFNG (326) | YYYGRDS (327) |
| Heavy | A1 | TFTDYSMH (328) | RINTETGEPTFADDFRG (329) | YYYGRDT (330) |
| Heavy | C6 | TFTDYSMH (331) | RINTETGEPTFADDFRG (332) | FYYGRDS (333) |
| Light Chains | Clone name | CDR1 Vk | CDR2 Vk | CDR3 Vk |
| Light | B2B2 | KASQDINSYLS (334) | RANRLVD (335) | LQYDEFPPLT (336) |
| Light | B13C4 | KSSQLLNSRTRKNYLA (337) | WASTRES (338) | KQSYNLLT (339) |
| Light | B13H3 | KSSQSLLNSRIRKNYLA (340) | WASTRES (341) | KQSYNLLT (342) |
| Light | B15B11.1 | SASSSVSYMH (343) | DTSNLAS (344) | QQWSSNPLT (345) |
| Light | B15B11.2 | SASSSVSYMH (346) | DTSNLAS (347) | QQWSSNPPT (348) |
| Light | B15B11.3 | KSSQSLLNSRTRKNYLA (349) | WASTRES (350) | KQSYNLLT (351) |
| Light | B13C12.1 | SASSSVSYMH (352) | DTSKLAS (353) | QQWSSNPFT (354) |
| Light | B13C12.2 | SASSSVSYMH (355) | GTSNLAS (356) | QQWSSNPPT (357) |
| Light | B13C12.3 | KSSQSLLHSRTRKNYLA (358) | WASTRES (359) | KQSYNLLT (360) |
| Light | D4 | KSSQSLLNSRTRKNYLA (361) | WASTRES (362) | KQSYNLLS (363) |

In some embodiments, the antibodies comprise one or more CDR (or all of the heavy chain CDRs of a clone, or all of the light chain CDRs of a clone) as follows:

| Heavy Chains | Clone name | CDR1 Vh (SEQ ID:) | CDR2 Vh (SEQ ID:) | CDR3 Vh (SEQ ID |
|---|---|---|---|---|
| Heavy | HuC6D4V1 | DYSMH (397) | RINTETGEPTFADDFRG (399) | FYYGRDS (401) |

| | | | | |
|---|---|---|---|---|
| Heavy | HuC6D4A3 | DYSMH (405) | RINTETGEPTFADDFRG (407) | FYYGRDS (409) |
| Heavy | HuC6D4B7 | DYSMH (413) | RINTETGEPTFADDFRG (415) | FYYGRDT (417) |
| Heavy | HuC6D4E5 | DYSMH (421) | RINTETGEPTFADDFRG (423) | FYYGRDT (425) |
| Heavy | HuC6D4 | DYSMH (429) | RINTETGEPTFADDFRG (431) | FYYGRDT (433) |
| Heavy | C6D4-RGD3 | DYSMH (437) | RINTETGEPTFADDFRG (439) | FYYGRDS (441) |
| Heavy | HuC6D4-RGD3 | DYSMH (445) | RINTETGEPTFADDFRG (447) | FYYGRDT (449) |
| Light Chains | Clone name | CDR1 Vk (SEQ ID:) | CDR2 Vk (SEQ ID:) | CDR3 Vk (SEQ ID: |
| Light | HuC6D4V1 | KSSQSLLNSRTRKNYLA (529) | WASTRES (530) | KQSYNLLS (531) |
| Light | HuC6D4A3 | KSSQSLLNSRSRKNYLA (532) | WASTRES (533) | KQSYNLIS (534) |
| Light | HuC6D4B7 | KSSQSLLNSRTRKNYLA (535) | WASTRES (536) | KQSSNLIS (537) |
| Light | HuC6D4E5 | KSSQSLLNSRSRKNYLA (538) | WASTRES (539) | KQSYNLLS (540) |
| Light | HuC6D4 | KSSQSLLNSRSRKNYLA (541) | WASTRES (542) | KQSYNLLS (543) |
| Light | C6D4-RGD3 | KSSQSLLGRGDLGRLKKNALA (544) | WASTRES (545) | KQSYNLLS (546) |
| Light | HuC6D4-RGD3 | KSSQSLLGRGDLGRLKKNALA (547) | WASTRES (548) | KQSYNLLS (549) |

In some embodiments, an antibody described herein comprises heavy and light chain CDRs as paired in the following table:

| Combinations (H + L) | Clone name | CDR1 (SEQ ID:) | CDR2 (SEQ ID:) | CDR3 (SEQ ID:) |
|---|---|---|---|---|
| H | B2B2 | TFTDYSMH (313) | RINTETGEPTFADDFGG (314) | YYYGRDS (315) |
| L | B2B2 | KASQDINSYLS (334) | RANRLVD (335) | LQYDEFPPLT (33) |
| H | B13H3 | TFTDYSMH (319) | WIKTETDEPTYADDFKE (320) | YYYGRDS (321) |
| L | B13H3 | KSSQSLLNSRIRKNYLA (340) | WASTRES (341) | KQSYNLLT (342) |
| H | B13C4 | TFTDYSMH (316) | WIKTETGEPTYADDFKG (317( | YYYGRDS (318) |
| L | B13C4 | KSSQSLLNSRTRKNYLA (337) | WASTRES (338) | KQSYNLLT (339) |
| H | B15B11 | TFTDYSMH (322) | RINTETGEPTFADDFRG (323) | YYYGRDS (324) |
| H | B15B11.1 | SASSSVSYMH (343) | DTSNLAS (344) | QQWSSNPLT (345) |
| H | B15B11 | TFTDYSMH (322) | RINTETGEPTFADDFRG (323) | YYYGRDS (324) |
| L | B15B11.2 | SASSSVSYMH (346) | DTSNLAS (347) | QQWSSNPPT (348) |
| H | B15B11 | TFTDYSMH (322) | RINTETGEPTFADDFRG (323 ) | YYYGRDS (324) |

-continued

| Combinations (H + L) | Clone name | CDR1 (SEQ ID:) | CDR2 (SEQ ID:) | CDR3 (SEQ ID:) |
|---|---|---|---|---|
| L | B15B11.3 | KSSQSLLNSRTRKNYLA (358) | WASTRES (359) | KQSYNLLT (360) |
| H | B13C12 | TFTDYSIH (325) | WIKTETGEPTYADDFNG (326) | YYYGRDS (327) |
| L | B13C12.1 | SASSSVSYMH (352) | DTSKLAS (353) | QQWSSNPFT (354) |
| H | B13C12 | TFTDYSIH (325) | WIKTETGEPTYADDFNG (326) | YYYGRDS (327) |
| L | B13C12.2 | SASSSVSYMH (355) | GTSNLAS (356) | QQWSSNPPT (357) |
| H | B13C12 | TFTDYSIH (325) | WIKTETGEPTYADDFNG (326) | YYYGRDS (327) |
| L | B13C12.3 | KSSQSLLHSRTRKNYLA (358) | WASTRES (359) | KQSYNLLT (360) |
| H | RSDLVH-3 | TFTDYSIH (367) | WIKTETGEPTYADDFNG (368) | YYYGRDS (369) |
| L | RSDLVK-10 | KSSQSLLNSRTRKNYLA (373) | WASTRES (374) | KQSYNLLT (375) |
| H | RSDLVH-1 | TFTDYSIH (364) | WIKTETGEPTYADDFKG (365) | YYYGRDS (366) |
| L | RSDLVK-10 | KSSQSLLNSRTRKNYLA (373) | WASTRES (374) | KQSYNLLT (375) |
| H | RSDLVH-3 | TFTDYSIH (367) | WIKTETGEPTYADDFNG (368) | YYYGRDS (369) |
| L | RSDLVK-13 | KSSQSLLHSRTRKNYLA (376) | WASTRES (377) | KQSYNLLT (378) |
| H | RSDLVH-16 | TFTDYSMH (370) | RINTETGEPTFADDFRG (37) | YYYGRDS (372) |
| L | RSDLVK-10 | KSSQLLNSRTRKNYLA (373) | WASTRES (374) | KQSYNLLT (375) |
| H | C6H | TFTDYSMH (766) | RINTETGEPTFADDFRG (767) | FYYGRDS (768) |
| L | C6K | KSSQSLLNSRTRKNYLA (382) | WASTRES (383) | KQSYNLLT (384) |
| H | D4H | TFTDYSMH (379) | RINTETGEPTFADDFRG (380) | YYYGRDS (381) |
| L | D4K | KSSQLLNSRTRKNYLA (361) | WASTRES (362) | KQSYNLLS (363) |
| H | C6H | TFTDYSMH (766) | RINTETGEPTFADDFRG (767) | FYYGRDS (768) |
| L | D4K | KSSQLLNSRTRKNYLA (361) | WASTRES (362) | KQSYNLLS (363) |

In some embodiments, an antibody described herein comprises heavy and light chain CDRs as paired in the following table:

| Combinations (H + L) | Clone name | CDR1 (SEQ ID:) | CDR2 (SEQ ID:) | CDR3 (SEQ ID:) |
|---|---|---|---|---|
| H | HuC6D4V1 | DYSMH (397) | RINTETGEPTFADDFRG (398) | FYYGRDS (399) |
| L | HuC6D4V1 | KSSQLLNSRTRKNYLA (529) | WASTRES (530) | KQSYNLLS (531) |
| H | HuC6D4A3 | DYSMH (405) | RINTETGEPTFADDFRG (407) | FYYGRDS (409) |
| L | HuC6D4A3 | KSSQSLLNSRSRKNYLA (532) | WASTRES (533) | KQSYNLIS (534) |
| H | HuC6D4B7 | DYSMH (413) | RINTETGEPTFADDFRG (415) | FYYGRDT (417) |
| L | HuC6D4B7 | KSSQSLLNSRTRKNYLA (535) | WASTRES (536) | KQSSNLIS (537) |

-continued

| Combinations (H + L) | Clone name | CDR1 (SEQ ID:) | CDR2 (SEQ ID:) | CDR3 (SEQ ID:) |
|---|---|---|---|---|
| H | HuC6D4E5 | DYSMH (421) | RINTETGEPTFADDFRG (423) | FYYGRDT (425) |
| L | HuC6D4E5 | KSSQSLLNSRSRKNYLA (538) | WASTRES (539) | KQSYNLLS (540) |
| H | HuC6D4 | DYSMH (429) | RINTETGEPTFADDFRG (431) | FYYGRDT (433) |
| L | HuC6D4 | KSSQLLNSRSRKNYLA (541) | WASTRES (542) | KQSYNLLS (543) |
| H | C6D4-RGD3 | DYSMH (437) | RINTETGEPTFADDFRG (439) | FYYGRDS (441) |
| L | C6D4-RGD3 | KSSQSLLGRGDLGRLKKNALA (544) | WASTRES (545) | KQSYNLLS (546) |
| H | HuC6D4-RGD3 | DYSMH (445) | RINTETGEPTFADDFRG (447) | FYYGRDT (449) |
| L | HuC6D4-RGD3 | KSSQLLGRGDLGRLKKNALA (547) | WASTRES (548) | KQSYNLLS (549) |
| H | C6D4 | DYSMH (123) | RINTETGEPTFADDFRG (125) | FYYGRDS (127) |
| L | C6D4 | KSSQSLLNSRSRKNYLA (291) | WASTRES (293) | KQSYNLLS (295) |
| H | C6RGD2 | DYSMH (769) | RINTETGEPTFADDFRG (770) | FYYGRDS (771) |
| L | C6RGD2 | KSSQSLLNSGRGDLGNALA (772) | WASTRES (773) | KQSYNLIS (774) |
| H | C6RGD3-1 | DYSMH (775) | RINTETGEPTFADDFRG (776) | FYYGRDT (777) |
| L | C6RGD3-1 | KSSQSLLGRGDLGRLKKQKDHNALA (778) | WASTRES (779) | KQSSNLIS (780) |
| H | C6RGD3-2 | DYSMH (781) | RINTETGEPTFADDFRG (782) | FYYGRDY (783) |
| L | C6RGD3-2 | KSSQSLLGRGDLGRLKXQKDNALA (784) | WASTRES (785) | KQSYNLLS (786) |
| H | C6RGD3-3 | DYSMH (787) | RINTETGEPTFADDFRG (788) | FYYGRDT (789) |
| L | C6RGD3-3 | KSSQLLGRGDLGRLKKQKNALA (790) | WASTRES (791) | KQSYNLLS (792) |
| H | C6RGD3-4 | DYSMH (793) | RINTETGEPTFADDFRG (794) | FYYGRDS (795) |
| L | C6RGD3-4 | KSSQSLLGRGDLGRLKKQNALA (796) | WASTRES (797) | KQSYNLLS (798) |
| H | C6RGD3 | DYSMH (799) | RINTETGEPTFADDFRG (800) | FYYGRDT (801) |
| L | C6RGD3 | KSSQSLLGRGDLGRLKKNALA (802) | WASTRES (803) | KQSYNLLS (804) |
| H | C6RGD3-6 | DYSMH (805) | RINTETGEPTFADDFRG (806) | FYYGRDS (807) |
| L | C6RGD3-6 | KSSQSLLGRGDLGRLKNALA (808) | WASTRES (809) | KQSYNLLS (810) |
| H | C6RDG3-7 | DYSMH (811) | RINTETGEPTFADDFRG (812) | FYYGRDS (813) |
| L | C6RGD3-7 | KSSQSLLGRGDLGRLNALA (814) | WASTRES (815) | KQSYNLIS (816) |
| H | C6RGD3-8 | DYSMH (817) | RINTETGEPTFADDFRG (818) | FYYGRDT (819) |
| L | C6RGD3-8 | KSSQSLLGRGDLGRNALA (820) | WASTRES (821) | KQSSNLIS (822) |
| H | C6RGD1 | DYSMH (823) | RINTETGEPTFADDFRG (824) | FYYGRDY (825) |
| L | C6RGD1 | KSSQSLLGRGDLGNALA (826) | WASTRES (827) | KQSYNLLS (828) |

| Combinations (H + L) | Clone name | CDR1 (SEQ ID:) | CDR2 (SEQ ID:) | CDR3 (SEQ ID |
|---|---|---|---|---|
| H | C6RGD3-9 | DYSMH (829) | RINTETGEPTFADDFRG (830) | FYYGRDT (831) |
| L | C6RGD3-9 | KSSQSLLGRGDLGRLKKQKDHH (832) | WASTRES (833) | KQSYNLLS (834) |
| H | C6RGD3-10 | DYSMH (835) | RINTETGEPTFADDFRG (836) | FYYGRDS (837) |
| L | C6RGD3-10 | KSSQSLLGRGDLGRLKKQKDH (838) | WASTRES (839) | KQSYNLLS (840) |
| H | C6RGD3-11 | DYSMH (841) | RINTETGEPTFADDFRG (842) | FYYGRDT (843) |
| L | C6RGD3-11 | KSSQSLLGRGDLGRLKKQKD (844) | WASTRES (845) | KQSYNLLS (846) |
| H | C6RGD3-12 | DYSMH (847) | RINTETGEPTFADDFRG (848) | FYYGRDT (849) |
| L | C6RGD3-12 | KSSQLLGRGDLGRLKKQK (850) | WASTRES (851) | KQSSNLIS (852) |
| H | C6RGD3-13 | DYSMH (853) | RINTETGEPTFADDFRG (854) | FYYGRDY (855) |
| L | C6RGD3-13 | KSSQSLLGRGDLGRLKKQ (856) | WASTRES (857) | KQSYNLLS (858) |
| H | C6RGD3-14 | DYSMH (859) | RINTETGEPTFADDFRG (860) | FYYGRDT (861) |
| L | C6RGD3-14 | KSSQSLLGRGDLGRLKK (862) | WASTRES (863) | KQSYNLLS (864) |
| H | C6RGD3-15 | DYSMH (865) | RINTETGEPTFADDFRG (866) | FYYGRDS (867) |
| L | C6RGD3-15 | KSSQSLLGRGDLGRLK (868) | WASTRES (869) | KQSYNLLS (870) |
| H | C6RGD3-16 | DYSMH (871) | RINTETGEPTFADDFRG (872) | FYYGRDT (873) |
| L | C6RGD3-16 | KSSQSLLGRGDLGRL (874) | WASTRES (875) | KQSYNLLS (876) |

In some embodiments, an antibody as described herein comprises one, two, three or all four of the framework sequences as provided here:

| Frameworks | Fr 1 (SEQ ID NO:) | Fr2 (SEQ ID NO:) |
|---|---|---|
| H | (Q)IQL(L)(Q)SGPELKKPGETVKISCKASGY (385)<br>E   M E<br>Where (X) can be specified AA | WVKQAPGKGLKW(V)A (386)<br>M |
| L | (D)IVM(T)QSPSSLAV(S)AGE(K)VT(M)SC (389)<br>E    S     P    N  V<br>Where (X) can be specified AA all alternatives listed under | WYQQKPGQSP(R)LLIY (390)<br>K |

| Frameworks | Fr3 (SEQ ID NO:) | Fr4 (SEQ ID NO:) |
|---|---|---|
| H | RFA(V)SLETSASTAYLQINNLKNEDTATYFCAI (387)<br>F | (WGQGTT(L)TVSS (388)<br>V |
| L | GVPDRFTGSGSGTDFTLTISSVQAEDLAVY(Y)C (391)<br>F | FGAGT(K)LE(L)K (392)<br>R    I |

In some embodiments, an antibody as described herein comprises one, two, three or all four of the framework sequences as provided here:

| Frameworks | Fr 1 (SEQ ID NO:) | Fr2 (SEQ ID NO:) |
|---|---|---|
| H | QIQLVQSG(P)(E)(L)KKPG(E)(T)VKISCKASGYTFT (550)<br>        A   K   V      A S<br>Where (X) can be specified AA | WV(K)QAPG(K)GL(K)WVA (551)<br>   R       Q    E |
| L | (D)IVMTQ(S)P(S)(S)L(A)VS(A)GE(K)VTMSC (554)<br> E      T    A  T   S    P      R<br>                 V          I | WYQQKPGQSPRLLIY (555)<br>             A |

| Frameworks | Fr3 (SEQ ID NO:) | |
|---|---|---|
| H | RF(A)V(S)L(E)TS(A)STAYL(Q)I(N)(N)L(K)(N)(E)DTA(T)YFCAI (552)<br>  T   T   D    T        E   R  S  R  S  D    V<br>  S                   T<br>Where (X) can be specified AA all alternatives listed under | |
| L | (G)VP(D)RF(T)GSGSGT(D)FTLTISSVQ(A)ED(L)AVYYC (556)<br>    D    A    S         E              S    F | |

| Frameworks | Fr4 (SEQ ID NO:) |
|---|---|
| H | WGQGT(T)LTVSS (553)<br>     A |
| L | FG(A)GT(K)LE(L)KR (557)<br>   Q     V    I |

In some embodiments, an antibody as described herein comprises one, two, three or all four of the framework sequences as provided here:

| Frameworks | Fr 1 (SEQ ID NO:) | Fr2 (SEQ ID NO:) |
|---|---|---|
| H | QIQL(V)QSG(P)(E)(L)KKPG(E)(T)VKISCKASGYTFT (550)<br>    L      A K V      A S<br>Where (X) can be specified AA | WV(K)QAPG(K)GL(K)W(V)(A) (877)<br>   R       Q      E  M  G |
| L | (D)IVM(T)Q(S)P(S)(S)L(A)VS(A)GE(K)VTMSC (880)<br> E     S   T   A  T   S    P      R<br>                 V          I | WYQQKPGQ(S)PRLLIY (881)<br>              A |

| Frameworks | Fr3 (SEQ ID NO:) | |
|---|---|---|
| H | RF(A)(V)(S)L(E)TS(A)(S)TA(Y)L(Q)I(N)(N)L(K)(N)(E)DTA(T)YFCAI (878)<br>  T  F  T   D    T  T     N      E   R  S  R  S  D    V<br>  S                             I                      K<br>                             T<br>Where (X) can be specified AA all alternatives listed under | |
| L | (G)VP(D)RF(T)GSGSGT(D)FTLTISSVQ(A)ED(L)AVYYC (882)<br>    D    A    S         E              S    F<br>                                          D | |

| Frameworks | Fr4 (SEQ ID NO:) |
|---|---|
| H | WGQGT(T)LTVSS (879)<br>     A |
| L | FG(A)GT(K)LE(I)KR (883)<br>   Q     V    L |

In some embodiments, the antibodies comprise the CDR1, CDR2, and CDR3 heavy chain sequences as provided herein, including but not limited to, e.g., SEQ ID NO:3, SEQ ID NO:5, and SEQ ID NO:7;
SEQ ID NO: 11, SEQ ID NO:13, and SEQ ID NO:15;
SEQ ID NO:19, SEQ ID NO:21, and SEQ ID NO:23;
SEQ ID NO:27, SEQ ID NO:29, and SEQ ID NO:31;
SEQ ID NO:35, SEQ ID NO:37, and SEQ ID NO:39;
SEQ ID NO:43, SEQ ID NO:45, and SEQ ID NO:47;
SEQ ID NO:51, SEQ ID NO:53, and SEQ ID NO:55;
SEQ ID NO:59, SEQ ID NO:61, and SEQ ID NO:63;
SEQ ID NO:67, SEQ ID NO:69, and SEQ ID NO:71;

SEQ ID NO:75, SEQ ID NO:77, and SEQ ID NO:79;
SEQ ID NO:83, SEQ ID NO:85, and SEQ ID NO:87;
SEQ ID NO:91, SEQ ID NO:93, and SEQ ID NO:95;
SEQ ID NO:99, SEQ ID NO:101, and SEQ ID NO:103;
SEQ ID NO: 107, SEQ ID NO:109, and SEQ ID NO: 111;
SEQ ID NO: 115, SEQ ID NO:117, and SEQ ID NO: 119;
SEQ ID NO: 123, SEQ ID NO: 125, and SEQ ID NO: 127,
SEQ ID NO:291, SEQ ID NO:293, and SEQ ID NO:295;
SEQ ID NO:313, SEQ ID NO:314, and SEQ ID NO:315;
SEQ ID NO:316, SEQ ID NO:317, and SEQ ID NO:318;
SEQ ID NO:319, SEQ ID NO:320, and SEQ ID NO:321;
SEQ ID NO:322, SEQ ID NO:323, and SEQ ID NO:324;
SEQ ID NO:325, SEQ ID NO:326, and SEQ ID NO:327;
SEQ ID NO:328, SEQ ID NO:329, and SEQ ID NO:330;
SEQ ID NO:331, SEQ ID NO:332, and SEQ ID NO:333;
SEQ ID NO:367, SEQ ID NO:368, and SEQ ID NO:369;
SEQ ID NO:364, SEQ ID NO:365, and SEQ ID NO:366;
SEQ ID NO:370, SEQ ID NO:371, and SEQ ID NO:372;
SEQ ID NO:379, SEQ ID NO:380, and SEQ ID NO:381;
SEQ ID NO:397, SEQ ID NO:399, and SEQ ID NO:401;
SEQ ID NO:405, SEQ ID NO:407, and SEQ ID NO:409;
SEQ ID NO:413, SEQ ID NO:415, and SEQ ID NO:417;
SEQ ID NO:421, SEQ ID NO:423, and SEQ ID NO:425; or
SEQ ID NO:429, SEQ ID NO:431, and SEQ ID NO:433.

In some embodiments, the antibodies comprise the heavy chain CDR1, CDR2, and CDR3 sequences described above but contain 1, 2, or 3 conservative amino acid substitutions in one, two or more CDR sequences compared to those listed above.

In some embodiments, the antibodies comprise the light chain CDR1, CDR2, and CDR3 sequences as provided herein, including but not limited to, e.g.,
SEQ ID NO:131, SEQ ID NO:133, and SEQ ID NO:135;
SEQ ID NO: 139, SEQ ID NO:141, and SEQ ID NO:143;
SEQ ID NO:147, SEQ ID NO:149, and SEQ ID NO:151;
SEQ ID NO: 155, SEQ ID NO:157, and SEQ ID NO: 159;
SEQ ID NO:163, SEQ ID NO:165, and SEQ ID NO:167;
SEQ ID NO:171, SEQ ID NO:173, and SEQ ID NO:175;
SEQ ID NO:179, SEQ ID NO:181, and SEQ ID NO: 183.
SEQ ID NO:187, SEQ ID NO:189, and SEQ ID NO:191;
SEQ ID NO:195, SEQ ID NO:197, and SEQ ID NO: 199.
SEQ ID NO:203, SEQ ID NO:205, and SEQ ID NO:207;
SEQ ID NO:211, SEQ ID NO:213, and SEQ ID NO:215.
SEQ ID NO:219, SEQ ID NO:221, and SEQ ID NO:223;
SEQ ID NO:227, SEQ ID NO:229, and SEQ ID NO:231.
SEQ ID NO:243, SEQ ID NO:245, and SEQ ID NO:247;
SEQ ID NO:251, SEQ ID NO:253, and SEQ ID NO:255;
SEQ ID NO:259, SEQ ID NO:261, and SEQ ID NO:263;
SEQ ID NO:267, SEQ ID NO:269, and SEQ ID NO:271;
SEQ ID NO:275, SEQ ID NO:277, and SEQ ID NO:279;
SEQ ID NO:283, SEQ ID NO:285, and SEQ ID NO:287;
SEQ ID NO:291, SEQ ID NO:293, and SEQ ID NO:295;
SEQ ID NO:307, SEQ ID NO:309, and SEQ ID NO:311;
SEQ ID NO:334, SEQ ID NO:335, and SEQ ID NO:336;
SEQ ID NO:337, SEQ ID NO:338, and SEQ ID NO:339;
SEQ ID NO:340, SEQ ID NO:341, and SEQ ID NO:342;
SEQ ID NO:343, SEQ ID NO:344, and SEQ ID NO:345;
SEQ ID NO:346, SEQ ID NO:347, and SEQ ID NO:348
SEQ ID NO:349, SEQ ID NO:350, and SEQ ID NO:351;
SEQ ID NO:352, SEQ ID NO:353, and SEQ ID NO:354;
SEQ ID NO:355, SEQ ID NO:356, and SEQ ID NO:357;
SEQ ID NO:358, SEQ ID NO:359, and SEQ ID NO:360
SEQ ID NO:361, SEQ ID NO:362, and SEQ ID NO:363;
SEQ ID NO:373, SEQ ID NO:374, and SEQ ID NO:375;
SEQ ID NO:376, SEQ ID NO:377, and SEQ ID NO:378;
SEQ ID NO:382, SEQ ID NO:383, and SEQ ID NO:384;
SEQ ID NO:453, SEQ ID NO:455, and SEQ ID NO:457;
SEQ ID NO:461, SEQ ID NO:463, and SEQ ID NO:465;
SEQ ID NO:469, SEQ ID NO:471, and SEQ ID NO:473;
SEQ ID NO:478, SEQ ID NO:480 and SEQ ID NO:482; or
SEQ ID NO:486, SEQ ID NO:488, and SEQ ID NO:490.

In some embodiments, the antibodies comprise the light chain CDR1, CDR2, and CDR3 sequences described above but contain 1, 2, or 3 conservative amino acid substitutions in one, two or more CDR sequences compared to those listed above. In some embodiments, the light chain CDR1 sequence is 12-18 amino acids long, e.g., 14-17, e.g., 12, 13, 14, 15, 16, 17, or 18 amino acids long.

In some embodiments, the antibodies comprise the heavy and light chain CDR1, CDR2, and CDR3 sequences as provided herein, including but not limited to, e.g.,
heavy chain CDRs SEQ ID NO:313, SEQ ID NO:314, and SEQ ID NO:315; and light chain CDRs SEQ ID NO:334, SEQ ID NO:335, and SEQ ID NO:336; or
heavy chain CDRs SEQ ID NO:319, SEQ ID NO:320, and SEQ ID NO:321; and light chain CDRs SEQ ID NO:340, SEQ ID NO:341, and SEQ ID NO:342; or
heavy chain CDRs SEQ ID NO:316, SEQ ID NO:317, and SEQ ID NO:318; and light chain CDRs SEQ ID NO:337, SEQ ID NO:338, and SEQ ID NO:339; or
heavy chain CDRs SEQ ID NO:322, SEQ ID NO:323, and SEQ ID NO:324; and light chain CDRs SEQ ID NO:343, SEQ ID NO:344, and SEQ ID NO:345; or
heavy chain CDRs SEQ ID NO:322, SEQ ID NO:323, and SEQ ID NO:324; and light chain CDRs SEQ ID NO:346, SEQ ID NO:347, and SEQ ID NO:348; or
heavy chain CDRs SEQ ID NO:322, SEQ ID NO:323, and SEQ ID NO:324; and light chain CDRs SEQ ID NO:349, SEQ ID NO:350, and SEQ ID NO:351; or
heavy chain CDRs SEQ ID NO:325, SEQ ID NO:326, and SEQ ID NO:327; and light chain CDRs SEQ ID NO:352, SEQ ID NO:353, and SEQ ID NO:354; or
heavy chain CDRs SEQ ID NO:325, SEQ ID NO:326, and SEQ ID NO:327; and light chain CDRs SEQ ID NO:355, SEQ ID NO:356, and SEQ ID NO:357; or
heavy chain CDRs SEQ ID NO:325, SEQ ID NO:326, and SEQ ID NO:327; and light chain CDRs SEQ ID NO:358, SEQ ID NO:359, and SEQ ID NO:360; or
heavy chain CDRs SEQ ID NO:367, SEQ ID NO:368, and SEQ ID NO:369; and light chain CDRs SEQ ID NO:373, SEQ ID NO:374, and SEQ ID NO:375; or
heavy chain CDRs SEQ ID NO:364, SEQ ID NO:365, and SEQ ID NO:366; and light chain CDRs SEQ ID NO:373, SEQ ID NO:374, and SEQ ID NO:375; or
heavy chain CDRs SEQ ID NO:367, SEQ ID NO:368, and SEQ ID NO:369; and light chain CDRs SEQ ID NO:376, SEQ ID NO:377, and SEQ ID NO:378; or
heavy chain CDRs SEQ ID NO:370, SEQ ID NO:371, and SEQ ID NO:372; and light chain CDRs SEQ ID NO:373, SEQ ID NO:374, and SEQ ID NO:375; or
heavy chain CDRs SEQ ID NO:331, SEQ ID NO:332, and SEQ ID NO:333; and light chain CDRs SEQ ID NO:382, SEQ ID NO:383, and SEQ ID NO:384; or
heavy chain CDRs SEQ ID NO:379, SEQ ID NO:380, and SEQ ID NO:381; and light chain CDRs SEQ ID NO:361, SEQ ID NO:362, and SEQ ID NO:363; or
heavy chain CDRs SEQ ID NO:331, SEQ ID NO:332, and SEQ ID NO:333; and light chain CDRs SEQ ID NO:361, SEQ ID NO:362, and SEQ ID NO:363; or heavy chain CDRs SEQ ID NO:508, SEQ ID NO:509, and SEQ ID NO:510; and light chain CDRs SEQ ID NO:529, SEQ ID NO:530, and SEQ ID NO:531; or
heavy chain CDRs SEQ ID NO:511, SEQ ID NO:512, and SEQ ID NO:513; and light chain CDRs SEQ ID NO:532, SEQ ID NO:533, and SEQ ID NO:534; or
heavy chain CDRs SEQ ID NO:514, SEQ ID NO:515, and SEQ ID NO:516; and light chain CDRs SEQ ID NO:535, SEQ ID NO:536, and SEQ ID NO:537; or
heavy chain CDRs SEQ ID NO:517, SEQ ID NO:518, and SEQ ID NO:519; and light chain CDRs SEQ ID NO:538, SEQ ID NO:539, and SEQ ID NO:540; or
heavy chain CDRs SEQ ID NO:520, SEQ ID NO:521, and SEQ ID NO:522; and light chain CDRs SEQ ID NO:541, SEQ ID NO:542, and SEQ ID NO:543; or
heavy chain CDRs SEQ ID NO:523, SEQ ID NO:524, and SEQ ID NO:525 and light chain CDRs SEQ ID NO:544, SEQ ID NO:545, and SEQ ID NO:546; or
heavy chain CDRs SEQ ID NO:526, SEQ ID NO: 527, and SEQ ID NO:528; and light chain CDRs SEQ ID NO: 547, SEQ ID NO:548, and SEQ ID NO:549.

In some embodiments, the antibodies comprise the heavy and light chain CDR1, CDR2, and CDR3 sequences described above but contain 1, 2, or 3 conservative amino acid substitutions in one, two or more CDR sequences compared to those listed above.

In some embodiments, any antibody described herein can comprise a light chain CDR1 comprising a RGD sequence, e.g., as provided in the following table:

| CDR$_{L1}$ | Vk |
|---|---|
| KSSQSLLNSRSRKNYLA (SEQ ID NO: 572) | D4 |
| KSSQSLLNSGRGDLGNALA (SEQ ID NO: 574) | RGD2 |
| KSSQSLLGRGDLGRLKKQKDHTNALA (SEQ ID NO: 576) | RGD3-1 |
| KSSQSLLGRGDLGRLKKQKDNALA (SEQ ID NO: 577) | RGD3-2 |
| KSSQSLLGRGDLGRLKKQKNALA (SEQ ID NO: 578) | RGD3-3 |
| KSSQSLLGRGDLGRLKKQNALA (SEQ ID NO: 579) | RGD3-4 |
| KSSQSLLGRGDLGRLKKNALA (SEQ ID NO: 575) | RGD3 |
| KSSQSLLGRGDLGRLKNALA (SEQ ID NO: 580) | RGD3-6 |
| KSSQSLLGRGDLGRINALA (SEQ ID NO: 581) | RGD3-7 |
| KSSQSLLGRGDLGRNALA (SEQ ID NO: 582) | RGD3-8 |
| KSSQSLLGRGDLGNALA (SEQ ID NO: 573) | RGD1 |
| KSSQSLLGRGDLGRLKKQKDHH (SEQ ID NO: 583) | RGD3-9 |
| KSSQSLLGRGDLGRLKKQKDH (SEQ ID NO: 584) | RGD3-10 |
| KSSQSLLGRGDLGRLKKQKD (SEQ ID NO: 585) | RGD3-11 |
| KSSQSLLGRGDLGRLKKQK (SEQ ID NO: 586) | RGD3-12 |
| KSSQSLLGRGDLGRLKKQ (SEQ ID NO: 587) | RGD3-13 |
| KSSQSLLGRGDLGRLKK (SEQ ID NO: 588) | RGD3-14 |
| KSSQSLLGRGDLGRLK (SEQ ID NO: 589) | RGD3-15 |
| KSSQSLLGRGDLGRL (SEQ ID NO: 590) | RGD3-16 |

In some embodiments, any of the antibodies described herein can comprise as CDR1 one of the CDRs selected from SEQ ID NO: 572, SEQ ID NO:573, SEQ ID NO: 574, SEQ ID NO:575, SEQ ID NO:576, SEQ ID NO:577, SEQ ID NO:578, SEQ ID NO:579, SEQ ID NO:580, SEQ ID NO:581, SEQ ID NO:582, SEQ ID NO:583, SEQ ID NO:584, SEQ ID NO:585, SEQ ID NO:586, SEQ ID NO:587, SEQ ID NO:588, SEQ ID NO:589, and SEQ ID NO:590.

In some embodiments, the antibody can comprise heavy and light chain CDR1, CDR2, and CDR3 sequences as provided below, including but not limited to, e.g.,
heavy chain CDRs SEQ ID NO:523, SEQ ID NO: 524, and SEQ ID NO:525; and light chain CDRs SEQ ID NO:572, SEQ ID NO:545, and SEQ ID NO:546; or
heavy chain CDRs SEQ ID NO:523, SEQ ID NO: 524, and SEQ ID NO:525; and light chain CDRs SEQ ID NO:573, SEQ ID NO:545, and SEQ ID NO:546; or
heavy chain CDRs SEQ ID NO:523, SEQ ID NO: 524, and SEQ ID NO:525; and light chain CDRs SEQ ID NO:574, SEQ ID NO:545, and SEQ ID NO:546; or
heavy chain CDRs SEQ ID NO:523, SEQ ID NO: 524, and SEQ ID NO:525; and light chain CDRs SEQ ID NO:575, SEQ ID NO:545, and SEQ ID NO:546; or
heavy chain CDRs SEQ ID NO:523, SEQ ID NO: 524, and SEQ ID NO:525; and light chain CDRs SEQ ID NO: 576, SEQ ID NO:545, and SEQ ID NO:546; or
heavy chain CDRs SEQ ID NO:523, SEQ ID NO: 524, and SEQ ID NO:525; and light chain CDRs SEQ ID NO: 577, SEQ ID NO:545, and SEQ ID NO:546; or
heavy chain CDRs SEQ ID NO:523, SEQ ID NO: 524, and SEQ ID NO:525; and light chain CDRs SEQ ID NO: 578, SEQ ID NO:545, and SEQ ID NO:546; or
heavy chain CDRs SEQ ID NO:523, SEQ ID NO: 524, and SEQ ID NO:525; and light chain CDRs SEQ ID NO:579, SEQ ID NO:545, and SEQ ID NO:546; or
heavy chain CDRs SEQ ID NO:523, SEQ ID NO:524, and SEQ ID NO:525; and light chain CDRs SEQ ID NO:580, SEQ ID NO:545, and SEQ ID NO:546; or
heavy chain CDRs SEQ ID NO:523, SEQ ID NO:524, and SEQ ID NO:525; and light chain CDRs SEQ ID NO:581, SEQ ID NO:545, and SEQ ID NO:546; or
heavy chain CDRs SEQ ID NO:523, SEQ ID NO: 524, and SEQ ID NO:525; and light chain CDRs SEQ ID NO:582, SEQ ID NO:545, and SEQ ID NO:546; or
heavy chain CDRs SEQ ID NO:523, SEQ ID NO: 524, and SEQ ID NO:525; and light chain CDRs SEQ ID NO:583, SEQ ID NO:545, and SEQ ID NO:546; or
heavy chain CDRs SEQ ID NO:523, SEQ ID NO: 524, and SEQ ID NO:525; and light chain CDRs SEQ ID NO:584, SEQ ID NO:545, and SEQ ID NO:546; or
heavy chain CDRs SEQ ID NO:523, SEQ ID NO: 524, and SEQ ID NO:525; and light chain CDRs SEQ ID NO:585, SEQ ID NO:545, and SEQ ID NO:546; or
heavy chain CDRs SEQ ID NO:523, SEQ ID NO: 524, and SEQ ID NO:525; and light chain CDRs SEQ ID NO:586, SEQ ID NO:545, and SEQ ID NO:546; or
heavy chain CDRs SEQ ID NO:523, SEQ ID NO: 524, and SEQ ID NO:525; and light chain CDRs SEQ ID NO: 587, SEQ ID NO:545, and SEQ ID NO:546; or
heavy chain CDRs SEQ ID NO:523, SEQ ID NO: 524, and SEQ ID NO:525; and light chain CDRs SEQ ID NO: 589, SEQ ID NO:545, and SEQ ID NO:546; or
heavy chain CDRs SEQ ID NO:523, SEQ ID NO: 524, and SEQ ID NO:525; and light chain CDRs SEQ ID NO: 590, SEQ ID NO:545, and SEQ ID NO:546; or
heavy chain CDRs SEQ ID NO:523, SEQ ID NO: 524, and SEQ ID NO:525; and light chain CDRs SEQ ID NO: 572, SEQ ID NO:545, and SEQ ID NO:534; or heavy chain CDRs SEQ ID NO:523, SEQ ID NO:524, and SEQ ID NO:525; and light chain CDRs SEQ ID NO:573, SEQ ID NO:545, and SEQ ID NO:534; or
heavy chain CDRs SEQ ID NO:523, SEQ ID NO:524, and SEQ ID NO:525; and light chain CDRs SEQ ID NO:574, SEQ ID NO:545, and SEQ ID NO:534; or
heavy chain CDRs SEQ ID NO:523, SEQ ID NO:524, and SEQ ID NO:525; and light chain CDRs SEQ ID NO:575, SEQ ID NO:545, and SEQ ID NO: 534; or
heavy chain CDRs SEQ ID NO:523, SEQ ID NO:524, and SEQ ID NO:525; and light chain CDRs SEQ ID NO:576, SEQ ID NO:545, and SEQ ID NO: 534; or
heavy chain CDRs SEQ ID NO:523, SEQ ID NO:524, and SEQ ID NO:525; and light chain CDRs SEQ ID NO:577, SEQ ID NO:545, and SEQ ID NO: 534; or
heavy chain CDRs SEQ ID NO:523, SEQ ID NO:524, and SEQ ID NO:525; and light chain CDRs SEQ ID NO:578, SEQ ID NO:545, and SEQ ID NO: 534; or
heavy chain CDRs SEQ ID NO:523, SEQ ID NO: 524, and SEQ ID NO:525; and light chain CDRs SEQ ID NO:579, SEQ ID NO:545, and SEQ ID NO:534; or
heavy chain CDRs SEQ ID NO:523, SEQ ID NO: 524, and SEQ ID NO:525; and light chain CDRs SEQ ID NO:580, SEQ ID NO:545, and SEQ ID NO:534; or
heavy chain CDRs SEQ ID NO:523, SEQ ID NO: 524, and SEQ ID NO:525; and light chain CDRs SEQ ID NO:581, SEQ ID NO:545, and SEQ ID NO:534; or
heavy chain CDRs SEQ ID NO:523, SEQ ID NO: 524, and SEQ ID NO:525; and light chain CDRs SEQ ID NO:582, SEQ ID NO:545, and SEQ ID NO:534; or
heavy chain CDRs SEQ ID NO:523, SEQ ID NO: 524, and SEQ ID NO:525; and light chain CDRs SEQ ID NO:583, SEQ ID NO:545, and SEQ ID NO:534; or
heavy chain CDRs SEQ ID NO:523, SEQ ID NO: 524, and SEQ ID NO:525; and light chain CDRs SEQ ID NO: 584, SEQ ID NO:545, and SEQ ID NO:534; or
heavy chain CDRs SEQ ID NO:523, SEQ ID NO: 524, and SEQ ID NO:525; and light chain CDRs SEQ ID NO: 585, SEQ ID NO:545, and SEQ ID NO:534; or
heavy chain CDRs SEQ ID NO:523, SEQ ID NO: 524, and SEQ ID NO:525; and light chain CDRs SEQ ID NO: 586, SEQ ID NO:545, and SEQ ID NO:534; or
heavy chain CDRs SEQ ID NO:523, SEQ ID NO: 524, and SEQ ID NO:525; and light chain CDRs SEQ ID NO: 587, SEQ ID NO:545, and SEQ ID NO:534; or
heavy chain CDRs SEQ ID NO:523, SEQ ID NO:524, and SEQ ID NO:525; and light chain CDRs SEQ ID NO:588, SEQ ID NO:545, and SEQ ID NO:534; or
heavy chain CDRs SEQ ID NO:523, SEQ ID NO:524, and SEQ ID NO:525; and light chain CDRs SEQ ID NO:589, SEQ ID NO:545, and SEQ ID NO:534; or
heavy chain CDRs SEQ ID NO:523, SEQ ID NO:524, and SEQ ID NO:525; and light chain CDRs SEQ ID NO:590, SEQ ID NO:545, and SEQ ID NO: 534; or
heavy chain CDRs SEQ ID NO:523, SEQ ID NO:524, and SEQ ID NO:525; and light chain CDRs SEQ ID NO:572, SEQ ID NO:545, and SEQ ID NO:537; or
heavy chain CDRs SEQ ID NO:523, SEQ ID NO:524, and SEQ ID NO:525; and light chain CDRs SEQ ID NO:573, SEQ ID NO:545, and SEQ ID NO:537; or
heavy chain CDRs SEQ ID NO:523, SEQ ID NO:524, and SEQ ID NO:525; and light chain CDRs SEQ ID NO:574, SEQ ID NO:545, and SEQ ID NO:537; or
heavy chain CDRs SEQ ID NO:523, SEQ ID NO: 524, and SEQ ID NO:525; and light chain CDRs SEQ ID NO:575, SEQ ID NO:545, and SEQ ID NO:537; or
heavy chain CDRs SEQ ID NO:523, SEQ ID NO: 524, and SEQ ID NO:525; and light chain CDRs SEQ ID NO:576, SEQ ID NO:545, and SEQ ID NO:537; or
heavy chain CDRs SEQ ID NO:523, SEQ ID NO: 524, and SEQ ID NO:525; and light chain CDRs SEQ ID NO:577, SEQ ID NO:545, and SEQ ID NO:537; or
heavy chain CDRs SEQ ID NO:523, SEQ ID NO: 524, and SEQ ID NO:525; and light chain CDRs SEQ ID NO:578, SEQ ID NO:545, and SEQ ID NO:537; or
heavy chain CDRs SEQ ID NO:523, SEQ ID NO: 524, and SEQ ID NO:525; and light chain CDRs SEQ ID NO:579, SEQ ID NO:545, and SEQ ID NO:537; or
heavy chain CDRs SEQ ID NO:523, SEQ ID NO: 524, and SEQ ID NO:525; and light chain CDRs SEQ ID NO: 580, SEQ ID NO:545, and SEQ ID NO:537; or
heavy chain CDRs SEQ ID NO:523, SEQ ID NO: 524, and SEQ ID NO:525; and light chain CDRs SEQ ID NO:581, SEQ ID NO:545, and SEQ ID NO:537; or
heavy chain CDRs SEQ ID NO:523, SEQ ID NO: 524, and SEQ ID NO:525; and light chain CDRs SEQ ID NO: 582, SEQ ID NO:545, and SEQ ID NO:537; or
heavy chain CDRs SEQ ID NO:523, SEQ ID NO: 524, and SEQ ID NO:525; and light chain CDRs SEQ ID NO: 583, SEQ ID NO:545, and SEQ ID NO:537; or
heavy chain CDRs SEQ ID NO:523, SEQ ID NO:524, and SEQ ID NO:525; and light chain CDRs SEQ ID NO:584, SEQ ID NO:545, and SEQ ID NO:537; or
heavy chain CDRs SEQ ID NO:523, SEQ ID NO:524, and SEQ ID NO:525; and light chain CDRs SEQ ID NO:585, SEQ ID NO:545, and SEQ ID NO:537; or
heavy chain CDRs SEQ ID NO:523, SEQ ID NO:524, and SEQ ID NO:525; and light chain CDRs SEQ ID NO:586, SEQ ID NO:545, and SEQ ID NO:537; or
heavy chain CDRs SEQ ID NO:523, SEQ ID NO:524, and SEQ ID NO:525; and light chain CDRs SEQ ID NO:587, SEQ ID NO:545, and SEQ ID NO:537; or
heavy chain CDRs SEQ ID NO:523, SEQ ID NO:524, and SEQ ID NO:525; and light chain CDRs SEQ ID NO:588, SEQ ID NO:545, and SEQ ID NO:537; or
heavy chain CDRs SEQ ID NO:523, SEQ ID NO:524, and SEQ ID NO:525; and light chain CDRs SEQ ID NO:589, SEQ ID NO:545, and SEQ ID NO:537; or
heavy chain CDRs SEQ ID NO:523, SEQ ID NO: 524, and SEQ ID NO:525; and light chain CDRs SEQ ID NO:590, SEQ ID NO:545, and SEQ ID NO:537.

In some embodiments, the antibodies comprise the heavy and light chain CDR1, CDR2, and CDR3 sequences described above but contain 1, 2, or 3 conservative amino acid substitutions in one, two or more CDR sequences compared to those listed above.

In some embodiments, any of the antibodies disclosed herein can comprise one of the heavy chain variable regions selected from SEQ ID NO: 1, SEQ ID NO:9, SEQ ID NO: 17, SEQ ID NO:25, SEQ ID NO:33, SEQ ID NO:41, SEQ ID NO:49, SEQ ID NO:57, SEQ ID NO:65, SEQ ID NO:73, SEQ ID NO:81, SEQ ID NO:89, SEQ ID NO:97, SEQ ID NO:105, SEQ ID NO:113, SEQ ID NO:121, or SEQ ID NO:297, or SEQ ID NO:395, SEQ ID NO:403, SEQ ID NO:411, SEQ ID NO:419, SEQ ID NO:427, SEQ ID NO:435, or SEQ ID NO:443.

In some embodiments, any of the antibodies disclosed herein can comprise one of the light chain variable regions selected from SEQ ID NO:129, SEQ ID NO:137, SEQ ID NO: 145, SEQ ID NO:153, SEQ ID NO:161, SEQ ID NO:169, SEQ ID NO:177, SEQ ID NO:185, SEQ ID NO:193, SEQ ID NO:201, SEQ ID NO:209, SEQ ID NO:217, SEQ ID NO:225, SEQ ID NO:233, SEQ ID NO:241, SEQ ID NO:249, SEQ ID NO:257, SEQ ID NO:265, SEQ ID NO:273, SEQ ID NO:281, SEQ ID NO:289, SEQ ID NO:305, or SEQ ID NO:451, SEQ ID NO:459, SEQ ID NO:467, SEQ ID NO:475, SEQ ID NO:484, SEQ ID NO:492, or SEQ ID NO: 500.

In some embodiments, the antibodies disclosed here can comprise one or more or all of the light chain variable regions (CDRs or framework regions) selected from SEQ ID NO:565, SEQ ID NO:566, SEQ ID NO:567, SEQ ID NO:568, SEQ ID NO:569, SEQ ID NO:570, or SEQ ID NO:571.

In some embodiments, any of the antibodies disclosed herein can comprise one or more or all of the heavy chain variable regions (CDRs or framework regions) selected from SEQ ID NO:558, SEQ ID NO:559, SEQ ID NO:560, SEQ ID NO:561, SEQ ID NO:562, SEQ ID NO: 563, or SEQ ID NO: 564.

Heavy chain variable regions can be paired with light chain regions as desired, including or not limited to for variable regions comprising the paired CDRs as set forth above.

In addition, as noted above, the inventors have discovered that an RGDL sequence (SEQ ID NO:756) can be inserted into a light chain CDR1 sequence in an αvβ8-binding antibody to obtain an antibody that has six CDRs in total and that binds both αvβ8 and αvβ6.

The antibodies at least partially block ligand binding function. See, e.g., FIGS. 38A-D. Thus in some embodiments, antibodies are provided that bind to αvβ8 and αvβ6 and comprise an RGDL sequence (SEQ ID NO:756) in the light chain CDR1 sequence. For instance, in some embodiments the light chain CDR1 is between 20-22 amino acids (e.g., 21 amino acids) an optionally comprises KSSQSLL-GRGDLGRLKK (SEQ ID NO:765) or a sequence containing 1, 2, or 3 conservative amino acid substitutions.

Additionally, the inventors have discovered that an RGDL sequence (SEQ ID NO:756) can be inserted into a light chain CDR1 sequence in an αvβ8-binding antibody to obtain an antibody that has six CDRs and that binds αvβ8, αvβ6 and αvβ3 (i.e., is tri-specific). See, Example 12.

In some embodiments, any antibody described herein can comprise a light chain CDR1 sequence selected from, but not limited to, SEQ ID NO:572, SEQ ID NO:573, SEQ ID NO:574, SEQ ID NO:575, SEQ ID NO:576, SEQ ID NO: 577, SEQ ID NO:578, SEQ ID NO:579, SEQ ID NO:580, SEQ ID NO:581, SEQ ID NO:582, SEQ ID NO: 583, SEQ ID NO:584, SEQ ID NO: 585, SEQ ID NO:586, SEQ ID NO:587, SEQ ID NO:588, SEQ ID NO: 589, and SEQ ID NO:590. In some embodiments, any of the light chain CDR1 sequences set forth in this paragraph can be combined with any light chain CDR2, light chain CDR3, heavy chain CDR1, heavy chain CDR2 and heavy chain CDR3, set forth herein.

In some embodiments, antibodies comprising the light chain CDR1 sequences described in the preceding paragraph can contain 1, 2, or 3 conservative amino acid substitutions in the CDR1 sequence compared to those listed above (i.e., SEQ ID NO:572-590).

In some embodiments, the antibodies can comprise the heavy chain CDR1, CDR2, and CDR3 sequences as provided herein, including but not limited to, e.g.,
SEQ ID NO:437, SEQ ID NO:439, and SEQ ID NO:441; or
SEQ ID NO:445, SEQ ID NO:447, and SEQ ID NO:449.

In some embodiments, the antibodies can comprise the heavy chain CDR1, CDR2, and CDR3 sequences described above but contain 1, 2, or 3 conservative amino acid substitutions in one, two or more CDR sequences compared to those listed above.

In some embodiments, the antibodies can comprise the light chain CDR1, CDR2, and CDR3 sequences as provided herein, including but not limited to, e.g.,
SEQ ID NO:494, SEQ ID NO:496, and SEQ ID NO:498; or
SEQ ID NO:502, SEQ ID NO:504, and SEQ ID NO:506.

In some embodiments, the antibodies can comprise the light chain CDR1, CDR2, and CDR3 sequences described above but contain 1, 2, or 3 conservative amino acid substitutions in one, two or more CDR sequences compared to those listed above.

Heavy chain variable regions can be paired with light chain regions as desired, including or not limited to for variable regions comprising the paired CDRs as set forth above.

For preparation and use of suitable antibodies as described herein, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see. e.g., Kuby, *Immunology* ($3^{rd}$ ed. 1997)). Techniques for the production of single chain antibodies or recombinant antibodies (U.S. Pat. Nos. 4,946, 778, 4,816,567) can be adapted to produce antibodies to polypeptides of this invention. Also, transgenic mice, or other organisms such as other mammals, can be used to express humanized or human antibodies (see, e.g., U.S. Pat. Nos. 5,545,807; 5,545,806; 5,569,825; 5,625,126; 5,633, 425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Inmmunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Antibodies can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a di-cistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

An antibody as described herein can also be produced in various formats, including as a Fab, a Fab', a F(ab')$_2$, a scFv, or a dAB. The antibody fragments can be obtained by a variety of methods, including, digestion of an intact antibody with an enzyme, such as pepsin (to generate (Fab')$_2$ fragments) or papain (to generate Fab fragments); or de novo synthesis. Antibody fragments can also be synthesized using recombinant DNA methodology. In some embodiments, an anti-β8 antibody comprises F(ab')$_2$ fragments that specifically bind β8. An antibody of the invention can also include a human constant region. See, e.g., Fundamental Immunology (Paul ed., 4d ed. 1999); Bird, et al., *Science* 242:423 (1988); and Huston, et al., *Proc. Natl. Acad. Sci. USA* 85:5879 (1988).

Methods for humanizing or primatizing non-human antibodies are also known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In some cases, the antibody or antibody fragment can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.* 17:780, 1999; and Humphreys, et al., *Protein Eng. Des.* 20:227, 2007). The antibody or antibody fragment can also be labeled, or conjugated to a therapeutic agent as described below.

The specificity of antibody binding can be defined in terms of the comparative dissociation constants (Kd) of the antibody for the target (e.g., β8) as compared to the dissociation constant with respect to the antibody and other materials in the environment or unrelated molecules in general. Typically, the Kd for the antibody with respect to the unrelated material will be at least 2-fold, 3-fold, 4-fold, 5-fold, 10-fold, 20-fold, 50-fold, 100-fold, 200-fold or higher than Kd with respect to the target.

The desired affinity for an antibody, e.g., high (pM to low nM), medium (low nM to 100 nM), or low (about 100 nM or higher), may differ depending upon whether it is being used as a diagnostic or therapeutic. For example, an antibody with medium affinity may be more successful in localizing to desired tissue as compared to one with a high affinity. Thus, antibodies having different affinities can be used for diagnostic and therapeutic applications.

A targeting moiety will typically bind with a Kd of less than about 1000 nM, e.g., less than 250, 100, 50, 20 or lower nM In some embodiments, the Kd of the affinity agent is less than 15, 10, 5, or 1 nM. In some embodiments, the Kd is 1-100 nM, 0.1-50 nM. 0.1-10 nM, or 1-20 nM. The value of the dissociation constant (Kd) can be determined by well-known methods, and can be computed even for complex mixtures by methods as disclosed, e.g., in Caceci et al., Byte (1984) 9:340-362.

Affinity of an antibody, or any targeting agent, for a target can be determined according to methods known in the art, e.g., as reviewed in Ernst et al. Determination of Equilibrium Dissociation Constants, *Therapeutic Monoclonal Antibodies* (Wiley & Sons ed. 2009).

Quantitative ELISA, and similar array-based affinity methods can be used. ELISA (Enzyme linked immunosorbent signaling assay) is an antibody-based method. In some cases, an antibody specific for target of interest is affixed to a substrate, and contacted with a sample suspected of containing the target. The surface is then washed to remove unbound substances. Target binding can be detected in a variety of ways, e.g., using a second step with a labeled antibody, direct labeling of the target, or labeling of the primary antibody with a label that is detectable upon antigen binding. In some cases, the antigen is affixed to the substrate (e.g., using a substrate with high affinity for proteins, or a Strepavidin-biotin interaction) and detected using a labeled antibody (or other targeting moiety). Several permutations of the original ELISA methods have been developed and are known in the art (see Lequin (2005) *Clin. Chem.* 51:2415-18 for a review).

The Kd, Kon, and Koff can also be determined using surface plasmon resonance (SPR), e.g., as measured by using a Biacore T100 system or using kinetic exclusion assays (e.g., KinExA®). SPR techniques are reviewed, e.g., in Hahnfeld et al. Determination of Kinetic Data Using SPR Biosensors, *Molecular Diagnosis of Infectious Diseases* (2004). In a typical SPR experiment, one interactant (target or targeting agent) is immobilized on an SPR-active, gold-coated glass slide in a flow cell, and a sample containing the other interactant is introduced to flow across the surface. When light of a given frequency is shined on the surface, the changes to the optical reflectivity of the gold indicate binding, and the kinetics of binding. Kinetic exclusion assays is the preferred method to determine affinity unless indicated otherwise. This technique is described in, e.g. Darling et al., *Assay and Drug Development Technologies* Vol. 2, number 6 647-657 (2004).

Binding affinity can also be determined by anchoring a biotinylated interactant to a streptavidin (SA) sensor chip. The other interactant is then contacted with the chip and detected, e.g., as described in Abdessamad et al. (2002) *Nuc. Acids Res.* 30:e45.

Also provided are polynucleotides encoding the antibodies described herein, or binding fragments thereof comprising at least heavy chain or light chain CDRs or both, e.g., polynucleotides, expression cassettes (e.g., a promoter linked to a coding sequence), or expression vectors encoding heavy or light chain variable regions or segments comprising the complementary determining regions as described herein. In some embodiments, the polynucleotide sequence is optimized for expression, e.g., optimized for mammalian expression or optimized for expression in a particular cell type.

III. Methods of treatment

The anti-αvβ8 antibodies described herein (including αvβ8 binding fragments thereof, labeled antibodies, immunoconjugates, pharmaceutical compositions, etc.) as well as antibodies that bind both αvβ8 and αvβ6 as described herein or binding fragments thereof can be used to detect, treat, ameliorate, or prevent chronic obstructive pulmonary disease (COPD) and asthma, inflammatory bowel disease, inflammatory brain autoimmune disease, multiple sclerosis, a demylinating disease (e.g., transverse myelitis, Devic's disease, Guillain-Barré syndrome), neuroinflammation, kidney disease, or glioma, arthritis, fibrotic disorders, such as airway fibrosis, idiopathic pulmonary fibrosis, non-specific interstitial pneumonia, post-infectious lung fibrosis, diffuse alveolar damage, collagen-vascular disease associated lung fibrosis, drug-induced lung fibrosis, silicosis, asbestos-related lung fibrosis, respiratory bronchiolitis, respiratory bronchiolitis interstitial lung disease, desquamative interstitial fibrosis, cryptogenic organizing pneumonia, chronic hypersensitivity pneumonia, drug-related lung or hepatic fibrosis, renal fibrosis, and liver fibrosis (e.g., induced by alcohol, drug use, steatohepatitis, viral infection (e.g., hepatitis B or C), choleostasis, etc., and cancer, including but not limited to adenocarcinoma, squamous carcinoma, breast carcinoma, and cancer growth and metastasis.

Accordingly, the antibodies and pharmaceutical compositions described herein can be administered to a human having or suspected of having one of the above-listed diseases in an appropriate dosage to ameliorate or treat one of the disease or at least one symptom thereof.

Without intending to limit the scope of the invention, in some embodiments it is believed that antibodies described herein function in part by triggering an increase in MHCII expression in antigen presenting cells. See, e.g., FIG. 36A-F.

Moreover, the anti-αvβ8 antibodies described herein (including αvβ8 binding fragments thereof, labeled antibodies, immunoconjugates, pharmaceutical compositions, etc.) can be used to treat, ameliorate, or prevent viral infections (e.g., by stimulating an immune response). Other antibodies that specifically bind to αvβ8 and that block binding of one or more αvβ8 ligand, for example such as described in WO2011/103490 or WO2015/026004 can also be used to treat, ameliorate, or prevent viral infections. Exemplary viral infections include but are not limited to hepatitis A, B (HBV), and C (HCV), herpes simplex virus (e.g., HSVI, HSVII), HIV, and influenza infections, all of which are enhanced by Treg-mediated immune suppression (Keynan, Y, et al., *Clin Infect Dis.* 2008 Apr. 1; 46(7): 1046-52.

Also provided are pharmaceutical compositions comprising the present anti-αvβ8 antibodies or antigen-binding molecules as well as antibodies that bind both αvβ8 and αvβ6 as described herein or binding fragments thereof, either of which can be formulated together with a pharmaceutically acceptable carrier. The compositions can additionally contain other therapeutic agents that are suitable for treating or preventing a given disorder. Pharmaceutically carriers can enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition as described herein can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, intranasal, inhalational, spinal or epidermal administration (e.g., by injection or infusion). Depending on the route of administration, the active compound, i.e., antibody, may be coated in a material to protect the compound from the action of acids and other natural conditions that may inactivate the compound.

The antibodies, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

In some embodiments, the composition is sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. Pharmaceutically acceptable carriers are determined in part by the particular composition being administered, as well as by the particular method used to administer the composition. Accordingly, there is a wide variety of suitable formulations of pharmaceutical compositions of the present invention. Applicable methods for formulating the antibodies and determining appropriate dosing and scheduling can be found, for example, in *Remington: The Science and Practice of Pharmacy,* 21$^{st}$ Ed., University of the Sciences in Philadelphia, Eds., Lippincott Williams & Wilkins (2005); and in *Martindale: The Complete Drug Reference*, Sweetman, 2005, London: Pharmaceutical Press., and in Martindale, *Martindale: The Extra Pharmacopoeia,* 31st Edition., 1996, Amer Pharmaceutical Assn, and Sustained and Controlled Release Drug Delivery Systems, J. R. Robinson, ed., Marcel Dekker, Inc., New York, 1978, each of which are hereby incorporated herein by reference. Pharmaceutical compositions are preferably manufactured under GMP conditions. Typically, a therapeutically effective dose or efficacious dose of the anti-αvβ8 antibody is employed in the pharmaceutical compositions of the invention. The anti-αvβ8 antibodies are formulated into pharmaceutically acceptable dosage forms by conventional methods known to those of skill in the art. Dosage regimens are adjusted to provide the desired response (e.g., a therapeutic response). In determining a therapeutically or prophylactically effective dose, a low dose can be administered and then incrementally increased until a desired response is achieved with minimal or no undesired side effects. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

In some embodiments, the pharmacological compositions comprise a mixture of the anti-αvβ8 antibody or antigen binding molecule (e.g. that blocks ligand binding or blocks activation by ligand binding) and a second pharmacological agent. Without intending to limit the invention, it is noted that the inventors have found that thymic stromal lymphopoietin (TSLP) is an inducer of viral clearance in a mouse model of acute and chronic HBV and thus is useful to combine TSLP with an antibody as described herein for anti-viral treatments. Moreover, the inventors have found that OX40 agonists are effective in stimulating an immune response to HBV in combination with an antibody as described herein.

As an alternative to mixing the anti-αvβ8 antibody and second pharmacological agent in a pharmacological composition, the anti-αvβ8 antibody and second pharmacological agent can be separately administered to the human in need thereof within a time frame (e.g., within 3, 2, or 1 day or within 24, 13, 6, or 3 hours of each other).

IV. Diagnostic Compositions and Applications

Integrin αvβ8 is expressed on fibroblasts, stellate cells, chondrocytes, activated macrophages and subsets of T and B-cells. Integrin αvβ8 is increased in expression in fibroblasts in COPD and pulmonary fibrosis, and can be used as a surrogate marker for increased fibroblast cell mass. Thus the presently disclosed antibodies can be broadly applicable to bioimaging strategies to detect fibroinflammatory processes. The presently described therapeutic and diagnostic antibodies can be applied to: inflammatory bowel disease (IBD), chronic obstructive pulmonary disease (COPD), asthma, arthritis, a hepatic fibroinflammatory disorder, alcohol induced liver injury, non-alcoholic steatohepatitis (NASH), viral hepatitis, and primary biliary cirrhosis (PBC), graft rejection after liver transplantation, autoimmune hepatitis, an autoimmune disorder, lupus erythematosus, scleroderma, dermatomyositis, bullous pemphigoid, pemphigus vulgaris, a pulmonary fibrotic disorder, an inflammatory brain autoimmune disease, multiple sclerosis, a demyelinating disease, neuroinflammation, kidney disease, glomerulonephritis, hepatocellular carcinoma (HCC), adenocarcinoma, squamous carcinoma, glioma, melanoma, prostate, ovarian, uterine and breast carcinoma.

The inventors have found that β8 and PD-L1 expression inversely correlate. Thus, anti-αvβ8 antibodies described herein can be used as a marker for PD-L1 expression and optionally for selecting invenniduals most likely to benefit from anti-αvβ8 treatment.

Anti-αvβ8 antibodies described herein (including αvβ8 binding fragments thereof, affinity matured variants, or scFvs) can be used for diagnosis, either in vivo or in vitro (e.g., using a biological sample obtained from an individual). In addition to the above-described antibodies, antibodies having the following CDRs can be used for diagnosis and prognosis: heavy chain CDRs SEQ ID NO:299, SEQ ID NO:301, and SEQ ID NO:303; and light chain CDRs SEQ ID NO:307, SEQ ID NO:309, and SEQ ID NO:311. In some embodiments, the antibodies have a heavy chain variable region comprising SEQ ID NO:297 and a light chain variable region of SEQ ID NO:305. Alternatively, any antibodies having heavy chain CDRs or a heavy chain variable region as set forth in FIG. 53 and light chain CDRs or a light chain variable region from a corresponding sequence as set forth in FIG. 54 can be used. The antibodies are particularly useful in detecting αvβ8 in samples that have been fixed, for example in formalin-fixed samples, including for example formalin-fixed paraffin-embedded (FFPE) biological (e.g., tissue or cell) samples.

When used for detection or diagnosis, the antibody is typically conjugated or otherwise associated with a detectable label. The association can be direct e.g., a covalent bond, or indirect, e.g., using a secondary binding agent, chelator, or linker.

A labeled antibody can be provided to an individual to determine the applicability of an intended therapy. For example, a labeled antibody may be used to detect the integrin β8 density within a diseased area. For therapies intended to target TGFβ or αvβ8 activity (to reduce TGFβ or αvβ8 activity), the density of β8 is typically high relative to non-diseased tissue. A labeled antibody can also indicate that the diseased area is accessible for therapy. Patients can thus be selected for therapy based on imaging results. Anatomical characterization, such as determining the precise boundaries of a cancer, can be accomplished using standard imaging techniques (e.g., CT scanning, MRI, PET scanning, etc.). Such in vivo methods can be carried out using any of the presently disclosed antibodies.

Any of the presently disclosed antibodies can also be used for in vitro diagnostic or monitoring methods, e.g., using cells or tissue from a patient sample. In some embodiments, labeled F9 (or a β8 binding fragment or affinity-matured variant) is used, as it can bind fixed cells as well as non-fixed cells.

In some embodiments, the diagnostic antibody is a single-chain variable fragment (scFv). Intact antibodies (e.g., IgG) can be used for radioimmunotherapy or targeted delivery of therapeutic agents because they exhibit high uptake and retention. In some cases, the persistence in circulation of intact mAbs can result in high background (Olafsen et al. (2012) *Tumour Biol.* 33:669-77; Cai et al. (2007) *J Nucl Med.* 48:304-10). ScFvs, typically with a molecular mass of ~25 kD, are rapidly excreted by the kidneys, but are monovalent and can have lower affinity. The issues of monovalency can be overcome with advanced antibody engineering (as shown herein), where affinities can be improved to the low nM to pM range. Such antibodies have short enough half-lives to be useful as imaging agents and have suitable binding characteristics for tissue targeting (Cortez-Retamozo et al. (2004) *Cancer Res.* 64:2853-7). As shown herein, we have created a very high affinity scFV antibody derivatives of 4F1, 6B9, called F9, that can be converted to humanized scFV platforms. These improved antibodies are not function blocking, and thus can be used in combination with a therapeutic agent that targets 138.

A diagnostic agent comprising an antibody described herein can include any diagnostic agent known in the art, as provided, for example, in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). The terms "detectable agent," "detectable moiety," "label," "imaging agent," and like terms are used synonymously herein. A diagnostic agent can be detected by a variety of ways, including as an agent providing and/or enhancing a detectable signal. Detectable signals include, but are not limited to, gamma-emitting, radioactive, echogenic, optical, fluorescent, absorptive, magnetic, or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like. PET is particularly sensitive and quantitative, and thus valuable for characterizing fibrotic processes in vivo (Olafsen et al. (2012) *Tumour Biol.* 33:669-77; Cai et al. (2007) *J Nucl Med.* 48:304-10). This is useful beyond a companion diagnostic and would be generally useful to diagnose, clinically stage and follow fibrotic patients during any treatment regimen.

A radioisotope can be incorporated into the diagnostic agents described herein and can include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga. In some embodiments, a nanoparticle can be labeled by incorporation of lipids attached to chelates, such as DTPA-lipid, as provided in the following references: Phillips et al., *Wiley Interdisciplinary Reviews: Nanomedicine and Nanobiotechnology*, 1(1): 69-83 (2008); Torchilin, V. P. & Weissig, V., Eds. *Liposomes 2nd Ed.*: Oxford Univ. Press (2003); Elbayoumi, T. A. & Torchilin, V. P., *Eur. J. Nucl. Med. Mol. Imaging* 33:1196-1205 (2006); Mougin-Degraef, M. et al., *Int'l J. Pharmaceutics* 344:110-117 (2007).

In some embodiments, a diagnostic agent can include chelators that bind, e.g., to metal ions to be used for a variety of diagnostic imaging techniques. Exemplary chelators include but are not limited to ethylenediaminetetraacetic acid (EDTA), [4-(1,4,8,11-tetraazacyclotetradec-1-yl) methyl] benzoic acid (CPTA), Cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7,10-tetraazacyclododecane-1,4,7,10-tetra(methylene phosphonic acid) (DOTP), 1,4,8,11-tetraazacyclotetradecane-1,4,8,11-tetraacetic acid (TETA), 1,4,7,10-tetraazacyclododecane-1,4,7,10-tetraacetic acid (DOTA), N$^1$,N$^1$-bis(pyridin-2-ylmethyl)ethane-1,2-diamine (ENPy2) and derivatives thereof.

In some embodiments, the diagnostic agent can be associated with a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Secondary binding ligands include, e.g., biotin and avidin or streptavidin compounds as known in the art.

In some embodiments, the diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives.

EXAMPLES

The following examples are offered to illustrate, but not to limit the claimed invention.

Example 1. Construction of Composite Antibody C6D4

ITGB-8 knockout mice were immunized with recombinant Human Integrin alpha V beta 8 (αvβ8) protein. Approximately 5000 hybridomas were generated and screened for their ability to bind to αvβ8 in an enzyme-linked immunosorbent assay (ELSA). Results were confirmed by cell staining, and function blocking was determined with the use of a transforming growth factor-beta (TGF-β) bioassay. Blocking antibodies were screened against a recombinant form of αvβ8 engineered to lack the specificity determining loop (SDL) of the β8 head domain. Antibodies not binding this engineered αvβ8 were then selected.

Variable (V) genes from eight hybridomas were next isolated, sequenced, and found to comprise seven $V_H$ and eleven $V_K$ genes that were unique but related. FIG. 1 and FIG. 2 provide sequence information for the products of these $V_H$ and $V_K$ genes. Sequence information is using the Kabat numbering scheme. Each V gene was amplified under mutagenic conditions, and a single-chain variable fragment (scFV) library was constructed by mixing the amplified cDNA and using splice overlap. The library served as an amplification template using primers designed to complement rabbit IgG expressing dual $V_H$ and $V_L$ vectors. Eleven distinct $V_H$ genes and sixteen distinct $V_K$ genes were identified after sequencing >100 random clones and transfected in 165 different combinations into 293 cells. The eight pairs that produced the best binders were determined by cell staining and FACS analysis, and by measuring binding affinity for CHO cells expressing αvβ8. The eight pairs each comprised a $V_H$ domain selected from RSDLVH-1, RSDLVH-3, and RSDLVH-16; and a $V_K$ domain selected from RSDLVK-1, RSDLVK-6, RSDLVK-10, and RSDLVK-13; the sequences of which are shown in FIG. 1 and FIG. 2.

These eight rabbit IgG $V_H/V_K$ pairs were then used to create a new mutagenic scFV yeast display library that was inserted into a yeast expression library vector. Two high-affinity binders from this selection and affinity maturation step were identified and designated clone 29 and clone 44. Random mutation mutagenic libraries were next made from genes of clones 29 and 44, and from these libraries the higher-affinity binding clones C6 and D4 were selected and determined (FIG. 1 and FIG. 2). Mutations in the complementarity-determining regions (CDRs) of C6 $V_H$ and D4 $V_K$ were identified, and the two chains were combined to create the composite antibody C6D4 (FIG. 1 and FIG. 2).

Example 2. Characterization of C6D4 Binding Affinity

A Kinetic Exclusion Assay (KINEXA®) was used to measure the binding affinity of C6D4. The affinity as a murine IgG2a was measured as 832 pM. As a recombinant IgG, C6D4 was found to result in substantially complete blockage of αvβ8-mediated TGF-β activation. This result implies blockage that is better than with B5, an allosteric inhibitor of αvβ8-mediated TGF-β activation. (Minagawa, et al, Sci Trans Med. 2014 Jun. 18; 6(241):241ra79)

C6D4 was also shown to block adhesion of cells to immobilized latent TGF-β. A peptide with the sequence DDHGRGDLGRLK (SEQ ID NO:713), which corresponds to as 257-268 of human TGF-β3 (NP_003230) was synthesized on an 8 lysine core (Multiple antigen presenting peptide, BioSyn) and used at 1 ug/ml to coat a 96 well ELISA plate. A truncated secreted form of αvβ8 which was fused in frame to alkaline phosphatase (Gline S E, et al. *J Biol Chem.* 2004 Dec. 24; 279(52):54567-72) was added with Mab at the indicated concentrations. The results (FIG. 19) show the superiority of C6D4 over B5 and the improvement of C6D4 compared to Clone 13C12. The table gives the IC50 values in µg/ml.

Further, a peptide with the sequence DDHGRGDLGRLK (SEQ ID NO:713), which corresponds to as 257-268 of human TGF-β3 (NP 003230) was synthesized on an 8 lysine core (Multiple antigen presenting peptide, BioSyn) and used at 0.51 ug/ml to coat a 96 well ELISA plate. CHO lec cells stably transfected with αvβ8 were allowed to bind to the peptide coated wells for 30 min at RT. Unbound cells were washed off with PBS. The Mab C6D4 was added at the indicated concentrations. Results were presented as stained cells detected after staining with crystal violet (OD590). The results (FIG. 20) show that C6D4 almost completely blocks cell adhesion to the peptide.

Example 3. Characterization of C6D4 Binding Structure

The current understanding of integrin structure is faced with the hurdle of having to reconcile two polar opposite views of integrin conformation. One camp proposes that integrins are always bent. The other believes that integrins must undergo a significant conformational "switchblade" change from a bent conformation to an extended conformation upon activation, opening the "headpieces" of the integrins to be fully functional. This model of integrin extension proposes one of the largest tertiary and quaternary structural rearrangements in biology.

Proof of such conformational extremes has been hampered by compromises and shortcomings associated with techniques routinely used in structural biology. Traditional crystallography produces crystal structures with atomic resolution but is reliant on the conformations and conditions under which crystals can be formed. In the case of integrins, only compact, closed conformations have been seen by crystallography. Alternatively, size exclusion chromatography (SEC) of integrins under activating conditions have demonstrated large shifts in size consistent with integrin extension. Such changes in conformation have been directly visualized using negative stain electron microscopy (EM) studies but at low resolution. Thus, the atomic details of the integrin ligand binding and the integrin activation mechanism remains unresolved.

Single-particle cryo-electron microscopy (cryoEM) can be used to determine the structure of biological macromolecules without crystals, thus offering an alternative that circumvents the obstacles of crystalizing integrins in the extended form. Recent hardware and software developments demonstrate that single-particle cryoEM has the power to provide atomic-level structural understanding of molecules that are traditionally challenging to study. Because single-particle cryoEM does not require the formation of crystals, and allows examination in the native functional conformations unaffected by crystal packing forces or high-salt crystallization buffers, this method is uniquely suited to understanding structures of proteins or integrin-ligand or integrin-Fab complexes that are difficult to crystallize. Here, we have used single particle cryoEM to address some of the biggest mysteries in structural biology, the structural mechanisms of integrin activation and conversely the mechanism of action of integrin inhibitors.

Previously published crystal structures of the latent TGF-β arginine-glycyine-aspartic acid (RGD) peptide of αvβ6 show the positioning of the TGF-β RGD in the αvβ6 binding pocket, as well as the positioning of the R of the TGF-β RGD proximate to the αv head. Cryo-electron microscopy of the new composite antibody C6D4 structure have now produced a ~4-5-angstrom-resolution structure of the C6D4 Fab binding to αvβ8. To generate the structures of αvβ8 in complex with C6D4, purified recombinant αvβ8 and C6D4 Fab complexes were isolated by size exclusion chromatography and then plunge frozen on grids in liquid nitrogen. Images of ~61,000 individual particle images captured by electron microscopy were selected to produce a 3D electron density map which was used to build model of αvβ8 in complex with C6D4 Fab using existing Protein Data Bank (PDB) entries for the integrin αvβ3, αIIbβ3, and Fabs with similar CDRs.

Figure 13A:
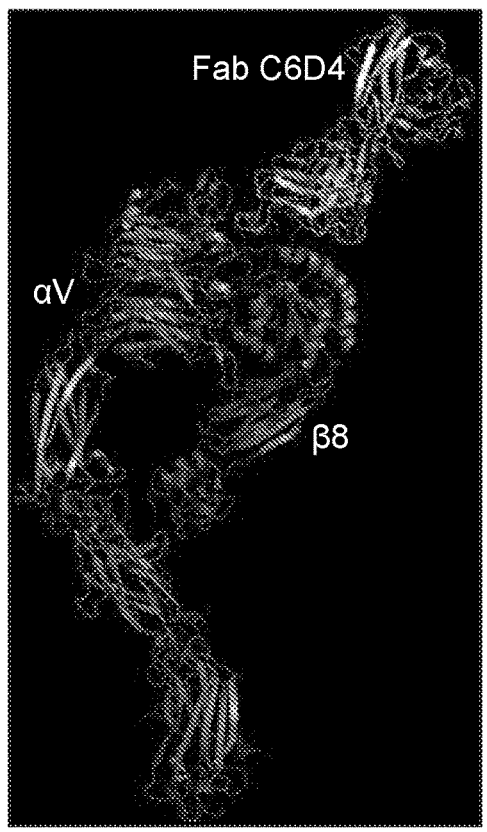
Figure 13B:
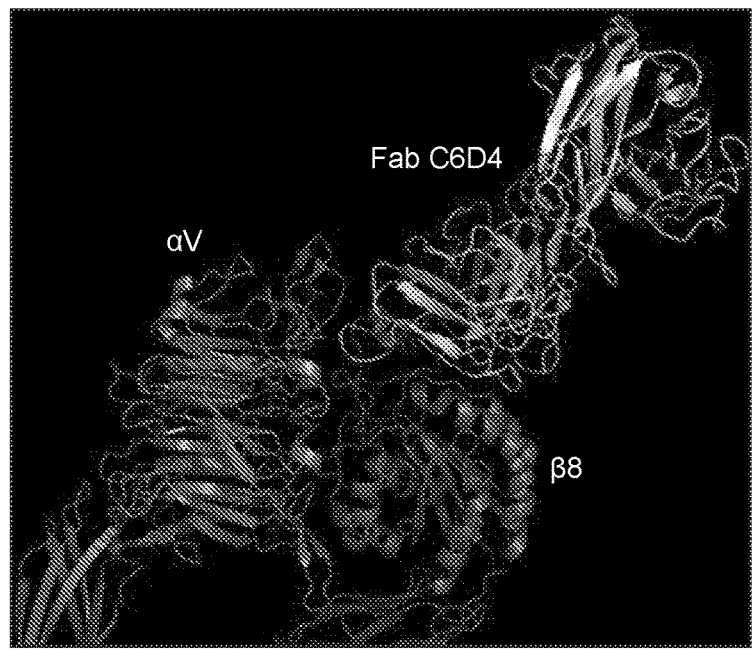

FIGS. 13A and 13B presents cryoEM results showing binding of the C6D4 Fab to the integrin αvβ8 at the head domain. FIGS. 13A and 13B illustrate this binding between C6D4 and αvβ8 in closer detail. From the C6D4 antibody footprint of FIG. 6, it can be seen that C6D4 binds primarily to the SDL loop of β8, making additional contacts with other secondary structures on the β8 α1 and α2 helices and on the head of αv. Together, these components of the binding configuration result in the almost complete occlusion of the ligand binding pocket. The residues of the β8 α1 and α2 helices and αv head that directly interact with C6D4 are further detailed in FIG. 7.

The elucidated structure shows that the CDR1 domain of the D4 $V_L$ binds close to the contact site for the R of RGD in the previously published αvβ6-RGD crystal structure. Because the αv subunit is shared by both αvβ6 and αvβ8, this finding suggests that the CDR1 loop of D4 $V_L$ is optimally positioned to sterically inhibit the binding of the R of RGD of latent TGF-β to αvβ8. On the other side of the SDL is a hydrophobic binding pocket having an L that immediately follows the RGD, forming an RGDL peptide. This hydrophobic pocket has been shown to be essential as a secondary binding site for the binding of the latent TGF-β RGD peptide to αvβ6. See, e.g., Shi M, et al., Nature 474(7351):343-9 (2011). The L or RGDL has also been shown to be essential for the binding of the latent TGF-β RGD peptide to αvβ8. (See, e.g., Ozawa, A, et al. *J Biol Chem.* 291(22): 11551-65 (2016). The CDR3 loop of C6 $V_H$ has now been shown to bind in such a way as to substantially cover the hydrophobic binding pocket located on the β8 subunit head domain. Additionally, C6D4 was found to interact extensively with the SDL of β8. FIG. 8 illustrates the overlapping of the C6D4 epitope with the ligand binding pocket of integrin αvβ8, showing how it can prevent the association of the integrin with latent TGF-β, and thus the activation of latent TGF-β. Importantly, all contact residues with C6D4 are believed to be conserved in αvβ8 across all mammalian species. This is in contrast to the allosteric inhibitor B5, which only reacts significantly against human αvβ8.

Example 4. Modeling of C6D4 Effects on Lung Cancer Survival

Syngeneic models for the study of lung cancer are very limited. The Lewis lung carcinoma (LLC) model is the only reproducible syngeneic lung cancer model currently widely in use. LLC is a cell line established from the lung of a C57BL mouse bearing a primary Lewis lung carcinoma. This line is highly tumorigenic and is used to model pulmonary metastasis that results after resection of the primary tumor. In this way the model mimics the clinical scenario closely. It is a useful model for evaluating the efficacy of chemotherapeutic agents in vivo. An advantage of the LLC model is that tumor cells are immunologically compatible, unlike the immunodeficient strains used in most other xenograft models. The LLC model was used as a preclinical model to evaluate vinorelbine prior to its use in clinical trials. The LLC cell line is injected subcutaneously into the subcutis of C57B6 mice, and within two weeks primary tumors reproducibly reach sizes of 10 mm. After resection of the primary tumor, lung metastasis appears in 2-4 weeks. The primary endpoints in this model are weight loss and lung metastasis number.

FIG. 9 presents result indicating that C6D4 increases survival in the LLC model. Mice received intraperitoneal injections of either C6D4 murine IgG2a or SV5 isotype control (7 mg/kg) at the time of primary tumor removal (day 0), and then once every week until weight loss exceeded 20%. The positive results indicate the first demonstration of an anti-β8 antibody inhibiting lung cancer metastasis. The fact that C6D4 inhibits lung cancer metastasis in this model indicates its potential as a treatment to prevent lung cancer metastasis. Because the mechanism of this antibody in cancer likely involves inhibiting the function or development of immunosuppressive Treg cells, C6D4 can have broad applications to any number of cancers where Treg cells play an immunosuppressive role.

FIG. 28 provides a schematic of the LLC model used herein to evaluate lung metastasis. The LLC tumor cell line is syngeneic to the host C57B/6 strain. This cell line does not express the integrins αvβ6 or αvβ8. The LLC. 1 cell line has been passed though mice one time and regrown from lung metastasis. After two weeks, subcutaneously injected tumor ($1\times10^6$) LLC.1 cells form large tumor nodules (~1 cm). The tumors are removed surgically and when animals lose 20% of their body weight they are euthanized.

The LLC model lung metastasis experiment described in the preceding paragraph was repeated eleven (11) times and the results in each of the eleven experiments were found to be similar (data not shown). FIGS. 29A and 29B present data from the eleventh experiment indicating that C6D4 increases survival in the LLC model. In each instance, mice received intraperitoneal injections of either C6D4 murine IgG2a or SV5 isotype control (7 mg/kg) at the time of primary tumor removal (day 0), and then once every week until weight loss exceeded 200%. The results indicate the anti-β8 antibody (C6D4) inhibits lung cancer metastasis. Survival curves in FIG. 29A represent mice euthanized for reasons of local recurrence or weight loss. In FIG. 29B, the animals removed for local recurrence are excluded. At autopsy, the animals with 20% weight loss all have metastatic implants in their lungs. The C6D4 antibodies were injected for up to 90 days in surviving animals. Interestingly, post-mortem examination did not reveal any abnormal inflammatory response in the tissues examined. The fact that C6D4 inhibits lung cancer metastasis in this model indicates its potential as a treatment to prevent lung cancer metastasis. Because the mechanism of this antibody in cancer likely involves inhibiting the function or development of immunosuppressive Treg cells, C6D4 can have broad applications to any number of cancers where Treg cells play an immunosuppressive role.

The effect of C6D4 was also evaluated with respect to tumor growth and tumor immune response. From the resected LLC. I1 primary tumors in mice that received two injections of isotype control (B5, which only cross reacts with human and not mouse b8) or C6D4 (which cross-reacts with mouse and human), the primary tumor weights were recorded and dimensions measured. The tumors were enzymatically disaggregated and immune cells isolated and counted. Flow cytometry was performed and tumor infiltrating immune cells separated from tumor cells using Percoll gradient centrifugation. FIGS. 30A-F is one of three experiments with similar results (remaining data not shown). In each experiment, n was greater than, or equal to, 10 in each test group.

Example 5. C6D4 Effects on Metastatic Disease Using a Melanoma Disease Model

A model for the study of metastasis was tested herein that utilized the B16-F10 tumor cell line. The B16-F10 highly metastatic tumor cell line is syngenic to the host C57B/6 strain. This line does not express the integrins αvβ6 or αvβ8. The B16-F10 cell line was transfected with murine ITGb8 and after selection in G418 and two rounds of sorting, a pool of high expressing αvβ8 cells were identified. When injected intravenously via the tail vein, visible lung metastases appeared within 14 days. A schematic of the metastatic disease melanoma model described in this paragraph is provided in FIG. 31. After three injections (i.p.) of isotype control (SV5) or C6D4, both at 7 mg/kg, at days 0, 7 and 14, the mice were euthanized at day 18. FIG. 34A shows photographs of representative lungs in anterior and posterior views; visible lung metastases were counted and the total lung surface area involved with metastases was assessed.

FIG. 34B shows the total number of metastases and FIG. 34C shows the percentage of total lung surface area involved in metastatic melanoma.

Example 6. Modeling of C6D4 Effects on Hepatitis B Infection and Disease Outcome Because the hepatitis B virus (HBV) does not infect mice, research has typically focused on using transgenic and knockout mouse models to study HBV immunity. In this model, viral antigens in the liver are exposed to an immune system that is not immunologically tolerant, and that has not been previously exposed to HBV. The goal is to mimic the immunologic events that would normally occur during primary HBV infection. In addition, this model permits manipulation of the immune system that is exposed to the virus, to be able to identify and dissect the cells, cytokines, and chemokines contributing to chronic hepatitis or disease resolution.

To generate the model, the resident (tolerized) immune system of the HBV-transgenic mice is ablated by backcrossing to immune-deficient strains (Mombaerts et al. (1992) Nature 360:225 and Mombaerts et al. (1992) Cell 68:869). This breeding strategy generates animals expressing high levels of viral antigen (HBV-Env) or virus (HBV-replication) in the liver, in the absence of a tolerant immune system (Baron et al. (2002) Immunity 16:583). Into these mice, HBV-naive syngeneic splenocytes (the equivalent of a whole spleen) are transferred from wildtype mice to reconstitute the immune system, mimic the point of primary infection, and test the importance of cellular and soluble mediators in HBV pathogenesis. Careful monitoring of immune responses and pathologic outcomes has revealed the utility of this model in mimicking or modifying acute and chronic HBV infection (Publicover et al. (2011) J. Clin. Investigation 2011:1154 and Publicover et al. (2013) J. Clin. Investigation 123:3728). In this way, the mouse model provides an experimental system to examine the reversibility of the altered immune priming that facilitates HBV persistence, and to test immune-modulatory therapeutics.

Results shown in FIG. 10 indicate that C6D4 induces HBV viral clearance in the chronic infection mouse model without causing hepatitis. In the figure, HepB surface antigen (HBSag) is a surrogate for intact HBV. Clearance of HBSag is a marker of HBV clearance. ALT is the liver enzyme monitored to measure liver inflammation and damage. The normal range of ALT in mice is 15-40. It can be seen from the data that the C6D4 antibody promoted HBsAg clearance in three of four chronic HBV model mice.

Example 7. Construction and Characterization of Composite Antibody 4F1F9

A yeast display scFV library was created using V-genes from hybridoma clones 6B9 and 4F1, a new clone 6B9.1 was selected from this library, then another yeast display scFV library was created using the V-gene of 6B9.1 and random mutagenesis, sixteen affinity-matured variant from this second library were characterized in terms of binding affinity and two clones C4 and D10 were transformed in to rabbit IgG format, both reacts weakly with human β8 in formalin-fixed paraffin-embedded tissue. A third mutagenic scFV library was then created from the variable regions of these two antibodies and inserted in a phage display vector and displayed as scFv on the phage surface (FIG. 11A-B). The induced phage library was screened against immobilized paraffin-embedded human αvβ8. Multiple rounds of selection were carried out, and fifteen phage clones were characterized in detail before the final clone F9 (FIG. 11A-B) was picked and transformed into IgG format for in vitro characterization.

Clone F9 in the IgG format was found to work efficiently in formalin-fixed paraffin-embedded tissues. The clone can be suitable for use as a companion diagnostic, for example to determine tumors expressing αvβ8 or infiltrated by immune cells expressing αvβ8 (i.e. dendritic cells, Treg cells), as a bioimaging reagent for measuring β8-specific tumor uptake and for informing C6D4 treatment decisions. The F9 antibody can also be used to detect αvβ8 in fluid or tissue lysate samples using ELISA.

Example 8. Methods to Inhibit and/or Treat H. Pylori Pathogenicity

The bacterium Helicobacter pylori (H. pylori) infects the stomachs of approximately half of the world's population and is associated with peptic ulcer disease, gastric carcinoma and gastric lymphoma (MALToma). The pathogenicity of Helicobacter pylori is linked to a type IV secretion system and the cytotoxicity-associated gene pathogenicity island cagPAI. The cagPAI proteins are transcribed from a 40 kb stretch of H. pylori DNA encoding ~31 genes of which one, cagL, contains an RGDL integrin binding motif. This RGDL motif is thought to act as a receptor for integrins so that the H. pylori pilus can interact with gastric epithelial cells and then penetrate the cell membrane and the oncogenic toxin cagA can be injected into the cell (see Kwok, et al, Nature, 2007449, 862-866, and Barden, et al, Journal of Molecular Biology, 2015, 427 (6) Part B, 1304-1315). We have used the anti-β8 clone F9 to stain human stomach biopsies and have found that the integrin αvβ8 is expressed by gastric crypt epithelial cells and this expression is increased in patients with chronic active gastritis due to H. pylori infection (see FIGS. 21 and 22). The ectodomain of integrins αvβ6 and αvβ8, but not other RGD-binding integrins (αvβ1, αvβ3, αvβ5 and α5β1) have been shown to preferentially bind to CagL via an RGDL dependent mechanism (see Barden, et al, Gastroenterology, 2010, 138(3). Previously, it was thought that the α5β1 integrin was the main CagL receptor on gastric epithelial cells (see Kwok, et al, Nature, 2007, 449 (7164): 862-6. We have found that the integrins αvβ6 and αvβ8 bind with similar efficiency to CagL while the αvβ3 integrin does not bind to CagL (See FIG. 23). The αvβ8-mediated binding to CagL can be efficiently blocked by C6D4 (See FIG. 24). The αvβ8 integrin also mediates strong cell adhesion to CagL (see FIG. 25) and CagL can compete for αvβ8-mediated cell adhesion to the TGF-β3 RGD peptide, indicating that αvβ8 binds to the RGD site of CagL (See FIG. 26). C6D4 can efficiently block cell adhesion to CagL (See FIG. 27).

Blocking αvβ8-mediated binding of CagL with C6D4 or its derivatives (i.e. IgA, monomeric or dimeric) can be used as a method to inhibit H. Pylori pathogenicity (i.e. peptic ulcer disease, gastric carcinoma or MALToma) by blocking entry of the oncogenic toxin CagA. In addition, C6D4 could provide protection against H. Pylori itself or from its indirect oncogenic and toxic effects by inhibiting Treg function and increasing more effective immunity against H. Pylori, gastric carcinoma, and MALToma. Such effects can be predicted by findings in murine models where H. Pylori immune escape has been shown to be mediated by dendritic cell-induced Treg skewing and Th17 suppression (see Kao, et al, Gastroenterology, 2010 138(3): 1046-54). Because the integrin αvβ8-mediated TGF-β activation has been shown to be required for Treg development and function (see Worthington, et al, *Immunity*, 2015, Volume 42, Issue 5, pp. 903-915), inhibiting αvβ8-mediated TGF-β activation using C6D4 or its derivatives will protect against the oncogenic effects of *H. Pylori* infection by enhancing immunity to *H. Pylori* itself while simultaneously increasing anti-tumoral immunity. Another possible mechanism by which blocking αvβ8-mediated TGF-β activation with C6D4 or its derivatives could block Treg function is by inhibiting migration of Tregs to the *H. Pylori* infected gastric mucosa. The chemokine CCL20 is a potent chemokine for Tregs and dendritic cells, which are required for Treg differentiation, and αvβ8-mediated TGF-β activation provides a major contribution to CCL20 production and function (see Cook, et al, *Gut* (2014), 63(10):1550-9; Brand, et al, *J Biol Chem*, 2015, 290(23): 14717-28, Hashimoto, et al, *J Immunol* 195(3):1182-90.). Therefore, treating patients with C6D4 or another anti-αvβ8 antibody alone, in combination with antibodies to other CagL binding integrins (α5β1, Act-1, or αvβ6, 3G9) or in combination with standard *H. Pylori* therapy (i.e. bismuth salts, proton pump inhibitors, macrolides, amoxicillin, metronidazole) would treat not only the pathogenic mechanism of *H. Pylori* but would enhance immunity to more efficiently eliminate *H. Pylori*, while at the same time protecting and/or treating the malignant complications of chronic *H. pylori* infection.

Example 9. Construction of Composite Humanized Antibody C6D4

FIG. 46, FIG. 50, and FIG. 51, show sequence alignment of various C6D4 humanized clones. FIGS. 50 and 51 also provide heavy chain and light chain amino acid consensus sequences for the humanized C6D4 related clones. The C6D4 antibody humanization focused on the V domain framework region of both the heavy and light chain. The humanization process was performed to include three criteria:
(1) The humanized version of antibody (HuC6D4) should have similar or improved affinity and specificity for αvβ8 as the murine version C6D4;
(2) The final amino acid in the HuC6D4 antibody framework region should be as close as possible to the translated antibody framework region of the human germline version that was selected as the target gene family (VH1/VK3);
(3) Production levels of the final humanized version (HuC6D4) in IgG or other format should be scalable for industry application.

We designed a potential humanized lead version of the murine C6D4 based on the chosen germline of human antibody (VH1/VK3), and the humanization algorithm developed at UCSF, and other published information for antibody human drug development, with main consideration on IgG general structure, VH-VL interface, IgG folding packing, surface accessibility, vernier zone impact, humanization hotspots and other risk factors.

These designed lead versions were synthesized and expressed as scFV using yeast display. The measured Kd showed an approximate 2-fold decrease from the parent murine C6D4 scFv.

Next, a random mutation based yeast scFv display library was created using the humanized lead version as the starting point, and FACS sorting performed to pick the best binders to αvβ from the displayed yeast library. Three mutant candidates (C6D4-RGD1, C6D4-RGD2 and C6D4-RGD3) were chosen for further testing in IgG format (See, for example FIG. 38C and FIG. 39).

Example 10. Characterization of Humanized C6D4 and CD64-RGD3 Binding Affinity

Shown in FIG. 39 is cell surface staining experiments of C6Vh expressed with either RGD1, RGD2, or RGD3 mutants (as disclosed in Example 8) as rabbit IgG. Binding to human Cho cells expressing αvβ8 was expressed as a percentage of binding of C6D4. The results show that RGD3 mutant has substantially higher relative binding to αvβ8 as compared to wildtype C6D4, RGD1 mutant or RDG2 mutant.

Figure 40:
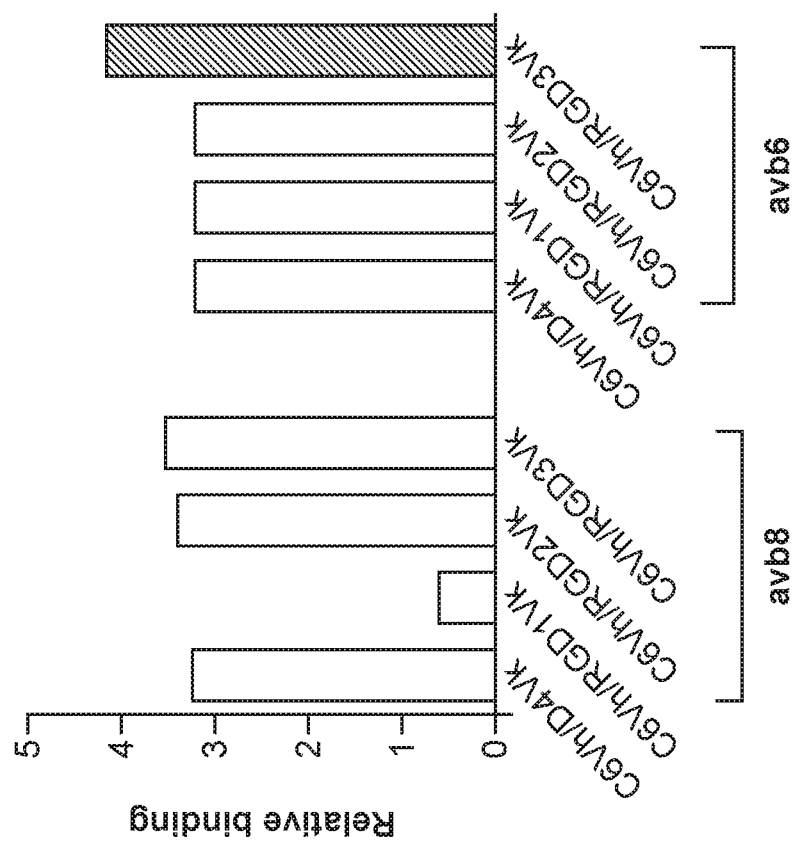

FIG. 40 shows cell surface staining experiments of C6Vh expressed with either D4 Vk or RGD1, RGD2 or RGD3 mutants (as disclosed in Example 8) as rabbit IgG. Binding to Cho cells expressing human αvβ8 or SW480 cells expressing αvβ6 are shown. Relative binding is defined as staining compared to staining of non-transfected Cho or SW480 cells. The results show that the C6D4-RGD3 mutant has substantially higher relative binding to αvβ6 as compared to wildtype C6D4, RGD1 mutant, or RDG2 mutant.

Figure 41:
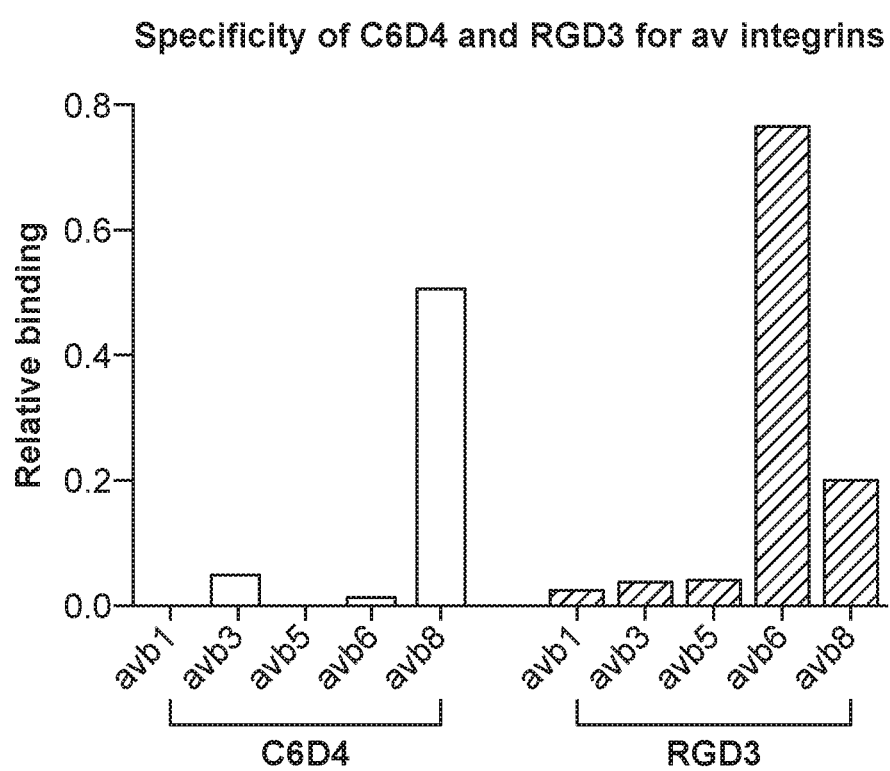
Figure 43A:
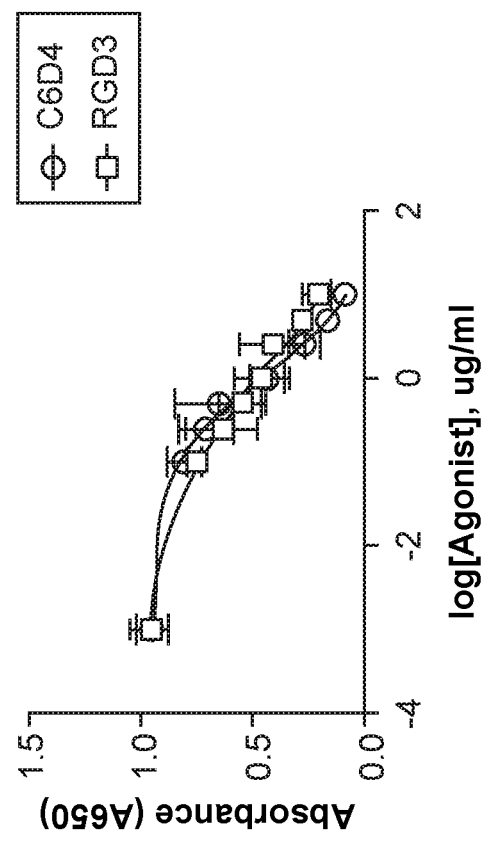
Figure 43B:
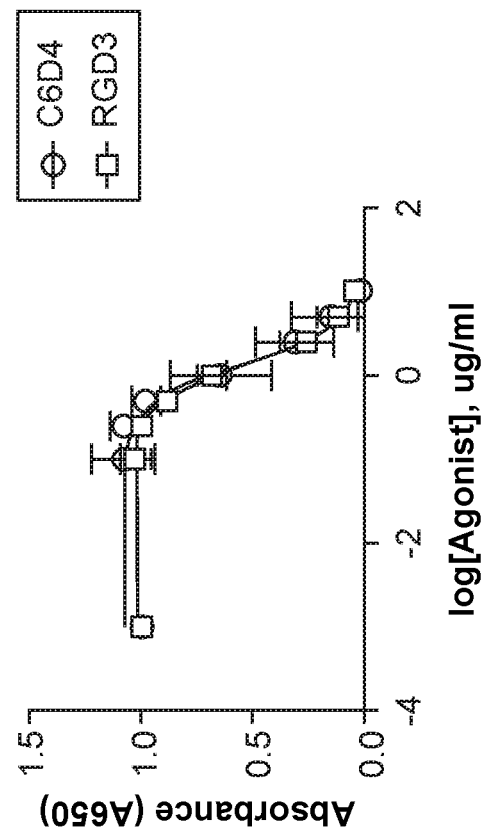
Figure 44A:
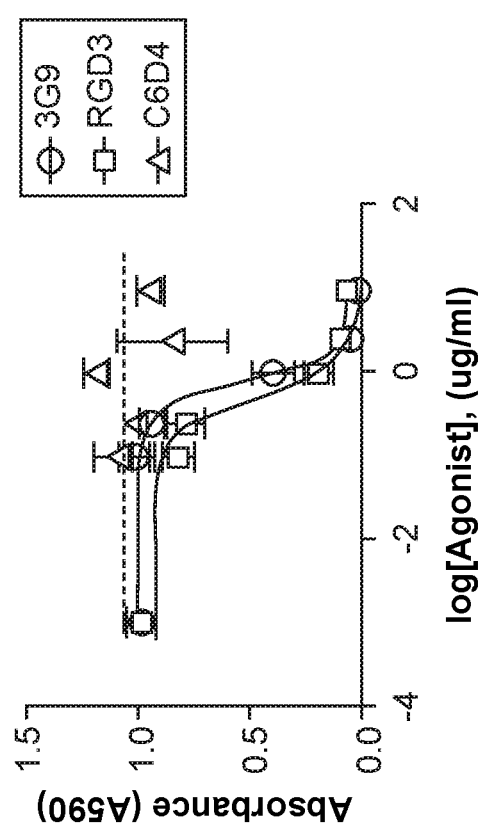
Figure 44B:
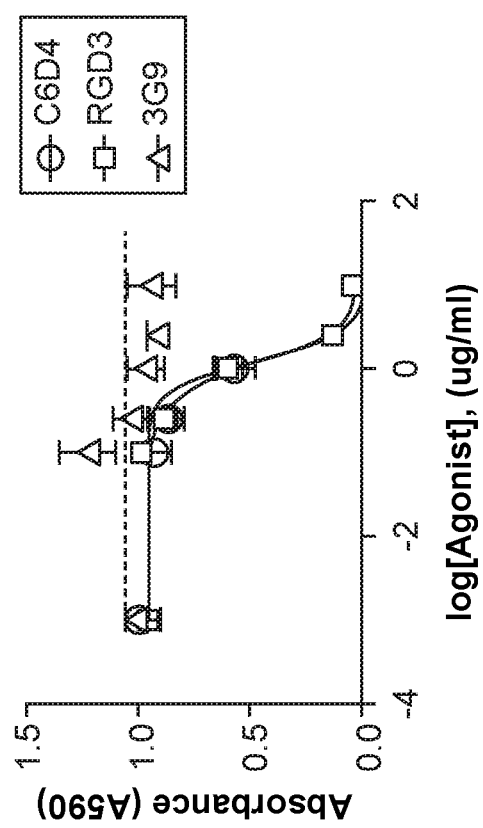
Figure 45:
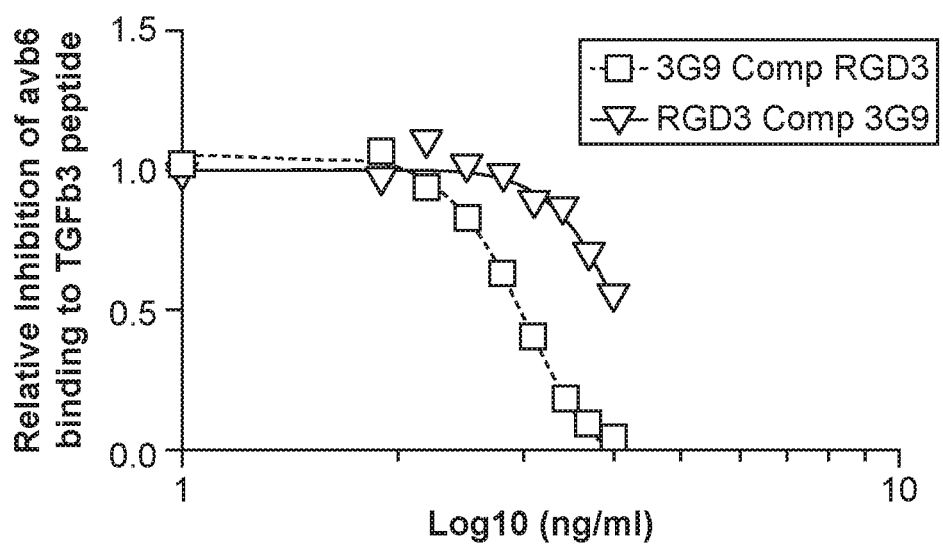

Shown in FIG. 41 is a binding experiment of C6Vh expressed with either D4 Vk or RGD1, RGD2 or RGD3 mutants (as disclosed in Example 8) as rabbit IgG to various av-integrins. The integrins αvβ1, αvβ3, αvβ5, αvβ6 and αvβ8 were purchased from R&D systems. All integrins were coated on ELISA plates at 2 mg/ml, blocked with BSA, and antibodies were allowed to bind. Binding of C6D4 and RGD3 was detected with anti-rabbit HRP. The results shown are relative to control wells coated with anti-av (clone 8B8) where av-integrins were detected with another av-antibody recognizing an non-overlapping epitope (L230-biotin), followed by SA-HRP. The results show that RGD3 mutant has substantially higher binding to αvβ6, while C6D4 has higher relative binding to αvβ8.

C6D4 and C6D4-RGD3 were also shown to bind avidly to αvβ8. Humanized C6D4 or C6D4-RGD3 (Frameworks and CH1 are human; hinge and CH2-3 are mouse) were immobilized on ELISA plates at the indicated concentrations. As a negative control, some wells were coated with anti-SV5 at the same concentrations. Non-specific binding sites were blocked with BSA. Recombinant αvβ8 ectodomain (0.5 ug/ml) was added to each well and after binding and washing in binding buffer (1 mM Ca"and Mg"), the bound αvβ8 was detected with biotinylated anti-αv (8b8) and detected with SA-HRP. The results of this experiment are shown as specific binding (minus SV5 control)(FIG. 47). The results show that C6D4 and C6D4-RGD3 outperform murine C6D4 and C6D4-RGD3 antibodies by avidly binding αvβ8.

Example 11. Characterization of Humanized C6D4-RGD3 Binding Structure

As set forth in Example 3, modeling and CryoEM maps can be used to provide structural information with respect to antibody binding. FIG. 48 presents a map of RGD3 binding to the ligand pocket of αvβ8. The map is derived from C6D4 in complex with αvβ8 and is compared to C6D4-RGD3 in complex with αvβ8. The density map when compared with the headpiece of αvβ6 in complex with LTGFβ1 shows the similarity of the position of the RGD residues of LTGFβ1 with the RGD residues of C6D4-RGD3. Magenta wire represent s RGD3+αvβ8 density map, Black represents C6D4+αvβ8 density map; Gold represents C6D4 Fab; Green represents the αv subunit; Blue represents the β8 subunit.

FIG. 49 is a cryoEM map showing the CDR Vk1 loop of C6D4-RGD3 occupies the ligand binding pocket of αvβ8. Here, models of C6D4 Fab-αvβ8 (FIG. 49A) are compared with RGD3-αvβ8 map (FIG. 49B) or in overlay (FIG. 49C) based on cryoEM derived density maps. The anti-αv 11D12V2 Fab was used to increase molecular mass of the complex and to assist in particle orientation. The results show that the C6D4 and C6D4-RGD3 complexes possess highly similar positioning.

Example 12. Characterization of D4-RGD3 Mutants Having Various Loop Length of the RGD and Flanking Sequence of Pro-TGF-Beta 3

There is an amphipathic alpha-helix following the R-G-D sequence of Latent-TGF-beta1 and Latent-TGF-beta3. Of the 3 engineered versions (RGD1, RGD2, RGD3) of D4 only RGD3 contained the amphipathic helix. Therefore, we engineered various loops containing portions of the RGD and flanking sequences of Pro-TGF-beta 3 to determine if loop length altered affinity, specificity or production of each clone. Because the Vh was not altered, we cloned all new constructs into the CDRL1 region of the C6D4 murine IgG expression vector and transfected the various new D4-RGD3-mutants into 293 cells. After 10 days, protein expression was compared using an murine IgG ELISA (shown as relative expression levels in the Table provided below). Integrins αvβ1, αvβ3, αvβ5, αvβ6 or αvβ8 (R&D systems) were coated on Immulon 4HBX ELISA plates (Thermo Scientific) for 1 hour at room temperature followed by blocking with a 5% bovine serum albumin solution (Sigma-Aldrich) overnight at 4° C. Supernatants with various RGD3 mutant antibodies were applied at 1/10 dilutions onto the wells for 1 hour at room temperature. Antibodies bound to the integrins were detected with an anti-mouse IgG-HRP antibody (GE Healthcare) and revealed with TMB substrate (Pierce). Binding was quantified by intensity as 0-4 (0 representing no apparent binding; 4 representing robust binding) and results normalized to expression. As can be seen from the data provided in the table below, different $CDR_{L1}$ swaps into Vk D4 show distinct binding specificities. As a result, we identified several mutants having bi-specific (e.g., RGD3-2 and RGD3-3) or tri-specific (e.g., RGD3-7 and RGD3-8) binding specificities.

| Inserted Vk $CDR_{L1}$ domain swap into D4 | Murine IgG H + L Vector | | IgG ELISA Expression | Binding to recombinant human integrins | | | | |
|---|---|---|---|---|---|---|---|---|
| $CDR_{L1}$ | Vh | Vk | Level | αvβ1 | αvβ3 | αvβ5 | αvβ6 | αvβ8 |
| KSSQSLLNSRSRKNYLA (SEQ ID NO: 572) | C6 | D4 | 4 | 0 | 0 | 0 | 0 | 4 |
| KSSQSLLNSGRGDLGNALA (SEQ ID NO: 574) | C6 | RGD2 | 4 | 0 | 0 | 0 | 0 | 2 |
| KSSQSLLGRGDLGRLKKQKDHNALA (SEQ ID NO: 576) | C6 | RGD3-1 | 3 | 0 | 0 | 0 | 4 | 1 |
| KSSQSLLGRGDLGRLKKQKDNALA (SEQ ID NO: 577) | C6 | RGD3-2 | 3 | 0 | 0 | 0 | 4 | 4 |
| KSSQSLLGRGDLGRLKKQKNALA (SEQ ID NO: 578) | C6 | RGD3-3 | 3 | 0 | 0 | 0 | 4 | 4 |
| KSSQSLLGRGDLGRLKKQNALA (SEQ ID NO: 579) | C6 | RGD3-4 | 3 | 0 | 0 | 0 | 4 | 4 |
| KSSQSLLGRGDLGRLKKNALA (SEQ ID NO: 575) | C6 | RGD3 | 3 | 0 | 0 | 0 | 4 | 4 |
| KSSQSLLGRGDLGRLKNALA (SEQ ID NO: 580) | C6 | RGD3-6 | 3 | 0 | 0 | 0 | 4 | 4 |
| KSSQSLLGRGDLGRLNALA (SEQ ID NO: 581) | C6 | RGD3-7 | 3 | 0 | 4 | 0 | 2 | 2 |
| KSSQSLLGRGDLGRNALA (SEQ ID NO: 582) | C6 | RGD3-8 | 3 | 0 | 3 | 0 | 3 | 3 |
| KSSQSLLGRGDLGNALA (SEQ ID NO: 573) | C6 | RGD1 | 2 | 0 | 0 | 0 | 0 | 1 |
| KSSQSLLGRGDLGRLKKQKDHH (SEQ ID NO: 583) | C6 | RGD3-9 | 1 | 0 | 0 | 0 | 3 | 0 |
| KSSQSLLGRGDLGRLKKQKDH (SEQ ID NO: 584) | C6 | RGD3-10 | 2 | 0 | 0 | 0 | 1 | 0 |
| KSSQSLLGRGDLGRLKKQKD (SEQ ID NO: 585) | C6 | RGD3-11 | 2 | 0 | 0 | 0 | 2 | 1 |
| KSSQSLLGRGDLGRLKKQK (SEQ ID NO: 586) | C6 | RGD3-12 | 2 | 0 | 1 | 0 | 2 | 0 |

-continued

| Inserted Vk CDR$_{L1}$ domain swap into D4 | Murine IgG H + L Vector | IgG ELISA Expression | Binding to recombinant human integrins | | | | |
|---|---|---|---|---|---|---|---|
| CDR$_{L1}$ | Vh Vk | Level | αvβ1 | αvβ3 | αvβ5 | αvβ6 | αvβ8 |
| KSSQSLLGRGDLGRLKKQ (SEQ ID NO: 587) | C6 RGD3-13 | 2 | 0 | 0 | 0 | 2 | 0 |
| KSSQSLLGRGDLGRLKK (SEQ ID NO: 588) | C6 RGD3-14 | 3 | 0 | 0 | 0 | 1 | 1 |
| KSSQSLLGRGDLGRLK (SEQ ID NO: 589) | C6 RGD3-15 | 3 | 0 | 0 | 0 | 0 | 0 |
| KSSQSLLGRGDLGRL (SEQ ID NO: 590) | C6 RGD3-16 | 3 | 0 | 0 | 0 | 0 | 0 |

Example 13. C6D4 Induces Th1 Bias and Increases CD8 IFN-γ Producing Cells

Seventeen C57B/7 mice were injected with $10^6$ Lewis lung carcinoma (LLC) tumor cells and 8 were injected IP with anti-SV5 (isotype control) or 9 mice with C6D4 (both groups at 7 mg/kg). Mab injections were repeated at day 7 and tumors were harvested at day 11. Tumor infiltrating lymphoid cells were isolated from tumors by enzyme digestion and Percoll gradient centrifugation and stained for CD45, TCRb, CD4, CD8 and surface capture assay for IFNg. Live CD45+ cells were gated and B220, Ly6g, CD11c, CD11b negative, TCRb positive cells were segregated in CD4, CD8, IFN-g positive subsets. The results from this experiment are shown in FIG. 54A-54D. Shown are percentages. *p<0.05, **p<0.01.

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

| Informal Sequence Listing | | |
|---|---|---|
| SEQ ID NO: 1 | B13C4 15-8 | EVQLQQSGPELKKPGETVKISCKASGY TFTDYSMH WVKQAPGKGLKWMG WIKTETGEPTYADDFKG RFAFSLETSATTAYLQINNLKNEDTAKYFCAI YYYGRDS WGQGTTLTVSS |
| SEQ ID NO: 2 | VH Framework 1 | EVQLQQSGPELKKPGETVKISCKASGY |
| SEQ ID NO: 3 | VH CDR1 | TFTDYSMH |
| SEQ ID NO: 4 | VH Framework 2 | WVKQAPGKGLKWMG |
| SEQ ID NO: 5 | VH CDR2 | WIKTETGEPTYADDFKG |
| SEQ ID NO: 6 | VH Framework 3 | RFAFSLETSATTAYLQINNLKNEDTAKYFCAI |
| SEQ ID NO: 7 | VH CDR 3 | YYYGRDS |
| SEQ ID NO: 8 | VH Framework 4 | WGQGTTLTVSS |
| SEQ ID NO: 9 | B13C4 15-10 | QIQLLQSGPELKKPGETVKISCKASGY TFTDYSMH WVKQAPGKGLKWMG WIKTETGEPTYADDFKG RFAFSLETSATTAYLQINNLKNEDTAKYFCAI YYYGRDS WGQGTTLTVSS |
| SEQ ID NO: 10 | VH Framework 1 | QIQLLQSGPELKKPGETVKISCKASGY |
| SEQ ID NO: 11 | VH CDR1 | TFTDYSMH |
| SEQ ID NO: 12 | VH Framework 2 | WVKQAPGKGLKWMG |
| SEQ ID NO: 13 | VH CDR2 | WIKTETGEPTYADDFKG |
| SEQ ID NO: 14 | VH Framework 3 | RFAFSLETSATTAYLQINNLKNEDTAKYFCAI |
| SEQ ID NO: 15 | VH CDR 3 | YYYGRDS |

Informal Sequence Listing

| | | |
|---|---|---|
| SEQ ID NO: 16 | VH Framework 4 | WGQGTTLTVSS |
| SEQ ID NO: 17 | B13H3.2 | QIQLLQSGPELKKPGETVKISCKASGY TFTDYSMH WVKQAPGKGLKWMG WIKTETDEPTYADDFKE RFAFSLETSASTANLQIINLKNEDTATYFCAI YYYGRDS WGQGTTLTVSSSEQ |
| SEQ ID NO: 18 | VH Framework 1 | QIQLLQSGPELKKPGETVKISCKASGY |
| SEQ ID NO: 19 | VH CDR1 | TFTDYSMH |
| SEQ ID NO: 20 | VH Framework 2 | WVKQAPGKGLKWMG |
| SEQ ID NO: 21 | VH CDR2 | WIKTETDEPTYADDFKE |
| SEQ ID NO: 22 | VH Framework 3 | RFAFSLETSASTANLQIINLKNEDTATYFCAI |
| SEQ ID NO: 23 | VH CDR 3 | YYYGRDS |
| SEQ ID NO: 24 | VH Framework 4 | WGQGTTLTVSSSEQ |
| SEQ ID NO: 25 | B13C1231015 | QIQLLQSGPELKKPGETVKISCKASGY TFTDYSIH WVKQAPGKGLKWMG WIKTETGEPTYADDFNG RFAFSLETSASTAYLQINNLKNEDTATYFCAI YYYGRDS WGQGTTLTVSS |
| SEQ ID NO: 26 | VH Framework 1 | QIQLLQSGPELKKPGETVKISCKASGY |
| SEQ ID NO: 27 | VH CDR1 | TFTDYSIH |
| SEQ ID NO: 28 | VH Framework 2 | WVKQAPGKGLKWMG |
| SEQ ID NO: 29 | VH CDR2 | WIKTETGEPTYADDFNG |
| SEQ ID NO: 30 | VH Framework 3 | RFAFSLETSASTAYLQINNLKNEDTATYFCAI |
| SEQ ID NO: 31 | VH CDR 3 | YYYGRDS |
| SEQ ID NO: 32 | VH Framework 4 | WGQGTTLTVSS |
| SEQ ID NO: 33 | B15B11Vh | QIQLLQSGPELKKPGETVKISCKASGY TFTDYSMH WVKQAPGKGLKWVA RINTETGEPTFADDFRG RFAVSLETSASTAYLQINNLKNEDTATYFCAI YYYGRDS WGQGTTLTVSS |
| SEQ ID NO: 34 | VH Framework 1 | QIQLLQSGPELKKPGETVKISCKASGY |
| SEQ ID NO: 35 | VH CDR1 | TFTDYSMH |
| SEQ ID NO: 36 | VH Framework 2 | WVKQAPGKGLKWVA |
| SEQ ID NO: 37 | VH CDR2 | RINTETGEPTFADDFRG |
| SEQ ID NO: 38 | VH Framework 3 | RFAVSLETSASTAYLQINNLKNEDTATYFCAI |
| SEQ ID NO: 39 | VH CDR 3 | YYYGRDS |
| SEQ ID NO: 40 | VH Framework 4 | WGQGTTLTVSS |
| SEQ ID NO: 41 | B2B2 15-9 | QIQLLQSGPELKKPGETVKISCLASGY TFTDYSMH WVKQAPGKGLKWVA RINTETGEPTFADDFGG RFAVSLETSASTAYLQINNLKENDTATYFCAI YYYGRDS WGQGTTLTVSS |
| SEQ ID NO: 42 | VH Framework 1 | QIQLLQSGPELKKPGETVKISCLASGY |
| SEQ ID NO: 43 | VH CDR1 | TFTDYSMH |
| SEQ ID NO: 44 | VH Framework 2 | WVKQAPGKGLKWVA |
| SEQ ID NO: 45 | VH CDR2 | RNTETGEPTFADDFGG |
| SEQ ID NO: 46 | VH Framework 3 | RFAVSLETSASTAYLQINNLKNEDTATYFCAI |
| SEQ ID NO: 47 | VH CDR 3 | YYYGRDS |
| SEQ ID NO: 48 | VH Framework 4 | WGQGTTLTVSSS |

| | | Informal Sequence Listing |
|---|---|---|
| SEQ ID NO: 49 | R11D12715.3 | EVQLVESGGGLVQPGGSLKLSCAASGF TFSSFGMS WVRQTPDKRLELVA TINSNGGSTYYPDNMKG TFTISRDNAKNTLYLQMNSSLKSEDTAMYYCAS ACYRYGAFFDY WGQGTTLTVSS |
| SEQ ID NO: 50 | VH Framework 1 | EVQLVESGGGLVQPGGSLKLSCAASGF |
| SEQ ID NO: 51 | VH CDR1 | TFSSFGMS |
| SEQ ID NO: 52 | VH Framework 2 | WVRQTPDKRLELVA |
| SEQ ID NO: 53 | VH CDR2 | TINSNGGSTYYPDNMKG |
| SEQ ID NO: 54 | VH Framework 3 | RFTISRDNAKNTLYLQMSSLKSEDTAMYYCAS |
| SEQ ID NO: 55 | VH CDR 3 | ACYRYGAFFDY |
| SEQ ID NO: 56 | VH Framework 4 | WGQGTTLTVSS |
| SEQ ID NO: 57 | RSDLVH-1 | EVQLLESGPELKKPGETVKISCKASGY TFTDYSIH WVKQAPGKGLKWMG WIKTETGEPTYADDFKG RFAFSLETSASTAYLQINNLKNEDTATYFCAI YYYGRDS WGQGTTVTVSS |
| SEQ ID NO: 58 | VH Framework 1 | EVQLLESGPELKKPGETVKISCKASGY |
| SEQ ID NO: 59 | VH CDR1 | TFTDYSIH |
| SEQ ID NO: 60 | VH Framework 2 | WVKQAPGKGLKWMG |
| SEQ ID NO: 61 | VH CDR2 | WIKTETPGETYADDFKG |
| SEQ ID NO: 62 | VH Framework 3 | RFAFSLETSASTAYLQINNLKNEDTATYFCAI |
| SEQ ID NO: 63 | VH CDR 3 | YYYGRDS |
| SEQ ID NO: 64 | VH Framework 4 | WGQGTTVTVSS |
| SEQ ID NO: 65 | RSDLVH-1 | EVQLLESGPELKKPGETVKISCKASGY TFTDYSIH WVKQAPGKGLKWMG WIKTETGEPTYADDFKG RFAFSLETSASTAYLQINNLKNEDTATYFCAI YYYGRDS WGQGTTVTVSS |
| SEQ ID NO: 66 | VH Framework 1 | EVQLLESGPELKKPGETVKISCKASGY |
| SEQ ID NO: 67 | VH CDR1 | TFTDYSIH |
| SEQ ID NO: 68 | VH Framework 2 | WVKQAPGKGLKWMG |
| SEQ ID NO: 69 | VH CDR2 | WIKTETGEPTYADDFKG |
| SEQ ID NO: 70 | VH Framework 3 | WFAFSLETSASTAYLQINNLKNEDTATYFCAI |
| SEQ ID NO: 71 | VH CDR 3 | YYYGRDS |
| SEQ ID NO: 72 | VH Framework 4 | WGQGTTVTVSS |
| SEQ ID NO: 73 | RSDLVH-3 | QVQLMQSGPELKKPGETVKISCKASGY TFTDYSIH WVKQAPGKGLKWMG WIKTETGEPTYADDFNG RFAFSLETSASTAYLQINNLKNEDTATYFCAI YYYGRDS WGQGTTLTVSS |
| SEQ ID NO: 74 | VH Framework 1 | QVQLMQSGPELKKPGETVKISCKASGY |
| SEQ ID NO: 75 | VH CDR1 | TFTDYSIH |
| SEQ ID NO: 76 | VH Framework 2 | WVKQAPGKGLKWMG |
| SEQ ID NO: 77 | VH CDR2 | WIKTETGEPTYADDFNG |
| SEQ ID NO: 78 | VH Framework 3 | RFAFSLETSASTAYLQINNLKNEDTATYFCAI |
| SEQ ID NO: 79 | VH CDR 3 | YYYGRDS |
| SEQ ID NO: 80 | VH Framework 4 | WGQGTTLTVSS |
| SEQ ID NO: 81 | RSDLVH-16 | QIQLQQSGPELKKPGETVKISCKASGY TFTDYSMH WVKQAPGKGLKWVA RINTETGEPTFADDFRG RFAVSLETSASTAYLQINNLKNEDTATYFCAI YYYGRDS WGQGTTLTVSS |
| SEQ ID NO: 82 | VH Framework 1 | QIQLQQSGPELKKPGETVKISCKASGY |
| SEQ ID NO: 83 | VH CDR1 | TFTDYSMH |
| SEQ ID NO: 84 | VH Framework 2 | WVKQAPGKGLKWVA |
| SEQ ID NO: 85 | VH CDR2 | RINTETGEPTFADDFRG |

| Informal Sequence Listing | | |
|---|---|---|
| SEQ ID NO: 86 | VH Framework 3 | RFAVSLETSASTAYLQINNLKNEDTATYFCAI |
| SEQ ID NO: 87 | VH CDR 3 | YYYGRDS |
| SEQ ID NO: 88 | VH Framework 4 | WGQGTTLTVSS |
| SEQ ID NO: 89 | 29 and 44 | QIQLLQSGPELKKPGETVKISCKASGY TFTDYSMH WVKQAPGKGLKWVA RINTETGEPTFADDFRG RFAVSLETSASTAYLQINNLKNEDTATYFCAI YYYGRDS WGQGTTLTVSS |
| SEQ ID NO: 90 | VH Framework 1 | QIQLLQSGPELKKPGETVKISCKASGY |
| SEQ ID NO: 91 | VH CDR1 | TFTDYSMH |
| SEQ ID NO: 92 | VH Framework 2 | WVKQAPGKGLKWVA |
| SEQ ID NO: 93 | VH CDR2 | RINTETGEPTFADDFRG |
| SEQ ID NO: 94 | VH Framework 3 | RFAVSLETSASTAYLQINNLKNEDTATYFCAI |
| SEQ ID NO: 95 | VH CDR 3 | YYYGRDS |
| SEQ ID NO: 96 | VH Framework 4 | WGQGTTLTVSS |
| SEQ ID NO: 97 | A1 = B4 = F9 | QIQLLQSGPELKKPGETVKISCKASGY TFTDYSMH WVKQAPGKGLKWVA RINTETGEPTFADDFRG RFAVSLETSASTAYLQINNLKNEDTATYFCAI YYYGRDT WGQGTTLSVSS |
| SEQ ID NO: 98 | VH Framework 1 | QIQLLQSGPELKKPGETVKISCKASGY |
| SEQ ID NO: 99 | VH CDR1 | TFTDYSMH |
| SEQ ID NO: 100 | VH Framework 2 | WVKQAPGKGLKWVA |
| SEQ ID NO: 101 | VH CDR2 | RINTETGEPTFADDFRG |
| SEQ ID NO: 102 | VH Framework 3 | RFAVSLETSASTAYLQINNLKNEDTATYFCAI |
| SEQ ID NO: 103 | VH CDR 3 | YYYGRDT |
| SEQ ID NO: 104 | VH Framework 4 | WGQGTTLSVSS |
| SEQ ID NO: 105 | A5 = C6 | QIQLLQSGPELKKPGETVKISCKASGY TFTDYSMH WVKQAPGKGLKWVA RINTETGEPTFADDFRG RFAVSLETSASTAYLQINNLKNEDTATYFCAI FYYGRDS WGQGTALTVSS |
| SEQ ID NO: 106 | VH Framework 1 | QIQLLQSGPELKKPGETVKISCKASGY |
| SEQ ID NO: 107 | VH CDR1 | TFTDYSMH |
| SEQ ID NO: 108 | VH Framework 2 | WVKQAPGKGLKWVA |
| SEQ ID NO: 109 | VH CDR2 | RINTETGEPTFADDFRG |
| SEQ ID NO: 110 | VH Framework 3 | RFAVSLETSASTAYLQINNLKNEDTATYFCAI |
| SEQ ID NO: 111 | VH CDR 3 | FYYGRDS |
| SEQ ID NO: 112 | VH Framework 4 | WGQGTALTVSS |
| SEQ ID NO: 113 | D4 = E6 | QIQLLQSGPELKKPGETVKISCKASGY TFTDYSMH WVKQAPGKGLKWVA RINTETGEPTFADDFRG RFAVSLETSASTAYLQINNLKNEDTATYFCAI YYYGRDS WGQGTTLTVSS |
| SEQ ID NO: 114 | VH Framework 1 | QIQLLQSGPELKKPGETVKISCKASGY |
| SEQ ID NO: 115 | VH CDR1 | TFTDYSMH |
| SEQ ID NO: 116 | VH Framework 2 | WVKQAPGKGLKWVA |
| SEQ ID NO: 117 | VH CDR2 | RINTETGEPTFADDFRG |
| SEQ ID NO: 118 | VH Framework 3 | RFAVSLETSASTAYLQINNLKNEDTATYFCAI |
| SEQ ID NO: 119 | VH CDR 3 | YYYGRDS |

| Informal Sequence Listing | |
|---|---|
| SEQ ID NO: 120 VH Framework 4 | WGQGTTLTVSS |
| SEQ ID NO: 121 C6D4 | QIQLLQSGPELKKPGETVKISCKASGY TFTDYSMH WVKQAPGKGLKWVA RINTETGEPTFADDFRG RFAVSLETSASTAYLQINNLKNEDTATYFCAI FYYGRDS WGQGTTLTVSS |
| SEQ ID NO: 122 VH Framework 1 | QIQLLQSGPELKKPGETVKISCKASGY |
| SEQ ID NO: 123 VH CDR1 | TFTDYSMH |
| SEQ ID NO: 124 VH Framework 2 | WVKQAPGKGLKWVA |
| SEQ ID NO: 125 VH CDR2 | RINTETGEPTFADDFRG |
| SEQ ID NO: 126 VH Framework 3 | RFAVSLETSASTAYLQINNLKNEDTATYFCAI |
| SEQ ID NO: 127 VH CDR 3 | FYYGRDS |
| SEQ ID NO: 128 VH Framework 4 | WGQGTTLVTVSS |
| SEQ ID NO: 129 35-20 | DIVMSQSPSSMYASLGERVTITC KASQDINSYLS WFQQKPGKSPKTLIY RANRLVD GVPSRFSGSGSGQDYSLTISSLEYEDMGIYYC LQYDEFPPLT FGAGTKLELKA |
| SEQ ID NO: 130 VL Framework 1 | DIVMSQSPSSMYASLGERVTITC |
| SEQ ID NO: 131 VL CDR1 | KASQDINSYLS |
| SEQ ID NO: 132 VL Framework 2 | WFQQKPGKSPKTLIY |
| SEQ ID NO: 133 VL CDR2 | RANRLVD |
| SEQ ID NO: 134 VL Framework 3 | GVPSRFSGSGSGQDYSLTISSLEYEDMGIYYC |
| SEQ ID NO: 135 VL CDR 3 | LQYDEFPPLT |
| SEQ ID NO: 136 VL Framework 4 | FGAGTKLELKA |
| SEQ ID NO: 137 B2B2 35-26 | QIVLTQSPSSMYASLGETVTITC KASQDINSYLS WFQQKPGKSPKTLIY RANRLVD GVPSRFSGSGSGQDYSLTISSLEYEDMGIYYC LQYDEFPPLT FGAGTKLELKA |
| SEQ ID NO: 138 VL Framework 1 | QIVLTQSPSSMYASLGERVTITC |
| SEQ ID NO: 139 VL CDR1 | KASQDINSYLS |
| SEQ ID NO: 140 VL Framework 2 | WFQQKPGKSPKTLIY |
| SEQ ID NO: 141 VL CDR2 | RANRLVD |
| SEQ ID NO: 142 VL Framework 3 | GVPSRFSGSGSGQDYSLTISSLEYEDMGIYYC |
| SEQ ID NO: 143 VL CDR 3 | LQYDEFPPLT |
| SEQ ID NO: 144 VL Framework 4 | FGAGTKLELKA |
| SEQ ID NO: 145 B15B11vk34-26 | QIVLTQSPAIMSASPGEKVTMTC SASSSVSYMH WYQQKPGTSPKLWIY STSNLAS GVPARFSGSGSGTSYSLTISSMEAEDAATYYC QQWSSNPLT RGSGTKLEIKA |
| SEQ ID NO: 146 VL Framework 1 | QIVLTQSPAIMSASPGEKVTMTC |
| SEQ ID NO: 147 VL CDR1 | SASSSVSYMH |
| SEQ ID NO: 148 VL Framework 2 | WYQQKPGTSPKLWIY |
| SEQ ID NO: 148 VL CDR2 | DTSNALS |
| SEQ ID NO: 150 VL Framework 3 | GVPARFSGSGSGTSYSLTISSMEAEDAATYYC |
| SEQ ID NO: 151 VL CDR 3 | QQWSSNPLT |
| SEQ ID NO: 152 VL Framework 4 | FGSGTKLEIKA |
| SEQ ID NO: 153 B15B11vk33-24 | EIVLTQSPAIMSASPGEKVTMTC SASSSVSYMH WYQQKPGSSPKLWIY DTSNLAS GVPARFSGSGSGTSYSLTISSMEAEDAATYYC QQWSSNPLT FGDGTRLEIKA |

| Informal Sequence Listing | | |
|---|---|---|
| SEQ ID NO: 154 | VL Framework 1 | EIVLTQSPAIMSASPGEKVTMTC |
| SEQ ID NO: 155 | VL CDR1 | SASSSVSYMH |
| SEQ ID NO: 156 | VL Framework 2 | WYQQKPGSSPKLWIY |
| SEQ ID NO: 157 | VL CDR2 | DTSNALS |
| SEQ ID NO: 158 | VL Framework 3 | GVPARFSGSGSGTSYSLTISSMEAEDAATYYC |
| SEQ ID NO: 159 | VL CDR 3 | QQWSSNPLT |
| SEQ ID NO: 160 | VL Framework 4 | FGDGTRLEIKA |
| SEQ ID NO: 161 | B15B11vk35-26 | QIVLTQSPAIMSASPGEKVTMTC SASSSVSYMH WYQQKSGTSPKLWIY DTSNALS GVPARFSGSGSGTSYSLTISSMEAEDAATYYC QQWSSNPPT FGAGTKLELKA |
| SEQ ID NO: 162 | VL Framework 1 | QIVLTQSPAIMSASPGEKVTMTC |
| SEQ ID NO: 163 | VL CDR1 | SASSSVSYMH |
| SEQ ID NO: 164 | VL Framework 2 | WYQQKSGTSPKLWIY |
| SEQ ID NO: 165 | VL CDR2 | DTSNLAS |
| SEQ ID NO: 166 | VL Framework 3 | GVPARFSGSGSGTSYSLTISSMEAEDAATYYC |
| SEQ ID NO: 167 | VL CDR 3 | QQWSSNPPT |
| SEQ ID NO: 168 | VL Framework 4 | FGSGTKLELKA |
| SEQ ID NO: 169 | B13C12134-25 | DIKMTQSPAIMSASPGEKVTMTC SASSSVSYMH WYQQKSGTSPKRWIY DTSKLAS GVPARFSGSGSGTSYSLTISSMEAEDAATYYC QQWSSNPFT FGSGTKLEIKA |
| SEQ ID NO: 170 | VL Framework 1 | DIKMTQSPAIMSASPGEKVTMTC |
| SEQ ID NO: 171 | VL CDR1 | SASSSVSYMH |
| SEQ ID NO: 172 | VL Framework 2 | WYQQKSGTSPKRWIY |
| SEQ ID NO: 173 | VL CDR2 | DTSKLAS |
| SEQ ID NO: 174 | VL Framework 3 | GVPARFSGSGSGTSYSLTISSMEAEDAATYYC |
| SEQ ID NO: 175 | VL CDR 3 | QQWSSNPFT |
| SEQ ID NO: 176 | VL Framework 4 | FGSGTKLEIKA |
| SEQ ID NO: 177 | B13C12133-26 | QMVLTHSPAIMSASPGEKVTMTC SASSSVSYMH WYQQKPGSSPKPWIY GTSNLAS GVPARFSGSGSGTSYSLTISRMEAEDAATYYC QQWSSNPPT FGDGTRLEIKA |
| SEQ ID NO: 178 | VL Framework 1 | QMVLTHSPAIMSASPGEKVTMTC |
| SEQ ID NO: 179 | VL CDR1 | SASSSVSYMH |
| SEQ ID NO: 180 | VL Framework 2 | WYQQKPGSSPKPWIY |
| SEQ ID NO: 181 | VL CDR2 | GTSNLAS |
| SEQ ID NO: 182 | VL Framework 3 | GVPARFSGSGSGTSYSLTISRMEAEDAATYYC |
| SEQ ID NO: 183 | VL CDR 3 | QQWSSNPPT |
| SEQ ID NO: 184 | VL Framework 4 | FGDGTRLEIKA |
| SEQ ID NO: 185 | B13C4-20 | DIVMSQSPSSLAVSAGEKVTMSC KSSQSLLNSRTRKNYLA WYQQKPGQSPRLLIY WASTRES GVPDRFTGSGSGTDFTLTISSVQAEDLAVYYC KQSYNLLT FGAGTKLELKA |
| SEQ ID NO: 186 | VL Framework 1 | DIVMSQSPSSLAVSAGEKVTMSC |
| SEQ ID NO: 187 | VL CDR1 | KSSQSLLNSRTRKNYLA |

| Informal Sequence Listing | | |
|---|---|---|
| SEQ ID NO: 188 | VL Framework 2 | WYQQKPGQSPRLLIY |
| SEQ ID NO: 189 | VL CDR2 | WASTRES |
| SEQ ID NO: 190 | VL Framework 3 | GVPDRFTGSGSGTDFTLTISSVQAEDLAVYYC |
| SEQ ID NO: 191 | VL CDR 3 | KQSYNLLT |
| SEQ ID NO: 192 | VL Framework 4 | FGAGTKLELKA |
| SEQ ID NO: 193 | B15B11vk35-20 | DIVMSQSPSSLAVSAGENVTVSC KSSQSLLNSRTRKNYLA WYQQKPGQSPKLLIY WASTRES QVPDRFTGSGSGTDFTLTISSVQAEDLAVYFC KQSYNLLT FGAGTKLELKA |
| SEQ ID NO: 194 | VL Framework 1 | DIVMSQSPSSLAVSAGENVTVSC |
| SEQ ID NO: 195 | VL CDR1 | DIVMSQSPSSLAVSAGENVTVSC |
| SEQ ID NO: 196 | VL Framework 2 | WYQQKPGQSPKLLIY |
| SEQ ID NO: 197 | VL CDR2 | WASTRES |
| SEQ ID NO: 198 | VL Framework 3 | GVPDRFTGSGSGTDFTLTISSVQAEDLAVYFC |
| SEQ ID NO: 199 | VL CDR 3 | KQSYNLLT |
| SEQ ID NO: 200 | VL Framework 4 | FGAGTKLELKA |
| SEQ ID NO: 201 | B13C12335-25 | DIKMTQSPSSLAVSPGEKVTMSC KSSQSLLHSRTRKNYLA WYQQKPGQSPKLLIY WASTRES GVPDRFTGSGSGTDFTLTISSVQAEDLAVYYC KQSYNLLT FGAGTKELEKA |
| SEQ ID NO: 202 | VL Framework 1 | DIKMTQSPSSLAVSPGKEVTMSC |
| SEQ ID NO: 203 | VL CDR1 | KSSQSLLHSRTRKNYLA |
| SEQ ID NO: 204 | VL Framework 2 | WYQQKPGQSPKLLIY |
| SEQ ID NO: 205 | VL CDR2 | WASTRES |
| SEQ ID NO: 206 | VL Framework 3 | GVPDRFTGSGSGTDFTLTISSVQAEDLAVYYC |
| SEQ ID NO: 207 | VL CDR 3 | KQSYNLLT |
| SEQ ID NO: 208 | VL Framework 4 | FGAGTKLELKA |
| SEQ ID NO: 209 | B13C1233520 | DIVMSQSPSSLAVSPGEKVTMSC KSSQSLLHSRTRKNYLA WYQQKPGQSPKLLIY WASTRES GVPDRFTGSGSGTDFTLTISSVQAEDLAVYYC KQSYNLLT FGAGTKLELKA |
| SEQ ID NO: 210 | VL Framework 1 | DIVMSQSPSSLAVSPGEKVTMSC |
| SEQ ID NO: 211 | VL CDR1 | KSSQSLLHSRTRKNYLA |
| SEQ ID NO: 212 | VL Framework 2 | WYQQKPGQSPKLLIY |
| SEQ ID NO: 213 | VL CDR2 | WASTRES |
| SEQ ID NO: 214 | VL Framework 3 | GVPDRFTGSGSGTDFTLTISSVQAEDLAVYYC |
| SEQ ID NO: 215 | VL CDR 3 | KQSYNLLT |
| SEQ ID NO: 216 | VL Framework 4 | FGAGTKLELKA |
| SEQ ID NO: 217 | RSDLVK-1 | DIVMTQSPSSLAVSAGEKVTMSC KSSQSLLNSRTRKNYLA WYQQKPGQSPRLLIY WASTRES GVPDRFTGSGSGTDFTLTISSVQAEDLAVYYC KQSYNLLT FGAGTKLELKR |
| SEQ ID NO: 218 | VL Framework 1 | DIVMTQSPSSLAVSAGEKVTMSC |
| SEQ ID NO: 219 | VL CDR1 | KSSQSLLNSRTRKNYLA |
| SEQ ID NO: 220 | VL Framework 2 | WYQQKPGQSPRLLIY |
| SEQ ID NO: 221 | VL CDR2 | WASTRES |
| SEQ ID NO: 222 | VL Framework 3 | WVPDRFTGSGSGTDFTLTISSVQAEDLAVYYC |

| Informal Sequence Listing | | |
|---|---|---|
| SEQ ID NO: 223 VL CDR 3 | | KQSYNLLT |
| SEQ ID NO: 224 VL Framework 4 | | FGAGTKLELKR |
| SEQ ID NO: 225 RSDLVK-6 | | DIVMTQSPSSLAVSAGEKVTMSC KSSQSLLNSRTRKNYLA WYQQKPGQSPRLLIY WASTRES GVPDRFTGSGSGTDFTLTISSVQAEDLAVYYC KQSYNLLT FGAGTRLEIKR |
| SEQ ID NO: 226 VL Framework 1 | | DIVMTQSPSSLAVSAGEKVTMSC |
| SEQ ID NO: 227 VL CDR1 | | KSSQSLLNSRTRKNYLA |
| SEQ ID NO: 228 VL Framework 2 | | WYQQKPGQSPRLLIY |
| SEQ ID NO: 229 VL CDR2 | | WASTRES |
| SEQ ID NO: 230 VL Framework 3 | | GVPDRFTGSGSGTDFTLTISSVQAEDLAVYYC |
| SEQ ID NO: 231 VL CDR 3 | | KQSYNLLT |
| SEQ ID NO: 232 VL Framework 4 | | FGAGTRLEIKR |
| SEQ ID NO: 233 RSDLVK-10 | | DIVMTQSPSSLAVSAGENVTVSC KSSQSLLNSRTRKNYLA WYQQKPGQSPKLLIY WASTRES GVPDRFTGSGSGTGFTLTISSVQAEDLAVYFC KQSYNLLT FGAGTRLEIKR |
| SEQ ID NO: 234 VL Framework 1 | | DIVMTQSPSSLAVSAGENVTVSC |
| SEQ ID NO: 235 VL CDR1 | | KSSQSLLNSRTRKNYLA |
| SEQ ID NO: 236 VL Framework 2 | | WYQQKPGQSPKLLIY |
| SEQ ID NO: 237 VL CDR2 | | WASTRES |
| SEQ ID NO: 238 VL Framework 3 | | GVPDRFTGSGSGTGFTLTISSVQAEDLAVYFC |
| SEQ ID NO: 239 VL CDR 3 | | KQSYNLLT |
| SEQ ID NO: 240 VL Framework 4 | | FGAGTRLEIKR |
| SEQ ID NO: 241 RSDLVK-13 | | DIVMSQSPSSLAVSPGEKVTMSC KSSQSLLHSRTRKNYLA WYQQKPGQSPKLLIY WASTRES GVPDRFTGSGSGTDFTLTISSVQAEDLAVYYC KQSYNLLT FGAGTKLELKR |
| SEQ ID NO: 242 VL Framework 1 | | DIVMSQSPSSLAVSPGEKVTMSC |
| SEQ ID NO: 243 VL CDR1 | | KSSQSLLHSRTRKNYLA |
| SEQ ID NO: 244 VL Framework 2 | | WYQQKPGQSPKLLIY |
| SEQ ID NO: 245 VL CDR2 | | WASTRES |
| SEQ ID NO: 246 VL Framework 3 | | GVPDRFTGSGSGTDFTLTISSVQAEDLAVYYC |
| SEQ ID NO: 247 VL CDR 3 | | KQSYNLLT |
| SEQ ID NO: 248 VL Framework 4 | | FGAGTKLELKR |
| SEQ ID NO: 249 29 | | DIVMSQSPSSLAVSAGEKVTMSC KSSQSLLNSRTRKNYLA WYQQKPGQSPRLLIY WASTRES GVPDRFTGSGSGTDFTLTISSVQAEDLAVYYC KQSYNLLT FGAGTKLELKA |
| SEQ ID NO: 250 VL Framework 1 | | DIVMSQSPSSLAVSAGEKVTMSC |
| SEQ ID NO: 251 VL CDR1 | | KSSQSLLNSRTRKNYLA |
| SEQ ID NO: 252 VL Framework 2 | | WYQQKPGQSPRLLIY |
| SEQ ID NO: 253 VL CDR2 | | WASTRES |
| SEQ ID NO: 254 VL Framework 3 | | GVPDRFTGSGSGTDFTLTISSVQAEDLAVYYC |
| SEQ ID NO: 255 VL CDR 3 | | KQSYNLLT |
| SEQ ID NO: 256 VL Framework 4 | | FGAGTKLELKA |

| Informal Sequence Listing | |
|---|---|
| SEQ ID NO: 257  44 | DIVMSQSPSSLAVSAGEKVTMSC KSSQSLLNSRTRKNYLA WYQQKPGQSPRLLIY WASTRES GVPDRFTGSGSGTDFTLTISSVQDEDLAVYYC KQSYNLLT FGAGTKLELKA |
| SEQ ID NO: 258  VL Framework 1 | DIVMSQSPSSLAVSAGEKVTMSC |
| SEQ ID NO: 259  VL CDR1 | KSSQSLLNSRTRKNYLA |
| SEQ ID NO: 260  VL Framework 2 | WYQQKPGQSPRLLIY |
| SEQ ID NO: 261  VL CDR2 | WASTRES |
| SEQ ID NO: 262  VL Framework 3 | GVPDRFTGSGSGTDFTLTISSVQDEDLAVYYC |
| SEQ ID NO: 263  VL CDR 3 | KQSYNLLT |
| SEQ ID NO: 264  VL Framework 4 | FGAGTKLELKA |
| SEQ ID NO: 265  A1 = B4 = F9 | DIVMSQSPSSLAVSAGEKVTMSC KSSQSLLNSRTRKNYLA WYQQKPGQSPRLLIY WASTRES GVPDRFTGSGSGTDFTLTISSVQAEDLAVYYC KQSYNLLT FGAGTKLELKA |
| SEQ ID NO: 266  VL Framework 1 | DIVMSQSPSSLAVSAGEKVTMSC |
| SEQ ID NO: 267  VL CDR1 | KSSQSLLNSRTRKNYLA |
| SEQ ID NO: 268  VL Framework 2 | WYQQKPGQSPRLLIY |
| SEQ ID NO: 269  VL CDR2 | WASTRES |
| SEQ ID NO: 270  VL Framework 3 | GVPDRFTGSGSGTDFTLTISSVQAEDLAVYYC |
| SEQ ID NO: 271  VL CDR 3 | KQSYNLLT |
| SEQ ID NO: 272  VL Framework 4 | FGAGTKLELKA |
| SEQ ID NO: 273  A5 = C6 | DIVMSQSPSSLAVSAGEKVTMSC KSSQSLLNSRTRKNYLA WYQQKPGQSPRLLIY WASTRES GVPDRFTGSGSGTDFTLTISSVQAEDLAVYYC KQSYNLLT FGAGTKLELKA |
| SEQ ID NO: 274  VL Framework 1 | DIVMSQSPSSLAVSAGEKVTMSC |
| SEQ ID NO: 275  VL CDR1 | KSSQSLLNSRTRKNYLA |
| SEQ ID NO: 276  VL Framework 2 | WYQQKPGQSPRLLIY |
| SEQ ID NO: 277  VL CDR2 | WASTRES |
| SEQ ID NO: 278  VL Framework 3 | GVPDRFTGSGSGTDFTLTISSVQAEDLAVYYC |
| SEQ ID NO: 279  VL CDR 3 | KQSYNLLT |
| SEQ ID NO: 280  VL Framework 4 | FGAGTKLELKA |
| SEQ ID NO: 281  D4 = E6 | DIVMSQSPSSLAVSAGEKVTMSC KSSQSLLNSRTRKNYLA WYQQKPGQXPRLLIY WASTRES GVPDRFTGSGSGTDFTLTISSVQDEDLAVYYC KQSYNLLS FGAGTKLELKA |
| SEQ ID NO: 282  VL Framework 1 | DIVMSQSPSSLAVSAGEKVTMSC |
| SEQ ID NO: 283  VL CDR1 | KSSQSLLNSRTRKNYLA |
| SEQ ID NO: 284  VL Framework 2 | WYQQKPGQXPRLLIY |
| SEQ ID NO: 285  VL CDR2 | WASTRES |
| SEQ ID NO: 286  VL Framework 3 | GVPDRFTGSGSGTDFTLTISSVQDEDLAVYYC |
| SEQ ID NO: 287  VL CDR 3 | KQSYNLLS |
| SEQ ID NO: 288  VL Framework 4 | FGAGTKLELKA |
| SEQ ID NO: 289  C6D4 | DIVMTQSPSSLAVSAGEKVTMSC KSSQSLLNSRTRKNYLA WYQQKPGQSPRLLIY WASTRES GVPDRFTGSGSGTDFTLTISSVQAEDLAVYYC KQSYNLLS FGAGTKLELKR |
| SEQ ID NO: 290  VL Framework 1 | DIVMTQSPSSLAVSAGEKVTMSC |

| Informal Sequence Listing | | |
|---|---|---|
| SEQ ID NO: 291 VL CDR1 | | KSSQSLLNSRTRKNYLA |
| SEQ ID NO: 292 VL Framework 2 | | WYQQKPGQSPRLLIY |
| SEQ ID NO: 293 VL CDR2 | | WASTRES |
| SEQ ID NO: 294 VL Framework 3 | | GVPDRFTGSGSGTDFTLTISSVQAEDLAVYYC |
| SEQ ID NO: 295 VL CDR 3 | | KQSYNLLS |
| SEQ ID NO: 296 VL Framework 4 | | FGAGTKLELKR |
| SEQ ID NO: 297 F9 VH | | QVQLQQSGAELVRPGTSVKVSCKASGY AFTDYLIQ WVKQRPGQGLEWIG VINPETGGTNYNAKFRG KATLTADKSSSSAYMQLSSLTSGDSAVYFCAR EAGNYIYAMDY WGQGTSVTVSS |
| SEQ ID NO: 298 VH Framework 1 | | QVQLQQSGAELVRPGTSVKVSCKASGY |
| SEQ ID NO: 299 VH CDR1 | | AFTDYLIQ |
| SEQ ID NO: 300 VH Framework 2 | | WVKQRPGQGLEWIG |
| SEQ ID NO: 301 VH CDR2 | | VINPETGGTNYNAKFRG |
| SEQ ID NO: 302 VH Framework 3 | | KATLTADKSSSSAYMQLSSLTSGDSAVYFCAR |
| SEQ ID NO: 303 VH CDR 3 | | EAGNYIYAMDY |
| SEQ ID NO: 304 VH Framework 4 | | WGQGTSVTVSS |
| SEQ ID NO: 305 F9 VL | | DIVMTQSPAFLSASVGETVTITC RASVNIYSYLV WYQQKQGKSPQLLVH NAKTLAE GVPSRFSGSGSGTQFSLKINSLQPEDFGSYYC QHHHGTPYT FGGGTKLEIKR |
| SEQ ID NO: 306 VL Framework 1 | | DIVMTQSPAFLSASVGETVTITC |
| SEQ ID NO: 307 VL CDR1 | | RASVNIYSYLV |
| SEQ ID NO: 308 VL Framework 2 | | WYQQKQGKSPQLLVH |
| SEQ ID NO: 309 VL CDR2 | | NAKTLAE |
| SEQ ID NO: 310 VL Framework 3 | | GVPSRFSGSGSGTQFSLKINSLQPEDFGSYYC |
| SEQ ID NO: 311 VL CDR 3 | | QHHHGTPYT |
| SEQ ID NO: 312 VL Framework 4 | | FGGGTKLEIKR |
| SEQ ID NO: 313 B2B2 VH CDR1 | | TFTDYSMH |
| SEQ ID NO: 314 B2B2 VH VDR2 | | RINTETGEPTFADDFGG |
| SEQ ID NO: 315 B2B2 VH CDR3 | | YYYGRDS |
| SEQ ID NO: 316 B13C4 VH CDR1 | | TFTDYSMH |
| SEQ ID NO: 317 B13C4 VH CDR2 | | WIKTETGEPTYADDFKG |
| SEQ ID NO: 318 B13C4 VH CDR3 | | YYYGRDS |
| SEQ ID NO: 319 B13H3 VH CDR1 | | TFTDYSMH |
| SEQ ID NO: 320 B13H3 VH CDR2 | | WIKTETDEPTYADDFKE |
| SEQ ID NO: 321 B13H3 VH CDR3 | | YYYGRDS |
| SEQ ID NO: 322 B15B11 VH CDR1 | | TFTDYSMH |
| SEQ ID NO: 323 B15B11 VH CDR2 | | RINTETGEPTFADDFRG |
| SEQ ID NO: 324 B15B11 VH CDR3 | | YYYGRDS |
| SEQ ID NO: 325 B13C12 VH CDR1 | | TFTDYSIH |
| SEQ ID NO: 326 B13C12 VH CDR2 | | WIKTETGEPTYADDFNG |

| Informal Sequence Listing | | |
|---|---|---|
| SEQ ID NO: 327 | B13C12 VH CDR3 | YYYGRDS |
| SEQ ID NO: 328 | A1 VH CDR1 | TFTDYSMH |
| SEQ ID NO: 329 | A1 VH CDR2 | RINTETGEPTFADDFRG |
| SEQ ID NO: 330 | A1 VH CDR3 | YYYGRDT |
| SEQ ID NO: 331 | C6 VH CDR1 | TFTDYSMH |
| SEQ ID NO: 332 | C6 VH CDR2 | RINTETGEPTFADDFRG |
| SEQ ID NO: 333 | C6 VH CDH4 | FYYGRDS |
| SEQ ID NO: 334 | B2B2 Vk CDR1 | KASQDINSYLS |
| SEQ ID NO: 335 | B2B2 Vk CDR2 | RANRLVD |
| SEQ ID NO: 336 | B2B2 Vk CDR3 | LQYDEFPPLT |
| SEQ ID NO: 337 | B13C4 Vk CDR1 | KSSQSLLNSRTRKNYLA |
| SEQ ID NO: 338 | B13C4 Vk CDR2 | WASTRES |
| SEQ ID NO: 339 | B13C4 Vk CDR3 | KQSYNLLT |
| SEQ ID NO: 340 | B13H3 Vk CDR1 | KSSQSLLNSRIRKNYLA |
| SEQ ID NO: 341 | B13H3 Vk CDR2 | WASTRES |
| SEQ ID NO: 342 | B13H3 Vk CDR3 | KQSYNLLT |
| SEQ ID NO: 343 | B15B11.1 Vk CDR1 | SASSSVSYMH |
| SEQ ID NO: 344 | B15B11.1 Vk CDR2 | DTSNLAS |
| SEQ ID NO: 345 | B15B11.1 Vk CDR3 | QQWSSNPLT |
| SEQ ID NO: 346 | B15B11.2 Vk CDR1 | SASSSVSYMH |
| SEQ ID NO: 347 | B15B11.2 Vk CDR2 | DTSNLAS |
| SEQ ID NO: 348 | B15B11.2 Vk CDR3 | QQWSSNPPT |
| SEQ ID NO: 349 | B15B11.3 Vk CDR1 | KSSQSLLNSRTRKNYLA |
| SEQ ID NO: 350 | B15B11.3 Vk CDR2 | WASTRES |
| SEQ ID NO: 351 | B15B11.3 Vk CDR3 | KQSYNLLT |
| SEQ ID NO: 352 | B13C12.1 Vk CDR1 | SASSSVSYMH |
| SEQ ID NO: 353 | B13C12.1 Vk CDR2 | DTSKLAS |
| SEQ ID NO: 354 | B13C12.1 Vk CDR3 | QQWSSNPFT |
| SEQ ID NO: 355 | B13C12.2 Vk CDR1 | SASSSVSYMH |
| SEQ ID NO: 356 | B13C12.2 Vk CDR2 | GTSNLAS |
| SEQ ID NO: 357 | B13C12.2 Vk CDR3 | QQWSSNPPT |
| SEQ ID NO: 358 | B13C12.3 Vk CDR1 | KSSQSLLHSRTRKNYLA |
| SEQ ID NO: 359 | B13C12.3 Vk CDR2 | WASTRES |
| SEQ ID NO: 360 | B13C12.3 Vk CDR3 | KQSYNLLT |
| SEQ ID NO: 361 | D4 Vk CDR1 | KSSQSLLNSRTRKNYLA |
| SEQ ID NO: 362 | D4 Vk CDR2 | WASTRES |
| SEQ ID NO: 363 | D4 Vk CDR3 | KQSYNLLS |
| SEQ ID NO: 364 | RSDLVH-1 VH CDR1 | TFTDYSIH |
| SEQ ID NO: 365 | RSDLVH-1 VH CDR2 | WIKTETGEPTYADDFKG |

| Informal Sequence Listing |
|---|

SEQ ID NO: 366 RSDLVH-1 VH CDR3    YYYGRDS

SEQ ID NO: 367 RSDLVH-3 VH CDR1    TFTDYSIH

SEQ ID NO: 368 RSDLVH-3 VH CDR2    WIKTETGEPTYADDFNG

SEQ ID NO: 369 RSDLVH-3 VH CDR3    YYYGRDS

SEQ ID NO: 370 RSDLVH-16 VH CDR1   TFTDYSMH

SEQ ID NO: 371 RSDLVH-16 VH CDR2   RINTETGEPTFADDFRG

SEQ ID NO: 372 RSDLVH-16 VH CDR3   YYYGRDS

SEQ ID NO: 373 RSDLVK-10 Vk CDR1   KSSQSLLNSRTRKNYLA

SEQ ID NO: 374 RSDLVK-10 Vk CDR2   WASTRES

SEQ ID NO: 375 RSDLVK-10 Vk CDR3   KQSYNLLT

SEQ ID NO: 376 RSDLVK-13 Vk CDR1   KSSQSLLHSRTRKNYLA

SEQ ID NO: 377 RSDLVK-13 Vk CDR2   WASTRES

SEQ ID NO: 378 RSDLVK-13 Vk CDR3   KQSYNLLT

SEQ ID NO: 379 D4H VH CDR1         TFTDYSMH

SEQ ID NO: 380 D4H VH CDR2         RINTETGEPTFADDFRG

SEQ ID NO: 381 D4H VH CDR3         YYYGRDS

SEQ ID NO: 382 C6k Vk CDR1         KSSQSLLNSRTRKNYLA

SEQ ID NO: 383 C6k Vk CDR2         WASTRES

SEQ ID NO: 384 C6k Vk CDR3         KQSYNLLT

SEQ ID NO: 385 heavy chain FR1     (Q/E)IQL(L/M)(Q/E)SGPELKKPGETVKISCKASGY

SEQ ID NO: 386 heavy chain FR2     WVKQAPGKGLKW(V/M)A

SEQ ID NO: 387 heavy chain FR3     RFA(V/F)SLETSASTAYLQINNLKNEDTATYFCAI

SEQ ID NO: 388 heavy chain FR4     WYQQKPGQSP(K/R)LLIY

SEQ ID NO: 389 light chain FR1     (D/E)IVM(T/S)QSPSSLAV(/PS)AGE(K/N)VT(M/V)SC

SEQ ID NO: 390 light chain FR2     WYQQKPGQSP(K/R)LLIY

SEQ ID NO: 391 light chain FR3     GVPDRFTGSGSGTDFTLTISSVQAEDLAVY(Y/F)C

SEQ ID NO: 392 light chain FR4     FGAGT(R/K)LE(L/I)K

SEQ ID NO: 393 Human αv
```
   1 FNLDVDSPAEYSGPEGSYFGFAVDFFVPSASSRMFLLVGAPKANTTQPGI    50
  51 VEGGQVLKCDWSSTRRCQPEIFDATGNRDYAKDDPLEFKSHQWFGASVRS   100
 101 KQDKILACAPLYHWRTEMKQEREPVGTCVLQDGTKTVEYAPCRSQDIDAD   150
 151 GQGFCQGGFSIDFTKADRVLLGGPGSFYWQGQLISDQVAEIVSKYDPNVY   200
 201 SIKYNNQLATRTAQAIFDDSYLGYSVAVGDFNGDGIDDFVSGVPRAARTL   250
 251 GMVYIYDGKNMSSLYNFTGEQMAAYFGFSVAATDINGDDYADVFIGAPLF   300
 301 MDRGSDGKLQEVGQVSVSLQRASGDFQTTKLNGFEVFARFGSAIAPLGDL   350
 351 DQDGFNDIAIAAPYGGEDKKGIVYIFNGRSTGLNAVPSQILEGQWAARSM   400
 401 PPSFGYSMKGATDIDKNGYPDLIVGAFGVDRAILYRARPVITVNAGLEVY   450
 451 PSILNQDNKTCSLPGTALKVSCFNVRFCLKADGKGVLPRKLNFQVELLLD   500
 501 KLKQKGAIRRALFLYSRSPSHSKNMTISRGGLMQCEELIAYLRDESEFRD   550
 551 KLTPITIFMEYRLDYRTAADTTGLQPILNQFTPANISRQAHILLDCGEDN   600
 601 VCKPKLEVSVDSDQKKIYIGDDNPLTLIVKAQNQGEGAYEAELIVSIPLQ   650
 651 ADFIGVVRNNEALARLSCAFKTENQTRQVVCDLGNPMKAGTQLLAGLRFS   700
 701 VHQQSEMDTSVKFDLQIQSSNLFDKVSPVVSHKVDLAVLAAVEIRGVSSP   750
 751 DHVFLPIPNWHEKENPETEEDVGPVVQHIYELRNNGPSSFSKAMLHLQWP   800
 801 YKYNNNTLLYILHYDIDGPMNCTSDMEINPLRIKISSLQTTEKNDTVAGQ   850
 851 GERDHLITKRDLALSEGDIHTLGCGVAQCLKIVCQVGRLDRGKSAILYVK   900
 901 SLLWTETFMNKENQNHSYSLKSSASFNVIEFPYKNLPIEDITNSTLVTTN   950
 951 VTWGIQPAPMPVPVWVIILAVLAGLLLLAVLVFVMYRMGFFKVRPPQEE  1000
1001 QEREQLQPEHNGEGNSET                                 1018
```

Informal Sequence Listing

```
SEQ ID NO: 394 Human β8
  1 EDNRCASSNAASCARCLALGPECGWCVQEDFISGGSRSERCDIVSNLISK    50
 51 GCSVDSIEYPSVHVIIPTENENITQVTPGEVSIQLRPGAEANFMLKVHPL   100
101 KKYPVDLYYLVDVSASMHNNIEKLNSVGNDLSRKMAFFSRDFRLGFGSYV   150
151 DKTVSPYISIHPERIHNQCSGYNLDCMPPHGYIHVLSLTENITEFEKAVH   200
201 RQKISGNIDTPEGGFDAMLQAAVCESHIGWRKEAKRLLLVMTDQTSHALA   250
251 DSKLAGIVVPNDGNCHLKNNVYVKSTTMEHPSLGQLSEKLIDNNINVIFA   300
301 VQGKQFHWYKDLLPLLPGTIAGEIESKAANLNNLVVEAYQKLISEVKVQV   350
351 ENQVQGIYFNITAICPDGSRKPGMEGCRNVTSNDEVLFNVTVTMKKCDVT   400
401 GGKNYAIIKPIGFNETAKIHIHRNCSQCEDNRGPKGKCVDETFLDSKCF    450
451 QCDENKCHFDEDQFSSESCKSHKDQPVCSGRGVCVCGKCSCHKIKLGKVY   500
501 GKYCEKDDFSCPYHHGNLCAGHGECEAGRCQCFSGWEGDRCQCPSAAAQH   550
551 CVNSKGQVCSGRGTCVCGRCECTDPRSIGRFCEHCPTCYTACKENWNCMQ   600
601 CLHPHNLSQAILDQCKTSCALMEQQHYVDQTSECFSSPSYLRIFFIIFIV   650
651 TFLIGLLKVLIIRQVILQWNSNKIKSSSDYRVSASKKDKLILQSVCTRAV   700
701 TYRREKPEEIKMDISKLNAHETFRCNF                          727

SEQ ID NO: 395 HuC6D4V1       QIQLVQSGAEVKKPGASVKISCKASGYTFT DYSMH WVRQAPGQGLEWVA
                              RINTETGEPTFADDFRG RFTVTLDTSTSTAYLEIRSLRSDDTAVYFCAI
                              FYYGRDS WGQGTTLVTVSS

SEQ ID NO: 396 VH Framework 1 QIQLVQSGAEVKKPGASVKISCKASGYTFT

SEQ ID NO: 397 VH CDR1        DYSMH

SEQ ID NO: 398 VH Framework 2 WVRQAPGQGLEWVA

SEQ ID NO: 399 VH CDR2        RINTETGEPTFADDFRG

SEQ ID NO: 400 VH Framework 3 RFTVTLDTSTSTAYLEIRSLRSDDTAVYFCAI

SEQ ID NO: 401 VH CDR 3       FYYGRDS

SEQ ID NO: 402 VH Framework 4 WGQGTTLTVSS

SEQ ID NO: 403 HuC6D4A3       QIQLVQSGAEVKKPGASVKISCKASGYTFT DYSMH WVRQAPGQGLEWVA
                              RINTETGEPTFADDFRG RFTVTLDTSTSTAYLEIRSLRSDDTAVYFCAI
                              FYYGRDS WGQGTTLTVSS

SEQ ID NO: 404 VH Framework 1 QIQLVQSGAEVKKPGASVKISCKASGYTFT

SEQ ID NO: 405 VH CDR1        DYSMH

SEQ ID NO: 406 VH Framework 2 WVRQAPGQGLEWVA

SEQ ID NO: 407 VH CDR2        RINTETGEPTFADDFRG

SEQ ID NO: 408 VH Framework 3 RFTVTLDTSTSTAYLEIRSLRSDDTAVYFCAI

SEQ ID NO: 409 VH CDR 3       FYYGRDS

SEQ ID NO: 410 VH Framework 4 WGQGTTLTVSS

SEQ ID NO: 411 HuC6D4B7       QIQLVQSGAKVKKPGASVKISCKASGYTFT DYSMH WVRQAPGQGLEWVA
                              RINTETGEPTFADDFRG RFSVTLDTSTSTAYLEITSLRSDDTAVYFCAI
                              FYYGRDT WGQGTALTVSS

SEQ ID NO: 412 VH Framework 1 QIQLVQSGAKVKKPGASVKISCKASGYTFT

SEQ ID NO: 413 VH CDR1        DYSMH

SEQ ID NO: 414 VH Framework 2 WVRQAPGQGLEWVA

SEQ ID NO: 415 VH CDR2        RINTETGEPTFADDFRG

SEQ ID NO: 416 VH Framework 3 RFSVTLDTSTSTAYLEIRSLRSDDTAVYFCAI

SEQ ID NO: 417 VH CDR 3       FYYGRDT

SEQ ID NO: 418 VH Framework 4 WGQGTALTVSS

SEQ ID NO: 419 HuC6D4E5       QIQLVQSGAEVKKPGASVKISCKASGYTFT DYSMH WVRQAPGQGLEWVA
                              RINTETGEPTFADDFRG RFTVTLDTSTSTAYLEIRSLRSDDTAVYFCAI
                              FYYGRDT WGQGTTLTVSS

SEQ ID NO: 420 VH Framework 1 QIQLVQSGAEVKKPGASVKISCKASGYTFT
```

-continued

| Informal Sequence Listing | | |
|---|---|---|
| SEQ ID NO: 421 | VH CDR1 | DYSMH |
| SEQ ID NO: 422 | VH Framework 2 | WVRQAPGQGLEWVA |
| SEQ ID NO: 423 | VH CDR2 | RINTETGEPTFADDFRG |
| SEQ ID NO: 424 | VH Framework 3 | RFTVTLDTSTSTAYLEIRSLRSDDTAVYFCAI |
| SEQ ID NO: 425 | VH CDR 3 | FYYGRDT |
| SEQ ID NO: 426 | VH Framework 4 | WGQGTTLTVSS |
| SEQ ID NO: 427 | HuC6D4 | QIQLVQSGAEVKKPGASVKISCKASGYTFT DYSMH WVRQAPGQGLEWVA RINTETGEPTFADDFRG RFTVTLDTSTSTAYLEIRSLRSDDTAVYFCAI FYYGRDT WGQGTTLTVSS |
| SEQ ID NO: 428 | VH Framework 1 | QIQLVQSGAEVKKPGASVKISCKASGYTFT |
| SEQ ID NO: 429 | VH CDR1 | DYSMH |
| SEQ ID NO: 430 | VH Framework 2 | WVRQAPGQGLEWVA |
| SEQ ID NO: 431 | VH CDR2 | RINTETGEPTFADDFRG |
| SEQ ID NO: 432 | VH Framework 3 | RFTVTLDTSTSTAYLEIRSLRSDDTAVYFCAI |
| SEQ ID NO: 433 | VH CDR 3 | FYYGRDT |
| SEQ ID NO: 434 | VH Framework 4 | WGQGTTLTVSS |
| SEQ ID NO: 435 | C6D4-RGD3 | QIQLLQSGPELKKPGETVKISCKASGYTFT DYSMH WVKQAPGKGLKWVA RINTETGEPTFADDFRG RFAVSLETSASTAYLQINNLKNEDTATYFCAI FYYGRDS WGQGTTLTVSS |
| SEQ ID NO: 436 | VH Framework 1 | QIQLLQSGPELKKPGETVKISCKASGYTFT |
| SEQ ID NO: 437 | VH CDR1 | DYSMH |
| SEQ ID NO: 438 | VH Framework 2 | WVKQAPGKGLKWVA |
| SEQ ID NO: 439 | VH CDR2 | RINTETGEPTFADDFRG |
| SEQ ID NO: 440 | VH Framework 3 | RFAVSLETSASTAYLQINNLKNEDTATYFCAI |
| SEQ ID NO: 441 | VH CDR 3 | FYYGRDS |
| SEQ ID NO: 442 | VH Framework 4 | WGQGTTLTVSS |
| SEQ ID NO: 443 | HuC6DR-RGD3 | QIQLVQSGAEVKKPGASVKISCKASGYTFT DYSMH WVRQAPGQGLEWVA RINTETGEPTFADDFRG RFTVTLDTSTSTAYLEIRSLRSDDTAVYFCAI FYYGRDT WGQGTTLTVSS |
| SEQ ID NO: 444 | VH Framework 1 | QIQLVQSGAEVKKPGASVKISCKASGYTFT |
| SEQ ID NO: 445 | VH CDR1 | DYSMH |
| SEQ ID NO: 446 | VH Framework 2 | WVRQAPGQGLEWVA |
| SEQ ID NO: 447 | VH CDR2 | RINTETGEPTFADDFRG |
| SEQ ID NO: 448 | VH Framework 3 | RFTVTLDTSTSTAYLEIRSLRSDDTAVYFCAI |
| SEQ ID NO: 449 | VH CDR 3 | FYYGRDT |
| SEQ ID NO: 450 | VH Framework 4 | WGQGTTLTVSS |
| SEQ ID NO: 451 | HuC6D4V1 | EIVMTQSPATLSVSPGERVTMSC KSSQSLLNSRTRKNYLA WYQQKPGQAPRLLIY WASTRES GVPARFSGSGSGTEFTLTISSVQSEDFAVYYC KQSYNLLS FGQGTVLEIKR |
| SEQ ID NO: 452 | Vk Framework 1 | EIVMTQSPATLSVSPGERVTMSC |
| SEQ ID NO: 453 | Vk CDR1 | KSSQSLLNSRTRKNYLA |
| SEQ ID NO: 454 | Vk Framework 2 | WYQQKPGQAPRLLIY |

| Informal Sequence Listing | |
|---|---|
| SEQ ID NO: 455 Vk CDR2 | WASTRES |
| SEQ ID NO: 456 Vk Framework 3 | GVPARFSGSGSGTEFTLTISSVQSEDFAVYYC |
| SEQ ID NO: 457 Vk CDR 3 | KQSYNLLS |
| SEQ ID NO: 458 Vk Framework 4 | FGQGTVLEIKR |
| SEQ ID NO: 459 HuC6D4A3 | EIVMTQSPATLSVSPGEIVTMSC KSSQSLLNSRSRKNYLA WYQQKPGQAPRLLIY WASTRES GVPARFSGSGSGTEFTLTISSVQSEDFAVYYC KQSYNLIS FGQGTVLEIKR |
| SEQ ID NO: 460 Vk Framework 1 | EIVMTQSPATLSVSPGEIVTMSC |
| SEQ ID NO: 461 Vk CDR1 | KSSQSLLNSRSRKNYLA |
| SEQ ID NO: 462 Vk Framework 2 | WYQQKPGQAPRLLIY |
| SEQ ID NO: 463 Vk CDR2 | WASTRES |
| SEQ ID NO: 464 Vk Framework 3 | GVPARFSGSGSGTEFTLTISSVQSEDFAVYYC |
| SEQ ID NO: 465 Vk CDR 3 | KQSYNLIS |
| SEQ ID NO: 466 Vk Framework 4 | FGQGTVLEIKR |
| SEQ ID NO: 467 HuC6D4B7 | EIVMTQTPVTLSVSPGERVTMSC KSSQSLLNSRTRKNYLA WYQQKPGQAPRLLIY WASTRES DVPARFSGSGSGTEFTLTISSVQSEDFAVYYC KQSSNLIS FGQGTVLEIKR |
| SEQ ID NO: 468 Vk Framework 1 | EIVMTQTPVTLSVSPGERVTMSC |
| SEQ ID NO: 469 Vk CDR1 | KSSQSLLNSRTRKNYLA |
| SEQ ID NO: 470 Vk Framework 2 | WYQQKPGQAPRLLIY |
| SEQ ID NO: 471 Vk CDR2 | WASTRES |
| SEQ ID NO: 472 Vk Framework 3 | DVPARFSGSGSGTEFTLTISSVQSEDFAVYYC |
| SEQ ID NO: 473 Vk CDR 3 | KQSSNLIS |
| SEQ ID NO: 474 Vk Framework 4 | FGQGTVLEIKR |
| SEQ ID NO: 475 HuC6D4E5 | EIVMTQSPATLSVSPGERVTMSC KSSQSLLNSRSRKNYLA WYQQKPGQAPRLLIY WASTRES GVPARFSGSGSGTEFTLTISSVQSEDFAVYYC KQSYNLLS FGQGTVLEIKR |
| SEQ ID NO: 476 Vk Framework 1 | EIVMTQSPATLSVSPGETVTMSC |
| SEQ ID NO: 478 Vk CDR1 | KSSQSLLNSRSRKNYLA |
| SEQ ID NO: 479 Vk Framework 2 | WYQQKPGQAPRLLIY |
| SEQ ID NO: 480 Vk CDR2 | WASTRES |
| SEQ ID NO: 481 Vk Framework 3 | GVPARFSGSGSGTEFTLTISSVQSEDFAVYYC |
| SEQ ID NO: 482 Vk CDR 3 | KQSYNLLS |
| SEQ ID NO: 483 Vk Framework 4 | FGQGTVLEIKR |
| SEQ ID NO: 484 HuC6D4 | EIVMTQSPATLSVSPGERVTMSC KSSQSLLNSRSRKNYLA WYQQKPGQAPRLLIY WASTRES GVPARFSGSGSGTEFTLTISSVQSEDFAVYYC KQSYNLLS FGQGTVLEIKR |
| SEQ ID NO: 485 Vk Framework 1 | EIVMTQSPATLSVSPGERVTMSC |
| SEQ ID NO: 486 Vk CDR1 | KSSQSLLNSRSRKNYLA |
| SEQ ID NO: 487 Vk Framework 2 | WYQQKPGQAPRLLIY |
| SEQ ID NO: 488 Vk CDR2 | WASTRES |
| SEQ ID NO: 489 Vk Framework 3 | GVPARFSGSGSGTEFTLTISSVQSEDFAVYYC |
| SEQ ID NO: 490 Vk CDR 3 | KQSYNLLS |

| Informal Sequence Listing | | |
|---|---|---|
| SEQ ID NO: 491 Vk Framework 4 | | FGQGTVLEIKR |
| SEQ ID NO: 492 C6D4-RGD3 | | DIVMTQSPSSLAVSAGEKVTMSC KSSQSLLGRGDLGRLKKNALA WYQQKPGQSPRLLIY WASTRES GVPDRFTGSGSGTDFTLTISSVQAEDLAVYYC KQSYNLLS FGAGTKLELKR |
| SEQ ID NO: 493 Vk Framework 1 | | DIVMTQSPSSLAVSAGEKVTMSC |
| SEQ ID NO: 494 Vk CDR1 | | KSSQSLLGRGDLGRLKKNALA |
| SEQ ID NO: 495 Vk Framework 2 | | WYQQKPGQSPRLLIY |
| SEQ ID NO: 496 Vk CDR2 | | WASTRES |
| SEQ ID NO: 497 Vk Framework 3 | | GVPDRFTGSGSGTDFTLTISSVQAEDLAVYYC |
| SEQ ID NO: 498 Vk CDR 3 | | KQSYNLLS |
| SEQ ID NO: 499 Vk Framework 4 | | FGAGTKLELKR |
| SEQ ID NO: 500 HuC6D4-RGD3 | | EIVMTQSPATLSVSPGERTMSC KSSQSLLGRGDLGRLKKNALA WYQQKPGQAPRLLIY WASTRES GVPARFSGSGSGTEFTLTISSVQSEDFAVYYC KQSYNLLS FGQGTVLEIKR |
| SEQ ID NO: 501 Vk Framework 1 | | EIVMTQSPATLSVSPGERVTMSC |
| SEQ ID NO: 502 Vk CDR1 | | KSSQSLLGRGDLGRLKKNALA |
| SEQ ID NO: 503 Vk Framework 2 | | WYQQKPGQAPRLLIY |
| SEQ ID NO: 504 Vk CDR2 | | WASTRES |
| SEQ ID NO: 505 Vk Framework 3 | | GVPARFSGSGSGTEFTLTISSVQSEDFAVYYC |
| SEQ ID NO: 506 Vk CDR 3 | | KQSYNLLS |
| SEQ ID NO: 507 Vk Framework 4 | | FGQGTVLEIKR |
| SEQ ID NO: 508 HuC6D4V1 VH CDR1 | | DYSMH |
| SEQ ID NO: 509 HuC6D4V1 VH CDR2 | | RINTETGEPTFADDFRG |
| SEQ ID NO: 510 HuC6D4V1 VH CDR3 | | FYYGRDS |
| SEQ ID NO: 511 HuC6D4A3 VH CDR1 | | DYSMH |
| SEQ ID NO: 512 HuC6D4A3 VH CDR2 | | RINTETGEPTFADDFRG |
| SEQ ID NO: 513 HuC6D4A3 VH CDR3 | | FYYGRDS |
| SEQ ID NO: 514 HuC6D4B7 VH CDR1 | | DYSMH |
| SEQ ID NO: 515 HuC6D4B7 VH CDR2 | | RINTETGEPTFADDFRG |
| SEQ ID NO: 516 HuC6D4B7 VH CDR3 | | FYYGRDT |
| SEQ ID NO: 517 HuC6D4E5 VH CDR1 | | DYSMH |
| SEQ ID NO: 518 HuC6D4E5 VH CDR2 | | DINTETGEPTFADDFRG |
| SEQ ID NO: 519 HuC6D4E5 VH CDR3 | | FYYGRDT |
| SEQ ID NO: 520 HuC6D4 VH CDR1 | | DYSMH |
| SEQ ID NO: 521 HuC6D4 VH CDR2 | | RINTETGEPTFADDFRG |
| SEQ ID NO: 522 HuC6D4 VH CDR3 | | FYYGRDT |
| SEQ ID NO: 523 C6D4-RGD3 VH CDR1 | | DYSMH |
| SEQ ID NO: 524 C6D4-RGD3 VH CDR2 | | RINTETGEPTFADDFRG |
| SEQ ID NO: 525 C6D4-RGD3 VH CDR3 | | FYYGRDS |
| SEQ ID NO: 526 HuC6D4-RGD3 VH CDR1 | | DYSMH |

| Informal Sequence Listing | | |
|---|---|---|
| SEQ ID NO: 527 HuC6D4-RGD3 VH CDR2 | RINTETGEPTFADDFRG |
| SEQ ID NO: 528 HuC6D4-RGD3 VH CDR3 | FYYGRDT |
| SEQ ID NO: 529 HuC6D4V1 Vk CDR1 | KSSQSLLNSRTRKNYLA |
| SEQ ID NO: 530 HuC6D4V1 Vk CDR2 | WASTRES |
| SEQ ID NO: 531 HuC6D4V1 Vk CDR3 | KQSYNLLS |
| SEQ ID NO: 532 HuC6D4A3 Vk CDR1 | KSSQSLLNSRSRKNYLA |
| SEQ ID NO: 533 HuC6D4A3 Vk CDR2 | WASTRES |
| SEQ ID NO: 534 HuC6D4A3 Vk CDR3 | KQSYNLIS |
| SEQ ID NO: 535 HuC6D4B7 Vk CDR1 | KSSQSLLNSRTRKNYLA |
| SEQ ID NO: 536 HuC6D4B7 Vk CDR2 | WASTRES |
| SEQ ID NO: 537 HuC6D4B7 Vk CDR3 | KQSSNLIS |
| SEQ ID NO: 538 HuC6D4E5 Vk CDR1 | KSSQSLLNSRSRKNYLA |
| SEQ ID NO: 539 HuC6D4E5 Vk CDR2 | WASTRES |
| SEQ ID NO: 540 HuC6D4E5 Vk CDR3 | KQSYNLLS |
| SEQ ID NO: 541 HuC6D4 Vk CDR1 | KSSQSLLNSRSRKNYLA |
| SEQ ID NO: 542 HuC6D4 Vk CDR2 | WASTRES |
| SEQ ID NO: 543 HuC6D4 Vk CDR3 | KQSYNLLS |
| SEQ ID NO: 544 C6D4-RGD3 Vk CDR1 | KSSQSLLGRGDLGRLKKNALA |
| SEQ ID NO: 545 C6D4-RGD3 Vk CDR2 | WASTRES |
| SEQ ID NO: 546 C6D4-RGD3 Vk CDR3 | KQSYNLLS |
| SEQ ID NO: 547 HuC6D4-RGD3 Vk CDR1 | KSSQSLLGRGDLGRLKKNALA |
| SEQ ID NO: 548 HuC6D4-RGD3 Vk CDR2 | WASTRES |
| SEQ ID NO: 549 HuC6D4-RGD3 Vk CDR3 | KQSYNLLS |
| SEQ ID NO: 550 heavy chain FR1 | QIQLVQSG(P/A)(E/K)(L/V)KKPG(E/A)(T/S)VKISCKASGYTFT |
| SEQ ID NO: 551 heavy chain FR2 | WV(K/R)WAPG(K/Q)GL(K/E)WVA |
| SEQ ID NO: 552 heavy chain FR3 | RF(A/T/S)V(S/T)L(E/D)TS(A/T)STAYL(Q/E)I(N/R/T)(N/S)L(K/R)(N/S)(E/D)DTA(T/V)YFCAI |
| SEQ ID NO: 553 heavy chain FR4 | WGQGT(T/A)LTVSS |
| SEQ ID NO: 554 light chain FR1 | (D/E)IVMTQ(S/T)P(S/A/V)(S/T)L(A/S)VS(A/P)GE(K/R/I)VTMSC |
| SEQ ID NO: 555 light chain FR2 | WYQQKPGQ(S/A)PRLLIY |
| SEQ ID NO: 556 light chain FR3 | (G/D)VP(D/A)RF(T/S)GSGSGT(D/E)FTLTISSVQ(A/S)ED(L/F)AVYYC |
| SEQ ID NO: 557 light chain FR4 | FG(A/Q)GT(K/V)LE(L/I)KR |
| SEQ ID NO: 558 heavy chain FR1 | QIQLxQSGx2x3x34KKPGx4x5VKISCKASGYTFT |
| SEQ ID NO: 559 heavy chain FR2 | WVx6QAPGx7GLx8Wx9x10 |
| SEQ ID NO: 560 heavy chain FR3 | RFx17x18x19Lx20TSx21x22TAx23Lx24Ix25x26Lx27x28x29DTAx30YFCAI |
| SEQ ID NO: 561 heavy chain FR4 | WGQGTx33LVTVSS |
| SEQ ID NO: 562 heavy chain CDR1 | DYSMH |
| SEQ ID NO: 563 heavy chain CDR2 | x11Ix12TETx13EPTx14ADDFx15x16 |

-continued

Informal Sequence Listing

SEQ ID NO: 564 heavy chain CDR3    x31YYGRDx32
where x1 = V or L, x2 = A or P, x3 = E or K, x4 = A or E, x5 = S or T, x6 = R or K,
x7 = Q or K, x8 = E or K, x9 = V or M, x10 = A or G, x11 = R or W, x12 = N or K, x13 =
G or D, x14 = F or Y, x15 = R, N, K or G, x16 = G or E, x17 = T, A, or S, x18 = V or F,
x19 = T or S, x20 = D or E, x21 = T or A, x22 = S or T, x23 = Y or N, x24 = E or Q,
x25 = R, N, I or T, x26 = S or N, x27 = R or K, x28 = S or N, x29 = D or E, x30 = V, T,
or K, x31 = F or Y, x32 = T or S, x33 = T or A, x34 = V or L SEQ ID NO: 565 light chain FR1     x40IVMx41Qx42Px43x44Lx45VSx46GEx47VTMSC SEQ ID NO: 566 light chain FR2     WYQQKPGQx49PRLLIY SEQ ID NO: 567 light chain FR3     x50VPx51RFx52GSGSGTx53FTLTISSVQx54EDx55AVYYC SEQ ID NO: 568 light chain FR4     FGx56GTx57LEx58KR SEQ ID NO: 569 light chain CDR1    KSSQSLLNSRx48RKNYLA SEQ ID NO: 570 light chain CDR2    WASTRES SEQ ID NO: 571 light chain CDR3    KQSYNLLS
where x40 = E or D, x41 = T or S, x42 = S or T, x43 = A, S or V, x44 = T, S, x45 = S or
A, x46 = P or A, x47 = R, K or I, x48 = S or T, x49 = A or S, x50 = G or D, x51 = A or
D, x52 = S or T, x53 = E or D, x54 = S, D or A, x55 = F or L, x56 = Q or A, x57 = V or
K, x58 = I or L.

SEQ ID NO: 572 (C6D4)              KSSQSLLNSRSRKNYLA

SEQ ID NO: 573 (RGD1)              KSSQSLLGRGDLGNALA

SEQ ID NO: 574 (RGD2)              KSSQSLLNSGRGDLGNALA

SEQ ID NO: 575 (RGD3)              KSSQSLLGRGDLGRLKKNALA

SEQ ID NO: 576 (RGD3-1)            KSSQSLLGRGDLGRLKKQKDHNALA

SEQ ID NO: 577 (RGD3-2)            KSSQSLLGRGDLGRLKKQKDNALA

SEQ ID NO: 578 (RGD3-3)            KSSQSLLGRGDLGRLKKQKNALA

SEQ ID NO: 579 (RGD3-4)            KSSQSLLGRGDLGRLKKQNALA

SEQ ID NO: 580 (RGD3-6)            KSSQSLLGRGDLGRLKNALA

SEQ ID NO: 581 (RGD3-7)            KSSQSLLGRGDLGRLNALA

SEQ ID NO: 582 (RGD3-8)            KSSQSLLGRGDLGRNALA

SEQ ID NO: 583 (RGD3-9)            KSSQSLLGRGDLGRLKKQKDHH

SEQ ID NO: 584 (RGD3-10)           KSSQSLLGRGDLGRLKKQKDH

SEQ ID NO: 585 (RGD3-11)           KSSQSLLGRGDLGRLKKQKD

SEQ ID NO: 586 (RGD3-12)           KSSQSLLGRGDLGRLKKQK

SEQ ID NO: 587 (RGD3-13)           KSSQSLLGRGDLGRLKKQ

SEQ ID NO: 588 (RGD3-14)           KSSQSLLGRGDLGRLKK

SEQ ID NO: 589 (RGD3-15)           KSSQSLLGRGDLGRLK

SEQ ID NO: 590 (RGD3-16)           KSSQSLLGRGDLGRL

SEQ ID NO: 591 Human αv            FLQDGTKTVEYAPCRSQDI*DADG*QGFCQGGFSIDFTKADRVLLGGPGSF*Y*WQGQ SEQ ID NO: 592 Chimp αv            FLQDGTKTVEYAPCRSQDI*DADG*QGFCQGGFSIDFTKADRVLLGGPGSF*Y*WQGQ SEQ ID NO: 593 Rhesus αv           FLQDGTKTVEYAPCRSQDI*DADG*QGFCQGGFSIDFTKADRVLLGGPGSF*Y*WQGQ SEQ ID NO: 594 Cyno αv             FLQDGTKTVEYAPCRSQDI*DADG*QGFCQGGFSIDFTKADRVLLGGPGSF*Y*WQGQ SEQ ID NO: 595 Cow αv              FLQDGTKTVEYAPCRSQDI*DADG*QGFCQGGFSIDFTKADRVLLGGPGSF*Y*WQGQ SEQ ID NO: 596 Pig αv              FLQDGTKTVEYAPCRSQDI*DADG*QGFCQGGFSIDFTKADRVLLGGPGSF*Y*WQGQ -continued

| Informal Sequence Listing | |
|---|---|
| SEQ ID NO: 597 Horse αv | FLQDGTKTVEYAPCRSQD_IDADG_QGFCQGGFSIDFTKADRVLLGGPGSF_Y_WQGQ |
| SEQ ID NO: 598 Mouse αv | FLQDGTKTVEYAPCRSQD_IDADG_QGFCQGGFSIDFTKADRVLLGGPGSF_Y_WQGQ |
| SEQ ID NO: 599 Rat αv | FLQDGTKTVEYAPCRSQD_IDADG_QGFCQGGFSIDFTKADRVLLGGPGSF_Y_WQGQ |
| SEQ ID NO: 600 Armadillo αv | FLQDGTKTVEYAPCRSQD_IDADG_QGFCQGGFSIDFTKADRVLLGGPGSF_Y_WQGQ |
| SEQ ID NO: 601 Platypus αv | FLQDGTKTVEYAPCRSQD_IDADG_QGFCQGGFSIDFTKADRVLLGGPGSF_Y_WQGQ |
| SEQ ID NO: 602 Human β8 | SASM_H_NNIEKLNSVGNDLSRKMAFFSRDFRLGFGSYVDKTVSPYISIHPER<br>IHNQC_SNYNLD_CMPPHGYIHVLSLTENITEFEKAV_HR_QKIS |
| SEQ ID NO: 603 Chimp β8 | SASM_H_NNIEKLNSVGNDLSRKMAFFSRDFRLGFGSYVDKTVSPYISIHPER<br>IHNQC_SNYNLD_CMPPHGYIHVLSLTENITEFERAV_HR_QKIS |
| SEQ ID NO: 604 Rhesus β8 | SASM_H_NNIEKLNSVGNDLSRKMAFFSRDFRLGFGSYVDKTVSPYISIHPER<br>IHNQC_SNYNLD_CMPPHGYIHVLSLTENITEFEKAV_HR_QKIS |
| SEQ ID NO: 605 Cyno β8 | SASM_H_NNIEKLNSVGNDLSRKMAFFSRDFRLGFGSYVDKTVSPYISIHPER<br>IHNQC_SNYNLD_CMPPHGYIHVLSLTENITEFEKAV_HR_QKIS |
| SEQ ID NO: 606 Cow β8 | SASM_H_NNIEKLNSVGNDLSRKMAFFSRDFRLGFGSYVDKTVSPYISIHPER<br>IHNQC_SNYNLD_CMPPHGYIHVLSLTENITEFEKAV_HR_QKIS |
| SEQ ID NO: 607 Pig β8 | SASM_H_NNIEKLNSVGNDLSRKMAFFSRDFRLGFGSYVDKTVSPYISIHPER<br>IHNQC_SNYNLD_CMPPHGYIHVLSLTENITEFEKAV_HR_QKIS |
| SEQ ID NO: 608 Horse β8 | SASM_H_NNIEKLNSVGNDLSRKMAFFSRDFRLGFGSYVDKTVSPYISIHPER<br>IHNQC_SNYNLD_CMPPHGYIHVLSLTENITEFEKAV_HR_QKIS |
| SEQ ID NO: 609 Mouse β8 | SASM_H_NNIEKLNSVGNDLSRKMAFFSRDFRLGFGSYVDKTVSPYISIHPER<br>IHNQC_SNYNLD_CMPPHGYIHVLSLTENITEFEKAV_HR_QKIS |
| SEQ ID NO: 610 Rat β8 | SASM_H_NNIEKLNSVGNDLSRKMAFFSRDFRLGFGSYVDKTVSPYISIHPER<br>IHNQC_SNYNLD_CMPPHGYIHVLSLTENITEFEKAV_HR_QKIS |
| SEQ ID NO: 611 Armadillo β8 | SASM_H_NNIEKLNSVGNDLSRKMAFFSRDFRLGFGSYVDKTVSPYISIHPER<br>IHNQC_SNYNLD_CMPPHGYIHVLSLTENITEFEKAV_HR_QKIS |
| SEQ ID NO: 612 Platypus β8 | SASM_H_NNIEKLNSVGNDLSQKMADFTRDFRLGFGSYVDKTVSPYISIHPGR<br>IRNQC_SQY_D_LD_CMPPHGYIHVLPLTENVTEFEKAVNKQKIS |
| SEQ ID NO: 613 C6D4 Vh CDR1 | YTFTDYSMH |
| SEQ ID NO: 614 C6D4 Vh CDR2 | RINTETGEPTFADDFRG |
| SEQ ID NO: 615 C6D4 Vh CFR3 | FYYGRDS |
| SEQ ID NO: 616 C6D4 Vk CDR1 | KSSQSLLNSRTRKNYLA |
| SEQ ID NO: 617 C6D4 Vk CDR2 | YWASTRES |
| SEQ ID NO: 618 C6D4 Vk CDR3 | KQSYNLLS |
| SEQ ID NO: 619 β8, α1 helix | SASMHNNIEKLNSVGNDLSRKMAFFS |
| SEQ ID NO: 620 β8, SDL | TVSPYISIHPERIHNQCSDYNLDCMPPH |
| SEQ ID NO: 621 β8, α2 helix | NITEFEKAVHR |
| SEQ ID NO: 622 αv, β-propeller domain blade W3 | KQDKILACAPLYHWRTEMKQEREPVGTCFLQDTKTVEYAPCRSQDIDADGQG<br>FCQGGFSIDFTKADRVLLGGPGSFYWQGQLISDQVAEIVSKYDPNVYSIKYNN<br>QLATRTAQAIFD |

SEQ ID NO: 623: head sequence of integrin αv
FNLDVDSPAEYSGPEGSYFGFAVDFFVPSASSRMFLLVGAPKANTTQPGIVEGGQVLKCDWSSTRRCQPIEFDATGNRDYAKDDPLEF
KSHQWFGASVRSKQDKILACAPLYHWRTEMKQEREPVGTCFLQDGTKTVEYAPCRSQDIDADGQGFCQGGFSIDFTKADRVLLGGPGS
FYWQGQLISDQVAEIVSKYDPNVYSIKYNNQLATRTAQAIFDDSYLGYSVAVGDFNGDGIDDFVSGVPRAARTLGMVYIYDGKNMSSL
YNFTGEQMAAYFGFSVAATDINGDDYADVFIGAPLFMDRGSDGKLQEVGQVSVSLQRASGDFQTTKLNGFEVFARFGSAIAPLGDLDQ
DGFNDIAIAAPYGGEDKKGIVYIFNGRSTGLNAVPSQILEGQWAARSMPPSFGYSMKGATDIDKNGYPDLIVGAFGVDRAILYRARP

| SEQ ID NO: 624 4F1 VH | QVQLQQSGAELVRPGTSVKVSCKASGY AFTNYLIE WVKQRPGQGLEWIG<br>VINPGTGGTNYNKKFKV KATLTADKSSSTAYMQLGGLTFDDSAVYFCAR<br>EGNARTYYYAMDY WGQGTSVTVSS |
| SEQ ID NO: 625 VH Framework 1 | QVQLQQSGAELVRPGTSVKVSCKASGY |
| SEQ ID NO: 628 VH CDR1 | AFTNYLIE |
| SEQ ID NO: 632 VH Framework 2 | WVKQRPGQGLEWIG |
| SEQ ID NO: 634 VH CDR2 | VINPGTGGTNYNKKFKV |
| SEQ ID NO: 637 VH Framework 3 | KATLTADKSSSTAYMQLGGLTFDDSAVYFCAR |

| Informal Sequence Listing | |
|---|---|
| SEQ ID NO: 651 VH CDR3 | EGNARTYYYAMDY |
| SEQ ID NO: 655 VH Framework 4 | WGQGTSVTVSS |
| SEQ ID NO: 656 6B9 VH | QVQLQQSGAELVRPGTSVKVSCKASGY AFTDYLIE WVKQRPGQGLEWIG VINPETGGTNYNAKFKG KATLTADKSSSSAYMQLSSLTSGDSAVYFCAR EAGNYIYAMDY WGQGTSVTVSS |
| SEQ ID NO: 625 VH Framework 1 | QVQLQQSGAELVRPGTSVKVSCKASGY |
| SEQ ID NO: 629 VH CDR1 | AFTDYLIE |
| SEQ ID NO: 632 VH Framework 2 | WVKQRPGQGLEWIG |
| SEQ ID NO: 635 VH CDR2 | VINPETGGTNYNAKFKG |
| SEQ ID NO: 638 VH Framework 3 | KATLTADKSSSSAYMQLSSLTSGDSAVYFCAR |
| SEQ ID NO: 652 VH CDR3 | EAGNYIYAMDY |
| SEQ ID NO: 655 VH Framework 4 | WGQGTSVTVSS |
| SEQ ID NO: 657 6B9.1 VH | QVQLQQSGAELVRPGTSVKVSCKASGY AFTDYLIE WVKQRPGQGLEWIG VINPETGGTNYNAKFRG KATLTADKSSSSAYMQLSSLTSGDSAVYFCAR AGNYIYAMDY WGQGTSVTVSS |
| SEQ ID NO: 625 VH Framework 1 | QVQLQQSGAELVRPGTSVKVSCKASGY |
| SEQ ID NO: 629 VH CDR1 | AFTDYLIE |
| SEQ ID NO: 632 VH Framework 2 | WVKQRPGQGLEWIG |
| SEQ ID NO: 636 VH CDR2 | VINPETGGTNYNAKFRG |
| SEQ ID NO: 638 VH Framework 3 | KATLTADKSSSSAYMQLSSLTSGDSAVYFCAR |
| SEQ ID NO: 653 VH CDR3 | AGNYIYAMDY |
| SEQ ID NO: 655 VH Framework 4 | WGQGTSVTVSS |
| SEQ ID NO: 658 A1 VH | QVQLQQSGAELVRPGASVKVSCKASGY AFTDYLIE WVRQRTGQGLEWIG VINPETGGTNYNAKFRG KATLTADKSSSSVYMQLSSLTSGDSAVYFCAR EAGNYIYAMDY WGQGTSVTVSS |
| SEQ ID NO: 626 VH Framework 1 | QVQLQQSGAELVRPGASVKVSCKASGY |
| SEQ ID NO: 629 VH CDR1 | AFTDYLIE |
| SEQ ID NO: 633 VH Framework 2 | WVRQRPGQGLEWIG |
| SEQ ID NO: 636 VH CDR2 | VINPETGGTNYNAKFRG |
| SEQ ID NO: 639 VH Framework 3 | KATLTADKSSSSVYMQLSSLTSGDSAVYFCAR |
| SEQ ID NO: 654 VH CDR3 | EAGNYIYAMDY |
| SEQ ID NO: 655 VH Framework 4 | WGQGTSVTVSS |
| SEQ ID NO: 659 A2 VH | QVQLQQSGAELVRPGTSVKVSCKASGY AFTDYLIE WVRQRTGQGLEWIG VINPETGGTNYNAKFRG KATLTADKSSSTAYMQLSSLTSGDSAVYFCAR EAGNYIYAMDY WGQGTSVTVSS |
| SEQ ID NO: 625 VH Framework 1 | QVQLQQSGAELVRPGTSVKVSCKASGY |
| SEQ ID NO: 629 VH CDR1 | AFTDYLIE |
| SEQ ID NO: 633 VH Framework 2 | WVRQRPGQGLEWIG |
| SEQ ID NO: 636 VH CDR2 | VINPETGGTNYNAKFRG |
| SEQ ID NO: 640 VH Framework 3 | KATLTADKSSSTAYMQLSSLTSGDSAVYFCAR |
| SEQ ID NO: 654 VH CDR3 | EAGNYIYAMDY |
| SEQ ID NO: 655 VH Framework 4 | WGQGTSVTVSS |

| | |
|---|---|
| Informal Sequence Listing | |
| SEQ ID NO: 660 A8 VH | QVQLQQSGALEVRPGTSVKVSCKASGY AFTDYLIE WVRQRTGQGLEWIG VINPETGGTNYNAKFRG KATLTADKSSSSAYMQLSGLTSGDSAVYFCAR EAGNYIYAMDY WGQGTSVTVSS |
| SEQ ID NO: 625 VH Framework 1 | QVQLQQSGAELVRPGTSVKVSCKASGY |
| SEQ ID NO: 629 VH CDR1 | AFTDYLIE |
| SEQ ID NO: 633 VH Framework 2 | WVRQRPGQGLEWIG |
| SEQ ID NO: 636 VH CDR2 | VINPETGGTNYNAKFRG |
| SEQ ID NO: 641 VH Framework 3 | KATLTADKSSSSAYMQLSGLTSGDSAVYFCAR |
| SEQ ID NO: 654 VH CDR3 | EAGNYIYAMDY |
| SEQ ID NO: 655 VH Framework 4 | WGQGTSVTVSS |
| SEQ ID NO: 661 A11 VH | QVQLQQSGALEVRPGTSVKVSCKASGY AFTDYLIE WVRQRTGQGLEWIG VINPETGGTNYNAKFRG KATLTADKSSSSAYMQLSGLTSGDSAVYFCAR EGANYIYAMDY WGQGTSVTVSS |
| SEQ ID NO: 625 VH Framework 1 | QVQLQQSGAELVRPGTSVKVSCKASGY |
| SEQ ID NO: 629 VH CDR1 | AFTDYLIE |
| SEQ ID NO: 633 VH Framework 2 | WVRQRPGQGLEWIG |
| SEQ ID NO: 636 VH CDR2 | VINPETGGTNYNAKFRG |
| SEQ ID NO: 638 VH Framework 3 | KATLTADKSSSSAYMQLSGLTSGDSAVYFCAR |
| SEQ ID NO: 654 VH CDR3 | EAGNYIYAMDY |
| SEQ ID NO: 655 VH Framework 4 | WGQGTSVTVSS |
| SEQ ID NO: 662 B1 VH | QVQLQQSGAELVRPGTSVKVSCKASGY AFTDYLIE WVKQRPGQGLEWIG VINPETGGTNYNAKFRG KATLTADKSSSSAYMQLSSLSSGDSAVYFCAR EAGNYIYAMDY WGQGTSVTVSS |
| SEQ ID NO: 625 VH Framework 1 | QVQLQQSGAELVRPGTSVKVSCKASGY |
| SEQ ID NO: 629 VH CDR1 | AFTDYLIE |
| SEQ ID NO: 632 VH Framework 2 | WVKQRPGQGLEWIG |
| SEQ ID NO: 636 VH CDR2 | VINPETGGTNYNAKFRG |
| SEQ ID NO: 642 VH Framework 3 | KATLTADKSSSSAYMQLSSLSSGDSAVYFCAR |
| SEQ ID NO: 654 VH CDR3 | EAGNYIYAMDY |
| SEQ ID NO: 655 VH Framework 4 | WGQGTSVTVSS |
| SEQ ID NO: 663 B3 VH | QVQLQQSGAELVRPGTSVKVSCKASGY AFTDYLIE WVRQRPGQGLEWIG VINPETGGTNYNAKFRG KATLTADKSSSSAYMQLSGLTSGDSAVYFCAR EAGNYIYAMDY WGQGTSVTVSS |
| SEQ ID NO: 625 VH Framework 1 | QVQLQQSGALEVRPGTSVKVSCKASGY |
| SEQ ID NO: 629 VH CDR1 | AFTDYLIE |
| SEQ ID NO: 633 VH Framework 2 | WVRQRPGQGLEWIG |
| SEQ ID NO: 636 VH CDR2 | VINPETGGTNYNAKFRG |
| SEQ ID NO: 643 VH Framework 3 | KATLTADKSSSSAYMQLSGLTSGDSAVYFCAR |
| SEQ ID NO: 654 VH CDR3 | EAGNYIYAMDY |
| SEQ ID NO: 655 VH Framework 4 | WGQGTSVTVSS |
| SEQ ID NO: 664 C4 = F10 VH | QVQLQQSGAELVRPGTSVKVSCKASGY AFTDYLIE WVRQRPGQGLEWIG VINPETGGTNYNAKFRG RATLTADKSSSSAYMQLSSLTSGDSAVYFCAR EAGNYIYAMDY WGQGTSVTVSS |
| SEQ ID NO: 625 VH Framework 1 | QVQLQQSGAELVRPGTSVKVSCKASGY |

-continued

Informal Sequence Listing

| | | |
|---|---|---|
| SEQ ID NO: 629 VH CDR1 | | AFTDYLIE |
| SEQ ID NO: 633 VH Framework 2 | | WVRQRPGQGLEWIG |
| SEQ ID NO: 636 VH CDR2 | | VINPETGGTNYNAKFRG |
| SEQ ID NO: 644 VH Framework 3 | | RATLTADKSSSSAYMQLSSLTSGDSAVYFCAR |
| SEQ ID NO: 654 VH CDR3 | | EAGNYIYAMDY |
| SEQ ID NO: 655 VH Framework 4 | | WGQGTSVTVSS |
| SEQ ID NO: 665 C7 = D1 VH | | QVQLQQSGAELVRPGTSVKVSCKASGY AFTDYLIE WVRQRPGQGLEWIG VINPETGGTNYNAKFRG KATLTADKSSGSAYMQLSSLTSGDSAVYFCAR EAGNYIYAMDY WGQGTSVTVSS |
| SEQ ID NO: 625 VH Framework 1 | | QVQLQQSGAELVRPGTSVKVSCKASGY |
| SEQ ID NO: 629 VH CDR1 | | AFTDYLIE |
| SEQ ID NO: 633 VH Framework 2 | | WVRQRPGQGLEWIG |
| SEQ ID NO: 636 VH CDR2 | | VINPETGGTNYNAKFRG |
| SEQ ID NO: 644 VH Framework 3 | | RATLTADKSSSSAYMQLSSLTSGDSAVYFCAR |
| SEQ ID NO: 654 VH CDR3 | | EAGNYIYAMDY |
| SEQ ID NO: 655 VH Framework 4 | | WGQGTSVTVSS |
| SEQ ID NO: 666 D3 = F1 VH | | QVQLQQSGAELVRPGTSVKVSCKASGY AFTDYLIE WVRQRPGQGLEWIG VINPETGGTNYNAKFRG KATLTADKSSSSAYMQLSSLTSDDSAVYFCAR EAGNYIYAMDY WGQGTSVTVSS |
| SEQ ID NO: 625 VH Framework 1 | | QVQLQQSGAELVRPGTSVKVSCKASGY |
| SEQ ID NO: 629 VH CDR1 | | AFTDYLIE |
| SEQ ID NO: 633 VH Framework 2 | | WVRQRPGQGLEWIG |
| SEQ ID NO: 636 VH CDR2 | | VINPETGGTNYNAKFRG |
| SEQ ID NO: 645 VH Framework 3 | | KATLTADKSSSSAYMQLSSLTSDDAAVYFCAR |
| SEQ ID NO: 654 VH CDR3 | | EAGNYIYAMDY |
| SEQ ID NO: 655 VH Framework 4 | | WGQGTSVTVSS |
| SEQ ID NO: 667 D10 = E5 VH | | QVQLQQSGAELVRPGTSVKVSCKASGY AFTDYLIE WVRQRPGQGLEWIG VINPETGGTNYNAKFRG KVTLTADKTSSSAYMQLSSLTSGDSAVYFCAR EAGNYIYAMDY WGQGTSVTVSS |
| SEQ ID NO: 625 VH Framework 1 | | QVQLQQSGAELVRPGTSVKVSCKASGY |
| SEQ ID NO: 629 VH CDR1 | | AFTDYLIE |
| SEQ ID NO: 633 VH Framework 2 | | WVRQRPGQGLEWIG |
| SEQ ID NO: 636 VH CDR2 | | VINPETGGTNYNAKFRG |
| SEQ ID NO: 646 VH Framework 3 | | KVTLTADKTSSSAYMQLSSLTSGDSAVYFCAR |
| SEQ ID NO: 654 VH CDR3 | | EAGNYIYAMDY |
| SEQ ID NO: 655 VH Framework 4 | | WGQGTSVTVSS |
| SEQ ID NO: 668 G4 VH | | QVQLQQSGAELVRPGTSVKVSCKASGY AFTDYLIE WVRQRPGQGLEWIG VINPETGGTNYNAKFRG KVTLTADKSSSSAYMQLNSLTSGDSAVYFCAR EAGNYIYAMDY WGQGTSVTVSS |
| SEQ ID NO: 625 VH Framework 1 | | QVQLQQSGALEVRPGTSVKVSCKASGY |
| SEQ ID NO: 629 VH CDR1 | | AFTDYLIE |
| SEQ ID NO: 633 VH Framework 2 | | WVRQRTGQGLEWIG |

| Informal Sequence Listing | |
|---|---|
| SEQ ID NO: 636 VH CDR2 | VINPETGGTNYNAKFRG |
| SEQ ID NO: 647 VH Framework 3 | KVTLTADKSSSSAYMQLNSLTSGDSAVYFCAR |
| SEQ ID NO: 654 VH CDR3 | EAGNYIYAMDY |
| SEQ ID NO: 655 VH Framework 4 | WGQGTSVTVSS |
| SEQ ID NO: 669 C4 VH | QVQLQQSGAELVRPGTSVKVSCKASGY AFTDYLIE WVRQRTGQGLEWIG VINPETGGTNYNAKFRG RATLTADKSSSSAYMQLSSLTSGDSAVYFCAR EAGNYIYAMDY WGQGTSVTVSS |
| SEQ ID NO: 625 VH Framework 1 | QVQLQQSGAELVRPGTSVKVSCKASGY |
| SEQ ID NO: 629 VH CDR1 | AFTDYLIE |
| SEQ ID NO: 633 VH Framework 2 | WVRQRPGQGLEWIG |
| SEQ ID NO: 636 VH CDR2 | VINPETGGTNYNAKFRG |
| SEQ ID NO: 650 VH Framework 3 | RATLTADKSSSSAYMQLSSLTSGDSAVYFCAR |
| SEQ ID NO: 654 VH CDR3 | EAGNYIYAMDY |
| SEQ ID NO: 655 VH Framework 4 | WGQGTSVTVSS |
| SEQ ID NO: 670 D10 VH | QVQLQQSGAELVRPGTSVKVSCKASGY AFTDYLIE WVRQRPGQGLEWIG VINPETGGTNYNAKFRG KVTLTADKTSSSAYMQLSSLTSGDSAVYFCAR EAGNYIYAMDY WGQGTSVTVSS |
| SEQ ID NO: 625 VH Framework 1 | QVQLQQSGAELVRPGTSVKVSCKASGY |
| SEQ ID NO: 629 VH CDR1 | AFTDYLIE |
| SEQ ID NO: 633 VH Framework 2 | WVRQRPGQGLEWIG |
| SEQ ID NO: 636 VH CDR2 | VINPETGGTNYNAKFRG |
| SEQ ID NO: 646 VH Framework 3 | KVTLTADKTSSSAYMQLSSLTSGDSAVYFCAR |
| SEQ ID NO: 654 VH CDR3 | EAGNYIYAMDY |
| SEQ ID NO: 655 VH Framework 4 | WGQGTSVTVSS |
| SEQ ID NO: 671 AF1A11 VH | QVQLQQSGALEVRPGTSVKVSCKASGY AFTDYLIE WVKQRPGQGLEWIG VINPETGGTNYNAKFRG RATLTADKSSSSAYMQLSSLTSGDSAVYFCAR EAGNYIYAMDY WGQGTSVTVSS |
| SEQ ID NO: 625 VH Framework 1 | QVQLQQSGALEVRPGTSVKVSCKASGY |
| SEQ ID NO: 629 VH CDR1 | AFTDYLIE |
| SEQ ID NO: 632 VH Framework 2 | WVKQRPGQGLEWIG |
| SEQ ID NO: 636 VH CDR2 | VINPETGGTNYNAKFRG |
| SEQ ID NO: 650 VH Framework 3 | RATLTADKSSSSAYMQLSSLTSGDSAVYFCAR |
| SEQ ID NO: 654 VH CDR3 | EAGNYIYAMDY |
| SEQ ID NO: 655 VH Framework 4 | WGQGTSVTVSS |
| SEQ ID NO: 672 AF1E1 VH | QVQLQQSGAELVRPGTSVKVSCKASGY AFTDYLIQ WVKQRPGQGLEWIG VINPETGGTNYNAKFRG KATLTADKSSSSAYMQLSSLTSGDSAVYFCAR EAGNYIYAMDY WGQGTSVTVSS |
| SEQ ID NO: 625 VH Framework 1 | QVQLQQSGAELVRPGTSVKVSCKASGY |
| SEQ ID NO: 631 VH CDR1 | AFTDYLIQ |
| SEQ ID NO: 632 VH Framework 2 | WVKQRTGQGLEWIG |
| SEQ ID NO: 636 VH CDR2 | VINPETGGTNYNAKFRG |
| SEQ ID NO: 638 VH Framework 3 | KATLTADKSSSSAYMQLSSLTSGDSAVYFCAR |
| SEQ ID NO: 654 VH CDR3 | EAGNYIYAMDY |

| Informal Sequence Listing | |
|---|---|
| SEQ ID NO: 655 VH Framework 4 | WGQGTSVTVSS |
| SEQ ID NO: 673 4F1G3 VH | QVQLQQSGAELVRPGTSVRVSCKASGY AFTDYLIQ WVKQRPGQGLEWIG VINPETGGTNYNAKFRG KATLTANKSSSSAYMQLSSLTSGDSAVYFCAR EAGNYIYAMDY WGQGTSVTVSS |
| SEQ ID NO: 625 VH Framework 1 | QVQLQQSGAELVRPGTSVKVSCKASGY |
| SEQ ID NO: 631 VH CDR1 | AFTDYLIQ |
| SEQ ID NO: 632 VH Framework 2 | WVKQRPGQGLEWIG |
| SEQ ID NO: 636 VH CDR2 | VINPETGGTNYNAKFRG |
| SEQ ID NO: 648 VH Framework 3 | KATLTANKSSSSAYMQLSSLTSGDSAVYFCAR |
| SEQ ID NO: 654 VH CDR3 | EAGNYIYAMDY |
| SEQ ID NO: 655 VH Framework 4 | WGQGTSVTVSS |
| SEQ ID NO: 674 4F1E10 VH | QVQLQQSGAELVRPGTSVKVPCKASGY AFTDYLIQ WVKQRPGQGLEWIG FINPETGGTNYNAKFRG KATLTADKSSSSAYMQLSSLTSGDSAVYFCAR EAGNYIYAMDY WGQGTSVTVSS |
| SEQ ID NO: 627 VH Framework 1 | QVQLQQSGAELVRPGTSVKVPCKASGY |
| SEQ ID NO: 631 VH CDR1 | AFTDYLIQ |
| SEQ ID NO: 632 VH Framework 2 | EVKQRPGQGLEWIG |
| SEQ ID NO: 636 VH CDR2 | VINPETGGTNYNAKFRG |
| SEQ ID NO: 638 VH Framework 3 | KATLTADKSSSSAYMQLSSLTSGDSAVYFCAR |
| SEQ ID NO: 654 VH CDR3 | EAGNYIYAMDY |
| SEQ ID NO: 655 VH Framework 4 | WGQGTSVTVSS |
| SEQ ID NO: 675 4F1E9 VH | QVQLQQSGAELVRPGTSVKVSCKASGY AFTDYLIE EVKQRPGQGLEWIG VINPETGGTNYNAKFRG KATLTADKSSSSAYMQLSSLTSGDSAVYFCAR EAGNYIYAMDY WGQGTSVTVSS |
| SEQ ID NO: 625 VH Framework 1 | QVQLQQSGAELVRPGTSVKVSCKASGY |
| SEQ ID NO: 629 VH CDR1 | AFTDYLIE |
| SEQ ID NO: 632 VH Framework 2 | WVKQRPGQGLEWIG |
| SEQ ID NO: 636 VH CDR2 | VINPETGGTNYNAKFRG |
| SEQ ID NO: 638 VH Framework 3 | KATLTADKSSSSAYMQLSSLTSGDSAVYFCAR |
| SEQ ID NO: 654 VH CDR3 | EAGNYIYAMDY |
| SEQ ID NO: 655 VH Framework 4 | WGQGTSVTVSS |
| SEQ ID NO: 676 4F1H12 VH | QVQLQQSGAELVRPGTSVKVSCKASGY AFTDYLIQ WVKQRPGQGLEWIG VINPETGGTNYNAKFRG KATLTADKSSSSAYLQLSSLTSGDSAVYFCAR EAVNYIYAMDY WGQGTSVTVSS |
| SEQ ID NO: 625 VH Framework 1 | QVQLQQSGAELVRPGTSVKVSCKASGY |
| SEQ ID NO: 631 VH CDR1 | AFTDYLIQ |
| SEQ ID NO: 632 VH Framework 2 | WVKQRPGQGLEWIG |
| SEQ ID NO: 636 VH CDR2 | VINPETGGTNYNAKFRG |
| SEQ ID NO: 649 VH Framework 3 | KATLTADKSSSSAYLQLSSLTSGDSAVYFCAR |
| SEQ ID NO: 654 VH CDR3 | EAGNYIYAMDY |
| SEQ ID NO: 655 VH Framework 4 | WGQGTSVTVSS |

-continued

| Informal Sequence Listing | |
|---|---|
| SEQ ID NO: 677 F9 VH | QVQLQQSGALEVRPGTSVKVSCKASGY AFTDYLIQ WVKQRPGQGLEWIG VINPETGGTNYNAKFRG KATLTADKSSSSAYMQLSSLTSGDSAVYFCAR EAGNYIYAMDY WGQGTSVTVSS |
| SEQ ID NO: 625 VH Framework 1 | QVQLQQSGAELVRPGTSVKVSCKASGY |
| SEQ ID NO: 631 VH CDR1 | AFTDYLIQ |
| SEQ ID NO: 632 VH Framework 2 | WVKQRPGQGLEWIG |
| SEQ ID NO: 636 VH CDR2 | VINPETGGTNYNAKFRG |
| SEQ ID NO: 638 VH Framework 3 | KATLTADKSSSSAYMQLSSLTSGDSAVYFCAR |
| SEQ ID NO: 654 VH CDR3 | EAGNYIYAMDY |
| SEQ ID NO: 655 VH Framework 4 | WGQGTSVTVSS |
| SEQ ID NO: 678 4F1 VL | DIQMTQSPASLSASVGETVTITC RASVNIYSYLV WYQQKQGKSPQLLVH NAKTLAE GVPSRFSGSGSGTQFSLKINSLQPEDFGSYYC QHHHGTPYT FGGGTKLEIKA |
| SEQ ID NO: 692 VL Framework 1 | DIQMTQSPASLSASVGETVTITC |
| SEQ ID NO: 693 VL CDR1 | RASVNIYSYLV |
| SEQ ID NO: 694 VL Framework 2 | WYQQKQGKSPQLLVH |
| SEQ ID NO: 695 VL CDR2 | NAKTLAE |
| SEQ ID NO: 696 VL Framework 3 | GVPSRFSGSGSGTQFSLKINSLQPEDFGSYYC |
| SEQ ID NO: 697 VL CDR3 | QHHHGTPYT |
| SEQ ID NO: 698 VL Framework 4 | FGGGTKLEIKA |
| SEQ ID NO: 679 6B9 VL | DIEMTQTPASLSASVGETVTITC RASENIYSYLV WYQQKQGKSPQVLVY NAKTLAE GVPSRFSGSGSGTQFSLKINSLQPEDFGSYYC QHHNGTPYT FGGGTKLEIKA |
| SEQ ID NO: 699 VL Framework 1 | DIEMTQTPASLSASVGETVTITC |
| SEQ ID NO: 700 VL CDR1 | RASENIYSYLV |
| SEQ ID NO: 701 VL Framework 2 | WYQQKQGKQPQVLVY |
| SEQ ID NO: 695 VL CDR2 | NAKTLAE |
| SEQ ID NO: 696 VL Framework 3 | GVPSRFSGSGSGTQFSLKINSLQPEDFGSYYC |
| SEQ ID NO: 702 VL CDR3 | QHHNGTPYT |
| SEQ ID NO: 698 VL Framework 4 | FGGGTKLEIKA |
| SEQ ID NO: 680 6B9.1 VL | DIVMTQSPASLSASVGETVTITC RASVNIYSYLV WYQQKQGKSPQLLVH NAKTLAE GVPSRFSGSGSGTQFSLKINSLQPEDFGSYYC QHHHGTPYT FGGGTKLEIKA |
| SEQ ID NO: 703 VL Framework 1 | DIVMTQSPASLSASVGETVTITC |
| SEQ ID NO: 693 VL CDR1 | RASVNIYSYLV |
| SEQ ID NO: 694 VL Framework 2 | WYQQKQGKSPQLLVH |
| SEQ ID NO: 695 VL CDR2 | NAKTLAE |
| SEQ ID NO: 696 VL Framework 3 | GVPSRFSGSGSGTQFSLKINSLQPEDFGSYYC |
| SEQ ID NO: 697 VL CDR3 | QHHHGTPYT |
| SEQ ID NO: 698 VL Framework 4 | FGGGTKLEIKA |
| SEQ ID NO: 681 A1 = A2 = C4 = C7 = D1 = D10 = E5 = F1 = F10 = G4 VL | DIVMTQSPASLSASVGETVTITC RASVNIYSYLV WYQQKQGKSPQLLVH NAKTLAE GVPSRFSGSGSGTQFSLKINSLQPEDFGSYYC QHHHGTPYT FGGGTKLEIKA |
| SEQ ID NO: 703 VL Framework 1 | DIVMTQSPASLSASVGETVTITC |

| Informal Sequence Listing | | |
|---|---|---|
| SEQ ID NO: 693 VL CDR1 | | RASVNIYSYLV |
| SEQ ID NO: 694 VL Framework 2 | | WYQQKQGKSPQLLVH |
| SEQ ID NO: 695 VL CDR2 | | NAKTLAE |
| SEQ ID NO: 696 VL Framework 3 | | GVPSRFSGSGSGTQFSLKINSLQPEDFGSYYC |
| SEQ ID NO: 697 VL CDR3 | | QHHHGTPYT |
| SEQ ID NO: 698 VL Framework 4 | | FGGGTKLEIKA |
| SEQ ID NO: 682 A8 VL | | DIVMTQSPASLSASVGETVTITC RASVNIYSYLV WYQQKQGKSPQLLVH NAKTLAE GVPSRFSGSGSGTQFSLKINSVQPEDFGSYYC QHHHGTPYT FGGGTKLEIKA |
| SEQ ID NO: 703 VL Framework 1 | | DIVMTQSPASLSASVGETVTITC |
| SEQ ID NO: 693 VL CDR1 | | RASVNIYSYLV |
| SEQ ID NO: 694 VL Framework 2 | | WYQQKQGKSPQLLVH |
| SEQ ID NO: 695 VL CDR2 | | NAKTLAE |
| SEQ ID NO: 696 VL Framework 3 | | GVPSRFSGSGSGTQFSLKINSLQPEDFGSYYC |
| SEQ ID NO: 697 VL CDR3 | | QHHHGTPYT |
| SEQ ID NO: 698 VL Framework 4 | | FGGGTKLEIKA |
| SEQ ID NO: 683 A11 VL | | HIVMTQSPASLSASVGETVTITC RASVNIYSYLV WYQQKQGKSPQLLVH NAKTLAE GVPSRFSGSGSGTQFSLKINSLQPEDFGSYYC QHHHGTPYT FGGGTKLEIKA |
| SEQ ID NO: 704 VL Framework 1 | | HIVMTQSPASLSASVGETVTITC |
| SEQ ID NO: 693 VL CDR1 | | RASVNIYSYLV |
| SEQ ID NO: 694 VL Framework 2 | | WYQQKQGKSPQLLVH |
| SEQ ID NO: 695 VL CDR2 | | NAKTLAE |
| SEQ ID NO: 696 VL Framework 3 | | GVPSRFSGSGSGTQFSLKINSLQPEDFGSYYC |
| SEQ ID NO: 697 VL CDR3 | | QHHHGTPYT |
| SEQ ID NO: 698 VL Framework 4 | | FGGGTKLEIKA |
| SEQ ID NO: 684 B1 VL | | DIVMTQSPASLSASVGETVTITC RASVNIYSYLV WYQQKQGKSPQLLVH NAKTLAE GVPSRFSGSGSGTQFSLINKSLQPEDVGSYYC QHHHGTPYT FGGGTKLEIKA |
| SEQ ID NO: 703 VL Framework 1 | | DIVMTQSPASLSASVGETVTITC |
| SEQ ID NO: 693 VL CDR1 | | RASVNIYSYLV |
| SEQ ID NO: 694 VL Framework 2 | | WYQQKQGKSPQLLVH |
| SEQ ID NO: 695 VL CDR2 | | NAKTLAE |
| SEQ ID NO: 696 VL Framework 3 | | GVPSRFSGSGSGTQFSLKINSLQPEDFGSYYC |
| SEQ ID NO: 697 VL CDR3 | | QHHHGTPYT |
| SEQ ID NO: 698 VL Framework 4 | | FGGGTKLEIKA |
| SEQ ID NO: 685 B3 VL | | DIVMQTSPASLSASVGETVTITC RASVNIYSYLV WYQQKQGKSPQLLVH NAKTLAE GVPSRFSGSGSGTQFSLKINSLQPEDFGSYYC QHHHGTPYT FGGGTKLEIKA |
| SEQ ID NO: 703 VL Framework 1 | | DIVMTQSPASLSASVGETVTITC |
| SEQ ID NO: 693 VL CDR1 | | RASVNIYSYLV |
| SEQ ID NO: 694 VL Framework 2 | | WYQQKQGKSPQLLVH |

| Informal Sequence Listing | | |
|---|---|---|
| SEQ ID NO: 695 | VL CDR2 | NAKTLAE |
| SEQ ID NO: 696 | VL Framework 3 | GVPSRFSGSGSGTQFSLKINSLQPEDFGSYYC |
| SEQ ID NO: 697 | VL CDR3 | QHHHGTPYT |
| SEQ ID NO: 698 | VL Framework 4 | FGGGTKLEIKA |
| SEQ ID NO: 686 | D10 = E5 VL | DIVMTQSPASLSASVGETVTITC RASVNIYSYLV WYQQKQGKSPQLLVH NAKTLAE GVPSRFSGSGSGTQFSLKINSLQPEDFGSYYC QHHHGTPYT FGGGTKLEIKA |
| SEQ ID NO: 703 | VL Framework 1 | DIVMTQSPASLSASVGETVTITC |
| SEQ ID NO: 693 | VL CDR1 | RASVNIYSYLV |
| SEQ ID NO: 694 | VL Framework 2 | WYQQKQGKSPQLLVH |
| SEQ ID NO: 695 | VL CDR2 | NAKTLAE |
| SEQ ID NO: 696 | VL Framework 3 | GVPSRFSGSGSGTQFSLKINSLQPEDFGSYYC |
| SEQ ID NO: 697 | VL CDR3 | QHHHGTPYT |
| SEQ ID NO: 698 | VL Framework 4 | FGGGTKLEIKA |
| SEQ ID NO: 687 | C4 VL | DIVMTQSPASLSASVGETVTITC RASVNIYSYLV WYQQKQGKSPQLLVH NAKTLAE GVPSRFSGSGSGTQFSLKINSLQPEDFGSYYC QHHHGTPYT FGGGTKLEIKR |
| SEQ ID NO: 703 | VL Framework 1 | DIVMTQSPASLSASVGETVTITC |
| SEQ ID NO: 693 | VL CDR1 | RASVNIYSYLV |
| SEQ ID NO: 694 | VL Framework 2 | WYQQKQGKSPQLLVH |
| SEQ ID NO: 695 | VL CDR2 | NAKTLAE |
| SEQ ID NO: 696 | VL Framework 3 | GVPSRFSGSGSGTQFSLKINSLQPEDFGSYYC |
| SEQ ID NO: 697 | VL CDR3 | QHHHGTPYT |
| SEQ ID NO: 706 | VL Framework 4 | FGGGTKLEIKR |
| SEQ ID NO: 688 | D10 VL | DIEMTQTPASLSASVGETVTITC RASVNIYSYLV WYQQKQGKSPQLLVH NAKTLAE GVPSRFSGSGSGTQFSLKINSLQPEDFGSYYC QHHHGTPYT GGGTKLEIKR |
| SEQ ID NO: 699 | VL Framework 1 | DIEMTQTPASLSASVGETVTITC |
| SEQ ID NO: 693 | VL CDR1 | RASVNIYSYLV |
| SEQ ID NO: 694 | VL Framework 2 | WYQQKQGKSPQLLVH |
| SEQ ID NO: 695 | VL CDR2 | NAKTLAE |
| SEQ ID NO: 696 | VL Framework 3 | GVPSRFSGSGSGTQFSLKINSLQPEDFGSYYC |
| SEQ ID NO: 697 | VL CDR3 | QHHHGTPYT |
| SEQ ID NO: 706 | VL Framework 4 | FGGGTKLEIKR |
| SEQ ID NO: 689 | 4F1E1 = 1F1G3 = 4F1B5 = 4F1G11 = AF1B9 = 4F1H9 = 4F1D10 = 4F1E9 = 4F1F10 = 4F1H11 = 4F1H12 VL | DIVMTQSPASLSASVGETVTITC RASVNIYSYLV WYQQKQGKSPQLLVH NAKTLAE GVPSRFSGSGSGTQFSLKINSLQPEDFGSYYC QHHHGTPYT FGGGTKLEIKA |
| SEQ ID NO: 703 | VL Framework 1 | DIVMTQSPASLSASVGETVTITC |
| SEQ ID NO: 693 | VL CDR1 | RASVNIYSYLV |
| SEQ ID NO: 694 | VL Framework 2 | WYQQKQGKSPQLLVH |
| SEQ ID NO: 695 | VL CDR2 | NAKTLAE |

| Informal Sequence Listing | |
|---|---|
| SEQ ID NO: 696 VL Framework 3 | GVPSRFSGSGSGTQFSLKINSLQPEDFGSYYC |
| SEQ ID NO: 697 VL CDR3 | QHHGTPYT |
| SEQ ID NO: 698 VL Framework 4 | FGGGTKLEIKA |
| SEQ ID NO: 690 4FA11 VL | DIVVTQSPASLSASVGETVTITC RASVNIYSYLV WYQQKQGKSPQLLVH NAKTLAE GVPSRFSGSGSGTQFSLKINSLQPEDFGSYYC QHHGTPYT FGGGTKLEIKA |
| SEQ ID NO: 705 VL Framework 1 | DIVVTQSPASLSASVGETVTITC |
| SEQ ID NO: 693 VL CDR1 | RASVNIYSYLV |
| SEQ ID NO: 694 VL Framework 2 | WYQQKQGKSPQLLVH |
| SEQ ID NO: 695 VL CDR2 | NAKTLAE |
| SEQ ID NO: 696 VL Framework 3 | GVSPRFSGSGSGTQFSLKINSLQPEDFGSYYC |
| SEQ ID NO: 697 VL CDR3 | QHHGTPYT |
| SEQ ID NO: 698 VL Framework 4 | FGGGTKLEIKA |
| SEQ ID NO: 691 F9 VL | DIVMTQSPAFLSASVGETVTITC RASVNIYSYLV WYQQKQGKSPQLLVH NAKTLAE GVPSRFSGSGSGTQFSLKINSLQPEDFGSYYC QHHGTPYT FGGGTKLEIKR |
| SEQ ID NO: 703 VL Framework 1 | DIVMTQSPASLSASVGETVTITC |
| SEQ ID NO: 693 VL CDR1 | RASVNIYSYLV |
| SEQ ID NO: 694 VL Framework 2 | WYQQKQGKSPQLLVH |
| SEQ ID NO: 695 VL CDR2 | NAKTLAE |
| SEQ ID NO: 696 VL Framework 2 | GVPSRFSGSGSGTQFSLKINSLQPEDFGSYYC |
| SEQ ID NO: 697 VL CDR2 | QHHGTPYT |
| SEQ ID NO: 706 VL Framework 4 | FGGGTKLEIKR |
| SEQ ID NO: 707 C6D4 Vh CDR1 | DYSMH |
| SEQ ID NO: 615 C6D4 Vh CDR3 | FTTGRDS |
| SEQ ID NO: 620 β8, SDL | TVSPYISIHPERIHNQCSDYNLDCMPPH |
| SEQ ID NO: 616 C6D4 Vk CDR1 | KSSQSLLNSRTRKNYLA |
| SEQ ID NO: 708 C6D4 Vk CDR2 | WASTRES |
| SEQ ID NO: 618 C6D4 Vk CDR3 | KQSYNLLS |
| SEQ ID NO: 709 αVβ6: | GRGDLGDLKK |
| SEQ ID NO: 710 αIIβ3: | GRGDSP |
| SEQ ID NO: 711 αIIβ3: | AKQRGDV |

SEQ ID NO: 712: RGDLGRLKK-loop of L-TGFβ

SEQ ID NO: 713: DDHGRGDLGRLK (TGFB3 sequence)

SEQ ID NO: 714 TGBF1
MPPSGLRLLLLLLPLLWLLVLTPGRPAAGLSTCKTIDMELVKRKRIEAIRGQILSKLRLASPPSQGEVPPGPLPEAVLALYNSTRDRV
AGESAEPEPEPEADYYAKEVTRVLMVETHNEIYDKFKQSTHSIYMFFNTSELREAVPEPVLLSRAELRLLRLKLKVEQHVELYQKYSN
NSWRYLSNRLLAPSDSPEWLSGDVTGVVRQWLSRGGEIEGFRLSAHCSCDSRDNTLQVDINGFTTGRRGDLATIHGMNRPFLLMATPL
ERAQHLQSSRHRRALDTNYCFSSTEKNCCVRQLYIDFRKDLGWKWIHEPKGYHANFCLGPCPYIWSLDTQYSKVLALYNQHNPGASAA
PCCVPQALEPLPIVYYVGRKPKVEQLSNMIVRSCKCS

SEQ ID NO: 715 TGFB2
MHYCVLSAFLILHLVTVALSLSTCSTLDMDQFMRKRIEAIRGQILSKLKLTSPPEDYPEPEEVPPEVISIYNSTRDLLQEKASRRAAA
CERERSDEEYYAKEVYKIDMPPFFPSENAIPPTFYRPYFRIVRFDVSAMEKNASNLVKAEFRVFRLQNPKARVPEQRIELYQILKSKD
DLTSPTQRYIDSKVVKTRAEGEWLSFDVTDAVHEWLPSYRLESQQTNTTKKTALDAAYCFRVQDNCCLRPLYIDFKRDLGWKWIHEPK
GYNANFCAGACPYLWSSDTQHSRVLSLYNTINPEASASPCCVSQDLEPLTILYYIGKTPKIEQLSNMIVKSCKCS

| Informal Sequence Listing |
|---|

SEQ ID NO: 716 TGFB3
MKMHLQRALVVLALLNFATVSLSLSTCTTLDFGHIKKKRVEAIRGQILSKLRLTSPPEPTVTHVPYQVLALYNSTRELLEEMHGEREE
GCTQENTESEYYAKEIHKFDMIQGLAEHNELAVCPKGITSKVFRFNVSSVEKNRTNLFRAEFRVLRVPNPSSKRNEQRIELFQILRPD
EHIAKQRYIGGKNLPTRGTAEWLSFDVTDTVREWLLRRESNLGLEISIHCPCHTFQPNGDILENIHEVMEIKFKGVDNEDDHGRGDLG
RLKKQKQHHNPHLILMMIPPHRLDNPGQGGQRKKRALDTNYVFRNLEENCCVRPLYIDFRQDLGWKWVHEPKGYYANFCSGPCPYLRS
ADTTHSTVLGLYNTLNPEASASPCCVPQDLEPLTILYYVGRTPKVEQLSNMVVKSCKCS

SEQ ID NO: 717 C6D4 vk
DIVMTQSPSSLAVSAGEKVTMSCKSSQSLLNSRTRKNYLAWYQQKGQSPRLLIYWASTRESGVPDRFTGSGSGTDFTLTISSVQAEDL
AVYYCKQSYNLLSFGAGTKLELKAADAAPTVSIFPPSSEQLTSGGASVVCFLNNFYPKDINVKWKIDGSERQNGVLNSWTDQDSKDST
YSMSSTLTLTKDEYERHNSYTCEATHKTSTSPIVKSFNRNEC

| SEQ ID NO: 718 C6D4-RDG1 | KSSQSLLGRGDLGNALA |
|---|---|
| SEQ ID NO: 719 C6D4-RGD2 | KSSQSLLNSRGDLGNALA |
| SEQ ID NO: 720 C6D4-RGD3 | KSSQSLLGRGDLGRLKKNALA |
| SEQ ID NO: 721 | GRGDLGRLK |
| SEQ ID NO: 722 C6D4 VH | QIQLVQSGPELKKPGETVKISCKASGYTFT DYSMH WVKQAPGKGLKWVA RINTETGEPTFADDFRG RFAVSLETSASTAYLQINNLKNEDTATYFCAI GYYGRDS WGQGTTLTVSS |
| SEQ ID NO: 732 VH Framework 1 | QIQLVQSGPELKKPGETVKISCKASGYTFT |
| SEQ ID NO: 733 VH CDR1 | DYSMH |
| SEQ ID NO: 734 VH Framework 2 | WVKQAPGKGLKWVA |
| SEQ ID NO: 735 VH CDR2 | RINTETGEPTFADDFRG |
| SEQ ID NO: 736 VH Framework 3 | RFAVSLETSASTAYLQINNLKNEDTATYFCAI |
| SEQ ID NO: 737 VH CDR3 | FYYGRDS |
| SEQ ID NO: 738 VH Framework 4 | WGQGTTLTVSS |
| SEQ ID NO: 723 HuC6D4 V1 VH | QIQLVQSAGEVKKPGASVKISCKASGYTFT DYSMH WVRQAPGQGLEWVA RINTETGEPTFADDFRG RFTVTLDTSTSTAYLEIRSLRSDDTAVYFCAI FYYGRDS WGQGTTLTVSS |
| SEQ ID NO: 739 VH Framework 1 | QIQLVQSAGEVKKGPASVKISCKASGYTFT |
| SEQ ID NO: 733 VH CDR1 | DYSMH |
| SEQ ID NO: 740 VH Framework 2 | WVRQAPGQGLEWVA |
| SEQ ID NO: 735 VH CDR2 | RINTETGEPTFADDFRG |
| SEQ ID NO: 741 VH Framework 3 | RFTVTLDTSTSTAYLEIRSLRSDDTAVYFCAI |
| SEQ ID NO: 737 VH CDR3 | FYYGRDS |
| SEQ ID NO: 738 VH Framework 4 | WGQGTTLVTVSS |
| SEQ ID NO: 724 Mutclone A3 VH | QIQLVQSGAEVKKPGASVKISCKASGYTFT DYSMH WVRQAPGQGLEWVA RINTETGEPTFADDFRG RFTVTLDTSTSTAYLEIRSLRSDDTAVYFCAI FYYGRDS WGQGTTLTVSS |
| SEQ ID NO: 739 VH Framework 1 | QIQLVQSGAEVKKPGASVKISCKASGYTFT |
| SEQ ID NO: 733 VH CDR1 | DYSMH |
| SEQ ID NO: 740 VH Framework 2 | WVRQAPGQGLEWVA |
| SEQ ID NO: 735 VH CDR2 | RINTETGEPTFADDFRG |
| SEQ ID NO: 741 VH Framework 3 | RFTVTLTSTSTAYLEIRSLRSDDTAVYCAI |
| SEQ ID NO: 737 VH CDR3 | FYYGRDS |
| SEQ ID NO: 738 VH Framework 4 | WGQGTTLTVSS |
| SEQ ID NO: 725 Mutclone B7 VH | QIQLVQSGAKVKKPGASVKISCKASGYTFT DYSMH WVRQAPGQGLEWVA RINTETGEPTFADDFRG RFSVTLDTSTSTAYLEIRSLRSDDTAVYFCAI FYYGRDT WGQGTTLTVSS |

| Informal Sequence Listing | |
|---|---|
| SEQ ID NO: 742 VH Framework 1 | QIQLVQSGAKVKKPGASVKISCKASGYTFT |
| SEQ ID NO: 733 VH CDR1 | DYSMH |
| SEQ ID NO: 740 VH Framework 2 | WVRQAPGQGLEWVA |
| SEQ ID NO: 735 VH CDR2 | RINTETGEPTFADDFRG |
| SEQ ID NO: 743 VH Framework 3 | RFSVTLDTSTSTAYLEIRSLRSDDTAVYFCAI |
| SEQ ID NO: 744 VH CDR3 | FYYGRDT |
| SEQ ID NO: 738 VH Framework 4 | WGQGTTLTVSS |
| SEQ ID NO: 726 Mutclone E5 VH | QIQLVQSGAEVKKPGASVKISCKASGYTFT DYSMH WVRQAPGQGLEWVA RINTETGEPTFADDFRG RFTVTLDTSTSTAYLEIRSLRSDDTAVYFCAI FYYGRDT WGQGTTLTVSS |
| SEQ ID NO: 739 VH Framework 1 | QIQLVQSGAEVKKPGASVKISCKASGYTFT |
| SEQ ID NO: 733 VH CDR1 | DYSMH |
| SEQ ID NO: 740 VH Framework 2 | WVRQAPGQGLEWVA |
| SEQ ID NO: 735 VH CDR2 | RINTETGEPTFADDFRG |
| SEQ ID NO: 741 VH Framework 3 | RFTVTLDTSTSTAYLEIRSLRSDDTAVYFCAI |
| SEQ ID NO: 744 VH CDR3 | FYYGRDT |
| SEQ ID NO: 738 VH Framework 4 | WGQGTTLTVSS |
| SEQ ID NO: 727 C6D4 VK | DIVMTQSPSSLAVSAGEKVTMSC KSSQSLLNSRTRKNYLA WYQQKPGQSPRLLIY WASTRES GVPDRFTGSGSGTDFTLTISSVQAEDLAVYYC KQSYNLLS FGAGTKLELKR |
| SEQ ID NO: 745 VK Framework 1 | DIVMTQSPSSLAVSAGEKVTMSC |
| SEQ ID NO: 746 VK CDR1 | KSSQSLLNSRTRKNYLA |
| SEQ ID NO: 747 VK Framework 2 | WYQQKPGQSPRLLIY |
| SEQ ID NO: 748 VK CDR2 | WASTRES |
| SEQ ID NO: 749 VK Framework 3 | GVPDRFTGSGSGTDFTLTISSVQAEDLAVYYC |
| SEQ ID NO: 750 VK CDR3 | KSQYNLLS |
| SEQ ID NO: 751 VK Framework 4 | FGAGTKLELKR |
| SEQ ID NO: 728 HuC6D4 V1 VK | EIVMTQSPATLSVSPGERVTMSC KSSQSLLNSRTRKNYLA WYQQKPGQAPRLLIY WASTRES GVPARFSGSGSGTEFTLTISSVQSEDFAVYYC KQSYNLLS FGQGTVLEIKR |
| SEQ ID NO: 752 VK Framework 1 | EIVMTQSPATLSVSPGERVTMSC |
| SEQ ID NO: 746 VK CDR1 | KSSQSLLNSRTRKNYLA |
| SEQ ID NO: 747 VK Framework 2 | WYQQKPGQSPRLLIY |
| SEQ ID NO: 748 VK CDR2 | WASTRES |
| SEQ ID NO: 753 VK Framework 3 | GVPARFSGSGSGTEFTLTISSVQSEDFAVYYC |
| SEQ ID NO: 750 VK CDR3 | KSQYNLLS |
| SEQ ID NO: 754 VK Framework 4 | FGQGTVLEIKR |
| SEQ ID NO: 729 Mutclone A3 VK | EIVMTQSPATLSVSPGEIVTMSC KSSQSLLNSRSRKNYLA WYQQKPGQAPRLLIY WASTRES GVPARFSGSGSGTEFTLTISSVQSEDFAVYYC KQSYNLLS FGQGTVLEIKR |
| SEQ ID NO: 755 VK Framework 1 | EIVMTQSPATLSVSPGEIVTMSC |
| SEQ ID NO: 756 VK CDR1 | KSSQSLLNSRSRKNYLA |

| Informal Sequence Listing | |
|---|---|
| SEQ ID NO: 747 VK Framework 2 | WYQQKPGQSPRLLIY |
| SEQ ID NO: 748 VK CDR2 | WASTRES |
| SEQ ID NO: 753 VK Framework 3 | GVPARFSGSGSGTEFTLTISSVQSEDFAVYYC |
| SEQ ID NO: 750 VK CDR3 | KQSYNLLS |
| SEQ ID NO: 754 VK Framework 4 | FGQGTVLEIKR |
| SEQ ID NO: 730 Mutclone B7 VK | EIVMTQTPVTLSVSPGERVTMSC KSSQSLLNSRTRKNYLA WYQQKPGQAPRLLIY WASTRES DVPARFSGSGSGTEFTLTISSVQSEDFAVYYC KQSSNLLS FGQGTVLEIKR |
| SEQ ID NO: 757 VK Framework 1 | EIVMTQTPVTLSVSPGERVTMSC |
| SEQ ID NO: 746 VK CDR1 | KSSQSLLNSRTRKNYLA |
| SEQ ID NO: 747 VK Framework 2 | WYQQKPGQSPRLLIY |
| SEQ ID NO: 748 VK CDR2 | WASTRES |
| SEQ ID NO: 758 VK Framework 3 | DVPARFSGSGSGTEFTLTISSVQSEDFAVYYC |
| SEQ ID NO: 750 VK CDR3 | KSQYNLLS |
| SEQ ID NO: 754 VK Framework 4 | FGQGTVLEIKR |
| SEQ ID NO: 731 Mutclone E5 VK | EIVMTQSPATLSVSPGERVTMSC KSSQSLLNSRSRKNYLA WYQQKPGQAPRLLIY WASTRES GVPARFSGSGSGTEFTLTISSVQSEDFAVYYC KQSYNLLS FGQGTVLEIKR |
| SEQ ID NO: 752 VK Framework 1 | EIVMTQSPATLSVSPGERVTMSC |
| SEQ ID NO: 756 VK CDR1 | KSSQSLLNSRSRKNYLA |
| SEQ ID NO: 747 VK Framework 2 | WYQQKPGQSPRLLIY |
| SEQ ID NO: 748 VK CDR2 | WASTRES |
| SEQ ID NO: 753 VK Framework 3 | GVPARFSGSGSGTEFTLTISSVQSEDFAVYYC |
| SEQ ID NO: 750 VK CDR3 | KQSYNLLS |
| SEQ ID NO: 754 VK Framework 4 | FGQGTVLEIKR |
| SEQ ID NO: 755 E8-VL Framework 3 | GVPSRFSGSGSGTRFSLKINSLQPEDFGSYYC |
| SEQ ID NO: 756 RGDL | |
| SEQ ID NO: 757 αv | DADGQ |
| SEQ ID NO: 758 αv | SFYWQ |
| SEQ ID NO: 759 αv | FDDSY |
| SEQ ID NO: 760 KQDKILACAPLYHWRTEMKQEREPVGTCFLQDGTKTVEYAPCRSQDIDADGQGFCQGGFSIDFTKADRVLLGGPGSFYWQGQLISDDQ VAEIVSKYDPNVYSIKYNNQLATRTAQAIFD | |
| SEQ ID NO: 761 β8 | YNLDC |
| SEQ ID NO: 762 β8 | QCSDYNL |
| SEQ ID NO: 763 β8 | SMHNN |
| SEQ ID NO: 764 β8 | AVHRQ |
| SEQ ID NO: 765 | KSSQSLLGRGDLGRLKK |
| SEQ ID NO: 766 C6H-VH CDR1 | TFTDYSMH |
| SEQ ID NO: 767 C6H-VH CDR2 | RINTETGEPTFADDFRG |
| SEQ ID NO: 768 C6H-VH CDR3 | FYYGRDS |
| SEQ ID NO: 877 heavy chain FR2 | WV(K/R)QAPG(K/Q)GL(K/E)W(V/M)(A/G) |

| Informal Sequence Listing | | |
|---|---|---|
| SEQ ID NO: 878 heavy chain FR3 | | RF(A/T/S)(V/F)(S/T)L(E/D)TS(A/T)(S/T)TA(Y/N)L(Q/E)I(N/R/I/T)(N/S)L(K/R)(N/S)(E/D)DTA(T/V/K)YFCAI |
| SEQ ID NO: 879 heavy chain FR4 | | WGQGT(T/A)LTVSS |
| SEQ ID NO: 880 light chain FR1 | | (D/E)IVM(T/S)Q(S/T)P(S/A/V)(S/T)L(A/S)VS(A/P)GE(K/R/I)VTMSC |
| SEQ ID NO: 881 light chain FR2 | | WYQQKPGQ(S/A)PRLLIY |
| SEQ ID NO: 882 light chain FR3 | | (G/D)VP(D/A)RF(T/S)GSGSGT(D/E)FTLTISSVQ(A/S/D)ED(L/F)AVYC |
| SEQ ID NO: 883 light chain FR4 | | FG(A/Q)GT(K/V)LE(i/LI)KR |

What is claimed is:

1. An antibody that specifically binds human αvβ8 and blocks binding of TGFβ peptide to αvβ8, wherein the antibody comprises:
   a heavy chain variable region comprising heavy chain complementarity determining regions (CDR) 1, 2, and 3 comprising SEQ ID NOS:520, 521 and 522, respectively; and
   a light chain variable region comprising light chain CDRs 1, 2 and 3 comprising SEQ ID NOS:541, 542 and 543, respectively.

2. The antibody of claim 1, wherein the heavy chain variable region comprises SEQ ID NO:427.

3. The antibody of claim 1, wherein the light chain variable region comprises SEQ ID NO:484.

4. The antibody of claim 1, wherein the heavy chain variable region comprises SEQ ID NO:427 and the light chain variable region comprises SEQ ID NO:484.

5. The antibody of claim 1, wherein the antibody is an IgG.

6. The antibody of claim 4, wherein the antibody is an IgG.

7. The antibody of claim 1, wherein the antibody is humanized.

8. The antibody of claim 1, wherein the antibody is linked to a detectable label.

9. A pharmaceutical composition comprising the antibody of claim 1 in a pharmaceutically acceptable excipient.

10. The pharmaceutical composition of claim 9, wherein the heavy chain variable region comprises SEQ ID NO:427.

11. The pharmaceutical composition of claim 9, wherein the light chain variable region comprises SEQ ID NO:484.

12. The pharmaceutical composition of claim 9, wherein the heavy chain variable region comprises SEQ ID NO:427 and the light chain variable region comprises SEQ ID NO:484.

13. The pharmaceutical composition of claim 9, wherein the antibody is an IgG.

14. The pharmaceutical composition of claim 12, wherein the antibody is an IgG.

15. The pharmaceutical composition of claim 9, wherein the antibody is humanized.

* * * * *

SEQUENCE LISTING

<160> NUMBER OF SEQ ID NOS: 887

<210> SEQ ID NO 1
<211> LENGTH: 116
<212> TYPE: PRT
<213> ORGANISM: Mus musculus

<400> SEQUENCE: 1

Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Lys Thr Glu Thr Gly Glu Pro Thr Tyr Ala Asp Asp Phe
    50                  55                  60

Lys Gly Arg Phe Ala Phe Ser Leu Glu Thr Ser Ala Thr Thr Ala Tyr
65                  70                  75                  80

Leu Gln Ile Asn Asn Leu Lys Asn Glu Asp Thr Ala Lys Tyr Phe Cys
                85                  90                  95

Ala Ile Tyr Tyr Tyr Gly Arg Asp Ser Trp Gly Gln Gly Thr Thr Leu
            100                 105                 110

Thr Val Ser Ser
        115

<210> SEQ ID NO 2
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 2

Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr
            20                  25

<210> SEQ ID NO 3
<211> LENGTH: 8
<212> TYPE: PRT
<213> ORGANISM: Unknown

```
<220> FEATURE:
<223> OTHER INFORMATION: Human (Homo sapiens), chimeric or humanized
      antibody peptide sequence

<400> SEQUENCE: 3

Thr Phe Thr Asp Tyr Ser Met His
1               5

<210> SEQ ID NO 4
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 4

Trp Val Lys Gln Ala Pro Gly Lys Gly Leu Lys Trp Met Gly
1               5                   10

<210> SEQ ID NO 5
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 5

Trp Ile Lys Thr Glu Thr Gly Glu Pro Thr Tyr Ala Asp Asp Phe Lys
1               5                   10                  15

Gly

<210> SEQ ID NO 6
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 6

Arg Phe Ala Phe Ser Leu Glu Thr Ser Ala Thr Thr Ala Tyr Leu Gln
1               5                   10                  15

Ile Asn Asn Leu Lys Asn Glu Asp Thr Ala Lys Tyr Phe Cys Ala Ile
                20                  25                  30

<210> SEQ ID NO 7
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 7

Tyr Tyr Tyr Gly Arg Asp Ser
1               5

<210> SEQ ID NO 8
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence
```

-continued

```
<400> SEQUENCE: 8

Trp Gly Gln Gly Thr Thr Leu Thr Val Ser Ser
1               5                   10

<210> SEQ ID NO 9
<211> LENGTH: 116
<212> TYPE: PRT
<213> ORGANISM: Mus musculus

<400> SEQUENCE: 9

Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Lys Thr Glu Thr Gly Glu Pro Thr Tyr Ala Asp Asp Phe
    50                  55                  60

Lys Gly Arg Phe Ala Phe Ser Leu Glu Thr Ser Ala Thr Thr Ala Tyr
65                  70                  75                  80

Leu Gln Ile Asn Asn Leu Lys Asn Glu Asp Thr Ala Lys Tyr Phe Cys
                85                  90                  95

Ala Ile Tyr Tyr Tyr Gly Arg Asp Ser Trp Gly Gln Gly Thr Thr Leu
            100                 105                 110

Thr Val Ser Ser
        115

<210> SEQ ID NO 10
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 10

Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr
            20                  25

<210> SEQ ID NO 11
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 11

Thr Phe Thr Asp Tyr Ser Met His
1               5

<210> SEQ ID NO 12
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 12
```

Trp Val Lys Gln Ala Pro Gly Lys Gly Leu Lys Trp Met Gly
1               5                   10

<210> SEQ ID NO 13
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 13

Trp Ile Lys Thr Glu Thr Gly Glu Pro Thr Tyr Ala Asp Asp Phe Lys
1               5                   10                  15

Gly

<210> SEQ ID NO 14
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 14

Arg Phe Ala Phe Ser Leu Glu Thr Ser Ala Thr Thr Ala Tyr Leu Gln
1               5                   10                  15

Ile Asn Asn Leu Lys Asn Glu Asp Thr Ala Lys Tyr Phe Cys Ala Ile
            20                  25                  30

<210> SEQ ID NO 15
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 15

Tyr Tyr Tyr Gly Arg Asp Ser
1               5

<210> SEQ ID NO 16
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 16

Trp Gly Gln Gly Thr Thr Leu Thr Val Ser Ser
1               5                   10

<210> SEQ ID NO 17
<211> LENGTH: 119
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 17

Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr

```
                    20                  25                  30
Ser Met His Trp Val Lys Gln Ala Pro Gly Lys Gly Leu Lys Trp Met
            35                  40                  45

Gly Trp Ile Lys Thr Glu Thr Asp Glu Pro Thr Tyr Ala Asp Asp Phe
        50                  55                  60

Lys Glu Arg Phe Ala Phe Ser Leu Glu Thr Ser Ala Ser Thr Ala Asn
65                  70                  75                  80

Leu Gln Ile Ile Asn Leu Lys Asn Glu Asp Thr Ala Thr Tyr Phe Cys
                85                  90                  95

Ala Ile Tyr Tyr Tyr Gly Arg Asp Ser Trp Gly Gln Gly Thr Thr Leu
                100                 105                 110

Thr Val Ser Ser Glu Gln
        115

<210> SEQ ID NO 18
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 18

Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr
            20                  25

<210> SEQ ID NO 19
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 19

Thr Phe Thr Asp Tyr Ser Met His
1               5

<210> SEQ ID NO 20
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 20

Trp Val Lys Gln Ala Pro Gly Lys Gly Leu Lys Trp Met Gly
1               5                   10

<210> SEQ ID NO 21
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 21

Trp Ile Lys Thr Glu Thr Asp Glu Pro Thr Tyr Ala Asp Asp Phe Lys
1               5                   10                  15
```

Glu

<210> SEQ ID NO 22
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 22

Arg Phe Ala Phe Ser Leu Glu Thr Ser Ala Ser Thr Ala Asn Leu Gln
1               5                   10                  15

Ile Ile Asn Leu Lys Asn Glu Asp Thr Ala Thr Tyr Phe Cys Ala Ile
            20                  25                  30

<210> SEQ ID NO 23
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 23

Tyr Tyr Tyr Gly Arg Asp Ser
1               5

<210> SEQ ID NO 24
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 24

Trp Gly Gln Gly Thr Thr Leu Thr Val Ser Ser Ser Glu Gln
1               5                   10

<210> SEQ ID NO 25
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 25

Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile His Trp Val Lys Gln Ala Pro Gly Lys Gly Leu Lys Trp Met
        35                  40                  45

Gly Trp Ile Lys Thr Glu Thr Gly Glu Pro Thr Tyr Ala Asp Asp Phe
    50                  55                  60

Asn Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ile Tyr Tyr Tyr Gly Arg Asp Ser Trp Gly Gln Gly Thr Thr Leu
            100                 105                 110

Thr Val Ser Ser
        115

<210> SEQ ID NO 26
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 26

Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr
            20                  25

<210> SEQ ID NO 27
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 27

Thr Phe Thr Asp Tyr Ser Ile His
1               5

<210> SEQ ID NO 28
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 28

Trp Val Lys Gln Ala Pro Gly Lys Gly Leu Lys Trp Met Gly
1               5                   10

<210> SEQ ID NO 29
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 29

Trp Ile Lys Thr Glu Thr Gly Glu Pro Thr Tyr Ala Asp Asp Phe Asn
1               5                   10                  15

Gly

<210> SEQ ID NO 30
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 30

Arg Phe Ala Phe Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Ile

```
                    20                  25                  30
```

<210> SEQ ID NO 31
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence <400> SEQUENCE: 31

```
Tyr Tyr Tyr Gly Arg Asp Ser
1               5
```

<210> SEQ ID NO 32
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence <400> SEQUENCE: 32

```
Trp Gly Gln Gly Thr Thr Leu Thr Val Ser Ser
1               5                   10
```

<210> SEQ ID NO 33
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence <400> SEQUENCE: 33

```
Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Val
        35                  40                  45

Ala Arg Ile Asn Thr Glu Thr Gly Glu Pro Thr Phe Ala Asp Asp Phe
    50                  55                  60

Arg Gly Arg Phe Ala Val Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ile Tyr Tyr Tyr Gly Arg Asp Ser Trp Gly Gln Gly Thr Thr Leu
            100                 105                 110

Thr Val Ser Ser
        115
```

<210> SEQ ID NO 34
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence <400> SEQUENCE: 34

```
Gln Ile Gln Leu Leu Gln Ser Gly Pro Glu Leu Lys Lys Pro Gly Glu
1               5                   10                  15
```

```
Thr Val Lys Ile Ser Cys Lys Ala Ser Gly Tyr
            20                  25
```

<210> SEQ ID NO 35
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 35

```
Thr Phe Thr Asp Tyr Ser Met His
1               5
```

<210> SEQ ID NO 36
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 36

```
Trp Val Lys Gln Ala Pro Gly Lys Gly Leu Lys Trp Val Ala
1               5                   10
```

<210> SEQ ID NO 37
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 37

```
Arg Ile Asn Thr Glu Thr Gly Glu Pro Thr Phe Ala Asp Asp Phe Arg
1               5                   10                  15

Gly
```

<210> SEQ ID NO 38
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 38

```
Arg Phe Ala Val Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Ile
            20                  25                  30
```

<210> SEQ ID NO 39
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 39

```
Tyr Tyr Tyr Gly Arg Asp Ser
1               5
```

```
<210> SEQ ID NO 40
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 40

Trp Gly Gln Gly Thr Thr Leu Thr Val Ser Ser
1               5                   10

<210> SEQ ID NO 41
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 41

Gln Ile Gln Leu Leu Gln Ser Gly Pro Glu Leu Lys Lys Pro Gly Glu
1               5                   10                  15

Thr Val Lys Ile Ser Cys Leu Ala Ser Gly Tyr Thr Phe Thr Asp Tyr
            20                  25                  30

Ser Met His Trp Val Lys Gln Ala Pro Gly Lys Gly Leu Lys Trp Val
        35                  40                  45

Ala Arg Ile Asn Thr Glu Thr Gly Glu Pro Thr Phe Ala Asp Asp Phe
    50                  55                  60

Gly Gly Arg Phe Ala Val Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ile Tyr Tyr Tyr Gly Arg Asp Ser Trp Gly Gln Gly Thr Thr Leu
            100                 105                 110

Thr Val Ser Ser
        115

<210> SEQ ID NO 42
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 42

Gln Ile Gln Leu Leu Gln Ser Gly Pro Glu Leu Lys Lys Pro Gly Glu
1               5                   10                  15

Thr Val Lys Ile Ser Cys Leu Ala Ser Gly Tyr
            20                  25

<210> SEQ ID NO 43
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 43

Thr Phe Thr Asp Tyr Ser Met His
1               5
```

<210> SEQ ID NO 44
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 44

Trp Val Lys Gln Ala Pro Gly Lys Gly Leu Lys Trp Val Ala
1               5                   10

<210> SEQ ID NO 45
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 45

Arg Ile Asn Thr Glu Thr Gly Glu Pro Thr Phe Ala Asp Asp Phe Gly
1               5                   10                  15

Gly

<210> SEQ ID NO 46
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 46

Arg Phe Ala Val Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Ile
                20                  25                  30

<210> SEQ ID NO 47
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 47

Tyr Tyr Tyr Gly Arg Asp Ser
1               5

<210> SEQ ID NO 48
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 48

Trp Gly Gln Gly Thr Thr Leu Thr Val Ser Ser
1               5                   10

<210> SEQ ID NO 49
<211> LENGTH: 120
<212> TYPE: PRT

-continued

<213> ORGANISM: Unknown
<220> FEATURE:
<223> OTHER INFORMATION: Human (Homo sapiens), chimeric or humanized
      antibody peptide sequence

<400> SEQUENCE: 49

Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Thr Phe Ser Ser Phe
            20                  25                  30
Gly Met Ser Trp Val Arg Gln Thr Pro Asp Lys Arg Leu Glu Leu Val
        35                  40                  45
Ala Thr Ile Asn Ser Asn Gly Gly Ser Thr Tyr Tyr Pro Asp Asn Met
    50                  55                  60
Lys Gly Arg Phe Thr Ile Ser Arg Asp Asn Ala Lys Asn Thr Leu Tyr
65                  70                  75                  80
Leu Gln Met Ser Ser Leu Lys Ser Glu Asp Thr Ala Met Tyr Tyr Cys
                85                  90                  95
Ala Ser Ala Cys Tyr Arg Tyr Gly Ala Phe Phe Asp Tyr Trp Gly Gln
            100                 105                 110
Gly Thr Thr Leu Thr Val Ser Ser
        115                 120

<210> SEQ ID NO 50
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 50

Glu Val Gln Leu Val Glu Ser Gly Gly Gly Leu Val Gln Pro Gly Gly
1               5                   10                  15
Ser Leu Lys Leu Ser Cys Ala Ala Ser Gly Phe
            20                  25

<210> SEQ ID NO 51
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 51

Thr Phe Ser Ser Phe Gly Met Ser
1               5

<210> SEQ ID NO 52
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 52

Trp Val Arg Gln Thr Pro Asp Lys Arg Leu Glu Leu Val Ala
1               5                   10

<210> SEQ ID NO 53
<211> LENGTH: 17

```
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 53

Thr Ile Asn Ser Asn Gly Gly Ser Thr Tyr Tyr Pro Asp Asn Met Lys
1               5                   10                  15

Gly

<210> SEQ ID NO 54
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 54

Arg Phe Thr Ile Ser Arg Asp Asn Ala Lys Asn Thr Leu Tyr Leu Gln
1               5                   10                  15

Met Ser Ser Leu Lys Ser Glu Asp Thr Ala Met Tyr Tyr Cys Ala Ser
            20                  25                  30

<210> SEQ ID NO 55
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 55

Ala Cys Tyr Arg Tyr Gly Ala Phe Phe Asp Tyr
1               5                   10

<210> SEQ ID NO 56
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 56

Trp Gly Gln Gly Thr Thr Leu Thr Val Ser Ser
1               5                   10

<210> SEQ ID NO 57
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 57

Glu Val Gln Leu Leu Glu Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile His Trp Val Lys Gln Ala Pro Gly Lys Gly Leu Lys Trp Met
        35                  40                  45

Gly Trp Ile Lys Thr Glu Thr Gly Glu Pro Thr Tyr Ala Asp Asp Phe
```

```
            50                  55                  60
Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Ile Tyr Tyr Tyr Gly Arg Asp Ser Trp Gly Gln Gly Thr Thr Val
                100                 105                 110

Thr Val Ser Ser
        115
```

<210> SEQ ID NO 58
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 58

```
Glu Val Gln Leu Leu Glu Ser Gly Pro Glu Leu Lys Lys Pro Gly Glu
 1               5                  10                  15

Thr Val Lys Ile Ser Cys Lys Ala Ser Gly Tyr
            20                  25
```

<210> SEQ ID NO 59
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 59

```
Thr Phe Thr Asp Tyr Ser Ile His
 1               5
```

<210> SEQ ID NO 60
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 60

```
Trp Val Lys Gln Ala Pro Gly Lys Gly Leu Lys Trp Met Gly
 1               5                  10
```

<210> SEQ ID NO 61
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 61

```
Trp Ile Lys Thr Glu Thr Gly Glu Pro Thr Tyr Ala Asp Asp Phe Lys
 1               5                  10                  15

Gly
```

<210> SEQ ID NO 62
<211> LENGTH: 32
<212> TYPE: PRT

```
<213> ORGANISM: Unknown
<220> FEATURE:
<223> OTHER INFORMATION: Human (Homo sapiens), chimeric or humanized
      antibody peptide sequence

<400> SEQUENCE: 62

Arg Phe Ala Phe Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Ile
            20                  25                  30

<210> SEQ ID NO 63
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 63

Tyr Tyr Tyr Gly Arg Asp Ser
1               5

<210> SEQ ID NO 64
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 64

Trp Gly Gln Gly Thr Thr Val Thr Val Ser Ser
1               5                   10

<210> SEQ ID NO 65
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 65

Glu Val Gln Leu Leu Glu Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile His Trp Val Lys Gln Ala Pro Gly Lys Gly Leu Lys Trp Met
        35                  40                  45

Gly Trp Ile Lys Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ile Tyr Tyr Tyr Gly Arg Asp Ser Trp Gly Gln Gly Thr Thr Val
            100                 105                 110

Thr Val Ser Ser
        115

<210> SEQ ID NO 66
<211> LENGTH: 27
```

```
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 66

Glu Val Gln Leu Leu Glu Ser Gly Pro Glu Leu Lys Lys Pro Gly Glu
1               5                   10                  15

Thr Val Lys Ile Ser Cys Lys Ala Ser Gly Tyr
            20                  25

<210> SEQ ID NO 67
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 67

Thr Phe Thr Asp Tyr Ser Ile His
1               5

<210> SEQ ID NO 68
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 68

Trp Val Lys Gln Ala Pro Gly Lys Gly Leu Lys Trp Met Gly
1               5                   10

<210> SEQ ID NO 69
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 69

Trp Ile Lys Thr Glu Thr Gly Glu Pro Thr Tyr Ala Asp Asp Phe Lys
1               5                   10                  15

Gly

<210> SEQ ID NO 70
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 70

Arg Phe Ala Phe Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Ile
            20                  25                  30

<210> SEQ ID NO 71
<211> LENGTH: 7
<212> TYPE: PRT
```

```
<213> ORGANISM: Unknown
<220> FEATURE:
<223> OTHER INFORMATION: Human (Homo sapiens), chimeric or humanized
      antibody peptide sequence

<400> SEQUENCE: 71

Tyr Tyr Tyr Gly Arg Asp Ser
1               5

<210> SEQ ID NO 72
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 72

Trp Gly Gln Gly Thr Thr Val Thr Val Ser Ser
1               5                   10

<210> SEQ ID NO 73
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 73

Gln Val Gln Leu Met Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Ile His Trp Val Lys Gln Ala Pro Gly Lys Gly Leu Lys Trp Met
            35                  40                  45

Gly Trp Ile Lys Thr Glu Thr Gly Glu Pro Thr Tyr Ala Asp Asp Phe
    50                  55                  60

Asn Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ile Tyr Tyr Tyr Gly Arg Asp Ser Trp Gly Gln Gly Thr Thr Leu
            100                 105                 110

Thr Val Ser Ser
        115

<210> SEQ ID NO 74
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 74

Gln Val Gln Leu Met Gln Ser Gly Pro Glu Leu Lys Lys Pro Gly Glu
1               5                   10                  15

Thr Val Lys Ile Ser Cys Lys Ala Ser Gly Tyr
                20                  25

<210> SEQ ID NO 75
<211> LENGTH: 8
```

```
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 75

Thr Phe Thr Asp Tyr Ser Ile His
1               5

<210> SEQ ID NO 76
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 76

Trp Val Lys Gln Ala Pro Gly Lys Gly Leu Lys Trp Met Gly
1               5                   10

<210> SEQ ID NO 77
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 77

Trp Ile Lys Thr Glu Thr Gly Glu Pro Thr Tyr Ala Asp Asp Phe Asn
1               5                   10                  15

Gly

<210> SEQ ID NO 78
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 78

Arg Phe Ala Phe Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Ile
            20                  25                  30

<210> SEQ ID NO 79
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 79

Tyr Tyr Tyr Gly Arg Asp Ser
1               5

<210> SEQ ID NO 80
<211> LENGTH: 11
<212> TYPE: PRT
<213> ORGANISM: Unknown
<220> FEATURE:
<223> OTHER INFORMATION: Human (Homo sapiens), chimeric or humanized
``` antibody peptide sequence

<400> SEQUENCE: 80

Trp Gly Gln Gly Thr Thr Leu Thr Val Ser Ser
1               5                   10

<210> SEQ ID NO 81
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 81

Gln Ile Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Val
        35                  40                  45

Ala Arg Ile Asn Thr Glu Thr Gly Glu Pro Thr Phe Ala Asp Asp Phe
    50                  55                  60

Arg Gly Arg Phe Ala Val Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ile Tyr Tyr Tyr Gly Arg Asp Ser Trp Gly Gln Gly Thr Thr Leu
            100                 105                 110

Thr Val Ser Ser
        115

<210> SEQ ID NO 82
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 82

Gln Ile Gln Leu Gln Gln Ser Gly Pro Glu Leu Lys Lys Pro Gly Glu
1               5                   10                  15

Thr Val Lys Ile Ser Cys Lys Ala Ser Gly Tyr
            20                  25

<210> SEQ ID NO 83
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 83

Thr Phe Thr Asp Tyr Ser Met His
1               5

<210> SEQ ID NO 84
<211> LENGTH: 14
<212> TYPE: PRT
<213> ORGANISM: Unknown
<220> FEATURE:

<223> OTHER INFORMATION: Human (Homo sapiens), chimeric or humanized
     antibody peptide sequence

<400> SEQUENCE: 84

Trp Val Lys Gln Ala Pro Gly Lys Gly Leu Lys Trp Val Ala
1               5                   10

<210> SEQ ID NO 85
<211> LENGTH: 17
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 85

Arg Ile Asn Thr Glu Thr Gly Glu Pro Thr Phe Ala Asp Asp Phe Arg
1               5                   10                  15

Gly

<210> SEQ ID NO 86
<211> LENGTH: 32
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 86

Arg Phe Ala Val Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Ile
                20                  25                  30

<210> SEQ ID NO 87
<211> LENGTH: 7
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 87

Tyr Tyr Tyr Gly Arg Asp Ser
1               5

<210> SEQ ID NO 88
<211> LENGTH: 11
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 88

Trp Gly Gln Gly Thr Thr Leu Thr Val Ser Ser
1               5                   10

<210> SEQ ID NO 89
<211> LENGTH: 116
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 89

```
Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Val
        35                  40                  45

Ala Arg Ile Asn Thr Glu Thr Gly Glu Pro Thr Phe Ala Asp Asp Phe
    50                  55                  60

Arg Gly Arg Phe Ala Val Ser Leu Glu Thr Ser Ala Ser Thr Ala Tyr
65              70                  75                  80

Leu Gln Ile Asn Asn Leu Lys Asn Glu Asp Thr Ala Thr Tyr Phe Cys
            85                  90                  95

Ala Ile Tyr Tyr Tyr Gly Arg Asp Ser Trp Gly Gln Gly Thr Thr Leu
            100                 105                 110

Thr Val Ser Ser
        115

<210> SEQ ID NO 90
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 90

Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr
            20                  25

<210> SEQ ID NO 91
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 91

Thr Phe Thr Asp Tyr Ser Met His
1               5

<210> SEQ ID NO 92
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 92

Trp Val Lys Gln Ala Pro Gly Lys Gly Leu Lys Trp Val Ala
1               5                   10

<210> SEQ ID NO 93
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence
```

```
<400> SEQUENCE: 93

Arg Ile Asn Thr Glu Thr Gly Glu Pro Thr Phe Ala Asp Asp Phe Arg
1               5                   10                  15

Gly

<210> SEQ ID NO 94
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 94

Arg Phe Ala Val Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Ile
            20                  25                  30

<210> SEQ ID NO 95
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 95

Tyr Tyr Tyr Gly Arg Asp Ser
1               5

<210> SEQ ID NO 96
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 96

Trp Gly Gln Gly Thr Thr Leu Thr Val Ser Ser
1               5                   10

<210> SEQ ID NO 97
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 97

Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Val
        35                  40                  45

Ala Arg Ile Asn Thr Glu Thr Gly Glu Pro Thr Phe Ala Asp Asp Phe
    50                  55                  60

Arg Gly Arg Phe Ala Val Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
```

```
                    85                  90                  95

Ala Ile Tyr Tyr Tyr Gly Arg Asp Thr Trp Gly Gln Gly Thr Thr Leu
                100                 105                 110

Ser Val Ser Ser
        115

<210> SEQ ID NO 98
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 98

Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr
            20                  25

<210> SEQ ID NO 99
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 99

Thr Phe Thr Asp Tyr Ser Met His
1               5

<210> SEQ ID NO 100
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 100

Trp Val Lys Gln Ala Pro Gly Lys Gly Leu Lys Trp Val Ala
1               5                   10

<210> SEQ ID NO 101
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 101

Arg Ile Asn Thr Glu Thr Gly Glu Pro Thr Phe Ala Asp Asp Phe Arg
1               5                   10                  15

Gly

<210> SEQ ID NO 102
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 102
```

```
Arg Phe Ala Val Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Ile
                20                  25                  30
```

<210> SEQ ID NO 103
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 103

```
Tyr Tyr Tyr Gly Arg Asp Thr
1               5
```

<210> SEQ ID NO 104
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 104

```
Trp Gly Gln Gly Thr Thr Leu Ser Val Ser Ser
1               5                   10
```

<210> SEQ ID NO 105
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 105

```
Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Met His Trp Val Lys Gln Ala Pro Gly Lys Gly Leu Lys Trp Val
            35                  40                  45

Ala Arg Ile Asn Thr Glu Thr Gly Glu Pro Thr Phe Ala Asp Asp Phe
        50                  55                  60

Arg Gly Arg Phe Ala Val Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ile Phe Tyr Tyr Gly Arg Asp Ser Trp Gly Gln Gly Thr Ala Leu
            100                 105                 110

Thr Val Ser Ser
        115
```

<210> SEQ ID NO 106
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

```
<400> SEQUENCE: 106

Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr
            20                  25

<210> SEQ ID NO 107
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 107

Thr Phe Thr Asp Tyr Ser Met His
1               5

<210> SEQ ID NO 108
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 108

Trp Val Lys Gln Ala Pro Gly Lys Gly Leu Lys Trp Val Ala
1               5                   10

<210> SEQ ID NO 109
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 109

Arg Ile Asn Thr Glu Thr Gly Glu Pro Thr Phe Ala Asp Asp Phe Arg
1               5                   10                  15

Gly

<210> SEQ ID NO 110
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 110

Arg Phe Ala Val Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Ile
            20                  25                  30

<210> SEQ ID NO 111
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 111
```

Phe Tyr Tyr Gly Arg Asp Ser
1               5

<210> SEQ ID NO 112
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 112

Trp Gly Gln Gly Thr Ala Leu Thr Val Ser Ser
1               5                   10

<210> SEQ ID NO 113
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 113

Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Val
        35                  40                  45

Ala Arg Ile Asn Thr Glu Thr Gly Glu Pro Thr Phe Ala Asp Asp Phe
    50                  55                  60

Arg Gly Arg Phe Ala Val Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ile Tyr Tyr Tyr Gly Arg Asp Ser Trp Gly Gln Gly Thr Thr Leu
            100                 105                 110

Thr Val Ser Ser
        115

<210> SEQ ID NO 114
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 114

Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr
            20                  25

<210> SEQ ID NO 115
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

```
<400> SEQUENCE: 115

Thr Phe Thr Asp Tyr Ser Met His
1               5

<210> SEQ ID NO 116
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 116

Trp Val Lys Gln Ala Pro Gly Lys Gly Leu Lys Trp Val Ala
1               5                   10

<210> SEQ ID NO 117
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 117

Arg Ile Asn Thr Glu Thr Gly Glu Pro Thr Phe Ala Asp Asp Phe Arg
1               5                   10                  15

Gly

<210> SEQ ID NO 118
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 118

Arg Phe Ala Val Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Ile
            20                  25                  30

<210> SEQ ID NO 119
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 119

Tyr Tyr Tyr Gly Arg Asp Ser
1               5

<210> SEQ ID NO 120
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 120

Trp Gly Gln Gly Thr Thr Leu Thr Val Ser Ser
1               5                   10
```

```
<210> SEQ ID NO 121
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 121

Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Val
        35                  40                  45

Ala Arg Ile Asn Thr Glu Thr Gly Glu Pro Thr Phe Ala Asp Asp Phe
    50                  55                  60

Arg Gly Arg Phe Ala Val Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ile Phe Tyr Tyr Gly Arg Asp Ser Trp Gly Gln Gly Thr Thr Leu
            100                 105                 110

Thr Val Ser Ser
        115

<210> SEQ ID NO 122
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 122

Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr
            20                  25

<210> SEQ ID NO 123
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 123

Thr Phe Thr Asp Tyr Ser Met His
1               5

<210> SEQ ID NO 124
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 124

Trp Val Lys Gln Ala Pro Gly Lys Gly Leu Lys Trp Val Ala
```

```
1               5                   10

<210> SEQ ID NO 125
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 125

Arg Ile Asn Thr Glu Thr Gly Glu Pro Thr Phe Ala Asp Asp Phe Arg
1               5                   10                  15

Gly

<210> SEQ ID NO 126
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 126

Arg Phe Ala Val Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Ile
                20                  25                  30

<210> SEQ ID NO 127
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 127

Phe Tyr Tyr Gly Arg Asp Ser
1               5

<210> SEQ ID NO 128
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 128

Trp Gly Gln Gly Thr Thr Leu Thr Val Ser Ser
1               5                   10

<210> SEQ ID NO 129
<211> LENGTH: 109
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 129

Asp Ile Val Met Ser Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
                20                  25                  30
```

```
Leu Ser Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Pro
                85                  90                  95

Leu Thr Phe Gly Ala Gly Thr Lys Leu Glu Leu Lys Ala
                100                 105

<210> SEQ ID NO 130
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 130

Asp Ile Val Met Ser Gln Ser Pro Ser Ser Met Tyr Ala Ser Leu Gly
1               5                   10                  15

Glu Arg Val Thr Ile Thr Cys
            20

<210> SEQ ID NO 131
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 131

Lys Ala Ser Gln Asp Ile Asn Ser Tyr Leu Ser
1               5                   10

<210> SEQ ID NO 132
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 132

Trp Phe Gln Gln Lys Pro Gly Lys Ser Pro Lys Thr Leu Ile Tyr
1               5                   10                  15

<210> SEQ ID NO 133
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 133

Arg Ala Asn Arg Leu Val Asp
1               5

<210> SEQ ID NO 134
<211> LENGTH: 32
<212> TYPE: PRT
```

```
<213> ORGANISM: Unknown
<220> FEATURE:
<223> OTHER INFORMATION: Human (Homo sapiens), chimeric or humanized
      antibody peptide sequence

<400> SEQUENCE: 134

Gly Val Pro Ser Arg Phe Ser Gly Ser Gly Ser Gly Gln Asp Tyr Ser
1               5                   10                  15

Leu Thr Ile Ser Ser Leu Glu Tyr Glu Asp Met Gly Ile Tyr Tyr Cys
            20                  25                  30

<210> SEQ ID NO 135
<211> LENGTH: 10
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 135

Leu Gln Tyr Asp Glu Phe Pro Pro Leu Thr
1               5                   10

<210> SEQ ID NO 136
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 136

Phe Gly Ala Gly Thr Lys Leu Glu Leu Lys Ala
1               5                   10

<210> SEQ ID NO 137
<211> LENGTH: 109
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 137

Gln Ile Val Leu Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Pro
                85                  90                  95

Leu Thr Phe Gly Ala Gly Thr Lys Leu Glu Leu Lys Ala
            100                 105

<210> SEQ ID NO 138
<211> LENGTH: 23
<212> TYPE: PRT
<213> ORGANISM: Unknown
<220> FEATURE:
```

```
<223> OTHER INFORMATION: Human (Homo sapiens), chimeric or humanized
      antibody peptide sequence

<400> SEQUENCE: 138

Gln Ile Val Leu Thr Gln Ser Pro Ser Ser Met Tyr Ala Ser Leu Gly
1               5                   10                  15

Glu Arg Val Thr Ile Thr Cys
            20

<210> SEQ ID NO 139
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 139

Lys Ala Ser Gln Asp Ile Asn Ser Tyr Leu Ser
1               5                   10

<210> SEQ ID NO 140
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 140

Trp Phe Gln Gln Lys Pro Gly Lys Ser Pro Lys Thr Leu Ile Tyr
1               5                   10                  15

<210> SEQ ID NO 141
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 141

Arg Ala Asn Arg Leu Val Asp
1               5

<210> SEQ ID NO 142
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 142

Gly Val Pro Ser Arg Phe Ser Gly Ser Gly Ser Gly Gln Asp Tyr Ser
1               5                   10                  15

Leu Thr Ile Ser Ser Leu Glu Tyr Glu Asp Met Gly Ile Tyr Tyr Cys
            20                  25                  30

<210> SEQ ID NO 143
<211> LENGTH: 10
<212> TYPE: PRT
<213> ORGANISM: Unknown
<220> FEATURE:
<223> OTHER INFORMATION: Human (Homo sapiens), chimeric or humanized
      antibody peptide sequence
```

```
<400> SEQUENCE: 143

Leu Gln Tyr Asp Glu Phe Pro Pro Leu Thr
1               5                   10

<210> SEQ ID NO 144
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 144

Phe Gly Ala Gly Thr Lys Leu Glu Leu Lys Ala
1               5                   10

<210> SEQ ID NO 145
<211> LENGTH: 107
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 145

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Pro Gly Thr Ser Pro Lys Leu Trp Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ser Gly Thr Lys Leu Glu Ile Lys Ala
            100                 105

<210> SEQ ID NO 146
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 146

Gln Ile Val Leu Thr Gln Ser Pro Ala Ile Met Ser Ala Ser Pro Gly
1               5                   10                  15

Glu Lys Val Thr Met Thr Cys
            20

<210> SEQ ID NO 147
<211> LENGTH: 10
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 147
```

Ser Ala Ser Ser Ser Val Ser Tyr Met His
1               5                   10

<210> SEQ ID NO 148
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 148

Trp Tyr Gln Gln Lys Pro Gly Thr Ser Pro Lys Leu Trp Ile Tyr
1               5                   10                  15

<210> SEQ ID NO 149
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 149

Asp Thr Ser Asn Leu Ala Ser
1               5

<210> SEQ ID NO 150
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 150

Gly Val Pro Ala Arg Phe Ser Gly Ser Gly Ser Gly Thr Ser Tyr Ser
1               5                   10                  15
Leu Thr Ile Ser Ser Met Glu Ala Glu Asp Ala Ala Thr Tyr Tyr Cys
                20                  25                  30

<210> SEQ ID NO 151
<211> LENGTH: 9
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 151

Gln Gln Trp Ser Ser Asn Pro Leu Thr
1               5

<210> SEQ ID NO 152
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 152

Phe Gly Ser Gly Thr Lys Leu Glu Ile Lys Ala
1               5                   10

<210> SEQ ID NO 153
<211> LENGTH: 107

<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 153

Glu Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Pro Gly Ser Ser Pro Lys Leu Trp Ile Tyr
            35                  40                  45

Asp Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Asp Gly Thr Arg Leu Glu Ile Lys Ala
            100                 105

<210> SEQ ID NO 154
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 154

Glu Ile Val Leu Thr Gln Ser Pro Ala Ile Met Ser Ala Ser Pro Gly
1               5                   10                  15

Glu Lys Val Thr Met Thr Cys
            20

<210> SEQ ID NO 155
<211> LENGTH: 10
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 155

Ser Ala Ser Ser Ser Val Ser Tyr Met His
1               5                   10

<210> SEQ ID NO 156
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 156

Trp Tyr Gln Gln Lys Pro Gly Ser Ser Pro Lys Leu Trp Ile Tyr
1               5                   10                  15

<210> SEQ ID NO 157
<211> LENGTH: 7
<212> TYPE: PRT
<213> ORGANISM: Unknown

```
<220> FEATURE:
<223> OTHER INFORMATION: Human (Homo sapiens), chimeric or humanized
      antibody peptide sequence

<400> SEQUENCE: 157

Asp Thr Ser Asn Leu Ala Ser
1               5

<210> SEQ ID NO 158
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 158

Gly Val Pro Ala Arg Phe Ser Gly Ser Gly Ser Gly Thr Ser Tyr Ser
1               5                   10                  15

Leu Thr Ile Ser Ser Met Glu Ala Glu Asp Ala Ala Thr Tyr Tyr Cys
            20                  25                  30

<210> SEQ ID NO 159
<211> LENGTH: 9
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 159

Gln Gln Trp Ser Ser Asn Pro Leu Thr
1               5

<210> SEQ ID NO 160
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 160

Phe Gly Asp Gly Thr Arg Leu Glu Ile Lys Ala
1               5                   10

<210> SEQ ID NO 161
<211> LENGTH: 107
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 161

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Thr Ser Pro Lys Leu Trp Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80
```

Asp Ala Ala Thr Tyr Tyr Cys Gln Gln Trp Ser Ser Asn Pro Pro Thr
            85                  90                  95

Phe Gly Ala Gly Thr Lys Leu Glu Leu Lys Ala
            100                 105

<210> SEQ ID NO 162
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 162

Gln Ile Val Leu Thr Gln Ser Pro Ala Ile Met Ser Ala Ser Pro Gly
1               5                   10                  15

Glu Lys Val Thr Met Thr Cys
            20

<210> SEQ ID NO 163
<211> LENGTH: 10
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 163

Ser Ala Ser Ser Ser Val Ser Tyr Met His
1               5                   10

<210> SEQ ID NO 164
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 164

Trp Tyr Gln Gln Lys Ser Gly Thr Ser Pro Lys Leu Trp Ile Tyr
1               5                   10                  15

<210> SEQ ID NO 165
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 165

Asp Thr Ser Asn Leu Ala Ser
1               5

<210> SEQ ID NO 166
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 166

Gly Val Pro Ala Arg Phe Ser Gly Ser Gly Ser Gly Thr Ser Tyr Ser
1               5                   10                  15

Leu Thr Ile Ser Ser Met Glu Ala Glu Asp Ala Ala Thr Tyr Tyr Cys
            20                  25                  30

<210> SEQ ID NO 167
<211> LENGTH: 9
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 167

Gln Gln Trp Ser Ser Asn Pro Pro Thr
1               5

<210> SEQ ID NO 168
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 168

Phe Gly Ala Gly Thr Lys Leu Glu Leu Lys Ala
1               5                   10

<210> SEQ ID NO 169
<211> LENGTH: 107
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 169

Asp Ile Lys Met Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Phe Thr
            85                  90                  95

Phe Gly Ser Gly Thr Lys Leu Glu Ile Lys Ala
            100                 105

<210> SEQ ID NO 170
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 170

Asp Ile Lys Met Thr Gln Ser Pro Ala Ile Met Ser Ala Ser Pro Gly
1               5                   10                  15

Glu Lys Val Thr Met Thr Cys
            20

<210> SEQ ID NO 171
<211> LENGTH: 10
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 171

Ser Ala Ser Ser Ser Val Ser Tyr Met His
1               5                   10

<210> SEQ ID NO 172
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 172

Trp Tyr Gln Gln Lys Ser Gly Thr Ser Pro Lys Arg Trp Ile Tyr
1               5                   10                  15

<210> SEQ ID NO 173
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 173

Asp Thr Ser Lys Leu Ala Ser
1               5

<210> SEQ ID NO 174
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 174

Gly Val Pro Ala Arg Phe Ser Gly Ser Gly Ser Gly Thr Ser Tyr Ser
1               5                   10                  15

Leu Thr Ile Ser Ser Met Glu Ala Glu Asp Ala Ala Thr Tyr Tyr Cys
            20                  25                  30

<210> SEQ ID NO 175
<211> LENGTH: 9
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 175

Gln Gln Trp Ser Ser Asn Pro Phe Thr
1               5

<210> SEQ ID NO 176
<211> LENGTH: 11
<212> TYPE: PRT

```
<213> ORGANISM: Unknown
<220> FEATURE:
<223> OTHER INFORMATION: Human (Homo sapiens), chimeric or humanized
      antibody peptide sequence

<400> SEQUENCE: 176

Phe Gly Ser Gly Thr Lys Leu Glu Ile Lys Ala
1               5                   10

<210> SEQ ID NO 177
<211> LENGTH: 107
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 177

Gln Met Val Leu Thr His Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Pro Gly Ser Ser Pro Lys Pro Trp Ile Tyr
        35                  40                  45

Gly Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Asp Gly Thr Arg Leu Glu Ile Lys Ala
            100                 105

<210> SEQ ID NO 178
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 178

Gln Met Val Leu Thr His Ser Pro Ala Ile Met Ser Ala Ser Pro Gly
1               5                   10                  15

Glu Lys Val Thr Met Thr Cys
            20

<210> SEQ ID NO 179
<211> LENGTH: 10
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 179

Ser Ala Ser Ser Ser Val Ser Tyr Met His
1               5                   10

<210> SEQ ID NO 180
<211> LENGTH: 15
<212> TYPE: PRT
<213> ORGANISM: Unknown
<220> FEATURE:
```

<223> OTHER INFORMATION: Human (Homo sapiens), chimeric or humanized
      antibody peptide sequence

<400> SEQUENCE: 180

Trp Tyr Gln Gln Lys Pro Gly Ser Ser Pro Lys Pro Trp Ile Tyr
1               5                   10                  15

<210> SEQ ID NO 181
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 181

Gly Thr Ser Asn Leu Ala Ser
1               5

<210> SEQ ID NO 182
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 182

Gly Val Pro Ala Arg Phe Ser Gly Ser Gly Ser Gly Thr Ser Tyr Ser
1               5                   10                  15

Leu Thr Ile Ser Arg Met Glu Ala Glu Asp Ala Ala Thr Tyr Tyr Cys
            20                  25                  30

<210> SEQ ID NO 183
<211> LENGTH: 9
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 183

Gln Gln Trp Ser Ser Asn Pro Pro Thr
1               5

<210> SEQ ID NO 184
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 184

Phe Gly Asp Gly Thr Arg Leu Glu Ile Lys Ala
1               5                   10

<210> SEQ ID NO 185
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 185

Asp Ile Val Met Ser Gln Ser Pro Ser Ser Leu Ala Val Ser Ala Gly

-continued

```
                1               5                  10                  15
Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Thr Phe Gly Ala Gly Thr Lys Leu Glu Leu Lys
                100                 105                 110

Ala
```

<210> SEQ ID NO 186
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 186

```
Asp Ile Val Met Ser Gln Ser Pro Ser Ser Leu Ala Val Ser Ala Gly
1               5                   10                  15

Glu Lys Val Thr Met Ser Cys
                20
```

<210> SEQ ID NO 187
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 187

```
Lys Ser Ser Gln Ser Leu Leu Asn Ser Arg Thr Arg Lys Asn Tyr Leu
1               5                   10                  15

Ala
```

<210> SEQ ID NO 188
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 188

```
Trp Tyr Gln Gln Lys Pro Gly Gln Ser Pro Arg Leu Leu Ile Tyr
1               5                   10                  15
```

<210> SEQ ID NO 189
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 189

Trp Ala Ser Thr Arg Glu Ser
1               5

<210> SEQ ID NO 190
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 190

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 191
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 191

Lys Gln Ser Tyr Asn Leu Leu Thr
1               5

<210> SEQ ID NO 192
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 192

Phe Gly Ala Gly Thr Lys Leu Glu Leu Lys Ala
1               5                   10

<210> SEQ ID NO 193
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 193

Asp Ile Val Met Ser Gln Ser Pro Ser Ser Leu Ala Val Ser Ala Gly
1               5                   10                  15

Glu Asn Val Thr Val Ser Cys Lys Ser Ser Gln Ser Leu Leu Asn Ser
            20                  25                  30

Arg Thr Arg Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Phe Cys Lys Gln
                85                  90                  95

Ser Tyr Asn Leu Leu Thr Phe Gly Ala Gly Thr Lys Leu Glu Leu Lys

Ala

<210> SEQ ID NO 194
<211> LENGTH: 23
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 194

Asp Ile Val Met Ser Gln Ser Pro Ser Ser Leu Ala Val Ser Ala Gly
1               5                   10                  15

Glu Asn Val Thr Val Ser Cys
            20

<210> SEQ ID NO 195
<211> LENGTH: 23
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 195

Asp Ile Val Met Ser Gln Ser Pro Ser Ser Leu Ala Val Ser Ala Gly
1               5                   10                  15

Glu Asn Val Thr Val Ser Cys
            20

<210> SEQ ID NO 196
<211> LENGTH: 15
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 196

Trp Tyr Gln Gln Lys Pro Gly Gln Ser Pro Lys Leu Leu Ile Tyr
1               5                   10                  15

<210> SEQ ID NO 197
<211> LENGTH: 7
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 197

Trp Ala Ser Thr Arg Glu Ser
1               5

<210> SEQ ID NO 198
<211> LENGTH: 32
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 198

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Phe Cys
            20                  25                  30

<210> SEQ ID NO 199
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 199

Lys Gln Ser Tyr Asn Leu Leu Thr
1               5

<210> SEQ ID NO 200
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 200

Phe Gly Ala Gly Thr Lys Leu Glu Leu Lys Ala
1               5                   10

<210> SEQ ID NO 201
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 201

Asp Ile Lys Met Thr Gln Ser Pro Ser Ser Leu Ala Val Ser Pro Gly
1               5                   10                  15

Glu Lys Val Thr Met Ser Cys Lys Ser Ser Gln Ser Leu Leu His Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Thr Phe Gly Ala Gly Thr Lys Leu Glu Leu Lys
            100                 105                 110

Ala

<210> SEQ ID NO 202
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 202

Asp Ile Lys Met Thr Gln Ser Pro Ser Ser Leu Ala Val Ser Pro Gly
1               5                   10                  15

Glu Lys Val Thr Met Ser Cys
            20

<210> SEQ ID NO 203
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 203

Lys Ser Ser Gln Ser Leu Leu His Ser Arg Thr Arg Lys Asn Tyr Leu
1               5                   10                  15

Ala

<210> SEQ ID NO 204
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 204

Trp Tyr Gln Gln Lys Pro Gly Gln Ser Pro Lys Leu Leu Ile Tyr
1               5                   10                  15

<210> SEQ ID NO 205
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 205

Trp Ala Ser Thr Arg Glu Ser
1               5

<210> SEQ ID NO 206
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 206

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 207
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 207

Lys Gln Ser Tyr Asn Leu Leu Thr
1               5

```
<210> SEQ ID NO 208
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 208

Phe Gly Ala Gly Thr Lys Leu Glu Leu Lys Ala
1               5                   10

<210> SEQ ID NO 209
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 209

Asp Ile Val Met Ser Gln Ser Pro Ser Ser Leu Ala Val Ser Pro Gly
1               5                   10                  15

Glu Lys Val Thr Met Ser Cys Lys Ser Ser Gln Ser Leu Leu His Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Thr Phe Gly Ala Gly Thr Lys Leu Glu Leu Lys
            100                 105                 110

Ala

<210> SEQ ID NO 210
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 210

Asp Ile Val Met Ser Gln Ser Pro Ser Ser Leu Ala Val Ser Pro Gly
1               5                   10                  15

Glu Lys Val Thr Met Ser Cys
            20

<210> SEQ ID NO 211
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 211

Lys Ser Ser Gln Ser Leu Leu His Ser Arg Thr Arg Lys Asn Tyr Leu
1               5                   10                  15
```

Ala

<210> SEQ ID NO 212
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 212

Trp Tyr Gln Gln Lys Pro Gly Gln Ser Pro Lys Leu Leu Ile Tyr
1               5                   10                  15

<210> SEQ ID NO 213
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 213

Trp Ala Ser Thr Arg Glu Ser
1               5

<210> SEQ ID NO 214
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 214

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 215
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 215

Lys Gln Ser Tyr Asn Leu Leu Thr
1               5

<210> SEQ ID NO 216
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 216

Phe Gly Ala Gly Thr Lys Leu Glu Leu Lys Ala
1               5                   10

<210> SEQ ID NO 217
<211> LENGTH: 113
<212> TYPE: PRT

```
<213> ORGANISM: Unknown
<220> FEATURE:
<223> OTHER INFORMATION: Human (Homo sapiens), chimeric or humanized
      antibody peptide sequence

<400> SEQUENCE: 217

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Thr Phe Gly Ala Gly Thr Lys Leu Glu Leu Lys
            100                 105                 110

Arg

<210> SEQ ID NO 218
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 218

Asp Ile Val Met Thr Gln Ser Pro Ser Ser Leu Ala Val Ser Ala Gly
1               5                   10                  15

Glu Lys Val Thr Met Ser Cys
            20

<210> SEQ ID NO 219
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 219

Lys Ser Ser Gln Ser Leu Leu Asn Ser Arg Thr Arg Lys Asn Tyr Leu
1               5                   10                  15

Ala

<210> SEQ ID NO 220
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 220

Trp Tyr Gln Gln Lys Pro Gly Gln Ser Pro Arg Leu Leu Ile Tyr
1               5                   10                  15

<210> SEQ ID NO 221
```

```
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 221

Trp Ala Ser Thr Arg Glu Ser
1               5

<210> SEQ ID NO 222
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 222

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 223
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 223

Lys Gln Ser Tyr Asn Leu Leu Thr
1               5

<210> SEQ ID NO 224
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 224

Phe Gly Ala Gly Thr Lys Leu Glu Leu Lys Arg
1               5                   10

<210> SEQ ID NO 225
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 225

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Arg Leu Leu Ile Tyr Trp Ala Ser Thr Arg Glu Ser Gly Val
    50                  55                  60
```

```
Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Asn Leu Leu Thr Phe Gly Ala Gly Thr Arg Leu Glu Ile Lys
            100                 105                 110

Arg
```

```
<210> SEQ ID NO 226
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 226

Asp Ile Val Met Thr Gln Ser Pro Ser Leu Ala Val Ser Ala Gly
 1               5                  10                  15

Glu Lys Val Thr Met Ser Cys
                 20
```

```
<210> SEQ ID NO 227
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 227

Lys Ser Ser Gln Ser Leu Leu Asn Ser Arg Thr Arg Lys Asn Tyr Leu
 1               5                  10                  15

Ala
```

```
<210> SEQ ID NO 228
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 228

Trp Tyr Gln Gln Lys Pro Gly Gln Ser Pro Arg Leu Leu Ile Tyr
 1               5                  10                  15
```

```
<210> SEQ ID NO 229
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 229

Trp Ala Ser Thr Arg Glu Ser
 1               5
```

```
<210> SEQ ID NO 230
<211> LENGTH: 32
<212> TYPE: PRT
<213> ORGANISM: Unknown
<220> FEATURE:
```

```
<223> OTHER INFORMATION: Human (Homo sapiens), chimeric or humanized
      antibody peptide sequence

<400> SEQUENCE: 230

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 231
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 231

Lys Gln Ser Tyr Asn Leu Leu Thr
1               5

<210> SEQ ID NO 232
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 232

Phe Gly Ala Gly Thr Arg Leu Glu Ile Lys Arg
1               5                   10

<210> SEQ ID NO 233
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 233

Asp Ile Val Met Thr Gln Ser Pro Ser Ser Leu Ala Val Ser Ala Gly
1               5                   10                  15

Glu Asn Val Thr Val Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Gly Phe Thr Leu Thr
65                  70                  75                  80

Ile Ser Ser Val Gln Ala Glu Asp Leu Ala Val Tyr Phe Cys Lys Gln
                85                  90                  95

Ser Tyr Asn Leu Leu Thr Phe Gly Ala Gly Thr Arg Leu Glu Ile Lys
                100                 105                 110

Arg

<210> SEQ ID NO 234
<211> LENGTH: 23
<212> TYPE: PRT
<213> ORGANISM: Unknown
<220> FEATURE:
```

<223> OTHER INFORMATION: Human (Homo sapiens), chimeric or humanized
     antibody peptide sequence

<400> SEQUENCE: 234

Asp Ile Val Met Thr Gln Ser Pro Ser Ser Leu Ala Val Ser Ala Gly
1               5                   10                  15

Glu Asn Val Thr Val Ser Cys
            20

<210> SEQ ID NO 235
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 235

Lys Ser Ser Gln Ser Leu Leu Asn Ser Arg Thr Arg Lys Asn Tyr Leu
1               5                   10                  15

Ala

<210> SEQ ID NO 236
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 236

Trp Tyr Gln Gln Lys Pro Gly Gln Ser Pro Lys Leu Leu Ile Tyr
1               5                   10                  15

<210> SEQ ID NO 237
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 237

Trp Ala Ser Thr Arg Glu Ser
1               5

<210> SEQ ID NO 238
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 238

Gly Val Pro Asp Arg Phe Thr Gly Ser Gly Ser Gly Thr Gly Phe Thr
1               5                   10                  15

Leu Thr Ile Ser Ser Val Gln Ala Glu Asp Leu Ala Val Tyr Phe Cys
            20                  25                  30

<210> SEQ ID NO 239
<211> LENGTH: 8
<212> TYPE: PRT
<213> ORGANISM: Unknown
<220> FEATURE:
<223> OTHER INFORMATION: Human (Homo sapiens), chimeric or humanized antibody peptide sequence

<400> SEQUENCE: 239

Lys Gln Ser Tyr Asn Leu Leu Thr
1               5

<210> SEQ ID NO 240
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 240

Phe Gly Ala Gly Thr Arg Leu Glu Ile Lys Arg
1               5                   10

<210> SEQ ID NO 241
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 241

Asp Ile Val Met Ser Gln Ser Pro Ser Ser Leu Ala Val Ser Pro Gly
1               5                   10                  15

Glu Lys Val Thr Met Ser Cys Lys Ser Gln Ser Leu Leu His Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Thr Phe Gly Ala Gly Thr Lys Leu Glu Leu Lys
            100                 105                 110

Arg

<210> SEQ ID NO 242
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 242

Asp Ile Val Met Ser Gln Ser Pro Ser Ser Leu Ala Val Ser Pro Gly
1               5                   10                  15

Glu Lys Val Thr Met Ser Cys
            20

<210> SEQ ID NO 243
<211> LENGTH: 17
<212> TYPE: PRT
<213> ORGANISM: Unknown
<220> FEATURE:
<223> OTHER INFORMATION: Human (Homo sapiens), chimeric or humanized antibody peptide sequence

<400> SEQUENCE: 243

Lys Ser Ser Gln Ser Leu Leu His Ser Arg Thr Arg Lys Asn Tyr Leu
1               5                   10                  15

Ala

<210> SEQ ID NO 244
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 244

Trp Tyr Gln Gln Lys Pro Gly Gln Ser Pro Lys Leu Leu Ile Tyr
1               5                   10                  15

<210> SEQ ID NO 245
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 245

Trp Ala Ser Thr Arg Glu Ser
1               5

<210> SEQ ID NO 246
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 246

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
                20                  25                  30

<210> SEQ ID NO 247
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 247

Lys Gln Ser Tyr Asn Leu Leu Thr
1               5

<210> SEQ ID NO 248
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 248

```
Phe Gly Ala Gly Thr Lys Leu Glu Leu Lys Arg
1               5                   10
```

<210> SEQ ID NO 249
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 249

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Lys Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Thr Phe Gly Ala Gly Thr Lys Leu Glu Leu Lys
            100                 105                 110

Ala
```

<210> SEQ ID NO 250
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 250

```
Asp Ile Val Met Ser Gln Ser Pro Ser Ser Leu Ala Val Ser Ala Gly
1               5                   10                  15

Glu Lys Val Thr Met Ser Cys
            20
```

<210> SEQ ID NO 251
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 251

```
Lys Ser Ser Gln Ser Leu Leu Asn Ser Arg Thr Arg Lys Asn Tyr Leu
1               5                   10                  15

Ala
```

<210> SEQ ID NO 252
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

```
<400> SEQUENCE: 252

Trp Tyr Gln Gln Lys Pro Gly Gln Ser Pro Arg Leu Leu Ile Tyr
1               5                   10                  15

<210> SEQ ID NO 253
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 253

Trp Ala Ser Thr Arg Glu Ser
1               5

<210> SEQ ID NO 254
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 254

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 255
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 255

Lys Gln Ser Tyr Asn Leu Leu Thr
1               5

<210> SEQ ID NO 256
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 256

Phe Gly Ala Gly Thr Lys Leu Glu Leu Lys Ala
1               5                   10

<210> SEQ ID NO 257
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 257

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
```

```
                20                  25                  30
Arg Thr Arg Lys Asn Tyr Leu Ala Trp Tyr Gln Gln Lys Pro Gly Gln
            35                  40                  45

Ser Pro Arg Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Asp Glu Asp Leu Ala Val Tyr Tyr Cys Lys Gln
                85                  90                  95

Ser Tyr Asn Leu Leu Thr Phe Gly Ala Gly Thr Lys Leu Glu Leu Lys
            100                 105                 110

Ala
```

<210> SEQ ID NO 258
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 258

```
Asp Ile Val Met Ser Gln Ser Pro Ser Ser Leu Ala Val Ser Ala Gly
1               5                   10                  15

Glu Lys Val Thr Met Ser Cys
            20
```

<210> SEQ ID NO 259
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 259

```
Lys Ser Ser Gln Ser Leu Leu Asn Ser Arg Thr Arg Lys Asn Tyr Leu
1               5                   10                  15

Ala
```

<210> SEQ ID NO 260
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 260

```
Trp Tyr Gln Gln Lys Pro Gly Gln Ser Pro Arg Leu Leu Ile Tyr
1               5                   10                  15
```

<210> SEQ ID NO 261
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 261

```
Trp Ala Ser Thr Arg Glu Ser
1               5
```

<210> SEQ ID NO 262
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 262

Gly Val Pro Asp Arg Phe Thr Gly Ser Gly Ser Gly Thr Asp Phe Thr
1               5                   10                  15

Leu Thr Ile Ser Ser Val Gln Asp Glu Asp Leu Ala Val Tyr Tyr Cys
            20                  25                  30

<210> SEQ ID NO 263
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 263

Lys Gln Ser Tyr Asn Leu Leu Thr
1               5

<210> SEQ ID NO 264
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 264

Phe Gly Ala Gly Thr Lys Leu Glu Leu Lys Ala
1               5                   10

<210> SEQ ID NO 265
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 265

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Thr Phe Gly Ala Gly Thr Lys Leu Glu Leu Lys
            100                 105                 110

Ala

-continued

<210> SEQ ID NO 266
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 266

Asp Ile Val Met Ser Gln Ser Pro Ser Ser Leu Ala Val Ser Ala Gly
1               5                   10                  15

Glu Lys Val Thr Met Ser Cys
            20

<210> SEQ ID NO 267
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 267

Lys Ser Ser Gln Ser Leu Leu Asn Ser Arg Thr Arg Lys Asn Tyr Leu
1               5                   10                  15

Ala

<210> SEQ ID NO 268
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 268

Trp Tyr Gln Gln Lys Pro Gly Gln Ser Pro Arg Leu Leu Ile Tyr
1               5                   10                  15

<210> SEQ ID NO 269
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 269

Trp Ala Ser Thr Arg Glu Ser
1               5

<210> SEQ ID NO 270
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 270

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

```
<210> SEQ ID NO 271
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 271

Lys Gln Ser Tyr Asn Leu Leu Thr
1               5

<210> SEQ ID NO 272
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 272

Phe Gly Ala Gly Thr Lys Leu Glu Leu Lys Ala
1               5                   10

<210> SEQ ID NO 273
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 273

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Lys Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Thr Phe Gly Ala Gly Thr Lys Leu Glu Leu Lys
            100                 105                 110

Ala

<210> SEQ ID NO 274
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 274

Asp Ile Val Met Ser Gln Ser Pro Ser Ser Leu Ala Val Ser Ala Gly
1               5                   10                  15

Glu Lys Val Thr Met Ser Cys
            20
```

```
<210> SEQ ID NO 275
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 275

Lys Ser Ser Gln Ser Leu Leu Asn Ser Arg Thr Arg Lys Asn Tyr Leu
1               5                   10                  15

Ala

<210> SEQ ID NO 276
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 276

Trp Tyr Gln Gln Lys Pro Gly Gln Ser Pro Arg Leu Leu Ile Tyr
1               5                   10                  15

<210> SEQ ID NO 277
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 277

Trp Ala Ser Thr Arg Glu Ser
1               5

<210> SEQ ID NO 278
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 278

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 279
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 279

Lys Gln Ser Tyr Asn Leu Leu Thr
1               5

<210> SEQ ID NO 280
<211> LENGTH: 11
<212> TYPE: PRT
```

```
<213> ORGANISM: Unknown
<220> FEATURE:
<223> OTHER INFORMATION: Human (Homo sapiens), chimeric or humanized
      antibody peptide sequence

<400> SEQUENCE: 280

Phe Gly Ala Gly Thr Lys Leu Glu Leu Lys Ala
1               5                   10

<210> SEQ ID NO 281
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: misc_feature
<222> LOCATION: (49)..(49)
<223> OTHER INFORMATION: Xaa can be any naturally occurring amino acid

<400> SEQUENCE: 281

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Xaa Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Asp Glu Asp Leu Ala Val Tyr Tyr Cys Lys Gln
                85                  90                  95

Ser Tyr Asn Leu Leu Ser Phe Gly Ala Gly Thr Lys Leu Glu Leu Lys
                100                 105                 110

Ala

<210> SEQ ID NO 282
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 282

Asp Ile Val Met Ser Gln Ser Pro Ser Ser Leu Ala Val Ser Ala Gly
1               5                   10                  15

Glu Lys Val Thr Met Ser Cys
            20

<210> SEQ ID NO 283
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 283

Lys Ser Ser Gln Ser Leu Leu Asn Ser Arg Thr Arg Lys Asn Tyr Leu
1               5                   10                  15
```

Ala

<210> SEQ ID NO 284
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: misc_feature
<222> LOCATION: (9)..(9)
<223> OTHER INFORMATION: Xaa can be any naturally occurring amino acid

<400> SEQUENCE: 284

Trp Tyr Gln Gln Lys Pro Gly Gln Xaa Pro Arg Leu Leu Ile Tyr
1               5                   10                  15

<210> SEQ ID NO 285
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 285

Trp Ala Ser Thr Arg Glu Ser
1               5

<210> SEQ ID NO 286
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 286

Gly Val Pro Asp Arg Phe Thr Gly Ser Gly Ser Gly Thr Asp Phe Thr
1               5                   10                  15

Leu Thr Ile Ser Ser Val Gln Asp Glu Asp Leu Ala Val Tyr Tyr Cys
            20                  25                  30

<210> SEQ ID NO 287
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 287

Lys Gln Ser Tyr Asn Leu Leu Ser
1               5

<210> SEQ ID NO 288
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 288

Phe Gly Ala Gly Thr Lys Leu Glu Leu Lys Ala
1               5                   10

<210> SEQ ID NO 289
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 289

Asp Ile Val Met Thr Gln Ser Pro Ser Ser Leu Ala Val Ser Ala Gly
1               5                   10                  15

Glu Lys Val Thr Met Ser Cys Lys Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Ser Phe Gly Ala Gly Thr Lys Leu Glu Leu Lys
            100                 105                 110

Arg

<210> SEQ ID NO 290
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 290

Asp Ile Val Met Thr Gln Ser Pro Ser Ser Leu Ala Val Ser Ala Gly
1               5                   10                  15

Glu Lys Val Thr Met Ser Cys
            20

<210> SEQ ID NO 291
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 291

Lys Ser Ser Gln Ser Leu Leu Asn Ser Arg Thr Arg Lys Asn Tyr Leu
1               5                   10                  15

Ala

<210> SEQ ID NO 292
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 292

Trp Tyr Gln Gln Lys Pro Gly Gln Ser Pro Arg Leu Leu Ile Tyr

<210> SEQ ID NO 293
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 293

Trp Ala Ser Thr Arg Glu Ser
1               5

<210> SEQ ID NO 294
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 294

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
                20                  25                  30

<210> SEQ ID NO 295
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 295

Lys Gln Ser Tyr Asn Leu Leu Ser
1               5

<210> SEQ ID NO 296
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 296

Phe Gly Ala Gly Thr Lys Leu Glu Leu Lys Arg
1               5                   10

<210> SEQ ID NO 297
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 297

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Tyr
                20                  25                  30

Leu Ile Gln Trp Val Lys Gln Arg Pro Gly Gln Gly Leu Glu Trp Ile

```
                35                  40                  45
Gly Val Ile Asn Pro Glu Thr Gly Gly Thr Asn Tyr Asn Ala Lys Phe
        50                  55                  60
Arg Gly Lys Ala Thr Leu Thr Ala Asp Lys Ser Ser Ser Ser Ala Tyr
65                  70                  75                  80
Met Gln Leu Ser Ser Leu Thr Ser Gly Asp Ser Ala Val Tyr Phe Cys
                85                  90                  95
Ala Arg Glu Ala Gly Asn Tyr Ile Tyr Ala Met Asp Tyr Trp Gly Gln
            100                 105                 110
Gly Thr Ser Val Thr Val Ser Ser
        115                 120
```

<210> SEQ ID NO 298
<211> LENGTH: 27
<212> TYPE: PRT
<213> ORGANISM: Unknown
<220> FEATURE:
<223> OTHER INFORMATION: Human (Homo sapiens), chimeric or humanized antibody peptide sequence

<400> SEQUENCE: 298

```
Gln Val Gln Leu Gln Gln Ser Gly Ala Glu Leu Val Arg Pro Gly Thr
1               5                   10                  15
Ser Val Lys Val Ser Cys Lys Ala Ser Gly Tyr
            20                  25
```

<210> SEQ ID NO 299
<211> LENGTH: 8
<212> TYPE: PRT
<213> ORGANISM: Unknown
<220> FEATURE:
<223> OTHER INFORMATION: Human (Homo sapiens), chimeric or humanized antibody peptide sequence

<400> SEQUENCE: 299

```
Ala Phe Thr Asp Tyr Leu Ile Gln
1               5
```

<210> SEQ ID NO 300
<211> LENGTH: 14
<212> TYPE: PRT
<213> ORGANISM: Unknown
<220> FEATURE:
<223> OTHER INFORMATION: Human (Homo sapiens), chimeric or humanized antibody peptide sequence

<400> SEQUENCE: 300

```
Trp Val Lys Gln Arg Pro Gly Gln Gly Leu Glu Trp Ile Gly
1               5                   10
```

<210> SEQ ID NO 301
<211> LENGTH: 17
<212> TYPE: PRT
<213> ORGANISM: Unknown
<220> FEATURE:
<223> OTHER INFORMATION: Human (Homo sapiens), chimeric or humanized antibody peptide sequence

<400> SEQUENCE: 301

```
Val Ile Asn Pro Glu Thr Gly Gly Thr Asn Tyr Asn Ala Lys Phe Arg
1               5                   10                  15
Gly
```

```
<210> SEQ ID NO 302
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 302

Lys Ala Thr Leu Thr Ala Asp Lys Ser Ser Ser Ala Tyr Met Gln
1               5                   10                  15

Leu Ser Ser Leu Thr Ser Gly Asp Ser Ala Val Tyr Phe Cys Ala Arg
                20                  25                  30

<210> SEQ ID NO 303
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 303

Glu Ala Gly Asn Tyr Ile Tyr Ala Met Asp Tyr
1               5                   10

<210> SEQ ID NO 304
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 304

Trp Gly Gln Gly Thr Ser Val Thr Val Ser Ser
1               5                   10

<210> SEQ ID NO 305
<211> LENGTH: 108
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 305

Asp Ile Val Met Thr Gln Ser Pro Ala Phe Leu Ser Ala Ser Val Gly
1               5                   10                  15

Glu Thr Val Thr Ile Thr Cys Arg Ala Ser Val Asn Ile Tyr Ser Tyr
                20                  25                  30

Leu Val Trp Tyr Gln Gln Lys Gln Gly Lys Ser Pro Gln Leu Leu Val
            35                  40                  45

His Asn Ala Lys Thr Leu Ala Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Gly Thr Pro Tyr
                85                  90                  95

Thr Phe Gly Gly Gly Thr Lys Leu Glu Ile Lys Arg
            100                 105

<210> SEQ ID NO 306
<211> LENGTH: 23
```

```
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 306

Asp Ile Val Met Thr Gln Ser Pro Ala Phe Leu Ser Ala Ser Val Gly
1               5                   10                  15

Glu Thr Val Thr Ile Thr Cys
            20

<210> SEQ ID NO 307
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 307

Arg Ala Ser Val Asn Ile Tyr Ser Tyr Leu Val
1               5                   10

<210> SEQ ID NO 308
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 308

Trp Tyr Gln Gln Lys Gln Gly Lys Ser Pro Gln Leu Leu Val His
1               5                   10                  15

<210> SEQ ID NO 309
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 309

Asn Ala Lys Thr Leu Ala Glu
1               5

<210> SEQ ID NO 310
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 310

Gly Val Pro Ser Arg Phe Ser Gly Ser Gly Ser Gly Thr Gln Phe Ser
1               5                   10                  15

Leu Lys Ile Asn Ser Leu Gln Pro Glu Asp Phe Gly Ser Tyr Tyr Cys
            20                  25                  30

<210> SEQ ID NO 311
<211> LENGTH: 9
<212> TYPE: PRT
<213> ORGANISM: Unknown
<220> FEATURE:
```

<223> OTHER INFORMATION: Human (Homo sapiens), chimeric or humanized
     antibody peptide sequence

<400> SEQUENCE: 311

Gln His His His Gly Thr Pro Tyr Thr
1               5

<210> SEQ ID NO 312
<211> LENGTH: 11
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 312

Phe Gly Gly Gly Thr Lys Leu Glu Ile Lys Arg
1               5                   10

<210> SEQ ID NO 313
<211> LENGTH: 8
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 313

Thr Phe Thr Asp Tyr Ser Met His
1               5

<210> SEQ ID NO 314
<211> LENGTH: 17
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 314

Arg Ile Asn Thr Glu Thr Gly Glu Pro Thr Phe Ala Asp Asp Phe Gly
1               5                   10                  15

Gly

<210> SEQ ID NO 315
<211> LENGTH: 7
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 315

Tyr Tyr Tyr Gly Arg Asp Ser
1               5

<210> SEQ ID NO 316
<211> LENGTH: 8
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 316

Thr Phe Thr Asp Tyr Ser Met His
1               5

<210> SEQ ID NO 317
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 317

Trp Ile Lys Thr Glu Thr Gly Glu Pro Thr Tyr Ala Asp Asp Phe Lys
1               5                   10                  15

Gly

<210> SEQ ID NO 318
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 318

Tyr Tyr Tyr Gly Arg Asp Ser
1               5

<210> SEQ ID NO 319
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 319

Thr Phe Thr Asp Tyr Ser Met His
1               5

<210> SEQ ID NO 320
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 320

Trp Ile Lys Thr Glu Thr Asp Glu Pro Thr Tyr Ala Asp Asp Phe Lys
1               5                   10                  15

Glu

<210> SEQ ID NO 321
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 321

Tyr Tyr Tyr Gly Arg Asp Ser
1               5

<210> SEQ ID NO 322
<211> LENGTH: 8
<212> TYPE: PRT

```
<213> ORGANISM: Unknown
<220> FEATURE:
<223> OTHER INFORMATION: Human (Homo sapiens), chimeric or humanized
      antibody peptide sequence

<400> SEQUENCE: 322

Thr Phe Thr Asp Tyr Ser Met His
1               5

<210> SEQ ID NO 323
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 323

Arg Ile Asn Thr Glu Thr Gly Glu Pro Thr Phe Ala Asp Asp Phe Arg
1               5                   10                  15

Gly

<210> SEQ ID NO 324
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 324

Tyr Tyr Tyr Gly Arg Asp Ser
1               5

<210> SEQ ID NO 325
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 325

Thr Phe Thr Asp Tyr Ser Ile His
1               5

<210> SEQ ID NO 326
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 326

Trp Ile Lys Thr Glu Thr Gly Glu Pro Thr Tyr Ala Asp Asp Phe Asn
1               5                   10                  15

Gly

<210> SEQ ID NO 327
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence
```

```
<400> SEQUENCE: 327

Tyr Tyr Tyr Gly Arg Asp Ser
1               5

<210> SEQ ID NO 328
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 328

Thr Phe Thr Asp Tyr Ser Met His
1               5

<210> SEQ ID NO 329
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 329

Arg Ile Asn Thr Glu Thr Gly Glu Pro Thr Phe Ala Asp Asp Phe Arg
1               5                   10                  15
Gly

<210> SEQ ID NO 330
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 330

Tyr Tyr Tyr Gly Arg Asp Thr
1               5

<210> SEQ ID NO 331
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 331

Thr Phe Thr Asp Tyr Ser Met His
1               5

<210> SEQ ID NO 332
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 332

Arg Ile Asn Thr Glu Thr Gly Glu Pro Thr Phe Ala Asp Asp Phe Arg
1               5                   10                  15
Gly
```

```
<210> SEQ ID NO 333
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 333

Phe Tyr Tyr Gly Arg Asp Ser
1               5

<210> SEQ ID NO 334
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 334

Lys Ala Ser Gln Asp Ile Asn Ser Tyr Leu Ser
1               5                   10

<210> SEQ ID NO 335
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 335

Arg Ala Asn Arg Leu Val Asp
1               5

<210> SEQ ID NO 336
<211> LENGTH: 10
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 336

Leu Gln Tyr Asp Glu Phe Pro Pro Leu Thr
1               5                   10

<210> SEQ ID NO 337
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 337

Lys Ser Ser Gln Ser Leu Leu Asn Ser Arg Thr Arg Lys Asn Tyr Leu
1               5                   10                  15

Ala

<210> SEQ ID NO 338
<211> LENGTH: 7
<212> TYPE: PRT
<213> ORGANISM: Unknown
<220> FEATURE:
<223> OTHER INFORMATION: Human (Homo sapiens), chimeric or humanized
``` antibody peptide sequence

<400> SEQUENCE: 338

Trp Ala Ser Thr Arg Glu Ser
1               5

<210> SEQ ID NO 339
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 339

Lys Gln Ser Tyr Asn Leu Leu Thr
1               5

<210> SEQ ID NO 340
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 340

Lys Ser Ser Gln Ser Leu Leu Asn Ser Arg Ile Arg Lys Asn Tyr Leu
1               5                   10                  15

Ala

<210> SEQ ID NO 341
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 341

Trp Ala Ser Thr Arg Glu Ser
1               5

<210> SEQ ID NO 342
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 342

Lys Gln Ser Tyr Asn Leu Leu Thr
1               5

<210> SEQ ID NO 343
<211> LENGTH: 10
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 343

Ser Ala Ser Ser Ser Val Ser Tyr Met His
1               5                   10

```
<210> SEQ ID NO 344
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 344

Asp Thr Ser Asn Leu Ala Ser
1               5

<210> SEQ ID NO 345
<211> LENGTH: 9
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 345

Gln Gln Trp Ser Ser Asn Pro Leu Thr
1               5

<210> SEQ ID NO 346
<211> LENGTH: 10
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 346

Ser Ala Ser Ser Ser Val Ser Tyr Met His
1               5                   10

<210> SEQ ID NO 347
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 347

Asp Thr Ser Asn Leu Ala Ser
1               5

<210> SEQ ID NO 348
<211> LENGTH: 9
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 348

Gln Gln Trp Ser Ser Asn Pro Pro Thr
1               5

<210> SEQ ID NO 349
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence
```

```
<400> SEQUENCE: 349

Lys Ser Ser Gln Ser Leu Leu Asn Ser Arg Thr Arg Lys Asn Tyr Leu
1               5                   10                  15

Ala

<210> SEQ ID NO 350
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 350

Trp Ala Ser Thr Arg Glu Ser
1               5

<210> SEQ ID NO 351
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 351

Lys Gln Ser Tyr Asn Leu Leu Thr
1               5

<210> SEQ ID NO 352
<211> LENGTH: 10
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 352

Ser Ala Ser Ser Ser Val Ser Tyr Met His
1               5                   10

<210> SEQ ID NO 353
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 353

Asp Thr Ser Lys Leu Ala Ser
1               5

<210> SEQ ID NO 354
<211> LENGTH: 9
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 354

Gln Gln Trp Ser Ser Asn Pro Phe Thr
1               5

<210> SEQ ID NO 355
```

```
<211> LENGTH: 10
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 355

Ser Ala Ser Ser Ser Val Ser Tyr Met His
1               5                   10

<210> SEQ ID NO 356
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 356

Gly Thr Ser Asn Leu Ala Ser
1               5

<210> SEQ ID NO 357
<211> LENGTH: 9
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 357

Gln Gln Trp Ser Ser Asn Pro Pro Thr
1               5

<210> SEQ ID NO 358
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 358

Lys Ser Ser Gln Ser Leu Leu His Ser Arg Thr Arg Lys Asn Tyr Leu
1               5                   10                  15

Ala

<210> SEQ ID NO 359
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 359

Trp Ala Ser Thr Arg Glu Ser
1               5

<210> SEQ ID NO 360
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence
```

```
<400> SEQUENCE: 360

Lys Gln Ser Tyr Asn Leu Leu Thr
1               5

<210> SEQ ID NO 361
<211> LENGTH: 18
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 361

Asp Lys Ser Ser Gln Ser Leu Leu Asn Ser Arg Thr Arg Lys Asn Tyr
1               5                   10                  15

Leu Ala

<210> SEQ ID NO 362
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 362

Asp Trp Ala Ser Thr Arg Glu Ser
1               5

<210> SEQ ID NO 363
<211> LENGTH: 9
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 363

Asp Lys Gln Ser Tyr Asn Leu Leu Ser
1               5

<210> SEQ ID NO 364
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 364

Thr Phe Thr Asp Tyr Ser Ile His
1               5

<210> SEQ ID NO 365
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 365

Trp Ile Lys Thr Glu Thr Gly Glu Pro Thr Tyr Ala Asp Asp Phe Lys
1               5                   10                  15

Gly
```

-continued

<210> SEQ ID NO 366
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 366

Tyr Tyr Tyr Gly Arg Asp Ser
1               5

<210> SEQ ID NO 367
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 367

Thr Phe Thr Asp Tyr Ser Ile His
1               5

<210> SEQ ID NO 368
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 368

Trp Ile Lys Thr Glu Thr Gly Glu Pro Thr Tyr Ala Asp Asp Phe Asn
1               5                   10                  15

Gly

<210> SEQ ID NO 369
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 369

Tyr Tyr Tyr Gly Arg Asp Ser
1               5

<210> SEQ ID NO 370
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 370

Thr Phe Thr Asp Tyr Ser Met His
1               5

<210> SEQ ID NO 371
<211> LENGTH: 17
<212> TYPE: PRT
<213> ORGANISM: Unknown
<220> FEATURE:
<223> OTHER INFORMATION: Human (Homo sapiens), chimeric or humanized antibody peptide sequence

<400> SEQUENCE: 371

Arg Ile Asn Thr Glu Thr Gly Glu Pro Thr Phe Ala Asp Asp Phe Arg
1               5                   10                  15

Gly

<210> SEQ ID NO 372
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 372

Tyr Tyr Tyr Gly Arg Asp Ser
1               5

<210> SEQ ID NO 373
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 373

Lys Ser Ser Gln Ser Leu Leu Asn Ser Arg Thr Arg Lys Asn Tyr Leu
1               5                   10                  15

Ala

<210> SEQ ID NO 374
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 374

Trp Ala Ser Thr Arg Glu Ser
1               5

<210> SEQ ID NO 375
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 375

Lys Gln Ser Tyr Asn Leu Leu Thr
1               5

<210> SEQ ID NO 376
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 376

Lys Ser Ser Gln Ser Leu Leu His Ser Arg Thr Arg Lys Asn Tyr Leu

```
1               5                   10                  15

Ala
```

<210> SEQ ID NO 377
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 377

```
Trp Ala Ser Thr Arg Glu Ser
1               5
```

<210> SEQ ID NO 378
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 378

```
Lys Gln Ser Tyr Asn Leu Leu Thr
1               5
```

<210> SEQ ID NO 379
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 379

```
Thr Phe Thr Asp Tyr Ser Met His
1               5
```

<210> SEQ ID NO 380
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 380

```
Arg Ile Asn Thr Glu Thr Gly Glu Pro Thr Phe Ala Asp Asp Phe Arg
1               5                   10                  15

Gly
```

<210> SEQ ID NO 381
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 381

```
Tyr Tyr Tyr Gly Arg Asp Ser
1               5
```

<210> SEQ ID NO 382
<211> LENGTH: 17

```
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 382

Lys Ser Ser Gln Ser Leu Leu Asn Ser Arg Thr Arg Lys Asn Tyr Leu
1               5                   10                  15

Ala

<210> SEQ ID NO 383
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 383

Trp Ala Ser Thr Arg Glu Ser
1               5

<210> SEQ ID NO 384
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 384

Lys Gln Ser Tyr Asn Leu Leu Thr
1               5

<210> SEQ ID NO 385
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (5)..(5)
<223> OTHER INFORMATION: Xaa is Leu or Met

<400> SEQUENCE: 385

Glx Ile Gln Leu Xaa Glx Ser Gly Pro Glu Leu Lys Lys Pro Gly Glu
1               5                   10                  15

Thr Val Lys Ile Ser Cys Lys Ala Ser Gly Tyr
            20                  25

<210> SEQ ID NO 386
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (13)..(13)
<223> OTHER INFORMATION: Xaa is Val or Met

<400> SEQUENCE: 386

Trp Val Lys Gln Ala Pro Gly Lys Gly Leu Lys Trp Xaa Ala
1               5                   10
```

```
<210> SEQ ID NO 387
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (4)..(4)
<223> OTHER INFORMATION: Xaa is Val or Phe

<400> SEQUENCE: 387

Arg Phe Ala Xaa Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Ile
            20                  25                  30

<210> SEQ ID NO 388
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (11)..(11)
<223> OTHER INFORMATION: Xaa is Lys or Arg

<400> SEQUENCE: 388

Trp Tyr Gln Gln Lys Pro Gly Gln Ser Pro Xaa Leu Leu Ile Tyr
1               5                   10                  15

<210> SEQ ID NO 389
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (1)..(1)
<223> OTHER INFORMATION: Xaa is Asp or Glu
<220> FEATURE:
<221> NAME/KEY: MISC_FEATURE
<222> LOCATION: (5)..(5)
<223> OTHER INFORMATION: Xaa is Thr or Ser
<220> FEATURE:
<221> NAME/KEY: MISC_FEATURE
<222> LOCATION: (14)..(14)
<223> OTHER INFORMATION: Xaa is Pro or Ser
<220> FEATURE:
<221> NAME/KEY: MISC_FEATURE
<222> LOCATION: (18)..(18)
<223> OTHER INFORMATION: Xaa is Lys or Asn
<220> FEATURE:
<221> NAME/KEY: MISC_FEATURE
<222> LOCATION: (21)..(21)
<223> OTHER INFORMATION: Xaa is Met or Val

<400> SEQUENCE: 389

Xaa Ile Val Met Xaa Gln Ser Pro Ser Ser Leu Ala Val Xaa Ala Gly
1               5                   10                  15

Glu Xaa Val Thr Xaa Ser Cys
            20

<210> SEQ ID NO 390
```

<211> LENGTH: 15
<212> TYPE: PRT
<213> ORGANISM: Unknown
<220> FEATURE:
<223> OTHER INFORMATION: Human (Homo sapiens), chimeric or humanized antibody peptide sequence
<220> FEATURE:
<221> NAME/KEY: MISC_FEATURE
<222> LOCATION: (11)..(11)
<223> OTHER INFORMATION: Xaa is Lys or Arg

<400> SEQUENCE: 390

Trp Tyr Gln Gln Lys Pro Gly Gln Ser Pro Xaa Leu Leu Ile Tyr
1               5                   10                  15

<210> SEQ ID NO 391
<211> LENGTH: 32
<212> TYPE: PRT
<213> ORGANISM: Unknown
<220> FEATURE:
<223> OTHER INFORMATION: Human (Homo sapiens), chimeric or humanized antibody peptide sequence
<220> FEATURE:
<221> NAME/KEY: MISC_FEATURE
<222> LOCATION: (31)..(31)
<223> OTHER INFORMATION: Xaa is Tyr or Phe

<400> SEQUENCE: 391

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Xaa Cys
            20                  25                  30

<210> SEQ ID NO 392
<211> LENGTH: 10
<212> TYPE: PRT
<213> ORGANISM: Unknown
<220> FEATURE:
<223> OTHER INFORMATION: Human (Homo sapiens), chimeric or humanized antibody peptide sequence
<220> FEATURE:
<221> NAME/KEY: MISC_FEATURE
<222> LOCATION: (6)..(6)
<223> OTHER INFORMATION: Xaa is Lys or Arg
<220> FEATURE:
<221> NAME/KEY: MISC_FEATURE
<222> LOCATION: (9)..(9)
<223> OTHER INFORMATION: Xaa is Leu or Ile

<400> SEQUENCE: 392

Phe Gly Ala Gly Thr Xaa Leu Glu Xaa Lys
1               5                   10

<210> SEQ ID NO 393
<211> LENGTH: 1018
<212> TYPE: PRT
<213> ORGANISM: Homo sapiens

<400> SEQUENCE: 393

Phe Asn Leu Asp Val Asp Ser Pro Ala Glu Tyr Ser Gly Pro Glu Gly
1               5                   10                  15

Ser Tyr Phe Gly Phe Ala Val Asp Phe Phe Val Pro Ser Ala Ser Ser
            20                  25                  30

Arg Met Phe Leu Leu Val Gly Ala Pro Lys Ala Asn Thr Thr Gln Pro
        35                  40                  45

Gly Ile Val Glu Gly Gly Gln Val Leu Lys Cys Asp Trp Ser Ser Thr
    50                  55                  60

-continued

```
Arg Arg Cys Gln Pro Ile Glu Phe Asp Ala Thr Gly Asn Arg Asp Tyr
 65                  70                  75                  80

Ala Lys Asp Asp Pro Leu Glu Phe Lys Ser His Gln Trp Phe Gly Ala
                 85                  90                  95

Ser Val Arg Ser Lys Gln Asp Lys Ile Leu Ala Cys Ala Pro Leu Tyr
            100                 105                 110

His Trp Arg Thr Glu Met Lys Gln Glu Arg Glu Pro Val Gly Thr Cys
        115                 120                 125

Phe Leu Gln Asp Gly Thr Lys Thr Val Glu Tyr Ala Pro Cys Arg Ser
    130                 135                 140

Gln Asp Ile Asp Ala Asp Gly Gln Gly Phe Cys Gln Gly Gly Phe Ser
145                 150                 155                 160

Ile Asp Phe Thr Lys Ala Asp Arg Val Leu Leu Gly Gly Pro Gly Ser
                165                 170                 175

Phe Tyr Trp Gln Gly Gln Leu Ile Ser Asp Gln Val Ala Glu Ile Val
            180                 185                 190

Ser Lys Tyr Asp Pro Asn Val Tyr Ser Ile Lys Tyr Asn Asn Gln Leu
        195                 200                 205

Ala Thr Arg Thr Ala Gln Ala Ile Phe Asp Asp Ser Tyr Leu Gly Tyr
    210                 215                 220

Ser Val Ala Val Gly Asp Phe Asn Gly Asp Gly Ile Asp Asp Phe Val
225                 230                 235                 240

Ser Gly Val Pro Arg Ala Ala Arg Thr Leu Gly Met Val Tyr Ile Tyr
                245                 250                 255

Asp Gly Lys Asn Met Ser Ser Leu Tyr Asn Phe Thr Gly Glu Gln Met
            260                 265                 270

Ala Ala Tyr Phe Gly Phe Ser Val Ala Ala Thr Asp Ile Asn Gly Asp
        275                 280                 285

Asp Tyr Ala Asp Val Phe Ile Gly Ala Pro Leu Phe Met Asp Arg Gly
    290                 295                 300

Ser Asp Gly Lys Leu Gln Glu Val Gly Gln Val Ser Val Ser Leu Gln
305                 310                 315                 320

Arg Ala Ser Gly Asp Phe Gln Thr Thr Lys Leu Asn Gly Phe Glu Val
                325                 330                 335

Phe Ala Arg Phe Gly Ser Ala Ile Ala Pro Leu Gly Asp Leu Asp Gln
            340                 345                 350

Asp Gly Phe Asn Asp Ile Ala Ile Ala Ala Pro Tyr Gly Gly Glu Asp
        355                 360                 365

Lys Lys Gly Ile Val Tyr Ile Phe Asn Gly Arg Ser Thr Gly Leu Asn
    370                 375                 380

Ala Val Pro Ser Gln Ile Leu Glu Gly Gln Trp Ala Ala Arg Ser Met
385                 390                 395                 400

Pro Pro Ser Phe Gly Tyr Ser Met Lys Gly Ala Thr Asp Ile Asp Lys
                405                 410                 415

Asn Gly Tyr Pro Asp Leu Ile Val Gly Ala Phe Gly Val Asp Arg Ala
            420                 425                 430

Ile Leu Tyr Arg Ala Arg Pro Val Ile Thr Val Asn Ala Gly Leu Glu
    435                 440                 445

Val Tyr Pro Ser Ile Leu Asn Gln Asp Asn Lys Thr Cys Ser Leu Pro
450                 455                 460

Gly Thr Ala Leu Lys Val Ser Cys Phe Asn Val Arg Phe Cys Leu Lys
465                 470                 475                 480

Ala Asp Gly Lys Gly Val Leu Pro Arg Lys Leu Asn Phe Gln Val Glu
```

-continued

```
                485                 490                 495
Leu Leu Leu Asp Lys Leu Lys Gln Lys Gly Ala Ile Arg Arg Ala Leu
                500                 505                 510
Phe Leu Tyr Ser Arg Ser Pro Ser His Ser Lys Asn Met Thr Ile Ser
                515                 520                 525
Arg Gly Gly Leu Met Gln Cys Glu Glu Leu Ile Ala Tyr Leu Arg Asp
                530                 535                 540
Glu Ser Glu Phe Arg Asp Lys Leu Thr Pro Ile Thr Ile Phe Met Glu
545                 550                 555                 560
Tyr Arg Leu Asp Tyr Arg Thr Ala Ala Asp Thr Thr Gly Leu Gln Pro
                565                 570                 575
Ile Leu Asn Gln Phe Thr Pro Ala Asn Ile Ser Arg Gln Ala His Ile
                580                 585                 590
Leu Leu Asp Cys Gly Glu Asp Asn Val Cys Lys Pro Lys Leu Glu Val
                595                 600                 605
Ser Val Asp Ser Asp Gln Lys Lys Ile Tyr Ile Gly Asp Asp Asn Pro
                610                 615                 620
Leu Thr Leu Ile Val Lys Ala Gln Asn Gln Gly Glu Gly Ala Tyr Glu
625                 630                 635                 640
Ala Glu Leu Ile Val Ser Ile Pro Leu Gln Ala Asp Phe Ile Gly Val
                        645                 650                 655
Val Arg Asn Asn Glu Ala Leu Ala Arg Leu Ser Cys Ala Phe Lys Thr
                660                 665                 670
Glu Asn Gln Thr Arg Gln Val Val Cys Asp Leu Gly Asn Pro Met Lys
                675                 680                 685
Ala Gly Thr Gln Leu Leu Ala Gly Leu Arg Phe Ser Val His Gln Gln
                690                 695                 700
Ser Glu Met Asp Thr Ser Val Lys Phe Asp Leu Gln Ile Gln Ser Ser
705                 710                 715                 720
Asn Leu Phe Asp Lys Val Ser Pro Val Val Ser His Lys Val Asp Leu
                        725                 730                 735
Ala Val Leu Ala Ala Val Glu Ile Arg Gly Val Ser Ser Pro Asp His
                740                 745                 750
Val Phe Leu Pro Ile Pro Asn Trp Glu His Lys Glu Asn Pro Glu Thr
                755                 760                 765
Glu Glu Asp Val Gly Pro Val Val Gln His Ile Tyr Glu Leu Arg Asn
                770                 775                 780
Asn Gly Pro Ser Ser Phe Ser Lys Ala Met Leu His Leu Gln Trp Pro
785                 790                 795                 800
Tyr Lys Tyr Asn Asn Asn Thr Leu Leu Tyr Ile Leu His Tyr Asp Ile
                        805                 810                 815
Asp Gly Pro Met Asn Cys Thr Ser Asp Met Glu Ile Asn Pro Leu Arg
                820                 825                 830
Ile Lys Ile Ser Ser Leu Gln Thr Thr Glu Lys Asn Asp Thr Val Ala
                835                 840                 845
Gly Gln Gly Glu Arg Asp His Leu Ile Thr Lys Arg Asp Leu Ala Leu
                850                 855                 860
Ser Glu Gly Asp Ile His Thr Leu Gly Cys Gly Val Ala Gln Cys Leu
865                 870                 875                 880
Lys Ile Val Cys Gln Val Gly Arg Leu Asp Arg Gly Lys Ser Ala Ile
                        885                 890                 895
Leu Tyr Val Lys Ser Leu Leu Trp Thr Glu Thr Phe Met Asn Lys Glu
                900                 905                 910
```

Asn Gln Asn His Ser Tyr Ser Leu Lys Ser Ser Ala Ser Phe Asn Val
            915                 920                 925

Ile Glu Phe Pro Tyr Lys Asn Leu Pro Ile Glu Asp Ile Thr Asn Ser
    930                 935                 940

Thr Leu Val Thr Thr Asn Val Thr Trp Gly Ile Gln Pro Ala Pro Met
945                 950                 955                 960

Pro Val Pro Val Trp Val Ile Ile Leu Ala Val Leu Ala Gly Leu Leu
                965                 970                 975

Leu Leu Ala Val Leu Val Phe Val Met Tyr Arg Met Gly Phe Phe Lys
            980                 985                 990

Arg Val Arg Pro Pro Gln Glu Glu  Gln Glu Arg Glu Gln  Leu Gln Pro
            995                 1000                1005

His Glu  Asn Gly Glu Gly Asn  Ser Glu Thr
    1010                 1015

<210> SEQ ID NO 394
<211> LENGTH: 727
<212> TYPE: PRT
<213> ORGANISM: Homo sapiens

<400> SEQUENCE: 394

Glu Asp Asn Arg Cys Ala Ser Ser Asn Ala Ser Cys Ala Arg Cys
1               5                   10                  15

Leu Ala Leu Gly Pro Glu Cys Gly Trp Cys Val Gln Glu Asp Phe Ile
                20                  25                  30

Ser Gly Gly Ser Arg Ser Glu Arg Cys Asp Ile Val Ser Asn Leu Ile
            35                  40                  45

Ser Lys Gly Cys Ser Val Asp Ser Ile Glu Tyr Pro Ser Val His Val
    50                  55                  60

Ile Ile Pro Thr Glu Asn Glu Ile Asn Thr Gln Val Thr Pro Gly Glu
65                  70                  75                  80

Val Ser Ile Gln Leu Arg Pro Gly Ala Glu Ala Asn Phe Met Leu Lys
                85                  90                  95

Val His Pro Leu Lys Lys Tyr Pro Val Asp Leu Tyr Tyr Leu Val Asp
                100                 105                 110

Val Ser Ala Ser Met His Asn Asn Ile Glu Lys Leu Asn Ser Val Gly
            115                 120                 125

Asn Asp Leu Ser Arg Lys Met Ala Phe Phe Ser Arg Asp Phe Arg Leu
    130                 135                 140

Gly Phe Gly Ser Tyr Val Asp Lys Thr Val Ser Pro Tyr Ile Ser Ile
145                 150                 155                 160

His Pro Glu Arg Ile His Asn Gln Cys Ser Asp Tyr Asn Leu Asp Cys
                165                 170                 175

Met Pro Pro His Gly Tyr Ile His Val Leu Ser Leu Thr Glu Asn Ile
                180                 185                 190

Thr Glu Phe Glu Lys Ala Val His Arg Gln Lys Ile Ser Gly Asn Ile
            195                 200                 205

Asp Thr Pro Glu Gly Gly Phe Asp Ala Met Leu Gln Ala Ala Val Cys
    210                 215                 220

Glu Ser His Ile Gly Trp Arg Lys Glu Ala Lys Arg Leu Leu Leu Val
225                 230                 235                 240

Met Thr Asp Gln Thr Ser His Leu Ala Leu Asp Ser Lys Leu Ala Gly
                245                 250                 255

Ile Val Val Pro Asn Asp Gly Asn Cys His Leu Lys Asn Asn Val Tyr

```
            260                 265                 270
Val Lys Ser Thr Thr Met Glu His Pro Ser Leu Gly Gln Leu Ser Glu
            275                 280                 285

Lys Leu Ile Asp Asn Asn Ile Asn Val Ile Phe Ala Val Gln Gly Lys
            290                 295                 300

Gln Phe His Trp Tyr Lys Asp Leu Leu Pro Leu Leu Pro Gly Thr Ile
305                 310                 315                 320

Ala Gly Glu Ile Glu Ser Lys Ala Ala Asn Leu Asn Asn Leu Val Val
                    325                 330                 335

Glu Ala Tyr Gln Lys Leu Ile Ser Glu Val Lys Val Gln Val Glu Asn
            340                 345                 350

Gln Val Gln Gly Ile Tyr Phe Asn Ile Thr Ala Ile Cys Pro Asp Gly
            355                 360                 365

Ser Arg Lys Pro Gly Met Glu Gly Cys Arg Asn Val Thr Ser Asn Asp
            370                 375                 380

Glu Val Leu Phe Asn Val Thr Val Thr Met Lys Lys Cys Asp Val Thr
385                 390                 395                 400

Gly Gly Lys Asn Tyr Ala Ile Ile Lys Pro Ile Gly Phe Asn Glu Thr
                    405                 410                 415

Ala Lys Ile His Ile His Arg Asn Cys Ser Gln Cys Glu Asp Asn
            420                 425                 430

Arg Gly Pro Lys Gly Lys Cys Val Asp Glu Thr Phe Leu Asp Ser Lys
            435                 440                 445

Cys Phe Gln Cys Asp Glu Asn Lys Cys His Phe Asp Glu Asp Gln Phe
450                 455                 460

Ser Ser Glu Ser Cys Lys Ser His Lys Asp Gln Pro Val Cys Ser Gly
465                 470                 475                 480

Arg Gly Val Cys Val Cys Gly Lys Cys Ser Cys His Lys Ile Lys Leu
                    485                 490                 495

Gly Lys Val Tyr Gly Lys Tyr Cys Glu Lys Asp Asp Phe Ser Cys Pro
            500                 505                 510

Tyr His His Gly Asn Leu Cys Ala Gly His Gly Glu Cys Glu Ala Gly
            515                 520                 525

Arg Cys Gln Cys Phe Ser Gly Trp Glu Gly Asp Arg Cys Gln Cys Pro
            530                 535                 540

Ser Ala Ala Gln His Cys Val Asn Ser Lys Gly Gln Val Cys Ser
545                 550                 555                 560

Gly Arg Gly Thr Cys Val Cys Gly Arg Cys Glu Cys Thr Asp Pro Arg
                    565                 570                 575

Ser Ile Gly Arg Phe Cys Glu His Cys Pro Thr Cys Tyr Thr Ala Cys
            580                 585                 590

Lys Glu Asn Trp Asn Cys Met Gln Cys Leu His Pro His Asn Leu Ser
            595                 600                 605

Gln Ala Ile Leu Asp Gln Cys Lys Thr Ser Cys Ala Leu Met Glu Gln
            610                 615                 620

Gln His Tyr Val Asp Gln Thr Ser Glu Cys Phe Ser Ser Pro Ser Tyr
625                 630                 635                 640

Leu Arg Ile Phe Phe Ile Ile Phe Ile Val Thr Phe Leu Ile Gly Leu
                    645                 650                 655

Leu Lys Val Leu Ile Ile Arg Gln Val Ile Leu Gln Trp Asn Ser Asn
            660                 665                 670

Lys Ile Lys Ser Ser Ser Asp Tyr Arg Val Ser Ala Ser Lys Lys Asp
            675                 680                 685
```

Lys Leu Ile Leu Gln Ser Val Cys Thr Arg Ala Val Thr Tyr Arg Arg
    690                 695                 700

Glu Lys Pro Glu Glu Ile Lys Met Asp Ile Ser Lys Leu Asn Ala His
705                 710                 715                 720

Glu Thr Phe Arg Cys Asn Phe
                725

<210> SEQ ID NO 395
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 395

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Val
        35                  40                  45

Ala Arg Ile Asn Thr Glu Thr Gly Glu Pro Thr Phe Ala Asp Asp Phe
    50                  55                  60

Arg Gly Arg Phe Thr Val Thr Leu Asp Thr Ser Thr Ser Thr Ala Tyr
65                  70                  75                  80

Leu Glu Ile Arg Ser Leu Arg Ser Asp Asp Thr Ala Val Tyr Phe Cys
                85                  90                  95

Ala Ile Phe Tyr Tyr Gly Arg Asp Ser Trp Gly Gln Gly Thr Thr Leu
            100                 105                 110

Thr Val Ser Ser
        115

<210> SEQ ID NO 396
<211> LENGTH: 30
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 396

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr
            20                  25                  30

<210> SEQ ID NO 397
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 397

Asp Tyr Ser Met His
1               5

<210> SEQ ID NO 398
<211> LENGTH: 14

```
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 398

Trp Val Arg Gln Ala Pro Gly Gln Gly Leu Glu Trp Val Ala
1               5                   10

<210> SEQ ID NO 399
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 399

Arg Ile Asn Thr Glu Thr Gly Glu Pro Thr Phe Ala Asp Asp Phe Arg
1               5                   10                  15

Gly

<210> SEQ ID NO 400
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 400

Arg Phe Thr Val Thr Leu Asp Thr Ser Thr Ser Thr Ala Tyr Leu Glu
1               5                   10                  15

Ile Arg Ser Leu Arg Ser Asp Asp Thr Ala Val Tyr Phe Cys Ala Ile
            20                  25                  30

<210> SEQ ID NO 401
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 401

Phe Tyr Tyr Gly Arg Asp Ser
1               5

<210> SEQ ID NO 402
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 402

Trp Gly Gln Gly Thr Thr Leu Thr Val Ser Ser
1               5                   10

<210> SEQ ID NO 403
<211> LENGTH: 116
<212> TYPE: PRT
<213> ORGANISM: Unknown
<220> FEATURE:
<223> OTHER INFORMATION: Human (Homo sapiens), chimeric or humanized
``` antibody peptide sequence

<400> SEQUENCE: 403

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
                20                  25                  30

Ser Met His Trp Val Arg Gln Ala Pro Gly Gln Gly Leu Glu Trp Val
            35                  40                  45

Ala Arg Ile Asn Thr Glu Thr Gly Glu Pro Thr Phe Ala Asp Asp Phe
        50                  55                  60

Arg Gly Arg Phe Thr Val Thr Leu Asp Thr Ser Thr Ser Thr Ala Tyr
65                  70                  75                  80

Leu Glu Ile Arg Ser Leu Arg Ser Asp Asp Thr Ala Val Tyr Phe Cys
                85                  90                  95

Ala Ile Phe Tyr Tyr Gly Arg Asp Ser Trp Gly Gln Gly Thr Thr Leu
            100                 105                 110

Thr Val Ser Ser
        115

<210> SEQ ID NO 404
<211> LENGTH: 30
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 404

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr
                20                  25                  30

<210> SEQ ID NO 405
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 405

Asp Tyr Ser Met His
1               5

<210> SEQ ID NO 406
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 406

Trp Val Arg Gln Ala Pro Gly Gln Gly Leu Glu Trp Val Ala
1               5                   10

<210> SEQ ID NO 407
<211> LENGTH: 17
<212> TYPE: PRT
<213> ORGANISM: Unknown
<220> FEATURE:

```
<223> OTHER INFORMATION: Human (Homo sapiens), chimeric or humanized
      antibody peptide sequence

<400> SEQUENCE: 407

Arg Ile Asn Thr Glu Thr Gly Glu Pro Thr Phe Ala Asp Asp Phe Arg
1               5                   10                  15

Gly

<210> SEQ ID NO 408
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 408

Arg Phe Thr Val Thr Leu Asp Thr Ser Thr Ser Thr Ala Tyr Leu Glu
1               5                   10                  15

Ile Arg Ser Leu Arg Ser Asp Asp Thr Ala Val Tyr Phe Cys Ala Ile
                20                  25                  30

<210> SEQ ID NO 409
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 409

Phe Tyr Tyr Gly Arg Asp Ser
1               5

<210> SEQ ID NO 410
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 410

Trp Gly Gln Gly Thr Thr Leu Thr Val Ser Ser
1               5                   10

<210> SEQ ID NO 411
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 411

Gln Ile Gln Leu Val Gln Ser Gly Ala Lys Val Lys Lys Pro Gly Ala
1               5                   10                  15

Ser Val Lys Ile Ser Cys Lys Ala Ser Gly Tyr Thr Phe Thr Asp Tyr
                20                  25                  30

Ser Met His Trp Val Arg Gln Ala Pro Gly Gln Gly Leu Glu Trp Val
            35                  40                  45

Ala Arg Ile Asn Thr Glu Thr Gly Glu Pro Thr Phe Ala Asp Asp Phe
        50                  55                  60

Arg Gly Arg Phe Ser Val Thr Leu Asp Thr Ser Thr Ser Thr Ala Tyr
```

```
                65                  70                  75                  80
Leu Glu Ile Thr Ser Leu Arg Ser Asp Asp Thr Ala Val Tyr Phe Cys
                    85                  90                  95

Ala Ile Phe Tyr Tyr Gly Arg Asp Thr Trp Gly Gln Gly Thr Ala Leu
                100                 105                 110

Thr Val Ser Ser
        115

<210> SEQ ID NO 412
<211> LENGTH: 30
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 412

Gln Ile Gln Leu Val Gln Ser Gly Ala Lys Val Lys Lys Pro Gly Ala
1               5                   10                  15

Ser Val Lys Ile Ser Cys Lys Ala Ser Gly Tyr Thr Phe Thr
            20                  25                  30

<210> SEQ ID NO 413
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 413

Asp Tyr Ser Met His
1               5

<210> SEQ ID NO 414
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 414

Trp Val Arg Gln Ala Pro Gly Gln Gly Leu Glu Trp Val Ala
1               5                   10

<210> SEQ ID NO 415
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 415

Arg Ile Asn Thr Glu Thr Gly Glu Pro Thr Phe Ala Asp Asp Phe Arg
1               5                   10                  15

Gly

<210> SEQ ID NO 416
<211> LENGTH: 32
<212> TYPE: PRT
<213> ORGANISM: Unknown
<220> FEATURE:
<223> OTHER INFORMATION: Human (Homo sapiens), chimeric or humanized
``` antibody peptide sequence

<400> SEQUENCE: 416

Arg Phe Ser Val Thr Leu Asp Thr Ser Thr Ser Ala Tyr Leu Glu
1               5                   10                  15

Ile Thr Ser Leu Arg Ser Asp Asp Thr Ala Val Tyr Phe Cys Ala Ile
            20                  25                  30

<210> SEQ ID NO 417
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 417

Phe Tyr Tyr Gly Arg Asp Thr
1               5

<210> SEQ ID NO 418
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 418

Trp Gly Gln Gly Thr Ala Leu Thr Val Ser Ser
1               5                   10

<210> SEQ ID NO 419
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 419

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Val
        35                  40                  45

Ala Arg Ile Asn Thr Glu Thr Gly Glu Pro Thr Phe Ala Asp Asp Phe
    50                  55                  60

Arg Gly Arg Phe Thr Val Thr Leu Asp Thr Ser Thr Ser Thr Ala Tyr
65                  70                  75                  80

Leu Glu Ile Arg Ser Leu Arg Ser Asp Asp Thr Ala Val Tyr Phe Cys
                85                  90                  95

Ala Ile Phe Tyr Tyr Gly Arg Asp Thr Trp Gly Gln Gly Thr Thr Leu
            100                 105                 110

Thr Val Ser Ser
        115

<210> SEQ ID NO 420
<211> LENGTH: 30
<212> TYPE: PRT
<213> ORGANISM: Unknown
<220> FEATURE:

<223> OTHER INFORMATION: Human (Homo sapiens), chimeric or humanized
     antibody peptide sequence

<400> SEQUENCE: 420

Gln Ile Gln Leu Val Gln Ser Gly Ala Glu Val Lys Pro Gly Ala
1               5                   10                  15

Ser Val Lys Ile Ser Cys Lys Ala Ser Gly Tyr Thr Phe Thr
            20                  25                  30

<210> SEQ ID NO 421
<211> LENGTH: 5
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 421

Asp Tyr Ser Met His
1               5

<210> SEQ ID NO 422
<211> LENGTH: 14
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 422

Trp Val Arg Gln Ala Pro Gly Gln Gly Leu Glu Trp Val Ala
1               5                   10

<210> SEQ ID NO 423
<211> LENGTH: 17
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 423

Arg Ile Asn Thr Glu Thr Gly Glu Pro Thr Phe Ala Asp Asp Phe Arg
1               5                   10                  15

Gly

<210> SEQ ID NO 424
<211> LENGTH: 32
<212> TYPE: PRT
<213> ORGANISM: Unknown
<220> FEATURE:
<223> OTHER INFORMATION: Human (Homo sapiens), chimeric or humanized
     antibody peptide sequence

<400> SEQUENCE: 424

Arg Phe Thr Val Thr Leu Asp Thr Ser Thr Ser Thr Ala Tyr Leu Glu
1               5                   10                  15

Ile Arg Ser Leu Arg Ser Asp Asp Thr Ala Val Tyr Phe Cys Ala Ile
            20                  25                  30

<210> SEQ ID NO 425
<211> LENGTH: 7
<212> TYPE: PRT
<213> ORGANISM: Unknown
<220> FEATURE:
<223> OTHER INFORMATION: Human (Homo sapiens), chimeric or humanized antibody peptide sequence

<400> SEQUENCE: 425

Phe Tyr Tyr Gly Arg Asp Thr
1               5

<210> SEQ ID NO 426
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 426

Trp Gly Gln Gly Thr Thr Leu Thr Val Ser Ser
1               5                   10

<210> SEQ ID NO 427
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 427

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Val
        35                  40                  45

Ala Arg Ile Asn Thr Glu Thr Gly Glu Pro Thr Phe Ala Asp Asp Phe
    50                  55                  60

Arg Gly Arg Phe Thr Val Thr Leu Asp Thr Ser Thr Ser Thr Ala Tyr
65                  70                  75                  80

Leu Glu Ile Arg Ser Leu Arg Ser Asp Asp Thr Ala Val Tyr Phe Cys
                85                  90                  95

Ala Ile Phe Tyr Tyr Gly Arg Asp Thr Trp Gly Gln Gly Thr Thr Leu
            100                 105                 110

Thr Val Ser Ser
        115

<210> SEQ ID NO 428
<211> LENGTH: 30
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 428

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr
            20                  25                  30

<210> SEQ ID NO 429
<211> LENGTH: 5
<212> TYPE: PRT
<213> ORGANISM: Unknown
<220> FEATURE:

<223> OTHER INFORMATION: Human (Homo sapiens), chimeric or humanized
      antibody peptide sequence

<400> SEQUENCE: 429

Asp Tyr Ser Met His
1               5

<210> SEQ ID NO 430
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 430

Trp Val Arg Gln Ala Pro Gly Gln Gly Leu Glu Trp Val Ala
1               5                   10

<210> SEQ ID NO 431
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 431

Arg Ile Asn Thr Glu Thr Gly Glu Pro Thr Phe Ala Asp Asp Phe Arg
1               5                   10                  15

Gly

<210> SEQ ID NO 432
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 432

Arg Phe Thr Val Thr Leu Asp Thr Ser Thr Ser Thr Ala Tyr Leu Glu
1               5                   10                  15

Ile Arg Ser Leu Arg Ser Asp Asp Thr Ala Val Tyr Phe Cys Ala Ile
                20                  25                  30

<210> SEQ ID NO 433
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 433

Phe Tyr Tyr Gly Arg Asp Thr
1               5

<210> SEQ ID NO 434
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 434

```
Trp Gly Gln Gly Thr Thr Leu Thr Val Ser Ser
1               5                   10
```

<210> SEQ ID NO 435
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 435

```
Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Val
        35                  40                  45

Ala Arg Ile Asn Thr Glu Thr Gly Glu Pro Thr Phe Ala Asp Asp Phe
    50                  55                  60

Arg Gly Arg Phe Ala Val Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ile Phe Tyr Tyr Gly Arg Asp Ser Trp Gly Gln Gly Thr Thr Leu
            100                 105                 110

Thr Val Ser Ser
        115
```

<210> SEQ ID NO 436
<211> LENGTH: 30
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 436

```
Gln Ile Gln Leu Leu Gln Ser Gly Pro Glu Leu Lys Lys Pro Gly Glu
1               5                   10                  15

Thr Val Lys Ile Ser Cys Lys Ala Ser Gly Tyr Thr Phe Thr
            20                  25                  30
```

<210> SEQ ID NO 437
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 437

```
Asp Tyr Ser Met His
1               5
```

<210> SEQ ID NO 438
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 438

Trp Val Lys Gln Ala Pro Gly Lys Gly Leu Lys Trp Val Ala
1               5                   10

<210> SEQ ID NO 439
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 439

Arg Ile Asn Thr Glu Thr Gly Glu Pro Thr Phe Ala Asp Asp Phe Arg
1               5                   10                  15

Gly

<210> SEQ ID NO 440
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 440

Arg Phe Ala Val Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Ile
                20                  25                  30

<210> SEQ ID NO 441
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 441

Phe Tyr Tyr Gly Arg Asp Ser
1               5

<210> SEQ ID NO 442
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 442

Trp Gly Gln Gly Thr Thr Leu Thr Val Ser Ser
1               5                   10

<210> SEQ ID NO 443
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 443

Gln Ile Gln Leu Val Gln Ser Gly Ala Glu Val Lys Lys Pro Gly Ala
1               5                   10                  15

```
Ser Val Lys Ile Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Val
            35                  40                  45

Ala Arg Ile Asn Thr Glu Thr Gly Glu Pro Thr Phe Ala Asp Asp Phe
50                  55                  60

Arg Gly Arg Phe Thr Val Thr Leu Asp Thr Ser Thr Ser Thr Ala Tyr
65                  70                  75                  80

Leu Glu Ile Arg Ser Leu Arg Ser Asp Asp Thr Ala Val Tyr Phe Cys
                85                  90                  95

Ala Ile Phe Tyr Tyr Gly Arg Asp Thr Trp Gly Gln Gly Thr Thr Leu
            100                 105                 110

Thr Val Ser Ser
        115

<210> SEQ ID NO 444
<211> LENGTH: 30
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 444

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr
            20                  25                  30

<210> SEQ ID NO 445
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 445

Asp Tyr Ser Met His
1               5

<210> SEQ ID NO 446
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 446

Trp Val Arg Gln Ala Pro Gly Gln Gly Leu Glu Trp Val Ala
1               5                   10

<210> SEQ ID NO 447
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 447

Arg Ile Asn Thr Glu Thr Gly Glu Pro Thr Phe Ala Asp Asp Phe Arg
```

Gly

<210> SEQ ID NO 448
<211> LENGTH: 32
<212> TYPE: PRT
<213> ORGANISM: Unknown
<220> FEATURE:
<223> OTHER INFORMATION: Human (Homo sapiens), chimeric or humanized
    antibody peptide sequence

<400> SEQUENCE: 448

Arg Phe Thr Val Thr Leu Asp Thr Ser Thr Ser Thr Ala Tyr Leu Glu
1               5                   10                  15

Ile Arg Ser Leu Arg Ser Asp Asp Thr Ala Val Tyr Phe Cys Ala Ile
            20                  25                  30

<210> SEQ ID NO 449
<211> LENGTH: 7
<212> TYPE: PRT
<213> ORGANISM: Unknown
<220> FEATURE:
<223> OTHER INFORMATION: Human (Homo sapiens), chimeric or humanized
    antibody peptide sequence

<400> SEQUENCE: 449

Phe Tyr Tyr Gly Arg Asp Thr
1               5

<210> SEQ ID NO 450
<211> LENGTH: 11
<212> TYPE: PRT
<213> ORGANISM: Unknown
<220> FEATURE:
<223> OTHER INFORMATION: Human (Homo sapiens), chimeric or humanized
    antibody peptide sequence

<400> SEQUENCE: 450

Trp Gly Gln Gly Thr Thr Leu Thr Val Ser Ser
1               5                   10

<210> SEQ ID NO 451
<211> LENGTH: 113
<212> TYPE: PRT
<213> ORGANISM: Unknown
<220> FEATURE:
<223> OTHER INFORMATION: Human (Homo sapiens), chimeric or humanized
    antibody peptide sequence

<400> SEQUENCE: 451

Glu Ile Val Met Thr Gln Ser Pro Ala Thr Leu Ser Val Ser Pro Gly
1               5                   10                  15

Glu Arg Val Thr Met Ser Cys Lys Ser Ser Gln Ser Leu Leu Asn Ser
            20                  25                  30

Arg Thr Arg Lys Asn Tyr Leu Ala Trp Tyr Gln Lys Pro Gly Gln
        35                  40                  45

Ala Pro Arg Leu Leu Ile Tyr Trp Ala Ser Thr Arg Glu Ser Gly Val
    50                  55                  60

Pro Ala Arg Phe Ser Gly Ser Gly Ser Gly Thr Glu Phe Thr Leu Thr
65                  70                  75                  80

Ile Ser Ser Val Gln Ser Glu Asp Phe Ala Val Tyr Tyr Cys Lys Gln
                85                  90                  95

Ser Tyr Asn Leu Leu Ser Phe Gly Gln Gly Thr Val Leu Glu Ile Lys

```
                100               105               110
Arg

<210> SEQ ID NO 452
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 452

Glu Ile Val Met Thr Gln Ser Pro Ala Thr Leu Ser Val Ser Pro Gly
1               5                   10                  15

Glu Arg Val Thr Met Ser Cys
            20

<210> SEQ ID NO 453
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 453

Lys Ser Ser Gln Ser Leu Leu Asn Ser Arg Thr Arg Lys Asn Tyr Leu
1               5                   10                  15

Ala

<210> SEQ ID NO 454
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 454

Trp Tyr Gln Gln Lys Pro Gly Gln Ala Pro Arg Leu Leu Ile Tyr
1               5                   10                  15

<210> SEQ ID NO 455
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 455

Trp Ala Ser Thr Arg Glu Ser
1               5

<210> SEQ ID NO 456
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 456

Gly Val Pro Ala Arg Phe Ser Gly Ser Gly Ser Gly Thr Glu Phe Thr
1               5                   10                  15
```

```
Leu Thr Ile Ser Ser Val Gln Ser Glu Asp Phe Ala Val Tyr Tyr Cys
            20                  25                  30

<210> SEQ ID NO 457
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 457

Lys Gln Ser Tyr Asn Leu Leu Ser
1               5

<210> SEQ ID NO 458
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 458

Phe Gly Gln Gly Thr Val Leu Glu Ile Lys Arg
1               5                   10

<210> SEQ ID NO 459
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 459

Glu Ile Val Met Thr Gln Ser Pro Ala Thr Leu Ser Val Ser Pro Gly
1               5                   10                  15

Glu Ile Val Thr Met Ser Cys Lys Ser Ser Gln Ser Leu Leu Asn Ser
            20                  25                  30

Arg Ser Arg Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ala Arg Phe Ser Gly Ser Gly Ser Gly Thr Glu Phe Thr Leu Thr
65                  70                  75                  80

Ile Ser Ser Val Gln Ser Glu Asp Phe Ala Val Tyr Tyr Cys Lys Gln
                85                  90                  95

Ser Tyr Asn Leu Ile Ser Phe Gly Gln Gly Thr Val Leu Glu Ile Lys
            100                 105                 110

Arg

<210> SEQ ID NO 460
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 460

Glu Ile Val Met Thr Gln Ser Pro Ala Thr Leu Ser Val Ser Pro Gly
1               5                   10                  15
```

Glu Ile Val Thr Met Ser Cys
            20

<210> SEQ ID NO 461
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 461

Lys Ser Ser Gln Ser Leu Leu Asn Ser Arg Ser Arg Lys Asn Tyr Leu
1               5                   10                  15

Ala

<210> SEQ ID NO 462
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 462

Trp Tyr Gln Gln Lys Pro Gly Gln Ala Pro Arg Leu Leu Ile Tyr
1               5                   10                  15

<210> SEQ ID NO 463
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 463

Trp Ala Ser Thr Arg Glu Ser
1               5

<210> SEQ ID NO 464
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 464

Gly Val Pro Ala Arg Phe Ser Gly Ser Gly Ser Gly Thr Glu Phe Thr
1               5                   10                  15

Leu Thr Ile Ser Ser Val Gln Ser Glu Asp Phe Ala Val Tyr Tyr Cys
            20                  25                  30

<210> SEQ ID NO 465
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 465

Lys Gln Ser Tyr Asn Leu Ile Ser
1               5

<210> SEQ ID NO 466
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 466

Phe Gly Gln Gly Thr Val Leu Glu Ile Lys Arg
1               5                   10

<210> SEQ ID NO 467
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 467

Glu Ile Val Met Thr Gln Thr Pro Val Thr Leu Ser Val Ser Pro Gly
1               5                   10                  15

Glu Arg Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Asp Val
    50                  55                  60

Pro Ala Arg Phe Ser Gly Ser Gly Ser Gly Thr Glu Phe Thr Leu Thr
65                  70                  75                  80

Ile Ser Ser Val Gln Ser Glu Asp Phe Ala Val Tyr Tyr Cys Lys Gln
                85                  90                  95

Ser Ser Asn Leu Ile Ser Phe Gly Gln Gly Thr Val Leu Glu Ile Lys
            100                 105                 110

Arg

<210> SEQ ID NO 468
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 468

Glu Ile Val Met Thr Gln Thr Pro Val Thr Leu Ser Val Ser Pro Gly
1               5                   10                  15

Glu Arg Val Thr Met Ser Cys
            20

<210> SEQ ID NO 469
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 469

Lys Ser Ser Gln Ser Leu Leu Asn Ser Arg Thr Arg Lys Asn Tyr Leu
1               5                   10                  15

Ala

```
<210> SEQ ID NO 470
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 470

Trp Tyr Gln Gln Lys Pro Gly Gln Ala Pro Arg Leu Leu Ile Tyr
1               5                   10                  15

<210> SEQ ID NO 471
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 471

Trp Ala Ser Thr Arg Glu Ser
1               5

<210> SEQ ID NO 472
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 472

Asp Val Pro Ala Arg Phe Ser Gly Ser Gly Ser Gly Thr Glu Phe Thr
1               5                   10                  15

Leu Thr Ile Ser Ser Val Gln Ser Glu Asp Phe Ala Val Tyr Tyr Cys
                20                  25                  30

<210> SEQ ID NO 473
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 473

Lys Gln Ser Ser Asn Leu Ile Ser
1               5

<210> SEQ ID NO 474
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 474

Phe Gly Gln Gly Thr Val Leu Glu Ile Lys Arg
1               5                   10

<210> SEQ ID NO 475
<211> LENGTH: 113
<212> TYPE: PRT
<213> ORGANISM: Unknown
```

-continued

```
<220> FEATURE:
<223> OTHER INFORMATION: Human (Homo sapiens), chimeric or humanized
      antibody peptide sequence

<400> SEQUENCE: 475

Glu Ile Val Met Thr Gln Ser Pro Ala Thr Leu Ser Val Ser Pro Gly
1               5                   10                  15

Glu Arg Val Thr Met Ser Cys Lys Ser Ser Gln Ser Leu Leu Asn Ser
            20                  25                  30

Arg Ser Arg Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Val
50                  55                  60

Pro Ala Arg Phe Ser Gly Ser Gly Ser Gly Thr Glu Phe Thr Leu Thr
65                  70                  75                  80

Ile Ser Ser Val Gln Ser Glu Asp Phe Ala Val Tyr Tyr Cys Lys Gln
                85                  90                  95

Ser Tyr Asn Leu Leu Ser Phe Gly Gln Gly Thr Val Leu Glu Ile Lys
            100                 105                 110

Arg

<210> SEQ ID NO 476
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 476

Glu Ile Val Met Thr Gln Ser Pro Ala Thr Leu Ser Val Ser Pro Gly
1               5                   10                  15

Glu Arg Val Thr Met Ser Cys
            20

<210> SEQ ID NO 477
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 477

Ala Val His Arg Gln
1               5

<210> SEQ ID NO 478
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 478

Lys Ser Ser Gln Ser Leu Leu Asn Ser Arg Ser Arg Lys Asn Tyr Leu
1               5                   10                  15

Ala

<210> SEQ ID NO 479
<211> LENGTH: 15
```

```
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 479

Trp Tyr Gln Gln Lys Pro Gly Gln Ala Pro Arg Leu Leu Ile Tyr
1               5                   10                  15

<210> SEQ ID NO 480
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 480

Trp Ala Ser Thr Arg Glu Ser
1               5

<210> SEQ ID NO 481
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 481

Gly Val Pro Ala Arg Phe Ser Gly Ser Gly Ser Gly Thr Glu Phe Thr
1               5                   10                  15

Leu Thr Ile Ser Ser Val Gln Ser Glu Asp Phe Ala Val Tyr Tyr Cys
                20                  25                  30

<210> SEQ ID NO 482
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 482

Lys Gln Ser Tyr Asn Leu Leu Ser
1               5

<210> SEQ ID NO 483
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 483

Phe Gly Gln Gly Thr Val Leu Glu Ile Lys Arg
1               5                   10

<210> SEQ ID NO 484
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence
```

-continued

<400> SEQUENCE: 484

Glu Ile Val Met Thr Gln Ser Pro Ala Thr Leu Ser Val Ser Pro Gly
1               5                   10                  15

Glu Arg Val Thr Met Ser Cys Lys Ser Ser Gln Ser Leu Leu Asn Ser
            20                  25                  30

Arg Ser Arg Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Val
50                  55                  60

Pro Ala Arg Phe Ser Gly Ser Gly Ser Gly Thr Glu Phe Thr Leu Thr
65                  70                  75                  80

Ile Ser Ser Val Gln Ser Glu Asp Phe Ala Val Tyr Tyr Cys Lys Gln
                85                  90                  95

Ser Tyr Asn Leu Leu Ser Phe Gly Gln Gly Thr Val Leu Glu Ile Lys
            100                 105                 110

Arg

<210> SEQ ID NO 485
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 485

Glu Ile Val Met Thr Gln Ser Pro Ala Thr Leu Ser Val Ser Pro Gly
1               5                   10                  15

Glu Arg Val Thr Met Ser Cys
            20

<210> SEQ ID NO 486
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 486

Lys Ser Ser Gln Ser Leu Leu Asn Ser Arg Ser Arg Lys Asn Tyr Leu
1               5                   10                  15

Ala

<210> SEQ ID NO 487
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 487

Trp Tyr Gln Gln Lys Pro Gly Gln Ala Pro Arg Leu Leu Ile Tyr
1               5                   10                  15

<210> SEQ ID NO 488
<211> LENGTH: 7
<212> TYPE: PRT
<213> ORGANISM: Unknown
<220> FEATURE:
<223> OTHER INFORMATION: Human (Homo sapiens), chimeric or humanized antibody peptide sequence

<400> SEQUENCE: 488

Trp Ala Ser Thr Arg Glu Ser
1               5

<210> SEQ ID NO 489
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 489

Gly Val Pro Ala Arg Phe Ser Gly Ser Gly Ser Gly Thr Glu Phe Thr
1               5                   10                  15

Leu Thr Ile Ser Ser Val Gln Ser Glu Asp Phe Ala Val Tyr Tyr Cys
            20                  25                  30

<210> SEQ ID NO 490
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 490

Lys Gln Ser Tyr Asn Leu Leu Ser
1               5

<210> SEQ ID NO 491
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 491

Phe Gly Gln Gly Thr Val Leu Glu Ile Lys Arg
1               5                   10

<210> SEQ ID NO 492
<211> LENGTH: 117
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 492

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Gly Arg
            20                  25                  30

Gly Asp Leu Gly Arg Leu Lys Lys Asn Ala Leu Ala Trp Tyr Gln Gln
        35                  40                  45

Lys Pro Gly Gln Ser Pro Arg Leu Leu Ile Tyr Trp Ala Ser Thr Arg
    50                  55                  60

Glu Ser Gly Val Pro Asp Arg Phe Thr Gly Ser Gly Ser Gly Thr Asp
65                  70                  75                  80

Phe Thr Leu Thr Ile Ser Ser Val Gln Ala Glu Asp Leu Ala Val Tyr

```
                    85                  90                  95
Tyr Cys Lys Gln Ser Tyr Asn Leu Leu Ser Phe Gly Ala Gly Thr Lys
            100                 105                 110

Leu Glu Leu Lys Arg
        115
```

<210> SEQ ID NO 493
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 493

```
Asp Ile Val Met Thr Gln Ser Pro Ser Ser Leu Ala Val Ser Ala Gly
1               5                   10                  15

Glu Lys Val Thr Met Ser Cys
            20
```

<210> SEQ ID NO 494
<211> LENGTH: 21
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 494

```
Lys Ser Ser Gln Ser Leu Leu Gly Arg Gly Asp Leu Gly Arg Leu Lys
1               5                   10                  15

Lys Asn Ala Leu Ala
            20
```

<210> SEQ ID NO 495
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 495

```
Trp Tyr Gln Gln Lys Pro Gly Gln Ser Pro Arg Leu Leu Ile Tyr
1               5                   10                  15
```

<210> SEQ ID NO 496
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 496

```
Trp Ala Ser Thr Arg Glu Ser
1               5
```

<210> SEQ ID NO 497
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 497

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 498
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 498

Lys Gln Ser Tyr Asn Leu Leu Ser
1               5

<210> SEQ ID NO 499
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 499

Phe Gly Ala Gly Thr Lys Leu Glu Leu Lys Arg
1               5                   10

<210> SEQ ID NO 500
<211> LENGTH: 117
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 500

Glu Ile Val Met Thr Gln Ser Pro Ala Thr Leu Ser Val Ser Pro Gly
1               5                   10                  15

Glu Arg Val Thr Met Ser Cys Lys Ser Ser Gln Ser Leu Leu Gly Arg
            20                  25                  30

Gly Asp Leu Gly Arg Leu Lys Lys Asn Ala Leu Ala Trp Tyr Gln Gln
        35                  40                  45

Lys Pro Gly Gln Ala Pro Arg Leu Leu Ile Tyr Trp Ala Ser Thr Arg
    50                  55                  60

Glu Ser Gly Val Pro Ala Arg Phe Ser Gly Ser Gly Thr Glu
65                  70                  75                  80

Phe Thr Leu Thr Ile Ser Ser Val Gln Ser Glu Asp Phe Ala Val Tyr
                85                  90                  95

Tyr Cys Lys Gln Ser Tyr Asn Leu Leu Ser Phe Gly Gln Gly Thr Val
            100                 105                 110

Leu Glu Ile Lys Arg
        115

<210> SEQ ID NO 501
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 501

Glu Ile Val Met Thr Gln Ser Pro Ala Thr Leu Ser Val Ser Pro Gly
1               5                   10                  15

Glu Arg Val Thr Met Ser Cys
            20

<210> SEQ ID NO 502
<211> LENGTH: 21
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 502

Lys Ser Ser Gln Ser Leu Leu Gly Arg Gly Asp Leu Gly Arg Leu Lys
1               5                   10                  15

Lys Asn Ala Leu Ala
            20

<210> SEQ ID NO 503
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 503

Trp Tyr Gln Gln Lys Pro Gly Gln Ala Pro Arg Leu Leu Ile Tyr
1               5                   10                  15

<210> SEQ ID NO 504
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 504

Trp Ala Ser Thr Arg Glu Ser
1               5

<210> SEQ ID NO 505
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 505

Gly Val Pro Ala Arg Phe Ser Gly Ser Gly Ser Gly Thr Glu Phe Thr
1               5                   10                  15

Leu Thr Ile Ser Ser Val Gln Ser Glu Asp Phe Ala Val Tyr Tyr Cys
            20                  25                  30

<210> SEQ ID NO 506
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence -continued

<400> SEQUENCE: 506

Lys Gln Ser Tyr Asn Leu Leu Ser
1               5

<210> SEQ ID NO 507
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 507

Phe Gly Gln Gly Thr Val Leu Glu Ile Lys Arg
1               5                   10

<210> SEQ ID NO 508
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 508

Asp Tyr Ser Met His
1               5

<210> SEQ ID NO 509
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 509

Arg Ile Asn Thr Glu Thr Gly Glu Pro Thr Phe Ala Asp Asp Phe Arg
1               5                   10                  15

Gly

<210> SEQ ID NO 510
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 510

Phe Tyr Tyr Gly Arg Asp Ser
1               5

<210> SEQ ID NO 511
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 511

Asp Tyr Ser Met His
1               5

```
<210> SEQ ID NO 512
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 512

Arg Ile Asn Thr Glu Thr Gly Glu Pro Thr Phe Ala Asp Asp Phe Arg
1               5                   10                  15

Gly

<210> SEQ ID NO 513
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 513

Phe Tyr Tyr Gly Arg Asp Ser
1               5

<210> SEQ ID NO 514
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 514

Asp Tyr Ser Met His
1               5

<210> SEQ ID NO 515
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 515

Arg Ile Asn Thr Glu Thr Gly Glu Pro Thr Phe Ala Asp Asp Phe Arg
1               5                   10                  15

Gly

<210> SEQ ID NO 516
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 516

Phe Tyr Tyr Gly Arg Asp Thr
1               5

<210> SEQ ID NO 517
<211> LENGTH: 5
<212> TYPE: PRT
<213> ORGANISM: Unknown
<220> FEATURE:
```

<223> OTHER INFORMATION: Human (Homo sapiens), chimeric or humanized
        antibody peptide sequence

<400> SEQUENCE: 517

Asp Tyr Ser Met His
1               5

<210> SEQ ID NO 518
<211> LENGTH: 17
<212> TYPE: PRT
<213> ORGANISM: Unknown
<220> FEATURE:
<223> OTHER INFORMATION: Human (Homo sapiens), chimeric or humanized
        antibody peptide sequence

<400> SEQUENCE: 518

Arg Ile Asn Thr Glu Thr Gly Glu Pro Thr Phe Ala Asp Asp Phe Arg
1               5                   10                  15

Gly

<210> SEQ ID NO 519
<211> LENGTH: 7
<212> TYPE: PRT
<213> ORGANISM: Unknown
<220> FEATURE:
<223> OTHER INFORMATION: Human (Homo sapiens), chimeric or humanized
        antibody peptide sequence

<400> SEQUENCE: 519

Phe Tyr Tyr Gly Arg Asp Thr
1               5

<210> SEQ ID NO 520
<211> LENGTH: 5
<212> TYPE: PRT
<213> ORGANISM: Unknown
<220> FEATURE:
<223> OTHER INFORMATION: Human (Homo sapiens), chimeric or humanized
        antibody peptide sequence

<400> SEQUENCE: 520

Asp Tyr Ser Met His
1               5

<210> SEQ ID NO 521
<211> LENGTH: 17
<212> TYPE: PRT
<213> ORGANISM: Unknown
<220> FEATURE:
<223> OTHER INFORMATION: Human (Homo sapiens), chimeric or humanized
        antibody peptide sequence

<400> SEQUENCE: 521

Arg Ile Asn Thr Glu Thr Gly Glu Pro Thr Phe Ala Asp Asp Phe Arg
1               5                   10                  15

Gly

<210> SEQ ID NO 522
<211> LENGTH: 7
<212> TYPE: PRT
<213> ORGANISM: Unknown
<220> FEATURE:
<223> OTHER INFORMATION: Human (Homo sapiens), chimeric or humanized
        antibody peptide sequence

<400> SEQUENCE: 522

Phe Tyr Tyr Gly Arg Asp Thr
1               5

<210> SEQ ID NO 523
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 523

Asp Tyr Ser Met His
1               5

<210> SEQ ID NO 524
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 524

Arg Ile Asn Thr Glu Thr Gly Glu Pro Thr Phe Ala Asp Asp Phe Arg
1               5                   10                  15

Gly

<210> SEQ ID NO 525
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 525

Phe Tyr Tyr Gly Arg Asp Ser
1               5

<210> SEQ ID NO 526
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 526

Asp Tyr Ser Met His
1               5

<210> SEQ ID NO 527
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 527

Arg Ile Asn Thr Glu Thr Gly Glu Pro Thr Phe Ala Asp Asp Phe Arg
1               5                   10                  15

Gly

<210> SEQ ID NO 528

```
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 528

Phe Tyr Tyr Gly Arg Asp Thr
1               5

<210> SEQ ID NO 529
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 529

Lys Ser Ser Gln Ser Leu Leu Asn Ser Arg Thr Arg Lys Asn Tyr Leu
1               5                   10                  15

Ala

<210> SEQ ID NO 530
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 530

Trp Ala Ser Thr Arg Glu Ser
1               5

<210> SEQ ID NO 531
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 531

Lys Gln Ser Tyr Asn Leu Leu Ser
1               5

<210> SEQ ID NO 532
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 532

Lys Ser Ser Gln Ser Leu Leu Asn Ser Arg Ser Arg Lys Asn Tyr Leu
1               5                   10                  15

Ala

<210> SEQ ID NO 533
<211> LENGTH: 7
<212> TYPE: PRT
<213> ORGANISM: Unknown
<220> FEATURE:
<223> OTHER INFORMATION: Human (Homo sapiens), chimeric or humanized
``` antibody peptide sequence

<400> SEQUENCE: 533

Trp Ala Ser Thr Arg Glu Ser
1               5

<210> SEQ ID NO 534
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 534

Lys Gln Ser Tyr Asn Leu Ile Ser
1               5

<210> SEQ ID NO 535
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 535

Lys Ser Ser Gln Ser Leu Leu Asn Ser Arg Thr Arg Lys Asn Tyr Leu
1               5                   10                  15

Ala

<210> SEQ ID NO 536
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 536

Trp Ala Ser Thr Arg Glu Ser
1               5

<210> SEQ ID NO 537
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 537

Lys Gln Ser Ser Asn Leu Ile Ser
1               5

<210> SEQ ID NO 538
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 538

Lys Ser Ser Gln Ser Leu Leu Asn Ser Arg Ser Arg Lys Asn Tyr Leu
1               5                   10                  15

Ala

<210> SEQ ID NO 539
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 539

Trp Ala Ser Thr Arg Glu Ser
1               5

<210> SEQ ID NO 540
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 540

Lys Gln Ser Tyr Asn Leu Leu Ser
1               5

<210> SEQ ID NO 541
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 541

Lys Ser Ser Gln Ser Leu Leu Asn Ser Arg Ser Arg Lys Asn Tyr Leu
1               5                   10                  15
Ala

<210> SEQ ID NO 542
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 542

Trp Ala Ser Thr Arg Glu Ser
1               5

<210> SEQ ID NO 543
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 543

Lys Gln Ser Tyr Asn Leu Leu Ser
1               5

<210> SEQ ID NO 544
<211> LENGTH: 21
<212> TYPE: PRT
<213> ORGANISM: Unknown

```
<220> FEATURE:
<223> OTHER INFORMATION: Human (Homo sapiens), chimeric or humanized
      antibody peptide sequence

<400> SEQUENCE: 544

Lys Ser Ser Gln Ser Leu Leu Gly Arg Gly Asp Leu Gly Arg Leu Lys
1               5                   10                  15

Lys Asn Ala Leu Ala
            20

<210> SEQ ID NO 545
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 545

Trp Ala Ser Thr Arg Glu Ser
1               5

<210> SEQ ID NO 546
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 546

Lys Gln Ser Tyr Asn Leu Leu Ser
1               5

<210> SEQ ID NO 547
<211> LENGTH: 21
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 547

Lys Ser Ser Gln Ser Leu Leu Gly Arg Gly Asp Leu Gly Arg Leu Lys
1               5                   10                  15

Lys Asn Ala Leu Ala
            20

<210> SEQ ID NO 548
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 548

Trp Ala Ser Thr Arg Glu Ser
1               5

<210> SEQ ID NO 549
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence
```

<400> SEQUENCE: 549

Lys Gln Ser Tyr Asn Leu Leu Ser
1               5

<210> SEQ ID NO 550
<211> LENGTH: 30
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (9)..(9)
<223> OTHER INFORMATION: Xaa is Pro or Ala
<220> FEATURE:
<221> NAME/KEY: MISC_FEATURE
<222> LOCATION: (10)..(10)
<223> OTHER INFORMATION: Xaa is Glu or Lys
<220> FEATURE:
<221> NAME/KEY: MISC_FEATURE
<222> LOCATION: (11)..(11)
<223> OTHER INFORMATION: Xaa is Lys or Val
<220> FEATURE:
<221> NAME/KEY: MISC_FEATURE
<222> LOCATION: (16)..(16)
<223> OTHER INFORMATION: Xaa is Glu or Ala
<220> FEATURE:
<221> NAME/KEY: MISC_FEATURE
<222> LOCATION: (17)..(17)
<223> OTHER INFORMATION: Xaa is Thr or Ser

<400> SEQUENCE: 550

Gln Ile Gln Leu Val Gln Ser Gly Xaa Xaa Xaa Lys Lys Pro Gly Xaa
1               5                   10                  15

Xaa Val Lys Ile Ser Cys Lys Ala Ser Gly Tyr Thr Phe Thr
                20                  25                  30

<210> SEQ ID NO 551
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (3)..(3)
<223> OTHER INFORMATION: Xaa is Lys or Arg
<220> FEATURE:
<221> NAME/KEY: MISC_FEATURE
<222> LOCATION: (8)..(8)
<223> OTHER INFORMATION: Xaa is Lys or Gln
<220> FEATURE:
<221> NAME/KEY: MISC_FEATURE
<222> LOCATION: (11)..(11)
<223> OTHER INFORMATION: Xaa is Lys or Glu

<400> SEQUENCE: 551

Trp Val Xaa Gln Ala Pro Gly Xaa Gly Leu Xaa Trp Val Ala
1               5                   10

<210> SEQ ID NO 552
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE -continued

```
<222> LOCATION: (3)..(3)
<223> OTHER INFORMATION: Xaa is Ala, Thr or Ser
<220> FEATURE:
<221> NAME/KEY: MISC_FEATURE
<222> LOCATION: (5)..(5)
<223> OTHER INFORMATION: Xaa is Ser or Thr
<220> FEATURE:
<221> NAME/KEY: MISC_FEATURE
<222> LOCATION: (7)..(7)
<223> OTHER INFORMATION: Xaa is Glu or Asp
<220> FEATURE:
<221> NAME/KEY: MISC_FEATURE
<222> LOCATION: (10)..(10)
<223> OTHER INFORMATION: Xaa is Ala or Thr
<220> FEATURE:
<221> NAME/KEY: MISC_FEATURE
<222> LOCATION: (18)..(18)
<223> OTHER INFORMATION: Xaa is Asn , Arg or Thr
<220> FEATURE:
<221> NAME/KEY: MISC_FEATURE
<222> LOCATION: (19)..(19)
<223> OTHER INFORMATION: Xaa is Asn or Ser
<220> FEATURE:
<221> NAME/KEY: MISC_FEATURE
<222> LOCATION: (21)..(21)
<223> OTHER INFORMATION: Xaa is Lys or Arg
<220> FEATURE:
<221> NAME/KEY: MISC_FEATURE
<222> LOCATION: (22)..(22)
<223> OTHER INFORMATION: Xaa is Asn or Ser
<220> FEATURE:
<221> NAME/KEY: MISC_FEATURE
<222> LOCATION: (23)..(23)
<223> OTHER INFORMATION: Xaa is Glu or Asp
<220> FEATURE:
<221> NAME/KEY: MISC_FEATURE
<222> LOCATION: (27)..(27)
<223> OTHER INFORMATION: Xaa is Thr or Val

<400> SEQUENCE: 552

Arg Phe Xaa Val Xaa Leu Xaa Thr Ser Xaa Ser Thr Ala Tyr Leu Glx
1               5                   10                  15

Ile Xaa Xaa Leu Xaa Xaa Xaa Asp Thr Ala Xaa Tyr Phe Cys Ala Ile
            20                  25                  30

<210> SEQ ID NO 553
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (6)..(6)
<223> OTHER INFORMATION: Xaa is Ala or Thr

<400> SEQUENCE: 553

Trp Gly Gln Gly Thr Xaa Leu Thr Val Ser Ser
1               5                   10

<210> SEQ ID NO 554
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (1)..(1)
<223> OTHER INFORMATION: Xaa is Asp or Glu
<220> FEATURE:
<221> NAME/KEY: MISC_FEATURE
```

```
<222> LOCATION: (7)..(7)
<223> OTHER INFORMATION: Xaa is Ser or Thr
<220> FEATURE:
<221> NAME/KEY: MISC_FEATURE
<222> LOCATION: (9)..(9)
<223> OTHER INFORMATION: Xaa is Ser , Ala or Val
<220> FEATURE:
<221> NAME/KEY: MISC_FEATURE
<222> LOCATION: (10)..(10)
<223> OTHER INFORMATION: Xaa is Ser or Thr
<220> FEATURE:
<221> NAME/KEY: MISC_FEATURE
<222> LOCATION: (12)..(12)
<223> OTHER INFORMATION: Xaa is Ala or Ser
<220> FEATURE:
<221> NAME/KEY: MISC_FEATURE
<222> LOCATION: (15)..(15)
<223> OTHER INFORMATION: Xaa is Ala or Pro
<220> FEATURE:
<221> NAME/KEY: MISC_FEATURE
<222> LOCATION: (18)..(18)
<223> OTHER INFORMATION: Xaa is Lys , Arg or Ile

<400> SEQUENCE: 554

Xaa Ile Val Met Thr Gln Xaa Pro Xaa Xaa Leu Xaa Val Ser Xaa Gly
1               5                   10                  15

Glu Xaa Val Thr Met Ser Cys
            20

<210> SEQ ID NO 555
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (9)..(9)
<223> OTHER INFORMATION: Xaa is Ser or Ala

<400> SEQUENCE: 555

Trp Tyr Gln Gln Lys Pro Gly Gln Xaa Pro Arg Leu Leu Ile Tyr
1               5                   10                  15

<210> SEQ ID NO 556
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (1)..(1)
<223> OTHER INFORMATION: Xaa is Glu or Asp
<220> FEATURE:
<221> NAME/KEY: MISC_FEATURE
<222> LOCATION: (4)..(4)
<223> OTHER INFORMATION: Xaa is Asp or Ala
<220> FEATURE:
<221> NAME/KEY: MISC_FEATURE
<222> LOCATION: (7)..(7)
<223> OTHER INFORMATION: Xaa is Thr or Ser
<220> FEATURE:
<221> NAME/KEY: MISC_FEATURE
<222> LOCATION: (14)..(14)
<223> OTHER INFORMATION: Xaa is Asp or Glu
<220> FEATURE:
<221> NAME/KEY: MISC_FEATURE
<222> LOCATION: (24)..(24)
<223> OTHER INFORMATION: Xaa is Ala or Ser
<220> FEATURE:
<221> NAME/KEY: MISC_FEATURE
```

```
<222> LOCATION: (27)..(27)
<223> OTHER INFORMATION: Xaa is Leu or Phe

<400> SEQUENCE: 556

Xaa Val Pro Xaa Arg Phe Xaa Gly Ser Gly Ser Gly Thr Xaa Phe Thr
1               5                   10                  15

Leu Thr Ile Ser Ser Val Gln Xaa Glu Asp Xaa Ala Val Tyr Tyr Cys
            20                  25                  30

<210> SEQ ID NO 557
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (3)..(3)
<223> OTHER INFORMATION: Xaa is Ala or Gln
<220> FEATURE:
<221> NAME/KEY: MISC_FEATURE
<222> LOCATION: (6)..(6)
<223> OTHER INFORMATION: Xaa is Lys or Val
<220> FEATURE:
<221> NAME/KEY: MISC_FEATURE
<222> LOCATION: (9)..(9)
<223> OTHER INFORMATION: Xaa is Leu or Ile

<400> SEQUENCE: 557

Phe Gly Xaa Gly Thr Xaa Leu Glu Xaa Lys Arg
1               5                   10

<210> SEQ ID NO 558
<211> LENGTH: 30
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid

<400> SEQUENCE: 558

Gln Ile Gln Leu Xaa Gln Ser Gly Xaa Xaa Xaa Lys Lys Pro Gly Xaa
1               5                   10                  15

Xaa Val Lys Ile Ser Cys Lys Ala Ser Gly Tyr Thr Phe Thr
            20                  25                  30

<210> SEQ ID NO 559
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (3)..(3)
<223> OTHER INFORMATION: Xaa is Arg or Lys
<220> FEATURE:
```

```
<221> NAME/KEY: MISC_FEATURE
<222> LOCATION: (8)..(8)
<223> OTHER INFORMATION: Xaa is Gln or Lys
<220> FEATURE:
<221> NAME/KEY: MISC_FEATURE
<222> LOCATION: (11)..(11)
<223> OTHER INFORMATION: Xaa is Gly or Lys
<220> FEATURE:
<221> NAME/KEY: MISC_FEATURE
<222> LOCATION: (13)..(13)
<223> OTHER INFORMATION: Xaa is Val or Met
<220> FEATURE:
<221> NAME/KEY: MISC_FEATURE
<222> LOCATION: (14)..(14)
<223> OTHER INFORMATION: Xaa is Ala or Gly

<400> SEQUENCE: 559

Trp Val Xaa Gln Ala Pro Gly Xaa Gly Leu Xaa Trp Xaa Xaa
1               5                   10

<210> SEQ ID NO 560
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (3)..(3)
<223> OTHER INFORMATION: Xaa is Thr , Ala or Ser
<220> FEATURE:
<221> NAME/KEY: MISC_FEATURE
<222> LOCATION: (4)..(4)
<223> OTHER INFORMATION: Xaa is Val or Phe
<220> FEATURE:
<221> NAME/KEY: MISC_FEATURE
<222> LOCATION: (5)..(5)
<223> OTHER INFORMATION: Xaa is Thr or Ser
<220> FEATURE:
<221> NAME/KEY: MISC_FEATURE
<222> LOCATION: (7)..(7)
<223> OTHER INFORMATION: Xaa is Asp or Glu
<220> FEATURE:
<221> NAME/KEY: MISC_FEATURE
<222> LOCATION: (10)..(10)
<223> OTHER INFORMATION: Xaa is Ala or Thr
<220> FEATURE:
<221> NAME/KEY: MISC_FEATURE
<222> LOCATION: (11)..(11)
<223> OTHER INFORMATION: Xaa is Ser or Thr
<220> FEATURE:
<221> NAME/KEY: MISC_FEATURE
<222> LOCATION: (14)..(14)
<223> OTHER INFORMATION: Xaa is Tyr or Asn
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: Xaa is Arg, Asn, Ile or Thr
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: Xaa is Arg or Lys
<220> FEATURE:
<221> NAME/KEY: MISC_FEATURE
<222> LOCATION: (21)..(21)
<223> OTHER INFORMATION: Xaa is Ser or Asn
<220> FEATURE:
<221> NAME/KEY: MISC_FEATURE
```

```
<222> LOCATION: (22)..(2)
<223> OTHER INFORMATION: Xaa is Asp or Glu
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: MISC_FEATURE
<222> LOCATION: (26)..(26)
<223> OTHER INFORMATION: Xaa is Val, Thr or Lys
<220> FEATURE:
<221> NAME/KEY: misc_feature
<222> LOCATION: (27)..(27)
<223> OTHER INFORMATION: Xaa can be any naturally occurring amino acid

<400> SEQUENCE: 560

Arg Phe Xaa Xaa Xaa Leu Xaa Thr Ser Xaa Xaa Thr Ala Xaa Leu Xaa
1               5                   10                  15

Ile Xaa Xaa Leu Xaa Xaa Xaa Asp Thr Ala Xaa Tyr Phe Cys Ala Ile
            20                  25                  30

<210> SEQ ID NO 561
<211> LENGTH: 12
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa is Thr or Ala

<400> SEQUENCE: 561

Trp Gly Gln Gly Thr Xaa Leu Val Thr Val Ser Ser
1               5                   10

<210> SEQ ID NO 562
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 562

Asp Tyr Ser Met His
1               5

<210> SEQ ID NO 563
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (1)..(1)
<223> OTHER INFORMATION: Xaa is Arg or Trp
<220> FEATURE:
<221> NAME/KEY: MISC_FEATURE
<222> LOCATION: (3)..(3)
<223> OTHER INFORMATION: Xaa is Asn or Lys
<220> FEATURE:
<221> NAME/KEY: MISC_FEATURE
<222> LOCATION: (7)..(7)
<223> OTHER INFORMATION: Xaa is Gly or Asp
```

```
<220> FEATURE:
<221> NAME/KEY: MISC_FEATURE
<222> LOCATION: (11)..(11)
<223> OTHER INFORMATION: Xaa is Phe or Tyr
<220> FEATURE:
<221> NAME/KEY: MISC_FEATURE
<222> LOCATION: (16)..(16)
<223> OTHER INFORMATION: Xaa is Arg, Asn, Lys or Gly
<220> FEATURE:
<221> NAME/KEY: MISC_FEATURE
<222> LOCATION: (17)..(17)
<223> OTHER INFORMATION: Xaa is Gly or Glu

<400> SEQUENCE: 563

Xaa Ile Xaa Thr Glu Thr Xaa Glu Pro Thr Xaa Ala Asp Asp Phe Xaa
 1               5                  10                  15

Xaa

<210> SEQ ID NO 564
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (1)..(1)
<223> OTHER INFORMATION: Xaa is Phe or Tyr
<220> FEATURE:
<221> NAME/KEY: MISC_FEATURE
<222> LOCATION: (7)..(7)
<223> OTHER INFORMATION: Xaa is Ser or Thr

<400> SEQUENCE: 564

Xaa Tyr Tyr Gly Arg Asp Xaa
 1               5

<210> SEQ ID NO 565
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (1)..(1)
<223> OTHER INFORMATION: Xaa is Glu or Asp
<220> FEATURE:
<221> NAME/KEY: MISC_FEATURE
<222> LOCATION: (5)..(5)
<223> OTHER INFORMATION: Xaa is Thr or Ser
<220> FEATURE:
<221> NAME/KEY: MISC_FEATURE
<222> LOCATION: (7)..(7)
<223> OTHER INFORMATION: Xaa is Ser or Thr
<220> FEATURE:
<221> NAME/KEY: MISC_FEATURE
<222> LOCATION: (9)..(9)
<223> OTHER INFORMATION: Xaa is Ala, Ser or Val
<220> FEATURE:
<221> NAME/KEY: MISC_FEATURE
<222> LOCATION: (10)..(10)
<223> OTHER INFORMATION: Xaa is Thr or Ser
<220> FEATURE:
<221> NAME/KEY: MISC_FEATURE
<222> LOCATION: (12)..(12)
<223> OTHER INFORMATION: Xaa is Ser or Ala
<220> FEATURE:
<221> NAME/KEY: MISC_FEATURE
<222> LOCATION: (15)..(15)
<223> OTHER INFORMATION: Xaa is Pro or Ala
<220> FEATURE:
```

```
<221> NAME/KEY: MISC_FEATURE
<222> LOCATION: (18)..(18)
<223> OTHER INFORMATION: Xaa is Arg, Lys or Ile

<400> SEQUENCE: 565

Xaa Ile Val Met Xaa Gln Xaa Pro Xaa Xaa Leu Xaa Val Ser Xaa Gly
1               5                   10                  15

Glu Xaa Val Thr Met Ser Cys
            20

<210> SEQ ID NO 566
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (9)..(9)
<223> OTHER INFORMATION: Xaa is Ala or Ser

<400> SEQUENCE: 566

Trp Tyr Gln Gln Lys Pro Gly Gln Xaa Pro Arg Leu Leu Ile Tyr
1               5                   10                  15

<210> SEQ ID NO 567
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (1)..(1)
<223> OTHER INFORMATION: Xaa is Glu or Asp
<220> FEATURE:
<221> NAME/KEY: MISC_FEATURE
<222> LOCATION: (4)..(4)
<223> OTHER INFORMATION: Xaa is Ala or Asp
<220> FEATURE:
<221> NAME/KEY: MISC_FEATURE
<222> LOCATION: (7)..(7)
<223> OTHER INFORMATION: Xaa is Ser or Thr
<220> FEATURE:
<221> NAME/KEY: MISC_FEATURE
<222> LOCATION: (14)..(14)
<223> OTHER INFORMATION: Xaa is Glu or Asp
<220> FEATURE:
<221> NAME/KEY: MISC_FEATURE
<222> LOCATION: (24)..(24)
<223> OTHER INFORMATION: Xaa is Ser, Asp or Ala
<220> FEATURE:
<221> NAME/KEY: MISC_FEATURE
<222> LOCATION: (27)..(27)
<223> OTHER INFORMATION: Xaa is Phe or Leu

<400> SEQUENCE: 567

Xaa Val Pro Xaa Arg Phe Xaa Gly Ser Gly Ser Gly Thr Xaa Phe Thr
1               5                   10                  15

Leu Thr Ile Ser Ser Val Gln Xaa Glu Asp Xaa Ala Val Tyr Tyr Cys
            20                  25                  30

<210> SEQ ID NO 568
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence
```

```
<220> FEATURE:
<221> NAME/KEY: MISC_FEATURE
<222> LOCATION: (3)..(3)
<223> OTHER INFORMATION: Xaa is Gln or Ala
<220> FEATURE:
<221> NAME/KEY: MISC_FEATURE
<222> LOCATION: (6)..(6)
<223> OTHER INFORMATION: Xaa is Val or Lys
<220> FEATURE:
<221> NAME/KEY: MISC_FEATURE
<222> LOCATION: (9)..(9)
<223> OTHER INFORMATION: Xaa is Ile or Leu

<400> SEQUENCE: 568

Phe Gly Xaa Gly Thr Xaa Leu Glu Xaa Lys Arg
1               5                   10

<210> SEQ ID NO 569
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (11)..(11)
<223> OTHER INFORMATION: Xaa is Ser or Thr

<400> SEQUENCE: 569

Lys Ser Ser Gln Ser Leu Leu Asn Ser Arg Xaa Arg Lys Asn Tyr Leu
1               5                   10                  15
Ala

<210> SEQ ID NO 570
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 570

Trp Ala Ser Thr Arg Glu Ser
1               5

<210> SEQ ID NO 571
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 571

Lys Gln Ser Tyr Asn Leu Leu Ser
1               5

<210> SEQ ID NO 572
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 572

Lys Ser Ser Gln Ser Leu Leu Asn Ser Arg Ser Arg Lys Asn Tyr Leu
1               5                   10                  15
```

Ala

<210> SEQ ID NO 573
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 573

Lys Ser Ser Gln Ser Leu Leu Gly Arg Gly Asp Leu Gly Asn Ala Leu
1               5                   10                  15

Ala

<210> SEQ ID NO 574
<211> LENGTH: 19
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 574

Lys Ser Ser Gln Ser Leu Leu Asn Ser Gly Arg Gly Asp Leu Gly Asn
1               5                   10                  15

Ala Leu Ala

<210> SEQ ID NO 575
<211> LENGTH: 21
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 575

Lys Ser Ser Gln Ser Leu Leu Gly Arg Gly Asp Leu Gly Arg Leu Lys
1               5                   10                  15

Lys Asn Ala Leu Ala
            20

<210> SEQ ID NO 576
<211> LENGTH: 25
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 576

Lys Ser Ser Gln Ser Leu Leu Gly Arg Gly Asp Leu Gly Arg Leu Lys
1               5                   10                  15

Lys Gln Lys Asp His Asn Ala Leu Ala
            20                  25

<210> SEQ ID NO 577
<211> LENGTH: 24
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 577

```
Lys Ser Ser Gln Ser Leu Leu Gly Arg Gly Asp Leu Gly Arg Leu Lys
1               5                   10                  15

Lys Gln Lys Asp Asn Ala Leu Ala
            20

<210> SEQ ID NO 578
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 578

Lys Ser Ser Gln Ser Leu Leu Gly Arg Gly Asp Leu Gly Arg Leu Lys
1               5                   10                  15

Lys Gln Lys Asn Ala Leu Ala
            20

<210> SEQ ID NO 579
<211> LENGTH: 22
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 579

Lys Ser Ser Gln Ser Leu Leu Gly Arg Gly Asp Leu Gly Arg Leu Lys
1               5                   10                  15

Lys Gln Asn Ala Leu Ala
            20

<210> SEQ ID NO 580
<211> LENGTH: 20
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 580

Lys Ser Ser Gln Ser Leu Leu Gly Arg Gly Asp Leu Gly Arg Leu Lys
1               5                   10                  15

Asn Ala Leu Ala
            20

<210> SEQ ID NO 581
<211> LENGTH: 19
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 581

Lys Ser Ser Gln Ser Leu Leu Gly Arg Gly Asp Leu Gly Arg Leu Asn
1               5                   10                  15

Ala Leu Ala

<210> SEQ ID NO 582
<211> LENGTH: 18
<212> TYPE: PRT
<213> ORGANISM: Unknown
```

```
<220> FEATURE:
<223> OTHER INFORMATION: Human (Homo sapiens), chimeric or humanized
      antibody peptide sequence

<400> SEQUENCE: 582

Lys Ser Ser Gln Ser Leu Leu Gly Arg Gly Asp Leu Gly Arg Asn Ala
1               5                   10                  15

Leu Ala

<210> SEQ ID NO 583
<211> LENGTH: 22
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 583

Lys Ser Ser Gln Ser Leu Leu Gly Arg Gly Asp Leu Gly Arg Leu Lys
1               5                   10                  15

Lys Gln Lys Asp His His
            20

<210> SEQ ID NO 584
<211> LENGTH: 21
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 584

Lys Ser Ser Gln Ser Leu Leu Gly Arg Gly Asp Leu Gly Arg Leu Lys
1               5                   10                  15

Lys Gln Lys Asp His
            20

<210> SEQ ID NO 585
<211> LENGTH: 20
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 585

Lys Ser Ser Gln Ser Leu Leu Gly Arg Gly Asp Leu Gly Arg Leu Lys
1               5                   10                  15

Lys Gln Lys Asp
            20

<210> SEQ ID NO 586
<211> LENGTH: 19
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 586

Lys Ser Ser Gln Ser Leu Leu Gly Arg Gly Asp Leu Gly Arg Leu Lys
1               5                   10                  15

Lys Gln Lys
```

```
<210> SEQ ID NO 587
<211> LENGTH: 18
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 587

Lys Ser Ser Gln Ser Leu Leu Gly Arg Gly Asp Leu Gly Arg Leu Lys
1               5                   10                  15

Lys Gln

<210> SEQ ID NO 588
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 588

Lys Ser Ser Gln Ser Leu Leu Gly Arg Gly Asp Leu Gly Arg Leu Lys
1               5                   10                  15

Lys

<210> SEQ ID NO 589
<211> LENGTH: 16
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 589

Lys Ser Ser Gln Ser Leu Leu Gly Arg Gly Asp Leu Gly Arg Leu Lys
1               5                   10                  15

<210> SEQ ID NO 590
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 590

Lys Ser Ser Gln Ser Leu Leu Gly Arg Gly Asp Leu Gly Arg Leu
1               5                   10                  15

<210> SEQ ID NO 591
<211> LENGTH: 54
<212> TYPE: PRT
<213> ORGANISM: Homo sapiens

<400> SEQUENCE: 591

Phe Leu Gln Asp Gly Thr Lys Thr Val Glu Tyr Ala Pro Cys Arg Ser
1               5                   10                  15

Gln Asp Ile Asp Ala Asp Gly Gln Gly Phe Cys Gln Gly Gly Phe Ser
                20                  25                  30

Ile Asp Phe Thr Lys Ala Asp Arg Val Leu Leu Gly Gly Pro Gly Ser
            35                  40                  45

Phe Tyr Trp Gln Gly Gln
    50
```

<210> SEQ ID NO 592
<211> LENGTH: 54
<212> TYPE: PRT
<213> ORGANISM: Pan troglodytes

<400> SEQUENCE: 592

Phe Leu Gln Asp Gly Thr Lys Thr Val Glu Tyr Ala Pro Cys Arg Ser
1               5                   10                  15

Gln Asp Ile Asp Ala Asp Gly Gln Gly Phe Cys Gln Gly Gly Phe Ser
            20                  25                  30

Ile Asp Phe Thr Lys Ala Asp Arg Val Leu Leu Gly Gly Pro Gly Ser
        35                  40                  45

Phe Tyr Trp Gln Gly Gln
    50

<210> SEQ ID NO 593
<211> LENGTH: 54
<212> TYPE: PRT
<213> ORGANISM: Macaca mulatta

<400> SEQUENCE: 593

Phe Leu Gln Asp Gly Thr Lys Thr Val Glu Tyr Ala Pro Cys Arg Ser
1               5                   10                  15

Gln Asp Ile Asp Ala Asp Gly Gln Gly Phe Cys Gln Gly Gly Phe Ser
            20                  25                  30

Ile Asp Phe Thr Lys Ala Asp Arg Val Leu Leu Gly Gly Pro Gly Ser
        35                  40                  45

Phe Tyr Trp Gln Gly Gln
    50

<210> SEQ ID NO 594
<211> LENGTH: 54
<212> TYPE: PRT
<213> ORGANISM: Macaca fascicularis

<400> SEQUENCE: 594

Phe Leu Gln Asp Gly Thr Lys Thr Val Glu Tyr Ala Pro Cys Arg Ser
1               5                   10                  15

Gln Asp Ile Asp Ala Asp Gly Gln Gly Phe Cys Gln Gly Gly Phe Ser
            20                  25                  30

Ile Asp Phe Thr Lys Ala Asp Arg Val Leu Leu Gly Gly Pro Gly Ser
        35                  40                  45

Phe Tyr Trp Gln Gly Gln
    50

<210> SEQ ID NO 595
<211> LENGTH: 54
<212> TYPE: PRT
<213> ORGANISM: Bos taurus

<400> SEQUENCE: 595

Phe Leu Gln Asp Gly Thr Lys Thr Val Glu Tyr Ala Pro Cys Arg Ser
1               5                   10                  15

Lys Asn Ile Asp Ala Asp Gly Gln Gly Phe Cys Gln Gly Gly Phe Ser
            20                  25                  30

Ile Asp Phe Thr Lys Ala Asp Arg Val Leu Leu Gly Gly Pro Gly Ser
        35                  40                  45

Phe Tyr Trp Gln Gly Gln
    50

-continued

<210> SEQ ID NO 596
<211> LENGTH: 54
<212> TYPE: PRT
<213> ORGANISM: Unknown
<220> FEATURE:
<223> OTHER INFORMATION: Sus sp.

<400> SEQUENCE: 596

Phe Leu Gln Asp Gly Thr Lys Thr Val Glu Tyr Ala Pro Cys Arg Ser
1               5                   10                  15

Lys Asn Ile Asp Ala Asp Gly Gln Gly Phe Cys Gln Gly Gly Phe Ser
            20                  25                  30

Ile Asp Phe Thr Lys Ala Asp Arg Val Leu Leu Gly Gly Pro Gly Ser
        35                  40                  45

Phe Tyr Trp Gln Gly Gln
    50

<210> SEQ ID NO 597
<211> LENGTH: 54
<212> TYPE: PRT
<213> ORGANISM: Equus ferus

<400> SEQUENCE: 597

Phe Leu Gln Asp Gly Ala Lys Thr Val Glu Tyr Ala Pro Cys Arg Ser
1               5                   10                  15

Lys Asn Ile Asp Ala Asp Gly Gln Gly Phe Cys Gln Gly Gly Phe Ser
            20                  25                  30

Ile Asp Phe Thr Lys Ala Asp Arg Val Leu Leu Gly Gly Pro Gly Ser
        35                  40                  45

Phe Tyr Trp Gln Gly Gln
    50

<210> SEQ ID NO 598
<211> LENGTH: 54
<212> TYPE: PRT
<213> ORGANISM: Mus musculus

<400> SEQUENCE: 598

Phe Leu Gln Asp Gly Thr Lys Thr Val Glu Tyr Ala Pro Cys Arg Ser
1               5                   10                  15

Lys Asn Ile Asp Ala Asp Gly Gln Gly Phe Cys Gln Gly Gly Phe Ser
            20                  25                  30

Ile Asp Phe Thr Lys Ala Asp Arg Val Leu Leu Gly Gly Pro Gly Ser
        35                  40                  45

Phe Tyr Trp Gln Gly Gln
    50

<210> SEQ ID NO 599
<211> LENGTH: 54
<212> TYPE: PRT
<213> ORGANISM: Unknown
<220> FEATURE:
<223> OTHER INFORMATION: Rattus sp.

<400> SEQUENCE: 599

Phe Leu Gln Asp Gly Thr Lys Thr Val Glu Tyr Ala Pro Cys Arg Ser
1               5                   10                  15

Lys Asn Ile Asp Ala Asp Gly Gln Gly Phe Cys Gln Gly Gly Phe Ser
            20                  25                  30

Ile Asp Phe Thr Lys Ala Asp Arg Val Leu Leu Gly Gly Pro Gly Ser
            35                  40                  45

Phe Tyr Trp Gln Gly Gln
            50

<210> SEQ ID NO 600
<211> LENGTH: 54
<212> TYPE: PRT
<213> ORGANISM: Unknown
<220> FEATURE:
<223> OTHER INFORMATION: Dasypus sp.

<400> SEQUENCE: 600

Phe Leu Gln Asp Gly Thr Lys Thr Val Glu Tyr Ala Pro Cys Arg Ser
1               5                   10                  15

Lys Asn Ile Asp Ala Asp Gly Gln Gly Phe Cys Gln Gly Gly Phe Ser
            20                  25                  30

Ile Asp Phe Thr Lys Ala Asp Arg Val Leu Leu Gly Gly Pro Gly Ser
            35                  40                  45

Phe Tyr Trp Gln Gly Gln
            50

<210> SEQ ID NO 601
<211> LENGTH: 54
<212> TYPE: PRT
<213> ORGANISM: Ornithorhynchus anatinus

<400> SEQUENCE: 601

Phe Leu Gln Asp Gly Thr Lys Thr Val Glu Tyr Ala Pro Cys Arg Ser
1               5                   10                  15

Arg Ser Ile Asp Ala Asp Gly Gln Gly Phe Cys Gln Gly Gly Phe Ser
            20                  25                  30

Ile Asp Phe Thr Lys Ala Asp Arg Val Leu Leu Gly Gly Pro Gly Ser
            35                  40                  45

Phe Tyr Trp Gln Gly Gln
            50

<210> SEQ ID NO 602
<211> LENGTH: 92
<212> TYPE: PRT
<213> ORGANISM: Homo sapiens

<400> SEQUENCE: 602

Ser Ala Ser Met His Asn Asn Ile Glu Lys Leu Asn Ser Val Gly Asn
1               5                   10                  15

Asp Leu Ser Arg Lys Met Ala Phe Phe Ser Arg Asp Phe Arg Leu Gly
            20                  25                  30

Phe Gly Ser Tyr Val Asp Lys Thr Val Ser Pro Tyr Ile Ser Ile His
            35                  40                  45

Pro Glu Arg Ile His Asn Gln Cys Ser Asp Tyr Asn Leu Asp Cys Met
        50                  55                  60

Pro Pro His Gly Tyr Ile His Val Leu Ser Leu Thr Glu Asn Ile Thr
65                  70                  75                  80

Glu Phe Glu Lys Ala Val His Arg Gln Lys Ile Ser
                85                  90

<210> SEQ ID NO 603
<211> LENGTH: 92
<212> TYPE: PRT
<213> ORGANISM: Pan troglodytes

<400> SEQUENCE: 603

Ser Ala Ser Met His Asn Asn Ile Glu Lys Leu Asn Ser Val Gly Asn
1               5                   10                  15

Asp Leu Ser Arg Lys Met Ala Phe Phe Ser Arg Asp Phe Arg Leu Gly
            20                  25                  30

Phe Gly Ser Tyr Val Asp Lys Thr Val Ser Pro Tyr Ile Ser Ile His
        35                  40                  45

Pro Glu Arg Ile His Asn Gln Cys Ser Asp Tyr Asn Leu Asp Cys Met
50                  55                  60

Pro Pro His Gly Tyr Ile His Val Leu Ser Leu Thr Glu Asn Ile Thr
65                  70                  75                  80

Glu Phe Glu Arg Ala Val His Arg Gln Lys Ile Ser
                85                  90

<210> SEQ ID NO 604
<211> LENGTH: 92
<212> TYPE: PRT
<213> ORGANISM: Macaca mulatta

<400> SEQUENCE: 604

Ser Ala Ser Met His Asn Asn Ile Glu Lys Leu Asn Ser Val Gly Asn
1               5                   10                  15

Asp Leu Ser Arg Lys Met Ala Phe Phe Ser Arg Asp Phe Arg Leu Gly
            20                  25                  30

Phe Gly Ser Tyr Val Asp Lys Thr Val Ser Pro Tyr Ile Ser Ile His
        35                  40                  45

Pro Glu Arg Ile His Asn Gln Cys Ser Asp Tyr Asn Leu Asp Cys Met
50                  55                  60

Pro Pro His Gly Tyr Ile His Val Leu Ser Leu Thr Glu Asn Ile Thr
65                  70                  75                  80

Glu Phe Glu Lys Ala Val His Arg Gln Lys Ile Ser
                85                  90

<210> SEQ ID NO 605
<211> LENGTH: 92
<212> TYPE: PRT
<213> ORGANISM: Macaca fascicularis

<400> SEQUENCE: 605

Ser Ala Ser Met His Asn Asn Ile Glu Lys Leu Asn Ser Val Gly Asn
1               5                   10                  15

Asp Leu Ser Arg Lys Met Ala Phe Phe Ser Arg Asp Phe Arg Leu Gly
            20                  25                  30

Phe Gly Ser Tyr Val Asp Lys Thr Val Ser Pro Tyr Ile Ser Ile His
        35                  40                  45

Pro Glu Arg Ile His Asn Gln Cys Ser Asp Tyr Asn Leu Asp Cys Met
50                  55                  60

Pro Pro His Gly Tyr Ile His Val Leu Ser Leu Thr Glu Asn Ile Thr
65                  70                  75                  80

Glu Phe Glu Lys Ala Val His Arg Gln Lys Ile Ser
                85                  90

<210> SEQ ID NO 606
<211> LENGTH: 92
<212> TYPE: PRT
<213> ORGANISM: Bos taurus

-continued

```
<400> SEQUENCE: 606

Ser Ala Ser Met His Asn Asn Ile Glu Lys Leu Asn Ser Val Gly Asn
1               5                   10                  15

Asp Leu Ser Arg Lys Met Ala Phe Phe Ser Arg Asp Phe Arg Leu Gly
            20                  25                  30

Phe Gly Ser Tyr Val Asp Lys Thr Val Ser Pro Tyr Ile Ser Ile His
        35                  40                  45

Pro Glu Arg Ile His Asn Gln Cys Ser Asp Tyr Asn Leu Asp Cys Met
    50                  55                  60

Pro Pro His Gly Tyr Ile His Val Leu Ser Leu Thr Glu Asn Ile Thr
65                  70                  75                  80

Glu Phe Glu Lys Ala Val His Arg Gln Lys Ile Ser
                85                  90

<210> SEQ ID NO 607
<211> LENGTH: 92
<212> TYPE: PRT
<213> ORGANISM: Unknown
<220> FEATURE:
<223> OTHER INFORMATION: Sus sp.

<400> SEQUENCE: 607

Ser Ala Ser Met His Asn Asn Ile Glu Lys Leu Asn Thr Val Gly Asn
1               5                   10                  15

Asp Leu Ser Arg Lys Met Ala Phe Phe Ser Arg Asp Phe Arg Leu Gly
            20                  25                  30

Phe Gly Ser Tyr Val Asp Lys Thr Val Ser Pro Tyr Ile Ser Ile His
        35                  40                  45

Pro Glu Arg Ile His Asn Gln Cys Ser Asp Tyr Asn Leu Asp Cys Met
    50                  55                  60

Pro Pro His Gly Tyr Ile His Val Leu Ser Leu Thr Glu Asn Ile Thr
65                  70                  75                  80

Glu Phe Glu Lys Ala Val His Arg Gln Lys Ile Ser
                85                  90

<210> SEQ ID NO 608
<211> LENGTH: 92
<212> TYPE: PRT
<213> ORGANISM: Equus ferus

<400> SEQUENCE: 608

Ser Ala Ser Met His Asn Asn Ile Glu Lys Leu Asn Ser Val Gly Asn
1               5                   10                  15

Asp Leu Ser Arg Lys Met Ala Phe Phe Ser Arg Asp Phe Arg Leu Gly
            20                  25                  30

Phe Gly Ser Tyr Val Asp Lys Thr Val Ser Pro Tyr Ile Ser Ile His
        35                  40                  45

Pro Glu Arg Ile His Asn Gln Cys Ser Asp Tyr Asn Leu Asp Cys Met
    50                  55                  60

Pro Pro His Gly Tyr Ile His Val Leu Ser Leu Thr Glu Asn Ile Thr
65                  70                  75                  80

Glu Phe Glu Lys Ala Val His Arg Gln Lys Ile Ser
                85                  90

<210> SEQ ID NO 609
<211> LENGTH: 92
<212> TYPE: PRT
<213> ORGANISM: Mus musculus
```

<400> SEQUENCE: 609

| Ser | Ala | Ser | Met | His | Asn | Asn | Ile | Glu | Lys | Leu | Asn | Ser | Val | Gly | Asn |
| 1 | | | | 5 | | | | | 10 | | | | | 15 | |

| Asp | Leu | Ser | Lys | Lys | Met | Ala | Leu | Tyr | Ser | Arg | Asp | Phe | Arg | Leu | Gly |
| | | | 20 | | | | | 25 | | | | | 30 | | |

| Phe | Gly | Ser | Tyr | Val | Asp | Lys | Thr | Val | Ser | Pro | Tyr | Ile | Ser | Ile | His |
| | | | 35 | | | | | 40 | | | | | 45 | | |

| Pro | Glu | Arg | Ile | His | Asn | Gln | Cys | Ser | Asp | Tyr | Asn | Leu | Asp | Cys | Met |
| | | 50 | | | | | 55 | | | | | 60 | | | |

| Pro | Pro | His | Gly | Tyr | Ile | His | Val | Leu | Ser | Leu | Thr | Glu | Asn | Ile | Thr |
| 65 | | | | | 70 | | | | | 75 | | | | | 80 |

| Glu | Phe | Glu | Lys | Ala | Val | His | Arg | Gln | Lys | Ile | Ser |
| | | | | 85 | | | | | 90 | | |

<210> SEQ ID NO 610
<211> LENGTH: 92
<212> TYPE: PRT
<213> ORGANISM: Unknown
<220> FEATURE:
<223> OTHER INFORMATION: Rattus sp.

<400> SEQUENCE: 610

| Ser | Ala | Ser | Met | His | Asn | Asn | Ile | Glu | Lys | Leu | Asn | Ser | Val | Gly | Asn |
| 1 | | | | 5 | | | | | 10 | | | | | 15 | |

| Asp | Leu | Ser | Lys | Lys | Met | Ala | Leu | Phe | Ser | His | Asp | Phe | Arg | Leu | Gly |
| | | | 20 | | | | | 25 | | | | | 30 | | |

| Phe | Gly | Ser | Tyr | Val | Asp | Lys | Thr | Val | Ser | Pro | Tyr | Ile | Ser | Ile | His |
| | | | 35 | | | | | 40 | | | | | 45 | | |

| Pro | Glu | Arg | Ile | His | Asn | Gln | Cys | Ser | Asp | Tyr | Asn | Leu | Asp | Cys | Met |
| | | 50 | | | | | 55 | | | | | 60 | | | |

| Pro | Pro | His | Gly | Tyr | Ile | His | Val | Leu | Ser | Leu | Thr | Glu | Asn | Ile | Thr |
| 65 | | | | | 70 | | | | | 75 | | | | | 80 |

| Glu | Phe | Glu | Lys | Ala | Val | His | Arg | Gln | Lys | Ile | Ser |
| | | | | 85 | | | | | 90 | | |

<210> SEQ ID NO 611
<211> LENGTH: 92
<212> TYPE: PRT
<213> ORGANISM: Unknown
<220> FEATURE:
<223> OTHER INFORMATION: Dasypus sp.

<400> SEQUENCE: 611

| Ser | Ala | Ser | Met | His | Asn | Asn | Ile | Glu | Lys | Leu | Asn | Ser | Val | Gly | Asn |
| 1 | | | | 5 | | | | | 10 | | | | | 15 | |

| Asp | Leu | Ser | Arg | Lys | Met | Ala | Phe | Phe | Ser | Leu | Asp | Phe | Arg | Leu | Gly |
| | | | 20 | | | | | 25 | | | | | 30 | | |

| Phe | Gly | Ser | Tyr | Val | Asp | Lys | Thr | Val | Ser | Pro | Tyr | Ile | Ser | Ile | His |
| | | | 35 | | | | | 40 | | | | | 45 | | |

| Pro | Glu | Arg | Ile | His | Asn | Gln | Cys | Ser | Asp | Tyr | Asn | Leu | Asp | Cys | Met |
| | | 50 | | | | | 55 | | | | | 60 | | | |

| Pro | Pro | His | Gly | Tyr | Ile | His | Val | Leu | Ser | Leu | Thr | Glu | Asn | Ile | Thr |
| 65 | | | | | 70 | | | | | 75 | | | | | 80 |

| Glu | Phe | Ala | Lys | Ala | Val | His | Arg | Gln | Lys | Ile | Ser |
| | | | | 85 | | | | | 90 | | |

<210> SEQ ID NO 612

<211> LENGTH: 92
<212> TYPE: PRT
<213> ORGANISM: Ornithorhynchus anatinus

<400> SEQUENCE: 612

Ser Ala Ser Met His Asn Asn Ile Glu Lys Leu Asn Ser Val Gly Asn
1               5                   10                  15

Asp Leu Ser Gln Lys Met Ala Asp Phe Thr Arg Asp Phe Arg Leu Gly
            20                  25                  30

Phe Gly Ser Tyr Val Asp Lys Thr Val Ser Pro Tyr Ile Ser Ile His
        35                  40                  45

Pro Gly Arg Ile Arg Asn Gln Cys Ser Gln Tyr Asp Leu Asp Cys Met
50                  55                  60

Pro Pro His Gly Tyr Ile His Val Leu Pro Leu Thr Glu Asn Val Thr
65                  70                  75                  80

Glu Phe Glu Lys Ala Val Asn Lys Gln Lys Ile Ser
                85                  90

<210> SEQ ID NO 613
<211> LENGTH: 9
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 613

Tyr Thr Phe Thr Asp Tyr Ser Met His
1               5

<210> SEQ ID NO 614
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 614

Arg Ile Asn Thr Glu Thr Gly Glu Pro Thr Phe Ala Asp Asp Phe Arg
1               5                   10                  15

Gly

<210> SEQ ID NO 615
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 615

Phe Tyr Tyr Gly Arg Asp Ser
1               5

<210> SEQ ID NO 616
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 616

```
Lys Ser Ser Gln Ser Leu Leu Asn Ser Arg Thr Arg Lys Asn Tyr Leu
1               5                   10                  15

Ala

<210> SEQ ID NO 617
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 617

Tyr Trp Ala Ser Thr Arg Glu Ser
1               5

<210> SEQ ID NO 618
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 618

Lys Gln Ser Tyr Asn Leu Leu Ser
1               5

<210> SEQ ID NO 619
<211> LENGTH: 26
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 619

Ser Ala Ser Met His Asn Asn Ile Glu Lys Leu Asn Ser Val Gly Asn
1               5                   10                  15

Asp Leu Ser Arg Lys Met Ala Phe Phe Ser
            20                  25

<210> SEQ ID NO 620
<211> LENGTH: 28
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 620

Thr Val Ser Pro Tyr Ile Ser Ile His Pro Glu Arg Ile His Asn Gln
1               5                   10                  15

Cys Ser Asp Tyr Asn Leu Asp Cys Met Pro Pro His
            20                  25

<210> SEQ ID NO 621
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 621

Asn Ile Thr Glu Phe Glu Lys Ala Val His Arg
```

```
1               5                   10
```

<210> SEQ ID NO 622
<211> LENGTH: 118
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 622

Lys Gln Asp Lys Ile Leu Ala Cys Ala Pro Leu Tyr His Trp Arg Thr
1               5                   10                  15

Glu Met Lys Gln Glu Arg Glu Pro Val Gly Thr Cys Phe Leu Gln Asp
            20                  25                  30

Gly Thr Lys Thr Val Glu Tyr Ala Pro Cys Arg Ser Gln Asp Ile Asp
        35                  40                  45

Ala Asp Gly Gln Gly Phe Cys Gln Gly Gly Phe Ser Ile Asp Phe Thr
    50                  55                  60

Lys Ala Asp Arg Val Leu Leu Gly Gly Pro Gly Ser Phe Tyr Trp Gln
65                  70                  75                  80

Gly Gln Leu Ile Ser Asp Gln Val Ala Glu Ile Val Ser Lys Tyr Asp
                85                  90                  95

Pro Asn Val Tyr Ser Ile Lys Tyr Asn Asn Gln Leu Ala Thr Arg Thr
            100                 105                 110

Ala Gln Ala Ile Phe Asp
        115

<210> SEQ ID NO 623
<211> LENGTH: 439
<212> TYPE: PRT
<213> ORGANISM: Homo sapiens

<400> SEQUENCE: 623

Phe Asn Leu Asp Val Asp Ser Pro Ala Glu Tyr Ser Gly Pro Glu Gly
1               5                   10                  15

Ser Tyr Phe Gly Phe Ala Val Asp Phe Phe Val Pro Ser Ala Ser Ser
            20                  25                  30

Arg Met Phe Leu Leu Val Gly Ala Pro Lys Ala Asn Thr Thr Gln Pro
        35                  40                  45

Gly Ile Val Glu Gly Gly Gln Val Leu Lys Cys Asp Trp Ser Ser Thr
    50                  55                  60

Arg Arg Cys Gln Pro Ile Glu Phe Asp Ala Thr Gly Asn Arg Asp Tyr
65                  70                  75                  80

Ala Lys Asp Asp Pro Leu Glu Phe Lys Ser His Gln Trp Phe Gly Ala
                85                  90                  95

Ser Val Arg Ser Lys Gln Asp Lys Ile Leu Ala Cys Ala Pro Leu Tyr
            100                 105                 110

His Trp Arg Thr Glu Met Lys Gln Glu Arg Glu Pro Val Gly Thr Cys
        115                 120                 125

Phe Leu Gln Asp Gly Thr Lys Thr Val Glu Tyr Ala Pro Cys Arg Ser
    130                 135                 140

Gln Asp Ile Asp Ala Asp Gly Gln Gly Phe Cys Gln Gly Gly Phe Ser
145                 150                 155                 160

Ile Asp Phe Thr Lys Ala Asp Arg Val Leu Leu Gly Gly Pro Gly Ser
                165                 170                 175

Phe Tyr Trp Gln Gly Gln Leu Ile Ser Asp Gln Val Ala Glu Ile Val

```
                180             185             190
Ser Lys Tyr Asp Pro Asn Val Tyr Ser Ile Lys Tyr Asn Asn Gln Leu
            195                 200                 205
Ala Thr Arg Thr Ala Gln Ala Ile Phe Asp Asp Ser Tyr Leu Gly Tyr
            210                 215                 220
Ser Val Ala Val Gly Asp Phe Asn Gly Asp Gly Ile Asp Asp Phe Val
225                 230                 235                 240
Ser Gly Val Pro Arg Ala Ala Arg Thr Leu Gly Met Val Tyr Ile Tyr
            245                 250                 255
Asp Gly Lys Asn Met Ser Ser Leu Tyr Asn Phe Thr Gly Glu Gln Met
            260                 265                 270
Ala Ala Tyr Phe Gly Phe Ser Val Ala Ala Thr Asp Ile Asn Gly Asp
            275                 280                 285
Asp Tyr Ala Asp Val Phe Ile Gly Ala Pro Leu Phe Met Asp Arg Gly
            290                 295                 300
Ser Asp Gly Lys Leu Gln Glu Val Gly Gln Val Ser Val Ser Leu Gln
305                 310                 315                 320
Arg Ala Ser Gly Asp Phe Gln Thr Thr Lys Leu Asn Gly Phe Glu Val
            325                 330                 335
Phe Ala Arg Phe Gly Ser Ala Ile Ala Pro Leu Gly Asp Leu Asp Gln
            340                 345                 350
Asp Gly Phe Asn Asp Ile Ala Ile Ala Ala Pro Tyr Gly Gly Glu Asp
            355                 360                 365
Lys Lys Gly Ile Val Tyr Ile Phe Asn Gly Arg Ser Thr Gly Leu Asn
            370                 375                 380
Ala Val Pro Ser Gln Ile Leu Glu Gly Gln Trp Ala Ala Arg Ser Met
385                 390                 395                 400
Pro Pro Ser Phe Gly Tyr Ser Met Lys Gly Ala Thr Asp Ile Asp Lys
            405                 410                 415
Asn Gly Tyr Pro Asp Leu Ile Val Gly Ala Phe Gly Val Asp Arg Ala
            420                 425                 430
Ile Leu Tyr Arg Ala Arg Pro
            435

<210> SEQ ID NO 624
<211> LENGTH: 122
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 624

Gln Val Gln Leu Gln Gln Ser Gly Ala Glu Leu Val Arg Pro Gly Thr
1               5                   10                  15
Ser Val Lys Val Ser Cys Lys Ala Ser Gly Tyr Ala Phe Thr Asn Tyr
            20                  25                  30
Leu Ile Glu Trp Val Lys Gln Arg Pro Gly Gln Gly Leu Glu Trp Ile
        35                  40                  45
Gly Val Ile Asn Pro Gly Thr Gly Gly Thr Asn Tyr Asn Lys Lys Phe
    50                  55                  60
Lys Val Lys Ala Thr Leu Thr Ala Asp Lys Ser Ser Ser Thr Ala Tyr
65                  70                  75                  80
Met Gln Leu Gly Gly Leu Thr Phe Asp Asp Ser Ala Val Tyr Phe Cys
                85                  90                  95
```

```
Ala Arg Glu Gly Asn Ala Arg Thr Tyr Tyr Ala Met Asp Tyr Trp
                100                 105                 110

Gly Gln Gly Thr Ser Val Thr Val Ser Ser
        115                 120
```

<210> SEQ ID NO 625
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 625

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr
            20                  25
```

<210> SEQ ID NO 626
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 626

```
Gln Val Gln Leu Gln Gln Ser Gly Ala Glu Leu Val Arg Pro Gly Ala
1               5                   10                  15

Ser Val Lys Val Ser Cys Lys Ala Ser Gly Tyr
            20                  25
```

<210> SEQ ID NO 627
<211> LENGTH: 27
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 627

```
Gln Val Gln Leu Gln Gln Ser Gly Ala Glu Leu Val Arg Pro Gly Thr
1               5                   10                  15

Ser Val Lys Val Pro Cys Lys Ala Ser Gly Tyr
            20                  25
```

<210> SEQ ID NO 628
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 628

```
Ala Phe Thr Asn Tyr Leu Ile Glu
1               5
```

<210> SEQ ID NO 629
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence -continued

```
<400> SEQUENCE: 629

Ala Phe Thr Asp Tyr Leu Ile Glu
1               5

<210> SEQ ID NO 630
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 630

Ala Phe Thr Asp Asn Leu Ile Glu
1               5

<210> SEQ ID NO 631
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 631

Ala Phe Thr Asp Tyr Leu Ile Gln
1               5

<210> SEQ ID NO 632
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 632

Trp Val Lys Gln Arg Pro Gly Gln Gly Leu Glu Trp Ile Gly
1               5                   10

<210> SEQ ID NO 633
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 633

Trp Val Arg Gln Arg Pro Gly Gln Gly Leu Glu Trp Ile Gly
1               5                   10

<210> SEQ ID NO 634
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 634

Val Ile Asn Pro Gly Thr Gly Gly Thr Asn Tyr Asn Lys Lys Phe Lys
1               5                   10                  15

Val
```

```
<210> SEQ ID NO 635
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 635

Val Ile Asn Pro Glu Thr Gly Gly Thr Asn Tyr Asn Ala Lys Phe Lys
1               5                   10                  15

Gly

<210> SEQ ID NO 636
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 636

Val Ile Asn Pro Glu Thr Gly Gly Thr Asn Tyr Asn Ala Lys Phe Arg
1               5                   10                  15

Gly

<210> SEQ ID NO 637
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 637

Lys Ala Thr Leu Thr Ala Asp Lys Ser Ser Ser Thr Ala Tyr Met Gln
1               5                   10                  15

Leu Gly Gly Leu Thr Phe Asp Asp Ser Ala Val Tyr Phe Cys Ala Arg
                20                  25                  30

<210> SEQ ID NO 638
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 638

Lys Ala Thr Leu Thr Ala Asp Lys Ser Ser Ser Ser Ala Tyr Met Gln
1               5                   10                  15

Leu Ser Ser Leu Thr Ser Gly Asp Ser Ala Val Tyr Phe Cys Ala Arg
                20                  25                  30

<210> SEQ ID NO 639
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 639

Lys Ala Thr Leu Thr Ala Asp Lys Ser Ser Ser Ser Val Tyr Met Gln
1               5                   10                  15
```

Leu Ser Ser Leu Thr Ser Gly Asp Ser Ala Val Tyr Phe Cys Ala Arg
            20                  25                  30

<210> SEQ ID NO 640
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 640

Lys Ala Thr Leu Thr Ala Asp Lys Ser Ser Ser Thr Ala Tyr Met Gln
1               5                   10                  15

Leu Ser Ser Leu Thr Ser Gly Asp Ser Ala Val Tyr Phe Cys Ala Arg
            20                  25                  30

<210> SEQ ID NO 641
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 641

Lys Ala Thr Leu Thr Ala Asp Lys Ser Ser Ser Ser Ala Tyr Met Gln
1               5                   10                  15

Leu Ser Gly Leu Thr Ser Gly Asp Ser Ala Val Tyr Phe Cys Ala Arg
            20                  25                  30

<210> SEQ ID NO 642
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 642

Lys Ala Thr Leu Thr Ala Asp Lys Ser Ser Ser Ser Ala Tyr Met Gln
1               5                   10                  15

Leu Ser Ser Leu Ser Ser Gly Asp Ser Ala Val Tyr Phe Cys Ala Arg
            20                  25                  30

<210> SEQ ID NO 643
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 643

Lys Ala Thr Leu Thr Ala Asp Lys Ser Ser Ser Ser Ala Tyr Met Gln
1               5                   10                  15

Leu Ser Gly Leu Thr Ser Gly Asp Ser Ala Val Tyr Phe Cys Ala Arg
            20                  25                  30

<210> SEQ ID NO 644
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence -continued

<400> SEQUENCE: 644

Arg Ala Thr Leu Thr Ala Asp Lys Ser Ser Ser Ala Tyr Met Gln
1               5                   10                  15

Leu Ser Ser Leu Thr Ser Gly Asp Ser Ala Val Tyr Phe Cys Ala Arg
            20                  25                  30

<210> SEQ ID NO 645
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 645

Lys Ala Thr Leu Thr Ala Asp Lys Ser Ser Ser Ala Tyr Met Gln
1               5                   10                  15

Leu Ser Ser Leu Thr Ser Asp Asp Ser Ala Val Tyr Phe Cys Ala Arg
            20                  25                  30

<210> SEQ ID NO 646
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 646

Lys Val Thr Leu Thr Ala Asp Lys Thr Ser Ser Ala Tyr Met Gln
1               5                   10                  15

Leu Ser Ser Leu Thr Ser Gly Asp Ser Ala Val Tyr Phe Cys Ala Arg
            20                  25                  30

<210> SEQ ID NO 647
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 647

Lys Val Thr Leu Thr Ala Asp Lys Ser Ser Ser Ala Tyr Met Gln
1               5                   10                  15

Leu Asn Ser Leu Thr Ser Gly Asp Ser Ala Val Tyr Phe Cys Ala Arg
            20                  25                  30

<210> SEQ ID NO 648
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 648

Lys Ala Thr Leu Thr Ala Asn Lys Ser Ser Ser Ala Tyr Met Gln
1               5                   10                  15

Leu Ser Ser Leu Thr Ser Gly Asp Ser Ala Val Tyr Phe Cys Ala Arg
            20                  25                  30

<210> SEQ ID NO 649

```
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 649

Lys Ala Thr Leu Thr Ala Asp Lys Ser Ser Ser Ser Ala Tyr Leu Gln
1               5                   10                  15
Leu Ser Ser Leu Thr Ser Gly Asp Ser Ala Val Tyr Phe Cys Ala Arg
            20                  25                  30

<210> SEQ ID NO 650
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 650

Arg Ala Thr Leu Thr Ala Asp Lys Ser Ser Ser Ser Ala Tyr Met Gln
1               5                   10                  15
Leu Ser Ser Leu Thr Ser Gly Asp Ser Ala Val Tyr Phe Cys Ala Arg
            20                  25                  30

<210> SEQ ID NO 651
<211> LENGTH: 13
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 651

Glu Gly Asn Ala Arg Thr Tyr Tyr Tyr Ala Met Asp Tyr
1               5                   10

<210> SEQ ID NO 652
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 652

Glu Ala Gly Asn Tyr Ile Tyr Ala Met Asp Tyr
1               5                   10

<210> SEQ ID NO 653
<211> LENGTH: 10
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 653

Ala Gly Asn Tyr Ile Tyr Ala Met Asp Tyr
1               5                   10

<210> SEQ ID NO 654
<211> LENGTH: 11
<212> TYPE: PRT
<213> ORGANISM: Unknown
```

```
<220> FEATURE:
<223> OTHER INFORMATION: Human (Homo sapiens), chimeric or humanized
      antibody peptide sequence

<400> SEQUENCE: 654

Glu Ala Gly Asn Tyr Ile Tyr Ala Met Asp Tyr
1               5                   10

<210> SEQ ID NO 655
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 655

Trp Gly Gln Gly Thr Ser Val Thr Val Ser Ser
1               5                   10

<210> SEQ ID NO 656
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 656

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Tyr
            20                  25                  30

Leu Ile Glu Trp Val Lys Gln Arg Pro Gly Gln Gly Leu Glu Trp Ile
        35                  40                  45

Gly Val Ile Asn Pro Glu Thr Gly Gly Thr Asn Tyr Asn Ala Lys Phe
    50                  55                  60

Lys Gly Lys Ala Thr Leu Thr Ala Asp Lys Ser Ser Ser Ser Ala Tyr
65                  70                  75                  80

Met Gln Leu Ser Ser Leu Thr Ser Gly Asp Ser Ala Val Tyr Phe Cys
                85                  90                  95

Ala Arg Glu Ala Gly Asn Tyr Ile Tyr Ala Met Asp Tyr Trp Gly Gln
            100                 105                 110

Gly Thr Ser Val Thr Val Ser Ser
        115                 120

<210> SEQ ID NO 657
<211> LENGTH: 119
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 657

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Tyr
            20                  25                  30

Leu Ile Glu Trp Val Lys Gln Arg Pro Gly Gln Gly Leu Glu Trp Ile
        35                  40                  45

Gly Val Ile Asn Pro Glu Thr Gly Gly Thr Asn Tyr Asn Ala Lys Phe
```

-continued

```
                50                  55                  60
Arg Gly Lys Ala Thr Leu Thr Ala Asp Lys Ser Ser Ser Ala Tyr
 65                  70                  75                  80

Met Gln Leu Ser Ser Leu Thr Ser Gly Asp Ser Ala Val Tyr Phe Cys
                 85                  90                  95

Ala Arg Ala Gly Asn Tyr Ile Tyr Ala Met Asp Tyr Trp Gly Gln Gly
            100                 105                 110

Thr Ser Val Thr Val Ser Ser
        115

<210> SEQ ID NO 658
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 658

Gln Val Gln Leu Gln Gln Ser Gly Ala Glu Leu Val Arg Pro Gly Ala
 1               5                  10                  15

Ser Val Lys Val Ser Cys Lys Ala Ser Gly Tyr Ala Phe Thr Asp Tyr
                20                  25                  30

Leu Ile Glu Trp Val Arg Gln Arg Pro Gly Gln Gly Leu Glu Trp Ile
             35                  40                  45

Gly Val Ile Asn Pro Glu Thr Gly Gly Thr Asn Tyr Asn Ala Lys Phe
         50                  55                  60

Arg Gly Lys Ala Thr Leu Thr Ala Asp Lys Ser Ser Ser Val Tyr
 65                  70                  75                  80

Met Gln Leu Ser Ser Leu Thr Ser Gly Asp Ser Ala Val Tyr Phe Cys
                 85                  90                  95

Ala Arg Glu Ala Gly Asn Tyr Ile Tyr Ala Met Asp Tyr Trp Gly Gln
            100                 105                 110

Gly Thr Ser Val Thr Val Ser Ser
        115                 120

<210> SEQ ID NO 659
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 659

Gln Val Gln Leu Gln Gln Ser Gly Ala Glu Leu Val Arg Pro Gly Thr
 1               5                  10                  15

Ser Val Lys Val Ser Cys Lys Ala Ser Gly Tyr Ala Phe Thr Asp Tyr
                20                  25                  30

Leu Ile Glu Trp Val Arg Gln Arg Pro Gly Gln Gly Leu Glu Trp Ile
             35                  40                  45

Gly Val Ile Asn Pro Glu Thr Gly Gly Thr Asn Tyr Asn Ala Lys Phe
         50                  55                  60

Arg Gly Lys Ala Thr Leu Thr Ala Asp Lys Ser Ser Ser Thr Ala Tyr
 65                  70                  75                  80

Met Gln Leu Ser Ser Leu Thr Ser Gly Asp Ser Ala Val Tyr Phe Cys
                 85                  90                  95

Ala Arg Glu Ala Gly Asn Tyr Ile Tyr Ala Met Asp Tyr Trp Gly Gln
```

```
                    100                 105                 110

Gly Thr Ser Val Thr Val Ser Ser
            115                 120

<210> SEQ ID NO 660
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 660

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Tyr
            20                  25                  30

Leu Ile Glu Trp Val Arg Gln Arg Pro Gly Gln Gly Leu Glu Trp Ile
        35                  40                  45

Gly Val Ile Asn Pro Glu Thr Gly Gly Thr Asn Tyr Asn Ala Lys Phe
    50                  55                  60

Arg Gly Lys Ala Thr Leu Thr Ala Asp Lys Ser Ser Ser Ser Ala Tyr
65                  70                  75                  80

Met Gln Leu Ser Gly Leu Thr Ser Gly Asp Ser Ala Val Tyr Phe Cys
                85                  90                  95

Ala Arg Glu Ala Gly Asn Tyr Ile Tyr Ala Met Asp Tyr Trp Gly Gln
            100                 105                 110

Gly Thr Ser Val Thr Val Ser Ser
            115                 120

<210> SEQ ID NO 661
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 661

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Asn
            20                  25                  30

Leu Ile Glu Trp Val Arg Gln Arg Pro Gly Gln Gly Leu Glu Trp Ile
        35                  40                  45

Gly Val Ile Asn Pro Glu Thr Gly Gly Thr Asn Tyr Asn Ala Lys Phe
    50                  55                  60

Arg Gly Lys Ala Thr Leu Thr Ala Asp Lys Ser Ser Ser Ser Ala Tyr
65                  70                  75                  80

Met Gln Leu Ser Ser Leu Thr Ser Gly Asp Ser Ala Val Tyr Phe Cys
                85                  90                  95

Ala Arg Glu Ala Gly Asn Tyr Ile Tyr Ala Met Asp Tyr Trp Gly Gln
            100                 105                 110

Gly Thr Ser Val Thr Val Ser Ser
            115                 120

<210> SEQ ID NO 662
<211> LENGTH: 120
<212> TYPE: PRT
```

-continued

<213> ORGANISM: Unknown
<220> FEATURE:
<223> OTHER INFORMATION: Human (Homo sapiens), chimeric or humanized
      antibody peptide sequence

<400> SEQUENCE: 662

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Tyr
                20                  25                  30

Leu Ile Glu Trp Val Lys Gln Arg Pro Gly Gln Gly Leu Glu Trp Ile
            35                  40                  45

Gly Val Ile Asn Pro Glu Thr Gly Gly Thr Asn Tyr Asn Ala Lys Phe
        50                  55                  60

Arg Gly Lys Ala Thr Leu Thr Ala Asp Lys Ser Ser Ser Ser Ala Tyr
65                  70                  75                  80

Met Gln Leu Ser Ser Leu Ser Ser Gly Asp Ser Ala Val Tyr Phe Cys
                85                  90                  95

Ala Arg Glu Ala Gly Asn Tyr Ile Tyr Ala Met Asp Tyr Trp Gly Gln
                100                 105                 110

Gly Thr Ser Val Thr Val Ser Ser
            115                 120

<210> SEQ ID NO 663
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 663

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Tyr
                20                  25                  30

Leu Ile Glu Trp Val Arg Gln Arg Pro Gly Gln Gly Leu Glu Trp Ile
            35                  40                  45

Gly Val Ile Asn Pro Glu Thr Gly Gly Thr Asn Tyr Asn Ala Lys Phe
        50                  55                  60

Arg Gly Lys Ala Thr Leu Thr Ala Asp Lys Ser Ser Ser Ser Ala Tyr
65                  70                  75                  80

Met Gln Leu Ser Gly Leu Thr Ser Gly Asp Ser Ala Val Tyr Phe Cys
                85                  90                  95

Ala Arg Glu Ala Gly Asn Tyr Ile Tyr Ala Met Asp Tyr Trp Gly Gln
                100                 105                 110

Gly Thr Ser Val Thr Val Ser Ser
            115                 120

<210> SEQ ID NO 664
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 664

Gln Val Gln Leu Gln Gln Ser Gly Ala Glu Leu Val Arg Pro Gly Thr
1               5                   10                  15

```
Ser Val Lys Val Ser Cys Lys Ala Ser Gly Tyr Ala Phe Thr Asp Tyr
            20                  25                  30

Leu Ile Glu Trp Val Arg Gln Arg Pro Gly Gln Gly Leu Glu Trp Ile
        35                  40                  45

Gly Val Ile Asn Pro Glu Thr Gly Gly Thr Asn Tyr Asn Ala Lys Phe
    50                  55                  60

Arg Gly Arg Ala Thr Leu Thr Ala Asp Lys Ser Ser Ser Ser Ala Tyr
65                  70                  75                  80

Met Gln Leu Ser Ser Leu Thr Ser Gly Asp Ser Ala Val Tyr Phe Cys
                85                  90                  95

Ala Arg Glu Ala Gly Asn Tyr Ile Tyr Ala Met Asp Tyr Trp Gly Gln
            100                 105                 110

Gly Thr Ser Val Thr Val Ser Ser
            115                 120

<210> SEQ ID NO 665
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 665

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Tyr
            20                  25                  30

Leu Ile Glu Trp Val Arg Gln Arg Pro Gly Gln Gly Leu Glu Trp Ile
        35                  40                  45

Gly Val Ile Asn Pro Glu Thr Gly Gly Thr Asn Tyr Asn Ala Lys Phe
    50                  55                  60

Arg Gly Lys Ala Thr Leu Thr Ala Asp Lys Ser Ser Gly Ser Ala Tyr
65                  70                  75                  80

Met Gln Leu Ser Ser Leu Thr Ser Gly Asp Ser Ala Val Tyr Phe Cys
                85                  90                  95

Ala Arg Glu Ala Gly Asn Tyr Ile Tyr Ala Met Asp Tyr Trp Gly Gln
            100                 105                 110

Gly Thr Ser Val Thr Val Ser Ser
            115                 120

<210> SEQ ID NO 666
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 666

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Tyr
            20                  25                  30

Leu Ile Glu Trp Val Arg Gln Arg Pro Gly Gln Gly Leu Glu Trp Ile
        35                  40                  45

Gly Val Ile Asn Pro Glu Thr Gly Gly Thr Asn Tyr Asn Ala Lys Phe
    50                  55                  60
```

```
Arg Gly Lys Ala Thr Leu Thr Ala Asp Lys Ser Ser Ser Ala Tyr
 65                  70                  75                  80

Met Gln Leu Ser Ser Leu Thr Ser Asp Asp Ser Ala Val Tyr Phe Cys
                 85                  90                  95

Ala Arg Glu Ala Gly Asn Tyr Ile Tyr Ala Met Asp Tyr Trp Gly Gln
            100                 105                 110

Gly Thr Ser Val Thr Val Ser Ser
        115                 120

<210> SEQ ID NO 667
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 667

Gln Val Gln Leu Gln Gln Ser Gly Ala Glu Leu Val Arg Pro Gly Thr
 1               5                  10                  15

Ser Val Lys Val Ser Cys Lys Ala Ser Gly Tyr Ala Phe Thr Asp Tyr
                20                  25                  30

Leu Ile Glu Trp Val Arg Gln Arg Pro Gly Gln Gly Leu Glu Trp Ile
            35                  40                  45

Gly Val Ile Asn Pro Glu Thr Gly Gly Thr Asn Tyr Asn Ala Lys Phe
        50                  55                  60

Arg Gly Lys Val Thr Leu Thr Ala Asp Lys Ser Ser Ser Ala Tyr
 65                  70                  75                  80

Met Gln Leu Ser Ser Leu Thr Ser Gly Asp Ser Ala Val Tyr Phe Cys
                 85                  90                  95

Ala Arg Glu Ala Gly Asn Tyr Ile Tyr Ala Met Asp Tyr Trp Gly Gln
            100                 105                 110

Gly Thr Ser Val Thr Val Ser Ser
        115                 120

<210> SEQ ID NO 668
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 668

Gln Val Gln Leu Gln Gln Ser Gly Ala Glu Leu Val Arg Pro Gly Thr
 1               5                  10                  15

Ser Val Lys Val Ser Cys Lys Ala Ser Gly Tyr Ala Phe Thr Asp Tyr
                20                  25                  30

Leu Ile Glu Trp Val Arg Gln Arg Pro Gly Gln Gly Leu Glu Trp Ile
            35                  40                  45

Gly Val Ile Asn Pro Glu Thr Gly Gly Thr Asn Tyr Asn Ala Lys Phe
        50                  55                  60

Arg Gly Lys Val Thr Leu Thr Ala Asp Lys Ser Ser Ser Ala Tyr
 65                  70                  75                  80

Met Gln Leu Asn Ser Leu Thr Ser Gly Asp Ser Ala Val Tyr Phe Cys
                 85                  90                  95

Ala Arg Glu Ala Gly Asn Tyr Ile Tyr Ala Met Asp Tyr Trp Gly Gln
            100                 105                 110
```

Gly Thr Ser Val Thr Val Ser Ser
        115                 120

<210> SEQ ID NO 669
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 669

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Tyr
                20                  25                  30

Leu Ile Glu Trp Val Arg Gln Arg Pro Gly Gln Gly Leu Glu Trp Ile
            35                  40                  45

Gly Val Ile Asn Pro Glu Thr Gly Gly Thr Asn Tyr Asn Ala Lys Phe
        50                  55                  60

Arg Gly Arg Ala Thr Leu Thr Ala Asp Lys Ser Ser Ser Ser Ala Tyr
65                  70                  75                  80

Met Gln Leu Ser Ser Leu Thr Ser Gly Asp Ser Ala Val Tyr Phe Cys
                85                  90                  95

Ala Arg Glu Ala Gly Asn Tyr Ile Tyr Ala Met Asp Tyr Trp Gly Gln
                100                 105                 110

Gly Thr Ser Val Thr Val Ser Ser
        115                 120

<210> SEQ ID NO 670
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 670

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Tyr
                20                  25                  30

Leu Ile Glu Trp Val Arg Gln Arg Pro Gly Gln Gly Leu Glu Trp Ile
            35                  40                  45

Gly Val Ile Asn Pro Glu Thr Gly Gly Thr Asn Tyr Asn Ala Lys Phe
        50                  55                  60

Arg Gly Lys Val Thr Leu Thr Ala Asp Lys Thr Ser Ser Ser Ala Tyr
65                  70                  75                  80

Met Gln Leu Ser Ser Leu Thr Ser Gly Asp Ser Ala Val Tyr Phe Cys
                85                  90                  95

Ala Arg Glu Ala Gly Asn Tyr Ile Tyr Ala Met Asp Tyr Trp Gly Gln
                100                 105                 110

Gly Thr Ser Val Thr Val Ser Ser
        115                 120

<210> SEQ ID NO 671
<211> LENGTH: 120
<212> TYPE: PRT
<213> ORGANISM: Unknown

```
<220> FEATURE:
<223> OTHER INFORMATION: Human (Homo sapiens), chimeric or humanized
      antibody peptide sequence

<400> SEQUENCE: 671

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Tyr
                20                  25                  30

Leu Ile Glu Trp Val Lys Gln Arg Pro Gly Gln Gly Leu Glu Trp Ile
            35                  40                  45

Gly Val Ile Asn Pro Glu Thr Gly Gly Thr Asn Tyr Asn Ala Lys Phe
        50                  55                  60

Arg Gly Arg Ala Thr Leu Thr Ala Asp Lys Ser Ser Ser Ser Ala Tyr
65                  70                  75                  80

Met Gln Leu Ser Ser Leu Thr Ser Gly Asp Ser Ala Val Tyr Phe Cys
                85                  90                  95

Ala Arg Glu Ala Gly Asn Tyr Ile Tyr Ala Met Asp Tyr Trp Gly Gln
            100                 105                 110

Gly Thr Ser Val Thr Val Ser Ser
        115                 120

<210> SEQ ID NO 672
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 672

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Tyr
                20                  25                  30

Leu Ile Gln Trp Val Lys Gln Arg Pro Gly Gln Gly Leu Glu Trp Ile
            35                  40                  45

Gly Val Ile Asn Pro Glu Thr Gly Gly Thr Asn Tyr Asn Ala Lys Phe
        50                  55                  60

Arg Gly Lys Ala Thr Leu Thr Ala Asp Lys Ser Ser Ser Ser Ala Tyr
65                  70                  75                  80

Met Gln Leu Ser Ser Leu Thr Ser Gly Asp Ser Ala Val Tyr Phe Cys
                85                  90                  95

Ala Arg Glu Ala Gly Asn Tyr Ile Tyr Ala Met Asp Tyr Trp Gly Gln
            100                 105                 110

Gly Thr Ser Val Thr Val Ser Ser
        115                 120

<210> SEQ ID NO 673
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 673

Gln Val Gln Leu Gln Gln Ser Gly Ala Glu Leu Val Arg Pro Gly Thr
1               5                   10                  15
```

```
Ser Val Arg Val Ser Cys Lys Ala Ser Gly Tyr Ala Phe Thr Asp Tyr
            20                  25                  30

Leu Ile Gln Trp Val Lys Gln Arg Pro Gly Gln Gly Leu Glu Trp Ile
        35                  40                  45

Gly Val Ile Asn Pro Glu Thr Gly Gly Thr Asn Tyr Asn Ala Lys Phe
    50                  55                  60

Arg Gly Lys Ala Thr Leu Thr Ala Asn Lys Ser Ser Ser Ser Ala Tyr
65                  70                  75                  80

Met Gln Leu Ser Ser Leu Thr Ser Gly Asp Ser Ala Val Tyr Phe Cys
                85                  90                  95

Ala Arg Glu Ala Gly Asn Tyr Ile Tyr Ala Met Asp Tyr Trp Gly Gln
            100                 105                 110

Gly Thr Ser Val Thr Val Ser Ser
        115                 120

<210> SEQ ID NO 674
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 674

Gln Val Gln Leu Gln Gln Ser Gly Ala Glu Leu Val Arg Pro Gly Thr
1               5                   10                  15

Ser Val Lys Val Pro Cys Lys Ala Ser Gly Tyr Ala Phe Thr Asp Tyr
            20                  25                  30

Leu Ile Gln Trp Val Lys Gln Arg Pro Gly Gln Gly Leu Glu Trp Ile
        35                  40                  45

Gly Val Ile Asn Pro Glu Thr Gly Gly Thr Asn Tyr Asn Ala Lys Phe
    50                  55                  60

Arg Gly Lys Ala Thr Leu Thr Ala Asp Lys Ser Ser Ser Ser Ala Tyr
65                  70                  75                  80

Met Gln Leu Ser Ser Leu Thr Ser Gly Asp Ser Ala Val Tyr Phe Cys
                85                  90                  95

Ala Arg Glu Ala Gly Asn Tyr Ile Tyr Ala Met Asp Tyr Trp Gly Gln
            100                 105                 110

Gly Thr Ser Val Thr Val Ser Ser
        115                 120

<210> SEQ ID NO 675
<211> LENGTH: 120
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 675

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Tyr
            20                  25                  30

Leu Ile Glu Trp Val Lys Gln Arg Pro Gly Gln Gly Leu Glu Trp Ile
        35                  40                  45

Gly Val Ile Asn Pro Glu Thr Gly Gly Thr Asn Tyr Asn Ala Lys Phe
    50                  55                  60
```

```
Arg Gly Lys Ala Thr Leu Thr Ala Asp Lys Ser Ser Ser Ala Tyr
 65                  70                  75                  80

Met Gln Leu Ser Ser Leu Thr Ser Gly Asp Ser Ala Val Tyr Phe Cys
                 85                  90                  95

Ala Arg Glu Ala Gly Asn Tyr Ile Tyr Ala Met Asp Tyr Trp Gly Gln
            100                 105                 110

Gly Thr Ser Val Thr Val Ser Ser
        115                 120
```

<210> SEQ ID NO 676
<211> LENGTH: 120
<212> TYPE: PRT
<213> ORGANISM: Unknown
<220> FEATURE:
<223> OTHER INFORMATION: Human (Homo sapiens), chimeric or humanized
    antibody peptide sequence

<400> SEQUENCE: 676

```
Gln Val Gln Leu Gln Gln Ser Gly Ala Glu Leu Val Arg Pro Gly Thr
  1               5                  10                  15

Ser Val Lys Val Ser Cys Lys Ala Ser Gly Tyr Ala Phe Thr Asp Tyr
                 20                  25                  30

Leu Ile Gln Trp Val Lys Gln Arg Pro Gly Gln Gly Leu Glu Trp Ile
             35                  40                  45

Gly Val Ile Asn Pro Glu Thr Gly Gly Thr Asn Tyr Asn Ala Lys Phe
         50                  55                  60

Arg Gly Lys Ala Thr Leu Thr Ala Asp Lys Ser Ser Ser Ala Tyr
 65                  70                  75                  80

Leu Gln Leu Ser Ser Leu Thr Ser Gly Asp Ser Ala Val Tyr Phe Cys
                 85                  90                  95

Ala Arg Glu Ala Gly Asn Tyr Ile Tyr Ala Met Asp Tyr Trp Gly Gln
            100                 105                 110

Gly Thr Ser Val Thr Val Ser Ser
        115                 120
```

<210> SEQ ID NO 677
<211> LENGTH: 120
<212> TYPE: PRT
<213> ORGANISM: Unknown
<220> FEATURE:
<223> OTHER INFORMATION: Human (Homo sapiens), chimeric or humanized
    antibody peptide sequence

<400> SEQUENCE: 677

```
Gln Val Gln Leu Gln Gln Ser Gly Ala Glu Leu Val Arg Pro Gly Thr
  1               5                  10                  15

Ser Val Lys Val Ser Cys Lys Ala Ser Gly Tyr Ala Phe Thr Asp Tyr
                 20                  25                  30

Leu Ile Gln Trp Val Lys Gln Arg Pro Gly Gln Gly Leu Glu Trp Ile
             35                  40                  45

Gly Val Ile Asn Pro Glu Thr Gly Gly Thr Asn Tyr Asn Ala Lys Phe
         50                  55                  60

Arg Gly Lys Ala Thr Leu Thr Ala Asp Lys Ser Ser Ser Ala Tyr
 65                  70                  75                  80

Met Gln Leu Ser Ser Leu Thr Ser Gly Asp Ser Ala Val Tyr Phe Cys
                 85                  90                  95

Ala Arg Glu Ala Gly Asn Tyr Ile Tyr Ala Met Asp Tyr Trp Gly Gln
            100                 105                 110
```

Gly Thr Ser Val Thr Val Ser Ser
         115                 120

<210> SEQ ID NO 678
<211> LENGTH: 108
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 678

Asp Ile Gln Met Thr Gln Ser Pro Ala Ser Leu Ser Ala Ser Val Gly
1               5                   10                  15

Glu Thr Val Thr Ile Thr Cys Arg Ala Ser Val Asn Ile Tyr Ser Tyr
            20                  25                  30

Leu Val Trp Tyr Gln Gln Lys Gln Gly Lys Ser Pro Gln Leu Leu Val
        35                  40                  45

His Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Gly Thr Pro Tyr
                85                  90                  95

Thr Phe Gly Gly Gly Thr Lys Leu Glu Ile Lys Ala
            100                 105

<210> SEQ ID NO 679
<211> LENGTH: 108
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 679

Asp Ile Glu Met Thr Gln Thr Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Val Trp Tyr Gln Gln Lys Gln Gly Lys Ser Pro Gln Val Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Asn Gly Thr Pro Tyr
                85                  90                  95

Thr Phe Gly Gly Gly Thr Lys Leu Glu Ile Lys Ala
            100                 105

<210> SEQ ID NO 680
<211> LENGTH: 108
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 680

Asp Ile Val Met Thr Gln Ser Pro Ala Ser Leu Ser Ala Ser Val Gly

```
                1               5                  10                  15
        Glu Thr Val Thr Ile Thr Cys Arg Ala Ser Val Asn Ile Tyr Ser Tyr
                        20                  25                  30

Leu Val Trp Tyr Gln Gln Lys Gln Gly Lys Ser Pro Gln Leu Leu Val
                    35                  40                  45

His Asn Ala Lys Thr Leu Ala Glu Gly Val Pro Ser Arg Phe Ser Gly
                    50                  55                  60

Ser Gly Ser Gly Thr Gln Phe Ser Leu Lys Ile Asn Ser Leu Gln Pro
        65                  70                  75                  80

Glu Asp Phe Gly Ser Tyr Tyr Cys Gln His His Gly Thr Pro Tyr
                            85                  90                  95

Thr Phe Gly Gly Gly Thr Lys Leu Glu Ile Lys Ala
                        100                 105
```

<210> SEQ ID NO 681
<211> LENGTH: 108
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 681

```
        Asp Ile Val Met Thr Gln Ser Pro Ala Ser Leu Ser Ala Ser Val Gly
        1               5                  10                  15

Glu Thr Val Thr Ile Thr Cys Arg Ala Ser Val Asn Ile Tyr Ser Tyr
                        20                  25                  30

Leu Val Trp Tyr Gln Gln Lys Gln Gly Lys Ser Pro Gln Leu Leu Val
                    35                  40                  45

His Asn Ala Lys Thr Leu Ala Glu Gly Val Pro Ser Arg Phe Ser Gly
                    50                  55                  60

Ser Gly Ser Gly Thr Gln Phe Ser Leu Lys Ile Asn Ser Leu Gln Pro
        65                  70                  75                  80

Glu Asp Phe Gly Ser Tyr Tyr Cys Gln His His Gly Thr Pro Tyr
                            85                  90                  95

Thr Phe Gly Gly Gly Thr Lys Leu Glu Ile Lys Ala
                        100                 105
```

<210> SEQ ID NO 682
<211> LENGTH: 108
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 682

```
        Asp Ile Val Met Thr Gln Ser Pro Ala Ser Leu Ser Ala Ser Val Gly
        1               5                  10                  15

Glu Thr Val Thr Ile Thr Cys Arg Ala Ser Val Asn Ile Tyr Ser Tyr
                        20                  25                  30

Leu Val Trp Tyr Gln Gln Lys Gln Gly Lys Ser Pro Gln Leu Leu Val
                    35                  40                  45

His Asn Ala Lys Thr Leu Ala Glu Gly Val Pro Ser Arg Phe Ser Gly
                    50                  55                  60

Ser Gly Ser Gly Thr Gln Phe Ser Leu Lys Ile Asn Ser Val Gln Pro
        65                  70                  75                  80

Glu Asp Phe Gly Ser Tyr Tyr Cys Gln His His Gly Thr Pro Tyr
```

```
                    85                  90                  95

Thr Phe Gly Gly Gly Thr Lys Leu Glu Ile Lys Ala
            100                 105

<210> SEQ ID NO 683
<211> LENGTH: 108
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 683

His Ile Val Met Thr Gln Ser Pro Ala Ser Leu Ser Ala Ser Val Gly
1               5                   10                  15

Glu Thr Val Thr Ile Thr Cys Arg Ala Ser Val Asn Ile Tyr Ser Tyr
            20                  25                  30

Leu Val Trp Tyr Gln Gln Lys Gln Gly Lys Ser Pro Gln Leu Leu Val
        35                  40                  45

His Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Gly Thr Pro Tyr
                85                  90                  95

Thr Phe Gly Gly Gly Thr Lys Leu Glu Ile Lys Ala
            100                 105

<210> SEQ ID NO 684
<211> LENGTH: 108
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 684

Asp Ile Val Met Thr Gln Ser Pro Ala Ser Leu Ser Ala Ser Val Gly
1               5                   10                  15

Glu Thr Val Thr Ile Thr Cys Arg Ala Ser Val Asn Ile Tyr Ser Tyr
            20                  25                  30

Leu Val Trp Tyr Gln Gln Lys Gln Gly Lys Ser Pro Gln Leu Leu Val
        35                  40                  45

His Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Val Gly Ser Tyr Tyr Cys Gln His His Gly Thr Pro Tyr
                85                  90                  95

Thr Phe Gly Gly Gly Thr Lys Leu Glu Ile Lys Ala
            100                 105

<210> SEQ ID NO 685
<211> LENGTH: 108
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 685
```

-continued

Asp Ile Val Met Thr Gln Ser Pro Ala Ser Leu Ser Ala Ser Val Gly
1               5                   10                  15

Glu Thr Val Thr Ile Thr Cys Arg Ala Ser Val Asn Ile Tyr Ser Tyr
                20                  25                  30

Leu Val Trp Tyr Gln Gln Lys Gln Gly Lys Ser Pro Gln Leu Leu Val
            35                  40                  45

His Asn Ala Lys Thr Leu Ala Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His His Gly Thr Pro Tyr
                85                  90                  95

Thr Phe Gly Gly Gly Thr Lys Leu Glu Ile Lys Ala
                100                 105

<210> SEQ ID NO 686
<211> LENGTH: 108
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 686

Asp Ile Val Met Thr Gln Ser Pro Ala Ser Leu Ser Ala Ser Val Gly
1               5                   10                  15

Glu Thr Val Thr Ile Thr Cys Arg Ala Ser Val Asn Ile Tyr Ser Tyr
                20                  25                  30

Leu Val Trp Tyr Gln Gln Lys Gln Gly Lys Ser Pro Gln Leu Leu Val
            35                  40                  45

His Asn Ala Lys Thr Leu Ala Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His His Gly Thr Pro Tyr
                85                  90                  95

Thr Phe Gly Gly Gly Thr Lys Leu Glu Ile Lys Ala
                100                 105

<210> SEQ ID NO 687
<211> LENGTH: 108
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 687

Asp Ile Val Met Thr Gln Ser Pro Ala Ser Leu Ser Ala Ser Val Gly
1               5                   10                  15

Glu Thr Val Thr Ile Thr Cys Arg Ala Ser Val Asn Ile Tyr Ser Tyr
                20                  25                  30

Leu Val Trp Tyr Gln Gln Lys Gln Gly Lys Ser Pro Gln Leu Leu Val
            35                  40                  45

His Asn Ala Lys Thr Leu Ala Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Gly Thr Pro Tyr
                85                  90                  95

Thr Phe Gly Gly Gly Thr Lys Leu Glu Ile Lys Arg
            100                 105

<210> SEQ ID NO 688
<211> LENGTH: 108
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 688

Asp Ile Glu Met Thr Gln Thr Pro Ala Ser Leu Ser Ala Ser Val Gly
1               5                   10                  15

Glu Thr Val Thr Ile Thr Cys Arg Ala Ser Val Asn Ile Tyr Ser Tyr
                20                  25                  30

Leu Val Trp Tyr Gln Gln Lys Gln Gly Lys Ser Pro Gln Leu Leu Val
            35                  40                  45

His Asn Ala Lys Thr Leu Ala Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Gly Thr Pro Tyr
                85                  90                  95

Thr Phe Gly Gly Gly Thr Lys Leu Glu Ile Lys Arg
            100                 105

<210> SEQ ID NO 689
<211> LENGTH: 108
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 689

Asp Ile Val Met Thr Gln Ser Pro Ala Ser Leu Ser Ala Ser Val Gly
1               5                   10                  15

Glu Thr Val Thr Ile Thr Cys Arg Ala Ser Val Asn Ile Tyr Ser Tyr
                20                  25                  30

Leu Val Trp Tyr Gln Gln Lys Gln Gly Lys Ser Pro Gln Leu Leu Val
            35                  40                  45

His Asn Ala Lys Thr Leu Ala Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Gly Thr Pro Tyr
                85                  90                  95

Thr Phe Gly Gly Gly Thr Lys Leu Glu Ile Lys Ala
            100                 105

<210> SEQ ID NO 690
<211> LENGTH: 108
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 690

Asp Ile Val Val Thr Gln Ser Pro Ala Ser Leu Ser Ala Ser Val Gly
1               5                   10                  15

Glu Thr Val Thr Ile Thr Cys Arg Ala Ser Val Asn Ile Tyr Ser Tyr
            20                  25                  30

Leu Val Trp Tyr Gln Gln Lys Gln Gly Lys Ser Pro Gln Leu Leu Val
        35                  40                  45

His Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Gly Thr Pro Tyr
                85                  90                  95

Thr Phe Gly Gly Gly Thr Lys Leu Glu Ile Lys Ala
            100                 105

<210> SEQ ID NO 691
<211> LENGTH: 108
<212> TYPE: PRT
<213> ORGANISM: Unknown
<220> FEATURE:
<223> OTHER INFORMATION: Human (Homo sapiens), chimeric or humanized antibody peptide sequence

<400> SEQUENCE: 691

Asp Ile Val Met Thr Gln Ser Pro Ala Phe Leu Ser Ala Ser Val Gly
1               5                   10                  15

Glu Thr Val Thr Ile Thr Cys Arg Ala Ser Val Asn Ile Tyr Ser Tyr
            20                  25                  30

Leu Val Trp Tyr Gln Gln Lys Gly Lys Ser Pro Gln Leu Leu Val
        35                  40                  45

His Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Gly Thr Pro Tyr
                85                  90                  95

Thr Phe Gly Gly Gly Thr Lys Leu Glu Ile Lys Arg
            100                 105

<210> SEQ ID NO 692
<211> LENGTH: 23
<212> TYPE: PRT
<213> ORGANISM: Unknown
<220> FEATURE:
<223> OTHER INFORMATION: Human (Homo sapiens), chimeric or humanized antibody peptide sequence

<400> SEQUENCE: 692

Asp Ile Gln Met Thr Gln Ser Pro Ala Ser Leu Ser Ala Ser Val Gly
1               5                   10                  15

Glu Thr Val Thr Ile Thr Cys
            20

<210> SEQ ID NO 693
<211> LENGTH: 11
<212> TYPE: PRT
<213> ORGANISM: Unknown
<220> FEATURE:

```
<223> OTHER INFORMATION: Human (Homo sapiens), chimeric or humanized
      antibody peptide sequence

<400> SEQUENCE: 693

Arg Ala Ser Val Asn Ile Tyr Ser Tyr Leu Val
1               5                   10

<210> SEQ ID NO 694
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 694

Trp Tyr Gln Gln Lys Gln Gly Lys Ser Pro Gln Leu Leu Val His
1               5                   10                  15

<210> SEQ ID NO 695
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 695

Asn Ala Lys Thr Leu Ala Glu
1               5

<210> SEQ ID NO 696
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 696

Gly Val Pro Ser Arg Phe Ser Gly Ser Gly Ser Gly Thr Gln Phe Ser
1               5                   10                  15

Leu Lys Ile Asn Ser Leu Gln Pro Glu Asp Phe Gly Ser Tyr Tyr Cys
            20                  25                  30

<210> SEQ ID NO 697
<211> LENGTH: 9
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 697

Gln His His His Gly Thr Pro Tyr Thr
1               5

<210> SEQ ID NO 698
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 698

Phe Gly Gly Gly Thr Lys Leu Glu Ile Lys Ala
```

```
1               5                   10
```

<210> SEQ ID NO 699
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 699

```
Asp Ile Glu Met Thr Gln Thr Pro Ala Ser Leu Ser Ala Ser Val Gly
1               5                   10                  15

Glu Thr Val Thr Ile Thr Cys
            20
```

<210> SEQ ID NO 700
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 700

```
Arg Ala Ser Glu Asn Ile Tyr Ser Tyr Leu Val
1               5                   10
```

<210> SEQ ID NO 701
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 701

```
Trp Tyr Gln Gln Lys Gln Gly Lys Ser Pro Gln Val Leu Val Tyr
1               5                   10                  15
```

<210> SEQ ID NO 702
<211> LENGTH: 9
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 702

```
Gln His His Asn Gly Thr Pro Tyr Thr
1               5
```

<210> SEQ ID NO 703
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 703

```
Asp Ile Val Met Thr Gln Ser Pro Ala Ser Leu Ser Ala Ser Val Gly
1               5                   10                  15

Glu Thr Val Thr Ile Thr Cys
            20
```

```
<210> SEQ ID NO 704
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 704

His Ile Val Met Thr Gln Ser Pro Ala Ser Leu Ser Ala Ser Val Gly
1               5                   10                  15

Glu Thr Val Thr Ile Thr Cys
            20

<210> SEQ ID NO 705
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 705

Asp Ile Val Val Thr Gln Ser Pro Ala Ser Leu Ser Ala Ser Val Gly
1               5                   10                  15

Glu Thr Val Thr Ile Thr Cys
            20

<210> SEQ ID NO 706
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 706

Phe Gly Gly Gly Thr Lys Leu Glu Ile Lys Arg
1               5                   10

<210> SEQ ID NO 707
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 707

Asp Tyr Ser Met His
1               5

<210> SEQ ID NO 708
<211> LENGTH: 6
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 708

Ala Ser Thr Arg Glu Ser
1               5

<210> SEQ ID NO 709
<211> LENGTH: 10
<212> TYPE: PRT
```

```
<213> ORGANISM: Unknown
<220> FEATURE:
<223> OTHER INFORMATION: Human (Homo sapiens), chimeric or humanized
      antibody peptide sequence

<400> SEQUENCE: 709

Gly Arg Gly Asp Leu Gly Arg Leu Lys Lys
1               5                   10

<210> SEQ ID NO 710
<211> LENGTH: 6
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 710

Gly Arg Gly Asp Ser Pro
1               5

<210> SEQ ID NO 711
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 711

Ala Lys Gln Arg Gly Asp Val
1               5

<210> SEQ ID NO 712
<211> LENGTH: 9
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 712

Arg Gly Asp Leu Gly Arg Leu Lys Lys
1               5

<210> SEQ ID NO 713
<211> LENGTH: 12
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 713

Asp Asp His Gly Arg Gly Asp Leu Gly Arg Leu Lys
1               5                   10

<210> SEQ ID NO 714
<211> LENGTH: 390
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 714

Met Pro Pro Ser Gly Leu Arg Leu Leu Leu Leu Leu Leu Pro Leu Leu
1               5                   10                  15
```

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
 50                  55                  60

Gln Gly Glu Val Pro Pro Gly Pro Leu Pro Glu Ala Val Leu Ala Leu
 65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
            115                 120                 125

His Ser Ile Tyr Met Phe Phe Asn Thr Ser Glu Leu Arg Glu Ala Val
130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
            165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
            195                 200                 205

Ser Arg Gly Gly Glu Ile Glu Gly Phe Arg Leu Ser Ala His Cys Ser
210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
            245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
            275                 280                 285

Thr Glu Lys Asn Cys Cys Val Arg Gln Leu Tyr Ile Asp Phe Arg Lys
            290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
            370                 375                 380

Arg Ser Cys Lys Cys Ser
385                 390

<210> SEQ ID NO 715
<211> LENGTH: 338
<212> TYPE: PRT
<213> ORGANISM: Unknown
<220> FEATURE:

<223> OTHER INFORMATION: Human (Homo sapiens), chimeric or humanized
     antibody peptide sequence

<400> SEQUENCE: 715

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Glu Glu Val Pro
    50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Asn Ala Ile Pro Pro Thr Phe Tyr Arg Pro Tyr Phe Arg
        115                 120                 125

Ile Val Arg Phe Asp Val Ser Ala Met Glu Lys Asn Ala Ser Asn Leu
130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val His
        195                 200                 205

Glu Trp Leu Pro Ser Tyr Arg Leu Glu Ser Gln Gln Thr Asn Arg Arg
210                 215                 220

Lys Lys Arg Ala Leu Asp Ala Ala Tyr Cys Phe Arg Val Gln Asp Asn
225                 230                 235                 240

Cys Cys Leu Arg Pro Leu Tyr Ile Asp Phe Lys Arg Asp Leu Gly Trp
                245                 250                 255

Lys Trp Ile His Glu Pro Lys Gly Tyr Asn Ala Asn Phe Cys Ala Gly
            260                 265                 270

Ala Cys Pro Tyr Leu Trp Ser Ser Asp Thr Gln His Ser Arg Val Leu
        275                 280                 285

Ser Leu Tyr Asn Thr Ile Asn Pro Glu Ala Ser Ala Ser Pro Cys Cys
290                 295                 300

Val Ser Gln Asp Leu Glu Pro Leu Thr Ile Leu Tyr Tyr Ile Gly Lys
305                 310                 315                 320

Thr Pro Lys Ile Glu Gln Leu Ser Asn Met Ile Val Lys Ser Cys Lys
                325                 330                 335

Cys Ser

<210> SEQ ID NO 716
<211> LENGTH: 411
<212> TYPE: PRT
<213> ORGANISM: Unknown
<220> FEATURE:
<223> OTHER INFORMATION: Human (Homo sapiens), chimeric or humanized
     antibody peptide sequence

```
<400> SEQUENCE: 716

Met Lys Met His Leu Gln Arg Ala Leu Val Leu Ala Leu Leu Asn
1               5                   10                  15

Phe Ala Thr Val Ser Leu Ser Leu Ser Thr Cys Thr Thr Leu Asp Phe
            20                  25                  30

Gly His Ile Lys Lys Arg Val Glu Ala Ile Arg Gly Gln Ile Leu
            35                  40                  45

Ser Lys Leu Arg Leu Thr Ser Pro Glu Pro Thr Val Thr His Val
    50                  55                  60

Pro Tyr Gln Val Leu Ala Leu Tyr Asn Ser Thr Arg Glu Leu Leu Glu
65                  70                  75                  80

Glu Met His Gly Glu Arg Glu Gly Cys Thr Gln Glu Asn Thr Glu
                85                  90                  95

Ser Glu Tyr Tyr Ala Lys Glu Ile His Lys Phe Asp Met Ile Gln Gly
                100                 105                 110

Leu Ala Glu His Asn Glu Leu Ala Val Cys Pro Lys Gly Ile Thr Ser
                115                 120                 125

Lys Val Phe Arg Phe Asn Val Ser Val Glu Lys Asn Arg Thr Asn
    130                 135                 140

Leu Phe Arg Ala Glu Phe Arg Val Leu Arg Val Pro Asn Pro Ser Ser
145                 150                 155                 160

Lys Arg Asn Glu Gln Arg Ile Glu Leu Phe Gln Ile Leu Arg Pro Asp
                165                 170                 175

Glu His Ile Ala Lys Gln Arg Tyr Ile Gly Gly Lys Asn Leu Pro Thr
                180                 185                 190

Arg Gly Thr Ala Glu Trp Leu Ser Phe Asp Val Thr Asp Thr Val Arg
        195                 200                 205

Glu Trp Leu Leu Arg Arg Glu Ser Asn Leu Gly Leu Glu Ile Ser Ile
        210                 215                 220

His Cys Pro Cys His Thr Phe Gln Pro Asn Gly Asp Ile Leu Glu Asn
225                 230                 235                 240

Ile His Glu Val Met Glu Ile Lys Phe Lys Gly Val Asp Asn Glu Asp
                245                 250                 255

Asp His Gly Arg Gly Asp Leu Gly Arg Leu Lys Lys Gln Lys His
                260                 265                 270

His Asn Pro His Leu Ile Leu Met Met Ile Pro Pro His Arg Leu Asp
                275                 280                 285

Asn Pro Gly Gln Gly Gly Gln Arg Lys Lys Arg Ala Leu Asp Thr Asn
                290                 295                 300

Tyr Cys Phe Arg Asn Leu Glu Glu Asn Cys Cys Val Arg Pro Leu Tyr
305                 310                 315                 320

Ile Asp Phe Arg Gln Asp Leu Gly Trp Lys Trp Val His Glu Pro Lys
                325                 330                 335

Gly Tyr Tyr Ala Asn Phe Cys Ser Gly Pro Cys Pro Tyr Leu Arg Ser
                340                 345                 350

Ala Asp Thr Thr His Ser Thr Val Leu Gly Leu Tyr Asn Thr Leu Asn
                355                 360                 365

Pro Glu Ala Ser Ala Ser Pro Cys Cys Val Pro Gln Asp Leu Glu Pro
        370                 375                 380

Leu Thr Ile Leu Tyr Tyr Val Gly Arg Thr Pro Lys Val Glu Gln Leu
385                 390                 395                 400

Ser Asn Met Val Val Lys Ser Cys Lys Cys Ser
                405                 410
```

<210> SEQ ID NO 717
<211> LENGTH: 219
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 717

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Arg Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Ser Phe Gly Ala Gly Thr Lys Leu Glu Leu Lys
                100                 105                 110

Ala Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
        210                 215

<210> SEQ ID NO 718
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 718

Lys Ser Ser Gln Ser Leu Leu Gly Arg Gly Asp Leu Gly Asn Ala Leu
1               5                   10                  15

Ala

<210> SEQ ID NO 719
<211> LENGTH: 19
<212> TYPE: PRT
<213> ORGANISM: Unknown
<220> FEATURE:
<223> OTHER INFORMATION: Human (Homo sapiens), chimeric or humanized
      antibody peptide sequence

```
<400> SEQUENCE: 719

Lys Ser Ser Gln Ser Leu Leu Asn Ser Gly Arg Gly Asp Leu Gly Asn
1               5                   10                  15

Ala Leu Ala

<210> SEQ ID NO 720
<211> LENGTH: 21
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 720

Lys Ser Ser Gln Ser Leu Leu Gly Arg Gly Asp Leu Gly Arg Leu Lys
1               5                   10                  15

Lys Asn Ala Leu Ala
            20

<210> SEQ ID NO 721
<211> LENGTH: 9
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 721

Gly Arg Gly Asp Leu Gly Arg Leu Lys
1               5

<210> SEQ ID NO 722
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 722

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Met His Trp Val Lys Gln Ala Pro Gly Lys Gly Leu Lys Trp Val
            35                  40                  45

Ala Arg Ile Asn Thr Glu Thr Gly Glu Pro Thr Phe Ala Asp Asp Phe
    50                  55                  60

Arg Gly Arg Phe Ala Val Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ile Phe Tyr Tyr Gly Arg Asp Ser Trp Gly Gln Gly Thr Thr Leu
            100                 105                 110

Thr Val Ser Ser
        115

<210> SEQ ID NO 723
<211> LENGTH: 116
<212> TYPE: PRT
<213> ORGANISM: Unknown
<220> FEATURE:
```

<223> OTHER INFORMATION: Human (Homo sapiens), chimeric or humanized
      antibody peptide sequence

<400> SEQUENCE: 723

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
                20                  25                  30

Ser Met His Trp Val Arg Gln Ala Pro Gly Gln Gly Leu Glu Trp Val
            35                  40                  45

Ala Arg Ile Asn Thr Glu Thr Gly Glu Pro Thr Phe Ala Asp Asp Phe
        50                  55                  60

Arg Gly Arg Phe Thr Val Thr Leu Asp Thr Ser Ser Thr Ala Tyr
65                  70                  75                  80

Leu Glu Ile Arg Ser Leu Arg Ser Asp Asp Thr Ala Val Tyr Phe Cys
                85                  90                  95

Ala Ile Phe Tyr Tyr Gly Arg Asp Ser Trp Gly Gln Gly Thr Thr Leu
                100                 105                 110

Thr Val Ser Ser
        115

<210> SEQ ID NO 724
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 724

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
                20                  25                  30

Ser Met His Trp Val Arg Gln Ala Pro Gly Gln Gly Leu Glu Trp Val
            35                  40                  45

Ala Arg Ile Asn Thr Glu Thr Gly Glu Pro Thr Phe Ala Asp Asp Phe
        50                  55                  60

Arg Gly Arg Phe Thr Val Thr Leu Asp Thr Ser Ser Thr Ala Tyr
65                  70                  75                  80

Leu Glu Ile Arg Ser Leu Arg Ser Asp Asp Thr Ala Val Tyr Phe Cys
                85                  90                  95

Ala Ile Phe Tyr Tyr Gly Arg Asp Ser Trp Gly Gln Gly Thr Thr Leu
                100                 105                 110

Thr Val Ser Ser
        115

<210> SEQ ID NO 725
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 725

Gln Ile Gln Leu Val Gln Ser Gly Ala Lys Val Lys Lys Pro Gly Ala
1               5                   10                  15

Ser Val Lys Ile Ser Cys Lys Ala Ser Gly Tyr Thr Phe Thr Asp Tyr

```
            20                  25                  30

Ser Met His Trp Val Arg Gln Ala Pro Gly Gln Gly Leu Glu Trp Val
        35                  40                  45

Ala Arg Ile Asn Thr Glu Thr Gly Glu Pro Thr Phe Ala Asp Asp Phe
    50                  55                  60

Arg Gly Arg Phe Ser Val Thr Leu Asp Thr Ser Thr Ser Thr Ala Tyr
65                  70                  75                  80

Leu Glu Ile Thr Ser Leu Arg Ser Asp Asp Thr Ala Val Tyr Phe Cys
                85                  90                  95

Ala Ile Phe Tyr Tyr Gly Arg Asp Thr Trp Gly Gln Gly Thr Thr Leu
            100                 105                 110

Thr Val Ser Ser
        115

<210> SEQ ID NO 726
<211> LENGTH: 116
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 726

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Val
        35                  40                  45

Ala Arg Ile Asn Thr Glu Thr Gly Glu Pro Thr Phe Ala Asp Asp Phe
    50                  55                  60

Arg Gly Arg Phe Thr Val Thr Leu Asp Thr Ser Thr Ser Thr Ala Tyr
65                  70                  75                  80

Leu Glu Ile Arg Ser Leu Arg Ser Asp Asp Thr Ala Val Tyr Phe Cys
                85                  90                  95

Ala Ile Phe Tyr Tyr Gly Arg Asp Thr Trp Gly Gln Gly Thr Thr Leu
            100                 105                 110

Thr Val Ser Ser
        115

<210> SEQ ID NO 727
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 727

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
```

```
              65                  70                  75                  80
Ile Ser Ser Val Gln Ala Glu Asp Leu Ala Val Tyr Tyr Cys Lys Gln
                    85                  90                  95

Ser Tyr Asn Leu Leu Ser Phe Gly Ala Gly Thr Lys Leu Glu Leu Lys
                    100                 105                 110

Arg

<210> SEQ ID NO 728
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 728

Glu Ile Val Met Thr Gln Ser Pro Ala Thr Leu Ser Val Ser Pro Gly
1               5                   10                  15

Glu Arg Val Thr Met Ser Cys Lys Ser Ser Gln Ser Leu Leu Asn Ser
                    20                  25                  30

Arg Thr Arg Lys Asn Tyr Leu Ala Trp Tyr Gln Gln Lys Pro Gly Gln
                35                  40                  45

Ala Pro Arg Leu Leu Ile Tyr Trp Ala Ser Thr Arg Glu Ser Gly Val
            50                  55                  60

Pro Ala Arg Phe Ser Gly Ser Gly Ser Gly Thr Glu Phe Thr Leu Thr
65                  70                  75                  80

Ile Ser Ser Val Gln Ser Glu Asp Phe Ala Val Tyr Tyr Cys Lys Gln
                    85                  90                  95

Ser Tyr Asn Leu Leu Ser Phe Gly Gln Gly Thr Val Leu Glu Ile Lys
                    100                 105                 110

Arg

<210> SEQ ID NO 729
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 729

Glu Ile Val Met Thr Gln Ser Pro Ala Thr Leu Ser Val Ser Pro Gly
1               5                   10                  15

Glu Ile Val Thr Met Ser Cys Lys Ser Ser Gln Ser Leu Leu Asn Ser
                    20                  25                  30

Arg Ser Arg Lys Asn Tyr Leu Ala Trp Tyr Gln Gln Lys Pro Gly Gln
                35                  40                  45

Ala Pro Arg Leu Leu Ile Tyr Trp Ala Ser Thr Arg Glu Ser Gly Val
            50                  55                  60

Pro Ala Arg Phe Ser Gly Ser Gly Ser Gly Thr Glu Phe Thr Leu Thr
65                  70                  75                  80

Ile Ser Ser Val Gln Ser Glu Asp Phe Ala Val Tyr Tyr Cys Lys Gln
                    85                  90                  95

Ser Tyr Asn Leu Leu Ser Phe Gly Gln Gly Thr Val Leu Glu Ile Lys
                    100                 105                 110

Arg
```

```
<210> SEQ ID NO 730
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 730

Glu Ile Val Met Thr Gln Thr Pro Val Thr Leu Ser Val Ser Pro Gly
1               5                   10                  15

Glu Arg Val Thr Met Ser Cys Lys Ser Gln Ser Leu Leu Asn Ser
            20                  25                  30

Arg Thr Arg Lys Asn Tyr Leu Ala Trp Tyr Gln Lys Pro Gly Gln
        35                  40                  45

Ala Pro Arg Leu Leu Ile Tyr Trp Ala Ser Thr Arg Glu Ser Asp Val
50                  55                  60

Pro Ala Arg Phe Ser Gly Ser Gly Ser Gly Thr Glu Phe Thr Leu Thr
65                  70                  75                  80

Ile Ser Ser Val Gln Ser Glu Asp Phe Ala Val Tyr Tyr Cys Lys Gln
                85                  90                  95

Ser Ser Asn Leu Leu Ser Phe Gly Gln Gly Thr Val Leu Glu Ile Lys
            100                 105                 110

Arg

<210> SEQ ID NO 731
<211> LENGTH: 113
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 731

Glu Ile Val Met Thr Gln Ser Pro Ala Thr Leu Ser Val Ser Pro Gly
1               5                   10                  15

Glu Arg Val Thr Met Ser Cys Lys Ser Ser Gln Ser Leu Leu Asn Ser
            20                  25                  30

Arg Ser Arg Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Val
50                  55                  60

Pro Ala Arg Phe Ser Gly Ser Gly Ser Gly Thr Glu Phe Thr Leu Thr
65                  70                  75                  80

Ile Ser Ser Val Gln Ser Glu Asp Phe Ala Val Tyr Tyr Cys Lys Gln
                85                  90                  95

Ser Tyr Asn Leu Leu Ser Phe Gly Gln Gly Thr Val Leu Glu Ile Lys
            100                 105                 110

Arg

<210> SEQ ID NO 732
<211> LENGTH: 30
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 732

Gln Ile Gln Leu Val Gln Ser Gly Pro Glu Leu Lys Lys Pro Gly Glu
```

```
                1               5                  10                  15
Thr Val Lys Ile Ser Cys Lys Ala Ser Gly Tyr Thr Phe Thr
                    20                  25                  30

<210> SEQ ID NO 733
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 733

Asp Tyr Ser Met His
1               5

<210> SEQ ID NO 734
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 734

Trp Val Lys Gln Ala Pro Gly Lys Gly Leu Lys Trp Val Ala
1               5                   10

<210> SEQ ID NO 735
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 735

Arg Ile Asn Thr Glu Thr Gly Glu Pro Thr Phe Ala Asp Asp Phe Arg
1               5                   10                  15

Gly

<210> SEQ ID NO 736
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 736

Arg Phe Ala Val Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Ile
                20                  25                  30

<210> SEQ ID NO 737
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 737

Phe Tyr Tyr Gly Arg Asp Ser
1               5
```

<210> SEQ ID NO 738
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 738

Trp Gly Gln Gly Thr Thr Leu Thr Val Ser Ser
1               5                   10

<210> SEQ ID NO 739
<211> LENGTH: 30
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 739

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr
            20                  25                  30

<210> SEQ ID NO 740
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 740

Trp Val Arg Gln Ala Pro Gly Gln Gly Leu Glu Trp Val Ala
1               5                   10

<210> SEQ ID NO 741
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 741

Arg Phe Thr Val Thr Leu Asp Thr Ser Thr Ser Thr Ala Tyr Leu Glu
1               5                   10                  15

Ile Arg Ser Leu Arg Ser Asp Asp Thr Ala Val Tyr Phe Cys Ala Ile
            20                  25                  30

<210> SEQ ID NO 742
<211> LENGTH: 30
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 742

Gln Ile Gln Leu Val Gln Ser Gly Ala Lys Val Lys Lys Pro Gly Ala
1               5                   10                  15

Ser Val Lys Ile Ser Cys Lys Ala Ser Gly Tyr Thr Phe Thr
            20                  25                  30

```
<210> SEQ ID NO 743
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 743

Arg Phe Ser Val Thr Leu Asp Thr Ser Thr Ser Thr Ala Tyr Leu Glu
1               5                   10                  15

Ile Thr Ser Leu Arg Ser Asp Asp Thr Ala Val Tyr Phe Cys Ala Ile
            20                  25                  30

<210> SEQ ID NO 744
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 744

Phe Tyr Tyr Gly Arg Asp Thr
1               5

<210> SEQ ID NO 745
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 745

Asp Ile Val Met Thr Gln Ser Pro Ser Ser Leu Ala Val Ser Ala Gly
1               5                   10                  15

Glu Lys Val Thr Met Ser Cys
            20

<210> SEQ ID NO 746
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 746

Lys Ser Ser Gln Ser Leu Leu Asn Ser Arg Thr Arg Lys Asn Tyr Leu
1               5                   10                  15

Ala

<210> SEQ ID NO 747
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 747

Trp Tyr Gln Gln Lys Pro Gly Gln Ser Pro Arg Leu Leu Ile Tyr
1               5                   10                  15
```

<210> SEQ ID NO 748
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 748

Trp Ala Ser Thr Arg Glu Ser
1               5

<210> SEQ ID NO 749
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 749

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 750
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 750

Lys Gln Ser Tyr Asn Leu Leu Ser
1               5

<210> SEQ ID NO 751
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 751

Phe Gly Ala Gly Thr Lys Leu Glu Leu Lys Arg
1               5                   10

<210> SEQ ID NO 752
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 752

Glu Ile Val Met Thr Gln Ser Pro Ala Thr Leu Ser Val Ser Pro Gly
1               5                   10                  15

Glu Arg Val Thr Met Ser Cys
            20

<210> SEQ ID NO 753
<211> LENGTH: 32

```
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 753

Gly Val Pro Ala Arg Phe Ser Gly Ser Gly Ser Gly Thr Glu Phe Thr
1               5                   10                  15

Leu Thr Ile Ser Ser Val Gln Ser Glu Asp Phe Ala Val Tyr Tyr Cys
            20                  25                  30

<210> SEQ ID NO 754
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 754

Phe Gly Gln Gly Thr Val Leu Glu Ile Lys Arg
1               5                   10

<210> SEQ ID NO 755
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 755

Glu Ile Val Met Thr Gln Ser Pro Ala Thr Leu Ser Val Ser Pro Gly
1               5                   10                  15

Glu Ile Val Thr Met Ser Cys
            20

<210> SEQ ID NO 756
<211> LENGTH: 4
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 756

Arg Gly Asp Leu
1

<210> SEQ ID NO 757
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 757

Glu Ile Val Met Thr Gln Thr Pro Val Thr Leu Ser Val Ser Pro Gly
1               5                   10                  15

Glu Arg Val Thr Met Ser Cys
            20

<210> SEQ ID NO 758
<211> LENGTH: 32
```

```
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 758

Asp Val Pro Ala Arg Phe Ser Gly Ser Gly Ser Gly Thr Glu Phe Thr
1               5                   10                  15

Leu Thr Ile Ser Ser Val Gln Ser Glu Asp Phe Ala Val Tyr Tyr Cys
            20                  25                  30

<210> SEQ ID NO 759
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 759

Phe Asp Asp Ser Tyr
1               5

<210> SEQ ID NO 760
<211> LENGTH: 118
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 760

Lys Gln Asp Lys Ile Leu Ala Cys Ala Pro Leu Tyr His Trp Arg Thr
1               5                   10                  15

Glu Met Lys Gln Glu Arg Glu Pro Val Gly Thr Cys Phe Leu Gln Asp
            20                  25                  30

Gly Thr Lys Thr Val Glu Tyr Ala Pro Cys Arg Ser Gln Asp Ile Asp
        35                  40                  45

Ala Asp Gly Gln Gly Phe Cys Gln Gly Gly Phe Ser Ile Asp Phe Thr
    50                  55                  60

Lys Ala Asp Arg Val Leu Leu Gly Gly Pro Gly Ser Phe Tyr Trp Gln
65                  70                  75                  80

Gly Gln Leu Ile Ser Asp Gln Val Ala Glu Ile Val Ser Lys Tyr Asp
                85                  90                  95

Pro Asn Val Tyr Ser Ile Lys Tyr Asn Asn Gln Leu Ala Thr Arg Thr
            100                 105                 110

Ala Gln Ala Ile Phe Asp
        115

<210> SEQ ID NO 761
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 761

Asn Leu Asp Cys Met
1               5

<210> SEQ ID NO 762
```

```
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 762

Tyr Asn Leu Asp Cys
1               5

<210> SEQ ID NO 763
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 763

Gln Cys Ser Asp Tyr Asn Leu
1               5

<210> SEQ ID NO 764
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 764

Ser Met His Asn Asn
1               5

<210> SEQ ID NO 765
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 765

Lys Ser Ser Gln Ser Leu Leu Gly Arg Gly Asp Leu Gly Arg Leu Lys
1               5                   10                  15

Lys

<210> SEQ ID NO 766
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 766

Thr Phe Thr Asp Tyr Ser Met His
1               5

<210> SEQ ID NO 767
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence
```

```
<400> SEQUENCE: 767

Arg Ile Asn Thr Glu Thr Gly Glu Pro Thr Phe Ala Asp Asp Phe Arg
1               5                   10                  15

Gly

<210> SEQ ID NO 768
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 768

Phe Tyr Tyr Gly Arg Asp Ser
1               5

<210> SEQ ID NO 769
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 769

Asp Tyr Ser Met His
1               5

<210> SEQ ID NO 770
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 770

Arg Ile Asn Thr Glu Thr Gly Glu Pro Thr Phe Ala Asp Asp Phe Arg
1               5                   10                  15

Gly

<210> SEQ ID NO 771
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 771

Phe Tyr Tyr Gly Arg Asp Ser
1               5

<210> SEQ ID NO 772
<211> LENGTH: 19
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 772

Lys Ser Ser Gln Ser Leu Leu Asn Ser Gly Arg Gly Asp Leu Gly Asn
1               5                   10                  15
```

Ala Leu Ala

<210> SEQ ID NO 773
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 773

Trp Ala Ser Thr Arg Glu Ser
1               5

<210> SEQ ID NO 774
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 774

Lys Gln Ser Tyr Asn Leu Ile Ser
1               5

<210> SEQ ID NO 775
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 775

Asp Tyr Ser Met His
1               5

<210> SEQ ID NO 776
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 776

Arg Ile Asn Thr Glu Thr Gly Glu Pro Thr Phe Ala Asp Asp Phe Arg
1               5                   10                  15

Gly

<210> SEQ ID NO 777
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 777

Phe Tyr Tyr Gly Arg Asp Thr
1               5

<210> SEQ ID NO 778
<211> LENGTH: 25
<212> TYPE: PRT
<213> ORGANISM: Unknown

```
<220> FEATURE:
<223> OTHER INFORMATION: Human (Homo sapiens), chimeric or humanized
      antibody peptide sequence

<400> SEQUENCE: 778

Lys Ser Ser Gln Ser Leu Leu Gly Arg Gly Asp Leu Gly Arg Leu Lys
1               5                   10                  15

Lys Gln Lys Asp His Asn Ala Leu Ala
            20                  25

<210> SEQ ID NO 779
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 779

Trp Ala Ser Thr Arg Glu Ser
1               5

<210> SEQ ID NO 780
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 780

Lys Gln Ser Ser Asn Leu Ile Ser
1               5

<210> SEQ ID NO 781
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 781

Asp Tyr Ser Met His
1               5

<210> SEQ ID NO 782
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 782

Arg Ile Asn Thr Glu Thr Gly Glu Pro Thr Phe Ala Asp Asp Phe Arg
1               5                   10                  15

Gly

<210> SEQ ID NO 783
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence
```

```
<400> SEQUENCE: 783

Phe Tyr Tyr Gly Arg Asp Tyr
1               5

<210> SEQ ID NO 784
<211> LENGTH: 24
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 784

Lys Ser Ser Gln Ser Leu Leu Gly Arg Gly Asp Leu Gly Arg Leu Lys
1               5                   10                  15

Lys Gln Lys Asp Asn Ala Leu Ala
            20

<210> SEQ ID NO 785
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 785

Trp Ala Ser Thr Arg Glu Ser
1               5

<210> SEQ ID NO 786
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 786

Lys Gln Ser Tyr Asn Leu Leu Ser
1               5

<210> SEQ ID NO 787
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 787

Asp Tyr Ser Met His
1               5

<210> SEQ ID NO 788
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 788

Arg Ile Asn Thr Glu Thr Gly Glu Pro Thr Phe Ala Asp Asp Phe Arg
1               5                   10                  15

Gly
```

<210> SEQ ID NO 789
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 789

Phe Tyr Tyr Gly Arg Asp Thr
1               5

<210> SEQ ID NO 790
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 790

Lys Ser Ser Gln Ser Leu Leu Gly Arg Gly Asp Leu Gly Arg Leu Lys
1               5                   10                  15

Lys Gln Lys Asn Ala Leu Ala
            20

<210> SEQ ID NO 791
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 791

Trp Ala Ser Thr Arg Glu Ser
1               5

<210> SEQ ID NO 792
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 792

Lys Gln Ser Tyr Asn Leu Leu Ser
1               5

<210> SEQ ID NO 793
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 793

Asp Tyr Ser Met His
1               5

<210> SEQ ID NO 794
<211> LENGTH: 17
<212> TYPE: PRT
<213> ORGANISM: Unknown

```
<220> FEATURE:
<223> OTHER INFORMATION: Human (Homo sapiens), chimeric or humanized
      antibody peptide sequence

<400> SEQUENCE: 794

Arg Ile Asn Thr Glu Thr Gly Glu Pro Thr Phe Ala Asp Asp Phe Arg
1               5                   10                  15

Gly

<210> SEQ ID NO 795
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 795

Phe Tyr Tyr Gly Arg Asp Ser
1               5

<210> SEQ ID NO 796
<211> LENGTH: 22
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 796

Lys Ser Ser Gln Ser Leu Leu Gly Arg Gly Asp Leu Gly Arg Leu Lys
1               5                   10                  15

Lys Gln Asn Ala Leu Ala
            20

<210> SEQ ID NO 797
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 797

Trp Ala Ser Thr Arg Glu Ser
1               5

<210> SEQ ID NO 798
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 798

Lys Gln Ser Tyr Asn Leu Leu Ser
1               5

<210> SEQ ID NO 799
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence
```

```
<400> SEQUENCE: 799

Asp Tyr Ser Met His
1               5

<210> SEQ ID NO 800
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 800

Arg Ile Asn Thr Glu Thr Gly Glu Pro Thr Phe Ala Asp Asp Phe Arg
1               5                   10                  15

Gly

<210> SEQ ID NO 801
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 801

Phe Tyr Tyr Gly Arg Asp Thr
1               5

<210> SEQ ID NO 802
<211> LENGTH: 21
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 802

Lys Ser Ser Gln Ser Leu Leu Gly Arg Gly Asp Leu Gly Arg Leu Lys
1               5                   10                  15

Lys Asn Ala Leu Ala
            20

<210> SEQ ID NO 803
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 803

Trp Ala Ser Thr Arg Glu Ser
1               5

<210> SEQ ID NO 804
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 804

Lys Gln Ser Tyr Asn Leu Leu Ser
1               5
```

<210> SEQ ID NO 805
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 805

Asp Tyr Ser Met His
1               5

<210> SEQ ID NO 806
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 806

Arg Ile Asn Thr Glu Thr Gly Glu Pro Thr Phe Ala Asp Asp Phe Arg
1               5                   10                  15

Gly

<210> SEQ ID NO 807
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 807

Phe Tyr Tyr Gly Arg Asp Ser
1               5

<210> SEQ ID NO 808
<211> LENGTH: 20
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 808

Lys Ser Ser Gln Ser Leu Leu Gly Arg Gly Asp Leu Gly Arg Leu Lys
1               5                   10                  15

Asn Ala Leu Ala
            20

<210> SEQ ID NO 809
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 809

Trp Ala Ser Thr Arg Glu Ser
1               5

<210> SEQ ID NO 810
<211> LENGTH: 8

```
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 810

Lys Gln Ser Tyr Asn Leu Leu Ser
1               5

<210> SEQ ID NO 811
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 811

Asp Tyr Ser Met His
1               5

<210> SEQ ID NO 812
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 812

Arg Ile Asn Thr Glu Thr Gly Glu Pro Thr Phe Ala Asp Asp Phe Arg
1               5                   10                  15

Gly

<210> SEQ ID NO 813
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 813

Phe Tyr Tyr Gly Arg Asp Ser
1               5

<210> SEQ ID NO 814
<211> LENGTH: 19
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 814

Lys Ser Ser Gln Ser Leu Leu Gly Arg Gly Asp Leu Gly Arg Leu Asn
1               5                   10                  15

Ala Leu Ala

<210> SEQ ID NO 815
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence
```

-continued

```
<400> SEQUENCE: 815

Trp Ala Ser Thr Arg Glu Ser
1               5

<210> SEQ ID NO 816
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 816

Lys Gln Ser Tyr Asn Leu Ile Ser
1               5

<210> SEQ ID NO 817
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 817

Asp Tyr Ser Met His
1               5

<210> SEQ ID NO 818
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 818

Arg Ile Asn Thr Glu Thr Gly Glu Pro Thr Phe Ala Asp Asp Phe Arg
1               5                   10                  15

Gly

<210> SEQ ID NO 819
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 819

Phe Tyr Tyr Gly Arg Asp Thr
1               5

<210> SEQ ID NO 820
<211> LENGTH: 18
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 820

Lys Ser Ser Gln Ser Leu Leu Gly Arg Gly Asp Leu Gly Arg Asn Ala
1               5                   10                  15

Leu Ala
```

<210> SEQ ID NO 821
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 821

Trp Ala Ser Thr Arg Glu Ser
1               5

<210> SEQ ID NO 822
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 822

Lys Gln Ser Ser Asn Leu Ile Ser
1               5

<210> SEQ ID NO 823
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 823

Asp Tyr Ser Met His
1               5

<210> SEQ ID NO 824
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 824

Arg Ile Asn Thr Glu Thr Gly Glu Pro Thr Phe Ala Asp Asp Phe Arg
1               5                   10                  15

Gly

<210> SEQ ID NO 825
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 825

Phe Tyr Tyr Gly Arg Asp Tyr
1               5

<210> SEQ ID NO 826
<211> LENGTH: 17
<212> TYPE: PRT
<213> ORGANISM: Unknown
<220> FEATURE:

-continued

```
<223> OTHER INFORMATION: Human (Homo sapiens), chimeric or humanized
      antibody peptide sequence

<400> SEQUENCE: 826

Lys Ser Ser Gln Ser Leu Leu Gly Arg Gly Asp Leu Gly Asn Ala Leu
1               5                   10                  15

Ala

<210> SEQ ID NO 827
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 827

Trp Ala Ser Thr Arg Glu Ser
1               5

<210> SEQ ID NO 828
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 828

Lys Gln Ser Tyr Asn Leu Leu Ser
1               5

<210> SEQ ID NO 829
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 829

Asp Tyr Ser Met His
1               5

<210> SEQ ID NO 830
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 830

Arg Ile Asn Thr Glu Thr Gly Glu Pro Thr Phe Ala Asp Asp Phe Arg
1               5                   10                  15

Gly

<210> SEQ ID NO 831
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 831
```

Phe Tyr Tyr Gly Arg Asp Thr
1               5

<210> SEQ ID NO 832
<211> LENGTH: 22
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 832

Lys Ser Ser Gln Ser Leu Leu Gly Arg Gly Asp Leu Gly Arg Leu Lys
1               5                   10                  15

Lys Gln Lys Asp His His
            20

<210> SEQ ID NO 833
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 833

Trp Ala Ser Thr Arg Glu Ser
1               5

<210> SEQ ID NO 834
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 834

Lys Gln Ser Tyr Asn Leu Leu Ser
1               5

<210> SEQ ID NO 835
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 835

Asp Tyr Ser Met His
1               5

<210> SEQ ID NO 836
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 836

Arg Ile Asn Thr Glu Thr Gly Glu Pro Thr Phe Ala Asp Asp Phe Arg
1               5                   10                  15

Gly

```
<210> SEQ ID NO 837
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 837

Phe Tyr Tyr Gly Arg Asp Ser
1               5

<210> SEQ ID NO 838
<211> LENGTH: 21
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 838

Lys Ser Ser Gln Ser Leu Leu Gly Arg Gly Asp Leu Gly Arg Leu Lys
1               5                   10                  15

Lys Gln Lys Asp His
            20

<210> SEQ ID NO 839
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 839

Trp Ala Ser Thr Arg Glu Ser
1               5

<210> SEQ ID NO 840
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 840

Lys Gln Ser Tyr Asn Leu Leu Ser
1               5

<210> SEQ ID NO 841
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 841

Asp Tyr Ser Met His
1               5

<210> SEQ ID NO 842
<211> LENGTH: 17
<212> TYPE: PRT
<213> ORGANISM: Unknown
<220> FEATURE:
<223> OTHER INFORMATION: Human (Homo sapiens), chimeric or humanized
``` antibody peptide sequence

<400> SEQUENCE: 842

Arg Ile Asn Thr Glu Thr Gly Glu Pro Thr Phe Ala Asp Asp Phe Arg
1               5                   10                  15

Gly

<210> SEQ ID NO 843
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 843

Phe Tyr Tyr Gly Arg Asp Thr
1               5

<210> SEQ ID NO 844
<211> LENGTH: 20
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 844

Lys Ser Ser Gln Ser Leu Leu Gly Arg Gly Asp Leu Gly Arg Leu Lys
1               5                   10                  15

Lys Gln Lys Asp
            20

<210> SEQ ID NO 845
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 845

Trp Ala Ser Thr Arg Glu Ser
1               5

<210> SEQ ID NO 846
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 846

Lys Gln Ser Tyr Asn Leu Leu Ser
1               5

<210> SEQ ID NO 847
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 847

Asp Tyr Ser Met His
1               5

<210> SEQ ID NO 848
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 848

Arg Ile Asn Thr Glu Thr Gly Glu Pro Thr Phe Ala Asp Asp Phe Arg
1               5                   10                  15

Gly

<210> SEQ ID NO 849
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 849

Phe Tyr Tyr Gly Arg Asp Thr
1               5

<210> SEQ ID NO 850
<211> LENGTH: 19
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 850

Lys Ser Ser Gln Ser Leu Leu Gly Arg Gly Asp Leu Gly Arg Leu Lys
1               5                   10                  15

Lys Gln Lys

<210> SEQ ID NO 851
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 851

Trp Ala Ser Thr Arg Glu Ser
1               5

<210> SEQ ID NO 852
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 852

Lys Gln Ser Ser Asn Leu Ile Ser
1               5

<210> SEQ ID NO 853

```
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 853

Asp Tyr Ser Met His
1               5

<210> SEQ ID NO 854
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 854

Arg Ile Asn Thr Glu Thr Gly Glu Pro Thr Phe Ala Asp Asp Phe Arg
1               5                   10                  15

Gly

<210> SEQ ID NO 855
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 855

Phe Tyr Tyr Gly Arg Asp Tyr
1               5

<210> SEQ ID NO 856
<211> LENGTH: 18
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 856

Lys Ser Ser Gln Ser Leu Leu Gly Arg Gly Asp Leu Gly Arg Leu Lys
1               5                   10                  15

Lys Gln

<210> SEQ ID NO 857
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 857

Trp Ala Ser Thr Arg Glu Ser
1               5

<210> SEQ ID NO 858
<211> LENGTH: 8
<212> TYPE: PRT
<213> ORGANISM: Unknown
<220> FEATURE:
<223> OTHER INFORMATION: Human (Homo sapiens), chimeric or humanized
``` antibody peptide sequence

<400> SEQUENCE: 858

Lys Gln Ser Tyr Asn Leu Leu Ser
1               5

<210> SEQ ID NO 859
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 859

Asp Tyr Ser Met His
1               5

<210> SEQ ID NO 860
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 860

Arg Ile Asn Thr Glu Thr Gly Glu Pro Thr Phe Ala Asp Asp Phe Arg
1               5                   10                  15

Gly

<210> SEQ ID NO 861
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 861

Phe Tyr Tyr Gly Arg Asp Thr
1               5

<210> SEQ ID NO 862
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 862

Lys Ser Ser Gln Ser Leu Leu Gly Arg Gly Asp Leu Gly Arg Leu Lys
1               5                   10                  15

Lys

<210> SEQ ID NO 863
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 863

Trp Ala Ser Thr Arg Glu Ser

```
<210> SEQ ID NO 864
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 864

Lys Gln Ser Tyr Asn Leu Leu Ser
1               5

<210> SEQ ID NO 865
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 865

Asp Tyr Ser Met His
1               5

<210> SEQ ID NO 866
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 866

Arg Ile Asn Thr Glu Thr Gly Glu Pro Thr Phe Ala Asp Asp Phe Arg
1               5                   10                  15

Gly

<210> SEQ ID NO 867
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 867

Phe Tyr Tyr Gly Arg Asp Ser
1               5

<210> SEQ ID NO 868
<211> LENGTH: 16
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 868

Lys Ser Ser Gln Ser Leu Leu Gly Arg Gly Asp Leu Gly Arg Leu Lys
1               5                   10                  15

<210> SEQ ID NO 869
<211> LENGTH: 7
<212> TYPE: PRT
<213> ORGANISM: Unknown
```

```
<220> FEATURE:
<223> OTHER INFORMATION: Human (Homo sapiens), chimeric or humanized
      antibody peptide sequence

<400> SEQUENCE: 869

Trp Ala Ser Thr Arg Glu Ser
1               5

<210> SEQ ID NO 870
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 870

Lys Gln Ser Tyr Asn Leu Leu Ser
1               5

<210> SEQ ID NO 871
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 871

Asp Tyr Ser Met His
1               5

<210> SEQ ID NO 872
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 872

Arg Ile Asn Thr Glu Thr Gly Glu Pro Thr Phe Ala Asp Asp Phe Arg
1               5                   10                  15

Gly

<210> SEQ ID NO 873
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 873

Phe Tyr Tyr Gly Arg Asp Thr
1               5

<210> SEQ ID NO 874
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 874

Lys Ser Ser Gln Ser Leu Leu Gly Arg Gly Asp Leu Gly Arg Leu
```

-continued

```
1               5                  10                 15
```

```
<210> SEQ ID NO 875
<211> LENGTH: 7
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 875

Trp Ala Ser Thr Arg Glu Ser
1               5

<210> SEQ ID NO 876
<211> LENGTH: 8
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 876

Lys Gln Ser Tyr Asn Leu Leu Ser
1               5

<210> SEQ ID NO 877
<211> LENGTH: 14
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (3)..(3)
<223> OTHER INFORMATION: Xaa is Lys or Arg
<220> FEATURE:
<221> NAME/KEY: MISC_FEATURE
<222> LOCATION: (8)..(8)
<223> OTHER INFORMATION: Xaa is Lys or Gln
<220> FEATURE:
<221> NAME/KEY: MISC_FEATURE
<222> LOCATION: (11)..(11)
<223> OTHER INFORMATION: Xaa is Lys or Glu
<220> FEATURE:
<221> NAME/KEY: MISC_FEATURE
<222> LOCATION: (13)..(13)
<223> OTHER INFORMATION: Xaa is Val or Met
<220> FEATURE:
<221> NAME/KEY: MISC_FEATURE
<222> LOCATION: (14)..(14)
<223> OTHER INFORMATION: Xaa is Ala or Gly

<400> SEQUENCE: 877

Trp Val Xaa Gln Ala Pro Gly Xaa Gly Leu Xaa Trp Xaa Xaa
1               5                  10

<210> SEQ ID NO 878
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (3)..(3)
<223> OTHER INFORMATION: Xaa is Ala, Thr or Ser
<220> FEATURE:
<221> NAME/KEY: MISC_FEATURE
<222> LOCATION: (4)..(4)
```

-continued

```
<223> OTHER INFORMATION: Xaa is Val or Phe
<220> FEATURE:
<221> NAME/KEY: MISC_FEATURE
<222> LOCATION: (5)..(5)
<223> OTHER INFORMATION: Xaa is Ser or Thr
<220> FEATURE:
<221> NAME/KEY: MISC_FEATURE
<222> LOCATION: (7)..(7)
<223> OTHER INFORMATION: Xaa is Glu or Asp
<220> FEATURE:
<221> NAME/KEY: MISC_FEATURE
<222> LOCATION: (10)..(10)
<223> OTHER INFORMATION: Xaa is Ala or Thr
<220> FEATURE:
<221> NAME/KEY: MISC_FEATURE
<222> LOCATION: (11)..(11)
<223> OTHER INFORMATION: Xaa is Ser or Thr
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: Xaa is Tyr or Asn
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: MISC_FEATURE
<222> LOCATION: (19)..(19)
<223> OTHER INFORMATION: Xaa is Asn, Arg, Ile or Thr
<220> FEATURE:
<221> NAME/KEY: MISC_FEATURE
<222> LOCATION: (20)..(20)
<223> OTHER INFORMATION: Xaa is Asn or Ser
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: MISC_FEATURE
<222> LOCATION: (22)..(22)
<223> OTHER INFORMATION: Xaa is Lys or Arg
<220> FEATURE:
<221> NAME/KEY: MISC_FEATURE
<222> LOCATION: (23)..(23)
<223> OTHER INFORMATION: Xaa is Asn or Ser
<220> FEATURE:
<221> NAME/KEY: MISC_FEATURE
<222> LOCATION: (24)..(24)
<223> OTHER INFORMATION: Xaa is Glu or Asp
<220> FEATURE:
<221> NAME/KEY: MISC_FEATURE
<222> LOCATION: (27)..(27)
<223> OTHER INFORMATION: Xaa is Thr, Val or Lys

<400> SEQUENCE: 878

Arg Phe Xaa Xaa Xaa Leu Xaa Thr Ser Xaa Xaa Thr Ala Xaa Leu Glx
1               5                   10                  15

Ile Xaa Xaa Leu Xaa Xaa Xaa Asp Thr Ala Xaa Tyr Phe Cys Ala Ile
            20                  25                  30

<210> SEQ ID NO 879
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (6)..(6)
<223> OTHER INFORMATION: Xaa is Thr or Ala
```

<400> SEQUENCE: 879

Trp Gly Gln Gly Thr Xaa Leu Thr Val Ser Ser
1               5                   10

<210> SEQ ID NO 880
<211> LENGTH: 23
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (1)..(1)
<223> OTHER INFORMATION: Xaa is Asp or Glu
<220> FEATURE:
<221> NAME/KEY: MISC_FEATURE
<222> LOCATION: (5)..(5)
<223> OTHER INFORMATION: Xaa is Thr or Ser
<220> FEATURE:
<221> NAME/KEY: MISC_FEATURE
<222> LOCATION: (7)..(7)
<223> OTHER INFORMATION: Xaa is Ser or Thr
<220> FEATURE:
<221> NAME/KEY: MISC_FEATURE
<222> LOCATION: (9)..(9)
<223> OTHER INFORMATION: Xaa is Ser, Ala or Val
<220> FEATURE:
<221> NAME/KEY: MISC_FEATURE
<222> LOCATION: (10)..(10)
<223> OTHER INFORMATION: Xaa is Ser or Thr
<220> FEATURE:
<221> NAME/KEY: MISC_FEATURE
<222> LOCATION: (12)..(12)
<223> OTHER INFORMATION: Xaa is Ala or Ser
<220> FEATURE:
<221> NAME/KEY: MISC_FEATURE
<222> LOCATION: (15)..(15)
<223> OTHER INFORMATION: Xaa is Ala or Pro
<220> FEATURE:
<221> NAME/KEY: MISC_FEATURE
<222> LOCATION: (18)..(18)
<223> OTHER INFORMATION: Xaa is Lys, Arg or Ile

<400> SEQUENCE: 880

Xaa Ile Val Met Xaa Gln Xaa Pro Xaa Xaa Leu Xaa Val Ser Xaa Gly
1               5                   10                  15

Glu Xaa Val Thr Met Ser Cys
            20

<210> SEQ ID NO 881
<211> LENGTH: 15
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (9)..(9)
<223> OTHER INFORMATION: Xaa is Ser or Ala

<400> SEQUENCE: 881

Trp Tyr Gln Gln Lys Pro Gly Gln Xaa Pro Arg Leu Leu Ile Tyr
1               5                   10                  15

<210> SEQ ID NO 882
<211> LENGTH: 32
<212> TYPE: PRT
<213> ORGANISM: Unknown
<220> FEATURE:
<223> OTHER INFORMATION: Human (Homo sapiens), chimeric or humanized

```
                              antibody peptide sequence
<220> FEATURE:
<221> NAME/KEY: MISC_FEATURE
<222> LOCATION: (1)..(1)
<223> OTHER INFORMATION: Xaa is Gly or Asp
<220> FEATURE:
<221> NAME/KEY: MISC_FEATURE
<222> LOCATION: (4)..(4)
<223> OTHER INFORMATION: Xaa is Asp or Ala
<220> FEATURE:
<221> NAME/KEY: MISC_FEATURE
<222> LOCATION: (7)..(7)
<223> OTHER INFORMATION: Xaa is Thr or Ser
<220> FEATURE:
<221> NAME/KEY: MISC_FEATURE
<222> LOCATION: (14)..(14)
<223> OTHER INFORMATION: Xaa is Asp or Glu
<220> FEATURE:
<221> NAME/KEY: MISC_FEATURE
<222> LOCATION: (24)..(24)
<223> OTHER INFORMATION: Xaa is Ala, Ser or Asp
<220> FEATURE:
<221> NAME/KEY: MISC_FEATURE
<222> LOCATION: (27)..(27)
<223> OTHER INFORMATION: Xaa is Leu or Phe

<400> SEQUENCE: 882

Xaa Val Pro Xaa Arg Phe Xaa Gly Ser Gly Ser Gly Thr Xaa Phe Thr
1               5                   10                  15

Leu Thr Ile Ser Ser Val Gln Xaa Glu Asp Xaa Ala Val Tyr Tyr Cys
            20                  25                  30

<210> SEQ ID NO 883
<211> LENGTH: 11
<212> TYPE: PRT
<213> ORGANISM: Unknown
<220> FEATURE:
<223> OTHER INFORMATION: Human (Homo sapiens), chimeric or humanized
      antibody peptide sequence
<220> FEATURE:
<221> NAME/KEY: MISC_FEATURE
<222> LOCATION: (3)..(3)
<223> OTHER INFORMATION: Xaa is Ala or Gln
<220> FEATURE:
<221> NAME/KEY: MISC_FEATURE
<222> LOCATION: (6)..(6)
<223> OTHER INFORMATION: Xaa is Lys or Val
<220> FEATURE:
<221> NAME/KEY: MISC_FEATURE
<222> LOCATION: (9)..(9)
<223> OTHER INFORMATION: Xaa is Leu or Ile

<400> SEQUENCE: 883

Phe Gly Xaa Gly Thr Xaa Leu Glu Xaa Lys Arg
1               5                   10

<210> SEQ ID NO 884
<211> LENGTH: 32
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 884

Gly Val Pro Ser Arg Phe Ser Gly Ser Gly Ser Gly Thr Arg Phe Ser
1               5                   10                  15

Leu Lys Ile Asn Ser Leu Gln Pro Glu Asp Phe Gly Ser Tyr Tyr Cys
            20                  25                  30

<210> SEQ ID NO 885
```

```
<211> LENGTH: 17
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 885

Lys Ser Ser Gln Ser Leu Leu Asn Ser Arg Ser Arg Lys Asn Tyr Leu
1               5                   10                  15

Ala

<210> SEQ ID NO 886
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 886

Asp Ala Asp Gly Gln
1               5

<210> SEQ ID NO 887
<211> LENGTH: 5
<212> TYPE: PRT
<213> ORGANISM: Unknown
<220> FEATURE:
<223> OTHER INFORMATION: Human (Homo sapiens), chimeric or humanized
      antibody peptide sequence

<400> SEQUENCE: 887

Ser Phe Tyr Trp Gln
1               5
```